US 7,229,774 B2
Jun. 12, 2007

(12) United States Patent
Chinnaiyan et al.

(10) Patent No.: US 7,229,774 B2
(45) Date of Patent: Jun. 12, 2007

(54) EXPRESSION PROFILE OF PROSTATE CANCER

(75) Inventors: Arul M. Chinnaiyan, Plymouth, MI (US); Mark A. Rubin, Ann Arbor, MI (US); Arun Sreekumar, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 453 days.

(21) Appl. No.: 10/210,120

(22) Filed: Aug. 1, 2002

(65) Prior Publication Data

US 2003/0175736 A1 Sep. 18, 2003

Related U.S. Application Data

(60) Provisional application No. 60/334,468, filed on Nov. 15, 2001, provisional application No. 60/309,581, filed on Aug. 2, 2001.

(51) Int. Cl.
G01N 33/53 (2006.01)
C12Q 1/68 (2006.01)
C07K 14/435 (2006.01)

(52) U.S. Cl. ............................. 435/7.1; 435/6; 530/350
(58) Field of Classification Search ................. 435/7.1; 514/2
See application file for complete search history.

(56) References Cited

U.S. PATENT DOCUMENTS

| | | | | |
|---|---|---|---|---|
| 5,871,960 | A | 2/1999 | Smith et al. | 435/69.1 |
| 5,871,961 | A | 2/1999 | Smith et al. | 435/69.1 |
| 5,981,830 | A | 11/1999 | Wu et al. | 800/18 |
| 6,335,170 | B1 * | 1/2002 | Orntoft | 435/6 |
| 6,518,028 | B1 | 2/2003 | O'Brien | |
| 2003/0108963 | A1 | 6/2003 | Schlegal et al. | 435/7.23 |

FOREIGN PATENT DOCUMENTS

| | | |
|---|---|---|
| WO | WO 97/18825 | 5/1997 |
| WO | WO 01/25272 | 4/2001 |
| WO | WO 01/57194 | 8/2001 |
| WO | WO 01/73032 | 10/2001 |
| WO | WO 01/77389 | 10/2001 |
| WO | WO 02/27324 | 6/2002 |

OTHER PUBLICATIONS

Grande et al., Clinical Cancer Research, vol. 6, pp. 1790-1795, May 2000.*
Scheurle et al., Anticancer Research, vol. 20, pp. 2091-2096, 2000 (Abstract provided).*
Gunster et al., Journal of Cellular Biochemistry, vol. 81, pp. 129-143, Mar. 2001.*
Abel et al., Genomics, vol. 37, pp. 161-171, 1996.*
Chen et al., Genomics, vol. 38, pp. 30-37, 1996.*
Wallner et al., Nature 320:77 [1986].
Cuypers et al., Cell 37:141 [1984].
Breuer et al., Nature 340:61 [1989].
Jacobs et al., Nature 397:164 [1999].
Weigart et al., Nature 402:429 [1999].
Alizadeh et al., Nature 403:503 [2000].
van Lohuizzen et al., Cell 65:737 [1991].
Etzioni et al., J. Natl. Cancer Inst., 91:1033 [1999].
Maattanen et al., Br. J. Cancer 79:1210 [1999].
Schroder et al., J. Natl. Cancer Inst., 90:1817 [1998].
Jacobsen et al., JAMA 274:1445 [1995].
Brown and Botstein, Nat. Gent., 21:33 [1999].
Schmitz et al., Eur J Biochem 231:815 [1995].
Tsao and Shibata, Am J Pathol 145: 531 [1994].
McNeal and Bostwick, Hum Pathol 17:64 [1986].
McNeal et al., Lancet 1:60 [1986].
De Marzo et al., Am J Pathol 155:1985 [1999].
Shah et al., Am J Pathol 158:1767 [2001].
Saez et al., Nat. Med. 4:1058 [1998].
Kubota et al., Cancer Res. 58:3344 [1998].
Hisatake et al., Cancer Res. 60:5494 [2000].
Smith et al., Trends. Genet. 10:241 [1994].
Mailliard et al., J Biol. Chem. 271:719 [1996].
Pepinsky et al., Nature 321:81 [1986].
Hubaishy et al., Biochemistry 34:14527 [1995].
Chan et al., J. Biol. Chem. 269:32464 [1994].
Selbert et al. Exp. Cell. Res. 222:199 [1996].
Eisen et al., PNAS 95:14863 [1998].
Shurbaji et al., Hum. Pathol., 27:917 [1996].
Tsuji et al., J. Biol. Chem., 266:16948 [1991].
Kurachi et al., Methods Enzymol., 244:100 [1994].
Kazama et al., J. Biol. Chem., 270:66 [1995].
Tanimoto et al., Cancer Res., 57:2884 [1997].
Shirogane, et al., Immunity 11:709 [1999].
Matikainen et al., Blood 93:1980 [1999].
Torres-Rosado et al., PNAS, 90:7181 [1993].
Sewalt et al., Mol. Cell. Biol. 18:3586 [1998].
Webber et al., Carcinogenesis 18:1225 [1997].
Yu et al., Nature 378:505 [1995].
Laible et al., Embo. J. 16:3219 [1997].
Jenuwein et al., Cell Mol. Life Sci. 54:80 [1998].
Satijn et al., Biochim. Biophys. Acta. 1447:1 [1999].
Sinclair et al., Genetics 148:211 [1998].
Emmert-Buck et al., Am. J. Pathol., 156:1109 [2000].
Ferdinandusse et al., J. Lipid Res., 41:1890 [2000].
Kotti et al., J. Biol.Chem., 275:20887 [2000].
Ferdinandusse et al., Nat. Genet., 24:188 [2000].

(Continued)

Primary Examiner—Marjorie A. Moran
Assistant Examiner—Marina Miller
(74) Attorney, Agent, or Firm—Medlen & Carroll, LLP

(57) ABSTRACT

The present invention relates to compositions and methods for cancer diagnostics, including but not limited to, cancer markers. In particular, the present invention provides gene expression profiles associated with prostate cancers. Genes identified as cancer markers using the methods of the present invention find use in the diagnosis and characterization of prostate cancer. In addition, the genes provide targets for cancer drug screens and therapeutic applications.

10 Claims, 137 Drawing Sheets

(6 of 137 Drawing Sheet(s) Filed in Color)

OTHER PUBLICATIONS

Ferdinandusse et al., J Lipid Res 42:137 [2001].
Moyad, Curr Opin Urol 11:457 [2001].
Willett, Oncologist 5:393 [2000].
Zomer et al., J. Lipid Res. 41:1801 [2000].
Yeldandi et al., Mutat. Res. 448:159 [2000].
Shappell et al., Cancer Res. 61:497 [2001].
Mueller et al., PNAS 97:10990 [2000].
Paweletz et al., Cancer Res. 60:6293 [2000].
Tomita et al., Cancer Res., 60:3650 [2000].
Hammond et al., Nature 404:293 [2000].
Macejak et al., Hepatology 31:769 [2000].
Epstein and Potter J. Urol, 166:402 [2001].
Debril et al., J. Mol. Med. 79:30 [2001].
Kotti et al., J. Biol.Chem., 275:20887 [2000].
Clayton et al., Biochem. Soc. Trans. 29:298 [2001].
Dhanasekaran et al., Nature 412: 822 [2001].
Hinoi et al., Am. J. Pathol. 159:2239 2001.
Kumar-Smith et al., J. Biol. Chem. 24:24 [2001].
Francis et al., Nat. Rev. Mol. Cell. Biol. 2:409 [2001].
Mahmoudi et al., Oncogene 20:3055 [2001].
O'Carroll et al., Mol. Cell. Biol. 21:4330 [2001].
Visser et al., Br. J. Hematol. 112:950 [2001].
Borck et al. Curr. Opin. Genet. Dev. 11:175 [2001].
Satijin et al., Mol. Cell. Biol. 21:1360 [2001].
Welsh et al., Cancer Res. 61:5974 [2001].
Magee et al., Cancer Res. 61:5692 [2001].
Brichory et al., PNAS 98:9824-9829.
Riefler et al., J. Biol. Chem. 276:48262 [2001].
Chinnadurai, Mol Cell. 9: 213 [2002].
Luo et al., Cancer Res. 61:4683 [2001].

* cited by examiner

Figure 4
a
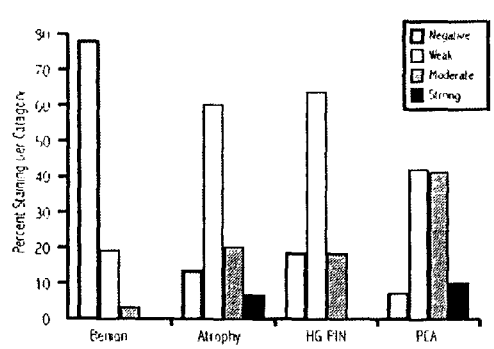
b
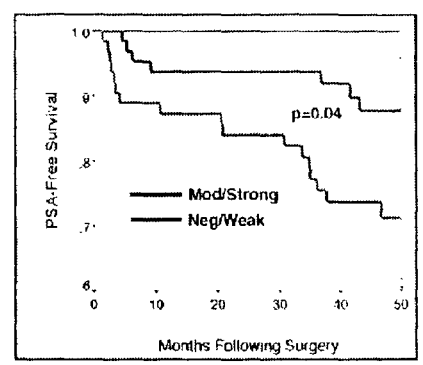

Figure 9

| SEQ ID NO | Name | Accession Number |
|---|---|---|
| 1 | Hepsin | M18930 |
| 2 | pim-1 | M54915 |
| 3 | FKBP5 | XM_004288 |
| 4 | FASN | NM_004104 |
| 5 | FOLH1 | M99487 |
| 6 | TNFSF10 | XM_045049 |
| 7 | PCM1 | XM_044711 |
| 8 | S100A11 | XM_047223 |
| 9 | IGFBP3 | XM_004689 |
| 10 | SLUG | XM_011634 |
| 11 | GSTM3 | J05459 |
| 12 | IL1R2 | X59770 |
| 13 | ITGB4 | X53587 |
| 14 | CCND2 | XM_034568 |
| 15 | EDNRB | S57283 |
| 16 | APP | X06989 |
| 17 | THROMBOSPONDIN 1 | X04665 |
| 18 | ANNEXIN A1 | XM_005665 |
| 19 | EPHA1 | M18391 |
| 20 | NCK1 | XM_051968 |
| 21 | MAPK6 | XM_017662 |
| 22 | SGK | XM_037045 |
| 23 | HEVIN | XM_011533 |
| 24 | MEIS2 | XM_012430 |
| 25 | MYLK | XM_042191 |
| 26 | FZD7 | NM_003507 |
| 27 | CAVEOLIN 2 | XM_004966 |
| 28 | TACC1 | XM_049505 |
| 29 | ARHB | XM_002689 |
| 30 | PSG9 | NM_002784 |
| 31 | GSTM1 | NM_000561 |
| 32 | Keratin 5 | XM_006847 |
| 33 | TIMP2 | XM_027036 |
| 34 | GELSOLIN | XM_016545 |
| 35 | ITM2C | AA034213 |
| 36 | GSTM5 | XM_002154 |
| 37 | VINCULIN | XM_011883 |
| 38 | FHL1 | XM_042931 |

Figure 9 (cont.)

| 39 | GSTP1 | XM_040116 |
|---|---|---|
| 40 | MEIS1 | XM_010880 |
| 41 | ETS2 | XM_009766 |
| 42 | PPP2CB | XM_005121 |
| 43 | CATHEPSIN B | XM_005133 |
| 44 | COL1A2 | XM_029246 |
| 45 | RIG | XM_006029 |
| 46 | VIMENTIN | XM_042952 |
| 47 | MOESIN | XM_013042 |
| 48 | MCAM | XM_006077 |
| 49 | FIBRONECTIN 1 | XM_030549 |
| 50 | NBL1 | XM_001434 |
| 51 | ANNEXIN A4 | XM_031594 |
| 52 | ANNEXIN A11 | XM_035906 |
| 53 | IL1R1 | XM_002686 |
| 54 | IGFBP5 | XM_046731 |
| 55 | CYSTATIN C | XM_009599 |
| 56 | COL15A1 | XM_005592 |
| 57 | ADAMTS1 | XM_047796 |
| 58 | SKI | XM_001535 |
| 59 | EGR1 | XM_033546 |
| 60 | FOSB | NM_006732 |
| 61 | CFLAR | XM_027980 |
| 62 | JUN | XM_001472 |
| 63 | YWHAB | XM_009519 |
| 64 | NRAS | XM_001317 |
| 65 | C7 | J03507 |
| 66 | SCYA2 | XM_038982 |
| 67 | ITGA1 | XM_032902 |
| 68 | LUMICAN | XM_006900 |
| 69 | C1S | XM_032536 |
| 70 | C4BPA | XM_052053 |
| 71 | COL3A1 | XM_044878 |
| 72 | FAT | XM_003477 |
| 73 | MMECD10 | XM_030168 |
| 74 | CLUSTERIN | XM_005113 |
| 75 | PLA2G2A | XM_027887 |
| 76 | MADH4 | XM_030100 |
| 77 | SEPP1 | XM_011306 |
| 78 | RAB2 | XM_037653 |
| 79 | PP1CB | NM_002709 |
| 80 | MPDZ | XM_051281 |

Figure 9 (cont.)

| 81 | PRKCL2 | XM_001880 |
|---|---|---|
| 82 | ATF2 | XM_027217 |
| 83 | RAB5A | NM_004162 |
| 84 | Cathepsin H | XM_007633 |
| 85 | CTBP1 | XM_003445 |
| 86 | MAP3K10 | XM_042665 |
| 87 | TBXA2R | XM_047633 |
| 88 | MTA1 | NM_004689 |
| 89 | RAP2 | NM_002886 |
| 90 | TRAP1 | XM_036666 |
| 91 | TFCP2 | XM_051171 |
| 92 | E2-EPF | XM_012615 |
| 93 | UBCH10 | XM_009488 |
| 94 | TASTIN | XM_006826 |
| 95 | EZH2 | XM_004774; NM004456 |
| 96 | FLS353 | AB024704 |
| 97 | MYBL2 | XM_009492 |
| 98 | LIMK1 | XM_051836 |
| 99 | TRAF4 | XM_031428 |
| 104 | AMACR | XM_043772; NM01324 |
| 114 | GP73 | AF236056 |
| 115 | CTBP2 | AF016507 |
| 116 | Annexin A2 | NM_004039 |
| 117 | Annexin A4 | XM_031596 |
| 118 | Annexin A11 | NM_001157 |
| 119 | ABCC5 (MDR5) | XM_002914 |
| 120 | ASNS | M27396 |
| 121 | TOP2A | NM_001067 |
| 122 | VaV2 | XM_005638 |

FIG. 10 A-1

```
SEQ ID NO:1
   1    tcgagcccgc tttccaggga ccctacctga gggcccacag gtgaggcagc ctggcctagc
  61    aggccccacg ccaccgcctc tgcctccagg ccgcccgctg ctgcggggcc accatgctcc
 121    tgcccaggcc tggagactga cccgaccccg gcactacctc gaggctccgc ccccacctgc
 181    tggaccccag ggtcccaccc tggcccagga ggtcagccag ggaatcatta acaagaggca
 241    gtgacatggc gcagaaggag ggtggccgga ctgtgccatg ctgctccaga cccaaggtgg
 301    cagctctcac tgcggggacc ctgctacttc tgacagccat cggggcggca tcctgggcca
 361    ttgtggctgt tctcctcagg agtgaccagg agccgctgta cccagtgcag gtcagctctg
 421    cggacgctcg gctcatggtc tttgacaaga cggaagggac gtggcggctg ctgtgctcct
 481    cgcgctccaa cgccagggta gccggactca gctgcgagga gatgggcttc ctcagggcac
 541    tgacccactc cgagctggac gtgcgaacgg cgggcgccaa tggcacgtcg ggcttcttct
 601    gtgtggacga ggggaggctg ccccacaccc agaggctgct ggaggtcatc tccgtgtgtg
 661    attgccccag aggccgtttc ttggccgcca tctgccaaga ctgtggccgc aggaagctgc
 721    ccgtggaccg catcgtggga ggccgggaca ccagcttggg ccggtggccg tgcaagtca
 781    gccttcgcta tgatggagca cacctctgtg ggggatccct gctctccggg gactgggtgc
 841    tgacagccgc ccactgcttc ccggagcgga accgggtcct gtcccgatgg cgagtgtttg
 901    ccggtgccgt ggcccaggcc tctccccacg gtctgcagct gggggtgcag gctgtggtct
 961    accacggggg ctatcttccc tttcgggacc ccaacagcga ggagaacagc aacgatattg
1021    ccctggtcca cctctccagt ccctgcccc tcacagaata catccagcct gtgtgcctcc
1081    cagctgccgg ccaggccctg gtggatggca agatctgtac cgtgacgggc tggggcaaca
1141    cgcagtacta tggccaacag gccgggtac tccaggaggc tcgagtcccc ataatcagca
1201    atgatctg caatggcgct gacttctatg gaaaccagat caagcccaag atgttctgtg
1261    ctggctaccc cgagggtggc attgatgcct gccaggcgca cagcggtggt cccttTgtgt
1321    gtgaggacag catctctcgg acgccacgtt ggcggctgtg tggcattgtg agttggggca
1381    ctggctgtgc cctggcccag aagccaggcg tctacaccaa agtcagtgac ttccgggagt
1441    ggatcttcca ggccataaag actcactccg aagccagcgg catggtgacc cagctctgac
1501    cggtggcttc tcgctgcgca gcctccaggg cccgaggtga tcccggtggt gggatccacg
1561    ctgggccgag gatgggacgt ttttcttctt gggcccggtc cacaggtcca aggacaccct
1621    ccctccaggg tcctctcttc cacagtggcg ggcccactca gccccgagac cacccaacct
1681    caccctcctg accccatgt aaatattgtt ctgctgtctg ggactcctgt ctaggtgccc
1741    ctgatgatgg gatgctcttt aaataataaa gatggttttg att SEQ ID NO:2
   1    gaggaggccc gagaggagtc ggtggcagcg gcggcggcgg gaccggcagc agcagcagca
  61    gcagcagcag caaccactag cctcctgccc cgcggcgttg cgacgagccc cacgagccgc
 121    tcaccccgcc gttctcagcg ctgcccgacc ccgctggcgc gcctcccgcc gcagtccggg
 181    cagcgcctca gttgtcctcc gactcgccct cggccttcgc gcagcgcagc acagccgcac
 241    gcaccgcagc acagcacagc acagcccagg catagcttcg gcacagcccc ggctccggct
 301    cctgcggcag ctcctctggc acgtccctgc gccgacattc tggaggttgg atgctcttgt
 361    ccaaaatcaa ctcgcttgcc cacctgcgcg ccgcgccctg caacgacctg cacgccacca
 421    agctggcgcc cggcaaggag aaggagcccc tggagtcgca gtaccaggtg ggcccgctac
 481    tgggcagcgg cggcttcggc tcggtctact caggcatccg cgtctccgac aacttgccgg
 541    tggccatcaa acacgtggag aaggaccgga tttccgactg gggagagctg cctaatggca
 601    ctcgagtgcc catggaagtg gtcctgctga gaaaggtgag ctcgggtttc tccggcgtca
 661    ttaggctcct ggactggttc gagaggcccg acagtttcgt cctgatcctg gagaggcccg
 721    agccggtgca agatctcttc gacttcatca cggaaagggg agccctgcaa gaggagctgg
 781    cccgcagctt cttctggcag gtgctggagg ccgtgcggca ctgccacaac tgcgggggtgc
```

FIG. 10 A-2

```
 841    tacaccgcga catcaaggac gaaaacatcc ttatcgacct caatcgcggc gagctcaagc
 901    tcatcgactt cgggtcgggg gcgctgctca aggacaccgt ctacacggac ttcgatggga
 961    cccgagtgta tagccctcca gagtggatcc gctaccatcg ctaccatggc aggtcggcgg
1021    cagtctggtc cctggggatc ctgctgtatg atatggtgtg tggagatatt cctttcgagc
1081    atgacgaaga gatcatcagg ggccaggttt tcttcaggca gagggtctct tcagaatgtc
1141    agcatctcat tagatggtgc ttggccctga gaccatcaga taggccaacc ttcgaagaaa
1201    tccagaacca tccatggatg caagatgttc tcctgcccca ggaaactgct gagatccacc
1261    tccacagcct gtcgccgggg cccagcaaat agcagccttt ctggcaggtc ctcccctctc
1321    ttgtcagatg cccgagggag gggaagcttc tgtctccagc ttcccgagta ccagtgacac
1381    gtctcgccaa gcaggacagt gcttgataca ggaacaacat ttacaactca ttccagatcc
1441    caggcccctg gaggctgcct cccaacagtg gggaagagtg actctccagg ggtcctaggc
1501    ctcaactcct cccatagata ctctcttctt ctcataggtg tccagcattg ctggactctg
1561    aaatatcccg ggggtggggg gtggggtggg gcagaaccct gccaatggaa ctctttcttc
1621    atcatgagtt ctgctgaatg ccgcgatggg tcaggtaggg gggaaacagg ttgggatggg
1681    ataggactag cacattttaa gtccctgtca cctcttccga ctctttctga gtgccttctg
1741    tggggactcc ggctgtgctg ggagaaatac ttgaacttgc ctcttttacc tgctgcttct
1801    ccaaaaatct gcctgggttt tgttccctat ttttctctcc tgtcctccct cacccccctcc
1861    ttcatatgaa aggtgccatg gaagaggcta cagggccaaa cgctgagcca cctgcccttt
1921    tttctgcctc ctttagtaaa actccgagtg aactggtctt cctttttggt ttttacttaa
1981    ctgtttcaaa gccaagacct cacacacaca aaaaaatgca caaaccaagc aatcaacaga
2041    aaagctgtaa atgtgtgtac agttggcatg gtagtataca aaaagattgt agtggatcta
2101    attttaagaa aattttgcct ttaagttatt ttacctgttt ttgtttcttg ttttgaaaga
2161    tgcgcattct aacctggagg tcaatgttat gtatttattt atttatttat ttggttccct
2221    tcctattcca agcttccata gctgctgccc tagttttctt tcctcctttc ctcctctgac
2281    ttggggacct tttgggggag ggctgcgacg cttgctctgt ttgtggggtg acgggactca
2341    ggcgggacag tgctgcagct ccctggcttc tgtgggggccc ctcacctact tacccaggtg
2401    ggtcccggct ctgtgggtga tgggagggggc cattgctgac tgtgtatata ggataattat
2461    gaaacacagt tctggatggt gtgccttcca gatcctctct ggggctgtgt tttgagcagc
2521    aggtagcctg ctggttttat ctgagtgaaa tactgtacag gggaataaaa gagatcttat
2581    ttttttttta tacttgcgtt tggaataaaa acccttggc ttt SEQ ID NO:3
   1    gaacaatgaa gaaagcccca cagccactgt tgctgagcag ggagaggata ttacctccaa
  61    aaaagacagg ggagtattaa agattgtcaa aagagtgggg aatggtgagg aaacgccgat
 121    gattggagac aaagtttatg tccattacaa aggaaaattg tcaaatggaa agaagtttga
 181    ttccagtcat gatagaaatg aaccatttgt ctttagtctt ggcaaaggcc aagtcatcaa
 241    ggcatgggac attgggggtgg ctaccatgaa gaaaggagag atatgccatt tactgtgcaa
 301    accagaatat gcatatggct cggctgcag tctcctaaa attcctcga atgcaactct
 361    ctttttgag attgagctcc ttgatttcaa aggagaggat ttatttgaag atggaggcat
 421    tatccggaga accaaacgga aaggagaggg atattcaaat ccaaacgaag gagcaacagt
 481    agaaatccac ctggaaggcc gctgtggtgg aaggatgttt gactgcagag atgtggcatt
 541    cactgtgggc gaaggagaag accacgacat tccaattgga attgacaaag ctctggagaa
 601    aatgcagcgg gaagaacaat gtatttata tcttggacca agatatggtt ttggagaggc
 661    agggaagcct aaatttggca ttgaacctaa tgctgagctt atatatgaag ttacacttaa
 721    gagcttcgaa aaggccaaag aatcctggga gatggatacc aaagaaaaat tggagcaggc
 781    tgccattgtc aaagagaagg gaaccgtata cttcaaggga ggcaaataca tgcaggcggt
 841    gattcagtat gggaagatag tgtcctggtt agagatgaa tatggtttat cagaaaagga
 901    atcgaaagct tctgaatcat ttctccttgc tgcctttctg aacctggcca tgtgctacct
 961    gaagcttaga gaatacacca aagctgttga atgctgtgac aaggcccttg gactggacag
1021    tgccaatgag aaaggcttgt ataggagggg tgaagcccag ctgctcatga acgagtttga
1081    gtcagccaag ggtgactttg agaaagtgct ggaagtaaac ccccagaata aggctgcaag
```

FIG. 10 A-3

```
1141    actgcagatc tccatgtgcc agaaaaaggc caaggagcac aacgagcggg accgcaggat
1201    atacgccaac atgttcaaga agtttgcaga gcaggatgcc aaggaagagg ccaataaagc
1261    aatgggcaag aagacttcag aaggggtcac taatgaaaaa ggaacagaca gtcaagcaat
1321    ggaagaagag aaacctgagg gccacgtatg acgccacgcc aaggagggaa gagtcccagt
1381    gaactcggcc cctcctcaat gggctttccc ccaactcagg acagaacagt gtttaatgta
1441    aagtttgtta tagtctatgt gattctggaa gcaaatggca aaaccagtag cttcccaaaa
1501    acagccccc tgctgctgcc cggagggttc actgagggt ggcacgggac cactccaggt
1561    ggaacaaaca gaaatgactg tggtgtggag ggagtgagcc agcagcttaa gtccagctca
1621    tttcagtttc tatcaacctt caagtatcca attcagggtc cctggagatc atcctaacaa
1681    tgtggggctg ttaggtttta cctttgaact ttcatagcac tgcagaaacc tttaaaaaaa
1741    aaatgcttca tgaatttctc ctttcctaca gttgggtagg gtagggaag gaggataagc
1801    ttttgttttt taaatgactg aagtgctata aatgtagtct gttgcatttt taaccaacag
1861    aacccacagt agagggtct catgtctccc cagttccaca gcagtgtcac agacgtgaaa
1921    gccagaacct cagaggccac ttgcttgctg acttagcctc ctcccaaagt cccctcctc
1981    agccagcctc cttgtgagag tggctttcta ccacacacag cctgtccctg ggggagtaat
2041    tctgtcattc ctaaaacacc cttcagcaat gataatgagc agatgagagt ttctggatta
2101    gctttctcc tttttcgatga agttctgaga tactgaaatg tgaaagagc aatcagaatt
2161    gtgctttttc tcccctcctc tattccttt agggaataat attcaataca cagtacttcc
2221    tcccag
```

SEQ ID NO:4

```
1       atggaggagg tggtgattgc cggcatgttc gggaagctgc cagagtcgga gaacttgcag
61      gagttctggg acaacctcat cggcggtgtg acatggtca cggacgatga ccgtcgctgg
121     aaggctgggc tctacggcct gccccggcgg tccggcaagc tgaaggacct gtctaggttt
181     gatgcctcct tcttcggagt ccaccccaag caggcacaca cgatggaccc tcagctgcgg
241     ctgctgctgg aagctaccta tgaagccatc gtgacggag gcatcaaccc agattcactc
301     cgaggaacac acactggcgt ctgggtgggc gtgagcggct ctgagacctc ggaggccctg
361     agccgagacc ccgagacact cgtgggctac agcatggtgg gctgccagcg agcgatgatg
421     gccaaccggc tctccttctt cttcgacttc agagggccca gcatcgcact ggacacagcc
481     tgctcctcca gcctgatggc cctgcagaac gcctaccagg ccatccacag cgggcagtgc
541     cctgccgcca tcgtgggggg catcaacctc ctgctgaagc ccaacaccct cgtgcagttc
601     ttgaggctgg ggatgctcag ccccgagggc acctgcaagg ccttcgacac agcgggggat
661     gggtactgcc gctcggaggg tgtggtggct gtcctgctga ccaagaagtc cctggcccgg
721     aaggtctaca ccaccatcct gaacaaaggc accaatacag atggcttcaa ggagcaaggc
781     gtgaccttcc ctcaggatat ccaggagcag cctatccgct cgttgtacca gtcggccgga
841     gtggccctg agtcatttga atacatcgaa gcccacggac caggcaccaa ggtgggcgac
901     ccccaggagc gtaatggcat caccgagcc ctgtgcgcca cccgccagga gccgctgctc
961     atcggctcca ccaagtccaa catgggcac ccggagccag cctcggggct cgacgccctg
1021    gccaaggtgc tgctgtccct ggagcacggg ctctgggccc caacctgca cttccatagc
1081    cccaacccctg agatcccagc gctgttggat gggcggctgc aggtggtgga ccagcccctg
1141    cccgtccgtg gcggcaacgt gggcatcaac tcctttggct tcggggctc caacatgcac
1201    atcatcctga ggccccaaca gcagtccgcc cccgcacccg ccccacatgc cacctgccc
1261    cgtctgctgc gggccagcgg acgcaccct gaggccgtgc agaagctgct ggagcagggc
1321    ctccggcaca gccagggcct ggcttcctg agcatgctga cgacatcgc ggctgtccc
1381    gccaccgcca tgccctttcg tggctacgct gtgctgggtg tgagacgcg gtggcccaga
1441    gtgcagcagg tgcccgctgg cgagcgcccg ctctggttca tctgctctgg gatgggcaca
1501    cagtggcgtg gaatgggct gagccttatg cgcctggacc gcttccgaga ttccatccta
1561    cgctccgatg aggctgtgaa ccgattcggc ctgaaggtgt cacagctgct gctgagcaca
1621    gacgagagca cctttgatga catcgtccat tcgtttgtga gcctgactgc catccagata
1681    ggcctcatag acctgctgag ctgcatggga cctgaggcag atggcatcgt cggccactcc
1741    ctggggagt ggctgtcggt acgcgacggc tgcctgtccc aggaggaggc cgtcctcgct
```

FIG. 10 A-4

```
1801 gcctactgga ggggacagtg catcaaagaa gccccacttc ccgccggcgc catggcagcc
1861 gtgggcttgt cctgggagga gtgtaaacag cgctgccccc ctgcggtggt gcccgcctgc
1921 cacaactcca aggacacagt caccatctcg ggacctcagg ccccggtgtt tgagttcgtg
1981 gagcagctga ggaaggaggg tgtgtttgcc aaggaggtgc ggaccggcgg tatggccttc
2041 cactcctact tcatggaggc catcgcaccc ccactgctgc aggagctcaa gaaggtgatc
2101 cgggagccga agccacgttc agcccgctgg ctcagcacct ctatcccga ggcccagtgg
2161 cacagcagcc tggcacgcac gtcttccgcc gagtacaatg tcaacaacct ggtgagccct
2221 gtgctgttcc aggaggccct gtggcacgtg cctgagcacg cggtggtgct ggagatcgcc
2281 ccgaccccgt gccctcaggc tgtcctgaag cgggtccgta agccgagctg caccatcatc
2341 ccccgtatga agaaggatca cagggacaac ctggagttct tcctggccgg catcggcagg
2401 ctgcacctct caggcatcga cgccaacccc aatgccttgt tcccacctgt ggagtcccca
2461 gctccccgag gaactcccct catctcccca ctcatcaagt gggaccacag cctggcctgg
2521 gacgcgccgg ccgccgagga cttccccaac ggttcaggtt ccccctcagc caccatctac
2581 acatgcacac caagctccga gtctcctgac cgctacctgg tggaccacac catcgacggt
2641 cgcgtcctct tccccgccac tggcctacctg agcatagtgt ggaagacgct ggcccgcgcc
2701 tgggctgggc tcgagcagct gcctgtggtg tttgaggatg tggtgcagca ccaggccacc
2761 atcctgccca agactgggac agtgtccttg gaggtacggc tcctggaggc caccggtgcc
2821 ttcgaggtgt cagagaacgg caacctggta gtgagtggga aggtgtacca gtgggatgac
2881 cctgacccca ggctcttcga ccacccggaa agtccccacc ccaattcccc acggagtccc
2941 ctcttcctgg cccaggcaga agtttacaag gagctgcgtc tgcgtggcta cgactacggc
3001 cctcatttcc agggcatcct ggaggccagc ctggaaggtg actcggggag gctgctgtgg
3061 aaggataact gggtgagctt catggacacc atgctgcaga tgtccatcct gggctcggcc
3121 aagcacggcc tgtacctacc cacccgtgtc accgccatcc acatcgaccc tgccacccac
3181 aggcagaagc tgtacacact gcaggacaag gcccaagtgg ctgacgtggt ggtgagcagg
3241 tggccgaggg tcacagtggc gggaggcgtc cacatctccg ggctccacac tgagtcggcc
3301 ccgcggcggc acgaggagca gcaggtgccc atcctggaga agttttgctt cactccccac
3361 acggaggagg ggtgcctgtc tgagcacgct gccctcgagg aggagctgca actgtgcaag
3421 gggctggtcg aggcactcga gaccaaggtg acccagcagg ggctggaagat ggtggtgccg
3481 gactggacgg ggcccagatc cccccgggac ccctcacagc aggaactgcc ccggctgtttg
3541 tcggctgcct gcaggcttca gctcaacggg aacctgcagc tggagctggc gcaggtgctg
3601 gcccaggaga ggcccaagct gccagaggac cctctgctca gcggcctcct ggactccccg
3661 gcactcaagg cctgcctgga cactgccgtg gagaacatgc ccagcctgaa gatgaaggtg
3721 gtggaggtgc tggccggcca cggtcacctg tattcccgca tccaggcct gctcagcccc
3781 catccctgc tgcagctgag ctacacggcc accgaccgcc accccaggc cctggaggct
3841 gcccaggccg agctgcagca gcacgacgtt gcccagggcc agtgggatcc cgcagaccct
3901 gcccccagcg ccctgggcag cgcggacctc ctggtgtgca actgtgctgt ggctgccctc
3961 ggggacccgg cctcagctct cagcaacatg gtggctgccc tgagagaagg gggctttctg
4021 ctcctgcaca cactgctccg ggggcaccct cgggacatcg tggccttcct cacctccact
4081 gagccgcagt atggccaggg catcctgagc caggacgcgt gggagagcct cttctccagg
4141 gtgtcgctgc gcctggtggg cctgaagaag tccttctacg gcgccacgct cttcctgtgc
4201 cgccggccca ccccgcagga cagccccatc ttcctgccgg tggacgatac cagcttccgc
4261 tgggtggagt ctctgaaggg catcctggct gacgaagact cttcccggcc tgtgtggctg
4321 aaggccatca actgtgccac ctcgggcgtg gtgggcttgg tgaactgtct ccgccgagag
4381 cccggcggaa ccgtccggtg tgtgctgctc tccaacctca gcagcacctc ccacgtcccg
4441 gaggtggacc cgggctccgc agaactgcag aaggtgttgc agggagacct ggtgatgaac
4501 gtctaccgcg acggggcctg ggggttttc cgccacttcc tgctggagga caagcctgag
4561 gagccgacgg cacatgcctt tgtgagcacc ctacccggg ggacctgtc ctccatccgc
4621 tgggtctgct cctcgctgcg ccatgcccag cccacctgcc ctggcgccca gctctgcacg
4681 gtctactacg cctccctcaa cttccgcgac atcatgctgg ccactggcaa gctgtcccct
4741 gatgccatcc cagggaagtg gacctcccag gacagcctgc taggtatgga gttctcgggc
4801 cgagacgcca gcggcaagcg tgtgatggga ctggtgcctg ccaagggcct ggccaccctct
```

FIG. 10 A-5

```
4861  gtcctgctgt caccggactt cctctgggat gtgccttcca actggacgct ggaggaggcg
4921  gcctcggtgc ctgtcgtcta cagcacggcc tactacgcgc tggtggtgcg tgggcgggtg
4981  cgccccgggg agacgctgct catccactcg ggctcgggcg gcgtgggcca ggccgccatc
5041  gccatcgccc tcagtctggg ctgccgcgtc ttcaccaccg tggggtcggc tgagaagcgg
5101  gcgtacctcc aggccaggtt cccccagctc gacagcacca gcttcgccaa ctcccgggac
5161  acatccttcg agcagcatgt gctgtggcac acgggcggga agggcgttga cctggtcttg
5221  aactccttgg cggaagagaa gctgcaggcc agcgtgaggt gcttcggtac gcacggtcgc
5281  ttcctggaaa ttggcaaatt cgaccttcct cagaaccacc cgctcggcat ggctatcttc
5341  ctgaagaacg tgacattcca cggggtccta ctggatgcgt tcttcaacga gagcagtgct
5401  gactggcggg aggtgtgggc gcttgtcgag gccgccatcc gggatggggt ggtacggccc
5461  ctcaagtgca cggtgttcca tggggcccag gtggaggacg ccttccgcta catggcccaa
5521  gggaagcaca ttggcaaagt cgtcgtgcag gtgcttgcgg aggagccggc agtgctgaag
5581  ggggccaaac ccaagctgat gtcggccatc tccaagacct tctgcccggc ccacaagagc
5641  tacatcatcg ctggtggtct gggtggcttc ggcctggagt tggcgcagtg gctgatacag
5701  cgtggggtgc agaagctcgt gttgacttct cgctccggga tccggacagg ctaccaggcc
5761  aagcaggtcc gccggtggag cgccagggg ctacaggtgc aggtgtccac cagcaacatc
5821  agctcactgg aggggcccg gggcctcatt gccgaggcgg cgcagcttgg gccgtgggg
5881  ggcgtcttca acctggccgt ggtcttgaga gatggcttgc tggagaacca gaccccagag
5941  ttcttccagg acgtctgcaa gcccaagtac agcggcaccc tgaacctgga cagggtgacc
6001  cgagaggcgt gccctgagct ggactacttt gtggtcttct cctctgtgag ctgcgggcgt
6061  ggcaatgcgg gacagagcaa ctacggcttt gccaattccg ccatggagcg tatctgtgag
6121  aaacgccggc acgaaggcct cccaggcctg gccgtgcagt ggggcgccat cggcaccgtg
6181  ggcattttgg tggagacgat gagcaccaac gacacgatcg tcagtggcac gctgcccacg
6241  cgcattggcg tccttggcct ggaggtgctg gacctcttcc tgaaccagcc ccacatggtc
6301  ctgagcagct ttgtgctggc tgagaaggct gcggcctata gggacaggga cagccagcgg
6361  gacctggtgg aggccgtggc acacatcctg ggcatccgcg acttggctgc tgtcaacctg
6421  ggcggctcac tggcggacct gggcctggac tcgctcatga gcgcgccggt gcgccagacg
6481  ctgagcgtg agctcaacct ggtgctgtcc gtgcgcgagg tgcggcaact cacgctccgg
6541  aaactgcagg agctgtcctc aaaggcggat gaagccagcg agctggcatg ccccacgccc
6601  aaggaggatg tctggcccca gcagcagact cagctgaacc tgcgctccct gctggtgaaa
6661  ccggagggcc ccaccctgat gcggctcaac tccgtgcaga gctcggagcg gcccctgttc
6721  ctggtgcaca caatcgaggc taccaccgtg ttccacaccc tcggtcccag tctcagcatc
6781  cccacctatg gcctgcagtg cacccccggc gcgccccttg acagcatcca cagcctggct
6841  gcctactaca tcgactgcat caggcaggtg cagcccgagg gccctaccg cgtggccggc
6901  tactcctacg gggcctgcgt ggcctttgaa atgtgctccc agctgcaggc ccagcagagc
6961  ccagccccca cccacaacag cctcttcctg ttcgacggct cgcccaccta cgtactggcc
7021  tacacccaga gctaccgggc aaagctgacc ccaggctgta aggctgaggc tgagacggag
7081  gccatatgct tcttcgtgca gcagttcacg gacatggagc acaacagggt gctggaggcg
7141  ctgctgccgc tgaagggcct agaggagcgt gtggcagccg ccgtggacct gatcatcaag
7201  agccaccagg gcctggaccg ccaggagctg agctttgcgg cccggtcctt ctactacagg
7261  ctgcgtgccg ctgaccagta tacacccaag gccaagtaca gtggcaacgt gatgctactg
7321  cgggccaaga cgggtggccg ctacggcgga gacctgggcg cggactacaa cctctcccag
7381  gtatgcgacg ggaaagtatc cgtccatatc atcgagggtg accaccgcac gctgctggag
7441  ggcagcggcc tggagtccat catcagcatc atccacagct ccctggctga gccacgtgtg
7501  agtcgggagg gctag SEQ ID NO:5
1    ctcaaaaggg gccggatttc cttctcctgg aggcagatgt tgcctctctc tctcgctcgg
61   attggttcag tgcactctag aaacactgct gtggtggaga aactggaccc caggtctgga
121  gcgaattcca gcctgcaggg ctgataagcg aggcattagt gagattgaga gagactttac
181  cccgccgtgg tggttggagg gcgcgcagta gagcagcagc acaggcgcgg gtcccgggag
```

FIG. 10 A-6

```
 241  gccggctctg ctcgcgccga gatgtggaat ctccttcacg aaaccgactc ggctgtggcc
 301  accgcgcgcc gcccgcgctg gctgtgcgct ggggcgctgg tgctggcggg tggcttcttt
 361  ctcctcggct tcctcttcgg gtggtttata aaatcctcca atgaagctac taacattact
 421  ccaaagcata atatgaaagc attttggat gaattgaaag ctgagaacat caagaagttc
 481  ttatataatt ttacacagat accacattta gcaggaacag aacaaaactt tcagcttgca
 541  aagcaaattc aatcccagtg gaaagaattt ggcctggatt ctgttgagct agcacattat
 601  gatgtcctgt tgtcctaccc aaataagact catcccaact acatctcaat aattaatgaa
 661  gatggaaatg agattttcaa cacatcatta tttgaaccac ctcctccagg atatgaaaat
 721  gtttcggata ttgtaccacc tttcagtgct ttctctcctc aaggaatgcc agagggcgat
 781  ctagtgtatg ttaactatgc acgaactgaa gacttcttta aattggaacg ggacatgaaa
 841  atcaattgct ctgggaaaat tgtaattgcc agatatggga aagttttcag aggaaataag
 901  gttaaaaatg cccagctggc aggggccaaa ggagtcattc tctactccga ccctgctgac
 961  tactttgctc ctggggtgaa gtcctatcca gatggttgga atcttcctgg aggtggtgtc
1021  cagcgtggaa atatcctaaa tctgaatggt gcaggagacc ctctcacacc aggttaccca
1081  gcaaatgaat atgcttatag gcgtggaatt gcagaggctg ttggtcttcc aagtattcct
1141  gttcatccaa ttggatacta tgatgcacag aagctcctag aaaaaatggg tggctcagca
1201  ccaccagata gcagctggag aggaagtctc aaagtgccct acaatgttgg acctggcttt
1261  actggaaact tttctacaca aaaagtcaag atgcacatcc actctaccaa tgaagtgaca
1321  agaatttaca atgtgatagg tactctcaga ggagcagtgg aaccagacag atatgtcatt
1381  ctgggaggtc accgggactc atgggtgttt ggtgtattga accctcagag tggagcagct
1441  gttgttcatg aaattgtgag gagctttgga acactgaaaa aggaagggtg gagacctaga
1501  agaacaattt tgtttgcaag ctgggatgca gaagaatttg gtcttcttgg ttctactgag
1561  tgggcagagg agaattcaag actccttcaa gagcgtggcg tggcttatat taatgctgac
1621  tcatctatag aaggaaacta cactctgaga gttgattgta caccgctgat gtacagcttg
1681  gtacacaacc taacaaaaga gctgaaaagc cctgatgaag ctttgaagg caaatctctt
1741  tatgaaagtt ggactaaaaa aagtccttcc ccagagttca gtggcatgcc caggataagc
1801  aaattgggat ctggaaatga ttttgaggtg ttcttccaac gacttggaat tgcttcaggc
1861  agagcacggt atactaaaaa ttgggaaaca aacaaattca gcggctatcc actgtatcac
1921  agtgtctatg aaacatatga gttggtggaa aagtttatg atccaatgtt taaatatcac
1981  ctcactgtgg cccaggttcg aggagggatg gtgtttgagc tagccaattc catagtgctc
2041  cctttgatt gtcagatta tgctgtagtt ttaagaaagt atgctgacaa aatctacagt
2101  atttctatga aacatccaca ggaaatgaag acatacagtg tatcatttga ttcactttt
2161  tctgcagtaa agaattttac agaaattgct tccaagttca gtgagagact ccaggacttt
2221  gacaaaagca acccaatagt attaagaatg atgaatgatc aactcatgtt tctggaaaga
2281  gcatttattg atccattagg gttaccagac aggccttttt ataggcatgt catctatgct
2341  ccaagcagcc acaacaagta tgcaggggag tcattcccag gaatttatga tgctctgttt
2401  gatattgaaa gcaaagtgga cccttccaag gcctggggag aagtgaagag acagatttat
2461  gttgcagcct tcacagtgca ggcagctgca gagactttga gtgaagtagc ctaagaggat
2521  tctttagaga atccgtattg aatttgtgtg gtatgtcact cagaaagaat cgtaatggt
2581  atattgataa attttaaaat tggtatattt gaaataaagt tgaatattat atataaaaaa
2641  aaaaaaaaaa aaa
```

SEQ ID NO:6
```
  1  cctcactgac tataaaagaa tagagaagga agggcttcag tgaccggctg cctggctgac
 61  ttacagcagt cagactctga caggatcatg gctatgatgg aggtccaggg gggacccagc
121  ctgggacaga cctgcgtgct gatcgtgatc ttcacagtgc tcctgcagtc tctctgtgtg
181  gctgtaactt acgtgtactt taccaacgag ctgaagcaga tgcaggacaa gtactccaaa
241  agtggcattg cttgttctt aaaagaagat gacagttatt gggaccccaa tgacgaagag
301  agtatgaaca gcccctgctg gcaagtcaag tggcaactcc gtcagctcgt tagaaagatg
361  attttgagaa cctctgagga aaccattcct acagttcaag aaaagcaaca aaatatttct
421  cccctagtga gagaaagagg tcctcagaga gtagcagctc acataactgg gaccagagga
```

FIG. 10 A-7

```
 481 agaagcaaca cattgtcttc tccaaactcc aagaatgaaa aggctctggg ccgcaaaata
 541 aactcctggg aatcatcaag gagtgggcat tcattcctga gcaacttgca cttgaggaat
 601 ggtgaactgg tcatccatga aaaagggttt tactacatct attcccaaac atactttcga
 661 tttcaggagg aaataaaaga aaacacaaag aacgacaaac aaatggtcca atatatttac
 721 aaatacacaa gttatcctga ccctatattg ttgatgaaaa gtgctagaaa tagttgttgg
 781 tctaaagatg cagaatatgg actctattcc atctatcaag ggggaatatt tgagcttaag
 841 gaaaatgaca gaatttttgt ttctgtaaca aatgagcact tgatagacat ggaccatgaa
 901 gccagttttt ttggggcctt tttagttggc taactgacct ggaaagaaaa agcaataacc
 961 tcaaagtgac tattcagttt tcaggatgat acactatgaa gatgtttcaa aaaatctgac
1021 caaaacaaac aaacagaaaa cagaaaacaa aaaacctct atgcaatctg agtagagcag
1081 ccacaaccaa aaaattctac aacacacact gttctgaaag tgactcactt atcccaagag
1141 aatgaaattg ctgaaagatc tttcaggact ctacctcata tcagtttgct agcagaaatc
1201 tagaagactg tcagcttcca aacattaatg caatggttaa catcttctgt ctttataatc
1261 tactccttgt aaagactgta gaagaaagag caacaatcca tctctcaagt agtgtatcac
1321 agtagtagcc tccaggtttc cttaagggac aacatcctta agtcaaaaga gagaagagc
1381 accactaaaa gatcgcagtt tgcctggtgc agtggctcac acctgtaatc ccaacatttt
1441 gggaacccaa ggtgggtaga tcacgagatc aagagatcaa gaccatagtg accaacatag
1501 tgaaacccca tctctactga aagtacaaaa attagctggg tgtgttggca catgcctgta
1561 gtcccagcta cttgagaggc tgaggcaaga gaattgtttg aacccgggag gcagaggttg
1621 cagtgtggtg agatcatgcc actacactcc agcctggcga cagagcgaga cttggtttca
1681 aaaaaaaaa aaaaaaaaac ttcagtaagt acgtgttatt tttttcaata aaattctatt
1741 acagtatgtc SEQ ID NO:7
    1 ggtcacatga ctccagtcta gctcgcattg cggctcccgc ccgggcgagt tctcgccccc
   61 gcgcggccgt tgccgaggag acggcgcatg tcccgccgcg cgttgccccc tctgcagtac
  121 ccccgccccc cttctcccac cacaatgaga tcctaagatg gcggtggctg cggcggttgg
  181 cgctgcgtag ctgaggtcga aaaggcggcc actggggccg aggcagccag gaaacgtgtg
  241 ggcctctctg ctgcggtctc cgagggccga ccgctgccgg cggcgggtcg tgggggctga
  301 ctgtcgctct gcctttgaca ggagaggctg cttcttgtag aggaaacagc tttgaagtgt
  361 ggagcgggaa aggagcagtt tctgagctgc aaaaactagt ttctaaacag agagttaatt
  421 gttaaatcca gtatgccac aggaggaggt cccttgaag atggcatgaa tgatcaggat
  481 ttaccaaact ggagtaatga gaatgttgat gacaggctca acaatatgga ttgggggtgcc
  541 caacagaaga aagcaaatag atcatcagaa aagaataaga aaaagtttgg tgtagaaagt
  601 gataaaagag taaccaatga tatttctccg gagtcgtcac caggagttgg aaggcgaaga
  661 acaaagactc cacatacgtt cccacacagt agatacatga gtcagatgtc tgtcccagag
  721 caggcagaat tagagaaact gaaacagcgg ataaacttca gtgatttaga tcagagaagc
  781 attggaagtg attcccaagg tagagcaaca gctgctaaca caaacgtca gcttagtgaa
  841 aaccgaaagc ccttcaactt tttgcctatg cagattaata ctaacaagag caaagatgca
  901 tctacaagtc ccccaaacag agaaacgatt ggatcagcac agtgtaaaga gttgtttgct
  961 tctgctttaa gtaatgacct cttgcaaaac tgtcaggtgt ctgaagaaga tgggaggga
 1021 gaacctgcaa tggagagcag ccagattgta agcaggcttg ttcaaattcg cgattatatt
 1081 actaaagcta gttccatgcg ggaagatctt gtagagaaaa atgagagatc tgctaatgtt
 1141 gagcgcctta ctcatctaat agatcaccft aaagaacaag agaagtcata tatgaaattt
 1201 cttaaaaaaa tccttgccag agatcctcag caggagccta tggaagagat agaaaatttg
 1261 aagaaacaac atgatttatt aaaagaatg ttacaacagc aggagcaact aagagctcta
 1321 caggacggc aggctgcact tctagctctg caacataag cagagcaagc tattgcagtg
 1381 atggatgatt ctgttgttgc agaaactgca ggtagcttat ctggcgtcag tatcacatct
 1441 gaactaaatg aagaattgaa tgacttaatt cagcgttttc ataatcagct tcgtgattct
 1501 cagcctccag ctgttccaga caatagaaga caggcagaaa gtctttcatt aactagggag
 1561 gtttcccaga gcaggaaacc atcagcttca gaacgtttac ctgatgagaa agtcgaactt
```

FIG. 10 A-8

```
1621 tttagcaaaa tgagagtgct acaggaaaag aaacaaaaaa tggacaaatt gcttggagaa
1681 cttcatacac ttcgagatca gcatcttaac aattcatcat cctctccaca aaggagtgtc
1741 gatcagagaa gtacttcagc tccctctgct tctgtaggct tggcaccggt tgtcaatgga
1801 gaatccaata gcctcacatc atctgttcct tatcctactg cttctctagt atctcagaat
1861 gagagtgaaa acgaaggcca cctcaatcca tctgaaaaac tccagaagtt aaatgaagtt
1921 cgaaagagat tgaatgagct aagagaatta gttcattatt atgaacaaac gtcagacatg
1981 atgacagatg ctgtgaatga aaacaggaaa gatgaagaaa ctgaagagtc agaatatgat
2041 tctgagcatg aaaattccga gcctgttact aacattcgaa atccacaagt agcttccact
2101 tggaatgaag taaatagtca tagtaatgca cagtgtgttt ctaataatag agatgggcga
2161 acagttaatt ctaattgtga aattaacaac agatctgctg ccaacataag ggctctaaac
2221 gtgcctcctt ctttagattg tcgatataat agagaagggg aacaggagat tcatgttgca
2281 caaggtgaag atgatgagga ggaggaggaa gaagcagaag aggagggagt cagtggagct
2341 tcattatcta gtcacaggag cagtctggtt gatgagcatc cagaagatgc tgaatttgaa
2401 cagaagatca accgacttat ggctgcaaaa cagaaactta gacagttaca agatcttgtt
2461 gctatggtac aggatgatga tgcagctcaa ggagttatct ctgccagtgc atcaaatttg
2521 gatgatttct acccagcaga agaagacacc aagcaaaatt caaataacac tagaggaaat
2581 gccaataaaa cacagaaaga tactggagta aatgaaaagg caagagagaa attttatgag
2641 gctaaactac agcagcaaca gagagagcta aaacaattgc aggaagaaag aaagaaactg
2701 attgacattc aggagaaaat tcaagcattg caaacggcat gccctgactt acagctgtca
2761 gctgctagtg tgggtaactg tcccaccaaa aaatatatgc cagctgttac ttcaacccca
2821 actgttaatc aacacgagac cagtacaagc aaatctgttt tgagcctga agattcttca
2881 atagtagata atgagttgtg gtcagaaatg agaagacatg aaatgttgag ggaggagctg
2941 cgacagagaa gaaagcagct tgaagctctg atggctgaac atcagaggag gcaaggtcta
3001 gctgaaactg catctccagt ggctgtgtca ttgagaagtg atggatctga gaacctatgt
3061 actcctcagc aaagtagaac agaaaaaacg atggcaactt ggggagggtc tacccagtgt
3121 gcactagatg aagaaggaga tgaagacggt tacctttctg aaggaattgt tcggacagat
3181 gaagaggagg aagaagagca agatgccagt tccaatgata acttttctgt gtgtccttct
3241 racagtgtga atcataactc ctacaatgga aaggaaacta aaaataggtg gaagaacaat
3301 tgcccttttt cggcagatga aaatttatcgt cctttagcca agacaaggca acagaatatc
3361 agcatgcaac ggcaagaaaa ccttcgttgg gtgtcagagc tctcttacgt agaagagaaa
3421 gaacaatggc aagaacaaat caatcagcta agaaacagc ttgattttag tgtcagtatt
3481 tgtcagactt tgatgcaaga ccagcagact ctatcttgtc tgctacaaac tcttctcacg
3541 ggtccttaca gtgttatgcc cagcaatgtt gcatcctc aagtacactt cataatgcac
3601 cagttgaacc agtgctatac tcagctaaca tggcaacaga ataatgttca gaggttgaaa
3661 caaatgctaa atgaacttat gcgccagcaa aatcagcatc cagaaaaacc tggaggcaag
3721 gaaagaggca gtagtgcatc gcacccctcc tctcccagtt tattgtcc tttcagcttt
3781 ccaacacagc ctgtaaatct cttcaatata cctggattta ctaacttttc atcatttgca
3841 ccaggtatga atttcagccc tttatttcct tctaattttg gagatttttc tcagaatatc
3901 tctacaccca gtgaacagca gcaaccctta gcccagaatt cttcaggaaa aacagaatat
3961 atggcttttc caaaaccttt tgaaagcagt tcctctattg gagcagagaa accaaggaat
4021 aaaaaactgc ctgaagagga ggtggaaagc agtaggacac catggttata tgaacaagaa
4081 ggtgaagtag agaaaccatt tatcaagact ggatttcag tgtctgtaga aaaatctaca
4141 agtagtaacc gcaaaaatca attagataca aacggaagaa gacgccagtt tgatgaagaa
4201 tcactggaaa gcttagcag tatgcctgat ccagtagatc caacaacagt gactaaaaca
4261 ttcaagacaa gaaaagcgtc tgcacaggcc taaagataa aactcccaag
4321 tcaaaaagta agaagaggaa ttctactcag ctgaaaagca gagttaaaaa catcaggtat
4381 gaaagtgcca gtatgtctag cacatgtgaa ccttgcaaaa gtaggaacag acattcagcc
4441 cagactgaag agcctgttca agcaaaagta ttcagcagaa agaatcatga gcaactggaa
4501 aaaataataa aatgtaatag gtctacagaa atatcttcag aaactgggag tgattttcc
4561 atgtttgaag ctttgcgaga tactatttat tctgaagtag ctacattaat ttctcaaaat
```

FIG. 10 A-9

```
4621 gaatctcgtc cacattttct tattgaactc ttccatgagc tgcagctactaaacacagac
4681 tacttgagac agagggcttt atatgcattg caggacatag tatccagaca tatttctgag
4741 agccatgaaa aaggagaaaa tgtaaagtca gtaaactctg gtacttggat agcatcaaac
4801 tcagaactta ctcctagtga gagccttgct actactgatg atgaaacttt tgagaagaac
4861 tttgaaagag aaacccataa aataagtgag caaaatgatg ctgataatgc tagtgtcctg
4921 tctgtatcat caaattttga gcctttgca acagatgatc taggtaacac cgtgattcac
4981 ttagatcaag cattagccag aatgagagaa tatgagcgta tgaagactga ggctgaaagt
5041 aactcaaata tgagatgcat ctgcaggatt attgaggatg gagatggtgc tggtgcaggt
5101 actacagtta ataatttaga agaaactccc gttattgaaa atcgtagttc acaacaacct
5161 gtaagtgaag tttctaccat cccatgtcct agaattgata ctcagcagct ggaccggcaa
5221 attaaagcaa ttatgaaaga agtcattcct tttttgaagg agcacatgga tgaagtatgc
5281 tcctcgcagc ttctaacttc agtaaggcgc atggttttga cccttaccca gcaaaatgat
5341 gagagcaaag agtttgtaaa gttctttcat aaacaacttg gaagtatatt acaggattca
5401 ctggcaaaat ttgctggcag aaaactgaaa gactgtggag aagatcttct tgtagagata
5461 tctgaagtgt tgttcaatga attggctttc tttaagctta tgcaagattt ggataataat
5521 agtataactg ttaaacagag atgcaaaagg aaaatagaag caactggagt gatacaatct
5581 tgtgccaaag agctaaaagg attcttgaag atcatggctc acctgctgga gagattgatg
5641 atgaagacaa agacaaggat gaaactgaaa cagttaagca gactcaaaca tctgaggtgt
5701 atgatggtcc caaaaatgta agatctgata tttctgatca agaggaagat gaagaaagtg
5761 aaggatgtcc agtgtctatt aatttgtcta aagctgaaac tcaggcttta actaattatg
5821 gaagtggaga agatgaaaat gaggatgaaa aaatggaaga atttgaagaa ggccctgtgg
5881 atgtccagac ttccctccag gctaacactg aagctactga agaaaatgaa catgatgaac
5941 aggtcctaca acgtgacttt aaaaagacag cagaaagcaa aaatgtccca ttggaacgag
6001 aagccactag taaaaatgac caaaataact gtcctgtgaa accctgttac ctcaatatct
6061 tggaagatga gcaaccttta aatagtgctg cccataagga gtcacctcct actgttgatt
6121 caactcaaca gcctaaccct ttgccgttac gtttacctga aatggaaccc ttagtgccta
6181 gagtcaaaga agttaaatct gctcaggaaa ctcctgaaag ctctctggct ggaagtcctg
6241 atactgaatc tccagtgtta gtgaatgact atgaagcaga atctggtaat ataagtcaaa
6301 agtctgatga agaagatttt gtaaaagttg aagatttacc actgaaactg acaatatatt
6361 cagaggcaga tctaagaaag aaaatggtag aagaagaaca gaaaaaccat ttatctggtg
6421 aaatatgtga aatgcagacc gaagaattag ctggaaattc tgagacacta aaagaacctg
6481 aaacggtggg agcccagagt atatgagatg tcttcagagg ctcatctaac tctgtcctta
6541 catactcaat gcatatatga aaacaatact aaataaacat ctgatctgta taaaaat
```

SEQ ID NO:8
```
  1 ctccaaaggc aaaaatctcc agccctacag agactgagcg gtgcatcgag tccctgattg
 61 ctgtcttcca gaagtatgct ggaaaggatg gttataacta cactctctcc aagacagagt
121 tcgtaagctt catgaataca gaactagctg ccttcacaaa gaaccagaag gaccctggtg
181 tccttgaccg catgatgaag aaactggaca ccaacagtga tggtcagcta gatttctcag
241 aatttcttaa tctgattggt ggcctagcta tggcttgcca tgactccttc ctcaaggctg
301 tcccttccca gaagcggacc tgaggaccca ttggccctgg ccttcaaacc caccccttt
361 ccttccagcc tttctgtcat catctccaca gccacccat cccctgagca cactaaccac
421 ctcatgcagg ccccacctgc caatagtaat aaagcaatgt cacttttta aaacatgaa
```

SEQ ID NO:9
```
  1 gccgcttcct gcctggattc cacagcttcg cgccgtgtac tgtcgcccca tccctgcgcg
 61 cccagcctgc caagcagcgt gccccggttg caggcgtcat gcagcgggcg cgacccacgc
121 tctgggccgc tgcgctgact ctgctggtgc tgctccgcgg gccgccggtg gcgcgggctg
181 gcgcgagctc ggcgggcttg ggtcccgtgg tgcgctgcga gccgtgcgac gcgcgtgcac
241 tggcccagtg cgccgcctcc cccgccgtgt gcgcggagct ggtgcgcgag ccggcgcg
301 gctgctgcct gacgtgcgca ctgagcgagg gccagccgtg cggcatctac accgagcgct
```

FIG. 10 A-10

```
 361 gtggctccgg ccttcgctgc cagccgtcgc ccgacgaggc gcgaccgctg caggcgctgc
 421 tggacggccg cgggctctgc gtcaacgcta gtgccgtcag ccgcctgcgc gcctacctgc
 481 tgccagcgcc gccagctcca ggaaatgcta gtgagtcgga ggaagaccgc agcgccggca
 541 gtgtggagag cccgtccgtc tccagcacgc accgggtgtc tgatcccaag ttccacccc
 601 tccattcaaa gataatcatc atcaagaaag ggcatgctaa agacagccag cgctacaaag
 661 ttgactacga gtctcagagc acagataccc agaacttctc ctccgagtcc aagcggggaga
 721 cagaatatgg tccctgccgt agagaaatgg aagacacact gaatcacctg aagttcctca
 781 atgtgctgag tcccaggggt gtacacattc ccaactgtga caagaaggga ttttataaga
 841 aaaagcagtg tcgccttcc aaaggcagga agcggggctt ctgctggtgt gtggataagt
 901 atgggcagcc ctcccaggc tacaccacca aggggaagga ggacgtgcac tgctacagca
 961 tgcagagcaa gtagacgcct gccgcaaggt taatgtggag ctcaaatatg ccttattttg
1021 cacaaaagac tgccaaggac atgaccagca gctggctaca gcctcgattt atatttctgt
1081 ttgtggtgaa ctgatttttt ttaaaccaaa gtttagaaag aggtttttga aatgcctatg
1141 gtttctttga atggtaaact tgagcatctt ttcactttcc agtagtcagc aaagagcagt
1201 ttgaattttc ttgtcgcttc ctatcaaaat attcagagac tcgagcacag cacccagact
1261 tcatgcgccc gtggaatgct caccacatgt tggtcgaagc ggccgaccac tgactttgtg
1321 acttaggcgg ctgtgttgcc tatgtagaga acacgcttca ccccactcc ccgtacagtg
1381 cgcacaggct ttatcgagaa taggaaaacc tttaaacccc ggtcatccgg acatcccaac
1441 gcatgctcct ggagctcaca gccttctgtg gtgtcatttc tgaaacaagg gcgtggatcc
1501 ctcaaccaag aagaatgttt atgtcttcaa gttgacctgta ctgcttgggg actattggag
1561 aaaataaggt ggagtcctac ttgtttaaaa aatatgtatc taagaatgtt ctagggcact
1621 ctgggaacct ataaaggcag gtatttcggg ccctcctctt caggaatctt cctgaagaca
1681 tggcccagtc gaaggcccag gatggcttt gctgcggccc cgtggggtag gagggacaga
1741 gagacaggga gagtcagcct ccacattcag aggcatcaca agtaatggca caattcttcg
1801 gatgactgca gaaaatagtg ttttgtagtt caacaactca agacgaagct tatttctgag
1861 gataagctct ttaaaggcaa agctttattt tcatctctca tcttttgtcc tccttagcac
1921 aatgtaaaaa agaatagtaa tatcagaaca ggaaggagga atggcttgct ggggagccca
1981 tccaggacac tgggagcaca tagagattca cccatgtttg ttgaacttag agtcattctc
2041 atgctttttct ttataattca cacatatatg cagagaagat atgttcttgt taacattgta
2101 tacaacatag ccccaaatat agtaagatct atactagata atcctagatg aaatgttaga
2161 gatgctattt gatacaactg tggccatgac tgaggaaagg agctcacgcc cagagactgg
2221 gctgctctcc cggaggccaa acccaagaag gtctggcaaa gtcaggctca gggagactct
2281 gccctgctgc agacctcggt gtggacacac gctgcataga gctctccttg aaaacagagg
2341 ggtctcaaga cattctgcct acctattagc ttttctttat ttttttaact ttttgggggg
2401 aaaagtattt ttgagaagtt tgtcttgcaa tgtatttata aatagtaaat aaagttttta
2461 ccatt SEQ ID NO:10
    1 atgccgcgct ccttcctggt caagaagcat ttcaacgcct ccaaaaagcc aaactacagc
   61 gaactggaca cacatacagt gattatttcc ccgtatctct atgagagtta ctccatgcct
  121 gtcataccac aaccagagat cctcagctca ggagcataca gccccatcac tgtgtggact
  181 accgctgctc cattccacgc ccagctaccc aatggcctct ctcctctttc cggatactcc
  241 tcatctttgg ggcgagtgag tcccctcct ccatctgaca cctcctccaa ggaccacagt
  301 ggctcagaaa gccccattag tgatgaagag gaaagactac agtccaagct ttcagacccc
  361 catgccattg aagctgaaaa gtttcagtgc aatttatgca ataagcccta ttcaactttt
  421 tctgggctgg ccaaacataa gcagctgcac tgcgatgccc agtctagaaa tctttccagc
  481 tgtaaaatact gtgacaagga atatgtgagc ctgggcgccc tgaagatgca tattcggacc
  541 cacacattac cttgtgtttg caagatctgc ggcaaggcgt tttccagacc ctggttgctt
  601 caaggacaca ttagaactca cacgggggag aagcttttt cttgccctca ctgcaacaga
  661 gcatttgcag acaggtcaaa tctgagggct catctgcaga cccattctga tgtaaagaaa
  721 taccagtgca aaaactgctc caaaaccttc tccagaatgt ctctcctgca caaacatgag
```

FIG. 10 A-11

```
781 gaatctggct gctgtgtagc acactga
```

SEQ ID NO:11
```
   1 ctcggaagcc cgtcaccatg tcgtgcgagt cgtctatggt tctcgggtac tgggatattc
  61 gtgggctggc gcacgccatc cgcctgctcc tggagttcac ggatacctct tatgaggaga
 121 aacgtacac gtgcggggaa gctcctgact atgatcgaag ccaatggctg gatgtgaaat
 181 tcaagctaga cctggacttt cctaatctgc cctacctcct ggatgggaag aacaagatca
 241 cccagagcaa tgccatcttg cgctacatcg ctcgcaagca caacatgtgt ggtgagactg
 301 aagaagaaaa gattcgagtg gacatcatag agaaccaagt aatggatttc gcacacaac
 361 tgataaggct ctgttacagc tctgaccacg aaaaactgaa gcctcagtac ttggaagagc
 421 tacctggaca actgaaacaa ttctccatgt ttctgtggaa attctcatgg tttgccgggg
 481 aaaagctcac ctttgtggat tttctcacct atgatatctt ggatcagaac cgtatatttg
 541 accccaagtg cctggatgag ttcccaaacc tgaaggcttt catgtgccgt tttgaggctt
 601 tggagaaaat cgctgcctac ttacagtctg atcagttctg caagatgccc atcaacaaca
 661 agatggccca gtggggcaac aagcctgtat gctgagcagg aggcagactt gcagagcttg
 721 ttttgtttca tcctgtccgt aagggggtcag cgctcttgct ttgctctttt caatgaatag
 781 cacttatgtt actggtgtcc agctgagttt ctcttgggta taaaggctaa aagggaaaaa
 841 ggatatgtgg agaatcatca agatatgaat tgaatcgctg cgatactgtg gcatttccct
 901 actcccaac tgagttcaag ggctgtaggt tcatgcccaa gccctgagag tgggtactag
 961 aaaaaacgag attgcacagt tggagagagc aggtgtgtta aatggactgg agtccctgtg
1021 aagactgggt gaggataaca caagtaaaac tgtggtactg atggacttaa ccggagttcg
1081 gaaaccgtcc tgtgtacaca tgggagttta gtgtgataaa ggcagtattt cagactggtg
1141 ggctagccaa tagagttggc aattgcttat tgaaactcat taaaaataat agagccccac
1201 ttgacactat tcactaaaat taatctggaa tttaaggccc aacattaaac acaaagctgt
1261 attgat
```

SEQ ID NO:12
```
   1 gccacgtgct gctgggtctc agtcctccac ttcccgtgtc ctctggaagt tgtcaggagc
  61 aatgttgcgc ttgtacgtgt tggtaatggg agttctgcc ttcacccttc agcctgcggc
 121 acacacaggg gctgccagaa gctgccggtt tcgtgggagg cattacaagc gggagttcag
 181 gctggaaggg gagcctgtag ccctgaggtg ccccaggtg ccctactggt tgtgggcctc
 241 tgtcagcccc cgcatcaacc tgacatggca taaaaatgac tctgctagga cggtcccagg
 301 agaagaagag acacggatgt gggcccagga cggtgctctg tggcttctgc cagccttgca
 361 ggaggactct ggcacctacg tctgcactac tagaaatgct tcttactgtg acaaaatgtc
 421 cattgagctc agagttttg agaataacaga tgctttcatct ccgttcatct catacccgca
 481 aatttaacc ttgtcaacct ctggggtatt agtatgccct gacctgagtg aattcacccg
 541 tgacaaaact gacgtgaaga ttcaatggta caaggattct cttcttttgg ataaagacaa
 601 tgagaaattt ctaagtgtga gggggaccac tcacttactc gtacacgatg tggccctgga
 661 agatgctggc tattaccgct gtgtcctgac atttgcccat gaaggccagc aatacaacat
 721 cactaggagt attgagctac gcatcaagaa aaaaaaagaa gagaccattc ctgtgatcat
 781 ttcccccctc aagaccatat cagcttctct ggggtcaaga ctgacaatcc cgtgtaaggt
 841 gtttctggga accggcacac ccttaaccac catgctgtgg tggacggcca atgacaccca
 901 catagagagc gcctacccgg gaggccgcgt gaccgagggg ccacgccagg aatattcaga
 961 aaataatgag aactacattg aagtgccatt gattttttgat cctgtcacaa gagaggattt
1021 gcacatggat tttaaatgtg ttgtccataa tacccctgat tttcagacac tacgcaccac
1081 agtcaaggaa gcctcctcca cgttctcctg gggcattgtg ctggccccac tttcactggc
1141 cttcttggtt ttgggggaa tatgctgatgca cagacggtgc aaacacagaa ctggaaaagc
1201 agatggtctg actgtgctat ggcctcatca tcaagacttt caatcctatc ccaagtgaaa
1261 taaatgaat gaaataattc aaacacaaaa aaaaaaaaa aaaaaaa
```

SEQ ID NO:13

FIG. 10 A-12

```
   1 gcgctgcccg cctcgtcccc acccccaac ccccgcgcc cgccctcgga cagtccctgc
  61 tcgcccgcgc gctgcagccc catctcctag cggcagccca ggcgcggagg gagcgagtcc
 121 gccccgaggt aggtccagga cgggcgcaca gcagcagccg aggctggccg ggagagggag
 181 gaagaggatg gcagggccac gccccagccc atgggccagg ctgctcctgg cagccttgat
 241 cagcgtcagc ctctctggga ccttggcaaa ccgctgcaag aaggccccag tgaagagctg
 301 cacggagtgt gtccgtgtgg ataaggactg cgcctactgc acagacgaga tgttcaggga
 361 ccggcgctgc aacacccagg cggagctgct ggccgcgggc tgccagcggg agagcatcgt
 421 ggtcatggag agcagcttcc aaatcacaga ggagacccag attgacacca ccctgcggcg
 481 cagccagatg tccccccaag gcctgcgggt ccgtctgcgg cccggtgagg agcggcattt
 541 tgagctggag gtgtttgagc cactggagag ccccgtggac ctgtacatcc tcatggactt
 601 ctccaactcc atgtccgatg atctggacaa cctcaagaag atggggcaga acctggctcg
 661 ggtcctgagc cagctcacca gcgactacac tattggattt ggcaagtttg tggacaaagt
 721 cagcgtcccg cagacggaca tgaggcctga gaagctgaag gagccctggc ccaacagtga
 781 ccccccttc tccttcaaga acgtcatcag cctgacagaa gatgtggatg agttccggaa
 841 taaactgcag ggagagcgga tctcaggcaa cctggatgct cctgagggcg gcttcgatgc
 901 catcctgcag acagctgtgt gcacgaggga cattggctgg cgcccggaca gcacccacct
 961 gctggtcttc tccaccgagt cagccttcca ctatgaggct gatggcgcca acgtgctggc
1021 tggcatcatg agccgcaacg atgaacggtg ccacctggac accacgggca cctacaccca
1081 gtacaggaca caggactacc cgtcggtgcc caccctggtg cgcctgctcg ccaagcacaa
1141 catcatcccc atctttgctg tcaccaacta ctcctatagc tactacgaga agcttcacac
1201 ctatttccct gtctcctcac tggggtgct gcaggaggac tcgtccaaca tcgtggagct
1261 gctggaggag gccttcaatc ggatccgctc caacctggac atccgggccc tagacagccc
1321 ccgaggcctt cggacagagg tcacctccaa gatgttccag aagacgagga ctgggtcctt
1381 tcacatccgg cgggggaag tgggtatata ccaggtgcag ctgcgggccc ttgagcacgt
1441 ggatgggacg cacgtgtgcc agctgccgga ggaccagaag ggcaacatcc atctgaaacc
1501 ttccttctcc gacggcctca agatggacgc gggcatcatc tgtgatgtgt gcacctgcga
1561 gctgcaaaaa gaggtgcggt cagctcgctg cagcttcaac ggagacttcg tgtgcggaca
1621 gtgtgtgtgc agcgagggct ggagtggcca gacctgcaac tgctccaccg gctctctgag
1681 tgacattcag ccctgcctgc ggagggcga ggacaagccg tgctccggcc gtggggagtg
1741 ccagtgcggg cactgtgtgt gctacggcga aggccgctac gagggtcagt ctgcgagta
1801 tgacaacttc cagtgtcccc gcacttccgg gttcctgtgc aatgaccgag acgctgctc
1861 catgggccag tgtgtgtgtg agcctggttg gacaggccca agctgtgact gtccctcag
1921 caatgccacc tgcatcgaca gcaatggggg catctgtaat ggacgtggcc actgtgagtg
1981 tggccgctgc cactgccacc agcagtcgct ctacacggac accatctgcg agatcaacta
2041 ctcggcgatc cacccgggcc tctgcgagga cctacgtcc tgcgtgcagt gccaggcgtg
2101 gggcaccggc gagaagaagg ggcgcacgtg tgaggaatgc aacttcaagg tcaagatggt
2161 ggacgagctt aagagagccg aggaggtggt ggtgcgctgc tccttccggg acgaggatga
2221 cgactgcacc tacagctaca ccatggaagg tgacgcgcc cctgggccca cagcactgt
2281 cctggtgcac aagaagaagg actgccctcc gggctccttc tggtggctca tcccctgct
2341 cctcctcctc ctgccgctcc tggccctgct actgctgcta tgctggaagt actgtgcctg
2401 ctgcaaggcg tgcctggcac ttctcccgtg ctgaacggga ggtcacatgg tgggctttaa
2461 ggaagaccac tacatgctgc gggagaacct gatggcctct gaccacttgg acacgcccat
2521 gctgcgcagc gggaacctca agggccgtga cgtggtccgc tggaaggtca ccaacaacat
2581 gcagcggcct ggctttgcca ctcatgccgc cagcatcaac cccacagagc tggtgcccta
2641 cgggctgtcc ttgcgcctgg cccgcctttg caccgagaac ctgctgaagc ctgacactcg
2701 ggagtgcgcc cagctgcgcc aggaggtgga ggagaacctg aacgaggtct acaggcagat
2761 ctccggtgta cacaagctcc agcagaccaa gttccggcag cagcccaatg ccgggaaaaa
2821 gcaagaccac accattgtgg acacagtgct gatggcgccc cgctcggcca gccggcct
2881 gctgaagctt acagagaagc aggtggaaca gagggccttc cacgacctca aggtggcccc
2941 cggctactac accctcactg cagaccagga cgcccgggc atggtggagt tccaggaggg
3001 cgtggagctg gtggacgtac gggtgcccct ctttatccgg cctgaggatg acgacgagaa
```

FIG. 10 A-13

```
3061 gcagctgctg gtggaggcca tcgacgtgcc cgcaggcact gccaccctcg gccgccgcct
3121 ggtaaacatc accatcatca aggagcaagc cagagacgtg gtgtcctttg agcagcctga
3181 gttctcggtc agccgcgggg accaggtggc ccgcatccct gtcatccggc gtgtcctgga
3241 cggcgggaag tcccaggtct cctaccgcac acaggatggc accgcgcagg gcaaccggga
3301 ctacatcccc gtggagggtg agctgctgtt ccagcctggg gaggcctgga aagagctgca
3361 ggtgaagctc ctggagctgc aagaagttga ctccctcctg cggggccgcc aggtccgccg
3421 tttccacgtc cagctcagca accctaagtt tggggcccac ctgggccagc cccactccac
3481 caccatcatc atcagggacc cagatgaact ggaccggagc ttcacgagtc agatgttgtc
3541 atcacagcca ccccctcacg gcgacctggg cgccccgcag aaccccaatg ctaaggccgc
3601 tgggtccagg aagatccatt tcaactggct gcccccttct ggcaagccaa tgggtacag
3661 ggtaaagtac tggattcagg gcgactccga atccgaagcc cacctgctcg acagcaaggt
3721 gccctcagtg gagctcacca acctgtaccc gtattgcgac tatgagatga aggtgtgcgc
3781 ctacggggct cagggcgagg gaccctacag ctccctggtg tcctgccgca cccaccagga
3841 agtgcccagc gagccagggc gtctggcctt caatgtcgtc tcctccacgg tgacccagct
3901 gagctgggct gagccggctg agaccaacgg tgagatcaca gcctacgagg tctgctatgg
3961 cctggtcaac gatgacaacc gacctattgg gcccatgaag aaagtgctgg ttgacaaccc
4021 taagaaccgg atgctgctta ttgagaacct tcgggagtcc cagccctacc gctacacggt
4081 gaaggcgcgc aacgggccgg ctgggggcc tgagcgggag gccatcatca acctggccac
4141 ccagcccaag aggcccatgt ccatccccat catccctgac atccctatcg tggacgccca
4201 gagcggggag gactacgaca gcttccttat gtacagcgat gacgttctac gctctccatc
4261 gggcagccag aggcccagcg tctccgatga cactggctgc ggctggaagt tcgagcccct
4321 gctgggggag gagctggacc tgcggcgcgt cacgtggcgg ctgccccgg agctcatccc
4381 gcgcctgtcg gccagcagcg ggcgctcctc cgacgccgag gcccccacgg cccccggac
4441 gacggcgggc cggcggggaa gggcggcagc cgtgcccgcc agtgcgacac ccgggccccc
4501 cggagagcac ctggtgaatg gccggatgga ctttgccttc ccgggcagca ccaactccct
4561 gcacaggatg accacgacca gtgctgctgc ctatggcacc cacctgagcc cacacgtgcc
4621 ccaccgcgtg ctaagcacat cctccaccct cacacgggac tacaactcac tgacccgctc
4681 agaacactca cactcgacca cactgcccag ggactactcc accctcacct ccgtctcctc
4741 ccacgactct cgcctgactg ctggtgtgcc cgacacgccc acccgcctgg tgttctctgc
4801 cctggggccc acatctctca gagtgagctg gcaggagccg cggtgcgagc ggccgctgca
4861 gggctacagt gtggagtacc agctgctgaa cggcggtgag ctgcatcggc tcaacatccc
4921 caaccctgcc cagacctcgg tggtggtgga agacctcctg cccaaccact cctacgtgtt
4981 ccgcgtgcgg gcccagagcc aggaaggctg gggccgagag cgtgagggtg tcatcaccat
5041 tgaatcccag gtgcaccgc agagcccact gtgtccctg ccaggctccg ccttcactttt
5101 gagcactccc agtgccccag gcccgctggt gttcactgcc ctgagcccag actcgctgca
5161 gctgagctgg gagcggccac ggaggcccaa tggggatatc gtcggctacc tggtgacctg
5221 tgagatggcc caaggaggag ggccagccac cgcattccgg gtggatggag acagccccga
5281 gagccggctg accgtgccgg gcctcagcga aacgtgccc tacaagttca aggtgcaggc
5341 caggaccact gagggcttcg gccagagcg cgagggcatc atcaccatag agtcccagga
5401 tggaggaccc ttcccgcagc tgggcagccg tgccgggctc ttccagcacc cgctgcaaag
5461 cgagtacagc agcatcacca ccacccacac cagcgccacc gagcccttcc tagtggatgg
5521 gctgaccctg ggggcccagc acctggaggc aggcggctcc ctcacccggc atgtgaccca
5581 ggagtttgtg agccggacac tgaccaccag cggaaccctt agcacccaca tggaccaaca
5641 gttcttccaa acttgaccgc accctgcccc accccgcca tgtcccacta ggcgtcctcc
5701 cgactcctct cccggagcct cctcagctac tccatccttg cacccctggg ggcccagccc
5761 acccgcatgc acagagcagg ggctaggtgt ctcctgggag gcatgaaggg ggcaaggtcc
5821 gtcctctgtg ggcccaaacc tatttgtaac caaagagctg ggagcagcac aaggacccag
5881 cctttgttct gcacttaata aatggttttg ctactgctaa aaaaaaaaa aaaaaaaaa
5941 aaaaaaaaaa aaaaaaaaaa aaaaaaaaaa aaaaaaaaaa aaaaaaaaaa aaaa
```

SEQ ID NO:14

FIG. 10 A-14

```
1    ccgccgggct ggccatggag ctgctgtgcc acgaggtgga cccggtccgc agggccgtgc
61   gggaccgcaa cctgctccga gacgaccgcg tcctgcagaa cctgctcacc atcgaggagc
121  gctaccttcc gcagtgctcc tacttcaagt gcgtgcagaa ggacatccaa ccctacatgc
181  gcagaatggt ggccacctgg atgctggagg tctgtgagga acagaagtgc gaagaagagg
241  tcttccctct ggccatgaat tacctggacc gttcttggc tggggtcccg actccgaagt
301  cccatctgca actcctgggt gctgtctgca tgttcctgca ctccaaactc aaagagacca
361  gcccgctgac cgcggagaag ctgtgcattt acaccgacaa ctccatcaag cctcaggagc
421  tgctggagtg ggaactggtg gtgctgggga agttgaagtg gaacctggca gctgtcactc
481  ctcatgactt cattgagcac atcttgcgca agctgcccca gcagcgggag aagctgtctc
541  tgatccgcaa gcatgctcag accttcattg ctctgtgtgc caccgacttt aagtttgcca
601  tgtacccacc gtcgatgatc gcaactggaa gtgtgggagc agccatctgt gggctccagc
661  aggatgagga agtgagctcg ctcacttgtg atgccctgac tgagctgctg gctaagatca
721  ccaacacaga cgtggattgt ctcaaagctt gccaggagca gattgaggcg tgctcctca
781  atagcctgca gcagtaccgt caggaccaac gtgacggatc caagtcggag gatgaactgg
841  accaagccag caccccctaca gacgtgcggg atatcgacct gtgaggatgc cagttgggcc
901  gaaagagaga gacgcgtcca taatctggtc tcttcttctt tctggttgtt tttgttcttt
961  gtgttttagg gtgaaactta aaaaaaaaat tctgccccca cctagatcat atttaaagat
1021 cttttagaag tgagagaaaa aggtcctacg aaaacggaat aataaaaagc atttggtgcc
1081 tatttgaagt acagcataag ggaatccctt gtatatgcga acagttattg tttgattatg
1141 taaaagtaat agtaaaatgc ttacaggaaa acctgcagag tagttagaga atatgtatgc
1201 ctgcaatatg ggaacaaatt agaggagact ttttttttc atgttatgag ctagcacata
1261 cacccccttg tagtataatt tcaaggaact gtgtacgcca tttatggcat gattagattg
1321 caaagcaatg aactcaagaa ggaattgaaa taaggaggga catgatgggg aaggagtaca
1381 aaacaatctc tcaacatgat tgaaccattt gggatggaga agcacctttg ctctcagcca
1441 cctgttacta agtcaggagt gtagttggat tctacatta atgtcctctt gctgtctaca
1501 gtagctgcta cctaaaaaaa gatgttttat tttgccagtt ggacacaggt gattggctcc
1561 tgggtttcat gttctgtgac atcctgcttc ttcttccaaa tgcagttcat tgcagacacc
1621 accatattgc tatctaatgg ggaaatgtag ctatgggcca taaccaaaac tcacatgaaa
1681 cggaggcaga tggagaccaa gggtgggatc cagaatggag tcttttctgt tattgtattt
1741 aaaagggtaa tgtggccttg gcatttcttc ttagaaaaaa actaattttt ggtgctgatt
1801 ggcatgtctg gttcacagtt tagcattgtt ataaaccatt ccattcgaaa agcactttga
1861 aaaattgttc ccgagcgata gatgggatgg tttatgca
```

SEQ ID NO:15

```
1    gagacattcc ggtgggggac tctggccagc ccgagcaacg tggatcctga gagcactccc
61   aggtaggcat ttgccccggt gggacgcctt gccagagcag tgtgtggcag cccccgtgg
121  aggatcaaca cagtggctga acactgggaa ggaactggta cttggagtct ggacatctga
181  aacttggctc tgaaactgcg cagcggccac cggacgcctt ctggagcagg tagcagcatg
241  cagccgcctc caagtctgtg cggacgcgcc ctggttgcgc tggttcttgc ctgcggcctg
301  tcgcggatct ggggagagga gagaggcttc ccgcctgaca gggccactcc gcttttgcaa
361  accgcagaga taatgacgcc acccactaag accttatggc caagggttc aacgccagt
421  ctggcgcggt cgttggcacc tgcggaggtg cctaaaggag acaggacggc aggatctccg
481  ccacgcacca tctcccctcc ccgtgccaa ggacccatcg agatcaagga gactttcaaa
541  tacatcaaca cggttgtgtc ctgccttgtg ttcgtgctgg ggatcatcgg gaactccaca
601  cttctgagaa ttatctacaa gaacaagtgc atgcgaaacg tcccaatat cttgatcgcc
661  agcttggctc tgggagacct gctgcacatc gtcattgaca tccctatcaa tgtctacaag
721  ctgctggcag aggactggcc atttggagct gagatgtgta agctggtgcc tttcatacag
781  aaagcctccg tgggaatcac tgtgctgagt ctatgtgctc tgagtattga cagatatcga
841  gctgttgctt cttggagtag aattaaagga attggggttc caaaatggac agcagtagaa
901  attgttttga tttgggtggt ctctgtggtt ctggctgtcc ctgaagccat aggttttgat
961  ataattacga tggactacaa aggaagttat ctgcgaatct gcttgcttca tcccgttcag
```

FIG. 10 A-15

```
1021 aagacagctt tcatgcagtt ttacaagaca gcaaaagatt ggtggctgtt cagtttctat
1081 ttctgcttgc cattggccat cactgcattt ttttatacac taatgacctg tgaaatgttg
1141 agaaagaaaa gtggcatgca gattgcttta aatgatcacc taaagcagag acgggaagtg
1201 gccaaaaccg tcttttgcct ggtccttgtc tttgccctct gctggcttcc ccttcacctc
1261 agcaggattc tgaagctcac tctttataat cagaatgatc ccaatagatg tgaacttttg
1321 agctttctgt tggtattgga ctatattggt atcaacatgg cttcactgaa ttcctgcatt
1381 aacccaattg ctctgtattt ggtgagcaaa agattcaaaa actgctttaa gtcatgctta
1441 tgctgctggt gccagtcatt tgaagaaaaa cagtccttgg aggaaaagca gtcgtgctta
1501 aagttcaaag ctaatgatca cggatatgac aacttccgtt ccagtaataa atacagctca
1561 tcttgaaaga agaactattc actgtatttc attttcttta tattggaccg aagtcattaa
1621 aacaaaatga aacatttgcc aaaacaaaac aaaaaactat gtatttgcac agcacactat
1681 taaaatatta agtgtaatta ttttaacact cacagctaca tatgacattt tatgagctgt
1741 ttacggcatg gaaagaaaat cagtgggaat taagaaagcc tcgtcgtgaa agcacttaat
1801 tttttacagt tagcacttca acatagctct taacaacttc caggatattc acacaacact
1861 taggcttaaa aatgagctca ctcagaattt ctattctttc taaaaagaga tttatttta
1921 aatcaatggg actctgatat aaaggaagaa taagtcactg taaaacagaa cttttaaatg
1981 aagcttaaat tactcaattt aaaattttaa aatcctttaa aacaacttt caattaatat
2041 tatcacacta ttatcagatt gtaattagat gcaaatgaga gagcagttta gttgttgcat
2101 ttttcggaca ctggaaacat ttaaatgatc aggagggagt aacagaaaga gcaaggctgt
2161 ttttgaaaat cattacactt tcactagaag cccaaacctc agcattctgc aatatgtaac
2221 caacatgtca caaacaagca gcatgtaaca gactggcaca tgtgccagct gaatttaaaa
2281 tataatactt ttaaaaagaa aattattaca tcctttacat tcagttaaga tcaaacctca
2341 caaagagaaa tagaatgttt gaaaggctat cccaaaagac ttttttgaat ctgtcattca
2401 catccctgt gaagacaata ctatctacaa ttttttcagg attattaaaa tcttcttttt
2461 tcactatcgt agcttaaact ctgttggtt ttgtcatctg taaatactta cctacataca
2521 ctgcatgtag atgattaaat gagggcaggc cctgtgctca tagctttacg atggagagat
2581 gccagtgacc tcataataaa gactgtgaac tgcctggtgc agtgtccaca tgacaaaggg
2641 gcaggtagca ccctctctca cccatgctgt ggttaaaatg gtttctagca tatgtataat
2701 gctatagtta aaatactatt tttcaaaatc atacagatta gtacatttaa cagctacctg
2761 taaagcttat tactaatttt tgtattattt ttgtaaatag ccaatagaaa agtttgcttg
2821 acatggtgct tttctttcat ctagaggcaa aactgctttt tgagaccgta agaacctctt
2881 agctttgtgc gttcctgcct aattttata tcttctaagc aaagtgcctt aggatagctt
2941 gggatgagat gtgtgtgaaa gtatgtacaa gagaaaacgg aagagagagg aaatgaggtg
3001 gggttggagg aaacccatgg ggacagattc ccattcttag cctaacgttc gtcattgcct
3061 cgtcacatca atgcaaaagg tcctgatttt gttccagcaa aacacagtgc aatgttctca
3121 gagtgacttt cgaaataaat tgggcccaag agctttaact cggtcttaaa atatgcccaa
3181 attttactt tgttttctt ttaataggct gggccacatg ttggaaataa gctagtaatg
3241 ttgttttctg tcaatattga atgtgatggt acagtaaacc aaaacccaac aatgtggcca
3301 gaaagaaaga gcaataataa ttaattcaca caccatatgg attctattta taaatcaccc
3361 acaaacttgt tctttaattt catcccaatc acttttcag aggcctgtta tcatagaagt
3421 cattttagac tctcaatttt aaattaattt tgaatcacta atattttcac agtttattaa
3481 tatatttaat ttctatttaa attttagatt attttattta ccatgtactg aattttaca
3541 tcctgatacc ctttccttct ccatgtcagt atcatgttct ctaattatct tgccaaattt
3601 tgaaactaca cacaaaaagc atacttgcat tatttataat aaaattgcat tcagtggctt
3661 tttaaaaaaa atgtttgatt caaaacttta acatactgat aagtaagaaa caattataat
3721 ttcttacat actcaaaacc aagatagaaa aaggtgctat cgttcaactt caaaacatgt
3781 ttcctagtat taaggacttt aatatagcaa cagacaaaat tattgttaac atggatgtta
3841 cagctcaaaa gatttataaa agatttttaac ctatttctc ccttattatc cactgctaat
3901 gtggatgtat gttcaaacac cttttagtat tgatagctta catatggcca aaggaataca
3961 gtttatagca aaacatgggt atgctgtagc taactttata aaagtgtaat ataacaatgt
4021 aaaaaattat atatctggga ggattttttg gttgcctaaa gtggctatag ttactgattt
```

FIG. 10 A-16

```
4081 tttattatgt aagcaaaacc aataaaaatt taagtttttt taacaactac cttatttttc
4141 actgtacaga cactaattca ttaaatacta attgattgtt taaaagaaat ataaatgtga
4201 caagtggaca ttatttatgt taaatataca attatcaagc aagtatgaag ttattcaatt
4261 aaaatgccac atttctggtc tctggg
```

SEQ ID NO:16

```
   1 gaattcccgc ggagcagcgt gcgcggggcc ccgggagacg gcggcggtag cggcgcgggc
  61 agagcaagga cgcggcggat cccactcgca cagcagcgca ctcggtgccc cgcgcaggot
 121 cgcgatgctg cccggtttgg cactgctcct gctggccgcc tggacggctc gggcgctgga
 181 ggtacccact gatggtaatg ctggcctgct ggctgaaccc cagattgcca tgttctgtgg
 241 cagactgaac atgcacatga atgtccagaa tgggaagtgg gattcagatc catcagggac
 301 caaaacctgc attgatacca aggaaggcat cctgcagtat tgccaagaag tctaccctga
 361 actgcagatc accaatgtgg tagaagccaa ccaaccagtg accatccaga actggtgcaa
 421 gcggggccgc aagcagtgca agaccccatcc ccactttgtg attccctacc gctgcttagt
 481 tggtgagttt gtaagtgatg cccttctcgt tcctgacaag tgcaaattct tacaccagga
 541 gaggatggat gtttgcgaaa ctcatcttca ctggcacacc gtcgccaaag agacatgcag
 601 tgagaagagt accaacttgc atgactacgg catgttgctg ccctgcggaa ttgacaagtt
 661 ccgaggggta gagtttgtgt gttgcccact ggctgaagaa agtgacaatg tggattctgc
 721 tgatgcggag gaggatgact cggatgtctg gtggggccga gcagacacag actatgcaga
 781 tgggagtgaa gacaaagtag tagaagtagc agaggaggaa gaagtggctg aggtggaaga
 841 agaagaagcc gatgatgacg aggacgatga ggatggtgat gaggtagagg aagaggctga
 901 ggaaccctac gaagaagcca cagagagaac caccagcatt gccaccacca ccaccaccac
 961 cacagagtct gtggaagagg tggttcgaga ggtgtgctct gaacaagccg agacggggcc
1021 gtgccgagca atgatctccc gctggtactt tgatgtgact gaagggaagt gtgcccatt
1081 cttttacggc ggatgttggc gcaaccggaa caactttgac acagaaagagt actgcatggc
1141 cgtgtgtggc agcgccattc ctacaacagc agccagtacc cctgatgccg ttgacaagta
1201 tctcgagaca cctgggggatg agaatgaaca tgcccatttc cagaaagcca aagagaggct
1261 tgaggccaag caccgagaga gaatgtccca ggtcatgaga gaatgggaag aggcagaacg
1321 tcaagcaaag aacttgccta agctgataaa gaaggcagtt atccagcatt tccaggagaa
1381 agtggaatct ttggaacagg aagcagccaa cgagagacag cagctggtgg agacacacat
1441 ggctcagagtg gaagccatgc tcaatgaccg ccgccgcctg gccctggaga actacatcac
1501 cgctctgcag gctgttcctc ctcggcctcg tcacgtgttc aatatgctaa agaagtatgt
1561 ccgcgcagaa cagaaggaca gacagcacac cctaaagcat ttcgagcatg tgcgcatggt
1621 ggatcccaag aaaagccgctc agatccggtc ccaggttatg acacacctcc gtgtgattta
1681 tgagcgcatg aatcagtctc tctccctgct ctacaacgtg cctgcagtgg ccgaggagat
1741 tcaggatgaa gttgatgagc tgcttcagaa agagcaaaac tattcagatg acgtcttggc
1801 caacatgatt agtgaaccaa ggatcagtta cggaaacgat gctctcatgc catctttgac
1861 cgaaacgaaa accaccgtgg agctccttcc cgtgaatgga gagttcagcc tggacgatct
1921 ccagccgtgg cattctttttg gggctgactc tgtgccagcc aacacagaaa acgaagttga
1981 gcctgttgat gcccgccctg ctgccgaccg aggactgacc actcgaccag gttctgggtt
2041 gacaaatatc aagacggagg agatctctga agtgaagatg gatgcagaat tccgacatga
2101 ctcaggatat gaagttcatc atcaaaaatt ggtgttcttt gcagaagatg tgggttcaaa
2161 caaaggtgca atcattggac tcatggtggg cggtgttgtc atagcgacag tgatcgtcat
2221 caccttggtg atgctgaaga gaaacagta cacatccatt catcatggtg tggtggaggt
2281 tgacgccgct gtcaccccag aggagcgcca cctgtccaag atgcagcaga acggctacga
2341 aaatccaacc tacaagttct tgagcagat gcagaactag accccgcca cagcagcctc
2401 tgaagttgga cagcaaaaccc attgcttcac tacccatcgg tgtccattta tagaataatg
2461 tgggaagaaa caaacccgtt ttatgattta ctcattatcg cctttgaca gctgtgctgt
2521 aacacaagta gatgcctgaa cttgaattaa tccacacatc agtaatgtat tctatctctc
2581 tttacatttt ggtctctata ctacattatt aatgggtttt gtgtactgta aagaatttag
2641 ctgtatcaaa ctagtgcatg aatagattct ctcctgatta tttatcacat agccccttag
```

FIG. 10 A-17

```
2701 ccagttgtat attattcttg tggtttgtga cccaattaag tcctacttta catatgcttt
2761 aagaatcgat gggggatgct tcatgtgaac gtgggagttc agctgcttct cttgcctaag
2821 tattcctttc ctgatcacta tgcattttaa agttaaacat ttttaagtat ttcagatgct
2881 ttagagagat ttttttttcca tgactgcatt ttactgtaca gattgctgct tctgctatat
2941 ttgtgatata ggaattaaga ggatacacac gtttgtttct tcgtgcctgt tttatgtgca
3001 cacattaggc attgagactt caagcttttc ttttttttgtc cacgtatctt tgggtctttg
3061 ataaagaaaa gaatccctgt tcattgtaag cacttttacg gggcgggtgg ggagggggtgc
3121 tctgctggtc ttcaattacc aagaattc
```

SEQ ID NO:17

```
   1 gccgccctcg ccaccgctcc cggccgccgc gctccggtac acacaggatc cctgctgggc
  61 accaacagct ccaccatggg gctggcctgg ggactaggcg tcctgttcct gatgcatgtg
 121 tgtggcacca accgcattcc agagtctggc ggagacaaca gcgtgtttga catctttgaa
 181 ctcaccgggg ccgcccgcaa ggggtctggg cgccgactgg tgaagggccc cgaccctttcc
 241 agccagcttt tccgcatcga ggatgccaac ctgatccccc ctgtgcctga tgacaagttc
 301 caagacctgg tggatgctgt gcggacagaa aagggtttcc tccttctggc atccctgagg
 361 cagatgaaga agacccgggg cacgctgctg gccctggagc ggaaagacca ctctggccag
 421 gtcttcagcg tggtgtccaa tggcaaggcg ggcacccctg acctcagcct gaccgtccaa
 481 ggaaagcagc acgtggtgtc tgtgaagaa gctctcctgg caaccggcca gtggaagagc
 541 atcaccctgt ttgtgcagga agacaggggcc cagctgtaca tcgactgtga aaagatggag
 601 aatgctgagt tggacgtccc catccaaagc gtcttcacca gagacctggc cagcatcgcc
 661 agactccgca tcgcaaaggg gggcgtcaat gacaatttcc aggggggtgct gcagaatgtg
 721 aggtttgtct ttggaaccac accagaagac atcctcagga caaaggctg ctccagctct
 781 accagtgtcc tcctcaccct tgacaacaac gtgttgaatg gttccagccc tgccatccgc
 841 actaactaca ttggccacaa gacaaaggac ttgcaagcca tctgcggcat ctcctgtgat
 901 gagctgtcca gcatggtcct ggaactcagg ggcctgcgca ccattgtgac cacgctgcag
 961 gacagcatcc gcaaagtgac tgaagagaac aaagagttgg ccaatgagct gaggcggcct
1021 cccctatgct atcacaacgg agttcagtac agaaataacg aggaatggac tgttgatagc
1081 tgcactgagt gtcactgtca gaactcagtt accatctgca aaaggtgtc ctgccccatc
1141 atgcccgct ccaatgccac agttcctgat ggagaatgct gtcctgctg ttggcccagc
1201 gactctgcgg acgatggctg gtctccatgg tccgagtgga cctcctgttc tacgagctgt
1261 ggcaatggaa ttcagcagcg cggccgctcc tgcgatagcc tcaacaaccg atgtgagggc
1321 tcctcggtcc agacacggac ctgccacatt caggagtgtg acaagagatt taaacaggat
1381 ggtggctgga gccactggtc cccgtggtca tcttgttctg tgacatgtgg tgatggtgtg
1441 atcacaagga tccggctctg caactctccc agcccccaga tgaacgggaa accctgtgaa
1501 ggcgaagcgc gggagaccaa agcctgcaag aaagcgcct gcccatcaa tggaggctgg
1561 ggtccttggt caccatggga catctgttct gtcacctgtg gaggagggggg acagaaacgt
1621 agtcgtctct gcaacaaccc cacacccag tttggaggca aggactcgt tggtgatgta
1681 acagaaaacc agatctgcaa caagcaggac tgtccaattg atggatgcct gtccaatccc
1741 tgctttgccg gcgtgaagtg tactagctac cctgatggca gctggaaatg tggtgcttgt
1801 cccctggtt acagtggaaa tggcatccag tgcacagatg ttgatgagtg caaagaagtg
1861 cctgatcct gcttcaacca caatggacga caccggtgtg agaacacgga ccccggctac
1921 aactgcctgc cctgcccccc acgcttcacc ggctcacagc ccttcggcca gggtgtcgaa
1981 catgccacgg ccaacaaaca ggtgtgcaag ccccgtaacc cctgcacgga tgggacccac
2041 gactgcaaca gaacgccaa gtcaactac ctggccact agcgaccc catgtaccgc
2101 tgcgagtgca gcctggcta cgctggcaat ggcatcatct gcggggagga cacagacctg
2161 gatggctggc caatgagaa cctggtgtgc gtggccaatg cgacttacca ctgcaaaaag
2221 gataattgcc caaccttcc caactcaggg caggaagact atgacaagga tggaattggt
2281 gatgcctgtg atgatgacga tgacaatgat aaaattccag atgacaggga caactgtcca
2341 ttccattaca acccagctca gtatgactat gacagagatg atgtgggaga ccgctgtgac
```

FIG. 10 A-18

```
2401 aactgtccct acaaccacaa cccagatcag gcagacacag acaacaatgg ggaaggagac
2461 gcctgtgctg cagacattga tggagacggt atcctcaatg aacgggacaa ctgccagtac
2521 gtctacaatg tggaccagag agacactgat atggatgggg ttggagatca gtgtgacaat
2581 tgcccttgg aacacaatcc ggatcagctg gactctgact cagaccgcat tggagatacc
2641 tgtgacaaca atcaggatat tgatgaagat ggccaccaga acaatctgga caactgtccc
2701 tatgtgccca atgccaacca ggctgaccat gacaaagatg gcaagggaga tgcctgtgac
2761 cacgatgatg acaacgatgg cattcctgat gacaaggaca actgcagact cgtgcccaat
2821 cccgaccaga aggactctga cggcgatggt cgaggtgatg cctgcaaaga tgattttgac
2881 catgacagtg tgccagacat cgatgacatc tgtcctgaga atgttgacat cagtgagacc
2941 gatttccgcc gattccagat gattcctctg gaccccaaag ggacatccca aaatgaccct
3001 aactgggttg tacgccatca gggtaaagaa ctcgtccaga ctgtcaactg tgatcctgga
3061 ctcgctgtag ttatgatga gtttaatgct gtggacttca gtggcacctt cttcatcaac
3121 accgaaaggg acgatgacta tgctggattt gtctttggct accagtccag cagccgcttt
3181 tatgttgtga tgtggaagca agtcacccag tcctactggg acaccaaccc cacgagggct
3241 cagggatact cgggcctttc tgtgaaagtt gtaaactcca ccacagggcc tggcgagcac
3301 ctgcggaacg ccctgtggca cacaggaaac acccctggcc aggtgcgcac cctgtggcat
3361 gaccctcgtc acataggctg gaaagattc accgcctaca gatggcgtct cagccacagg
3421 ccaaagacgg gtttcattag agtggtgatg tatgaaggga agaaaatcat ggctgactca
3481 ggaccatct atgataaaac ctatgctggt ggtagactag ggttgtttgt cttctctcaa
3541 gaaatggtgt tcttctctga cctgaaatac gaatgtagag atccctaatc atcaaattgt
3601 tgattgaaag actgatcata aaccaatgct ggtattgcac cttctggaac tatgggcttg
3661 agaaaacccc caggatcact tctccttggc ttccttcttt tctgtgcttg catcagtgtg
3721 gactcctaga acgtgcgacc tgcctcaaga aaatgcagtt ttcaaaaaca gactcagcat
3781 tcagcctcca atgaataaga catcttccaa gcatataaac aattgctttg gtttcctttt
3841 gaaaaagcat ctacttgctt cagttgggaa ggtgcccatt ccactctgcc tttgtcacag
3901 agcagggtgc tattgtgagg ccatcctctga gcagtggact caaaagcatt ttcaggcatg
3961 tcagagaagg gaggactcac tagaattagc aaacaaaacc accctgacat cctccttcag
4021 gaacacgggg agcagaggcc aaagcactaa ggggaggggcg catacccgag acgattgtat
4081 gaagaaaata tggaggaact gttacatgtt cggtactaag tcattttcag gggattgaaa
4141 gactattgct ggatttcatg atgctgactg gcgttagctg attaacccat gtaaataggc
4201 acttaaatag aagcaggaaa gggagacaaa gactggcttc tggacttcct ccctgatccc
4261 cacccttact catcacctgc agtggccaga attagggaat cagaatcgaa accagtgtaa
4321 ggcagtgctg gctgccattg cctggtcaca ttgaaattgg tggcttcatt ctagatgtag
4381 cttgtgcaga tgtagcagga aaataggaaa acctaccatc tcagtgagca ccag SEQ ID NO:18
   1 atttctcttt agttctttgc aagaaggtag agataaagac acttttttcaa aaatggcaat
  61 ggtatcagaa ttcctcaagc aggcctggtt tattgaaaat gaagagcagg aatatgttca
 121 aactgtgaag tcatccaaag gtggtcccgg atcagcggtg agccccatc ctaccttcaa
 181 tccatcctcg gatgtcgctg ccttgcataa ggccataatg gttaaggtg tggatgaagc
 241 aaccatcatt gacattctaa ctaagcgaaa caatgcacag cgtcaacaga tcaaagcagc
 301 atatctccag gaaacaggaa agcccctgga tgaaacactg aagaaagccc ttacaggtca
 361 ccttgaggag gttgttttag ctctgctaaa aactccagcg caatttgatg ctgatgaact
 421 tcgtgctgcc atgaagggcc ttgaactga tgaagatact ctaattgaga ttttggcatc
 481 aagaactaac aaagaaatca gagacattaa cagggtctac agagaggaac tgaagagaga
 541 tctggccaaa gacataacct cagacacatc tggagatttt cggaacgctt tgctttctct
 601 tgctaagggt gaccgatctg aggactttgg tgtgaatgaa gacttggctg attcagatgc
 661 cagggccttg tatgaagcag gagaaaggag aaaggggaca gacgtaaacg tgttcaatac
 721 catccttacc accagaagct atccacaact tcgcagagtg tttcagaaat acaccaagta
 781 cagtaagcat gacatgaaca aagttctgga cctggagttg aaaggtgaca ttgagaaatg
```

FIG. 10 A-19

```
 841 cctcacagct atcgtgaagt gcgccacaag caaaccagct ttctttgcag gaagcttca
 901 tcaagccatg aaaggtgttg gaactcgcca taaggcattg atcaggatta tggtttcccg
 961 ttctgaaatt gacatgaatg atatcaaagc attctatcag aagatgtatg gtatctccct
1021 ttgccaagcc atcctggatg aaaccaaagg agattatgag aaaatcctgg tggctctttg
1081 tggaggaaac taaacattcc cttgatggtc tcaagctatg atcagaagac tttaattata
1141 tatttcatc ctataagctt aaataggaaa gtttcttcaa caggattaca gtgtagctac
1201 ctacatgctg aaaaatatag cctttaaatc attttatat tataactctg tataatagag
1261 ataagtccat tttttaaaaa tgttttcccc aaaccataaa accctataca agttgttcta
1321 gtaacaatac atgagaaaga tgtctatgta gctgaaaata aaatgacgtc acaagac
```

SEQ ID NO:19
```
   1 gcccccgccc ggcccgcccc gctctcctag tcccttgcaa cctggcgctg catccgggcc
  61 actgtcccag gtcccaggtc ccggccggga gctatggagc ggcgctggcc cctggggcta
 121 gggctggtgc tgctgctctg cgccccgctg ccccggggg cgcgcgccaa ggaagttact
 181 ctgatggaca caagcaaggc acagggagag ctgggctggc tgctggatcc cccaaaagat
 241 gggtggagtg aacagcaaca gatactgaat gggacacccc tctacatgta ccaggactgc
 301 ccaatgcaag gacgcagaga cactgaccac tggcttcgct ccaattggat ctaccgcggg
 361 gaggaggctt cccgcgtcca cgtggagctg cagttcaccg tgcgggactg caagagtttc
 421 cctgggggag ccgggcctct gggctgcaag gagaccttca accttctgta catggagagt
 481 gaccaggatg tgggcattca gctccgacgg cccttgttcc agaaggtaac cacggtggct
 541 gcagaccaga gcttcaccat tcgagacctt gcgtctggct ccgtgaagct gaatgtggag
 601 cgctgctctc tgggccgcct gacccgccgt ggcctctacc tgctttcca aacccgggt
 661 gcctgtgtgg ccctggtgtc tgtccgggtc ttctaccagc gctgtcctga gaccctgaat
 721 ggcttggccc aattcccaga cactctgcct ggccccgctg ggttggtgga agtggcgggc
 781 acctgcttgc cccacgcgcg ggccagcccc aggccctcag gtgcacccg catgcactgc
 841 agccctgatg gcgagtggct ggtgcctgta ggacggtgcc actgtgagcc tggctatgag
 901 gaaggtggca gtggcgaagc atgtgttgcc tgccctagcg gctcctaccg gatggacatg
 961 gacacacccc attgtctcac gtgccccag cagagcactg ctgagtctga ggggccacc
1021 atctgtacct gtgagagcgg ccattacaga gctcccgggg agggccccca ggtggcatgc
1081 acaggtcccc cctcggcccc ccgaaacctg agcttctctg cctcagggac tcagctctcc
1141 ctgcgttggg aacccccagc agatacgggg ggacgccagg atgtcagata cagtgtgagg
1201 tgttcccagt gtcagggcac agcacaggac ggggggccct gccagccctg tggggtgggc
1261 gtgcactttg cgccgggcc ccgggcgctc accacactgc cagtgcatgt caatggcctt
1321 gaaccttatg ccaactacac ctttaatgtg gaagcccaaa atggagtgtc agggctgggc
1381 agctctggcc atgccagcac ctcagtcagc atcagcatgg ggcatgcaga gtcactgtca
1441 ggcctgtctc tgagactggt gaagaaagaa ccgaggcaac tagagctgac ctgggcgggg
1501 tcccggcccc gaagccctgg ggcgaacctg acctatgagc tgcacgtgct gaaccaggat
1561 gaagaacggt accagatggt tctagaaccc agggtcttgc tgacagagct gcagcctgac
1621 accacataca tcgtcagagt ccgaatgctg acccactgg gtcctggccc tttctcccct
1681 gatcatgagt ttcggaccag cccaccagtg tccaggggcc tgactggagg agagattgta
1741 gccgtcatct ttgggctgct gcttggtgca gccttgctgc ttgggattct cgttttccgg
1801 tccaggagag cccagcggca gaggcagcag aggcacgtga ccgcgccacc gatgtggatc
1861 gagaggacaa gctgtgctga agcctatgt ggtacctcca ggcatacgag gaccctgcac
1921 agggagcctt ggactttacc cggaggctgg tctaattttc cttcccggga gcttgatcca
1981 gcgtggctga tggtggacac tgtcatagga gaaggagagt ttggggaagt gtatcgaggg
2041 accctcaggc tccccagcca ggactgcaag actgtggcca ttaagacctt aaaagacaca
2101 tccccaggtg gccagtggtg gaacttcctt cgagaggcaa ctatcatggg ccagtttagc
2161 cacccgcata ttctgcatct ggaaggcgtc gtcacaaagc gaaagccgat catgatcatc
2221 acagaattta tggagaatgc agccctggat gccttcctga gggagcggga ggaccagctg
2281 gtccctggc agctagtggc catgctgcag gcatagcat ctggcatgaa ctacctcagt
2341 aatcacaatt atgtccaccg ggacctggct gccagaaaca tcttggtgaa tcaaaacctg
```

FIG. 10 A-20

```
2401 tgctgcaagg tgtctgactt tggcctgact cgcctcctgg atgactttga ggcacatac
2461 gaaacccagg gaggaaagat ccctatccgt tggacagccc ctgaagccat tgcccatcgg
2521 atcttcacca cagccagcga tgtgtggagc tttgggattg tgatgtggga ggtgctgagc
2581 tttggggaca agccttatgg ggagatgagc aatcaggagg ttatgaagag cattgaggat
2641 gggtaccggt tgcccctcc tgtggactgc cctgccctc tgtatgagct catgaagaac
2701 tgctgggcat atgaccgtgc ccgccggcca cacttccaga agcttcaggc acatctggag
2761 caactgcttg ccaaccccca ctccctgcgg accattgcca actttgaccc cagggtgact
2821 cttcgcctgc ccagcctgag tggctcagat gggatcccgt atcgaaccgt ctctgagtgg
2881 ctcgagtcca tacgcatgaa acgctacatc ctgcacttcc actcggctgg gctggacacc
2941 atggagtgtg tgctggagct gaccgctgag gacctgacgc agatgggaat cacactgccc
3001 gggcaccaga agcgcattct ttgcagtatt cagggattca aggactgatc cctcctctca
3061 ccccatgccc aatcagggtg caaggagcaa ggacggggcc aaggtcgctc atggtcactc
3121 cctgcgcccc ttcccacaac ctgccagact aggctatcgg tgctgcttct gcccgcttta
3181 aggagaaccc tgctctgcac cccagaaaac ctctttgttt taaaagggag gtgggggtag
3241 aagtaaaagg atgatcatgg gagggagctc aggggttaat atatatacat acatacacat
3301 atatatattg ttgtaaataa acaggaaatg attttctgcc tccatcccac ccatcagggc
3361 tgcaggcact
```

SEQ ID NO:20

```
   1 ccaagagcta cgcggcggcg gcggagcgca ggcctcgtgc cgttacggcc atcacggcgg
  61 ccgcagtggc gtcctggagc cctcctcagt gctgaagctg ctgaaagatg gcagaagaag
 121 tggtggtagt agccaaattt gattatgtgg cccaacaaga acaagagttg gacatcaaga
 181 agaatgagag attatggctt ctggatgatt ctaagtcctg gtggcgagtt cgaaattcca
 241 tgaataaaac aggttttgtg ccttctaact atgtggaaag gaaaaacagt gctcggaaag
 301 catctattgt gaaaaaccta aaggatacct taggcattgg aaaagtgaaa agaaaaccta
 361 gtgtgccaga ttctgcatct cctgctgatg atagttttgt tgacccaggg gaacgtctct
 421 atgacctcaa catgcccgct tatgtgaaat ttaactacat ggctgagaga gaggatgaat
 481 tatcattgat aaaggggaca aaggtgatcg tcatggagaa atgcagtgat gggtggtggc
 541 gtggtagcta caatggacaa gttggatggt tcccttcaaa ctatgtaact gaagaaggtg
 601 acagtccttt gggtgaccat gtgggttctc tgtcagagaa attagcagca gtcgtcaata
 661 acctaaatac tgggcaagtg ttgcatgtgg tacaggctct ttacccattc agctcatcta
 721 atgatgaaga acttaatttc gagaaaggag atgtaatgga tgttattgaa aaacctgaaa
 781 atgacccaga gtggtggaaa tgcaggaaga tcaatggtat ggttggtcta gtaccaaaaa
 841 actatgttac cgttatgcag aataatccta taacttcagg tttggaacca tcacctccac
 901 agtgtgatta cattaagcct tcactcactg gaaagtttgc tggcaatcct tggtattatg
 961 gcaaagtcac caggcatcaa gcagaaatgg cattaaatga aagaggacat gaaggggatt
1021 tcctcattcg tgatagtgaa tcttcgccaa atgatttctc agtatcacta aaagcacaag
1081 ggaaaaacaa gcattttaaa gtccaactaa aagagactgt ctactgcatt gggcagcgta
1141 aattcagcac catggaagaa cttgtagaac attacaaaaa ggcaccaatt tttacaagtg
1201 aacaaggaga aaaattatat cttgtcaagc atttatcatg atactgctga ccagaagtga
1261 ctgctgtgta gctgtaattt gtcatgtaat tgaagactga gaaatgttgg ggtccagtcg
1321 tgcttgattg gaaattgttg tttctaaatc tatatgagaa ttgacaataa gtattttat
1381 tataactcag cccatacata tatactatgt atgcagtgca tctgcataga acagttcctt
1441 atccttggcc ttctgtttta ttgttttttt ctttgctgtt ttcccctttgc ttctaatatt
1501 acagttttgt attttgtaaa caaaaatcaa ataatgcata tcagaatctt tatatggaag
1561 aaatccttta ttgcctttcc tttgtttcct tgtaaaggca ccctgttctg ttatggtttt
1621 tcattatata aaattattat atctatatat gacatatgct aaaatttctt ggagagtgtt
1681 aatcttttct gtgactaaat agcaataata agtggaaaat tagaaattat ttccaggtat
1741 tatatttgtc acaggccatt gtaaatacca agtatattgt gtctgccata ttttaaaa
1801 atacattcat tgtcttcagt catacagcaa gacacatgag acatagatta gaaacatgt
```

FIG. 10 A-21

```
1861 tgtacaattt taatttacaa ctgttggaaa taaaaatcac ttaatttttt tcc
```

SEQ ID NO:21

```
   1 catggcggcg actgcggcaa agcgagagcc tcggagacgc cgctgccgcc agcacagccg
  61 gagacctgag ccgacactgg gggcagtccg cgagccccgc actctctcga tgagtcggag
 121 aagtcccgtt gtatcagagt aagatggacg gtagctttga ttgtgattgt ggtgagctgg
 181 agccacctga tcactaacaa aagacatctt ctgttaacca acagccgcca gggcttcctg
 241 ttgaaataaa tatatagcaa caaaggaaaa aaagaagcaa aacggaaata gtgcttacca
 301 gcaccttaga atgatgctgc tcaggaccag tccaacactg aatgtatctg cactgtgagg
 361 agaatgttca tagaagcctg ttgtgtgcat atttattcac attttgtta aatgttaaat
 421 cgtttagcac ggtaatctga gtgcacagta tgtcatttca ttccgtttga gtttcttgtt
 481 ttcgttaaat gtctgcagag ttgctgcccc tttcttgaac tatgagtact gcaatctttt
 541 taattctcaa tatgaataga gcttttgag ctttaaatct aaggggaact cgacaggcct
 601 gtttggcata tgcaatgaac atcaagaaac catcttgctg tggaagcata attattttc
 661 ttctcccttt tgaaagatc tttccttttg atgccagttt tcttccttgt ttacacaagt
 721 tcaatttgaa aggaaaaggc aatagtaagg gtttcaaaat ggcagagaaa tttgaaagtc
 781 tcatgaacat tcatggtttt gatctgggtt ctaggtatat ggacttaaaa ccattgggtt
 841 gtggaggcaa tggcttggtt ttttctgctg tagacaatga ctgtgacaaa agagtagcca
 901 tcaagaaaat tgtccttact gatccccaga gtgtcaaaca tgctctacgt gaaatcaaaa
 961 ttattagaag acttgaccat gataacattg tgaaagtgtt tgagattctt ggtcccagtg
1021 gaagccaatt aacagacgat gtgggctctc ttacggaact gaacagtgtt tacattgttc
1081 aggagtacat ggagacagac ttggctaatg tgctggagca gggcccttta ctggaagagc
1141 atgccaggct tttcatgtat cagctgctca gggggctcaa gtatattcac tctgcaaatg
1201 tactgcacag agatctcaaa ccagctaatc ttttcattaa tacggaagac ttggtgctga
1261 agataggtga ctttggtctt gcacggatca tggatcctca ttattcccat aagggtcatc
1321 tttctgaagg attggttact aaatggtaca gatctccacg tctttactt tctcctaata
1381 attatactaa agccattgac atgtgggctg caggctgcat ctttgctgaa atgctgactg
1441 gtaaaaccct ttttgcaggt gcacatgaac ttgaacagat gcagctgatt ttagaatcta
1501 ttcctgttgt acatggaaa gatcgtcagg agcttctcag cgtaattcca gtttacatta
1561 gaaatgacat gactgagcca cacaaacctt taactcagct gcttccagga attagtcgag
1621 aagcactgga tttcctggaa caaatttga catttagccc catggatcgg ttaacagcag
1681 aagaagcact ctcccatcct tacatgagca tatattcttt tccaatggat gagccaattt
1741 caagccatcc ttttcatatt gaagatgaag ttgatgatat tttgcttatg gatgaaactc
1801 acagtcacat ttataactgg gaaaggtatc atgattgtca gttttcagag catgattggc
1861 ctgtacataa caacttgat attgatgaa ttcagcttga tccaagagct ctgtccgatg
1921 tcactgatga agaagaagta caagttgatc cccgaaaata tttggattga gatcgggaaa
1981 agtatctgga ggatcctgct tttgatacca attactctac tgagccttgt tggcaatact
2041 cagatcatca tgaaaacaaa tattgtgatc tggagtgtag ccatacttgt aactacaaaa
2101 cgaggtcatc atcatattta gataacttag tttggagaga gagtgaagtt aaccattact
2161 atgaacccaa gcttattata gatctttcca attggaaaga acaaagcaaa gaaaaatctg
2221 ataagaaagg caaatcaaaa tgtgaaagga atggattggt taaagcccag atagcgctag
2281 aggaagcatc acagcaactg gctggaaaag aaagggaaaa gaatcaggga tttgattttg
2341 attccttat tgcaggaact attcagctta gttcccagca tgagcctact gatgttgttg
2401 ataaattaaa tgacttgaat agctcagtgt cccaactaga attgaaaagt ttgatatcaa
2461 agtcagtaag ccaagaaaaa caggaaaaag aatggcaaa tctggctcaa ttagaagcct
2521 tgtaccagtc ttcttgggac agccagtttg tgagtggtgg ggaggactgt tttttcataa
2581 atcagttttg tgaggtaagg aaggatgaac aagttgagaa ggaaaacact tacactagtt
2641 acttggacaa gttctttagc aggaaagaag atactgaaat gctagaaact gagccagtag
2701 aggatgggaa gcttggggag agaggacatg aggaaggatt tctgaacaac agtgggggagt
2761 tcctcttaa caagcagctc gagtccatag gcatcccaca gtttcacagt ccagttgggt
2821 caccacttaa gtcaatacag gccacattaa caccttctgc tatgaaatct tcccctcaaa
```

FIG. 10 A-22

```
2881 ttcctcatca aacatacagc agcattctga aacatctgaa ctaaaacact cagcagacat
2941 ttatctttgt attcttcatg aaatgtgttt tgtcttttt tattactagt gtttaagtca
3001 ttttttactt gaatcagatg gtgtcattta gtaaggattt tatgagttct tgtttttaa
3061 aatccagact ttcttttct acatgtgaga tagttttcat tttaactggc atgtcatttg
3121 cacacaaaaa taaagactag agcaaaataa tgcaacgcag gaggagaaaa gaaatgcact
3181 aagacaagaa cattctctca tagaacattg atctgtttta caggaaacaa accttgcctt
3241 gaaatttaca cagtgag
```

SEQ ID NO:22
```
   1 ggtctttgag cgctaacgtc tttctgtctc cccgcggtgg tgatgacggt gaaaactgag
  61 gctgctaagg gcaccctcac ttactccagg atgaggggca tggtggcaat tctcatcgct
 121 ttcatgaagc agaggaggat gggtctgaac gactttattc agaagattgc caataactcc
 181 tatgcatgca aacaccctga agttcagtcc atcttgaaga tctcccaacc tcaggagcct
 241 gagcttatga atgccaaccc ttctcctcca ccaagtcctt ctcagcaaat caaccttggc
 301 ccgtcgtcca atcctcatgc taaaccatct gactttcact tcttgaaagt gatcggaaag
 361 ggcagttttg gaaaggttct tctagcaaga cacaaggcag aagaagtgtt ctatgcagtc
 421 aaagttttac agaagaaagc aatcctgaaa aagaaagagg agaagcatat tatgtcggag
 481 cggaatgttc tgttgaagaa tgtgaagcac cctcctggtg gggccttca cttctctttc
 541 cagactgctg acaaattgta ctttgtccta gactacatta atggtggaga gttgttctac
 601 catctccaga gggaacgctg cttcctggaa ccacgggctc gtttctatgc tgctgaaata
 661 gccagtgcct tgggctacct gcattcactg aacatcgttt atagagactt aaaaccagag
 721 aatatttgc tagattcaca gggacacatt gtccttactg acttcggact ctgcaaggag
 781 aacattgaac acaacagcac aacatccacc ttctgtggca cgccggagta tctcgcacct
 841 gaggtgcttc ataagcagcc ttatgacagg actgtggact ggtggtgcct gggagctgtc
 901 ttgtatgaga tgctgtatgg cctgccgcct ttttatagcc gaaacacagc tgaaatgtac
 961 gacaacattc tgaacaagtc tctccagctg aaaccaaata ttacaaattc cgcaagacac
1021 ctcctggagg gcctcctgca gaaggacagg acaaagcggc tcggggccaa ggatgacttc
1081 atggagatta agagtcatgt cttcttctcc ttaattaact gggatgatct cattaataag
1141 aagattactc ccctttaa cccaaatgtg agtgggccca acgacctacg gcactttgac
1201 cccgagttta ccgaagagcc tgtccccaac tccattggca gtcccctga cagcgtcctc
1261 gtcacagcca gcgtcaagga agctgccgag gcttcctag gcttttccta tgcgcctccc
1321 acggactctt tcctctgaac cctgttaggg cttggttta aaggatttta tgtgtgtttc
1381 cgaatgtttt agttagcctt ttggtggagc cgccagctga caggacatct tacaagagaa
1441 tttgcacatc tctggaagct tagcaatctt attgcacact gttcgctgga agcttttga
1501 agagcacatt ctcctcagtg agctcatgag gttttcattt ttattcttcc ttccaacgtg
1561 gtgctatctc tgaaacgagc gttagagtgc cgccttagac ggaggcagga gtttcgttag
1621 aaagcggacg ctgttctaaa aaaggtctcc tgcagatctg tctgggctgt gatgacgaat
1681 attatgaaat gtgccttttc tgaagagatt gtgttagctc caaagctttt cctatcgcag
1741 tgtttcagtt ctttattttc ccttgtggat atgctgtgtg aaccgtcgtg tgagtgtggt
1801 atgcctgatc acagatggat tttgttataa gcatcaatgt gacacttgca ggacactaca
1861 acgtgggaca ttgttttgttt cttccatatt tggaagataa atttatgtgt agactttttt
1921 gtaagatacg gttaataact aaaatttatt gaaatggtct tgcaatgact cgtattcaga
1981 tgcttaaaga aagcattgct gctacaaata tttctatttt tagaaagggt ttttatggac
2041 caatgcccca gttgtcagtc agagccgttg gtgtttttca ttgtttaaaa tgtcacctgt
2101 aaaatgggca ttatttatgt ttttttttt gcattcctga taattgtatg tattgtataa
2161 agaacgtctg tacattgggt tataacacta gtatatttaa acttacaggc ttatttgtaa
2221 tgtaaaccac catttaaatg tactgtaatt aacatggtta taatacgtac aatccttccc
2281 tcatcccatc acacaacttt ttttgtgtgt gataaactga ttttggtttg caataaaacc
2341 ttgaaaaata ttta
```

FIG. 10 A-23

SEQ ID NO:23
```
   1 gagcagcaga atttcaactc cagtagactt gaatatgcct ctgggcaaag aagcagagct
  61 aacgaggaaa gggatttaaa gagtttttct tgggtgtttg tcaaactttt attccctgtc
 121 tgtgtgcaga ggggattcaa cttcaatttt tctgcagtgg ctctgggtcc agccccttac
 181 ttaaagatct ggaaagcatg aagactgggc ttttttcct atgtctcttg ggaactgcag
 241 ctgcaatccc gacaaatgca agattattat ctgatcattc caaaccaact gctgaaacgg
 301 tagcacctga caacactgca atccccagtt taagggctga agctgaagaa aatgaaaaag
 361 aaacagcagt atccacagaa gacgattccc accataaggc tgaaaaatca tcagtactaa
 421 agtcaaaaga ggaaagccat gaacagtcag cagaacaggg caagagttct agccaagagc
 481 tgggattgaa ggatcaagag gacagtgatg gtcacttaag tgtgaatttg gagtatgcac
 541 caactgaagg tacattggac ataaaagaag atatgagtga gcctcaggag aaaaaactct
 601 cagagaacac tgattttttg gctcctggtg ttagttcctt cacagattct aaccaacaag
 661 aaagtatcac aaagagagag gaaaaccaag aacaacctag aaattattca catcatcagt
 721 tgaacaggag cagtaaacat agccaaggcc taagggatca aggaaaccaa gagcaggatc
 781 caaatatttc caatggagaa gaggaagaag aaaaagagcc aggtgaagtt ggtacccaca
 841 atgataacca agaagaaag acagaattgc ccaggagca tgctaacagc aagcaggagg
 901 aagacaatac ccaatctgat gatattttgg aagagtctga tcaaccaact caagtaagca
 961 agatgcagga ggatgaattt gatcagggta accaagaaca agaagataac tccaatgcag
1021 aaatggaaga ggaaaatgca tcgaacgtca ataagcacat tcaagaaact gaatggcaga
1081 gtcaagaggg taaaactggc ctagaagcta tcagcaacca caaagagaca gaagaaaaga
1141 ctgtttctga ggctctgctc atggaaccta ctgatgatgg taataccacg cccagaaatc
1201 atggagttga tgatgatggc gatgatgatg gcgatgatgg cggcactgat ggccccaggc
1261 acagtgcaag tgatgactac ttcatcccaa gccaggcctt tctggaggcc gagagagctc
1321 aatccacctc aaaattgagg agcaaagaga aaaatcat gaaaatgaaa
1381 atataggtac cactgagcct ggagagcacc aagaggccaa gaaagcagag aactcatcaa
1441 atgaggagga aacgtcaagt gaaggcaaca tgagggtgca tgctgtggat tcttgcatga
1501 gcttccagtg taaaagaggc cacatctgta aggcagacca acagggaaaa cctcactgtg
1561 tctgccagga tccagtgact tgtcctccaa caaacccct tgatcaagtt tgtggcactg
1621 acaatcagac ctatgctagt tcctgtcatc tattcgctac taaatgcaga ctggaggga
1681 ccaaaaaggg gcatcaactc cagctggatt attttggagc ctgcaaat
```

SEQ ID NO:24
```
   1 cggataagga caaaaaacgc cagaagaaaa gaggcatttt ccccaaagta gcaacaaata
  61 tcatgagagc atggctcttc cagcatctca cacatccgta cccttccgaa gagcagaaga
 121 aacagttagc gcaagacaca ggacttacaa ttctccaagt aaacaactgg tttattaatg
 181 ccagaagaag aatagtacag cccatgattg accagtcaaa tcgagcagtg agccaaggag
 241 cagcatatag tccagagggt cagcccatgg ggagctttgt gttggatggt cagcaacaca
 301 tggggatccg gcctgcagga cctatgagtg aatgggcat gaatatgggc atggatgggc
 361 aatggcacta catgtaacct tcatcatgta aagcaatcgc aaagcaaggg ggaagtttgc
 421 agagcatgcc aggggactac gtttctcagg tggtcctat gggaatgagt atggcacagc
 481 caagttacac tcctccccag atgaccccac accctactca attaagacat ggacccccaa
 541 tgcattcata tttgccaagc catccccacc acccagccat gatgatgcac ggaggacccc
 601 ctacccaccc tggaatgact atgtcagcac agagccccac aatgttaaat tctgtagatc
 661 ccaatgttgg cggacaggtt atggacattc atgcccaata gtataaggga actcaaggga
 721 aaggaaaca cacgcaaaaa ctattttaag actttctgaa ctttgaccag atgttgacac
 781 ttaatatgaa attccagaca gctgtgatta ttttttactt ttgtcatttt tcatcaagca
 841 acagaggacc aatgcaacaa gaacacaaat gtgaaatcat gggctgactg agacaattct
 901 gtccatgtaa agatcctctg gaaaaagact ccgagagtta taactactgt agtataaata
 961 taggaactaa gttaaacttg tacatttctg ttgatcacgc cgttatgttg cctcaaatag
1021 ttttagaaga gaaaaaaaaa tatatccttg ttttccacac tatgtgtgtt gttcccaaaa
1081 gaatgactgt tttggttcat cagtgaattc accatccagg agagactgtg gtatatattt
```

FIG. 10 A-24

```
1141 taaacctgtt gggccaatga gaaaagaacc acactggaga tcatgatgaa cttttggctg
1201 aacctcatca ctcgaactcc agcttcaaga atgtgttttc atgcccggcc tttgttcctc
1261 cataaatgtg tcctttagtt tcaaacagat ctttatagtt cgtgcttcat aagccaattc
1321 ttattattat ttttggggga ctcttcttca aagagcttgc caatgaagat ttaaagacag
1381 agcaggagct tcttccagga gttctgagcc ttggttgtgg acaaaacaat cttaagttgg
1441 gcagctttcc tcaacacaaa aaaaagttat taatggtcat tgaaccataa ctaggacttt
1501 atcagaaact caaagcttgg gggataaaaa ggagcaagag aatactgtaa caaacttcgt
1561 acagagttcg gtctattaat tgtttcatgt tagatattct atgtgtttac ctcaattgaa
1621 aaaaaaaaga atgttttgc tagtatcaga tctgctgtgg aattggtatt gtatgtccat
1681 gaattcttct tttctcagca cgtgttcctc actagaagaa aatgctgtta cctttaagct
1741 ttgtcaaatt tacattaaaa tacttgtatg aggactgtga cgttatgtta aaaaaaaaaa
1801 ggtgttaagt cacaaaaagc ggtaataaat atttcatttt tgattttt
```

SEQ ID NO:25

```
   1 agcacactga ggaggcgatc cgccagcagg aggtggagca gctggacttc cgagacctcc
  61 tggggaagaa ggtgagtaca aagaccctat cggaagacga cctgaaggag atcccagccg
 121 agcagatgga tttccgtgcc aacctgcagc ggcaagtgaa gccaaagact gtgtctgagg
 181 aagagaggaa ggtgcacagc ccccagcagg tcgattttcg ctctgtcctg gccaagaagg
 241 ggacttccaa gaccccgtg cctgagaagg tgccaccgcc aaaacctgcc accccggatt
 301 ttcgctcagt gctgggtggc aagaagaaat taccagcaga gaatggcagc agcagtgccg
 361 agaccctgaa tgccaaggca gtggagagtt ccaagcccct gagcaatgca cagccttcag
 421 ggccccttgaa accgtgggc aacgccaagc ctgcgaagcc atgggcaacg atgggcaacg
 481 ccaagcctgc cgagaccctg aagcccatgg gcaatgccaa gcctgatgag aacctgaaat
 541 ccgctagcaa agaagaactc aagaaagacg ttaagaatga tgtgaactgc aagagaggcc
 601 atgcagggac cacagataat gaaaagagat cagagagcca ggggacagcc ccagccttca
 661 agcagaagct gcaagatgtt catgtggcag agggcaagaa gctgctgctc cagtgccagg
 721 tgtcttctga ccccccagcc accatcatct ggacgctgaa cggaaagacc atcaagacca
 781 ccaagttcat catcctctcc caggaaggct cactctgctc cgtctccatc gagaaggcac
 841 tgcctgagga cagaggctta tacaagtgtg tagccaagaa tgacgctggc caggcggagt
 901 gctccaccgc cagtcaccgtg gatgatgctc cagccagtga gaacaccaag gccccagaga
 961 tgaaatcccg gaggcccaag agctctcttc ctccccgtgct aggaactgga agtgatgcga
1021 ctgtgaaaaa gaaacctgcc cccaagacac tccgaaggc agcaatgccc cctcagatca
1081 tccagttccc tgaggaccag aaggtacgcg caggagagtc agtggagctg tttggcaaag
1141 tgacaggcac tcagcccatc acctgtacct ggatgaagtt ccgaaagcag atccaggaaa
1201 gcgagcacat gaaggtggag aacagcgaga atggcagcaa gctcaccatc ctggccgcgc
1261 gccaggagca ctgcggctgc tacacactgc tggtggagaa caagctgggc agcaggcagg
1321 cccaggtcaa cctcactgtc gtggataagc cagaccccc agctggcaca ccttgtgcct
1381 ctgacattcg gagctcctca ctgaccctgt cctggtatgg ctcctcatat gatggggca
1441 gtgctgtaca gtcctacagc atcgatatct gggactcagc caacaagacg tggaaggaac
1501 tagccacatg ccgcagcacc tctttcaacg tccaggacct gctgcctgac cacgaatata
1561 agttccgtgt acgtgcaatc aacgtgtatg aaccagtga gccaagccag gagtctgaac
1621 tcacaacggt aggagagaaa cctgaagagc cgaaggatga agtggaggtg tcagacgatg
1681 atgagaagga gcccgaggtt gattaccgga cagtgacaat caatactgaa caaaaagtat
1741 ctgacttcta cgacattgag gagagattag gatctgggaa atttggacag gtctttcgac
1801 ttgtagaaaa gaaaactcga aaagtctggg cagggaagtt cttcaaggca tattcagcaa
1861 aagagaaaga gaatatccgg caggagatta gcatcatgaa ctgcctccac caccctaagc
1921 tggtccagtg tgtggatgcc tttgaagaaa aggccaacat cgtcatggtc ctggagatcg
1981 tgtcaggagg ggagctgttt gagcgcatca ttgacgagga ctttgagctg acggagcgtg
2041 agtgcatcaa gtacatgcgg cagatctcgg agggagtgga gtacatccac aagcagggca
2101 tcgtgcacct ggacctcaag ccggagaaca tcatgtgtgt caacaagacg ggcaccagga
```

FIG. 10 A-25

```
2161 tcaagctcat cgactttggt ctggccagga ggctggagaa cgcggggtct ctgaaggtcc
2221 tctttggcac cccagaattt gtggctcctg aagtgatcaa ctatgagccc atcggctacg
2281 ccacagacat gtggagcatc ggggtcatct gctacatcct agtcagtggc ctttccccct
2341 tcatgggaga caacgataac gaaaccttgg ccaacgttac ctcagccacc tgggacttcg
2401 acgacgaggc attcgatgag atctccgacg atgccaagga tttcatcagc aatctgctga
2461 agaaagatat gaaaaaccgc ctggactgca cgcagtgcct tcagcatcca tggctaatga
2521 aagataccaa gaacatggag gccaagaaac tctccaagga ccggatgaag aagtacatgg
2581 caagaaggaa atggcagaaa acgggcaatg ctgtgagagc cattggaaga ctgtcctcta
2641 tggcaatgat ctcagggctc agtggcagga aatcctcaac agggtcacca accagcccgc
2701 tcaatgcaga aaaactagaa tctgaagaag atgtgtccca agctttcctt gaggctgttg
2761 ctgaggaaaa gcctcatgta aaaccctatt tctctaagac cattcgcgat ttagaagttg
2821 tggagggaag tgctgctaga tttgactgca agattgaagg atacccagac ccgaggttg
2881 tctggttcaa agatgaccag tcaatcaggg agtcccgcca cttccagata gactacgatg
2941 aggacgggaa ctgctcttta attattagtg atgtttgcgg ggatgacgat gccaagtaca
3001 cctgcaaggc tgtcaacagt cttggagaag ccacctgcac agcagagctc attgtggaaa
3061 cgatggagga aggtgaaggg gaagggaag aggaagaaga gtgaaacaaa gccagagaaa
3121 agcagtttct aagtcatatt aaaaggacta tttctctaaa actc
```

SEQ ID NO:26
```
   1 ctctcccaac cgcctcgtcg cactcctcag gctgagagca ccgctgcact cgcggccggc
  61 gatgcgggac cccggcgcgg ccgctccgct ttcgtccctg ggctctgtg ccctggtgct
 121 ggcgctgctg ggcgcactgt ccgcgggcgc cggggcgcag ccgtaccacg gagagaaggg
 181 catctccgtg ccggaccacg gcttctgcca gccatctcc atcccgctgt gcacggacat
 241 cgcctacaac cagaccatcc tgcccaacct gctgggccac acgaaccaag aggacgcggg
 301 cctcgaggtg caccagttct acccgctggt gaaggtgcag tgttctcccg aactccgctt
 361 tttcttatgc tccatgtatg cgcccgtgtg caccgtgctc gatcaggcca tcccgccgtg
 421 tcgttctctg tgcgagcgcg cccgccaggg ctgcgaggcg ctcatgaaca gttcggctt
 481 ccagtggccc gagcggctgc gctgcgagaa cttcccggtg cacggtgcgg gcgagatctg
 541 cgtgggccag aacacgtcgg acggctccgg gggcccaggc ggcggcccca ctgcctaccc
 601 tacccgcctg tacctgccgg acctgccctt caccgccgtg ccccgggggg cctcagatgg
 661 caggggggcgt cccgccttcc ccttctcatg ccccgtcag ctcaaggtgc ccccgtacct
 721 gggctaccgc ttcctgggtg agcgcgattg tggcgccccg tgcgaaccgg gccgtgccaa
 781 cggcctgatg tactttaagg aggaggagag gcgcttcgcc cgcctctggg tgggcgtgtg
 841 gtccgtgctg tgctgcgcct cgacgctctt taccgttctc acctacctgg tggacatgcg
 901 gcgcttcagc tacccagagc ggcccatcat cttcctgtcg ggctgctact tcatggtggc
 961 cgtggcgcac gtggccggct ccttctaga ggaccgcgcc gtgtgcgtgg agcgcttctc
1021 ggacgatggc taccgcacgg tggcgcaggg caccaagaag gagggctgca ccatcctctt
1081 catggtgctc tacttcttcg gcatggccag ctccatctgg tgggtcattc tgtctctcac
1141 ttggttcctg gcggccggca tgaagtgggg ccacgaggcc atcgaggcca actcgcagta
1201 cttccacctg gccgcgtggg ccgtgcccgc cgtcaagacc atcactatcc tggccatggg
1261 ccaggtagac ggggacctgc tgagcggggt gtgctacgtt ggcctctcca gtgtggacgc
1321 gctgcgggc ttcgtgctgg cgcctctgtt cgtctacctc ttcataggca cgtccttctt
1381 gctggccggc ttcgtgtccc tcttccgtat ccgcaccatc atgaaacacg acggcaccaa
1441 gaccgagaag ctggagaagc tcatggtgcg catcggcgtc ttcagcgtgc tctacacagt
1501 gcccgccacc atcgtcctgg cctgctactt ctacgagcag gccttccgcg agcactggga
1561 gcgcacctgg ctcctgcaga cgtgcaagag ctatgccgtg ccctgcccgc ccggccactt
1621 cccgcccatg agccccgact tcaccgtctt catgatcaag tacctgatga ccatgatcgt
1681 cggcatcacc actggcttct ggatctggtc gggcaagacc ctgcagtcgt ggcgccgctt
1741 ctaccacaga cttagccaca gcagcaaggg ggagactgcg gtatgagccc cggcccctcc
1801 ccaccttcc cacccagcc ctcttgcaag aggagaggca cggtagggaa aagaactgct
```

FIG. 10 A-26

```
1861 gggtgggggc ctgtttctgt aactttctcc ccctctactg agaagtgacc tggaagtgag
1921 aagttctttg cagatttggg gcgaggggtg atttggaaaa gaagacctgg gtggaaagcg
1981 gtttggatga aaagatttca ggcaaagact tgcaggaaga tgatgataac ggcgatgtga
2041 atcgtcaaag gtacgggcca gcttgtgcct aatagaaggt tgagaccagc agagactgct
2101 gtgagtttct cccggctccg aggctgaacg gggactgtga gcgatccccc tgctgcaggg
2161 cgagtggcct gtccagaccc ctgtgaggcc ccgggaaagg tacagccctg tctgcggtgg
2221 ctgctttgtt ggaaagaggg agggcctcct gcggtgtgct tgtcaagcag tggtcaaacc
2281 ataatctctt ttcactgggg ccaaactgga gcccagatgg gttaatttcc agggtcagac
2341 attacggtct ctcctcccct gcccctccc gcctgttttt cctcccgtac tgctttcagg
2401 tcttgtaaaa taagcatttg gaagtcttgg gaggcctgcc tgctagaatc ctaatgtgag
2461 gatgcaaaag aaatgatgat aacattttga gataaggcca aggagacgtg gagtaggtat
2521 ttttgctact ttttcatttt ctggggaagg caggaggcag aaagacgggt gttttatttg
2581 gtctaatacc ctgaaaagaa gtgatgactt gttgcttttc aaaacaggaa tgcattttc
2641 cccttgtctt tgttgtaaga gacaaaagag gaaacaaaag tgtctccctg tggaaggca
2701 taactgtgac gaaagcaact tttataggca aagcagcgca aatctgaggt ttcccgttgg
2761 ttgttaattt ggttgagata aacattcctt tttaaggaaa agtgaagagc agtgtgctgt
2821 cacacaccgt taagccagag gttctgactt cgctaaagga aatgtaagag gttttgttgt
2881 ctgttttaaa taaatttaat tcggaacaca tgatccaaca gactatgtta aaatattcag
2941 ggaaatctct cccttcattt acttttctt gctataagcc tatatttagg tttctttct
3001 attttttct cccatttgga tcctttgagg taaaaaaaca taatgtcttc agcctcataa
3061 taaaggaaag ttaattaaaa aaaaaaagca aagagccatt tgtcctgtt ttcttggttc
3121 catcaatctg tttattaaac atcatccata tgctgaccct gtctctgtgt ggttgggttg
3181 ggaggcgatc agcagatacc atagtgaacg aagaggaagg tttgaaccat gggccccatc
3241 tttaaagaaa gtcattaaaa gaaggtaaac ttcaaagtga ttctggagtt ctttgaaatg
3301 tgctggaaga cttaaattta ttaatcttaa atcatgtact tttttctgt aatagaactc
3361 ggattctttt gcatgatggg gtaaagctta gcagagaatc atgggagcta acctttatcc
3421 cacctttgac actaccctcc aatcttgcaa cactatcctg tttctcagaa cagtttttaa
3481 atgccaatca tagagggtac tgtaaagtgt acaagttact ttatatatgt aatgttcact
3541 tgagtggaac tgcttttac attaaagtta aaatcgatct tgtgtttctt caaccttcaa
3601 aactactctca tctgtcagat tttttaaaact ccaacacagg ttttggcatc ttttgtgctg
3661 tatctttttaa gtgcatgtga aatttgtaaa atagagataa gtacagtatg tatattttgt
3721 aaatctccca ttttttgtaag aaaatatata ttgtatttat acattttac tttggatttt
3781 tgttttgttg gctttaaagg tctaccccac tttatcacat gtacagatca caaataaatt
3841 tttttaaata c
```

SEQ ID NO:27
```
   1 ggggctcggg acggccgggc tgggagctgg agcccacagc gggaagcggc cgccgcccgg
  61 gcctcgcagg gctaggcgag gcgagggggg gcggggccgg gcgctacggg aaggggaggc
 121 cgcgcggacc gggagccgca ccgcgccagc cgggctgcag cggccgcgca ccaaggctgc
 181 gatgggctg gagacggaga aggcggacgt acagctcttc atggacgacg actcctacag
 241 ccaccacagc ggcctcgagt acgccgaccc cgagaagttc gcggactcgg accaggaccg
 301 ggatccccac cggctcaact cgcatctcaa gctgggcttc gaggatgtga tcgcagagcc
 361 ggtgactacg cactcctttg acaaagtgtg gatctgcagc catgccctct ttgaaatcag
 421 caaatacgta atgtacaagt tcctgacggt gttcctggcc attccctgg ccttcattgc
 481 gggaattctc tttgccaccc tcagctgtct gcacatctgg attttaatgc cttttgtaaa
 541 gacctgccta atggttctgc cttcagtgca gacaatatgg aagagtgtga cagatgttat
 601 cattgctcca ttgtgtacga gcgtaggacg atgcttctct tctgtcagcc tgcaactgag
 661 ccaggattga atacttggac cccaggtctg gagattggga tactgtaata cttcttgtt
 721 attataacat aaaagcacca ctgttctgtt catttcctag ctgttctaat taagaaaact
 781 attaagatga gcaaccacat ttagaaatgt ttattgacag gtcttttcaa ataatgcttt
```

FIG. 10 A-27

```
 841 tctaattaat agccaaagat ttcatatcta actttgtaac cagaattata cagtaagttg
 901 acaccactta gatttaaagg cagacagttt tgctttagta caatagtata cattttataa
 961 tgatgaactt ataatgatta agggacattt ctataaaaat actacaaatg ttttatgcac
1021 aacttcccat taaaaatgag atttcttatt tgtttgtctg tttttactct gggagtaata
1081 cttttaaat taccttaca tatatagtca ctggcatact gagaatatac aatgatcctg
1141 gaaattgcag taacaaaagc acacaacgat tatagtaact ataagataca ataaaacaaa
1201 taaatatgaa agtagattca tgaaaatgta ttcctttaaa atattgtttt cctacaggcc
1261 tatttaacaa gatgtttcat tttactgtat attttgtagt taatataaat gttgctctaa
1321 tcagattgct taaaagcatt tttattatat ttatgttgtt gaactaatat atgaaataag
1381 taaatgtagc tcccacaagg taaacttcat tggtaagatt gcactgttct gattatgtaa
1441 gcatttgtac atcttctttg gaataaaag ataaaa
```

SEQ ID NO:28
```
   1 gtttagaaca gcctacagac ccagtggcac gagacgggcc tctctcccaa acatcttcca
  61 agccagatcc tagtcagtgg gaaagcccca gcttcaaccc ctttgggagc cactctgttc
 121 tgcagaactc cccacccctc tcttctgagg gctcctacca ctttgaccca gataactttg
 181 acgaatccat ggatcccttt aaaccaacta cgaccttaac aagcagtgac ttttgttctc
 241 ccactgtaa tcacgttaat gaaatcttag aatcacccaa gaaggcaaag tcgcgtttaa
 301 taacgactac tgaacaagtg aaatttctct gttttctgtt gagtggctgt aaggtgaaga
 361 agcatgaaac tcagtctctc gccctggatg catgttctcg ggatgaaggg gcagtgatct
 421 cccagatttc agacatttct aatagggatg gccatgctac tgatgaggag aaactggcat
 481 ccacgtcatg tggtcagaaa tcagctggtg ccgaggtgaa aggtgagcca gaggaagacc
 541 tggagtactt tgaatgttcc aatgttcctg tgtctaccat aaatcatgcg ttttcatcct
 601 cagaagcagg catagagaag gagacgtgcc agaagatgga agaagacggg tccactgtgc
 661 ttgggctgct ggagtcctct gcagagaagg cccctgtgtc ggtgtcctgt ggaggtgaga
 721 gcccctgga tgggatctgc ctcagcgaat cagacaagac agccgtgctc accttaataa
 781 gagaagagat aattactaaa gagattgaag caaatgaatg gaagaagaaa tacgaagaga
 841 cccggcaaga agttttggag atgaggaaaa ttgtagctga atatgaaaag actattgctc
 901 aaatgattga tgaacaaagg acaagtatga cctctcagaa gagcttccag caactgacca
 961 tggagaagga acaggccctg gctgacctta actctgtgga aggtcccttt tctgatctct
1021 tcaggagata tgagaacctg aaaggtgttc tggaagggtt caagaagaat gaagaagcct
1081 tgaagaaatg tgctcaggat tacttagcca gagttaaaca agaggagcag cgataccagg
1141 ccctgaaaat ccacgcagaa gagaaactgg acaaagccaa tgaagagatt gctcaggttc
1201 gaacaaaagc aaaggctgag agtgcagctc tccatgctgg actccgcaaa gagcagatga
1261 aggtggagtc cctgagaagg gccctgcagc agaagaacca agaaattgaa gaactgacaa
1321 aaatctgtga tgagctgatt gcaaagctgg gaaagactga ctgagacact ccccctgtta
1381 gctcaacaga tctgcatttg gctgcttctc ttgtgaccac aattatcttg ccttatccag
1441 gaataattgc cctttgcag agaaaaaaaa aaacttaaaa aaagcacatg cctactgctg
1501 cctgtcccgc tttgctgcca atgcaacagc cctggaagaa accctagagg gttgcatagt
1561 ctagaaagga gtgtgacctg acagtgctgg agcctcctag tttcccccta tgaaggttcc
1621 cttaggctgc tgagtttggg tttgtgattt atctttagtt tgtttttaaag tcatctttac
1681 tttcccaaat gtgttaaatt tgtaactcct ctttggggtc ttctccacca cctgtctgat
1741 tttttgtga tctgttttaat cttttaattt tttagtatca gtggttttat ttaaggagac
1801 agtttggcct attgttactt ccaatttata atcaagaagg ggctctggat cccctttaa
1861 attacacaca ctctcacaca catacatgta tgtttataga tgctgctgct cttttccctg
1921 aagcatagtc aagtaagaac tgctctacag aaggacatat ttccttggat gtgagaccct
1981 attttgaaat agagtcctga ctcagaacac caacttaaga atttggggga ttaaagatgt
2041 gaagaccaca gtcttgggtt ttcatatctg gagaagacta tttgccatga cgtttgttg
2101 ccctggtatt tggacactcc tcagctttaa tgggtgtggc cccttaggg ttagtcctca
2161 gactaatgat agtgtctgct ttctgcatga acggcaatat gggactccct ccaagctagg
2221 gtttggcaag tctgccctag agtcatttac tctcctctgc ctccatttgt taatacagaa
```

FIG. 10 A-28

```
2281 tcaacattta gtcttcatta tctttttttt ttttttgag acagagtttc gatctatttt
2341 aagtatgtga agaaaatcta cttgtaaaag gctcagatct taattaaaag gtaattgtag
2401 cacattacca attataaggt gaagaaatgt ttttttccca agtgtgatgc attgttcttc
2461 agatgttgaa aagaaagcaa aaaatacctt ctaacttaag acagaatttt taacaaaatg
2521 agcagtaaaa gtcacatgaa ccactccaaa aatcagtgca ttttgcatat ttttaaacaa
2581 agacagcttg ttgaatactg agaagaggag tgcaaggaga aggtctgtac taacaaagcc
2641 aaattcctca agctcttact ggactcagtt cagagtggtg ggccattaac cccaacatgg
2701 aattttttcca tataaatctc aatgaattcc ctttcatttg aataggcaaa cccaaatcca
2761 tgcaagtgtt ttaaagcact gtcctgtctt aatcttacat gctgaaagtc ttcatggtga
2821 tatgcactat attcagtata cgtatgtttt cctacttctc ttgtaaaact gttgcatgat
2881 ccaacttcag caatgaattg tgcctagtgg agaacctcta tagatcttaa aaaatgaatt
2941 attctttagc agtgtattac tcacatgggt gcaatcttta gccccaggga ggtcaataat
3001 gtcttttaaa gccagaagtc acattttacc aatatgcatt tatcataatt ggtgcttagg
3061 ctgtatattc aagcctgttg tcttaacatt ttgtataaaa aagaacaaca gaaattatct
3121 gtcatttgag aagtggcttg acaatcattt gagctttgaa agcagtcact gtggtgtaat
3181 atgaatgctg tcctagtggt catagtacca agggcacgtg tctcccttg gtataactga
3241 tttcctttt agtcctctac tgctaaataa gttaattttg cattttgcag aaagaaacat
3301 tgattgctaa atcttttttgc tgctgtgttt tggtgttttc atgtttactt gttttatatt
3361 gatctgtttt aagtatgaga ggcttatagt gccctccatt gtaaatccat agtcatcttt
3421 ttaagcttat tgtgtttaag aaagtagcta tgtgttaaac agaggtgatg gcagccttc
3481 cctagcacac tggtggaaga gacccttaa gaacctgacc ccagtgaatg aagctgatgc
3541 acaggagca ccaaaggacc ttcgttaagt gataattgtc ctggcctctc agccatgacc
3601 gttatgagga aatatccccc attcgaactt aacagatgcc tcctctccaa agagaattaa
3661 aatcgtagct tgtacagatc aagagaatat actgggcaga atgaagtatg tttgtttatt
3721 tttctttaaa aataaaggat tttggaactc tggagagtaa gaatatagta tagagtttgc
3781 ctcaacacat gtgagggcca aataacctgc tagctaggca gtaataaact ctgttacaga
3841 agagaaaaag ggccgggcac agtggcttat tcctgtaatc ccaacactgt ggaaggccga
3901 ggcaggagga tcacttgagt ccaggagttt gaaacctacc taggcaacat ggtgaaacct
3961 tgtctctacc aaaataaaaa ttagctgggc atggtggcac gtgcctgtgg tcccagctac
4021 ttgggaggct gaggtgggag cctgggaggt caaggctgca gtgagccatg atcatgccac
4081 tgcactccat cctgggtgac agcaagatct tgtctc
```

SEQ ID NO:29

```
  1 cgagttcccc gaggtgtacg tgcccaccgt cttcgagaac tatgtggccg acattgaggt
 61 ggacggcaag caggtggagc tggcgctgtg ggacacggcg ggccaggagg actacgaccg
121 cctgcggccg ctctcctacc cggacaccga cgtcattctc atgtgcttct cggtggacag
181 cccggactcg ctggagaaca tccccgagaa gtgggtcccc gaggtgaagc acttctgtcc
241 caatgtgccc atcatcctgg tggccaacaa aaaagacctg cgcagcgacg agcatgtccg
301 cacagagctg gcccgcatga agcaggaacc cgtgcgcacg gatgacggcg cgccatggc
361 cgtgcgcatc caagcctacg actacctcga gtgtctgcc aagaccaagg aaggcgtgcg
421 cgaggtcttc gagacggcca cgcgcgccg gctgcagaag cgctacggct cccagaacgg
481 ctgcatcaac tgctgcaagg tgctatgagg ccgcgcccg tcgcgcctgc cctgccggc
```

SEQ ID NO:30

```
  1 cggggagacc atgggcccc tctcagcccc ttcctgcaca cacctcatca cttggaaggg
 61 ggtcctgctc acagcatcac tttaaacttt ctggaatccg ccaccactg ccgaagtcac
121 gattgaagcc cagccaccca aagtttctga ggggaaggat gttcttctac ttgttcacaa
181 tttgccccag aatcttcctg gctacttctg gtacaaaggg gaaatgacgg acctctacca
241 ttacattata tcgtatatag ttgatggtaa aataattata tatgggcctg catacagtgg
301 aagagaaaca gtatattcca acgcatccct gctgatccag aatgtcaccc ggaaggatgc
```

FIG. 10 A-29

```
 361 aggaacctac accttacaca tcataaagcg aggtgatgag actagagaag aaattcgaca
 421 tttcaccttc acctttatact atggtccaga cctcccagaa atttacccctt cattcaccta
 481 ttacggttca ggagaaaacc tcgacttgtc ctgcttcacg aatctaacc caccggcaga
 541 gtattttgg acaattaatg ggaagtttca gcaatcagga caaaagctct ttatccccca
 601 aattactaga aatcatagcg ggctctatgt ttgctctgtt cataactcag ccactggcaa
 661 ggaaatctcc aaatccatga cagtcaaagt ctctggtccc tgccatggag acctgacaga
 721 gtttcagtca tgactgcaac aactgagaca ctgagaaaaa gaacaggctg ataccttcat
 781 gaaattcaag acaaagaaga aaaaaactca atgttattgg actaaataat caaaaggata
 841 atgtttcat aattttttat tggaaaatgt gctgattctt tgaatgtttt attctccaga
 901 tttatgaact tttttttcttc agcaattggt aaagtatact tttgtaaaca aaaattgaaa
 961 tatttgcttt tgctgtctat ctgaatgccc cagaattgtg aaactactca tgagtactca
1021 taggttttatg gtaataaagt tatttgcaca tgttccgtag ttt
```

SEQ ID NO:31
```
   1 gcaccaacca gcaccatgcc catgatactg gggtactggg acatccgcgg gctggcccac
  61 gccatccgcc tgctcctgga atacacagac tcaagctatg aggaaaagaa gtacacgatg
 121 ggggacgctc ctgattatga cagaagccag tggctgaatg aaaaattcaa gctgggcctg
 181 gactttccca atctgcccta cttgattgat ggggctcaca agatcaccca gagcaacgcc
 241 atcttgtgct acattgcccg caagcacaac ctgtgtgggg agacagaaga ggagaagatt
 301 cgtgtggaca ttttggagaa ccagaccatg acaaccata tgcagctggg catgatctgc
 361 tacaatccag aatttgagaa actgaagcca aagtacttgg aggaactccc tgaaaagcta
 421 aagctctact cagagtttct ggggaagcgg ccatggtttg caggaaacaa gatcactttt
 481 gtagattttc tcgtctatga tgtccttgac ctccaccgta tatttgagcc caactgcttg
 541 gacgccttcc caaatctgaa ggacttcatc tcccgctttg agggcttgga gaagatctct
 601 gcctacatga agtccagccg cttcctccca agcctgtgt tctcaaagat ggctgtctgg
 661 ggcaacaagt agggccttga aggcaggagg tgggagtgag gagcccatac tcagcctgct
 721 gcccaggctg tgcagcgcag ctggactctg catcccagca cctgcctcct cgttccttttc
 781 tcctgtttat tcccatcttt actcccaaga cttcattgtc cctcttcact ccccctaaac
 841 ccctgtccca tgcaggccct tgaagcctc agctacccac tatccttcgt gaacatcccc
 901 tcccatcatt acccttccct gcactaaagc cagcctgacc ttccttcctg ttagtggttg
 961 tgtctgcttt aaagcctgcc tggccccctcg cctgtggagc tcagccccga gctgtccccg
1021 tgttgcatga aggagcagca ttgactggtt tacaggccct gctcctgcag catggtccct
1081 gcctaggcct acctgatgga agtaaagcct caaccac
```

SEQ ID NO:32
```
   1 ttcaggaacc ggtttggtgc tggtgctgga ggcggctatg gctttggagg tggtgccggt
  61 agtggatttg gtttcggcg tggagctggt ggtggctttg ggctcggtgg cggagctggc
 121 tttggaggtg gcttcggtgg ccctggcttt cctgtctgcc ctcctggagg tatccaagag
 181 gtcactgtca accagagtct cctgactccc ctcaacctgc aaatcgaccc cagcatccag
 241 agggtgagga ccgaggagcg cgagcagatc aagaccctca caataagtt tgcctccttc
 301 atcgacaagg tgcggttcct ggagcagcag aacaaggttc tggacaccaa gtggaccctg
 361 ctgcaggagc agggcaccaa gactgtgagg cagaacctgg agccgttgtt cgagcagtac
 421 atcaacaacc tcaggaggca gctggacagc atcgtggggg aacgggccg cctggactca
 481 gagctgagaa acatgcagga cctggtggaa gacttcaaga caagtatga ggatgaaatc
 541 aacaagcgta ccactgctga gaatgagttt gtgatgctga gaaggatgt agatgctgcc
 601 tacatgaaca aggtggagct ggaggccaag gttgatgcac tgatggatga gattaacttc
 661 atgaagatgt tctttgatgc ggagctgtcc cagatgcaga cgcatgtctc tgacacctca
 721 gtggtcctct ccatggacaa caaccgcaac ctgaccctgg atagcatcat cgctgaggtc
 781 aaggcccagt atgaggagat tgccaaccgc agccggacag aagccgagtc ctggtatcag
 841 accaagtatg aggagctgca gcagacagct ggccggcatg gcgatgacct ccgcaacacc
 901 aagcatgaga tctctgagat gaaccggatg atccagaggc tgagagccga gattgacaat
```

FIG. 10 A-30

```
 961 gtcaagaaac agtgcgccaa tctgcagaac gccattgcgg atgccgagca gcgtggggag
1021 ctggccctca aggatgccag gaacaagctg gccgagctgg aggaggccct gcagaaggcc
1081 aagcaggaca tggcccggct gctgcgtgag taccaggagc tcatgaacac caagctggcc
1141 ctggacgtgg agatcgccac ttaccgcaag ctgctggagg gcgaggaatg cagactcagt
1201 ggagaaggag ttggaccagt caacatctct gttgtcacaa gcagtgtttc ctctggatat
1261 ggcagtggca gtggctatgg cggtggcctc ggtggaggtc ttggcggcgg cctcggtgga
1321 ggtcttgccg gaggtagcag tggaagctac tactccagca gcagtggggg tgtcggccta
1381 ggtggtgggc tcagtgtggg gggctctggc ttcagtgcaa gcagtggccg agggctgggg
1441 gtgggctttg gcagtggcgg gggtagcagc tccagcgtca aatttgtctc caccacctcc
1501 tcctcccgga agagcttcaa gagctaagaa cctgctgcaa gtcactgcct tccaagtgca
1561 gcaacccagc ccatggagat tgcctcttct aggcagttgc tcaagccatg ttttatcctt
1621 ttctggagag tagtctagac caagccaatt gcagaaccac attctttggt tcccaggaga
1681 gccccattcc cagccctgg tctcccgtgc cgcagttcta tattctgctt caaatcagcc
1741 ttcaggtttc ccacagcatg gcccctgctg acacgagaac ccaaagtttt cccaaatcta
1801 aatcatcaaa acagaatccc caccccaatc ccaaattttg ttttggttct aactacctcc
1861 agaatgtgt
```

SEQ ID NO:33
```
   1 agtgatcagg gccaaagcgg tcagtgagaa ggaagtggac tctggaaacg acatttatgg
  61 caaccctatc aagaggatcc agtatgagat caagcagata aagatgttca aagggcctga
 121 gaaggatata gagtttatct acacggcccc ctcctcggca gtgtgtgggg tctcgctgga
 181 cgttggagga aagaaggaat atctcattgc aggaaaggcc gagggggacg gcaagatgca
 241 catcaccctc tgtgacttca tcgtgcctg ggacaccctg agcaccaccc agaagaagag
 301 cctgaaccac aggtaccaga tgggctgcga gtgcaagatc acgcgctgcc ccatgatccc
 361 gtgctacatc tcctccccga acgagtgcct ctggatgacg tgggtcacag agaagaacat
 421 caacgggcac caggccaagt tcttcgcctg catcaagaga agtgacggct cctgtgcgtg
 481 gtaccgcggc gcggcgcccc ccaagcagga gtttctcgac atcgaggacc ataagcagg
 541 cctccaacgc ccctgtggcc aactgcaaaa aaagcctcca agggtttcga ctggtccagc
 601 tctgacatcc cttcctggaa acagcatgaa taaaacactc atcccatggg tccaaattaa
 661 tatg
```

SEQ ID NO:34
```
   1 tgtcgccacc atggctccgc accgcccgc gcccgcgctg ctttgcgcgc tgtccctggc
  61 gctgtgcgcg ctgtcgctgc ccgtccgcgc ggccactgcg tcgcgggggg cgtcccaggc
 121 gggggcgccc caggggcggg tgcccgaggc gcgcccccaac agcatggtgg tggaacaccc
 181 cgagttcctc aaggcaggga aggagcctgg cctgcagatc tggcgtgtgg agaagttcga
 241 tctggtgccc gtgcccacca acctttatgg agacttcttc acgggcgacg cctacgtcat
 301 cctgaagaca gtgcagctga ggaacggaaa tctgcagtat gacctccact actggctggg
 361 caatgagtgc agccaggatg agagcgggc ggccgccatc tttaccgtgc agctggatga
 421 ctacctgaac ggccgggccg tgcagcaccg tgaggtccag ggcttcgagt cggccacctt
 481 cctaggctac ttcaagtctg gcctgaagta caagaaagga ggtgtggcat caggattcaa
 541 gcacgtggta cccaacgagg tggtggtgca gagactcttc caggtcaaag gcggcgtgt
 601 ggtccgtgcc accaggtac ctgtgtcctg ggagagcttc aacaatggcg actgcttcat
 661 cctggaccctg ggcaacaaca tccaccagtg gtgtggttcc aacagcaatg ggtatgaaag
 721 actgaaggcc acacaggtgt ccaagggcat ccgggacaac gagcggagtg gccgggcccg
 781 agtgcacgtg tctgaggagg gcactgagcc cgaggcgatg ctccaggtgc tgggccccaa
 841 gccggctctg cctgcaggta ccgaggacac cgccaaggag gatgcggcca ccgcaagct
 901 ggccaagctc tacaaggtct ccaatggtgc agggaccatg tccgtctccc tcgtggctga
 961 tgagaacccc ttcgcccagg ggcctgaa gtcagaggac tgcttcatcc tggaccacgg
1021 caaagatggg aaaatctttg tctggaaagg caagcaggca aacacggagg agaggaaggc
1081 tgccctcaaa acagcctctg acttcatcac caagatggac taccccaagc agactcaggt
```

FIG. 10 A-31

```
1141 ctcggtcctt cctgagggcg gtgagacccc actgttcaag cagttcttca agaactggcg
1201 ggacccagac cagacagatg gcctgggctt gtcctacctt tccagccata tcgccaacgt
1261 ggagcgggtg cccttcgacg ccgccaccct gcacacctcc actgccatgg ccgcccagca
1321 cggcatggat gacgatggca caggccagaa acagatctgg agaatcgaag gttccaacaa
1381 ggtgcccgtg gaccctgcca catatggaca gttctatgga ggcgacagct acatcattct
1441 gtacaactac cgccatggtg gccgccaggg gcagataatc tataactggc agggtgccca
1501 gtctacccag gatgaggtcg ctgcatctgc catcctgact gctcagctgg atgaggagct
1561 gggaggtacc cctgtccaga gccgtgtggt ccaaggcaag gagcccgccc acctcatgag
1621 cctgtttggt gggaagccca tgatcatcta caagggcggc acctcccgcg agggcgggca
1681 gacagcccct gccagcaccc gcctcttcca ggtccgcgcc aacagcgctg agccacccg
1741 ggctgttgag gtattgccta aggctggtgc actgaactcc aacgatgcct tgttctgaa
1801 aacccctca gccgcctacc tgtgggtggg tacaggagcc agcgaggcag agaagacggg
1861 ggcccaggag ctgctcaggg tgctgcgggc ccaacctgtg caggtggcag aaggcagcga
1921 gccagatggc ttctgggagg ccctgggcgg gaaggctgcc taccgcacat ccccacggct
1981 gaaggacaag aagatggatg cccatcctcc tcgcctcttt gcctgctcca acaagattgg
2041 acgttttgtg atcgaagagg ttcctggtga gctcatgcag gaagacctgg caacggatga
2101 cgtcatgctt ctggacacct gggaccaggt ctttgtctgg gttggaaagg attctcaaga
2161 agaagaaaag acagaagcct tgacttctgc taagcggtac atcgagacgg acccagccaa
2221 tcgggatcgg cggacgccca tcaccgtggt gaagcaaggc tttgagcctc ctcctttgt
2281 gggctggttc cttggctggg atgatgatta ctggtctgtg gacccccttgg acagggccat
2341 ggctgagctg gctgcctgag gaggggcagg gcccacccat gtcaccggtc agtgcctttt
2401 ggaactgtcc ttccctcaaa gaggccttag agcgagcaga gcagctctgc tatgagtgtg
2461 tgtgtgtgtg tgtgttgttt cttttttttt tttttacagt atccaaaaat agccctgcaa
2521 aaattcagag tccttgcaaa attgtctaaa atgtcagtgt ttgggaaatt aaatccaata
2581 aaaacatttt gaagtgtg
```

SEQ ID NO:35
gaagtaaaagatttttattgttctatagacacttctgaaaagagatctaattgagaaat
atacaaagcatttaagagtttcatccccagagactgactgaaggcgttacagccctcctc
tccaaggctcagggctgagaacggttagcatatcgaatgatcagtaaaaacatgcaaaag
tgagaaggaaagggaaaaaggtgcattcccctaagctgaggggatggaatttcagaaca
gaggangcagggtggacaagtaccaaggtggctctcccttccctctgtgtnatctttca
aaaccanttccaagcntggatnaaagcaa

SEQ ID NO:36

```
   1 caaagtctga gccccgctcc gctgatgcct gtctgcagaa tccgcaccaa ccagcaccat
  61 gccatgact ctggggtact gggacatccg tgggctggcc cacgccatcc gcttgctcct
 121 ggaatacaca gactcaagct atgtggaaaa gaagtacacg ctggggacg ctcctgacta
 181 tgacagaagc cagtggctga tgaaaaatt caagctgggc ctggacttc ccaatctgcc
 241 ctacttgatt gatgggctc acaagatcac ccagagcaat gccatcctgc gctacattgc
 301 ccgcaagcac aacctgtgtg gggagacaga agaggagaag attcgtgtgg acattttgga
 361 gaaccaggtt atggataacc acatggagct ggtcagactg tgctatgacc agatttttga
 421 gaaactgaag ccaaaatact tggaggaact ccctgaaaag ctaaagctct actcagagtt
 481 tctggggaag cggccatggt ttgcaggaga caagatcacc tttgtggatt tccttgccta
 541 tgatgtcctt gacatgaagc gtatatttga gcccaagtgc ttggacgcct tcctaaactt
 601 gaaggacttc atctcccgct tgagggttt gaagaagatc tctgcctaca tgaagtccag
 661 ccaattcctc gaggtctttt tgtttggaaa gtcagctaca tggaacagca aatagggccc
 721 agtgatgcca gaagatggga gggaggagcc aaccttgctg cctgcgaccc tggaggacag
 781 cctgactccc tggacctgcc ttcttcctt tccttctttt ctactctctt ctcttcccca
 841 aggcctcatt ggcttccttt cttctaacat catccctccc cgcatcgagg ctctttaaag
```

FIG. 10 A-32

```
 901 cttcagctcc ccactgtcct ccatcaaagt cccctccta acgtcttcct ttccctgcac
 961 taacgccaac ctgactgctt ttcctgtcag tgcttttctc ttctttgaga agccagactg
1021 atctctgagc tccctagcac tgtcctcaaa gaccatctgt atgccctgct cccctttgctg
1081 ggtccctacc ccagctccgt gtgatgccca gtaaagcctg aaccatgcct gccatgtctt
1141 gtcttattcc ctgaggctcc cttgactcag gactgtgctc gaattgtggg tggtttttg
1201 tcttctgttg tccacagcca gagcttagtg gatgggtgtg tgtgtgtgtg tgttgggggt
1261 ggtgatcagg caggttcata aatttccttg gtcatttctg ccctctagcc acatccctct
1321 gttcctcact gtggggatta ctacagaaag gtgctctgtg ccaagttcct cactcattcg
1381 cgctcctgta ggccgtctag aactggcatg gttcaaagag gggctaggct gatggggaag
1441 ggggctgagc agctcccagg cagactgcct tctttcaccc tgtcctgata gacttccctg
1501 atctagatat ccttcgtcat gacacttctc aataaaacgt atcccaccgt attgt SEQ ID NO:37
   1 ggttgagaat gcttgcacca agcttgtcca ggcagctcag atgcttcagt cagacccta
  61 ctcagtgcct gctcgagatt atctaattga tgggtcaagg ggcatcctct ctggaacatc
 121 agacctgctc cttaccttcg atgaggctga ggtccgtaaa attattagag tttgcaaagg
 181 aattttggaa tatcttacag tggcagaggt ggtggagact atggaagatt tggtcactta
 241 cacaaagaat cttgggccag gaatgactaa gatggccaag atgattgacg agagacagca
 301 ggagctcact caccaggagc accgagtgat gttggtgaac tcgatgaaca ccgtgaaaga
 361 gttgctgcca gttctcattt cagctatgaa gattttgta acaactaaaa actcaaaaaa
 421 ccaaggcata gaggaagctt taaaaatcg caatttact gtagaaaaaa tgagtgctga
 481 aattaatgag ataattcgtg tgttacaact cacctcttgg gatgaagatg cctgggccag
 541 caaggacact gaagccatga agagagcatt ggcctccata gactccaaac tgaaccaggc
 601 caaaggttgg ctccgtgacc ctagtgcctc cccaggggat gctggtgagc aggccatcag
 661 acagatctta gatgaagctg gaaaagttgg tgaactctgt gcaggcaaag aacgcaggga
 721 gattctggga acttgcaaaa tgctagggca gatgactgat caagtggctg acctccgtgc
 781 cagnnnnnnn nnnnnnnnnn nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnnnn nnnnnnnnnn nnnnnnnnnn nnnnnnnnnn nnnnnnnnnn nnnnnnnnnn
1081 nnnnnnnnnn nnnnnnnnnn nnnnnnnnnn nnnnnnnnnn nnnnnnnnnn nnnaggctcg
1141 agccttggcc aaacaggtgg ccacggccct gcagaacctg cagaccaaaa ccaaccgggc
1201 tgtggccaac agcagaccgg ccaaagcagc tgtacacctt gagggcaaga ttgagcaagc
1261 acagcggtgg attgataatc ccacagtgga tgaccgtgga gtcggtcagg ctgccatccg
1321 ggggcttgtg gccgaagggc atcgtctggc taatgttatg atggggcctt atcggcaaga
1381 tcttctcgcc aagtgtgacc gagtggacca gctgacagcc cagctggctg acctggctgc
1441 cagaggggaa ggggagagtc tcaggcacg agcacttgca tctcagctcc aagactcctt
1501 aaaggatcta aaagctcgga tgcaggaggc catgactcag gaagtgtcag atgtttcag
1561 cgataccaca actcccatca agctgttggc agtggcagcc acggcgcctc ctgatgcgcc
1621 taacagggaa gaggtatttg atgagagggc agctaacttt gaaaaccatt caggaaagct
1681 tggtgctacg gccgagaagg cggctgcggt tggtactgct aataaatcaa cagtggaagg
1741 cattcaggcc tcagtgaaga cggcccgaga actcacaccc caggtggtct cggctgctcg
1801 tatcttactt aggaaccctg gaaatcaagc tgcttatgaa cattttgaga ccatgaagaa
1861 ccagtggatc gataatgttg aaaaaatgac agggctggtg gacgaagcca ttgataccaa
1921 atctctgttg gatgcttcag aagaagcaat taaaaagac ctggacaagt gcaaggtagc
1981 tatggccaac attcagcctc agatgctggt tgctggggca accagtattg ctcgtcgggc
2041 caaccggatc ctgctggtgg ctaagaggga ggtggagaat tccgaggatc ccaagttccg
2101 tgaggctgtg aaagctgcct ctgatgaatt gagcaaaacc atctccccga tggtgatgga
2161 tgcaaaagct gtggctggaa acatttccga ccctggactg caaaagagct tcctggactc
```

FIG. 10 A-33

```
2221 aggatatcgg atcctgggag ctgtggccaa ggtcagagaa gccttccaac ctcaggagcc
2281 tgacttcccg ccgcctccac cagaccttga acaactccga ctaacagatg agcttgctcc
2341 tcccaaacca cctctgcctg aaggtgaggt ccctccacct aggcctccac caccagagga
2401 aaaggatgaa gagttccctg agcagaaggc cggggaggtg attaaccagc caatgatgat
2461 ggctgccaga cagctccatg atgaagctcg caaatggtcc agcaagggca atgacatcat
2521 tgcagcagcc aagcgcatgg ctctgctgat ggctgagatg tctcggctgg taagaggggg
2581 cagtggtacc aagcgggcac tcattcagtg tgccaaggac atcgccaagg cctcagatga
2641 ggtgactcgg ttggccaagg aggttgccaa gcagtgcaca gataaacgga ttagaaccaa
2701 cctcttacag gtatgtgagc gaatcccaac cataagcacc cagctcaaaa tcctgtccac
2761 agtgaaggcc accatgctgg ccggaccaa catcagtgat gaggagtctg agcaggccac
2821 agagatgctg gttcacaatg cccagaacct catgcagtct gtgaaggaga ctgtgcggga
2881 agctgaagct gcttcaatca aaattcgaac agatgctgga tttacactgc gctgggttag
2941 aaagactccc tggtaccagt aggcacctgg ctgagcctgg ctggcacaga aacctctact
3001 aaaaagaagg aaaatgatct gagtcccagg agctgcccag agttgctggg agctgaaaaa
3061 tcacatcctg gcctggcaca tcagaaagga atgggggcct cttcaaatta gaagacattt
3121 atactctttt tcatggaca ctttgaaatg tgtttctgta taaagcctgt attctcaaac
3181 acagttacac ttgtgcaccc tctatcccaa taggcagact gggtttctag cccatggact
3241 tcacataagc tcagaatcca agtgaacact agccagacac tctgctctgc ccttgttccc
3301 taggggacac ttccctctgt ttctctttcc ttggctccca ttcactcttc agaatccca
3361 agacccaggg cccaggcaaa tcagttacta agaagaaaat tgctgtgcct cccaaaattg
3421 ttttgagctt tccatgttgc tgccaaccat accttccttc cctgggctgt gctacctggg
3481 tccttttcag aagtgagctt tgctgctaca ggggaaggtg gcctctgtgg agcccagca
3541 tatggggggcc tggattcatt tcctgccctt cctcagttta atccttctag tttcccacaa
3601 tataaaactg tacttcactg tcaggaagaa atcacagaat catatgattc tgcttttacc
3661 atgcccctga gcaatgtctg tgctagggaa acttcccgtc ccatatcctg cctcagcccg
3721 ccaaggtagc catcccatga acacactgtg tcctggtgct ctctgccact ggaagggcag
3781 agtagccagg gtgtggccct gccatcttcc cagcagggcc actcccggca ctccatgctt
3841 agtcactgcc tgcagaggtc tgtgctgagg ccttatcatt cattcttagc tcttaattgt
3901 tcattttgag ctgaaatgct gcattttaat tttaaccaaa acatgtctcc tatcctggtt
3961 tttgtagcct tcctcacat cctttctaaa caagatttta aagacatgta ggtgtttgtt
4021 catctgtaac tctaaaagat ccttttaaa ttcagtccta agaaagagga gtgcttgtcc
4081 cctaagagtg tttaatggca aggcagccct gtctgaagga cacttcctgc ctaagggaga
4141 gtggtatttg cagactagaa ttctagtgct gctgaagatg aatcaatggg aaatactact
4201 cctgtaattc ctacctccct gcaaccaact acaaccaagc tctctgcatc tactcccaag
4261 tatggggttc aagagagtaa tgggtttcat atttcttatc accacagtaa gttcctacta
4321 ggcaaaatga gagggcagtg tttcctttt ggtacttatt actgctaagt atttcccagc
4381 acatgaaacc ttattttttc ccaaagccag aaccagatga gtaaaggagt aagaaccttg
4441 cctgaacatc cttccttccc acccatcgct gtgtgttagt tcccaacatc gaatgtgtac
4501 aacttaagtt ggtcctttac actcaggctt tcactatttc ctttataatg aggatgatta
4561 ttttcaaggc cctcagcata tttgtatagt tgcttgcctg atataaatgc aatattaatg
4621 cctttaaagt atgaatctat gccaaagatc acttgttgtt ttactaaaga aagattactt
4681 agaggaaata agaaaaatca tgtttgctct cccggttctt ccagtggttt gagacactgg
4741 tttacacttt atgccggatg tgcttttctc caatatcagt gctcgagaca cagtgaagca
4801 aattaaaaaa aa
```

SEQ ID NO:38

```
  1 atatccagcc tttgccgaat acatcctatc tgccacacat ccagcgtgag gtccctccag
 61 ctacaaggtg ggcaccatgg cggagaagtt tgactgccac tactgcaggg atccttgca
121 ggggaagaag tatgtgcaaa aggatggcca ccactgctgc tgaaatgct tgacaagtt
181 ctgtgccaac acctgtgtgg aatgccgcaa gcccatcggt gcggactcca aggaggtgca
```

FIG. 10 A-34

```
 241 ctataagaac cgcttctggc atgacacctg cttccgctgt gccaagtgcc ttcaccccTt
 301 ggccaatgag acctttgtgg ccaaggacaa caagatcctg tgcaacaagt gcaccactcg
 361 ggaggactcc cccaagtgca aggggtgctt caaggccatt gtggcaggag atcaaaacgt
 421 ggagtacaag gggaccgtct ggcacaaaga ctgcttcacc tgtagtaact gcaagcaagt
 481 catcgggact ggaagcttct tccctaaagg ggaggacttc tactgcgtga cttgccatga
 541 gaccaagttt gccaagcatt gcgtgaagtg caacaaggcc atcacatctg gaggaatcac
 601 ttaccaggat cagccctggc atgccgattg ctttgtgtgt gttacctgct ctaagaagct
 661 ggctgggcag cgtttcaccg ctgtggagga ccagtattac tgcgtggatt gctacaagaa
 721 ctttgtggcc aagaagtgtg ctggatgcaa gaacccatc actgggaaaa ggactgtgtc
 781 aagagtgagc cacccagtct ctaaagctag gaagccccca gtgtgccacg ggaaacgctt
 841 gcctctcacc ctgtttccca gcgccaacct ccggggcagg catccgggtg gagagaggac
 901 ttgtccctcg tgggtggtgg ttctttatag aaaaaatcga agcttagcag ctcctcgagg
 961 cccgggtttg gtaaaggctc cagtgtggtg gcctatgaag acaatcctg gcacgactac
1021 tgcttccact gcaaaaaatg ctccgtgaat ctggccaaca agcgctttgt tttccaccag
1081 gagcaagtgt attgtcccga ctgtgccaaa aagctgtaaa ctgacagggg ctcctgtcct
1141 gtaaaatggc atttgaatct cgttcttTgt gtccttactt tctgccctat accatcaata
1201 ggggaagagt ggtccttccc ttctttaaag ttctccttcc gtcttttctc ccatttTaca
1261 gtattactca aataaggcca cacagtgatc atattagcat ttagcaaaaa gcaaccctgc
1321 agcaaagtga atttctgtcc ggctgcaatt taaaaatgaa aacttaggta gattgactct
1381 tctgcatgtt tctcatagag cagaaaagtg ctaatcattt agccacttag tgatgtaagc
1441 aagaagcata ggagataaaa cccccactga gatgcctctc atgcctcagc tgggacccac
1501 cgtgtagaca cacgacatgc aagagttgca gcggctgctc caactcactg ctcaccctct
1561 tctgtgagca ggaaaagaac cctactgaca tgcatggttt aacttcctca tcagaactct
1621 gcccttcctt ctgttctttt gtgctttcaa ataactaaca cgaacttcca gaaaattaac
1681 atttgaactt agctgtaatt ctaaactgac ctttcccgt actaacgttt ggtttccccg
1741 tgtggcatgt tttctgagcg ttcctacttt aaagcatgga acatgcaggt gatttgggaa
1801 gtgtagaaag acctgagaaa acgagcctgt tcagaggaa catcgtcaca acgaatactt
1861 ctggaagctt aacaaaacta accctgctgt ccttttTatt gttttTaatt aatattttTg
1921 ttttaattga tagcaaaata gtttatgggt ttggaaactt gcatgaaaat atttTagccc
1981 cctcagatgt tcctgcagtg ctgaaattca tcctacggaa gtaaccgcaa aactctag SEQ ID NO:39
    1 tgccgcccta caccgtggtc tatttcccag ttcgagnnnn nnnnnnnnnn nnnnnnnnnn
   61 nnnnnnnnnn nnnnnnnngc tgctggcaga tcagggccag agctggaagg aggaggtggt
  121 gaccgtggag acgtggcagg agggctcact caaagcctcc tgcctatacg ggcagctccc
  181 caagttccag gacggagacc tcaccctgta ccagtccaat accatcctgc gtcacctggn
  241 nnnnnnnnnn nnnnnnnnnn nnnnnnnngg ctctatggga aggaccagca ggaggcagcc
  301 ctggtggaca tggtgaatga cggcgtggag gacctccgct gcaaatatact ctccctcatc
  361 tacaccaact atgaggcggg caaggatgac tatgtgaagg cactgccggg gcaactgaag
  421 cctttTgaga ccctgctgtc ccagaaccag ggaggcaaga ccttcattgt gggagaccag
  481 atctccttcg ctgactacaa cctgctggac ttgctgctga tccatgaggt cctagcccct
  541 ggctgcctgg atgcgttccc cctgctctca gcatatgtgg ggcgcctcag tgcccggccc
  601 aagctcaagg ccttcctggc ctccctgag tacgtgaacc tccccatcaa tggcaacggg
  661 aaacagtgag ggttgggggg actctgagcg g SEQ ID NO:40
    1 cttTtcacac tggccttaaa gaggatatat tagaagttga agtaggaagg gagccagaga
   61 ggccgatggc gcaaaggtac gacgatctac cccattacgg gggcatggat ggagtaggca
  121 tccctccac gatgtatggg gacccgcatg cagccaggtc catgcagccg gtccaccacc
  181 tgaaccacgg gcctcctctg cactcgcatc agtacccgca cacagctcat accaacgcca
```

FIG. 10 A-35

```
 241 tggccccag catgggctcc tctgtcaatg acgctttaaa gagagataaa gatgccattt
 301 atggacaccc cctcttccct ctcttagcac tgattttga gaaatgtgaa ttagctactt
 361 gtaccccccg cgagccgggg gtggcgggcg gggacgtctg ctcgtcagag tcattcaatg
 421 aagatatagc cgtgttcgcc aaacagattc gcgcagaaaa acctctattt tcttctaatc
 481 cagaactgga taacttgatg attcaagcca tacaagtatt aaggtttcat ctattggaat
 541 tagagaaggt acacgaatta tgtgacaatt tctgccaccg gtatattagc tgtttgaaag
 601 ggaaaatgcc tatcgatttg gtgatagacg atagagaagg aggatcaaaa tcagacagtg
 661 aagatataac aagatcagca aatctaactg accagccctc ttggaacaga gatcatgatg
 721 acacggcatc tactcgttca ggaggaaccc caggcccttc cagcggtggc cacacgtcac
 781 acagtgggga caacagcann nnnnnnnnn nnnnnnnnnn nnnnnnnnn nnnnnnnnn
 841 nnnnnnnnnn nnnnnnnnnn nnnnnnnnn nnnnnnnnn nnnnnnnnn nnnnnnnnnn
 901 nnnnnnnnnn nnnnnnnnnn nnnnnnnnn nnnnnnnnn nnnnnnnnnn nnncacccctt
 961 acccttctga agaacagaaa aagcagttgg cacaagacac gggactcacc atccttcaag
1021 tgaacaattg gtttattaat gcccggagaa gaatagtgca gcccatgata gaccagtcca
1081 accgagcagt aagtcaagga acaccttata atcctgatgg acagcccatg ggaggtttcg
1141 taatggacgg tcagcaacat atgggaatta gagcaccagg acctatgagt ggaatgggca
1201 tgaatatggg catggagggg cagtggcact acatgtaacc ttcatctagt taaccaatcg
1261 caaagcaagg gggaaggctg caaagtatgc caggggagta tgtagcccgg ggtggtccaa
1321 tgggtgtgag tatgggacag ccaagttata cccaacccca gatgcccccc catcctgctc
1381 agctccgtca tgggccccc atgcatacgt acattcctgg acaccctcac cacccaacag
1441 tgatgatgca tggaggaccg ccccacccctg gaatgccaat gtcagcatca agccccacag
1501 ttcttaatac aggagaccca acaatgagtg gacaagtcat ggacattcat gctcagtagc
1561 ttaagggaat atgcattgtc tgcaatggtg actgatttca aatcatgttt tttctgcaat
1621 gactgtggag ttccattctt ggcatctact ctggaccaag gagcatccct aattcttcat
1681 agggaccttt aaaaagcagg aaataccaac tgaagtcaat ttgggggaca tgctaaataa
1741 ctatataaga cattaagaga acaaagatg aatattgta aatgctatta tactgttatc
1801 catattacgt tgtttcttat agatttttta aaaaaaatgt gaaatttttc cacactatgt
1861 gtgttgtttc catagctctt cacttcctcc agaagcctcc ttacattaaa aagccttaca
1921 gttatcctgc aagggacagg aaggtctgat ttgcaggatt tttagagcat taaaataact
1981 atcaggcaga agaatctttc ttctcgccta ggatttcagc catgcgcgcg ctctctctct
2041 ttctctctct tttcctctct ctccctcttt ctagcctggg gcttgaattt gcatgtctaa
2101 ttcatttact caccatattt gaattggcct gaacagatgt aaatcgggaa ggatgggaaa
2161 aactgcagtc atcaacaatg attaatcagc tgttgcaggc agtgtctaa ggagactggt
2221 aggaggaggc atggaaacca aaaggccgtg tgtttagaag cctaattgtc acatcaagca
2281 tcattgtccc catgcaacaa ccaccaccttt atacatcact tcctgtttta agcagctcta
2341 aaacatagac tgaagattta ttttaatat gttgacttta tttctgagca aagcatcggt
2401 catgtgtgta ttttttcata gtcccacctt ggagcattta tgtagacatt gtaaataaat
2461 tttgtgcaaa aaggactgga aaatgaact gtattattgc aatttttttt t
```

SEQ ID NO:41

```
   1 ctcaataagc caaccatgtc tttcaaggat tacatccaag agaggagtga cccagtggag
  61 caaggcaaac cagttatacc tgcagctgtg ctggccggct tcacaggaag tggacctatt
 121 cagctgtggc agtttctcct ggagctgcta tcagacaaat cctgccagtc attcatcagc
 181 tggactggag acggatggga gtttaagctc gccgaccccg atgaggtggc ccgccggtgg
 241 ggaaagagga aaaataagcc caagatgaac tacgagaagc tgagccgggg cttacgctac
 301 tattacgaca gaacatcat ccacaagacg tcggggaagc gctacgtgta ccgcttcgtg
 361 tgcgacctcc agaacttgct ggggttcacg cccgaggaac tgcacgccat cctgggcgtc
 421 cagcccgaca cggaggactg a
```

SEQ ID NO:42

```
   1 ggacgacaag gcgttcacca aggagctgga ccagtgggtc gagcagctga cgagtgtaa
```

FIG. 10 A-36

```
  61 gcagctgaac gagaaccaag tgcggacgct gtgcgagaag gcaaaggaaa ttttaacaaa
 121 agaatcaaat gtgcaagagg ttcgttgccc tgttactgtc tgtggagatg tgcatggtca
 181 atttcatgat cttatggaac tctttagaat tggtggaaaa tcaccggata caaactactt
 241 attcatgggt gactatgtag acagaggata ttattcagtg gagactgtga ctcttcttgt
 301 agcattaaag gtgcgttatc cagaacgcat tacaatattg agaggaaatc acgaaagccg
 361 acaaattacc caagtatatg gcttttatga tgaatgtctg cgaaagtatg ggaatgccaa
 421 cgtttggaaa tattttacag atctctttga ttatcttcca cttacagctt tagtagatgg
 481 acagatattc tgcctccatg gtggcctctc tccatccata gacacactgg atcatataag
 541 agccctggat cgtttacagg aagttccaca tgagggccca atgtgtgatc tgttatggtc
 601 agatccagat gatcgtggtg gatggggtat ttcaccacgt ggtgctggct acacatttgg
 661 acaagacatt tctgaaacct ttaaccatgc caatgatctc acactggttt ctcgtgccca
 721 ccagcttgta atggagggat acaattggtg tcatgatcgg aatgtggtta ccatttttcag
 781 tgcacccaat tactgttatc gttgtgggaa ccaggctgct atcatggaat tagatgacac
 841 tttaaaatat tccttccttc aatttgaccc agcgcctcgt cgtggtgagc ctcatgttac
 901 acggcgcacc ccagactact tcctataaat ttctcctggg aaacctgcct ttgtatgtgg
 961 aagtatacct ggcttttaa aatatatgta tttaaaaaca aaaagcaaca gtaatctatg
1021 tgtttctgta acaaattggg atctgtcttg gcattaaacc acatcatgga ccaaatgtgc
1081 catactaatg atgagcattt agcacaattt gagactgaaa tttagtacac tatgttctag
1141 gtcagtctaa cagtttgcct gctgtattta tagtaaccat tttcctttgg actgttcaag
1201 caaaaaaggt aactaactgc ttcatctcct tttgcgctta tttggaaatt ttagttatag
1261 tgtttaactg gcatggatta atagagttgg agtttatttt ttaagaaaaa ttcacaagct
1321 aacttccact aatccattat cctttatttt attgaaatgt ataattaact taactgaaga
1381 aaaggttctt cttgggagta tgttgtcata acatttaaag agatttccct tcatttaaac
1441 taaattactg ttttatgttg atctgcatat ttctgtatat ttgtcatgac agtgcttgca
1501 tcctatttgg tgtactcagc aaataaactt t
```

SEQ ID NO:43

```
   1 cctgtgagca ccacgtcaac ggctcccggc ccccatgcac gggggaggga gatacccca
  61 agtgtagcaa gatctgtgag cctggctaca gcccgaccta caaacaggac aagcactacg
 121 gatacaattc ctacagcgtc tccaatagcg agaaggacat catggccgag atctacaaaa
 181 acggccccgt ggagggagct ttctctgtgt attcggactt cctgctctac aagtcaggag
 241 tgtaccaaca cgtcaccgga gagatgatgg gtggccatgc catccgcatc ctggctgggg
 301 gagtggagaa tggcacaccc tactggctgg ttgccaactc ctggaacact gactggggtg
 361 acaatggctt cttttaaaata ctcagagcaa aggatcactg tggaatcgaa tcagaagtgg
 421 tggctggaat tccacgcacc gatcagtact gggaaaagat ctaatctgcc gtgggcctgt
 481 cgtgccagtc ctggggcga gatggggta gaaatgcatt ttattcttta agttcacgta
 541 agatacaagt ttcagacagg gtctgaagga ctggattggc caaacatcag acctgtcttc
 601 caaggagacc aagtcctggc tacatcccag cctgtggtta cagtgcagac aggccatgtg
 661 agccaccgct gccagcacag agcgtccttc ccctgtaga ctagtgccgt agggagtacc
 721 tgttgcccca gctgactgtg gcccctccg tgatccatcc atctccaggg agcaagacag
 781 agcccagga atggaaagcg gagttcctaa caggatgaaa gttcccccat cagttccccc
 841 agtacctcca agcaagtagc tttccacatt tgtcacagaa atcagaggag agatggtgtt
 901 gggagccctt tggagaacgc cagtctccca ggccccctgc atctatcgag tttgcaatgt
 961 cacaacctct ctgatcttgt gctcagcatg attctttaat agaagtttta ttttttcgtg
1021 cactctgcta atcatgtggg tgagccagtg aacagcggg agacctgtgc tagttttaca
1081 gattgcctcc ttatgacgcg gctcaaaagg aaaccaagtg gtcaggagtt gtttctgacc
1141 cactgatctc tactaccaca aggagaatag tttaggagaa accagctttt actgttttg
1201 aaaaattaca gcttcaccct gtcaagttaa caaggaatgc ctgtgccaat aaaaggtttc
```

SEQ ID NO:44

```
   1 gtgtcccata gtgtttccaa acttggaaag ggcgggggag ggcgggagga tgcggagggc
```

FIG. 10 A-37

```
  61 ggaggtatgc agacaacgag tcagagtttc cccttgaaag cctcaaaagt gtccacgtcc
 121 tcaaaaagaa tggaaccaat ttaagaagcc agccccgtgg ccacgtccct tcccccattc
 181 gctccctcct ctgcgccccc gcaggctcct cccagctgtg gctgcccggg ccccagccc
 241 cagccctccc attggtggag gcccttttgg aggcacccta gggccaggga aacttttgcc
 301 gtataaatag ggcagatccg ggctttatta ttttagcacc acggcagcag gaggtttcgg
 361 ctaagttgga ggtactggcc acgactgcat gcccgcgccc gccaggtgat acctccgccg
 421 gtgacccagg ggctctgcga cacaaggagt ctgcatgtct aagtgctaga catgctcagc
 481 tttgtggata cgcggacttt gttgctgctt gcagtaacct tatgcctagc aacatgccaa
 541 tctttacaag aggaaactgt aagaaagggc ccagccggag atagaggacc acgtggagaa
 601 aggggtccac caggccccc aggcagagat ggtgaagatg gtcccacagg ccctcctggt
 661 ccacctggtc ctcctggccc ccctggtctc ggtgggaact tgctgctca gtatgatgga
 721 aaaggagttg gacttggccc tggaccaatg ggcttaatgg gacctagagg cccacctggt
 781 gcagctggag ccccaggccc tcaaggtttc caaggacctg ctggtgagcc tggtgaacct
 841 ggtcaaactg gtcctgcagg tgctcgtggt ccagctggcc ctcctggcaa ggctggtgaa
 901 gatggtcacc ctggaaaacc cggacgacct ggtgagagag gagttgttgg accacagggt
 961 gctcgtggtt tccctggaac tcctggactt cctggcttca aaggcattag gggacacaat
1021 ggtctggatg gattgaaggg acagcccggt gctcctggtg tgaagggtga acctggtgcc
1081 cctggtgaaa atggaactcc aggtcaaaca ggagcccgtg ggcttcctgg tgagagagga
1141 cgtgttggtg ccctggccc agctggtgcc cgtggcagtg atggaagtgt gggtcccgtg
1201 ggtcctgctn nnnnnnnng gtctgctggc cctccaggct tcccaggtgc ccctggcccc
1261 aagggtgaaa ttggagctat tggtaacgct ggtcctgctg gtcccgccgg tccccgtggt
1321 gaagtgggtc ttccaggcct ctccggcccc gttggacctc ctggtaatcc tggagcaaac
1381 ggccttactg gtgccaaggg tgctgctggc cttccggcg ttgctgggc tcccggcctc
1441 cctggacccc gcggtattcc tggccctgtt ggtgctgccg gtgctactgg tgccagagga
1501 cttgttggtg agcctggtcc agctggctcc aaaggagaga gcggtaacaa gggtgagccc
1561 ggctctgctg gccccaagg tcctcctggt cccagtggtg aagaaggaaa gagaggccct
1621 aatggggaag ctggatctgc cggccctcca ggacctcctg ggctgagagg tagtcctggt
1681 tctcgtggtc ttcctggagc tgatggcaga gctggcgtca tgggccctcc tggtagtcgt
1741 ggtgcaagtg gccctgctgg agtccgagga cctaatggag atgctggtcg ccctggggag
1801 cctggtctca tgggacccag aggtcttcct ggttccccta gaaatatcgg ccccgctgga
1861 aaagaaggtc ctgtcggcct ccctggcatc gacggcaggc ctggcccaat tggccccgtt
1921 ggagcaagag gagagcctgg caacattgga ttccctggac ccaaaggccc cactggtgac
1981 cctggcaaaa acggtgataa aggtcatgct ggtcttgctg gtgctcgggg tgctccaggt
2041 cctgatggaa acaatggtgc tcagggacct cctggaccac agggtgttca aggtggaaaa
2101 ggtgaacagg gtcccgctgg tcctccaggc ttcaggggtc tgcctggccc ctcaggtccc
2161 gctggtgaag ttggcaaacc aggagaaagg ggtctccatg gtgagtttgg tctccctggt
2221 cctgctggtc caagagggga acgcggtccc caggtgaga gtggtgctgc cggtcctact
2281 ggtcctattg gaagccgagg tccttctgga ccccagggc ctgatgaaaa caagggtgaa
2341 cctggtgtgg ttggtgctgt gggcactgct ggtccatctg tcctagtgg actcccagga
2401 gagaggggtg ctgctggcat acctggaggc aagggagaaa agggtgaacc tggtctcaga
2461 ggtgaaattg gtaaccctgg cagagatggt gctcgtggtc tcatggtgc tgtaggtgcc
2521 cctggtcctg ctggagccac aggtgaccgg ggcgaagctg gggctgctgg tcctgctggt
2581 cctgctggtc ctcggggaag ccctggtgaa cgtggcgagg tcggtcctgc tggccccaac
2641 ggatttgctg gtccggctgg tgctgctggt caacccgggtg ctaaaggaga aagaggaggc
2701 aaagggccta agggtgaaaa cggtgttgtt ggtcccacag gccccgttgg agctgctggc
2761 ccagctggtc caaatggtcc ccccggtcct gctggaagtc gtggtgatgg aggcccccct
2821 ggtatgactg gtttccctgg tgctgctgga cggactggtc ccccaggacc ctctggtatt
2881 tctggccctc ctggtccccc tggtcctgct gggaagaag gcttcgtgg tcctcgtggt
2941 gaccaaggtc cagttggccg aactggagaa gtaggtcag ttggtccccc tggcttcgct
3001 ggtgagaagg gtccctctgg agaggctggt actgctggac ctcctggcac tccaggtcct
3061 cagggtcttc ttggtgctcc tggtattctg ggtctccctg gctcgagagg tgaacgtggt
```

FIG. 10 A-38

```
3121 ctacctggtg ttgctggtgc tgtgggtgaa cctggtcctc ttggcattgc cggccctcct
3181 ggggcccgtg gtcctcctgg tgctgtgggt agtcctggag tcaacggtgc tcctggtgaa
3241 gctggtcgtg atggcaaccc tgggaacgat ggtcccccag gtcgcgatgg tcaacccgga
3301 cacaagggag agcgcggtta ccctggcaat attggtcccg ttggtgctgc aggtgcacct
3361 ggtcctcatg gccccgtggg tcctgctggc aaacatgaaa accgtggtga aactggtcct
3421 tctggtcctg ttggtcctgc tggtgctgtt ggcccaagag gtcctagtgg cccacaaggc
3481 attcgtggcg ataagggaga gcccggtgaa aagggcccca gaggtcttcc tggcttcaag
3541 ggacacaatg gattgcaagg tctgcctggt atcgctggtc accatggtga tcaaggtgct
3601 cctggctccg tgggtcctgc tggtcctagg ggccctgctg gtccttctgg ccctgctgga
3661 aaagatggtc gcactggaca tcctggtacg gttggacctg ctggcattcg aggccctcag
3721 ggtcaccaag gccctgctgg cccccctggt ccccctggcc ctcctggacc tccaggtgta
3781 agcggtggtg gttatgactt tggttacgat ggagacttct acagggctga ccagcctcgc
3841 tcagcacctt ctctcagacc caaggactat gaagttgatg ctactctgaa gtctctcaac
3901 aaccagattg agaccttct tactcctgaa ggctctagaa agaacccagc tcgcacatgc
3961 cgtgacttga gactcagcca cccagagtgg agcagtggtt actactggat tgaccccaac
4021 caaggatgca ctatggaagc catcaaagta tactgtgatt tccctaccgg cgaaacctgt
4081 atccgggccc aacctgaaaa catcccagcc aagaactggt ataggagctc caaggacaag
4141 aaacacgtct ggctaggaga aactatcaat gctggcagcc agtttgaata taatgttgaa
4201 ggagtgactt ccaaggaaat ggctacccaa cttgccttca tgcgcctgct ggccaactat
4261 gcctctcaga acatcaccta ccactgcaag aacagcattg catacatgga tgaggagact
4321 ggcaacctga aaaaggctgt cattctacag ggctctaatg atgttgaact tgttgctgag
4381 ggcaacagca ggttcactta cactgttctt gtagatggct gctctaaaaa gacaaatgaa
4441 tggggaaaga caatcattga atacaaaaca aataagccat cacgcctgcc cttccttgat
4501 attgcacctt ggacatcgg tggtgctgac catgaattct ttgtggacat tggcccagtc
4561 tgtttcaaat aaatgaactc aatctaaatt aaaaaagaaa gaatttgaa aaaactttct
4621 ctttgccatt tcttcttctt cttttttaac tgaaagctga atccttccat ttcttctgca
4681 catctacttg cttaaattgt gggcaaaaga gaaaagaag gattgatcag agcattgtgc
4741 aatacagttt cattaactcc ttccccgct ccccaaaaa tttgaatttt ttttcaaca
4801 ctcttacacc tgttatgaaa aatgtcaacc tttgtaagaa aaccaaaata aaaattgaaa
4861 aataaaaacc ataaacattt gcaccacttg tggcttttga atatcttcca cagagggaag
4921 tttaaaaccc aaacttccaa aggtttaaac tacctcaaaa cactttccca tgagtgtgat
4981 ccacattgtt aggtgctgac ctagacagag atgaactgag gtccttgttt tgttttgttc
5041 ataatacaaa ggtgctaatt aatagtattt cagatacttg aagaatgttg atggtgctag
5101 aagaatttga gaagaaatac tcctgtattg agttgtatcg tgtgtgttat tttttaaaaa
5161 atttgattta gcattcatat tttccatctt attccaatt aaaagtatgc agattatttg
5221 cccaaagttg tcctcttctt cagattcagc atttgttctt tgccagtctc attttcatct
5281 tcttccatgg ttccacagaa gctttgtttc ttgggcaagc agaaaaatta aattgtacct
5341 attttgtata tgtgagatgt ttaaataaat tgtgaaaaaa atgaaataaa gcatgtttgg
5401 ttttccaaaa gaacatat
```

SEQ Id NO:45

```
  1 cagaccacag gaatacctaa tgcctttttt ctcttcctgt ctttgtccct cacactacag
 61 caggcccctc ccttccctct tcaacctcat cctccctccc cacaggccca gagaaccagt
121 tgggctttgt tctcctgcag gctatggttc atcatgcaaa tagctcctgt gtcagaaatg
181 cttttggct tcaaataaca gaaaagctaa caccagcttt atcaataata atatcggtgg
241 tttacttaag gtgtccagag atggtggaga acaggattgg tttcctcctc aatgtcaagg
301 actcaaagac tctttctgtg gtagggccac atcctaaacc ctgtatcctg tgattattta
361 cctgacaggg caaaagagat tttgcagatg caattaaggt taaggacctt gacgtgggaa
421 gattgtgatt atttacctga cagggcaaaa gagattttgc agatgcaatt aaggttaagg
481 accttgacgt gggaagatta ttctggatta tctaggtggg cgcaatttga tcacatgggt
```

FIG. 10 A-39

```
 541 ccccagaagt ggagaacctt tcccacctgt agaaagccag agagctggca cctgagaagg
 601 acagaactgt cactgcagga tttgaagatg aaggggccca tgagccaagg aatgccagtg
 661 acctatagag gctaaaaaac agcaaggaaa tggactctcc ccagagcctc cagaggaatg
 721 cagccctgtt gatcacatga tcaccagatg gctgcccag agccaaatgt cgcttcctga
 781 gcaccatact caaaggcagg ggaagtggat ggagggcagg agctccattc ttgtttgcca
 841 ctctccttt gtcaattggg aaaaaattcc agaaactctg ggagccctcc ccttacattt
 901 cctgggtcat ggggccagcc ctagctgctg gagggactga gaactgctgt tgagcagttt
 961 acctgacggc atctgccatg gcttggcagg aactctggct ttgggagaga gcagcagcaa
1021 ggtattcaag caccacctcc acccagcccc tcccacattt cactcaggac tgagtaaagg
1081 agacactcag atgctactca gatgctggct tcagctaagt attttgcaaa gcctctcgtg
1141 ttcttacaag tttgtggcta tcatgacaaa atggagcagc ctactatatc tacatataca
1201 actatggggg acctagtttt atctcattta ccacaatgtt ttcaatcatt ttttggatga
1261 cataattttt agcctcttct ctaaatgctt cctcaagctt tccttgcctt ccagccactg
1321 caaatgactt gcagtttccc ctacatggca cctgaccctt gtgcctccct ccctctgccc
1381 atggcccaga agcccttc ctgtgccctc tggcttcctg ataaactcct atcatcttca
1441 agagccagtt cccatgccag ctctcccaa gtgctccact gaggcttccg taacacctct
1501 gttcccacat cgggttgact gtctttgttt tgtcattgct tgctctggct gtgtctccct
1561 cattagactg ggatgccttc aaggtaggga ccctatctgg gtcagcttgg caccccaaag
1621 cgtaccacag cacctgattc tgaggaggct ctcagtagat atctgttgag taaccagaat
1681 gtagggtggt cctgatggtt tctgacattg aatagaaaac agctccctat ttgatcttaa
1741 aataatcact ataacctgga catactgtac tagatgctgt ttttgtctga cttctactct
1801 gtcaatctct ttgcacctcc atttgttcat ctgtgaaatg aagaaaatgc tcatggagtt
1861 cagtgaagat taaatgaatg aatataggta gactgcctaa tctggcactt gccacgcagc
1921 tgacttcaat atagtagctc taatattatg gtccttgagg atcttactgt cttatggccc
1981 agaactgcat ttgattaaag aaggctcccc taaaaaaaga gtcatacata ttccatttgt
2041 cctttcagaa ggccgtgaag catttacact ctttaagaca aattcccatc caaaaatagt
2101 taagatttct aaaatatttt gatgctgaaa gaggtgtgct tcagttgggt ggcaaatttg
2161 cttctatgga agattttaa tacaggttgt ttctattta cttttctgg ctgaaaggat
2221 tttacattta ttcaaagtca aagggaaaa gaaatccaag aactacagaa gagcagttga
2281 agtgatttat gcttgatttc taaatgcaac ttatgtttat acataattta aaactcaaag
2341 aaagcatgct tatacaatca tgtgcaactt taaactttaa gaactctgga tgaatacatg
2401 gtggcaacag tccatgacac ctgaaaacat catttgtgga gtggcgtaga gttcagtgtt
2461 cgcagtcgca tattacaacc atgtttcaca cagccctgct cggtttgatt ttctccacgt
2521 ggttgataat tgtcttcagt tgctgctaag tgattttgca aatttc SEQ ID NO:46
   1 gtccccgcgc cagagacgca gccgcgctcc caccacccac acccaccgcg ccctcgttcg
  61 cctcttctcc gggagccagt ccgcgccacc gccgccgccc aggccatcgc cacccctccgc
 121 agccatgtcc accaggtccg tgtcctcgtc ctcctaccgc aggatgttcg gcggcccggg
 181 caccgcgagc cggccgagct ccagccggag ctacgtgact acgtccaccc gcacctacag
 241 cctgggcagc gcgctgcgcc ccagccaccag ccgcagcctc tacgcctcgt ccccgggcgg
 301 cgtgtatgcc acgcgctcct ctgccgtgcg cctgcggagc agcgtgcccg gggtgcggct
 361 cctgcaggac tcggtggact tctcgctggc cgacgccatc aacaccgagt tcaagaacac
 421 ccgcaccaac gagaaggtgg agctgcagga gctgaatgac cgcttcgcca actacatcga
 481 caaggtgcgc ttcctggagc agcagaataa gatcctgctg gccgagctcg agcagctcaa
 541 gggccaaggc aagtcgcgcc tgggggacct tacgaggag gagatgcggg agctgcgccg
 601 gcaggtggac cagctaacca acgacaaagc ccgcgtcgag gtggagcgcg caacctggc
 661 cgaggacatc atgcgcctcc gggagaaatt gcaggaggag atgcttcaga gagaggaagc
 721 cgaaaacacc ctgcaatctt tcagacagga tgttgacaat gcgtctctgg cacgtcttga
 781 ccttgaacgc aaagtggaat ctttgcaaga agagattgcc ttttgaaga aactccacga
 841 agaggaaatc caggagctgc aggctcagat tcaggaacag catgtccaaa tcgatgtgga
```

FIG. 10 A-40

```
 901 tgtttccaag cctgacctca cggctgccct gcgtgacgta cgtcagcaat atgaaagtgt
 961 ggctgccaag aacctgcagg aggcagaaga atggtacaaa tccaagtttg ctgacctctc
1021 tgaggctgcc aaccggaaca atgacgccct gcgccaggca aagcaggagt ccactgagta
1081 ccggagacag gtgcagtccc tcacctgtga agtggatgcc cttaaaggaa ccaatgagtc
1141 cctggaacgc cagatgcgtg aaatggaaga gaactttgcc gttgaagctg ctaactacca
1201 agacactatt ggccgcctgc aggatgagat tcagaatatg aaggaggaaa tggctcgtca
1261 ccttcgtgaa taccaagacc tgctcaatgt taagatggcc cttgacattg agattgccac
1321 ctacaggaag ctgctggaag gcgaggagag caggatttct ctgcctcttc caaactttc
1381 ctccctgaac ctgagggaaa ctaatctgga ttcactccct ctggttgata cccactcaaa
1441 aaggacactt ctgattaaga cggttgaaac tagagatgga caggttatca cgaaacttc
1501 tcagcatcac gatgaccttg aataaaaatt gcacacactc agtgcagcaa tatattacca
1561 gcaagaataa aaagaaatc catatcttaa agaaacagct ttcaagtgcc tttctgcagt
1621 ttttcaggag cgcaagatag atttggaata ggaataagct ctagttctta acaaccgaca
1681 ctcctacaag atttagaaaa aagtttacaa cataatctag tttacagaaa aatcttgtgc
1741 tagaatactt tttaaaaggt attttgaata ccattaaaac tgcttttttt tttccagcaa
1801 gtatccaacc aacttggttc tgcttcaata aatctttgga aaaactc
```

SEQ ID NO:47

```
   1 ggccagccga atccaagccg tgtgtactgc gtgctcagca ctgcccgaca gtcctagcta
  61 aacttcgcca actccgctgc ctttgccgcc accatgccca aaacgatcag tgtgcgtgtg
 121 accaccatgg atgcagagct ggagtttgcc atccagccca acaccaccgg gaagcagcta
 181 tttgaccagg tggtgaaaac tattggcttg agggaagttt ggttctttgg tctgcagtac
 241 caggacacta aaggtttctc cacctggctg aaactcaata agaaggtgac tgcccaggat
 301 gtgcggaagg aaagccccct gctctttaag ttccgtgcca agttctaccc tgaggatgtg
 361 tccgaggaat tgattcagga catcactcag cgcctgttct ttctgcaagt gaaagagggc
 421 attctcaatg atgatattta ctgcccgcct gagaccgctg tgctgctggc ctcgtatgct
 481 gtccagtcta agtatggcga cttcaataag gaagtgcata agtctggcta cctggccgga
 541 gacaagttgc tcccgcagag agtcctggaa cagcacaaac tcaacaagga ccagtgggag
 601 gagcggatcc aggtgtggca tgaggaacac cgtggcatgc tcagggagga tgctgtcctg
 661 gaatatctga agattgctca agatctggta tgaactactt cagcatcaag
 721 aacaagaaag gctcagagct gtggctgggg gtggatgccc tgggtctcaa catctctatgag
 781 cagaatgaca gactaactcc caagataggc ttccctggaa gtgaaatcag gaacatctct
 841 ttcaatgata gaaatttgt catcaagccc attgacaaaa agccccgga cttcgtcttc
 901 tatgctcccc ggctgcggat taacaagcgg atcttggcct tgtgcatggg gaaccatgaa
 961 ctatacatgc gccgtcgcaa gcctgatacc attgaggtgc agcagatgaa ggcacaggcc
1021 cgggaggaga agcaccagaa gcagatggag cgtgctatgc tggaaaatga aagaagaag
1081 cgtgaaatgg cagagaagga gaaagagaag attgaacggg agaaggagga gctgatggag
1141 aggctgaagc agatcgagga acagactaag aagaactgga aagaactgga agaacagacc
1201 cgtagggctc tggaacttga gcaggaacg aagcgtgccc agagcgaggc tgaaaagctg
1261 gccaaggagc gtcaagaagc tgaagaggcc aaggaggcct tgctgcaggc ctcccgggac
1321 cagaaaaaga ctcaggaaca gctggccttg gaaatggcag agctgacagc tcgaatctcc
1381 cagctggaga tggcccgaca gaaggaggag agtaggctg tgggtggca gcagaaggcc
1441 cagatggtac aggaagactt ggagaagacc cgtgctgagc tgaagactgc catgagtaca
1501 cctcatgtgg cagagcctgc tgagaatgag caggatgagc aggatgagaa tggggcagag
1561 gctagtgctg acctacgggc tgatgctatg gccaaggacc gcagtgagga ggaacgtacc
1621 actgaggcag agaagaatga gcgtgtgcag aagcacctga aggccctcac ttcggagctg
1681 gccaatgcca gagtgagtc caagaagact gccaatgaca tgatccatgc tgagaacatg
1741 cgactgggcc gagacaaata caagaccctg cgccagatcc ggcagggcaa caccaagcag
1801 cgcattgacg aatttgagtc tatgtaatgg gcacccagcc tctagggacc cctcctcct
1861 ttttccttgt ccccacactc ctacacctaa ctcacctaac tcatactgtg ctggagccac
1921 taactagagc agccctggag tcatgccaag catttaatgt agccatggga ccaaacctag
```

FIG. 10 A-41

```
1981 cccctttagcc cccacccact tccctgggca aatgaatggc tcactatggt gccaatggaa
2041 cctcctttct cttctctgtt ccattgaatc tgtatggcta gaatatccta cttctccagc
2101 ctagaggtac tttccacttg attttgcaaa tgcccttaca cttactgttg tcctatggga
2161 gtcaagtgtg gagtaggttg gaagctagct cccctcctct ccctaccac tgtcttcttc
2221 agggtcctga gatttacacg gttggagtgt tatgcggtct agggaatgag acaggaccta
2281 ggatatcttc tccaggatgt caactgacct aaaatttgcc ctcccatccc gtttagagtt
2341 atttaggctt tgtaacgatt gggggataaa aagatgttca gtcattttg tttctacctc
2401 ccagatcgga tctgttgcaa actcagcctc aataagcctt gtcgttgact ttagggactc
2461 aatttctccc cagggtggat gggggaaatg gtgccttcaa gaccttcacc aaacatacta
2521 gaagggcatt ggccattcta ttgtggcaag gctgagtaga agatcctacc ccaattcctt
2581 gtaggagtat aggccggtct aaagtgagct ctatgggcag atctaccccct tacttattat
2641 tccagatctg cagtcacttc gtgggatctg cccctccctg cttcaatacc caaatcctct
2701 ccagctataa cagtagggat gagtacccaa aagctcagcc agccccatca ggactcttgt
2761 gaaaagagag gatatgttca cacctagcgt cagtattttc cctgctaggg gttttaggtc
2821 tcttcccctc tcagagctac ttgggccata gctcctgctc cacagccatc ccagccttgg
2881 catctagagc ttgatgccag taggctcaac tagggagtga gtgcaaaaag ctgagtatgg
2941 tgagagaagc ctgtgccctg atccaagttt actcaaccct ctcaggtgac caaaatcccc
3001 ttctcatcac tcccctccaa agaggtgact gggccctgcc tctgtttgac aaacctctaa
3061 cccaggtctt gacaccagct gttctgtccc ttggagctgt aaaccagaga gctgctgggg
3121 attctggcct agtcccttcc acaccccac ccctgctct caaccagga gcatccacct
3181 ccttctctgt ctcatgtgtg ctcttcttct ttctacagta ttatgtactc tactgatatc
3241 taaatattga tttctgcctt ccttgctaat gcaccattag aagatattag tcttggggca
3301 ggatgatttt ggcctcatta ctttaccacc cccacacctg gaaagcatat actatattac
3361 aaaatgacat tttgccaaaa ttattaatat aagaagcttt cagtattagt gatgtcatct
3421 gtcactatag gtcatacaat ccattcttaa agtacttgtt atttgttttt attattactg
3481 tttgtcttct ccccagggtt cagtcctcaa ggggccatcc tgtcccacca tgcagtgccc
3541 ctagcttaga gcctccctca attcccctg gccaccaccc ccactctgt gcctgacctt
3601 gaggagtctt gtgtgcattg ctgtgaatta gctcacttgg tgatatgtcc tatattggct
3661 aaattgaaac ctggaattgt ggggcaatct attaatagct gccttaaagt cagtaactta
3721 cccttaggga ggctgggga aaaggttaga ttttgtattc aggggttttt tgtgtacttt
3781 ttgggtttt taaaaattgt ttttggaggg gtttatgctc aatccatgtt ctatttcagt
3841 gccaataaaa tttaggaaga cttc
```

SEQ ID NO:48
```
  1 ggtgtgcccg gagaggctga gcagcctgcg cctgagctgg tggaggtgga agtgggcagc
 61 acagcccttc tgaagtgcgg cctctcccag tccaaggca acctcagcca tgtcgactgg
121 ttttctgtcc acaaggagaa gcggacgctc atcttccgtg tgcgccaggg ccagggccag
181 agcgaacctg gggagtacga gcagcctgcc agcctccagg acagaggggc tactctggcc
241 ctgactcaag tcacccccca agacgagcgc atcttcttgt gccagggcaa gcgccctcgg
301 tcccaggagt accgcatcca gctccgcgtc tacaaagctc cggaggagcc aaacatccag
361 gtcaaccccc tgggcatccc tgtgaacagt aaggagcctg aggaggtcgc tacctgtgta
421 gggaggaacg ggtaccccat tcctcaagtc atctggtaca agaatggcc gcctctgaag
481 gaggagaaga accgggtcca cattcagtcg tcccagactg tggagtcgag tggtttgtac
541 accttgcaga gtattctgaa ggcacagctg gttaaagaag acaaagatgc ccagttttac
601 tgtgagctca actaccggct gcccagtggg aaccacatga aggagtccag ggaagtcacc
661 gtccctgttt tctacccgac agaaaaagtg tggctggaag tggagcccgt gggaatgctg
721 aaggaagggg accgcgtgga aatcaggtgt gttggctgatg gcaaccctcc accacacttc
781 agcatcagca gcagaaccc cagcaccagg gaggcagagg aagagacaac caacgacaac
841 ggggtcctgg tgctggagcc tgcccggaag gaacacagtg ggcgctatga atgtcaggc
901 ctggacttgg acaccatgat atcgctgctg agtgaaccac aggaactact ggtgaactat
```

FIG. 10 A-42

```
 961 gtgtctgacg tccgagtgag tcccgcagca cactgagaga caggaaggca gcagcctcac
1021 cctgacctgt gaggcagaga gtagccagga cctcgagttc cagtggctga gagaagagac
1081 aggccaggtg ctggaaaggg ggcctgtgct tcagttgcat gacctgaaac gggaggcagg
1141 aggcggctat cgctgcgtgg cgtctgtgcc cagcataccc ggcctgaacc gcacacagct
1201 ggtcaacgtg gccattttg gccccccttg gatggcattc aaggagagga aggtgtgggt
1261 gaaagagaat atggtgttga atctgtcttg tgaagcgtca gggcacccc ggcccaccat
1321 ctcctggaac gtcaacggca cggcaagtga acaagaccaa gatccacagc gagtcctgag
1381 caccctgaat gtcctcgtga ccccggagct gttggagaca ggtgttgaat gcacggcctc
1441 caacgacctg ggcaaaaaca ccagcatcct cttcctggag ctggtcaatt taaccaccct
1501 cacaccagac tccaacacaa ccactggcct cagcacttcc actgccagtc ctcataccag
1561 agccaacagc acctccacag agaaaagct gccggagccg gagagccggg gcgtggtcat
1621 cgtggctgtg attgtgtgca tcctggtcct ggcggtgctg ggcgctgtcc tctatttcct
1681 ctataagaag ggcaagctgc cgtgcaggcg ctcagggaag caggagatca cgctgccccc
1741 gtctcgtaag agcgaacttg tagttgaagt taagtcagat aagctcccag aagagatggg
1801 cctcctgcag ggcagcagcg gtgacaagag ggctccggga gaccagggag agaaatacat
1861 cgatctgagg cattagcccc gaatcacttc agctcccttc cctgcctgga ccattcccag
1921 ctccctgctc actcttctct cagccaaagc ctccaaaggg actagagaga agcctcctgc
1981 tcccctcgcc tgcacacccc ctttcagagg gccactgggt taggacctga ggacctcact
2041 tggccctgca aggcccgctt ttcagggacc agtccaccac catctccacg ttgagtgaag
2101 ctcatcccaa gcaaggagcc ccagtctccc gagcgggtag gagagtttct tgtagaacgt
2161 gtttttcttt tacacacatt atggctgtaa ataccctggct cctgccagca gctgagctgg
2221 gtagcctctc tgagctggga ttacaggtgt gagccactgc gcccagccaa
```

SEQ ID NO:49

```
   1 caaacttggt ggcaacttgc ctcccggtgc gggcgtctct cccccaccgt ctcaacatgc
  61 ttaggggtcc ggggcccggg ctgctgctgc tggccgtcct gtgcctgggg acagcggtgc
 121 cctccacggg agcctcgaag agcaagaggc aggctcagca aatggttcag ccccagtccc
 181 cggtggctgt cagtcaaagc aagcccggtt gttatgacaa tggaaaacac tatcagataa
 241 atcaacagtg ggagcggacc tacctaggca atgcgttggt ttgtacttgt tatggaggaa
 301 gccgaggttt taactgcgag agtaaacctg aagctgaaga gacttgcttt gacaagtaca
 361 ctgggaacac ttaccgagtg ggtgacactt atgagcgtcc taaagactcc atgatctggg
 421 actgtacctg catcggggct gggcgaggga gaataagctg taccatcgca aaccgctgcc
 481 atgaagggg tcagtcctac aagattggtg acacctggag gagaccacat gagactggtg
 541 gttacatgtt agagtgtgtg tgtcttggta atggaaaagg agaatggacc tgcaagccca
 601 tagctgagaa gtgttttgat catgctgctg ggacttccta tgtggtcgga gaaacgtggg
 661 agaagcccta ccaaggctgg atgatggtag attgtacttg cctgggagaa ggcagcggac
 721 gcatcacttg cacttctaga aatagatgca acgatcagga cacaaggaca tcctatagaa
 781 ttggagacac ctggagcaag aaggataatc gaggaaacct gctccagtgc atctgcacag
 841 gcaacggccg aggagagtgg aagtgtgaga ggcacacctc tgtgcagacc acatcgagcg
 901 gatctgggcc cttcaccgat gttcgtgcag ctgtttacca accgcagcct cacccccagc
 961 ctcctcccta tggccactgt gtcacagaca gtggtgtggt ctactctgtg gggatgcagt
1021 ggctgaagac acaaggaaat aagcaaatgc tttgcacgtg cctgggcaac ggagtcagct
1081 gccaagagac agctgtaacc cagacttacg gtggcaactc aaatggagag ccatgtgtct
1141 taccattcac ctacaatggc aggacgtgca gcacaacttc gaattatgag caggaccaga
1201 aatactcttt ctgcacagac cacactgttt tggttcagac tcgaggagga aattccaatg
1261 gtgccttgtg ccacttcccc ttcctataca caaccacaa ttacactgat tgcacttctg
1321 agggcagaag agacaacatg aagtggtgtg ggaccacaca gaactatgat gccgaccaga
1381 agtttgggtt ctgccccatg gctgcccacg aggaaatctg cacaaccaat gaagggtca
1441 tgtaccgcat tggagatcag tgggataagc agcatgacat gggtcacatg atgaggtgca
1501 cgtgtgttgg gaatggtcgt ggggaatgga catgcattgc ctactcgcag cttcgagatc
1561 agtgcattgt tgatgacatc acttacaatg tgaacgacac attccacaag cgtcatgaag
```

FIG. 10 A-43

```
1621 agggcacat gctgaactgt acatgcttcg gtcagggtcg gggcaggtgg aagtgtgatc
1681 ccgtcgacca atgccaggat tcagagactg ggacgtttta tcaaattgga gattcatggg
1741 agaagtatgt gcatggtgtc agataccagt gctactgcta tggccgtggc attggggagt
1801 ggcattgcca acctttacag acctatccaa gctcaagtgg tcctgtcgaa gtatttatca
1861 ctgagactcc gagtcagccc aactccacc ccatccagtg gaatgcacca cagccatctc
1921 acatttccaa gtacattctc aggtggagac ctgtgagtat cccacccaga aaccttggat
1981 actgagtctc ctaatcttat caattctgat ggtttctttt tttcccagct tttgagccaa
2041 caactctgat taactattcc tatagcattt actatatttg tttagtgaac aaacaatatg
2101 tggtcaatta aattgacttg tagactg
```

SEQ ID NO:50
```
   1 acccccgcac ccagctccgc aggaccggcg ggcgcgcgcg ggctctggag gccacgggca
  61 tgatgcttcg ggtcctggtg ggggctgtcc tcctgccat gctactggct gccccaccac
 121 ccatcaacaa gctggcactg ttcccagata agagtgcctg gtgcgaagcc aagaacatca
 181 cccagatcgt gggccacagc ggctgtgagg ccaagtccat ccagaacagg gcgtgcctag
 241 gacagtgctt cagctacagc gtccccaaca ccttcccaca gtccacagag tccctggttc
 301 actgtgactc ctgcatgcca gccagtcca tgtgggagat tgtgacgctg gagtgcccgg
 361 gccacgagga ggtgcccagg gtggacaagc tggtggagaa gatcctgcac tgtagctgcc
 421 aggcctgcgg caaggagcct agtcacgagg ggctgagcgt ctatgtgcag ggcgaggacg
 481 ggccgggatc ccagcccggc acccaccctc accccatcc ccacccat cctggcgggc
 541 agaccctga gcccgaggac cccctgggg cccccacac agaggaagag ggggctgagg
 601 actgaggccc cccaactct tcctcccctc tcatccccct gtggaatgtt gggtctcact
 661 ctctggggaa gtcaggggag aagctgaagc cccccctttgg cactggatgg acttggcttc
 721 agactcggac ttgaatgctg cccggttgcc atggagatct gaaggggcgg ggttagagcc
 781 aagctgcaca atttaatata ttcaagagtg ggggaggaa gcagaggtct tcagggctct
 841 ttttttgggg ggggtggtct cttcctgtct ggcttctaga gatgtgcctg tgggaggggg
 901 aggaagttgg ctgagccatt gagtgctggg aggccatc caagatggca tgaatcgggc
 961 taaggtccct gggggtgcag atggtactgc tgaggtcccg ggcttagtgt gagcatcttg
1021 ccagcctcag gcttgaggga gggctgggct agaaagacca ctggcagaaa caggaggctc
1081 cggcccacag gtttccccaa ggcctctcac cccacttccc atctccaggg aagcgtcgcc
1141 ccagtggcac tgaagtggcc ctccctcagc ggagggggttt gggagtcagg cctgggcagg
1201 accctgctga ctcgtggcgc gggagctggg agccaggctc tccgggcctt tctctggctt
1261 ccttggcttg cctggtgggg aaggggagg aggggaagaa ggaaagggaa gagtcttcca
1321 aggccagaag gaggggaca accccccaag accatccctg aagacgagca tccccctcct
1381 ctccctgtta gaaatgttag tgcccccgcac tgtgcccccaa gttctaggcc ccccagaaag
1441 ctgccagagc cggccgcctt ctcccctctc caggggatgc tcttttgtaaa tatccggatg
1501 gtgtgggagt gaggggttac ctccctcgcc ccaaggttcc agaggcccta ggcgggatgg
1561 gctcgctgaa cctcgaggaa ctccaggacg aggaggacat gggacttgcg tggacagtca
1621 gggttcactt gggctctctc tagctcccca attctgcctg cctcctccct cccagctgca
1681 ctttaaccct agaaggtggg gacctggggg gagggacagg gcaggcgggc ccatgaagaa
1741 agcccctcgt tgcccagcac tgtctgcgtc tgctcttctg tgcccagggt ggctgccagc
1801 ccactgcctc ctgcctgggg tggcctggcc ctcctggctg ttgcgacgcg ggcttctgga
1861 gcttgtcacc attggacagt ctccctgatg gaccctcagt cttctcatga ataaattc
```

SEQ ID NO:51
```
   1 atccgtcccg gataagaccc gctgtctggc cctgagtagg gtgtgacctc cgcagccgca
  61 gaggaggagc gcagcccggc ctcgaagaac ttctgcttgg gtggctgaac tctgatcttg
 121 acctagagtc atggccatgg caaccaaagg aggtactgtc aaagctgctt caggattcaa
 181 tgccatggaa gatgcccaga cctgaggaa ggccatgaaa gggctcggca ccgatgaaga
 241 cgccattatt agcgtccttg cctaccgcaa caccgcccag cgccaggaga tcaggacagc
```

FIG. 10 A-44

```
 301 ctacaagagc accatcggca gggacttgat agacgacctg aagtcagaac tgagtggcaa
 361 cttcgagcag gtgattgtgg ggatgatgac gcccacggtg ctgtatgacg tgcaagagct
 421 gcgaagggcc atgaaggagc ccggcactga tgagggctgc ctaattgaga tcctggcctc
 481 ccggacccct gaggagatcc ggcgcataag ccaaacctac cagcagcaat atggacggag
 541 ccttgaagat gacattcgct ctgacacatc gttcatgttc cagcgagtgc tggtgtctct
 601 gtcagctggt gggagggatg aaggaaatta tctgacgat gctctcgtga gacaggatgc
 661 ccaggacctg tatgaggctg agagaagaa atgggggaca gatgaggtga aatttctaac
 721 tgttctctgt tcccggaacc gaaatcacct gttgcatggt ttgatgaata caaaaggata
 781 tcacagaagg atattgaaca gagtattaaa tctgaaacat ctggtagctt tgaagatgct
 841 ctgctggcta tagtaaagtg catgaggaac aaatctgcat attttgctga aaagctctat
 901 aaatcgatga agggcttggg caccgatgat aacacccctca tcagagtgat ggtttctcga
 961 gcagaaattg acatgttgga tatccgggca cacttcaaga gactctatgg aaagtctctg
1021 tactcgttca tcaagggtga cacatctgga gactacagga agtactgct tgttctctgt
1081 ggaggagatg attaaaataa aaatcccaga aggacaggag gattctcaac actttgaatt
1141 ttttttaactt cattttttcta cactgctatt atcattatct cagaatgctt atttccaatt
1201 aaaacgcccta cagctgcctc ct
```

SEQ ID NO:52
```
   1 tggggcagcc gcgcccgcgg tgttttccgc ccggcgctgg cggctgctgc gcccgcggct
  61 ccccagtgcc ccgagtgccc cgcgggcccc gcgagcggga gtgggaccca gcccctaggc
 121 agaacccagg cgccgcgccc gggacgcccg cggagagagc cactcccgcc cacgtccat
 181 ttcgccccctc gcgtccggag tcctcgtggc cagatctaac catgagctac cctggctatc
 241 ccccgcccccc aggtggctac ccaccagctg caccaggtgg tggtccctgg ggaggtgctg
 301 cctaccctcc tccgcccagc atgccccca tcgggctgga taacgtggcc acctatgcgg
 361 ggcagttcaa ccaggactat ctctcgggaa tggcggccaa catgtctggg acatttggag
 421 gagccaacat gccaacctg taccctgggg cccctggggc tggctaccca ccagtgcccc
 481 ctggcgagctt tgggcagccc cctctcgtc agcagcctgt tcctccctat gggatgtatc
 541 caccccagg aggaaaccca ccctccagga tgccctcata tccgccatac ccaggggccc
 601 ctgtgccggg ccagcccatg ccacccccg acagcagcc cccaggggcc tacccgtggc
 661 agccaccagt gacctaccct ggtcagcctc cagtgccact ccctgggcag cagcagccag
 721 tgccgagcta cccaggatac ccggggtctg ggactgtcac ccccgctgtg ccccaaccc
 781 agtttggaag ccgaggcacc atcactgatg ctcccggctt tgacccctg cgagatgccg
 841 aggtcctgcg gaaggccatg aaaggcttcg ggacggatga gcaggccatc attgactgcc
 901 tggggagtcg ctccaacaag cagcggcagc agatcctact ttccttcaag acggcttacg
 961 gcaaggattt gatcaaagat ctgaaatctg aactgtcagg aaactttgag aagacaatct
1021 tggctctgat gaagaccca gtcctctttg acatttatga gataaaggaa gccatcaagg
1081 gggttggcac tgatgaagcc tgcctgattg agatcctcgc ttcccgcagc aatgagcaca
1141 tccgagaatt aaacagagcc tacaaagcag aattcaaaaa gaccctggaa gaggccattc
1201 gaagcgacac atcagggcac ttccagcggc tcctcatctc tctctctcag ggaaaccgtg
1261 atgaaagcac aaacgtggac atgtcactcg cccagagaga tgcccaggag ctgtatgcgg
1321 ccggggagaa ccgcctggga acagacgagt ccaagttcaa tgcggttctg tgctcccgga
1381 gccgggccca cctggtagca gttttcaatg agtaccagag aatgacaggc cgggacattg
1441 agaagagcat ctgccgggag atgtccgggg acctggagga gggcatgctg gccgtggtga
1501 aatgtctcaa gaatacccca gccttctttg cggagaggct caatcaaggcc atgaggggg
1561 caggaacaaa ggaccggacc ctgattcgca tcatggtgtc tcgcagcgag accgacctcc
1621 tggacatcag atcagagtat aagcggatgt acggcaagtc gctgtaccac gacatctcgg
1681 gagatacttc aggggattac cggaagattc tgctgaagat ctgtggtggc aatgactgaa
1741 cagtgactgg tggctcactt ctgcccacct gccggcaaca ccagtgccag gaaaaggcca
1801 aaagaatgtc tgtttctaac aaatccacaa atagccccga gattcaccgt cctagagctt
1861 aggcctgtct tccaccccctc ctgacccgta tagtgtgcca caggacctgg gtcggtctag
1921 aactctctca ggatgccttt tctacccat ccctcacagc ctcttgctgc taaaatagat
```

FIG. 10 A-45

```
1981 gtttcattt tctgactcat gcaatcattc cccttttgcct gtggctaaga cttggcttca
2041 tttcgtcatg taattgtata ttttttatttg gaggcatatt ttcttttctt acagtcattg
2101 ccagacagag gcatacaagt ctgtttgctg catacacatt tctggtgagg gcgactgggt
2161 gggtgaagca ccgtgtcctc gctgaggaga gaaagggagg cgtgcctgag aaggtagcct
2221 gtgcatctgt tgagtgtgtc acgagctttg ttactgccaa actcactcct ttttagaaaa
2281 aacaaaaaaa aagggccaga aagtcattcc ttccatcttc cttgcagaaa ccacgagaac
2341 aaagccagtt ccctgtcagt gacagggctt cttgtaattt gtggtatgtg ccttaaacct
2401 gaatgtctgt agccaaaact tgtttccaca ttaagagtca gccagctctg gaatggtctg
2461 gaaatgtc
```

SEQ ID NO:53

```
   1 tagacgcacc ctctgaagat ggtgactccc tcctgagaag ctggacccct tggtaaaaga
  61 caaggccttc tccaagaaga atatgaaagt gttactcaga cttatttgtt tcatagctct
 121 actgatttct tctctggagg ctgataaatg caaggaacgt gaagaaaaaa taattttagt
 181 gtcatctgca aatgaaattg atgttcgtcc ctgtcctctt aacccaaatg aacacaaagg
 241 cactataact tggtataaag atgacagcaa gacacctgta tctacagaac aagcctccag
 301 gattcatcaa cacaaagaga aactttggtt tgttcctgct aaggtggagg attcaggaca
 361 ttactattgc gtggtaagaa attcatctta ctgcctcaga attaaaataa gtgcaaaatt
 421 tgtgggagaat gagcctaact tatgtttataa tgcacaagcc atatttaagc agaaactacc
 481 cgttgcagga gacggaggac ttgtgtgccc ttatatggag tttttttaaaa atgaaaataa
 541 tgagttacct aaattacagt ggtataagga ttgcaaacct ctacttcttg acaatataca
 601 ctttagtgga gtcaaagata ggctcatcgt gatgaatgtg gctgaaaagc atagagggaa
 661 ctatacttgt catgcatcct acacatactt gggcaagcaa tatcctatta cccgggtaat
 721 agaatttatt actctagagg aaaacaaacc cacaaggcct gtgattgtga gcccagctaa
 781 tgagacaatg gaagtagact tgggatccca gatcaatgta atctgtaatg tcaccggcca
 841 gttgagtgac attgcttact ggaagtggaa tgggtcagta attgatgaag atgacccagt
 901 gctaggggaa gactattaca gtgtggaaaa tcctgcaaac aaaagaagga gtaccctcat
 961 cacagtgctt aatatatcgg aaattgaaag tagattttat aaacatccat ttacctgttt
1021 tgccaagaat acacatggta tagatgcagc atatatccag ttaatatatc cagtcactaa
1081 tttccagaag cacatgattg gtatatgtgt cacgttgaca gtcataattg tgtgttctgt
1141 tttcatctat aaaatcttca agattgacat tgtgctttgg tacagggatt cctgctatga
1201 ttttctccca ataaaagctt cagatggaaa gacctatgag gcatatatac tgtatccaaa
1261 gactgttggg gaaggtctca cctctgactg tgatattttt gtgtttaaag tcttgcctga
1321 ggtcttggaa aaacagtgtg gatataagct gttcatttat ggaagggatg actacgttgg
1381 ggaagacatt gttgaggtca ttaatgaaaa cgtaaagaaa agcagaagac tgattatcat
1441 tttagtcaga gaaacatcag gcttcagctg gctgggtggt tcatctgaag agcaaatagc
1501 catgtataat gctcttgttc aggatggaat taaagttgtc ctgctgagc tggagaaaat
1561 ccaagactat gagaaaatgc cagaatcgat taaattcatt aagcagaaac atggggctat
1621 ccgctggtca ggggacttta cacagggacc acagtctgca aagacaaggt tctggaagaa
1681 tgtcaggtac cacatgccag tccagcgacg gtcaccttca tctaaacacc agttactgtc
1741 accagccact aaggagaaac tgcaaagaga ggctcacgtg cctctcgggt agcatggaga
1801 agttgccaag agttctttag gtgcctcctg tcttatggcg ttgcaggcca ggttatgcct
1861 catgctgact tgcagagttc atgaatgta actatatcat cctttatccc tgaggtcacc
1921 tggaatcaga ttattaaggg aataagccat gacgtcaata gcagcccagg gcacttcaga
1981 gtagagggct tgggaagatc ttttaaaaag gcagtaggcc cggtgtggtg gctcacgcct
2041 ataatcccag cactttggga ggctgaagtg ggtggatcac cagaggtcag gagttcgaga
2101 ccagcccagc caacatggca aaacccccatc tctactaaaa atacaaaaat gagctaggca
2161 tggtggcaca cgcctgtaat cccagctaca cctgaggctg aggcaggaga attgcttgaa
2221 ccggggagac ggaggttgca gtgagccgag tttgggccac tgcactctag cctggcaaca
```

FIG. 10 A-46

```
2281 gagcaagact ccgtctcaaa aaaagggcaa taaatgccct ctctgaatgt ttgaactgcc
2341 aagaaaaggc atggagacag cgaactagaa gaaagggcaa gaaggaaata gccaccgtct
2401 acagatggct tagttaagtc atccacagcc caagggcggg gctatgcctt gtctggggac
2461 cctgtagagt cactgaccct ggagcggctc tcctgagagg tgctgcaggc aaagtgagac
2521 tgacacctca ctgaggaagg gagacatatt cttggagaac tttccatctg cttgtatttt
2581 ccatacacat ccccagccag aagttagtgt ccgaagaccg aatttttattt tacagagctt
2641 gaaaactcac ttcaatgaac aaagggattc tccaggattc caaagttttg aagtcatctt
2701 agctttccac aggagggaga gaacttaaaa aagcaacagt agcagggaat tgatccactt
2761 cttaatgctt tcctccctgg catgaccatc ctgtcctttg ttattatcct gcatttacg
2821 tctttggagg aacagctccc tagtggcttc ctccgtctgc aatgtccctt gcacagccca
2881 cacatgaacc atccttccca tgatgccgct cttctgtcat cccgctcctg ctgaaacacc
2941 tcccaggggc tccacctgtt caggagctga agcccatgct ttcccaccag catgtcactc
3001 ccagaccacc tccctgccct gtcctccagc ttccoctcgc tgtcctgctg tgtgaattcc
3061 caggttggcc tggtggccat gtcgcctgcc cccagcactc ctctgtctct gctcttgcct
3121 gcacccttcc tcctcctttg cctaggaggc cttctcgcat tttctctagc tgatcagaat
3181 tttaccaaaa ttcagaacat cctccaattc cacagtctct gggagacttt ccctaagagg
3241 cgacttcctc tccagccttc tctctctggt caggcccact gcagagatgg tggtgagcac
3301 atctgggagg ctggtctccc tccagctgga attgctgctc tctgagggag aggctgtggt
3361 ggctgtctct gtccctcact gccttccagg agcaatttgc acatgtaaca tagatttatg
3421 taatgcttta tgtttaaaaa cattccccaa ttatcttatt taattttttgc aattattcta
3481 attttatata tagagaaagt gacctatttt ttaaaaaaat cacactctaa gttctattga
3541 acctaggact tgagcctcca tttctggctt ctagtctggt gttctgagta cttgatttca
3601 ggtcaataac ggtccccct cactccacac tggcacgttt gtgagaagaa atgacatttt
3661 gctaggaagt gaccgagtct aggaatgctt ttattcaaga caccaaattc caaacttcta
3721 aatgttggaa ttttcaaaaa ttgtgtttag attttatgaa aaactcttct actttcatct
3781 attcttcccc tagaggcaaa catttcttaa aatgtttcat tttcattaaa aatgaaagcc
3841 aaatttatat gccaccgatt gcaggacaca agcacagttt taagagttgt atgaacatgg
3901 agaggacttt tggtttttat atttctcgta tttaatatgg gtgaacacca actttttattt
3961 ggaataataa ttttcctcct aaacaaaaac acattgagtt taagtctctg actcttgcct
4021 ttccacctgc tttctcctgg gcccgctttg cctgcttgaa ggaacagtgc tgttctggag
4081 ctgctgttcc aacagacagg gcctagcttt catttgacac acagactaca gccagaagcc
4141 catggagcag ggatgtcacg tcttgaaaag cctattagat gttttacaaa tttaattttg
4201 cagattattt tagtctgtca tccagaaaat gtgtcagcat gcatagtgct aagaaagcaa
4261 gccaatttgg aaacttaggt tagtgacaaa attggccaga gagtggggt gatgatgacc
4321 aagaattaca agtagaatgc cagctggaat ttaaggaggg acaagaatca atggataagc
4381 gtgggtggag gaagatccaa acagaaaagt gcaaagttat tccccatctt ccaagggttg
4441 aattctggag gaagaagaca cattcctagt tccccgtgaa cttcctttga cttattgtcc
4501 ccactaaaac aaaacaaaaa acttttaatg ccttccacat taattagatt ttcttgcagt
4561 tttttttatgg catttttta aagatgccct aagtgttgaa gaagagtttg caaatgcaac
4621 aaaatattta attaccggtt gttaaaactg gtttagcaca atttatattt tccctctctt
4681 gcctttctta tttgcaataa aaggtattga gccatttttt aaatgacatt tttgataaat
4741 tatgttgta ctagttgatg aaggagtttt ttttaacctg tttatataat tttgcagcag
4801 aagccaaatt ttttgtatat taaagcacca aattcatgta cagcatgcat cacggatcaa
4861 tagactgtac ttattttcca ataaaatttt caaactttgt actgtta SEQ ID NO:54
   1 ccctgcactc tcgctctcct gccccacccc gaggtaaagg gggcgactaa gagaagatgg
  61 tgttgctcac cgcggtcctc ctgctgctgg ccgcctatgc ggggccggcc cagagcctgg
 121 gctccttcgt gcactgcgag ccctgcgacg agaaagccct ctccatgtgc cccccagcc
 181 ccctgggctg cgagctggtc aaggagccgg gctgcggctg ctgcatgacc tgcgccctgg
```

FIG. 10 A-47

```
241 ccgaggggca gtcgtgcggc gtctacaccg agcgctgcgc ccaggggctg cgctgcctcc
301 cccggcagga cgaggagaag ccgctgcacg ccctgctgca cggccgcggg gtttgcctca
361 acgaaaagag ctaccgcgag caagtcaaga tcgagagaga ctcccgtgag cacgaggagc
421 ccaccacctc tgagatggcc gaggagacct actcccccaa gatcttccgg cccaaacaca
481 cccgcatctc cgagctgaag gctgaagcag tgaagaagga ccgcagaaag aagctgaccc
541 agtccaagtt tgtcggggga gccgagaaca ctgcccaccc ccggatcatc tctgcacctg
601 agatgagaca ggagtctgag cagggcccct gccgcagaca catggaggct tccctgcagg
661 agctcaaagc cagcccacgc atggtgcccc gtgctgtgta cctgcccaat tgtgaccgca
721 aaggattcta caagagaaag cagtgcaaac cttcccgtgg ccgcaaacgt ggcatctgct
781 ggtgcgtgga caagtacggg atgaagctgc aggcatgga gtacgttgac ggggactttc
841 agtgccacac cttcgacagc agcaacgttg agtgatgcgt ccccccccaa cctttccctc
901 accccctccc accccagcc ccgactccag ccagcgcctc cctccacccc aggacgccac
961 tcatttcatc tcatttaagg gaaaaatata tatctatcta tttg
```

SEQ ID NO:55

```
  1 cgcagcgggt cctctctatc tagctccagc ctctcgcctg cgccccactc cccgcgtccc
 61 gcgtcctagc cgaccatggc cgggcccctg cgcgccccgc tgctcctgct ggccatcctg
121 gccgtggccc tggccgtgag ccccgcggcc ggctccagtc ccggcaagcc gccgcgccta
181 gtgggaggcc ccatgacgc cagcgtggag gaggagggtg tgcggcgtgc actggacttt
241 gccgtcggcg agtacaacaa agccagcaac gacatgtacc acagccgcgc gctgcaggtg
301 gtgcgcgccc gcaagcagat cgtagctggg gtgaactact tcttggacgt ggagctgggc
361 cgaaccacgt gtaccaagac ccagcccaac ttggacaact gcccttcca tgaccagcca
421 catctgaaaa ggaaagcatt ctgctctttc cagatctacg ctgtgccttg cagggcaca
481 atgaccttgt cgaaatccac ctgtcaggac gcctagggg ctgtaccggg ctggcctgtg
541 cctatcacct cttatgcaca cctcccaccc cctgtattcc caccgtgga ctggtggccc
601 ctgccttggg gaaggtctcc ccatgctgcct gcaccaggag acagacagag aaggcagcag
661 gcggcctttg ttgctcagca aggggctctg ccctccctcc ttccttcttg cttctcatag
721 ccccggtgtg cggtgcatac acccccacct cctgcaataa aatagtagca tc
```

SEQ ID NO:56

```
   1 gaaagatgga tcactccagc tcaaagagaa catgtgggaa tgaaaggaca ggctgggccc
  61 aaaggagaaa aggtgatgc tggggaggag cttcctggcc ctcctgaacc ttctgggcct
 121 gttggaccca cggcaggagc agaagcagag ggctctggcc taggctgggg ctcggacgtc
 181 ggctctggct ctggtgacct ggtgggcagt gagcagctgc tgagaggtcc tccaggaccc
 241 ccagggccac ctggcttacc tgggattcca ggaaaaccag gaactgatgt tttcatggga
 301 cccctggat ctcctggaga ggatggacct gctggtgaac ctgggccccc gggccctgag
 361 ggacagcctg gagttgatgg agccaccggc cttcccggga tgaaggggga gaaggagca
 421 agagggccta atggctcagt tggtgaaaag ggtgaccctg caacagagg cttacctgga
 481 cccccgggga aaagggaca agctggccct cctgggtca tgggacccc agggcctcct
 541 ggaccccctg ggccccagg cctggatgc acaatgggac ttggattcga ggataccgaa
 601 ggctctggaa gcacccagct attgaatgaa cccaaactct ccagaccaac ggctgcaatt
 661 ggtctcaaag gagagaaagg agaccgggga cccaagggag aaaggggga ggatgagcc
 721 agtattgtgg gaccccctgg ccgagaggg ccacctggc acatcaaggt cttgtctaat
 781 tccttgatca atatcaccca tggattcatg aatttctcgg acattcctga gctggtgggg
 841 cctccggggc cggacgggtt gcctgggctg ccaggatttc cagggtccta gaggaccaaa
 901 aggtgacact ggtttacctg gctttccagg actaaaagga gaacagggcg agaagggaga
 961 gccgggtgcc atcctgacag aggacattcc tctggaaagg ctgatgggga aaaagggtga
1021 acctggaatg catggagccc caggaccaat ggggcccaaa ggaccaccag gacataaagg
1081 agaatttggc cttcccgggc gacctggtcg cccaggactg aatggcctca agggtaccaa
```

FIG. 10 A-48

```
1141   aggagatcca ggggtcatta tgcagggccc acctggctta cctggccctc caggcccccc
1201   tgggccacct ggagctgtga ttaacatcaa aggagccatt ttcccaatac ccgtccgacc
1261   acactgcaaa atgccagttg atactgctca tcctgggagt ccagagctca tcacttttca
1321   cggtgttaaa ggagagaaag gatcctgggg tcttcctggc tcaaagggag aaaaaggcga
1381   ccagggagcc cagggaccac caggtcctcc acttgatcta gcttacctga gacactttct
1441   gaacaacttg aaggggggaga atggagacaa ggggttcaaa ggtgaaaaag gagaaaaagg
1501   agacattaat ggcagcttcc ttatgtctgg gcctccaggc ctgcccggaa atccaggccc
1561   ggctggccaa aaaggggaga cagtcgttgg gccccaagga cccccaggtg ctcctggtct
1621   gcctgggcca cctggctttg gaagacctgg tgatcctggg ccaccggggc ccccggggcc
1681   accaggacct ccagctatcc tgggagcagc tgtggcccct ccaggtcccc ctggccctcc
1741   aggacagcca gggcttcccg gatccagaaa cctggtcaca gcattcagca acatggatga
1801   catgctgcag aaagcgcatt tggttataga aggaacattc atctacctga gggacagcac
1861   tgagttttc attcgtgtta gagatggctg gaaaaaatta cagctgggag aactgatccc
1921   cattcctgcc gacagccctc caccccctgc gctttccagc aacccacatc agcttctgcc
1981   tccaccaaac cctatttcaa gtgccaatta tgagaagcct gctctgcatt tggctgctct
2041   gaacatgcca tttttctgggg acattcgagc tgattttcag tgcttcaagc aggccagagc
2101   tgcaggactg ttgtccacct accgagca SEQ ID NO:57
   1   tagaaattgt taatttttaac aatccagagc aggccaacga ggctttgctc tcccgacccg
  61   aactaaaggt ccctcgctcc gtgcgctgct acgacgcggtg tctcctgggg ctccaatgca
 121   gcgagctgtg cccgaggggt tcggaaggcg caagctgggc agcgacatgg ggaacgcgga
 181   gcgggctccg gggtctcgga gctttgggcc agtacccacg ctgctgctgc tcgccgcggc
 241   gctactggcc gtgtcggacg cactcgggcg cccctccgag gaggacgagg agctagtggt
 301   gccggagctg gagcgcgccc cggacacgg gaccacgcgc ctccgcctgc acgcctttga
 361   ccagcagctg gatctggagc tgcggcccga cagcagcttt ttggcgcccg gcttcacgct
 421   ccagaacgtg gggcgcaaat ccgggtccga gacgccgctt ccggaaaccg acctggcgca
 481   ctgcttctac tccggcaccg tgaatggcga tcccagctcg gctgccgccc tcagcctctg
 541   cgagggcgtg cgcggcgcct tctacctgct ggggggaggcg tatttcatcc agccgctgcc
 601   cgccgccagc gagcgcctcg ccaccgccgc ccaggggggag aagccgccgg caccactaca
 661   gttccacctc ctgcggcgga atcggcaggg cgacgtcggc ggcacgtgcg gggtcgtgga
 721   cgacgagccc cggccgactg ggaaagcgga gaccgaagac gaggacgaag ggactgaggg
 781   cgaggacgaa ggggctcagt ggtcgccgca ggacccggca ctgcaaggcg taggacagcc
 841   cacaggaact ggaagcataa gaaagaagcg atttgtgtcc agtcaccgct atgtggaaac
 901   catgcttgtg gcagaccagt cgatggcaga attccacggc agtggtctaa agcattacct
 961   tctcacgttg ttttcggtgg cagccagatt gtacaaacac cccagcattc gtaattcagt
1021   tagcctggtg tgtggtgaaga tcttggtcat ccacgatgaa cagaaggggc cggaagtgac
1081   ctccaatgct gccctcactc tgcggaactt ttgcaactgg cagaagcagc acaacccacc
1141   cagtgaccgg gatgcagagc actatgacac agcaattctt ttcaccagac aggacttgtg
1201   tgggtccag acatgtgata ctcttgggat ggctgatgtt ggaactgtgt gtgatccgag
1261   cagaagctgc tccgtcatag aagatgatgg tttcaaagct gccttcacca cagcccatga
1321   attaggccac gtgtttaaca tgccacatga tgatgcaaag cagtgtgcca gccttaatgg
1381   tgtgaaccag gattcccaca tgatggcgtc aatgctttcc aacctggacc acagccagcc
1441   ttggtctcct tgcagtgcct acatgattac atcatttctg gataatggtc atgggggaatg
1501   tttgatggac aagcctcaga atccatacac gctcccaggc gatctccctg gcacctcgta
1561   cgatgccaac cggcagtgcc agtttacatt tggggaggac tccaaacact gccccgatgc
1621   agccagcaca tgtagcacct tgtggtgtac cggcacctct ggtggggtgc tggtgtgtca
1681   aaccaaacac ttcccgtggg cggatggcac cagctgtgga aagggaaat ggtgtatcaa
1741   cggcaagtgt gtgaacaaaa ccgacagaaa gcatttgat acgcctttc atggaagctg
1801   ggaatgtgg ggccttggg gagactgttc gagaacgtgc ggtggaggag tccagtcacac
1861   gatgagggaa tgtgacaacc cagtcccaaa gaatggaggg aagtactgtg aaggcaaacg
```

FIG. 10 A-49

```
1921 agtgcgctac agatcctgta accttgagga ctgtccagac aataatggaa aaacctttag
1981 agaggaacaa tgtgaagcac acaacgagtt ttcaaaagct tcctttggga gtgggcctgc
2041 ggtggaatgg attcccaagt acgctggcgt ctcaccaaag gacaggtgca agctcatctg
2101 ccaagccaaa ggcattggct acttcttcgt tttgcagccc aaggttgtag atggtactcc
2161 atgtagccca gattccacct ctgtctgtgt gcaaggacag tgtgtaaaag ctggttgtga
2221 tcgcatcata gactccaaaa agaagtttga taaatgtggt gtttgcgggg gaaatggatc
2281 tacttgtaaa aaaatatcag gatcagttac tagtgcaaaa cctggatatc atgatatcat
2341 cacaattcca actggagcca ccaacatcga agtgaaacag cggaaccaga ggggatccag
2401 gaacaatggc agctttcttg ccatcaaagc tgctgatggc acatatattc ttaatggtga
2461 ctacactttg tccaccttag agcaagacat tatgtacaaa ggtgttgtct tgaggtacag
2521 cggctcctct gcggcattgg aaagaattcg cagctttagc cctctcaaag agcccttgac
2581 catccaggtt cttactgtgg gcaatgccct tcgacctaaa attaaataca cctacttcgt
2641 aaagaagaag aaggaatctt tcaatgctat ccccactttt tcagcatggg tcattgaaga
2701 gtggggcgaa tgttctaagt catgtgaatt gggttggcag agaagactgg tagaatgccg
2761 agacattaat ggacagcctg cttccgagtg tgcaaaggaa gtgaagccag ccagcaccag
2821 accttgtgca gaccatccct gccccagtg gcagtgggg gagtggtcat catgttctaa
2881 gacctgtggg aagggttaca aaaaagaag cttgaagtgt ctgtcccatg atggagggt
2941 gttatctcat gagagctgtg atcctttaaa gaaacctaaa catttcatag acttttgcac
3001 aatggcagaa tgcagttaag tggtttaagt ggtgttagct ttgagggcaa ggcaaagtga
3061 ggaagggctg gtgcagggaa agcaagaagg ctggagggat ccagcgtatc ttgccagtaa
3121 ccagtgaggt gtatcagtaa ggtgggatta tgggggtaga tagaaaagga gttgaatcat
3181 cagagtaaac tgccagttgc aaatttgata ggatagttag tgaggattat taacctctga
3241 gcagtgatat agcataataa agccccgggc attattatta ttatttcttt tgttacatct
3301 attacaagtt tagaaaaaac aaagcaattg tcaaaaaaag ttagaactat tacaacccct
3361 gtttcctggt acttatcaaa tacttagtat catgggggtt gggaaatgaa agtaggaga
3421 aaagtgagat tttactaaga cctgttttac tttacctcac taacaatggg gggagaaagg
3481 agtacaaata ggatctttga ccagcactgt ttatggctgc tatgtttca gagaatgttt
3541 atacattatt tctaccgaga attaaaactt cagattgttc aacatgagag aaaggctcag
3601 caacgtgaaa taacgcaaat ggcttcctct ttccttttt ggaccatctc agtctttatt
3661 tgtgtaattc attttgagga aaaacaact ccatgtattt attcaagtgc attaaagtct
3721 acaatggaaa aaagcagtg aagcattaga tgctggtaaa agctagagga gacacaatga
3781 gcttagtacc tccaacttcc tttctttcct accatgtaac cctgctttgg gaatatggat
3841 gtaaagaagt aacttgtgtc tcatgaaaat cagtacaatc acacaaggag gatgaaacgc
3901 cggaacaaaa atgaggtgtg tagaacaggg tcccacaggt ttggggacat tgagatcact
3961 tgtcttgtgg tggggaggct gctgagggat agcaggtcca tctccagcag ctgtccaac
4021 agtcgtatcc tggtgaatgt ctgttcagct cttctgtgag aatatgattt tttccatatg
4081 tatatagtaa aatatgttac tataaattac atgtacttta taagtattgg tttgggtgtt
4141 ccttccaaga aggactatag ttagtaataa atgcctataa taacatattt attttatac
4201 atttatttct aatgaaaaaa actttaaat tatatcgctt ttgtggaagt gcatataaaa
4261 tagagtattt atacaatata tgttactaga aataaagaa cacttttgg SEQ ID NO:58
   1 gggcccgggc gcgcgggagc gggagcggcc gggggagccg gagcgcacca tggaggcggc
  61 ggcaggcggc cgcggctgtt ccagccgca cccggggctg cagaagacgc tggagcagtt
 121 ccacctgagc tccatgagct cgctgggcgg cccggccgct ttctcggcgc gctgggcgca
 181 ggaggcctac aagaaggaga gcgccaagga ggcgggcgcg gccgcggtgc cggcgccggt
 241 gcccgcagcc accgagccgc cgcccgtgct gcacctgccc gccatccagc cgccgccgcc
 301 cgtgctgccc gggcccttct tcatgccgtc cgaccgctcc accgacgct gcgagaccgt
 361 actggaaggc gagaccatct cgtgcttcgt ggtgggaggc gagaagcgcc tgtgtctgcc
 421 gcagattctc aactcggtgc tgcgcgactt ctcgctgcag cagatcaacg cggtgtgcga
 481 cgagctccac atctactgct cgcgctgcac ggccgaccag ctggagatcc tcaaagtcat
```

FIG. 10 A-50

```
 541 gggcatcctg cccttctcgg cgccctcgtg cgggctcatc accaagacgg acgccgagcg
 601 cctgtgcaac gcgctgctct acggcggcgc ctacccgccg ccctgcaaga aggagctggc
 661 cgccagcctg gcgctgggcc tggagctcag cgagcgcagc gtccgcgtgt accacgagtg
 721 cttcggcaag tgtaaggggc tgctggtgcc cgagctctac agcagcccga gcgccgcctg
 781 catccagtgc ctggactgcc gcctcatgta cccgccgcac aagttcgtgg tgcactcgca
 841 caaggccctg gagaaccgga cctgccactg gggcttcgac tcggccaact ggcgggccta
 901 catcctgctg agccaggatt acacgggcaa ggaggagcag gcgcgcctcg gccgctgcct
 961 ggacgacgtg aaggagaaat tcgactatgg caacaagtac aagcggcggg tgccccgggt
1021 ctcctctgag cctccggcct ccataagacc caaaacagat gacacctctt cccagtcccc
1081 cgcgccttcc gaaaaggaca agccgtccag ctggctgcgg accttggccg gctcttccaa
1141 taagagcctg ggctgtgttc accctcgcca gcgcctctct gctttccgac cctggtcccc
1201 cgcagtgtca gcgagtgaga aagagctctc cccacacctc ccggccctca tccgagacag
1261 cttctactcc tacaagagct ttgagacagc cgtggcgccc aacgtggccc tcgcaccgcc
1321 ggcccagcag aaggttgtga gcagccctcc gtgtgccgcc gccgtctccc gggcccccga
1381 gcctctcgcc acttgcaccc agcctcggaa gcggaagctg actgtggaca ccccaggagc
1441 cccagacgcg ctggcgcccg tggctgccc agaggaggac aaggactcgg aggcggaggt
1501 ggaagttgaa agcagggagg aattcacctc ctccttgtcc tcgctctctt cccgtccttt
1561 tacctcatcc agctccgcca aggacctggg ctccccgggt gcgcgtgccc tgccctcggc
1621 cgtccctgat gctgcggccc ctgccgacgc ccccagtggg ctggaggcgg agctggagca
1681 cctgcggcag gcactggagg gcggcctgga caccaaggaa gccaagagaa gttcctgca
1741 tgaggtggtc aagatgcgcg tgaagcagga ggagaagctc agcgcagccc tgcaggccaa
1801 gcgcagcctc caccaggagc tggagttcct acgcgtggcc aagaaggaga agctgcggga
1861 ggccacggag gccaagcgta acctgcggaa ggagatcgag cgtctccgcg acgagaacga
1921 gaagaagatg aaagaggcca acgagtcacg gctgcgcctg aagcgggagc tggagcaggc
1981 gcggcaggcc cgggtgtgcg acaagggctg cgaggcgggc cgcctgcgcg ccaagtactc
2041 ggcccagatc gaagacctgc aggtgaagct gcagcacgcg gaggcggacc gggagcagct
2101 gcgggccgac ctgctgcggg agcgcgaggc ccggggcac ctggagaagg tggtgaagga
2161 gctgcaggaa cagctgtggc cgcgggcccg ccccgaggct gcgggcagcg agggcgctgc
2221 ggagctggag ccgtagattc cgtgcctgcc gccgacaac gccggtgcag
2281 gggggcgcgg ctgggcggtg cagctccgcc cggctccgcc cctgcagccc acacagcaca
2341 acgtcttacc gtgcctatta ccaagcgagt gtttgtaacc atgtagtttt ggaacccact
2401 gcaaaatttt ctactggcca agttcaagtg agtaagccgc gtccccaac tacagctgga
2461 gacggggcca gctcggcggc ctgctggtcc tctgcttgct ggaacattct aacatttaca
2521 cttttgttat aagctattta aaaccagtaa ggagacttga aattcagaaa atcaacacat
2581 ttttaaatga ctaacttcta aaagccccaa cacatgcagc catctgaaga cccgcaacgg
2641 agtgggggtg gcggccgccc caccctcccc acccggggaa gccatcacag ctcatctgcc
2701 cgcggctgcg tgaggacagc aggggttttt cttcagagtc tatttttca gcgacaagga
2761 cccaggtctt cctgctgctg ccagggagag cagggacagt gccgcgtgcg agatgagctc
2821 gaacactgcc cgccttactg ccgcctaccc cgccgccac gccgccgtcg atgccagcgc
2881 tgtccccacg ggtaccagga agtgcagagc cgcacaggag ctgcccgga gctgagggga
2941 cggtcttcgg ctcctctgca ccccgtgatt ctgcccacgc tcctccacca cgaggcactg
3001 acctgcgtcg ggtggtgacc gtggctggcg gtcacgccct cagcccctcc gggcacacgt
3061 gccgcctgac cgggcgaccc ttttcagttc ggcaaacgtc gctcccttca ttttgggact
3121 gaggctgcag cattggaaca aaagagcatt atttcaattt ttctttcttt tttttttgttc
3181 gttcatttaa acgtatattt agaactgcac tttgtccaca accttccctt ctctttctat
3241 tccccagtga actgaggttt ttaccgattt atagagcagt caaatccgaa gtgctcgagt
3301 gcttagaaac cccctctggt gcttggttga acaagggaat cacaagaaaa cgaaaatgca
3361 aaaactgaac ttcgggggtc gttctgtgcc ttccagcatc ttgtacagca aatcctgact
3421 cgtgtctttt taccccaag atatctgtct tcagtagcga ctgaatctgc cactctcaga
3481 ataagttc
```

FIG. 10 A-51

SEQ Id NO:59

```
   1 gccgccgccg ccatccgccg ccgcagccag cttccgccgc cgcaggaccg gcccctgccc
  61 cagcctccgc agccgcggcg cgtccacgcc cgcccgcgcc cagggcgagt cggggtcgcc
 121 gcctgcacgc ttctcagtgt tccccgcgcc ccgcatgtaa cccggccagg cccccgcaac
 181 tgtgtcccct gcagctccag ccccgggctg catcccccg ccccgacacc agctctccag
 241 cctgctcgtc caggatggcc gcggccaagg ccgagatgca gctgatgtcc ccgctgcaga
 301 tctctgaccc gttcggatcc tttcctcact cgcccaccat ggacaactac cctaagctgg
 361 aggagatgat gctgctgagc aacgggctc cccagttcct cggcgccgcc ggggcccag
 421 agggcagcgg cagcaacagc agcagcagca gcagcggggg cggtggaggc ggcgggggcg
 481 gcagcaacag cagcagcagc agcagcacct caacccctca ggcggacacg ggcgagcagc
 541 cctacgagca cctgaccgca gagtcttttc ctgacatctc tctgaacaac gagaaggtgc
 601 tggtggagac cagttacccc agccaaacca ctcgactgcc ccccatcacc tatactggcc
 661 gcttttccct ggagcctgca cccaacagtg caacaccttg tggcccgag ccctcttca
 721 gcttggtcag tggcctagtg agcatgacca acccaccggc ctcctcgtcc tcagcaccat
 781 ctccagcggc ctcctccgcc tccgcctccc agagcccacc cctgagctgc gcagtgccat
 841 ccaacgacag cagtcccatt tactcagcgg cacccacctt ccccacgccg aacactgaca
 901 ttttccctga gccacaaagc caggccttcc cgggctcggc agggacagcg ctccagtacc
 961 cgcctcctgc ctaccctgcc gccaaggtg gcttccaggt tcccatgatc ccgactacc
1021 tgtttccaca gcagcagggg gatctgggcc tgggcacccc agaccagaag cccttccagg
1081 gcctggagag ccgcacccag cagccttcgc taaccccctct gtctactatt aaggcctttg
1141 ccactcagtc gggctccag gacctgaagg ccctcaatac cagctaccag tcccagctca
1201 tcaaacccag ccgcatgcgc aagtacccca accggccag caagacgccc ccccacgaac
1261 gccctacgc ttgcccagtg gagtcctgtg atcgccgctt ctcccgctcc gacgagctca
1321 cccgccacat ccgcatccac acaggccaga agcccttcca gtgccgcatc tgcatgcgca
1381 acttcagccg cagcgaccac ctcaccaccc acatccgcac ccacacaggc gaaaagccct
1441 tcgcctgcga catctgtgga agaaagtttg ccaggagcga tgaacgcaag aggcatacca
1501 agatccactt gcggcagaag gacaagaaag cagacaaaag tgttgtggcc tcttcggcca
1561 cctcctctct ctcttcctac ccgtccccgg ttgctacctc ttacccgtcc ccggttacta
1621 cctcttatcc atccccggcc accacctcat acccatcccc tgtgcccacc tcttctcct
1681 ctcccggctc ctcgcctac ccatcccctg tgcacagtgg cttcccctcc ccgtcggtgg
1741 ccaccacgta ctcctctgtt ccccctgctt tcccggccca ggtcagcagc ttcccttcct
1801 cagctgtcac caactccttc agcgcctcca cagggctttc ggacatgaca gcaaccttt
1861 ctcccaggac aattgaaatt tgctaaaggg aaaggggaaa gaagggaaa agggagaaaa
1921 agaaacacaa gagacttaaa ggacaggagg aggagatggc cataggagag gagggttcct
1981 cttaggtcag atggaggttc tcagagccaa gtcctccctc tctactggag tggaaggtct
2041 attggccaac aatcctttct gcccacttcc ccttccccaa ttactattcc ctttgacttc
2101 agctgcctga acagccatg tccaagttct tcacctctat ccaaagaact tgatttgcat
2161 ggattttgga taaatcattt cagtatcatc tccatcatat gcctgacccc ttgctccctt
2221 caatgctaga aaatcgagtt ggcaaaatgg ggtttgggcc cctcagagcc ctgccctgca
2281 cccttgtaca gtgtctgtgc catggatttc gttttttcttg gggtactctt gatgtgaaga
2341 taatttgcat attctattgt attatttgga gttaggtcct cacttggggg aaaaaaaaaa
2401 aagaaaagcc aagcaaacca atggtgatcc tctattttgt gatgatgctg tgacaataag
2461 tttgaacctt ttttttgaa acagcagtcc cagtattctc agagcatgtg tcagagtgtt
2521 gttccgttaa ccttttttgta aatactgctt gaccgtactc tcacatgtgg caaaatatgg
2581 tttggttttt ctttttttttt tttttgaaa gtgttttttc ttcgtccttt tggtttaaaa
2641 agtttcacgt cttggtgcct tttgtgtgat gcgccttgct gatggcttga catgtgcaat
2701 tgtgagggac atgctcacct ctagccttaa gggggcagg gagtgatgat ttgggggagg
2761 ctttgggagc aaaataagga agagggctga gctgagcttc ggttctccag aatgtaagaa
2821 aacaaaatct aaaacaaaat ctgaactctc aaaagtctat ttttttaact gaaaatgtaa
2881 atttataaat atattcagga gttggaatgt tgtagttacc tactgagtag gcggcgattt
2941 ttgtatgtta tgaacatgca gttcattatt ttgtggttct attttacttt gtacttgtgt
```

FIG. 10 A-52

```
3001 ttgcttaaac aaagtgactg tttggcttat aaacacattg aatgcgcttt attgcccatg
3061 ggatatgtgg tgtatatcct tccaaaaaat taaaacgaaa ataaagta SEQ ID NO:60
   1 cattcataag actcagagct acggccacgg cagggacacg cggaaccaag acttggaaac
  61 ttgattgttg tggttcttct tgggggttat gaaatttcat taatcttttt tttttccggg
 121 gagaaagttt ttggaaagat tcttccagat atttcttcat tttcttttgg aggaccgact
 181 tacttttttt ggtcttcttt attactcccc tcccccgtg ggacccgccg gacgcgtgga
 241 ggagaccgta gctgaagctg attctgtaca gcgggacagc gctttctgcc cctggggag
 301 caacccctcc ctcgcccctg ggtcctacgg agcctgcact ttcaagaggt acagcggcat
 361 cctgtggggg cctgggcacc gcaggaagac tgcacagaaa ctttgccatt gttggaacgg
 421 gacgttgctc cttcccgag cttccccgga cagcgtactt tgaggactcg ctcagctcac
 481 cggggactcc cacggctcac cccggacttg caccttactt ccccaacccg gccatagcct
 541 tggcttcccg gcgacctcag cgtggtcaca ggggcccccc tgtgcccagg gaaatgtttc
 601 aggctttccc cggagactac gactccggct cccggtgcag ctcctcaccc tctgccgagt
 661 ctcaatatct gtcttcggtg gactccttcg gcagtccacc caccgccgcg gcctcccagg
 721 agtgcgccgg tctcggggaa atgcccggtt ccttcgtgcc cacggtcacc gcgatcacaa
 781 ccagccagga cctccagtgg cttgtgcaac ccaccctcat ctcttccatg gcccagtccc
 841 aggggcagcc actggcctcc cagcccccgg tcgtcgaccc ctacgacatg ccgggaacca
 901 gctactccac accaggcatg agtggctaca gcagtggcgg agcgagtggc agtggtgggc
 961 cttccaccag cggaactacc agtgggcctg ggcctgcccg cccagcccga gcccggccta
1021 ggagacccg agaggagacg ctcaccccag aggaagagga gaagcgaagg gtgcgccggg
1081 aacgaaataa actagcagca gctaaatgca ggaaccggcg gagggagctg accgaccgac
1141 tccaggcgga gacagatcag ttggaggaag aaaaagcaga gctggagtcg gagatcgccg
1201 agctccaaaa ggagaaggaa cgtctggagt ttgtgctggt ggcccacaaa ccgggctgca
1261 agatccccta cgaagagggg cccgggccgg gcccgctggc ggaggtgaga gatttgccgg
1321 gctcagcacc ggctaaggaa gatggcttca gctggctgct gccgccccg ccaccaccgc
1381 ccctgccctt ccagaccagc caagacgcac ccccaacct gacggcttct ctctttacac
1441 acagtgaagt tcaagtcctc ggcgaccct tcccgttgt taaccttcg tacacttctt
1501 cgtttgtcct cacctgcccg gaggtctccg cgttcgccgg cgcccaacgc accagcggca
1561 gtgaccagcc ttccgatccc ctgaactcgc cctccctcct cgctcggtga actctttaga
1621 cacacaaaac aaacaaacac atgggggaga gagacttgga agaggaggag gaggaggaga
1681 aggaggagag agagggaag agacaaagtg ggtgtgtggc ctccctggct cctccgtctg
1741 accctctgcg gccactgcgc cactgccatc ggacaggagg attccttgtg tttttgtcctg
1801 cctcttgttt ctgtgccccg gcgaggccgg agagctggtg acttttgggga cagggggtgg
1861 gaaggggatg gacacccca gctgactgtt ggctctctga cgtcaaccca agctctgggg
1921 atgggtgggg aggggggcgg gtgacgccca cctcggcga gtcctgtgtg aggatgaagg
1981 gacggggtg ggaggtaggc tgtggggtgg gctggagtcc tctccagaga ggctcaacaa
2041 ggaaaaatgc cactccctac ccaatgtctc ccacacccac ccttttttgt gggtgcccag
2101 gttggtttcc cctgcactcc cgacttagc ttattgatcc cacatttcca tggtgtgaga
2161 tcctctttac tctgggcaga agtgagcccc cccttaaagg gaattcgatg ccccccctaga
2221 ataatctcat ccccccaccc gacttctttt gaaatgtgaa cgtccttcct tgactgtcta
2281 gccactccct cccagaaaaa ctggctctga ttggaatttc tggcctccta aggctcccca
2341 cccgaaatc agccccccagc cttgtttctg atgacagtgt tatcccaaga ccctgccccc
2401 tgccagccga ccctcctggc cttcctcgtt gggccgctct gatttcaggc agcagggct
2461 gctgtgatgc cgtcctgctg gagtgattta tactgtgaaa tgagttggcc agattgtggg
2521 gtgcagctgg gtggggcagc acacctctgg ggggataatg tccccactcc cgaaagcctt
2581 tcctcggtct cccttccgtc catccccctt cttcctcccc tcaacagtga gttagactca
2641 agggggtgac agaaccgaga agggggtgac agtcctccat ccacgtggcc tctctctctc
2701 tcctcaggac cctcagccct ggcctttttc tttaaggtcc cccgaccaat ccccagccta
```

FIG. 10 A-53

```
2761 ggacgccaac ttctcccacc ccttggcccc tcacatcctc tccaggaagg cagtgagggg
2821 ctgtgacatt tttccggaga agatttcaga gctgaggctt tggtaccccc aaacccccaa
2881 tattttggga ctggcagact caaggggctg gaatctcatg attccatgcc cgagtccgcc
2941 catccctgac catggttttg gctctcccac cccgccgttc cctgcgcttc atctcatgag
3001 gatttcttta tgaggcaaat ttatatttt taatatcggg gggtggacca cgccgccctc
3061 catccgtgct gcatgaaaaa cattccacgt gccccttgtc gcgcgtctcc catcctgatc
3121 ccagacccat tccttagcta tttatccctt tcctggtttc cgaaaggcaa ttatatctat
3181 tatgtataag taaatatatt atatatggat gtgtgtgtgt gcgtgcgcgt gagtgtgtga
3241 gcgcttctgc agcctcggcc taggtcacgt tggccctcaa agcgagccgt tgaattggaa
3301 actgcttcta gaaactctgg ctcagcctgt ctcgggctga ccctttctg atcgtctcgg
3361 ccctctgat tgttccgat ggtctctctc cctctgtctt ttctcctccg cctgtgtcca
3421 tctgaccgtt ttcacttgtc tcctttctga ctgtccctgc caatgctcca gctgtcgtct
3481 gactctgggt tcgttgggga catgagattt tatttttttgt gagtgagact gagggatcgt
3541 agattttac aatctgtatc tttgacaatt ctgggtgcga gtgtgagagt gtgagcaggg
3601 cttgctcctg ccaaccacaa ttcaatgaat ccccgacccc cctaccccat gctgtacttg
3661 tggttctctt tttgtatttt gcatctgacc ccgggggggct gggacagatt ggcaatgggc
3721 cgtcccctct cccctttggtt ctgcactgtt gccaataaaa agctcttaaa aacgc
```

SEQ ID NO:61

```
   1 agcgagcttg cagcctcacc gacgagtctc aactaaaagg gactcccgga gctaggggtg
  61 gggactcggc ctcacacagt gagtgccggc tattggactt ttgtccagtg acagctgaga
 121 caacaaggac cacgggagga ggtgtaggag agaagcgccg cgaacagcga tcgcccagca
 181 ccaagtccgc ttccaggctt tcggtttctt ttgcctccat ctggggtgcgc cttcccggcg
 241 tctaggggag cgaaggctga ggtggcagcg gcaggagagt ccggccgcga caggccgaac
 301 tccccccactg gaaaggattc tgaaagaaat gaagtcagcc ctcagaaatg aagttgactg
 361 cctgctggct ttctgttgac tggcccggag ctgtactgca agacccttgt gagcttccct
 421 agtctaagag taggatgtct gctgaagtca tccatcaggt tgaaaagca cttgatacag
 481 atgagaagga gatgctgctc ttttttgtgcc gggatgttgc tatagatgtg gttccaccta
 541 atgtcaggga ccttctggat attttacggg aaagaggtaa gctgtctgtc ggggacttgg
 601 ctgaactgct ctacagagtg aggcgatcttg acgtatcttg aagatggaca
 661 gaaaagctgt ggagacccac ctgctcagga accctcacct tgtttcggac tatagagtgc
 721 tgatggcaga gattggtgag gatttggata aatctgatgt gtcctcatta attttcctca
 781 tgaaggatta catgggccga ggcaagataa gcaaggagaa ggtttcttgg accttgtggt
 841 tgagttggag aaactaaatc tggttgcccc agatcaactg gatttattag aaaaatgcct
 901 aaagaacatc cacagaatag acctgaagac aaaaatccag aagtacaagc agtctgttca
 961 aggagcaggg acaagttaca ggaatgttct ccaagcagca atccaaaaga gtctcaagga
1021 tccttcaaa aacttcaggc tccataaagg gaagaagaca ttaaggaaca
1081 gcttggcgct caacaagaac cagtgaagaa atccattcag gaatcagaag ctttttttgcc
1141 tcagagcata cctgaagaga gatacaagat gaagagcaag ccccctaggaa tctgcctgat
1201 aatcgattgc attggcaatg agacagagct tcttcgagac accttcactt ccctgggcta
1261 tgaagtccag aaattcttgc atctcagtat gcatggtata tcccagattc ttggccaatt
1321 tgcctgtatg cccgagcacc gagactacga cagctttgtg tgtgtcctgg tgagccgagg
1381 aggctcccag agtgtgtatg gtgtggatca gactcactca gggctccccc tgcatcacat
1441 caggaggatg ttcatgggag attcatgccc ttatctagca gggaagccaa agatgttttt
1501 tattcagaac tatgtggtgt cagagggcca gctggaggac agcagcctct tggaggtgga
1561 tgggccagcg atgaagaatg tggaattcaa ggctcagaag cgagggctgt gcacagttca
1621 ccgagaagct gacttcttct ggagcctgtg tactgcggac atgtccctgc tggagcagtc
1681 tcacagctca ccatccctgt acctgcagtg cctctcccag aaactgagac aagaaagaaa
1741 acgcccactc ctggatcttc acattgaact caatggctac atgtatgatt ggaacagcag
1801 agtttctgcc aaggagaaat attatgtctg gctgcagcac actctgagaa agaaacttat
```

FIG. 10 A-54

```
1861 cctctcctac acataagaaa ccaaaaggct gggcgtagtg gctcacacct gtaatcccag
1921 cactttggga ggccaaggag ggcagatcac ttcaggtcag gagttcgaga ccagcctggc
1981 caacatggta aacgctgtcc ctagtaaaaa tacaaaaatt a SEQ ID NO:62
   1 agagttgcac tgagtgtggc tgaagcagcg aggcgggagt ggaggtgcgc ggagtcaggc
  61 agacagacag acacagccag ccagccaggt cggcagtata gtccgaactg caaatcttat
 121 tttcttttca ccttctctct aactgcccag agctagcgcc tgtggctccc gggctggtgt
 181 ttcgggagtg tccagagagc ctggtctcca gccgccccg ggaggagagc cctgctgccc
 241 aggcgctgtt gacagcggcg gaaagcagcg gtacccacgc gcccgccggg ggaagtcggc
 301 gagcggctgc agcagcaaag aactttcccg gctgggagga ccggagacaa gtggcagagt
 361 cccggagcca acttttgcaa gcctttcctg cgtcttaggc ttctccacgg cggtaaagac
 421 cagaaggcgg cggagagcca gcaagagaa gaaggacgtg cgctcagctt cgctcgcacc
 481 ggttgttgaa cttgggcgag cgcgagccgc ggctgccggg cgccccctcc ccctagcagc
 541 ggaggagggg acaagtcgtc ggagtccggg cggccaagac ccgccgccgg ccggccactg
 601 cagggtccgc actgatccgc tccgcgggga gagccgctgc tctgggaagt gagttcgcct
 661 gcggactccg aggaaccgct gcgcacgaag agcgctcagt gagtgaccgc gacttttcaa
 721 agccgggtag cgcgcgcgag tcgacaagta agagtgcggg aggcatctta attaaccctg
 781 cgctccctgg agcgagctgg tgaggagggc gggctgctc agctggcgtg cgacagccag cgggtgcgtg
 841 cgctcttaga gaaactttcc ctgtcaaagg ctccgggggg cgcgggtgtc cccgcttgc
 901 cacagccctg ttgcgccccc gaaacttgtg cgcgcagccc aaactaacct cacgtgaagt
 961 gacggactgt tctatgactg caaagatgga aacgaccttc tatgacgatg ccctcaacgc
1021 ctcgttcctc ccgtccgaga gcggacctta tggctacagt aaccccaaga tcctgaaaca
1081 gagcatgacc ctgaacctgg ccgacccagt ggggagcctg aagccgcacc tccgcgccaa
1141 gaactcggac ctcctcacct cgcccgacgt gggctgctc aagctggcgt cgccgcgagct
1201 ggagcgcctg ataatccagt ccagcaacgg gcacatcacc accacgccga ccccccaccca
1261 gttcctgtgc cccaagaacg tgacagatga gcaggagggc ttcgccgagg gcttcgtgcg
1321 cgccctggcc gaactgcaca gccagaacac gctgcccagc gtcacgtcgg cggcgcagcc
1381 ggtcaacggg gcaggcatgg tggctcccgc ggtagcctcg gtggcagggg gcagcggcag
1441 cggcggcttc agcgccagcc tgcacagcga gccgccggtc tacgcaaacc tcagcaactt
1501 caacccaggc gcgctgagca gcggcggcgg ggcgcccctcc tacggcgcgg ccggcctggc
1561 cttcccgcg caaccccagc agcagcagca gccgccgcac cacctgcccc agcagatgcc
1621 cgtgcagcac ccgcggctgc aggccctgaa ggaggagcct cagacagtgc ccgagatgcc
1681 cggcgagaca ccgcccctgt ccccatcga catggagtcc caggagcgga tcaaggcgga
1741 gaggaagcgc atgaggaacc gcatcgctgc ctccaagtgc cgaaaaagga agctggagag
1801 aatcgcccgg ctggaaggaa aagtgaaaac cttgaaagct cagaactcgg agctggcgtc
1861 cacggccaac atgctcaggg aacaggtggc acagcttaaa cagaaagtca tgaaccacgt
1921 taacagtggg tgccaactca tgctaacgca gcagttgcaa acatttgaa gagagaccgt
1981 cggggctga ggcaacga agaaaaaaa taacacagag agacagactt gagaacttga
2041 caagttgcga cggagagaaa aaagaagtgt ccgagaacta aagccaaggg tatccaagtt
2101 ggactgggtt gcgtcctgac ggcgccccca gtgtgcacga gtgggaagga cttggcgcgc
2161 cctcccttgg cgtggagcca gggagcggcc gcctgcgggc tgccccgctt tgcggacggg
2221 ctgtcccgc gcgaacggaa cgttggactt ttcgttaaca ttgaccaaga actgcatgga
2281 cctaacattc gatctcattc agtattaaag gggggagggg gagggggtta caaactgcaa
2341 tagagactgt agattgcttc tgtagtactc cttaagaaca caaagcgggg ggagggttgg
2401 ggaggggcgg caggagggag gtttgtgaga gcgaggctga gcctacagat gaactctttc
2461 tggcctgcct tcgttaactg tgtatgtaca tatatatatt ttttaatttg atgaaagctg
2521 attactgtca ataaacagct tcatgccttt gtaagttatt tcttgtttgt ttgtttgggt
2581 atcctgccca gtgttgtttg taaataagag atttggagca ctctgagttt accatttgta
2641 ataaagtata aattttttt atgttttgtt tctgaaaatt ccagaaagga tatttaagaa
```

FIG. 10 A-55

```
2701 aatacaataa actattggaa agtactcccc taacctcttt tctgcatcat ctgtagatac
2761 tagctatcta ggtggagttg aaagagttaa gaatgtcgat taaaatcact ctcagtgctt
2821 cttactatta agcagtaaaa actgttctct attagacttt agaaataaat gtacctgatg
2881 tacctgatgc tatggtcagg ttatactcct cctcccccag ctatctatat ggaattgctt
2941 accaaaggat agtgcgatgt ttcaggaggc tggaggaagg ggggttgcag tggagaggga
3001 cagcccactg agaagtcaaa catttcaaag tttggattgt atcaagtggc atgtgctgtg
3061 accatttata atgttagtag aaattttaca ataggtgctt attctcaaag caggaattgg
3121 tggcagattt tacaaaagat gtatccttcc aatttggaat cttctctttg acaattccta
3181 gataaaaaga tggcctttgc ttatgaatat ttataacagc attcttgtca caataaatgt
3241 attcaaatac caat
```

SEQ ID NO:63
```
   1 gtggagctac cgccaccgcc gccgccgatt ccggagccgg ggtagtcgcc gccgccgccg
  61 ccgctgcagc cactgcaggc accgctgccg ccgcctgagt agtgggctta ggaaggaaga
 121 ggtcatctcg ctcggagctt cgctcggaag ggtctttgtt ccctgcagcc ctcccacggg
 181 aatgacaatg gataaaagtg agctggtaca gaaagccaaa ctcgctgagc aggctgagcg
 241 atatgatgat atggctgcag ccatgaaggc agtcacagaa cagggcatg aactctccaa
 301 cgaagagaga atctgctct ctgttgccta caagaatgtg gtaggcgccc gccgctcttc
 361 ctggcgtgtc atctccagca ttgagcagaa aacagagagg aatgagaaga agcagcagat
 421 gggcaaagag taccgtgaga agatagaggc agaactgcag gacatctgca atgatgttct
 481 ggagctgttg gacaaaatatc ttattcccaa tgctacacaa ccagaaagta aggtgttcta
 541 cttgaaaatg aaaggagatt attttaggta tctttctgaa gtggcatctg gagacaacaa
 601 acaaaccact gtgtcgaact cccagcaggc ttaccaggaa gcatttgaaa ttagtaagaa
 661 agaaatgcag cctacacacc caattcgtct tggtctggca ctaaatttct cagtcttta
 721 ctatgagatt ctaaactctc ctgaaaaggc ctgtagcctg gcaaaaacgg catttgatga
 781 agcaattgct gaattggata cgctgaatga agagtcttat aaagacagca ctctgatcat
 841 gcagttactt agggacaatc tcactctgtg gacatcggaa aaccagggag acgaaggaga
 901 cgctggggag ggagagaact aatgtttctc gtgctttgtg atctgttcag tgtcactctg
 961 taccctcaac atatatccct tgtgcgat
```

SEQ ID NO:64
```
   1 gtgccgctcc ttggtggggg ctgttcatgg cggttccggg gtctccaaca ttttcccgg
  61 ctgtgtcct aaatctgtcc aaagcagagg cagtgaagct tgaggttctt gctggtgtga
 121 aatgactgag tacaaactgg tggtggttgg agcaggtggt gttgggaaaa gcgcactgac
 181 aatccagcta atccagaacc actttgtaga tgaatatgat cccaccatag aggattctta
 241 cagaaaacaa gtggttatag atggtgaaac ctgtttgttg gacatactgg atacagctgg
 301 acaagaagag tacagtgcca tgagagacca atacatgagg acaggcgaag gcttcctctg
 361 tgtatttgcc atcaataata gcaagtcatt tgcggatatt aacctctaca gggagcgat
 421 taagcgagta aaagactcgg atgatgtacc tatgtgcta gtgggaaaca agtgtgattt
 481 gccaacaagg acagttgata caaaacaagc ccacgaactg gccaagagtt acgggattcc
 541 attcattgaa acctcagcca agaccagaca gggtgttgaa gatgcttttt acacactggt
 601 aagagaaata cgccagtacc gaatgaaaaa actcaacagc agtgatgatg ggactcaggg
 661 ttgtatggga ttgccatgtg tggtgatgta acaagatact tttaaagttt tgtcagaaaa
 721 gagccacttt caagctgcac tgacaccctg gtcctgactt ccctggagga gaagtattcc
 781 tgttgctgtc ttcagtctca cagagaagct cctgctactt ccccagctct cagtagttta
 841 gtacaataat ctctatttga gaagttctca gaataactac ctcctcactt ggctgtctga
 901 ccagagaatg cacctcttgt tactccctgt tatttttctg ccctgggttc ttccacagca
 961 caaacacacc tctgccaccc caggtttttc atctgaaaag cagttcatgt ctgaaacaga
1021 gaaccaaacc gcaaacgtga aattctattg aaaacagtgt cttgagctct aaagtagcaa
1081 ctgctggtga tttttttttt cttttactg ttgaacttag aactatgcta attttggag
```

FIG. 10 A-56

```
1141 aaatgtcata aattactgtt ttgccaagaa tatagttatt attgctgttt ggtttgttta
1201 taatgttatc ggctctattc tctaaactgg catctgctct agattcataa atacaaaaat
1261 gaatactgaa ttttgagtct atcctagtct tcacaacttt gacgtaatta aatccaactt
1321 tcacagtgaa gtgcctttt cctagaagtg gtttgtagac ttcctttata atatttcagt
1381 ggaatagatg tctcaaaaat ccttatgcat gaaatgaatg tctgagatac gtctgtgact
1441 tatctaccat tgaaggaaag ctatatctat ttgagagcag atgccatttt gtacatgtat
1501 gaaattggtt ttccagaggc ctgttttggg gcttcccag gagaaagatg aaactgaaag
1561 cacatgaata atttcactta ataattttta cctaatctcc actttttca taggttacta
1621 cctatacaat gtatgtaatt tgtttcccct agcttactga taaacctaat attcaatgaa
1681 cttccatttg tattcaaatt tgtgtcatac cagaaagctc tacatttgca gatgttcaaa
1741 tattgtaaaa ctttggtgca ttgttattta atagctgtga tcagtgattt tcaaacctca
1801 aatatagtat attaacaaat tacattttca ct
```

SEQ ID NO:65

```
   1 atgaaggtga taagcttatt cattttggtg ggatttatag gagagttcca aagttttca
  61 agtgcctcct ctccagtcaa ctgccagtgg gacttctatg ccccttggtc agaatgcaat
 121 ggctgtacca agactcagac tcgcaggcgg tcagttgctg tgtatgggca gtatggaggc
 181 cagccttgtg ttggaaatgc ttttgaaaca cagtcctgtg aacctacaag aggatgtcca
 241 acagaggagg gatgtggaga gcgtttcagg tgcttttcag gtcagtgcat cagcaaatca
 301 ttggtttgca atggggattc tgactgtgat gaagacagtg ctgatgaaga cagatgtgag
 361 gactcagaaa ggagaccttc ctgtgatatc gataaacctc ctcctaacat agaacttact
 421 ggaaatggtt acaatgaact cactggccag tttaggaaca gagtcatcaa taccaaaagt
 481 tttggtggtc aatgtagaaa ggtgtttagt ggggatggaa agatttcta caggctgagt
 541 ggaaatgtcc tgtcctatac attccaggtg aaaataaata atgatttaa ttatgaattt
 601 tacaatagta cttggtctta tgtaaaacat acgtcgacag aacacacatc atctagtcgg
 661 aagcgctcct tttagatc ttcatcatct tcttcacgca gttatacttc acataccaat
 721 gaaatccata aaggaaagag ttaccaactg ctggttgttg agaacactgt tgaagtggct
 781 cagttcatta ataacaatcc agaatttta caacttgctg agccattctg gaaggagctt
 841 tcccacctcc cctctctgta tgactacagt gcctaccgaa gattaatcga ccagtacggg
 901 acacattatc tgcaatctgg gtcgttagga ggagaataca gagttctatt ttatgtggac
 961 tcagaaaaat taaaacaaaa tgatttaat tcagtcgaag aaaagaaatg taaatcctca
1021 ggttggcatt ttgtcgttaa attttcaagt catggatgca aggaactgga aaacgcttta
1081 aaagctgctt caggaaccca gaacaatgta ttgcgaggag aaccgttcat cagaggggga
1141 ggtgcaggct tcatatctgg ctagagctgg ctagagctgg ctagagctgg tggaaacaaa
1201 aggcgatatt ctgcctggc agaatctgtg actaatcttc ctcaagtcat aaaacaaaag
1261 ctgacacctt tatatgagct ggtaaaggaa gtaccttgtg cctctgtgaa aaaactatac
1321 ctgaaatggg ctcttgaaga gtatctggat gaatttgacc cctgtcattg ccggccttgt
1381 caaaatggtg gtttggctac tgttgagggg acccattgtc tgtgccattg caaaccgtac
1441 acatttggtg cggcgtgtga gcaaggagtc ctcgtaggga atcaagcagg aggggttgat
1501 ggaggttgga gttgctggtc ctcttggagc ccctgtgtcc aagggaagaa aacaagaagc
1561 cgtgaatgca ataacccacc tcccagtggg ggtgggagat cctgcgttgg agaaacgaca
1621 gaaagcacac aatgcgaaga tgaggagctg gagcacttga ggttgcttga accacattgc
1681 tttcctttgt ctttggttcc aacagaattc tgtccatcac ctcctgcctt gaaagatgga
1741 tttgttcaag atgaaggtcc aatgttcct gtgggggaaaa atgtagtgta cacttgcaat
1801 gaaggatact ctcttattgg aaacccagtg ccagatgtg gagaagattt acggtggctt
1861 gttggggaaa tgcattgtca gaaaattgcc tgtgttctac ctgtactgat ggatggcata
1921 cagagtcacc cccaaaaacc tttctacaca gttggtgaga aggtgactgt ttcctgttca
1981 ggtggcatgt ccttagaagg tccttcagca tttctctgtg gctccagcct taagtggagt
2041 cctgagatga agaatgcccg ctgtgtacaa aagaaaatc cgttaacaca ggcagtgcct
2101 aaatgtcagc gctgggagaa actgcagaat tcaagatgtg tttgtaaaat gccctacgaa
```

FIG. 10 A-57

```
2161 tgtggacctt ccttggatgt atgtgctcaa gatgagagaa gcaaaaggat actgcctctg
2221 acagtttgca agatgcatgt tctccactgt cagggtagaa attacaccct tactggtagg
2281 gacagctgta ctctgcctgc ctcagctgag aaagcttgtg gtgcctgccc actgtgggga
2341 aaatgtgatg ctgagagcag caaatgtgtc tgccgagaag catcggagtg cgaggaagaa
2401 gggtttagca tttgtgtgga agtgaacggc aaggagcaga cgatgtctga gtgtgaggcg
2461 ggcgctctga gatgcagagg gcagagcatc tctgtcacca gcataaggcc ttgtgctgcg
2521 gaaacccagt aggctcctgg aggccatggt cagcttgctt ggaatccagc aggcagctgg
2581 ggctgagtga aaacatctgc acaactgggc actggacagc ttttccttct tctccagtgt
2641 ctaccttcct cctcaactcc cagccatctg tataaacaca atcctttgtt ctcccaaatc
2701 tgaatcgaat tactcttttg cctcctttt aatgtcagta aggatatgag cctttgcaca
2761 ggctggctgc gtgttcttga aataggtgtt accttctctg ggccttggtt ttttaaaatc
2821 tgtaaaatta gaggattgca ctagagaaac ttgaatgctc cattcaggcc tatcatttta
2881 ttaagtatga ttgacacagc ccatgggcca gaacacactc tacaaaatga ctaggataac
2941 agaaagaacg tgatctcctg attagagagg gtggttttcc tcaatggaac caaatataaa
3001 gaggacttga acaaaaatga cagatacaaa ctatttctat cctgagtagt aatctcacac
3061 ttcatcctat agagtcaacc accacagata ggaattcctt attctttttt taattttttt
3121 aagacagagt ctcactttgt tgcccaggct ggagcgcagt ggggtgatct catctccctg
3181 caacctccgc ctcctgggtt gaagcgattc ttgtgcctca gcttcccaag cagctgggat
3241 tacaggtgcc cgccaccacg cccagctaat ttttgcattt ttagtagaga tgggtttcac
3301 catgttggcc atgctcgtct ccaactcctg acctcaggta atccgtctgc cttggcctcc
3361 caaatgctgg gattacagac atgaaccacc acgcctggct ggaatactta ctcttgtcgg
3421 gagattgaac cactaaaatg ttagagcaga attcattatg ctgtggtcac aggggtgtct
3481 tgtctgagaa caaatacaat tcagtcttct ctttggggtt ttagtatgtg tcaaacatag
3541 gactggaagt ttgcccctgt tctttttttct tttgaaagaa catcagttca tgcctgaggc
3601 atgagtgact gtgcatttga gatagttttc cctattctgt ggatacagtc ccagagtttt
3661 cagggagtac acaggtagat tagtttgaag cattgacctt ttatttattc cttatttctc
3721 tttcatcaaa acaaaacagc agctgtggga ggagaaatga gagggcttaa atgaaattta
3781 aaataagcta tattatacaa atactatctc tgtattgttc tgaccctggt aaatatattt
3841 caaaacttca gatgacaagg attagaacac tcattaagat gctattcttc
```

SEQ ID NO:66
```
  1 ctaacccaga aacatccaat tctcaaactg aagctcgcac tctcgcctcc agcatgaaag
 61 tctctgccgc ccttctgtgc ctgctgctca tagcagccac cttcattccc caagggctcg
121 ctcagccaga tgcaatcaat gccccagtca cctgctgtta aacttcacc aataggaaga
181 tctcagtgca gaggctcgcg agctatagaa gaatcaccag cagcaagtgt cccaaagaag
241 ctgtgatctt caagaccatt gtggcaaagg agatctgtgc tgacccaag cagaagtggg
301 ttcaggattc catggaccac ctggacaagc aaacccaaac tccgaagact tgaacactca
361 ctccacaacc caagaatctg cagctaactt atttccccct agctttcccc agacaccctg
421 ttttatttta ttataatgaa ttttgtttgt tgatgtgaaa cattatgcct taagtaatgt
481 taattcttat ttaagttatt gatgtttta gtttatcttt catggtacta gtgtttttta
541 gatacagaga cttggggaaa ttgcttctacc tcttgaacca cagttctacc cctgggatgt
601 tttgagggtc tttgcaagaa tcattaatac aaagaatttt ttttaacatt ccaatgcatt
661 gctaaaatat tattgtggaa atgaatattt tgtaactatt acaccaaata aatatatttt
721 tgtac
```

SEQ ID NO:67
```
  1 ttcaatgttg atgtgaaaaa ttcaatgact ttcagcggcc cggtggaaga catgtttgga
 61 tatactgttc aacaatatga aaatgaagaa ggaaaatggg tgcttattgg ttctccgtta
121 gttggccaac ccaaaaacag aactggagat gtctataagt gtccagttgg gagaggtgaa
181 tcattacctt gcgtaaagtt ggatctacca gttaatacat caattcccaa tgtcacagaa
```

FIG. 10 A-58

```
 241 gtaaaggaga acatgacatt tggatcaact ttagtcacca acccaaatgg aggatttctg
 301 gcttgtgggc cctatatgc ctatagatgt ggacatttgc attacacaac tggaatctgt
 361 tctgacgtca gccccacatt tcaagtcgtg aattccattg ccctgtaca agaatgcagc
 421 actcaactgg acatagtcat agtgctggat ggttccaaca gtatttaccc atgggacagt
 481 gttacagctt ttttaaatga ccttcttgaa agaatggata ttggtcctaa acagacacag
 541 gttggaattg tacagtatgg agaaaacgtg acccatgagt tcaacctcaa taagtattct
 601 tccaccgaag aggtacttgt tgcagcaaag aaaatagtcc agagaggtgg ccgccagact
 661 atgacagctc ttggaataga cacagcaaga aaggaggcat tcacggaagc ccggggtgcc
 721 cgaagaggag ttaaaaaagt catggttatt gtgacagatg gagagtctca tgacaatcat
 781 cgactgaaga aggtcatcca agactgtgaa gatgaaaaca ttcaacggtt ttccatagct
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnctt catatgaaat ggaaatgtct cagactggct tcagtgctca ttattcacag
1081 nnnnnnnnnn nnnnnnnnnn nnnnnnnnnn nnnnnnnnnn nnnnnnnnnn nnnnnnnnnn
1141 nnnnnnnnnn nnnnnnnnnn nnnnnnnnnn nnnnnnnnnn nnnnnnnnnn nnnnnnnnnn
1201 nnnnnnnnnn nnnnnnnnnn nnnnngttac actgtaaact ctgctactgc ttcttctgga
1261 gatgtgctct atattgctgg acagcctcgg tacaatcata caggccaggt cattatctac
1321 aggatggaag atggaaacat caaaattctc cagacgctca gtggagaaca gattggttcc
1381 tactttggca gtattttaac aacaactgac attgacaagg attctaatac tgacattctt
1441 ctagtcggag ccctatgta catgggaaca gagaaggagg agcaaggaaa agtgtatgtg
1501 tatgctctca atcagacaag gtttgaatat caaatgagcc tggaacctat taagcagacg
1561 tgctgttcat ctcggcagca caattcatgc acaacagaaa acaaaaatga gccatgcggg
1621 gctcgttttg gaactgcaat gctgctgta aaagacctca atcttgatgg atttaatgac
1681 atcgtgatag gagctccgct ggagatcatt acggggagc tgtgtacatt tatcatggaa
1741 gtggcaagac tataaggaaa gagtatgcac aacgtattcc atcaggtggg gatgtaaga
1801 cactgaaatt ttttggccag tctatccacg gagaaatgga tttaaatggt gacggtctga
1861 cagatgtgac tattgggggc cttggtgtgt ctgccctctt ctggtcccga gatgtggccg
1921 tagttaaagt gaccatgaat tttgagccaa ataaagtgaa tattcaaaag aaaaactgcc
1981 atatggaggg aaaggaaaca gtatgcataa atgctacagt gtgttttgat gtgaaattaa
2041 agtctaaaga agacacgatt tatgaagctc atttgcagta ccgtgtcacc ctagattcac
2101 taagacaaat atcacgaagt tttttctctg gaactcaaga gagaaaggtt caaaggaaca
2161 tcacagttcg aaaatcagaa tgcactaagc actccttcta catgttgaca agcatgactt
2221 tcaggactct gtgagaataa cgttggactt taatcttacc gatccagaaa atgggcctgt
2281 tcttgatgat tctctaccaa actcagtaca tgaatatatt cccctttgcca aagattgtgg
2341 aaataaggaa aaatgtatct cagacctcag cctgcagtc gccaccactg aaaaggacct
2401 gctgattgtc cgatcccaga atgataagtt caacgttagc ctcacagtca aaaatacaaa
2461 ggacagtgcc tataacacca ggacaatagt gcattattct ccaaatctag tttttttcagg
2521 aattgaggct atccaaaaag acagttgtga atctaatcat aatatcacat gtaaagttgg
2581 atatcccttc ctgagaagag gagagatggt aactttcaaa atattgtttc agtttaacac
2641 atcctatctc atggaaaatg tgaccatttta tttaagtgca acaagtgaca gcgaagaacc
2701 tcctgaaacc ctttctgata atgtagtaaa catttctatc ccggtaaaat atgaagttgg
2761 actacagttt tacagctctg caagtgaata ccacatttca attgctgcca atgagacagt
2821 ccctgaagtt attaattcta ctgaggacat tggaaatgaa attaatatct tctacttgat
2881 tagaaaaagt ggatcttttc caatgccaga gcttaagctg tcaatttcat tccccaatat
2941 gacatcaaat ggttaccctg tgctgtaccc aactggattg tcatcttctg agaatgcaaa
3001 ctgcagaccc catatctttg aggatccttt cagtatcaac tctggaaaga aaatgactac
3061 atcaactgac catctcaaac gaggcacaat tctggactgc aatacatgta aatttgctac
3121 catcacatgt aatctcactt cttctgacat cagccaagtc aatgtttcgc ttatcttgtg
3181 gaaaccaact tttataaaat catatttttc cagcttaaat cttactataa ggggagaact
3241 tcggagtgaa aatgcatctc tggttttaag tagcagcaat caaaaaagag agcttgctat
```

FIG. 10 A-59

```
3301 tcaaatatcc aaagatgggc taccgggcag agtgccatta tgggtcatcc tgctgagtgc
3361 ttttgccgga ttgttgctgt taatgctgct cattttagca ctgtggaaga ttggattctt
3421 caaaagacca ctgaaaaaga aaatggagaa a
```

SEQ ID NO:68
```
   1 gtatcactca gaatctggca gccagttccg tcctgacaga gttcacagca tatattggtg
  61 gattcttgtc catagtgcat ctgctttaag aattaacgaa agcagtgtca agacagtaag
 121 gattcaaacc atttgccaaa aatgagtcta agtgcattta ctctcttcct ggcattgatt
 181 ggtggtacca gtggccagta ctatgattat gattttcccc tatcaattta tgggcaatca
 241 tcaccaaact gtgcaccaga atgtaactgc cctgaaagct acccaagtgc catgtactgt
 301 gatgagctga aattgaaaag tgtaccaatg gtgcctcctg gaatcaagta tctttacctt
 361 aggaataacc agattgacca tattgatgaa aaggcctttg agaatgtaac tgatctgcag
 421 tggctcattc tagatcacaa ccttctagaa aactccaaga taaaagggag agttttctct
 481 aaattgaaac aactgaagaa gctgcatata aaccacaaca acctgacaga gtctgtgggc
 541 ccacttccca aatctctgga ggatctgcag cttactcata acaagatcac aaagctggc
 601 tcttttgaag gattggtaaa cctgaccttc atccatctcc agcacaatcg gctgaaagag
 661 gatgctgttt cagctgcttt taaaggtctt aaatcactcg ataccttga cttgagcttc
 721 aatcagatag ccagactgcc ttctggtctc cctgtctctc ttctaactct ctacttagac
 781 aacaataaga tcagcaacat ccctgatgag tatttcaagc gttttaatgc attgcagtat
 841 ctgcgtttat ctcacaacga actggctgat agtgaaatc ctggaaattc tttcaatgtg
 901 tcatccctgg ttgagctgga tctgtcctat aacaagctta aaaacatacc aactgtcaat
 961 gaaaaccttg aaaactatta cctggaggtc aatcaacttg agaagttga cataaagagc
1021 ttctgcaaga tcctggggcc attatcctac tccaagatca agcatttgcg tttgatggc
1081 aatcgcatct cagaaaccag tcttccaccg gatatgtatg aatgtctacg tgttgctaac
1141 gaagtcactc ttaattaata tctgtatcct ggaacaatat tttatggtta tgtttttctg
1201 tgtgtcagtt ttcatagtat ccatattta ttactgttta ttacttccat gaattttaaa
1261 atctgaggga aatgttttgt aaacatttat ttttttaaa gaaaagatga aaggcaggcc
1321 tatttcatca caagaacaca cacatataca cgaatagaca tcaaactcaa tgctttattt
1381 gtaaattag tgttttttta tttctactgt caatgatgt gcaaaaccttt ttactggttg
1441 catggaaatc agccaagttt tataatcctt aaatcttaat gttcctcaaa gcttggatta
1501 aatacatatg gatgttactc tcttgcacca aattatcttg atacattcaa atttgtctgg
1561 ttaaaaaata ggtggtagat attgaggcca agaatattgc aaaatacatg aagcttcatg
1621 cacttaaaga agtatttta gaataagaat ttgcatactt acctagtgaa acttttctag
1681 aattatttt cactctaagt catgtatgtt tctctttgat tatttgcatg ttatgtttaa
1741 taagctacta gcaaaataaa acatagcaaa tg
```

SEQ ID NO:69
```
   1 tggacagagg agcagtaaca atccccactc tccaattgtg gaagagttcc aagtcccata
  61 caacaaactc caggtgatct ttaagtcaga cttttccaat gaagagcgtt ttacggggtt
 121 tgctgcatac tatgttgcca cagacataaa tgaatgcaca gattttgtag atgtcccttg
 181 tagccacttc tgcaacaatt tcattggtgg ttacttctgc tcctgccccc ggaatatt
 241 cctccatgat gacatgaaga attgcggagt taattgcagt ggggatgtat tcactgcact
 301 gattggggag attgcaagtc ccaattatcc caaaccatat ccagagaact caaggtgtga
 361 ataccagatc cggttggaga aagggttcca agtggtgtg accttgcgga gagaagattt
 421 tgatgtggaa gcagctgact cagcgggaaa ctgccttgac agtttagttt ttgttgcagg
 481 agatcggcaa tttggtccttt actgtggtca tggattccct gggcctctaa atattgaaac
 541 caagagtaat gctcttgata tcatcttcca aactgatcta acagggcaaa aaaagggctg
 601 gaaacttcgc tatcatggag atccaatgcc ctgcctaag gaagacactc ccaattctgt
 661 ttgggagcct gcgaaggcaa aatatgtctt tagagatgtg gtgcagataa cctgtctgga
 721 tgggtttgaa gttgtggagg gacgtgttgg tgcaacatct ttctattcga cttgtcaaag
```

FIG. 10 A-60

```
 781 caatggaaag tggagtaatt ccaaactgaa atgtcaacct gtggactgtg gcattcctga
 841 atccattgag aatggtaaag ttgaagaccc agagagcact ttgtttggtt ctgtcatccg
 901 ctacacttgt gaggagccat attactacat ggaaaatgga ggaggtgggg agtatcactg
 961 tgctggtaac gggagctggg tgaatgaggt gctgggcccg gagctgccga aatgtgttcc
1021 aggtctgtgg agtccccaga gaacccttg aagaaaaaca gaggataatt ggaggatccg
1081 atgcagatat taaaaacttc ccctggcaag tcttctttga caacccatgg gctggtggag
1141 cgctcattaa tgagtactgg gtgctgacgg ctgctcatgt tgtggaggga aacagggagc
1201 caacaatgta tgttgggtcc acctcagtgc agacctcacg gctggcaaaa tccaagatgc
1261 tcactcctga gcatgtgttt attcatccgg gatggaagct gctggaagtc ccagaaggac
1321 gaaccaattt tgataatgac attgcactgg tgcggctgaa agacccagtg aaaatgggac
1381 ccaccgtctc tcccatctgc ctaccaggca cctcttccga ctacaacctc atggatgggg
1441 acctgggact gatctcaggc tggggccgaa cagagaagag agatcgtgct gttcgcctca
1501 aggcggcaag gttacctgta gctcctttaa gaaaatgcaa agaagtgaaa gtggagaaac
1561 ccacagcaga tgcagaggcc tatgttttca ctcctaacat gatctgtgct ggaggagaga
1621 agggcatgga tagctgtaaa ggggacagtg gtggggcctt tgctgtacag gatcccaatg
1681 acaagaccaa attctacgca gctggcctgg tgtcctgggg gccccagtgt gggacctatg
1741 ggctctacac acgggtaaag aactatgttg actggataat gaagactatg caggaaaata
1801 gcaccccccg tgaggactaa tccagataca tcccaccagc ctctccaagg gtggtgacca
1861 atgcattacc ttctgttcct tatgatattc tcattatttc atcatgactg aaagaagaca
1921 cgagcgaatg atttaaatag aacttgattg ttgagacgcc ttgctagagg tagagtttga
1981 tcatagaatt gtgctggtca tacatttgtg gtctgactcc ttggggtcct ttccccggag
2041 tacctattgt agataacact atgggtgggg cactcctttc ttgcactatt ccacagggat
2101 accttaattc tttgtttcct ctttacctgt tcaaaattcc atttacttga tcattctcag
2161 tatccactgt ctatgtacaa taaaggatgt ttataagc SEQ ID NO:70
   1 aaactctgat ctggggagga accaggacta catagatcaa ggcagttttc ttctttgaga
  61 aactatccca gatatcatca tagagtcttc tgctcttcct caactaccaa agaaaaacat
 121 cagcgaagca gcaggccatg caccccccaa aaactccatc tggggctctt catagaaaaa
 181 ggaaaatggc agcctggccc ttctccaggc tgtggaaagt ctctgatcca attctcttcc
 241 aaatgacctt gatcgctgct ctgttgcctg ctgttcttgg caattgtggt cctccaccca
 301 ctttatcatt tgctgccccg atggatatta cgttgactga gacacgctc aaaactggaa
 361 ctactctgaa atacacctgc ctccctggct acgtcagatc ccattcaact cagacgctta
 421 cctgtaattc tgatggcgaa tgggtgtata acaccttctg tatctacaaa cgatgcagac
 481 acccaggaga gttacgtaat gggcaagtag agattaagac agatttatct tttggatcac
 541 aaatagaatt cagctgttca gaaggatttt tcttaattgg ctcaaccact agtcgttgtg
 601 aagtccaaga tagaggagtt ggctggagtc atcctctccc acaatgtgaa attgtcaagt
 661 gtaagcctcc tccagacatc aggaatggaa ggcacagcgg tgaagaaaat ttctacgcat
 721 acggcttttc tgtcacctac agctgtgacc cccgcttctc actcttgggc catgcctcca
 781 tttcttgcac tgtggagaat gaaacaatag gtgtttggag accaagccct cctacctgtg
 841 aaaaaatcac ctgtcgcaag ccagatgttt cacatgggga atggtctct ggatttggac
 901 ccatctataa ttacaaagac actattgtgt taagtgcca aaaaggtttt gttctcagag
 961 gcagcagtgt aattcattgt gatgctgata gcaaatggaa tccttctcct cctgcttgtg
1021 agcccaatag ttgtattaat ttaccagaca ttccacatgc ttcctgggaa acatatccta
1081 ggccgacaaa agaggatgtg tatgttgttg ggactgtgtt aaggtaccgc tgtcatcctg
1141 gctacaaacc cactacagat gagcctacga ctgtgatttg tcagaaaaat ttgagatgga
1201 ccccatacca aggatgtgag gcgttatgtt gccctgaacc aaagctaaat aatggtgaaa
1261 tcactcaaca caggaaaagt cgtcctgcca atcactgtgt ttatttctat ggagatgaga
1321 tttcattttc atgtcatgag accagtaggt tttcagctat atgccaagga gatggcacgt
1381 ggagtccccg aacaccatca tgtggagaca tttgcaattt cctcctaaa attgcccatg
1441 ggcattataa acaatctagt tcatacagct ttttcaaaga agagattata tatgaatgtg
```

FIG. 10 A-61

```
1501 ataaaggcta cattctggtc ggacaggcga aactctcctg cagttattca cactggtcag
1561 ctccagcccc tcaatgtaaa gctctgtgtc ggaaaccaga attagtgaat ggaaggttgt
1621 ctgtggataa ggatcagtat gttgagcctg aaaatgtcac catccaatgt gattctggct
1681 atggtgtggt tggtccccaa agtatcactt gctctgggaa cagaacctgg tacccagagg
1741 tgcccaagtg tgagtgggag accccgaag gctgtgaaca agtgctcaca ggcaaaagac
1801 tcatgcagtg tctcccaaac ccagaggatg tgaaaatggc cctgaggta tataagctgt
1861 ctctggaaat tgaacaactg gaactacaga gagacagcgc aagacaatcc actttggata
1921 aagaactata ttttctca aaagaaggag gaaaaggtgt cttgctggct tgcctcttgc
1981 aattcaatac agatcagttt agcaaatcta ctgtcaattt ggcagtgata ttcatcataa
2041 taaatatcta gaaatgataa tttgctaaag tttagtgctt tgagattgtg aaattattaa
2101 tcatcctctg tgtggctcat gttttgctt ttcaacacac aaagcacaaa ttttttttcg
2161 attaaaaatg tatgtat
```

SEQ Id NO:71
```
   1 gccctgctgg ccctgctggt gctcccnnnn nnnnnnnnnn nnnnnnnnnn nnnggtcctc
  61 aaggcccacg tggtgacaaa ggtgaaacag gtgaacgtgg agctgctggc atcaaaggac
 121 atcgaggatt ccctggtaat ccaggtgccc caggttctcc agggccctgc tggtcagcag
 181 ggtgcaatcg gcagtccagg acctgcaggc cccagaggac ctgttggacc cagtggacct
 241 cctggcaaag atggaaccag tggacatcca ggtcccattg gaccaccagg gcctcgaggt
 301 aacagaggtg aaagaggatc tgagggctcc ccaggccacc cagggcaacc aggccctcct
 361 ggacctcctg gtgcccctgg tccttgc
```

SEQ Id NO:72
```
   1 gggcgcgggg agagggcgcg ggagcggctc gcgcggcagg taccatgcgg acgcgcgagc
  61 ccggcgaggg ccccggcagg cccggtccct gctcggggc gcgctgagac ggcggtgag
 121 ctccacgaga gcgccgtcgc cacttcgggc caactttgcg attcccgaca gttaagcaat
 181 ggggagacat ttggctttgc tcctgcttct gctccttctc ttccaacatt ttggagacag
 241 tgatgcgagc caacgagttg aacagactcg tctgcagttt acacaccgtg agtacaacgt
 301 caccgtgcag gagaactctg cagctaagac ttatgtgggg catcctgtca agatgggtgt
 361 ttacattaca catccagcgt gggaagtaag gtacaaaatt gtttccggag acagtgaaaa
 421 cctgttcaaa gctgaagagt acattctcgg agacttttgc tttctaagaa taaggaccaa
 481 aggaggaaat acagctattc ttaatagaga agtgaaggat cactacacat tgatagtgaa
 541 agcacttgaa aaaaatacta atgtggaggc gcgaacaaag gtcagggtgc aggtgctgga
 601 tacaaatgac ttgagaccgt tattctcacc cacctcatac agcgtttctt tacctgaaaa
 661 cacagctata aggaccagta tcgcaagagt cagcgccacg gatgcagaca taggaaccaa
 721 cgggggaattt tactacagtt ttaaagatcg aacagatatg tttgctattc acccaaccag
 781 tggtgtgata gtgttaactg gtagacttga ttacctagag accaagctct atgagatgga
 841 aatcctcgct gcggaccgtg gcatgaagtt gtatgggagc agtggcacag gcagcagtgg
 901 caagctaacg gtgcacatcg aacaggccaa tgaatgtgct ccggtgataa cagcagtgac
 961 attgtcacca tcagaactgg acagggaccc agcatatgca attgtgacag tggatgactg
1021 cgatcagggt gccaatggtg acatagcatc tttaagcatc gtggcaggtg accttctcca
1081 gcagtttaga acagtgaggt cctttccagg gagtaaggag tataaagtca aagccatcgg
1141 tggcattgat tgggacagtc atccttcggg ctacaatctc acactcagg ctaaagataa
1201 aggaactccg ccccagttct cttctgttaa agtcattcac gtgacttctc cacagttcaa
1261 agccgggcca gtcaagtttg aaaaggatgt ttacagagca gaaataagtg aatttgctcc
1321 tcccaacaca cctgtggtca tggtaaaggc cattcctgct tattcccatt tgaggtatgt
1381 ttttaaaagt acacctggaa aagctaaatt cagtttaaat tacaacactg gtctcatttc
1441 tattttagaa ccagttaaaa gacagcaggc agcccatttt gaacttgaag taacaacaag
1501 tgacagaaaa gcgtccacca aggtcttggt gaaagtctta ggtgcaaata gcaatccccc
1561 tgaatttacc cagacagcgt acaaagctgc ttttgatgag aacgtgccca ttggtactac
```

FIG. 10 A-62

```
1621 tgtcatgagc ctgagtgccg tagaccctga tgagggtgag aacgggtacg tgacatacag
1681 tatcgcaaat ttaaatcatg tgccgtttgc gattgaccat ttcactggtg ccgtgagtac
1741 gtcagaaaac ctggactacg aactgatgcc tcgggtttat actctgagga ttcgtgcatc
1801 agactggggc ttgccgtacc gccgggaagt cgaagtcctt gctacaatta ctctcaataa
1861 cttgaatgac aacacacctt tgtttgagaa aataaattgt gaagggacaa ttcccagaga
1921 tctaggcgtg ggagagcaaa taaccactgt ttctgctatt gatgcagatg aacttcagtt
1981 ggtacagtat cagattgaag ctggaaatga actggatttc tttagtttaa accccaactc
2041 gggggtattg tcattaaagc gatcgctaat ggatggctta ggtgcaaagg tgtctttcac
2101 agtctgagaa tcacagctac agatggagaa aattttgcca caccattata tatcaacata
2161 acagtggctg ccagtcacaa gctggtaaac ttgcagtgtg aagagactgg tgttgccaaa
2221 atgctggcag agaagctcct gcaggcaaat aaattacaca accagggaga ggtggaggat
2281 attttcttcg attctcactc tgtcaatgct cacataccgc agtttagaag cactcttccg
2341 actggtattc aggtaaagga aaaccagcct gtgggttcca gtgtaatttt catgaactcc
2401 actgaccttg acactggctt caatgcaaaa ctggtctatg ctgtttctgg aggaaatgag
2461 gatagttgct tcatgattga tatggaaaca ggaatgctga aaattttatc tcctcttgac
2521 cgtgaaacaa cagacaaata caccctgaat attaccgtct atgaccttgg gatacccag
2581 aaggctgcgt ggcgtcttct acatgtcgtg gttgtcgatg ccaatgataa tccacccgag
2641 ttttacagg agagctattt tgtggaagtg agtgaagaca aggaggtaca tagtgaaatc
2701 atccaggttg aagccacaga taaagacctg gggcccaacg gacacgtgac gtactcaatt
2761 gttacagaca cagacacatt ttcaattgac agcgtgacgg gtgttgttaa catcgcacgc
2821 cctctggatc gagagctgca gcatgagcac tccttaaaga ttgaggccag ggaccaagcc
2881 agagaagagc ctcagctgtt ctccactgtc gttgtgaaag tatcactaga agatgttaat
2941 gacaaacccac ctacatttat tccacctaat tatcgtgtga aagtccgaga ggatcttcca
3001 gaaggaaccg tcatcatgtg gttagaagcc cacgatcctg atttaggtca gtctggtcag
3061 gtcagcacac agccttctgg accacggaga aggaaacttc gatgtggata aactcagtgg
3121 agcagttagg atcgtccagc agttggactt tgagaagaag caagtgtata atctcactgt
3181 gagggccaaa gacaagggaa agccagtttc tctgtcttct acttgctatg ttgaagttga
3241 ggtggttgat gtgaatgaga acctgcaccc acccgtgttt tccagctttg tggaaagggg
3301 gacagtgaaa gaagatgcac ctgttggttc attggtaatg acggtgtcgg ctcatgatga
3361 ggacgccaga agagatgggg agatccgata ctccattaga gatggctctg gcgttggtgt
3421 tttcaaaata ggtgaagaga caggtgtcat agagacgtca gatcgactgg accgtgaatc
3481 gacctcccat tattggctaa cagtctttgc aaccgatcag ggtgtcgtgc ctctttcatc
3541 gttcatagag atctacatag aggttgagga tgtcaatgac aatgcaccac agacatcaga
3601 gcctgtttat tacccagaaa tcatggaaaa ttctcctaaa gatgtatctg tggtccagat
3661 cgaggcattt gatccagatt cgagctctaa tgacaagctc atgtacaaaa ttacaagtgg
3721 aaatccacaa ggattctttt caatacatcc taaaacaggt ctcatcacaa ctacgtcaag
3781 gaagctagac cgagaacagc aagatgaaca catattagag gttactgtga cagacaatgg
3841 tagtcccccc aaatcaacca ttgcaagagt cattgtgaaa atccttgatg aaaatgacaa
3901 caaacctcag tttctgcaaa agttctacaa aatcagactc cctgagcggg aaaagccaga
3961 ccgagaaaga aatgccagac gggagccgct ctatcgcgtc atagccaccg acaaggatga
4021 gggcccccaat gcagaaatct cctacagcat cgaagacggg aatgagcatg gcaaattttt
4081 catcgaaccg aaaactggag tggtttcgtc caagaggttt tcagcagctg gagaatatga
4141 tattctttca attaaggcag ttgacaatgg tcgccctcaa aagtcatcaa ccaccagact
4201 ccatattgaa tggatctcca agcccaaacc gtccctggag cccatttcat ttgaagaatc
4261 attttttacc tttactgtga tggaaagtga ccccgttgct cacatgattg gagtaatatc
4321 tgtggagcct cctggcatac ccctttggtt tgacatcact ggtggcaact acgacagtca
4381 cttcgatgtg gacaagggaa ctggaaccat cattgttgcc aaacctcttg atgcagaaca
4441 gaagtcaaac tacaacctca cagtcgaggc tacagatgga accaccacta tcctcactca
4501 ggtattcatc aaagtaatag acacaaatga ccatcgtcct cagttttcta catcaaagta
4561 tgaagttgtt attcctgaag atacagcgcc agaaacagaa attttgcaaa tcagtgctgt
```

FIG. 10 A-63

```
4621 ggatcaggat gagaaaaaca aactaatcta cactctgcag agcagtagag atccactgag
4681 tctcaagaaa tttcgtcttg atcctgcaac cggctctctc tatacttctg agaaactgga
4741 tcatgaagct gttcaccagc acaccctcac ggtcatggta cgagatcaag atgtgcctgt
4801 aaaacgcaac tttgcaagga ttgtggtcaa tgtcagcgac acgaatgacc acgcccccgtg
4861 gttcaccgct tcctcctaca aagggcgggt ttatgaatcg gcagccgttg gctcagttgt
4921 gttgcaggtg acggctctgg acaaggacaa agggaaaaat gctgaagtgc tgtactcgat
4981 cgagtcagnn nnnnnnngaa atattggaaa ttcttttatg attgatcctg tcttgggctc
5041 tattaaaact gccaaagaat tagatcgaag taaccaagcg gagtatgatt taatggtaaa
5101 agctacagat aagggcagtc caccaatgag tgaaataact tctgtgcgta tctttgtcac
5161 aattgctgac aacgcctctc cgaagtttac atcaaaagaa tattctgttg aacttagtga
5221 aactgtcagc attgggagtt tcgttgggat ggttacagcc catagtcaat catcagtggt
5281 gtatgaaata aaagatggaa atacaggtga tgcttttgat attaatccac attctggaac
5341 tatcatcact cagaaagccc tggactttga aactttgccc atttacacat tgataataca
5401 aggaactaac atggctggtt tgtccactaa tacaacggtt ctagttcact tgcaggatga
5461 gaatgacaac gcgccagttt ttatgcaggc agaatataca ggactcatta gtgaatcagc
5521 ctcaattaac agcgtggtcc taacagacag gaatgtccca ctggtgattc gagcagctga
5581 tgctgataaa gactcaaatg ctttgcttgt atatcacatt gttgaaccat ctgtacacac
5641 atattttgct attgattcta gcactggtgc tattcataca gtactaagtc tggactatga
5701 agaaacaagt attttttcact ttaccgtcca agtgcatgac atgggaaccc cacgtttatt
5761 tgctgagtat gcagcgaatg taacagtaca tgtaattgac attaatgact gcccccctgt
5821 gtttgccaag ccattatatg aagcatctct tttgttacca acatacaaag gagtaaaagt
5881 catcacagta aatgctacag atgctgattc aagtgcattc tcacagttga tttactccat
5941 caccgaaggc aacatcgggg agaagttttc tatggactac aagactggtg ctctcactgt
6001 ccaaaacaca actcagttaa gaagccgcta cgagctaacc gttagagctt ccgatgcag
6061 atttgccggc cttacctctg tcaaaattaa tgtgaaagaa agcaaagaaa gtcacctaaa
6121 gtttacccag gatgtctact ctgcggtagt gaaagagaat tccaccgagg ccgaaacatt
6181 agctgtcatt actgctattg ggaatccaat caatgagcct ttgttttatc acatcctcaa
6241 cccagatcgc agatttaaaa taagccgcac ttcaggagtt ctgtcaacca ctggcacgcc
6301 cttcgatcgt gagcagcagg aggcgtttga tgtggttgta gaagtgacag aggaacataa
6361 gccttctgca gtgcccacg ttgtcgtgaa ggtcattgta gaagaccaaa atgataatgc
6421 gccggtgttt gtcaaccttc cctactacgc cgttgttaaa gtggacactg aggtgggcca
6481 tgtcattcgc tatgtcactg ctgtagacag agacagtggc agaaacgggg aagtgcatta
6541 ctacctcaag gaacatcatg aacactttca aattggaccc ttgggtgaaa tttcactgaa
6601 aaagcaattt gagcttgaca ccttaaataa agaaatatct gttacagtgg ttgcaaaaga
6661 tggagggaac ccggcctttt cagcggaagt tatcgttccg atcactgtca tgaataaagc
6721 catgcctgtg tttgaaaaac ctttctacag tgcagagatt gcagagagca tccaggtgca
6781 cagccctgtg gtccacgtgc aggctaacag cccgaaggc ctgaaagtgt tctacagcat
6841 cacagacgga gacccttca gccagttcac tattaacttc aatactggag ttatcaatgt
6901 catagctcct ctggactttg aggcccaccc ggcatataag ctgagcatac gcgcaactga
6961 ctccttgacg ggcgctcatg ctgaagtatt tgtgacatca atagtagacg acatcaatga
7021 taaccctcct gtgtttgctc agcagtctta tgcggtgacc ctgtctgagg catctgtaat
7081 tggaacgtct gttgttcaag ttagagccac cgattctgat tcagaaccaa atagaggaat
7141 ctcataccag atgtttggga tcacagcaa gagtcatgat cattttcatg tagacagcag
7201 cactggcctc atctcactac tcagaaccct ggattacgag cagtcccggc agcacacgat
7261 ttttgtgagg gcagttgatg gtggtatgcc cacgctgagc agtgatgtga ttgtcacggt
7321 ggacgttacc gacctcaatg ataatccacc actctttgaa caacagattt atgaagccag
7381 aattagcgag cacgccctc atgggcattt cgtgacctgt gtaaaagcct atgatgcaga
7441 cagttcagac atagacaagt tgcagtattc cattctgtct ggcaatgatc ataaacattt
7501 tgtcattgac agtgcaacag ggattatcac cctctcaaac ctgcaccggc acgccctgaa
7561 gccatttac agtcttaacc tgtcagtgtc tgatggagtt tttagaagtt ccacccaggt
```

FIG. 10 A-64

```
7621 tcatgtaact gtaattggag gcaatttgca cagtcctgct ttccttcaga acgaatatga
7681 agtggaacta gctgaaaacg ctcccctaca tacccctggtg atggaggtga aaactacgga
7741 tggggattct ggtatttatg gtcacgttac ttaccatatt gtaaatgact ttgccaaaga
7801 cagattttac ataaatgaga gaggacagat atttactttg gaaaaacttg atcgagaaac
7861 cccggcggag aaagtgatct cagtccgttt aatggctaag gatgctggag gaaaagttgc
7921 tttctgcacc gtgaatgtca tccttacaga tgacaatgac aatgcaccac aatttcgagc
7981 aaccaaatac gaagtgaata tcgggtccag tgctgctaaa gggacttcag tcgttaaagt
8041 tcttgcaagt gatgccgatg agggctccaa tgccgacatc acctatgcca ttgaagcaga
8101 ctctgaaagt gtaaaagaga atttgaaaat taacaaactg tccggcgtaa tcactacaaa
8161 ggagagcctc attggcttgg aaaatgaatt cttcactttc tttgttagag ctgtggataa
8221 tgggtctcca tcaaaagaat ctgttgttct tgtctatgtt aaaatccttc caccggaaat
8281 gcagcttcca aaattttcag aacctttcta taccttaca gtgtcagagg acgtgcctat
8341 tggaacagag atagatctca tccgagcaga acatagtggg actgttcttt acagcctggt
8401 caaagggaat actccagaaa gcaataggga tgagtccttt gtgattgaca gacagagcgg
8461 gagactgaag ttggagaaga gtcttgatca tgagacaact aagtggtatc agttttccat
8521 actggccagg tgcactcaag atgaccatga gatggtggct tctgtagatg ttagtatcca
8581 agtgaaagat gcaaatgaca acagcccggt ctttgaatct agtccatatg aggcattcat
8641 tgttgaaaac ctgccaggggg gaagtagagt aattcagatc agggcatctg atgctgactc
8701 aggaaccaac ggccaagtta tgtatagcct ggatcagtca caaagtgtgg aagtcattga
8761 atcctttgcc attaacatgg aaacaggctg gattacaact ttaaaggaac ttgaccatga
8821 aaagagagac aattaccaga ttaaagtggt tgcatcagat catggtgaaa agatccagct
8881 atcctccaca gccattgtgg atgttaccgt caccgatgtc aacgatagtc caccacgatt
8941 cacggccgag atctataaag ggactgtgag tgaggatgac ccccaaggtg gggtgattgc
9001 catcttaagt accacggatg ctgattctga agagatcaac agacaagtta catatttcat
9061 aacaggaggg gatcctttag gacagttttgc cgttgaaact atacagaatg aatggaaggt
9121 atatgtgaag aaacctctag acagggaaaa aagggacaat taccttctta ctatcacggc
9181 aactgatggc accttctcat caaaagcgat agttgaagtg aaagttctgg atgcaaatga
9241 caacagtcca gttgtgaaa agacttata ttcagcact attcctgaag acgtccttcc
9301 tggaaaattg atcatgcaga tctctgctac agacgcagac atccgctcta acgctgaaat
9361 tacttacacg ttattgggtt caggtgcaga aaaattcaaa ctaaatccag acacaggtga
9421 actgaaaacg tcaaccccc ttgatcgtga ggagcaagct gtttatcatc ttctcgtcag
9481 ggccacagat ggaggaggaa gattctgcca agccagtatt gtgctcacgc tagaagatgt
9541 gaacgataac gcccccgaat tctctgccga tccttatgcc atcaccgtgt ttgaaaacac
9601 agagccggga acgctgctga caagagtgca ggccacagat gccgacgcag gattaaatcg
9661 gaagatttta tactcactga ttgactctgc tgatgggcag ttctccatta acgaattatc
9721 tggaattatt cagttagaaa aacctttgga cagagaactc caggcagtat acaccctctc
9781 tttgaaagct gtgatcaag gcttgccaag gaggctgact gccactggca ctgtgattgt
9841 atcagttctt gacataaatg acaacccccc tgtgtttgag taccgtgaat atggtgccac
9901 cgtgtctgag gacattcttg ttggaactga agttcttcaa gtgtatgcag caagtcggga
9961 tattgaagca aatgcagaaa tcacctactc aataataagt ggaaatgaac atgggaaatt
10021 cagcatagat tctaaaacag nnnnnnnnnn nnnnnnnnnn nnnnnnnnnn nnnnnnnnnn
10081 nnnnnnnnnn nnnnnnnnnn nnnnnnnnnn nnnnnnnnnn nnnnnnnnnn nnnnnnnnnn
10141 nnnnnnnnnn nnnnnnnnnn nnnnnnnnnn nnnnnnnnnn nnnnnnnnnn nnnnnnnnnn
10201 nnnnnnnnnn nnnnnnnnnn nnnnnnnnnn nnnnnnnnnn nnnnnnnnnn nnnnnnnnnn
10261 nnnnnnnnnn nnnnnnnnnn nnnnnnnnnn nnnnnnnnnn nnnnnnnnnn nnnnnnnnnn
10321 nnnnnnnnnn nnnnnnnnnn nnnnnnnnnn nnnnnnnnnn nnnnnnnnnn nnnnnnnnnn
10381 nnnnnnnnnn nnnnnnnnnn nnnnnnnnnn nnnnnnnnnn nnnnnnnnnn nnnnnnnnnn
10441 nnnnnnnnnn nnnnnnnnnn nnnnnnnnnn nnnnnnnnnn nnnnnnnnnn nnnnnnnnnn
10501 nnnnnnnnnn nnnnnnnnnn nnnnnnnnnn nnnnnngaa aataagccag tgggcttcag
10561 cgtgctgcag ctggtagtaa cagatgagga ttcttcccat aacggtccac ccttcttctt
```

FIG. 10 A-65

```
10621 tactattgta actggaaatg atgagaaggc ttttgaagtt aacccgcaag gagtcctcct
10681 gacatcatct gccatcaaga ggaaggagaa agatcattac ttactgcagg tgaaggtggc
10741 agataatgga aagcctcagt tgtcatcttt gacatacatt gacattaggg taattgagga
10801 gagcatctat ccgcctgcga ttttgcccct ggagattttc atcacctctt ctggagaaga
10861 atactcaggt ggcgtcattg ggaagatcca tgccacagac caggacgtgt atgatactct
10921 aacctacagt ctcgaccctc agatggacaa cctgttctct gtttccagca caggggggcaa
10981 gctgatagca cacaaaaagc tagacatagg gcaataccttc ctcaatgtca gcgtaacaga
11041 tgggaagttc acgacggtgg ccgacatcac agtgcatatc agacaagtca cacaggagat
11101 gttgaaccac accatcgcga tccgctttgc caacctcact ccggaagaat tcgttggtga
11161 ctactggcgc aacttccagc gagctttacg gaacatcctg ggtgtgagga ggaacgacat
11221 acagattgtt agtttgcagt cctctgaacc tcacccacat ctggacgtct tactttttgt
11281 agagaaacca ggtagtgctc agatctcaac aaaacaactt ctgcacaaga ttaactcttc
11341 cgtgactgac attgaggaaa tcattggagt taggatactg aatgtattcc agaaactctg
11401 cgcgggactg gactgcccct ggaagttctg cgatgaaaag gtgtctgtgg atgaaagtgt
11461 gatgtcaaca cacagcacag ccagactgag ttttgtgact ccccgccacc acagggcagc
11521 ggtgtgtctc tgcaaagagg gaaggtgccc acctgtccac catggctgtg aagatgatcc
11581 gtgccctgag ggatccgaat gtgtgtctga tccctgggag gagaaacaca cctgtgtctg
11641 tcccagcggc aggtttggtc agtgcccagg gagttcatct atgacactga ctggaaacag
11701 ctacgtgaaa taccgtctga cggaaaatga aaacaaatta gagatgaaac tgaccatgag
11761 gctcagaaca tattccacgc atgcggttgt catgtatgct cgaggaactg actatagcat
11821 cttggagatt catcatggaa ggtgcagtca annnnnnnnn nnnnnnnnnn nnnnnnnnnn
11881 nnnnnnnnnn nnncattcag gtcaatgatg ggcagtggca cgcagtggcc ctggaagtga
11941 atggaaacta tgctcgcttg gttctagacc aagttcatac tgcatcgggc acagcccag
12001 ggactctgaa aaccctgaac ctggataact atgtgttttt tggtggccac atccgtcagc
12061 agggaacaag gcatggaaga agtcctcaag ttggtaatgg tttcaggggt tgtatggact
12121 ccatttattt gaatgggcag gagctccctt taaacagcaa acccagaagc tatgcacaca
12181 tcgaagagtc ggtggatgta tctccaggct gcttcctgac ggccacggaa gactgcgcca
12241 gcaacccttg ccagaatgga ggcgtttgca atccgtcacc tgctggaggt tattactgca
12301 aatgcagtgc cttgtacata gggacccact gtgagataag cgtcaatccg tgttcctcca
12361 agccatgcct ctatgggggc acgtgtgttg tcgacaacgg aggctttgtt tgccagtgta
12421 gaggattata tactggtcag aggtgtcagc ttagtccata ctgcaaagat gaacctgta
12481 agaatggcgg aacatgcttt gacagtttgg atggcgccgt tgtcagtgt gattcgggtt
12541 ttaggggaga aaggtgtcag agtgatatcg acgagtgctc tggaaaccct tgcctgcacg
12601 gggccctctg tgagaacacg cacggctcct atcactgcaa ctgcagccac gagtacaggg
12661 gacgtcactg cgaggatgct gcgcccaacc agtatgtgtc cacgccgtgg aacattgggt
12721 tggcggaagg aattggaatc gttgtgtttg ttgcagggat attttactg gtggtggtgt
12781 ttgttctctg ccgtaagatg attagtcgga aaaagaagca tcaggctgaa cctaaagaca
12841 agcacctggg acccgctacg gctttcttgc aaagaccgta ttttgattcc aagctaaata
12901 agaacattta ctcagacata ccaccccagg tgcctgtccg gcctattcc tacacccga
12961 gtattccaag tgactcaaga aacaatctgg accgaaattc cttcgaagga tctgctatcc
13021 cagagcatcc cgaattcagc acttttaacc ccgagtctgt gcacgggcac cgaaaagcag
13081 tggcggtctg cagcgtggcg ccaaacctgc ctccccacc ccttcaaac tcccccttctg
13141 acagcgactc catccagaag cctagctggg actttgacta tgacacaaaa gtggtggatc
13201 ttgatccctg tctttccaag aagcctctag aggaaaagcc ttcccagcca tacagtgccc
13261 gggaaagcct gtctgaagtg cagtctctga gtcctccta gtccgatcg tgcatgaca
13321 atgggtatca ctgggataca tcagattgga tgccaagcgt tcctctgccg gacataagg
13381 agttccccaa ctatgaggtg attgatgagc agacccccct gtactcagca gatccaaacg
13441 ccatcgatac ggactattac cctggaggct acgacatcga aagtgatttt ctccacccc
13501 cagaagactt ccccgcagct gatgagctac caccgttacc gcccgaattc agcaatcagt
13561 ttgaatccat ccaccctcct agagacatgc ctgccgcggg tagctgggt tcttcatcaa
```

FIG. 10 A-66

```
13621 gaaaccggca gaggttcaac ttgaatcagt atttgcccaa tttttatccc ctcgatatgt
13681 ctgaacctca aacaaaaggc actggtgaga atagtacttg tagagaaccc catgcccctt
13741 acccgccagg gtatcaaaga cacttcgagg cgccgctgt cgagagcatg cccatgtctg
13801 tgtacgcctc caccgcctcc tgctctgacg tgtcagcctg ctgcgaagtg gagtccgagg
13861 tcatgatgag tgactatgag agcggggacg acggccactt cgaagaggtg acgatcccgc
13921 ccctggattc ccagcagcac acggaagtct gactctcaac tccccccaaa gtgcctgact
13981 ttagtgaacc tagaggtgat gtgagtaatc cgcgctgttc tttgcagcag tgcttccaag
14041 ctttttttgg tgagccgaat gggcatggct gcgctggatc ctgcgcctct ggacgtgcta
14101 gccatttcca gtgtcccaac tactgtcatc gtgaggtttt catcggctgt gccatttccc
14161 aacgtctttt gggatttaca tctgtctgtg ttaaaataat caaacgaaaa atcagtcctg
14221 tgttgtcagc atgattcatg tatttatata gatttgatta ttttaatttt cctgtctctt
14281 tttttgtaa atttatgta cagatttgat ttttcatagt tttaactaga tttccaagat
14341 attttgtgca tttgtttcaa ctgaattttg gtggtgtcag tgccattatc tagcaccctg
14401 attttttttt ttttactata accagggttt cattctgtct ttttccactg aagtgtgaca
14461 ttttgttagt acatttcagt gtagtcattc atttctagct gtacatagga tgaaggagag
14521 atcagataca tgaacatgtc ttacatggct tgctgtattt agaattataa acatttttca
14581 ttattggaaa gtgtaacggg gaccttctgc ataccgtttt agaaccaaaa ccaccatgac
14641 acagttttta tagtgtctgt atatttgtga tgcaatggtc ttgtaaaggt ttttaatgaa
14701 aactaccatt agccagtctt tcttactgac aataaattat taataaaat SEQ Id NO:73
    1 gattttaggt gatgggcaag tcagaaagtc agatggatat aactgatatc aacactccaa
   61 agccaaagaa gaaacagcga tggactccac tggagatcag cctctcggtc cttgtcctgc
  121 tcctcaccat catagctgtg acaatgatcg cactctatgc aacctacgat gatggtattt
  181 gcaagtcatc agactgcata aaatcagctg ctcgactgat ccaaaacatg gatgccacca
  241 ctgagccttg tacagacttt ttcaaatatg cttgcggagg ctggttgaaa cgtaatgtca
  301 ctcccgagac cagctcccgt tacggcaact tgacatttt aagagatgaa ctagaagtcg
  361 ttttgaaaga tgtccttcaa gaacccaaaa ctgaagatat agtagcagtg cagaaagcaa
  421 aagcattgta caggtcttgt ataaatgaat ctgctattga tagcagaggt ggagaacctc
  481 tactcaaact gttaccagac atatatgggt ggccagtagc aacagaaaac tgggagcaaa
  541 aatatggtgc ttcttggaca gctgaaaaag ctattgcaca actgaattct aaatatggga
  601 aaaagtcct tattaatttg tttgttggca ctgatgataa gaattctgtg atcatgtaa
  661 ttcatattga ccaacctcga cttggcctcc cttctagaa ttactatgaa tgcactggaa
  721 tctataaaga ggcttgtaca gcatatgtgg attttatgat ttctgtggcc agattgattc
  781 gtcaggaaga aagattgccc atcgatgaaa accagcttgc tttggaaatg aataaagtta
  841 tggaattgga aaaagaaatt gccaatgcta cggctaaacc tgaagatcga aatgatccaa
  901 tgcttctgta taacaagatg acattggccc agatccaaaa taacttttca ctagagatca
  961 atgggaagcc attcagctgg ttgaatttca caatgaaat catgtcaact gtgaatatta
 1021 gtattacaaa tgaggaagat gtggttgttt atgctccaga atatttaacc aaacttaagc
 1081 ccattcttac caaatattct gccagagatc ttcaaaattt aatgtcctgg agattcataa
 1141 tggatcttgt aagcagcctc agccgaacct acaaggagtc cagaaatgct ttccgcaagg
 1201 cccttttatg tacaacctca gaaacagcaa cttggagacg ttgtgcaaac tatgtcaatg
 1261 ggaatatgga aaatgctgtg gggaggcttt atgtggaagc agcatttgct ggagagagta
 1321 aacatgtggt cgaggatttg attgcacaga tccgagaagt ttttattcag actttagatg
 1381 acctcacttg gatggatgcc gagacaaaaa agagagctga agaaaaggcc ttagcaatta
 1441 aagaaaggat cggctatcct gatgacattg tttcaaatga taacaaactg aataatgagt
 1501 acctcgagtt gaactacaaa gaagatgaat acttcgagaa cataattcaa aatttgaaat
 1561 tcagccaaag taaacaactg aagaagctcc gagaaaaggt ggacaaagat gagtggataa
 1621 gtggagcagc tgtagtcaat gcatttact cttcaggaag aaatcagata gtcttcccag
 1681 ccggcattct gcagccccc ttctttagtg cccagcagtc caactcattg aactatgggg
```

FIG. 10 A-67

```
1741 gcatcggcat ggtcatagga cacgaaatca cccatggctt cgatgacaat ggcagaaact
1801 ttaacaaaga tggagacctc gttgactggt ggactcaaca gtctgcaagt aactttaagg
1861 agcaatccca gtgcatggtg tatcagtatg gaaactttc ctgggacctg gcaggtggac
1921 agcaccttaa tggaattaat acactgggag aaaacattgc tgataatgga ggtcttggtc
1981 aagcatacag agcctatcag aattatatta aaaagaatgg cgaagaaaaa ttacttcctg
2041 gacttgacct aaatcacaaa caactatttt tcttgaactt tgcacaggtg tggtgtggaa
2101 cctataggcc agagtatgcg gttaactcca ttaaaacaga tgtgcacagt ccaggcaatt
2161 tcaggattat tgggactttg cagaactctg cagagttttc agaagccttt cactgccgca
2221 agaattcata catgaatcca gaaaagaagt gccgggtttg gtgatcttca aaagaagcat
2281 tgcagccctt ggctagactt gccaacacca cagaaatggg gaattctcta atcgaaagaa
2341 aatgggccct aggggtcact gtactgactt gagggtgatt aacagagagg gcaccatcac
2401 aatacagata acattaggtt gtcctagaaa gggtgtggag ggaggaaggg ggtctaaggt
2461 ctatcaagtc aatcatttct cactgtgtac ataatgctta atttctaaag ataatattac
2521 tgtttatttc tgtttctcat atggtctacc agtttgctga tgtccctaga aaacaatgca
2581 aaacctttga ggtagaccag gatttctaat caaaagggaa aagaagatgt tgaagaatac
2641 agttaggcac cagaagaaca gtaggtgaca ctatagttta aaacacattg cctaactact
2701 agttttact tttatttgca acatttacag tccttcaaaa tccttccaaa gaattcttat
2761 acacattggg gccttggagc ttacatagtt ttaaactcat ttttgccata catcagttat
2821 tcattctgtg atcatttatt ttaagcactc ttaaagcaaa aatgaatgt ctaaaattgt
2881 tttttgttgt acctgctttg actgatgctg agattcttca ggcttcctgc aattttctaa
2941 gcaatttctt gctctatctc tcaaaacttg gtattttca gagatttata taaatgtaaa
3001 aataataatt tttatattta attattaact acatttatga gtaactatta ttataggtaa
3061 tcaatgaata ttgaagtttc agcttaaaat aaacagttgt gaaccaagat ctataaagcg
3121 atatacagat gaaaatttga gactatttaa acttataaat catattgatg aaaagattta
3181 agcacaaact ttagggtaaa aattgccatt ggacagttgt ctagagatat atatacttgt
3241 ggttttcaaa ttggactttc aaaattaaat ctgtccctga gagtgtctct gataaaaggg
3301 caaatctgca cctatgtagc tctgcatctc ctgtcttttc aggtttgtca tcagatggaa
3361 atattttgat aataaattga aattgtgaac tcattgctcc ctaagactgt gacaactgtc
3421 taactttaga agtgcatttc tgaatagaaa tgggaggcct ctgatggacc ttctagaatt
3481 ataagtcaca aagagttctg gaaaagaact gtttactgct tgataggaat tcatctttg
3541 aggcttctgt tcctctcttt tcctgttgta ttgactattt tcgttcatta cttgattaag
3601 attttacaaa agaggagcac ttccaaaatt cttattttc ctaacaaaag atgaaagcag
3661 ggaatttcta tctaaatgat gagtattagt tccctgtctc ttgaaaaatg cccatttgcc
3721 tttaaaaaaa aaagttacag aaatactata acatatgtac ataaattgca taaagcataa
3781 gtatacagtt caataaactt aactttaact gaacaatggc cctgtagcca gcacctgtaa
3841 gaaacagagc agtaccagcg ctctaaaagc acctccttgt cactttatta ctcccagaac
3901 aacaactatc ctgacttcta atatcattca ctagctttgc ctggttttgt cttttatgca
3961 gatagaatca atcagtatgt attcttttgt gcctggcttc tttctctcag ccttacattt
4021 gtgagattcc tctgtattgt gctgattgtg gatcttttca ttctcattgc agaataatgt
4081 tctattgtgg gacttattac aatttgttca tcctattgtt gatgggcact tgagaacttt
4141 ccatttttggc gctattacaa atagtgcaac tatgaatgta ctgcatgtta ccatcttact
4201 tgagccttta atggacttat ttcttcaaat ccttccaaaa attattataa gcattgaaat
4261 tatagtttca agccaactgt ggatacccctt accctttcct cctttatcac aaccaccgtt
4321 acaagtatac ttatatttcc ctaaaataca tttaaaactt acctaagtga catttgtagt
4381 tggagtaata ggagcttcca gctctaataa aacagctgtc tctaacttat tttatttcca
4441 tcatgtcaga gcaggtgaag agccagaagt gaagagtgac tagtacaaat tataaaaagc
4501 cactagactc ttcactgtta gctttttaaa acattaggct cccatcccta tggaggaaca
4561 actctccagt gcctggatcc cctctgtcta caaatataag atttttctggg cctaaaggat
4621 agatcaaagt caaaaatagc aatgcctccc tatccctcac acatccagac atcatgaatt
4681 ttacatggta ctcttgttga gttctgtaga gccttctgat gtctctaaag cactaccgat
```

FIG. 10 A-68

```
4741 tctttggagt tgtcacatca gataagacat atctctaatt ccatccataa atccagttct
4801 actatggctg agttctggtc aaagaaagaa agtttagaag ctgagacaca aagggttggg
4861 agctgatgaa actcacaaat gatggtagga agaagctctc gacaatoccc gttggcaagg
4921 agtctgcctc catgctgcag tgttcgagtg gattgtaggt gcaagatgga aaggattgta
4981 ggtgcaagct gtccagagaa aagagtcctt gttccagccc tattctgcca ctcctgacag
5041 ggtgaccttg ggtatttgca atattccttt gggcctctgc ttctctcacc taaaaaaaga
5101 gaattagatt atattggtgg ttctcagcaa gagaaggagt atgtgtccaa tgctgccttc
5161 ccatgaatct gtctcccagt tatgaatcag tgggcaggat aaactgaaaa ctcccattta
5221 cgtgtctgaa tcgagtgaga caaaattta gtccaaataa caagtaccaa agttttatca
5281 agtttgggtc tgtgctgctg ttactgttaa ccatttaagt ggggcaaaac cttgctaatt
5341 ttctcaaaag catttatcat tcttgttgcc acagctggag ctctcaaact aaaagacatt
5401 tgttattttg gaaagaagaa agactctatt ctcaaagttt cctaatcaga aatttttatc
5461 agtttccagt ctcaaaaata caaaataaaa acaaacgttt ttaatact
```

SEQ ID NO:74
```
   1 atgtccaatc agggaagtaa gtacgtcaat aaggaaattc aaaatgctgt caacggggtg
  61 aaacagataa agactctcat agaaaaaaca aacgaagagc gcaagacact gctcagcaac
 121 ctagaagaag ccaagaagaa gaaagaggat gccctaaatg agaccaggga atcagagaca
 181 aagctgaaga agctcccagg agtgtgcaat gagaccatga tggccctctg ggaagagtgt
 241 aagccctgcc tgaaacagac ctgcatgaag ttctacgcac gcgtctgcag aagtggctca
 301 ggcctggttg gccgccagct tgaggagttc ctgaaccaga gctcgccctt ctacttctgg
 361 atgaatggtg accgcatcga ctccctgctg gagaacgacc ggcagcagac gcacatgctg
 421 gatgtcatgc aggaccactt cagccgcgcg tccagcatca tagacgagct cttccaggac
 481 aggttcttca cccggggagcc ccaggatacc taccactacc tgcccttcca cctgccccac
 541 cggaggcctc acttcttctt tcccaagtcc cgcatcgtcc gcagcttgat gcccttctct
 601 ccgtacgagc ccctgaactt ccacgccatg ttccagccct tccttgagat gatacacgag
 661 gctcagcagg ccatggacat ccacttccat agcccggcct tccagcaccc gccaacagaa
 721 ttcatacgag aaggcgacga tgaccggact gtgtgccggg agatccgcca caactccacg
 781 ggctgcctgc ggatgaagga ccagtgtgac aagtgccggg agatcttgtc tgtggactgt
 841 tccaccaaca accccctccca ggctaagctg cggcgggagc tcgacgaatc cctccaggtc
 901 gctgagaggt tgaccaggaa atacaacgag ctgctaaagt cctaccagtg gaagatgctc
 961 aacacctcct ccttgctgga gcagctgaac gagcagttta ctgggtgtc ccggctggca
1021 aacctcacgc aaggcgaaga ccagtactat ctgcgggtca ccacggtggc ttcccacact
1081 tctgactcgg acgttccttc cggtgtcact gaggtggtcg tgaagctctt tgactctgat
1141 cccatcactg tgacggtccc tgtagaagtc tccaggaaga accctaaatt tatggagacc
1201 gtggcggaga aagcgctgca ggaataccgc aaaaagcacc gggaggagtg agatgtggat
1261 gttgcttttg cacctacggg ggcatctgag tccagctccc cccaagatga gctgcagccc
1321 cccagagaga gctctgcacg tcaccaagta accaggcccc agcctccagg cccccaactc
1381 cgcccagcct ctccccgctc tggatcctgc actctaacac tcgactctgc tgctcatggg
1441 aagaacagaa ttgctcctgc atgcaactaa ttcaataaaa ctgtcttgtg agctg
```

SEQ ID NO:75
```
   1 gaaggaaaaa gagcaacaga tccagggagc attcacctgc cctgtctcca aacagccttg
  61 tgcctcacct acccccaacc tcccagaggg agcagctatt taagggagc aggagtgcag
 121 aacaaacaag acggcctggg gatacaactc tggagtcctc tgagagagcc accaaggagg
 181 agcaggggag cgacggccgg ggcagaagtt gagaccaccc agcagaggag ctaggccagt
 241 ccatctgcat ttgtcaccca agaactctta ccatgaagac cctcctactg ttggcagtga
 301 tcatgatctt tggcctactg caggcccatg ggaatttggt gaatttccac agaatgatca
 361 agttgacgac aggaaaggaa gccgcactca gttatggctt ctacggctgc cactgtggcg
```

FIG. 10 A-69

```
 421 tgggtggcag aggatccccc aaggatgcaa cggatcgctg ctgtgtcact catgactgtt
 481 gctacaaacg tctggagaaa cgtggatgtg gcaccaaatt tctgagctac aagtttagca
 541 actcggggag cagaatcacc tgtgcaaaac aggactcctg cagaagtcaa ctgtgtgagt
 601 gtgataaggc tgctgccacc tgttttgcta gaaacaagac gacctacaat aaaaagtacc
 661 agtactattc caataaacac tgcagaggga gcacccctcg ttgctgagtc ccctcttccc
 721 tggaaacctt ccacccagtg ctgaatttcc ctctctcata ccctccctcc ctacccctaac
 781 caagttcctt ggccatgcag aaagcatccc tcacccatcc tagaggccag gcaggagccc
 841 ttctataccc acccagaatg agacatccag cagatttcca gccttctact gctctcctcc
 901 acctcaactc cgtgcttaac caaagaagct gtactccggg gggtctcttc tgaataaagc
 961 aattagc
```

SEQ ID NO:76

```
    1 gctccatcaa gtatgatggt gaaggatgaa tatgtgcatg actttgaggg acagccatcg
   61 ttgtccactg aaggacattc aattcaaacc atccagcatc caccaagtaa tcgtgcatcg
  121 acagagacat acagcacccc agctctgtta gccccatctg agtctaatgc taccagcact
  181 gccaactttc ccaacattcc tgtggcttcc acaagtcagc ctgccagtat actgggggc
  241 agccatagtg aaggactgtt gcagatagca tcagggcctc agccaggaca gcagcagaat
  301 ggatttactg gtcagccagc tacttaccat cataacagca ctaccacctg gactggaagt
  361 aggactgcac catacaccc taatttgcct caccacaaca acggccatct tcagcaccac
  421 ccgcctatgc cgccccatcc cggacattac tggcctgttc acaatgagct tgcattccag
  481 cctcccattt ccaatcatcc tgctcctgag tattggtgtt ccattgctta ctttgaaatg
  541 gatgttcagg taggagagac atttaaggtt ccttcaagct gcccctattgt tactgttgat
  601 ggatacgtgg acccttctgg aggagatcgc ttttgtttgg gtcaactctc caatgtccac
  661 aggacagaag ccattgagag agcaaggttg cacataggca aaggtgtgca gttgaatgt
  721 aaaggtgaag gtgatgtttg ggtcaggtgc cttagtgacc acgcggtctt tgtacagagt
  781 tactacttag acagagaagc tgggcgtgca cctggagatg ctgttcataa gatctaccca
  841 agtgcatata taaaggtctt tgatttgcgt cagtgtcatc gacagatgca gcagcaggcg
  901 gctactgcac aagctgcagc agctgcccag gcagcagccg tggcaggaaa catccctgc
  961 ccaggatcag taggtggaat agctccagct atcagtctgt cagctgctgc tggaattggt
 1021 gttgatgacc ttcgtcgctt atgcatactc aggatgagtt ttgtgaaagg ctggggaccg
 1081 gattacccaa gacagagcat caaagaaaca ccttgctgga ttgaaattca cttacaccgg
 1141 gccctccagc tcctagacga agtacttcat accatgccga ttgcagaccc acaaccttta
 1201 gactgaggtc ttttaccgtt ggggcccta accttatcag gatggtggac tacaaaatac
 1261 aatcctgttt ataatctgaa gatatatttc acttttgttc tgctttatct tttcataaag
 1321 ggttgaaaat gtgtttgctg ccttgctcct agcagacaga aactggatta aaacaatttt
 1381 ttttttcctc ttcagaactt gtcaggcatg gctcagagct tgaagattag gagaaacaca
 1441 ttcttattaa ttcttcacct gttatgtatg aaggaatcat tccagtgcta gaaaatttag
 1501 cccttttaaa cgtcttagag ccttttatct gcagaacatc gatatgtata tcattctaca
 1561 gaataatcca gtattgctga ttttaaaggc agagaagttc tcaaagttaa ttcacctatg
 1621 ttattttgtg tacaagttgt tattgttgaa catacttcaa aaataatgtg ccatgtgggt
 1681 gagttaattt taccaagagt aactttactc tgtgtttaaa aagtaagtta ataatgtatt
 1741 gtaatctttc atccaaaata tttttttgcaa gttatattag tgaagatggt ttcaattcag
 1801 attgtcttgc aacttcagtt ttattttgc caaggcaaaa aactcttaat ctgtgtgtat
 1861 attgagaatc ccttaaaatt accagacaaa aaaatttaaa attacgtttg ttattcctag
 1921 tggatgactg ttgatgaagt atacttttcc cctgttaaac agtagttgta ttcttctgta
 1981 tttctaggca caaggttggt tgctaagaag cctataagag gaatttcttt tccttcattc
 2041 atagggaaag gttttgtatt ttttaaaaca ctaaaagcag cgtcactcta cctaatgtct
 2101 cactgttctg caaaggtggc aatgcttaaa ctaaataatg aataaactga atattttgga
 2161 aactgctaaa ttctatgtta aatactgtgc agaataatgg aaacattaca gttcataata
 2221 ggtagtttgg atatttttgt acttgatttg atgtgacttt ttttggtata atgtttaaat
```

FIG. 10 A-70

```
2281 catgtatgtt atgatattgt ttaaaattca gtttttgtat cttggggcaa gactgcaaac
2341 ttttttatat cttttggtta ttctaagccc tttgccatca atgatcatat caattggcag
2401 tgactttgta tagagaattt aagtagaaaa gttgcagatg tattgactgt accacagaca
2461 caatatgtat gctttttacc tagctggtag cataaataaa actgaatctc aacat
```

SEQ ID NO:77
```
   1 gcaggcccgt tggaagtggt tgtgacaacc ccagcaatgt ggagaagcct ggggcttgcc
  61 ctggctctct gtctcctccc atcgggagga acagagagcc aggaccaaag ctccttatgt
 121 aagcaacccc cagcctggag cataagagat caagatccaa tgctaaactc caatggttca
 181 gtgactgtgg ttgctcttct tcaagccagc tgatacctgt gcatactgca ggcatctaaa
 241 ttagaagacc tgcgagtaaa actgaagaaa gaaggatatt ctaatatttc ttatattgtt
 301 gttaatcatc aaggaatctc ttctcgatta aaatacacac atcttaagaa taaggtttca
 361 gagcatattc ctgtttatca acaagaagaa aaccaaacag atgtctggac tcttttaaat
 421 ggaagcaaag atgacttcct catatatgat agatgtggcc gtcttgtata tcatcttggt
 481 ttgccttttt ccttcctaac tttcccatat gtagaagaag ccattaagat tgcttactgt
 541 gaaaagaaat gtggaaactg ctctctcacg actctcaaag atgaagactt ttgtaaacgt
 601 gtatctttgg ctactgtgga taaaacagtt gaaactccat cgcctcatta ccatcatgag
 661 catcatcaca atcatggaca tcagcacctt ggcagcagtg agctttcaga gaatcagcaa
 721 ccaggagcac caaatgctcc tactcatcct gctcctccag gccttcatca ccaccataag
 781 cacaagggtc agcataggca gggtcaccca gagaaccgag atatgccagc aagtgaagat
 841 ttacaagatt tacaaaagaa gctctgtcga aagagatgta taaatcaatt actctgtaaa
 901 ttgcccacag attcagagtt ggctcctagg agctgatgct gccattgtcg acatctgata
 961 tttgaaaaaa cagggtctgc aatcacctga cagtgtaaag aaaacctccc atctttatgt
1021 agctgacagg gacttcgggc agaggagaac ataactgaat cttgtcagtg acgtttgcct
1081 ccagctgcct gacaaataag tcagcagctt atacccacag aagccagtgc cagttgacgc
1141 tgaaagaatc aggcaaaaaa gtgagaatga ccttcaaact aaatatttaa aataggacat
1201 actccccaat ttagtctaga cacaatttca tttccagcat ttttataaac taccaaatta
1261 gtgaaccaaa aatagaaatt agatttgtgc aaacatggag aaatctactg aattggcttc
1321 cagatttttaa atttttatgtc atagaaatat tgactcaaac catatttttt atgatggagc
1381 aactgaaagg tgattgcagc ttttggttaa tatgtctttt tttttcttttt tccagtgttc
1441 tatttgcttt aatgagaata gaaacgtaaa ctatgaccta gggtttctg ttggataatt
1501 agcagtttag aatggaggaa gaacaacaaa gacatgcttt ccattttttt cttacttat
1561 ctctcaaaac aatattactt tgtcttttca atcttctact tttaactaat aaaataagtg
1621 gattttgtat tttaagatcc agaaatactt aacacgtgaa tattttgcta aaaaagcata
1681 tataactatt ttaaatatcc atttatcttt tgtatatcta agactcatcc tgattttac
1741 tatcacacat gaataaagcc tttgtatctt tcttctctca atgttgtatc atactcttct
1801 aaaacttgag tggctgtctt aaaagatata aggggaaaga taatattgtc tgtctctata
1861 ttgcttagta agtatttcca tagtcaatga tggtttaata ggtaaaccaa accctataaa
1921 cctgacctcc tttatggtta atactattaa gcaagaatgc agtacagaat tggatacagt
1981 acggatttgt ccaaataaat tcaataaaaa ccttaaa
```

SEQ ID NO:78
```
   1 caaccacttg acaacctggt tagaagatgc ccgccagcat tccaattcca acatggtcat
  61 tatgcttatt ggaaataaaa gtgatttaga atctagaaga gaagtaaaaa aagaagaagg
 121 tgaagctttt gcacgagaac atggactcat cttcatggaa acgtctgcta agactgcttc
 181 caatgtagaa gaggcatttaa ttaatacagc aaaagaaatt tatgaaaaaa ttcaagaagg
 241 agtctttgac attaataatg aggcaaatgg cattaaaatt ggccctcagc atgctgctac
 301 caatgcaaca catgcaggca atcagggagg acagcaggct gggggcggct gctgttgagt
 361 ctgtttttac tgtctagctg cccaacgggg cctactcact tattctttca cccctctcc
```

FIG. 10 A-71

```
 421 tcctgctcag ctgagacatg aaactatttg aaatggcttt atgtcacaga agactttaat
 481 ccgtcaaatt cttgtataac tttgaataaa tggttaatgt tcacttaaaa gacagatttt
 541 ggagattgta ttcatatcta tttgcatttg atttctaggt caattgatgt gattattttt
 601 gttaaatgtt gtcttgtgcc cttaactacg aactgaattg tattaaacac tacaaagtca
 661 tcttgagtat tttaaatcgg tttgtgtagt taggtttccc aacatctgtg gttacctaat
 721 gtttaatatt atagaactgt cctcagaaac tttgtcaatt ttcacggcta taaggaaaca
 781 gaaggactct tttaattctg tatttatcat ttactttctg tatatatagt ttaataacct
 841 gcttgggtgt aatttgccaa gcttgaattc tttaatgcat ttgcataaat tctatactgt
 901 ttagagctta aagctacaga agcattgtta ggaattgctt ggacactgaa ttttaaactt
 961 tttgacattg ttaacaagca tgttcatctt ttcttgtcac tagtccaaga aaaatatgct
1021 taatgtatat tacaaaggct ttgtatatgt taacctgttt taatgccaaa agtttgcttt
1081 gtccacaatt tccttaagac ctcttcagaa agggatttgt ttgccttaat gaatactgtt
1141 gggaaaaaac acagtataat gagtgaaaag ggcagaagca agaaatttct acatcttagc
1201 gactccaaga agaatgagta tccacattta gatggcacat tatgaggact ttaatctttc
1261 cttaaacaca ataatgtttt ctttttttctt ttattcacat gatttctaag tatattttc
1321 atgcaggaca gttttttcaac cttgatgtac agtgactgtg taaaattttt ctttcagtgg
1381 caacctctat aatctttaaa atatggtgag catcttgtct gttttgaagg ggatatgaca
1441 ataaatctat cagatggaaa atcctgtt SEQ ID NO:79
   1 cctgggtctg acgcggccct gttcgagggg gcctctcttg tttatttatt tattttccgt
  61 gggtgcctcc gagtgtgcgc gcgctctcgc tacccggcgg ggaggggggtg gggggagggc
 121 ccgggaaaag ggggagttgg agccggggtc gaaacgccgc gtgacttgta ggtgagagaa
 181 cgccgagccg tcgccgcagc ctccgccgcc gagaagcccc tgttcccgct gctggaagg
 241 agagtctgtg ccgacaagat ggcggacggg gagctgaacg tggacagcct catcacccgg
 301 ctgctggagg tacgaggatg tcgtccagga aagattgtgc agatgactga agcagaagtt
 361 cgaggcttat gtatcaagtc tcgggagatc tttctcagcc agcctattct tttggaattg
 421 gaagcaccgc tgaaaatttg tggagatatt catggacaat atacagattt actgagatta
 481 tttgaatatg gaggtttccc accagaaagcc aactatcttt tcttaggaga ttatgtggac
 541 agaggaaagc agtctttgga aaccatttgt ttgctattgg cttataaaat caaatatcca
 601 gagaacttct ttctcttaag aggaaaccat gagtgtgcta gcatcaatcg catttatgga
 661 ttctatgatg aatgcaaacg aagatttaat attaaattgt ggaagacctt cactgattgt
 721 tttaactgtc tgcctatagc agccattgtg gatgagaaga tcttctgttg tcatggagga
 781 ttgtcaccag acctgcaatc tatgagcag attcggagaa ttatgagacc tactgatgtc
 841 cctgatacag gtttgctctg tgatttgcta tggtctgatc cagataagga tgtgcaaggc
 901 tggggagaaa atgatcgtgg tgtttccttt acttttggag ctgatgtagt cagtaaattt
 961 ctgaatcgtc atgatttaga tttgatttgt cgagctcatc aggtggtgga agatggatat
1021 gaatttttg ctaaacgaca gttggtaacc ttatttcag ccccaaatta ctgtggcgag
1081 tttgataatg ctggtggaat gatgagtgtg atgaaactt tgatgtgttc atttcagata
1141 ttgaaaccat ctgaaaagaa agctaaatac cagtagtggtg gactgaattc tggacgtcct
1201 gtcactccac ctcgaacagc taatccgccg aagaaaaggt gaagaaagga attctgtaaa
1261 gaaaccatca gatttgttaa ggacatactt cataatatat aagtgtgcac tgtaaaacca
1321 tccagccatt tgacacccctt tatgatgtca cacctttaac ttaaggagac gggtaaagga
1381 tcttaaattt ttttctaata gaaagatgtg ctacactgta ttgtaataag tatactctgt
1441 tatagtcaac aaagttaaat ccaaattcaa aattatccat taaagttaca tcttcatgta
1501 tcacaattt taaagttgaa aagcatccca gttaaactag atgtgatagt taaaccagat
1561 gaaagcatga tgatccatct gtgtaatgtg gttttagtgt tgcttggttg tttaattatt
1621 ttgagcttgt tttgtttttg tttgttttca ctagaataat ggcaaatact tctaattttt
1681 ttccctaaac attttaaaa gtgaaatatg ggaagagctt tacagacatt caccaactat
1741 tattttccct tgtttatcta cttagatatc tgtttaatct tactaagaaa actttcgcct
1801 cattacatta aaaggaatt ttagagattg attgttttaa aaaaaaatac gcacattgtc
```

FIG. 10 A-72

```
1861 caatccagtg attttaatca tacagtttga ctgggcaaac tttacagctg atagtgaata
1921 ttttgcttta tacaggaatt gacactgatt tggatttgtg cactctaatt tttaacttat
1981 tgatgctcta ttgtgcagta gcatttcatt taagataagg ctcatatagt attacccaac
2041 tagttggtaa tgtgattatg tggtaccttg gctttaggtt ttcattcgca cggaacacct
2101 tttggcatgc ttaacttcct ggtaacacct tcacctgcat tggttttctt tttctttttt
2161 cttctttttt tttttttttt ttttttttga gttgttgttt gttttagat ccacagtaca
2221 tgagaatcct ttttgacaa gccttggaaa gctgacactg tctcttttc ctccctctat
2281 acgaaggatg tatttaaatg aatgctggtc agtgggacat tttgtcaact atgggtattg
2341 ggtgcttaac tgtctaatat tgccatgtga atgttgtata cgattgtaag gcttatgtca
2401 ctaaagattt ttattctgat tttttcataa tcaaaggtca tatgatactg tatagacaag
2461 ctttgtagtg aagtatagta gcaataattt ctgtacctga tcaagtttat tgcagccttt
2521 cttttcctat ttcttttttt taagggttag tattaacaaa tggcaatgag tagaaaagtt
2581 aacatgaaga ttttagaagg agagaactta caggacacag atttgtgatt ctttgactgt
2641 gacactattg gatgtgattc taaaagcttt tattgagcat tgtcaaattt gtaagcttca
2701 tagggatgga catcatatct ataatgccct tctatatgtg ctaccataga tgtgacattt
2761 ttgaccttaa tatcgtcttt gaaaatgtta aattgagaaa cctgttaact tacattttat
2821 gaattggcac attgtattac ttactgcaag agatatttca ttttcagcac agtgcaaaag
2881 ttctttaaaa tgcatatgtc ttttttcta attccgttct gttttaaagc acattttaaa
2941 tgtagttttc tcatttagta aaagttgtct aattgatatg aagcctgact gattttttt
3001 ttccttacag tgagacattt aagcacacat tttattcaca tagatactat gtccttgaca
3061 tattgaaatg attcttttct gaaagtattc atgatctgca tatgatgtat taggttaggt
3121 cacaaaggtt ttatctgagg tgatttaaat aacttcctga ttggagtgtg taagctgagc
3181 gatttctaat aaaattttag ttgtacactt ttagtagtca tagtgaagca ggtctagaaa
3241 ataagccttt ggcagggaaa aagggcaatg ttgattaatc tcagtattaa accacattaa
3301 tctgtatccc attgtctggc ttttgtaaat tcatccaggt caagactaag tatgttggtt
3361 aataggaatc cttttttttt tttaaagact aaatgtgaaa aaataatcac tacttaagct
3421 aattaatatt ggtcattaaa tttaaggat ggaaatttat catgtttaaa aattattcaa
3481 gcactcttaa aaccacttaa acagcctcca gtcataaaaa tgtgttcttt acaaatattt
3541 gcttggcaac acgacttgaa ataaataaaa ctttgtttct taggagaaaa
```

```
SEQ ID NO:80
   1 gcaacctgcc ccattatccc tggctgcgaa acaaccatcg agatttccaa agggcgaaca
  61 gggctgggcc tgagcatcgt tggggggttca gacacgctgc tgggtgccat tattatccat
 121 gaagtttatg aagaaggagc agcatgtaaa gatggaagac tctgggctgg agatcagatc
 181 ttagaggtga atggaattga cttgagaaag gccacacatg atgaagcaat caatgtcctg
 241 agacagacgc cacagagagt gcgcctgaca ctctacagag atgaggcccc atacaaagag
 301 gaggaagtgt gtgacaccct cactattgag ctgcagaaga agccgggaaa aggcctagga
 361 ttaagtattg ttggtaaaag aaacgatact ggagtatttg tgtcagacat tgtcaaagga
 421 ggaattgcag atgccgatgg aagactgatg cagggagacc agatattaat ggtgaatggg
 481 gaagacgttc gtaatgccac ccaagaagcg gttgccgctt tgctaaagtg ttccctaggc
 541 acagtaacct tggaagttgg aagaatcaaa gctggtccat tccattcaga gaggaggcca
 601 tctcaaagca gccaggtgag tgaaggcagc ctgtcatctt tcacttttcc actctctgga
 661 tccagtacat ctgagtcact ggaaagtagc tcaaagaaga atgcattggc atctgaaata
 721 cagggattaa gaacagtcga atgaaaaag ggccctactg actcactggg aatcagcatt
 781 gctggaggag taggcagccc acttggtgat gtgcctatat ttattgcaat gatgcaccca
 841 actggagttg cagcacagac ccaaaaactc agagttgggg ataggattgt caccatctgt
 901 ggcacatcca ctgagggcat gactcacacc caagcagtta acctactgaa aaatgcatct
 961 ggctccattg aaatgcaggt ggttgctgga ggagacgtga gtgtggtcac aggtcatcag
1021 caggagcctg caagttccag tctttcttc actgggctga cgtcaagcag tatatttcag
1081 gatgatttag gacctcctca atgtaagtct attacactag agcgaggacc agatggctta
```

```
1141 ggcttcagta tagttggagg atatggcagc cctcatggag acttacccat ttatgttaaa
1201 acagtgtttg caaagggagc agcctctgaa gacggacgtc tgaaaagggg cgatcagatc
1261 attgctgtca atgggcagag tctagaagga gtcacccatg aagaagctgt tgccatcctt
1321 aaacggacaa aaggcactgt cactttgatg gttctctctt gaattggctg ccagaattga
1381 accaacccaa cccctagctc acctcctact gtaaagagaa tgcactggtc ctgacaattt
1441 ttatgctgtg ttcagccggg tcttcaaaac tgtaggggggg aaataacact taagtttctt
1501 tttctcatct agaaatgctt tccttactga caacctaaca tcattttct tttcttcttg
1561 cattttgtga acttaaagag aaggaatatt tgtgtaggtg aatctcgttt ttatttgtgg
1621 agatatctaa tgttttgtag tcacatgggc aagaattatt acatgctaag ctggttagta
1681 taaagaaaga taattctaaa gctaaccaaa gaaaatggct tcagtaaatt aggatgaaaa
1741 atgaaaatat
```

SEQ ID NO:81

```
   1 ggagcgcaat ggcgtccaac cccgaacggg gggagattct gctcacggaa ctgcaggggg
  61 attcccgaag tcttccgttt tctgagaatg tgagtgctgt tcaaaaatta gactttcag
 121 atacaatggt gcagcagaaa ttggatgata tcaaggatcg aattaagaga gaaataagga
 181 aagaactgaa aatcaaagaa gggagctgaaa atctgaggaa agtcacaaca gataaaaaaa
 241 gtttggctta tgtagacaac attttgaaaa aatcaaataa aaaattagaa gaactacatc
 301 acaagctgca ggaattaaat gcacatattg ttgtatcaga tccagaagat attacagatt
 361 gcccaaggac tccagatact ccaaataatg accctcgttg ttctactagc aacaatagat
 421 tgaaggcctt acaaaaacaa ttggatatag aacttaaagt aaaacaaggt gcagagaata
 481 tgatacagat gtattcaaat ggatcttcaa aggatcggaa actccatggt acagctcagc
 541 aactgctcca ggacagcaag acaaaaatag aagtcatacg aatgcagatt cttcaggcag
 601 tccagactaa tgaattggct tttgataatg caaaacctgt gataagtcct cttgaacttc
 661 ggatggaaga attaaggcat cattttagga tagagtttgc agtagcagaa ggtgcaaaga
 721 atgtaatgaa attacttggc tcaggaaaag taacagacag aaaagcactt tcagaagctc
 781 aagcaagatt taatgaatca agtcagaagt tggacctttt aaagtattca ttagagcaaa
 841 gattaaacga agtcccaag aatcatccca aagcaggat tattattgaa gaactttcac
 901 ttgttgctgc atcaccaaca ctaagtccac gtcaaagtat gatatctacg caaaatcaat
 961 atagtacact atccaaacca gcagcactaa caggtacttt ggaagttcgt cttatgggct
1021 gccaagatat cctagagaat gtccctggac ggtcaaaagc aacatcagtt gcactgcctg
1081 gttggagtcc aagtgaaacc agatcatctt tcatgagcag aacgagtaaa agtaaaagcg
1141 gaagtagtcg aaatcttcta aaaaccgatg acttgtccaa tgatgtctgt gctgtttga
1201 agctcgataa tactgtggtt ggccaaacta gctgaaaacc catttccaat cagtcatggg
1261 accagaagtt tacactggaa ctggacaggt cacgtgaact ggaaatttca gtttattggc
1321 gtgattggcg gtctctgtgt gctgtaaaat ttctgaggtt agaagatttt ttagacaacc
1381 aacggcatgg catgtgtctc tatttggaac cacagggtac tttattgca gaggttacct
1441 ttttttaatcc agttattgaa agaagaccaa aacttcaaag acaaaagaaa attttttcaa
1501 agcaacaagg caaaacattt ctcagagctc ctcaaatgaa tattaatatt gccacttggg
1561 gaaggctagt aagaagagct attcctacag tggcaccttc agccctcaag
1621 ctcctgtgcc tactacagtg ccagtggttg atgtacgcat ccctcaacta gcacctccag
1681 ctagtgattc tacagtaacc aaattggact ttgatcttga gcctgaacct cctccagccc
1741 caccacgagc ttcttctctt ggagaaatag atgaatcttc tgaattaaga gttttggata
1801 taccaggaca ggattcgag actgttttg atattcagaa tgacagaaat agtatacttc
1861 caaaatctca atctgaatac aagcctgata ctcctcagtc aggcctagaa tatagtggta
1921 ttcaagaact tgaggacaga agatctcagc aaaggtttca gttaatctca caagatttca
1981 ggtgttgtgc tgtcttggga agaggacatt tggaaaggt gcttttagct gaatataaaa
2041 acacaaatga gatgtttgct ataaaagcct taaagaaagg agatattgtg gctcgagatg
2101 aagtagacag cctgatgtgt gaaaaagaa tttttgaaac tgtgaatagt gtaaggcatc
2161 cctttttggt gaacctttt gcatgtttcc aaaccaaaga gcatgtttgc tttgtaatgg
```

FIG. 10 A-74

```
2221 aatatgctgc cggtggggac ctaatgatgc acattcatac tgatgtcttt tctgaaccaa
2281 gagctgtatt ttatgctgct tgtgtagttc ttgggttgca gtatttacat gaacacaaaa
2341 ttgtttatag agatttgaaa ttggataact tattgctaga tacagagggc tttgtgaaaa
2401 ttgctgattt tggtctttgc aaagaaggaa tgggatatgg agatagaaca agcacatttt
2461 gtggcactcc tgaatttctt gccccagaag tattaacaga aacttcttat acaagggctg
2521 tagattggtg gggccttggc gtgcttatat atgaaatgct tgttggtgag tctcccttc
2581 ctggtgatga tgaagaggaa gttttgaca gtattgtaaa tgatgaagta aggtatccaa
2641 ggttcttatc tacagaagcc atttctataa tgagaaggct gttaagaaga aatcctgaac
2701 ggcgccttgg ggctagcgag aaagatgcag aggatgtaaa aaagcaccca ttttccggc
2761 taattgattg gagcgctctg atggacaaaa aagtaaagcc accatttata cctaccataa
2821 gaggacgaga agatgttagt aattttgatg atgaatttac ctcagaagca cctattctga
2881 ctccacctcg agaaccaagg atactttcgg aagaggagca ggaaatgttc agagattttg
2941 actacattgc tgattggtgt taagttgcta gacactgcga aaccaagctg actcacaaga
3001 agacctctta aaaatagcaa cccttcattt gctctctgtg ccaccaatag cttctgagtt
3061 ttttgttgtt gttgtttta ttgaaacacg tgaagatttg tttaaaagta ccattctaat
3121 acttcttcaa aagtggctcc tcattgtact tcagcgtaaa tatgagcact ggaaacagtt
3181 tcatggagtt taagttgagt gaacatcggc catgaaaatc catcacgaat acttttggat
3241 caatagtcta tttt SEQ ID NO:82
   1 atgaaattca agttacatgt gaattctgcc aggcaataca aggacctgtg gaatatgagt
  61 gatgacaaac cctttctatg tactgcgcct ggatgtggcc agagtgaagt caccctgctg
 121 agaaatgaag tggcacagct gaaacagctt cttctggctc ataaagattg ccctgtaacc
 181 gccatgcaga agaaatctgg ctatcatact gctgataaag atgatagttc agaagacatt
 241 tcagtgccga gtagtccaca tacagaagct atacagcata gttcggtcag cacatccaat
 301 ggagtcagtt caacctccaa ggcagaagct gtagccactt cagtcctcac ccagatggcg
 361 gaccagagta cagagcctgc tcttcacag atcgttatgg ctccttcctc ccagtcacag
 421 ccctcaggaa gttgattaaa aacctgcagt acaacagttt tagatactca ttagtgactt
 481 caaagggaaa tcaaggaaag accagtttc SEQ ID NO:83
   1 gaattctgga agttcattga agagtctgaa attagggact tatttcaaat ttggacatgg
  61 ctagtcgagg cgcaacaaga cccaacggcc caaatactgg aaataaaata tgccagttca
 121 aactagtact tctgggagag tccgctgttg gcaaatcaag cctagtgctt cgttttgtga
 181 aaggccaatt tcatgaattt caagagagta ccattggggc tgcttttcta acccaaactg
 241 tatgtcttga tgacactaca gtaaagtttg aaatctggga tacagctggt caagaaggat
 301 accatagcct agcaccaatg tactacagag gagcacaagc agccatagtt gtatatgata
 361 tcacaaatga ggagtccttt gcaagagcaa aaaattgggt taaagaactt cagaggcaag
 421 caagtcctaa cattgtaata gctttatcgg gaaacaaggc cgacctagca aataaaagag
 481 cagtagattt ccaggaagca cagtcctatg cagatgacaa tagtttatta ttcatggaga
 541 catccgctaa acatcaatg aatgtaaatg aaatattcat ggcaatagct aaaaaattgc
 601 caaagaatga accacaaaat ccaggagcaa attctgccag aggaggagga gtagacctta
 661 ccgaacccac acaaccaacc aggaatcagt gttgtagtaa ctaaacctct agtttgaac SEQ Id NO:84
   1 gacgctctgg gccgccacct ccgcggaccc tgagcgcaag agccaagccc cagcgctgc
  61 gatgtgggcc acgctgccgc tgctctgcgc cggggcctgg ctcctgggag tccccgtctg
 121 cggtgccgcc gaactgtgcg tgaactcctt agagaagttt cacttcaagt catggatgtc
 181 taagcaccgt aagacctaca gtacggagga gtaccaccac aggctgcaga cgtttgccag
 241 caactggagg aagataaacg cccacaacaa tgggaaccac acatttaaaa tggcactgaa
```

FIG. 10 A-75

```
 301 ccaattttca gacatgagct ttgctgaaat aaaacacaag tatctctggt cagagcctca
 361 gaattgctca gccaccaaaa gtaactacct tcgaggtact ggtccctacc caccttccgt
 421 ggactggcgg aaaaaaggaa attttgtctc acctgtgaaa aatcagggtg cctgcggcag
 481 ttgctggact ttctccacca ctggggccct ggagtctgcg atcgccatcg caaccggaaa
 541 gatgctgtcc ttggcggaac agcagctggt ggactgcgcc caggacttca ataatcacgg
 601 ctgccaaggg ggtctcccca gccaggcttt cgagtatatc ctgtacaaca aggggatcat
 661 gggtgaagac acctacccct accagggcaa ggatggttat tgcaagttcc aacctggaaa
 721 ggccatcggc tttgtcaagg atgtagccaa catcacaatc tatgacgagg aagcgatggt
 781 ggaggctgtg gccctctaca accctgtgag ctttgccttt gaggtgactc aggacttcat
 841 gatgtataga accggcatct actccagtac ttcctgccat aaaactccag ataaagtaaa
 901 ccatgcagta ctggctgttg ggtatggaga aaaaaatggg atcccttact ggatcgtgaa
 961 aaactcttgg ggtccccagt ggggaatgaa cgggtacttc ctcatcgagc gcggaaagaa
1021 catgtgtggc ctggctgcct gcgcctccta ccccatccct ctggtgtgag ccgtggcagc
1081 cgcagcgcag actggcggag aaggagagga acgggcagcc tgggcctggg tggaaatcct
1141 gccctggagg aagttgtggg gagatccact gggaccccca acattctgcc ctcacctctg
1201 tgcccagcct ggaaacctac agacaaggag gagttccacc atgagctcac ccgtgtctat
1261 gacgcaaaga tcaccagcca tgtgccttag tgtccttctt aacagactca aaccacatgg
1321 accacgaata ttctttctgt ccagaagggc tactttccac atatagagct ccagggactg
1381 tcttttctgt attcgctgtt caataaacat tgagtgagca cctccccaga tgg
```

SEQ ID NO:85
```
   1 ggtcggggcc cgcggccgct cgcgcctctc gatgggcagc tcgcacttgc tcaacaaggg
  61 cctgccgctt ggcgtccgac ctccgatcat gaacgggccc ctgcaccgc ggccccctggt
 121 ggcattgctg gatggccggg actgcacagt ggagatgccc atcctgaagg acgtggccac
 181 tgtggccttc tgcgacgcgc agtccacgca ggagatccat gagaaggtcc tgaacgaggc
 241 tgtggggggcc ctgatgtacc acaccatcac tctcaccagg gaggacctgg agaagttcaa
 301 agccctccgc atcatcgtcc ggattggcag tggttttgac aacatcgaca tcaagtcggc
 361 cggggattta ggcattgccg tctgcaacgt gcccgcggcg tctgtggagg agacggccga
 421 ctcgacgctg tgccacatcc tgaacctgta ccggcgggcc acctggctgc accaggcgct
 481 gcgggagggc acacgagtcc agagcgtcga gcagatccgc gaggtggcgt ccggcgctgc
 541 caggatccgc ggggagacct tgggcatcat cggacttgtc gcgtggggca ggcagtggcg
 601 ctgcgggcca aggccttcgg cttcaacgtg ctcttctacg acccttactt gtcggatggc
 661 gtggagcggg cgctggggct gcagcgtgtc agcaccctgc aggacctgct cttccacagc
 721 gactgcgtga ccctgcactg cggcctcaac gagcacaacc accacctcat caacgacttc
 781 accgtcaagc agatgagaca aggggccttc ctgtgaaca cagcccgggt tggcctggtg
 841 gatgagaagg cgctggccca ggccctgaag gagggccgga tccgcggcgc ggccctggat
 901 gtgcacgagt cggaacccct cagctttagc cagggccctc tgaaggatgc acccaacctc
 961 atctgcaccc cccatgctgc atggtacagc gagcaggcat ccatcgagat gcgagaggag
1021 gcggcacggg agatccgcag agccatcaca ggccggatcc cagacagcct gaagaactgt
1081 gtcaacaagg accatctgac agccgccacc cactgggcca gcatgagccc cgccgtcgtg
1141 cacccctgagc tcaatggggc tgcctatagg taccctccgg gcgtggtggg cgtggcccc
1201 actggcatcc cagctgctgt ggaaggtatc gtccccagcg ccatgtccct gtcccacggc
1261 ctgccccctg tgcccaccc gccccacgcc ccttctcctg gccaaaccgt caagcccgag
1321 gcggatagag accacgccag tgaccagttg tagcccggga ggagctctcc agcctcggcg
1381 cctgggcaga gggcccggaa accctcggac cagagtgtgt ggaggaggca tctgtgtggt
1441 ggccctggca ctgcagagac tggtccgggc tgtcaggagg cgggaggggg cagcgctggg
1501 cctcgtgtcg cttgtcgtcg tccgtcctgt gggcgctctg ccctgtgtcc ttcgcgttcc
1561 tcgttaagca gaagaagtca gtagttattc tcccatgaac gttcttgtct gtgtacagtt
1621 tttagaacat tacaaaggat ctgtttgctt agctgtcaac aaaaagaaaa cctgaaggag
1681 catttggaag tcaatttgag gttttttttt ttgttttttt tttttttgta tgttggaacg
1741 tgccccagaa tgaggcagtt ggcaaacttc tcaggacaat gaatccttcc cgttttttctt
```

FIG. 10 A-76

```
1801 tttatgccac acagtgcatt gttttttcta cctgcttgtc ttatttttag aataatttag
1861 aaaaacaaaa caaaggctgt ttttcctaat tttggcatga accccccctt gttccaaatg
1921 aagacggcat cacgaagcag ctccaaaagg aaaagcttgg gcggtgccca gcgtgcccgc
1981 tgcccatcga cgtctgtcct ggggacgtgg agggtggcag cgtccccgcc tgcaccagtg
2041 ccgtcctgct gatgtggtag gctagcaata ttttggttaa aatcatgttt gtg
```

SEQ ID NO:86

```
   1 cgcgcggcca ggccctctta gccctctgcc gtttgggggg cacgggtgaa cctgccgccc
  61 cactcccacc ccgccccgcc ccgcccgtac agccaaatcg gaagggacga gcctgcccct
 121 tgaaagggtt ttttttcttg ctcctgcgga gggcgcccca gccatggccc tcaggagctc
 181 cctagacccc gcagggactg ccctccatcc cggccgccgg ggcccgccct ctgcatcccg
 241 cgggcagcct gtgtgaagcg gcctccgca gcccccggcc cctcccccat ggaggaggag
 301 gagggggcgg tggccaagga gtggggcacg acccccgcgg ggcccgtctg gaccgcggtg
 361 ttcgactacg aggcggcggg cgacgaggag ctgaccctgc ggaggggcga tcgcgtccag
 421 gtgctttccc aagactgtgc ggtgtccggc gacgagggct ggtggaccgg gcagctcccc
 481 agcggccgcg tgggcgtctt cccagcaac tacgtggccc ccggcgcccc cgctgcaccc
 541 gcgggcctcc agctgcccca ggagatcccc ttccacgagc tgcagctaga ggagatcatc
 601 ggtgtggggg gctttggcaa ggtctatcgg gccctgtggc gtggcgagga ggtggcagtc
 661 aaggccgccc ggctggaccc tgagaaggac ccggcagtga cagcggagca ggtgtgccag
 721 gaagcccgc tctttggagc cctgcagcac cccaaacataa ttgcccttag gggcgcctgc
 781 ctcaaccccc cacacctctg cctagtgatg gagtatgccc ggggtggtgc actgagcagg
 841 gtgctggcag gtcgccgggt gccacctcac gtgctggtca actgggctgt gcaggtggcc
 901 cggggcatga actacctaca caatgatgcc cctgtgccca tcatccaccg ggacctcaag
 961 tccatcaaca tcctgatcct ggaggccatc gagaaccaca acctcgcaga cacggtgctc
1021 aagatcacgg acttcggcct cgcccgcgag tggcacaaga ccaccaagat gagcgctgcg
1081 gggacctacg cctggatggc gccggaggtt atccgtctct ccctcttctc aaaagcagt
1141 gatgtctgga gcttcgggt gctgctgtgg gagctgctga cggggaggt cccctaccgt
1201 gagatcgacg ccttggccgt ggcgtatgg gtggctatga ataagctgac gctgcccatt
1261 ccctccacgt gccccgagcc ctttgcccgc ctcctggagg aatgctggga cccagacccc
1321 cacgggcggc cagatttcgg tagcatcttg aagcggcttg aagtcatcga acagtcagcc
1381 ctgttccaga tgccactgga gtccttccac tcgctgcagg aagactggaa gctggagatt
1441 cagcacatgt ttgatgacct tcggaccaag gagaaggagc ttcggagccg tgaggaggag
1501 ctgctgcggg cggcacagga gcagcgcttc caggaggcag agctgcggcg gcgggacgag
1561 gagctggcag aacgtgagat ggacatcgtg gaacgggagc tgcacctgct catgtgccag
1621 ctgagccagg agaagccccg ggtccgcaag cgcaagggca acttcaagcg cagccgcctg
1681 ctcaagctgc gggaaggcgg cagccacatc agcctgccct ctggctttga gcataagatc
1741 acagtccagg cctctccaac tctggataag cggaaaggat ccgatggggc cagccccccct
1801 gcaagcccca gcatcatccc ccggctgagg gccattcgcc tgactcccgt ggactgtggt
1861 ggcagcagca gtgcagcag cagtggagga agtgggacat ggagccgcgg tgggcccca
1921 aagaaggaag aactggtcgg gggcaagaag aagggacgaa cgtggggccc cagctccacc
1981 ctgcagaagg agcgggtggg aggagaggag aggctgaagg ggctggggga aggaagcaaa
2041 cagtggtcat caagtgcccc caacctgggc aagtccccca acacacacc cagtcgccgc
2101 tggcttcgcc agcctcaatg agatggagga gttcgcggag gcagaggatg gaggcagcag
2161 cgtgcccccct tccccctact cgacccccgtc ctacctctca gtgccactgc ctgccgagcc
2221 ctccccgggg gcgcgggcgc cgtgggagcc gacgccgtcc gcgccccccg ctcggtgggg
2281 acacggcgcc cggcggcgct gcgacctggc gctgctaggc tgcgccacgc tgctgggggc
2341 tgtgggcctg ggcgccgacg tggccgaggc gcgcgcggcc gacggtgagg agcagcggcg
2401 ctggctcgac ggcctcttct ttccccgcgc cggccgcttc ccgcgggccc tcagcccacc
2461 cgcgcgtccc cacggccgcc gcgaagacgt gggccccggc ctgggcctgg cgccctcggc
2521 caccctcgtg tcgctgtcgt ccgtgtccga ctgcaactcc acgcgttcac tgctgcgctc
```

FIG. 10 A-77

```
2581 tgacagtgac gaggccgcac cggccgcgcc ctccccacca ccctccccgc ccgcgcccac
2641 acccacgccc tcgcccagca ccaaccccct ggtggacctg gagctggaga gcttcaagaa
2701 ggaccccgc cagtcgctca cgcccaccca cgtcacggct gcatgcgctg tgagccgcgg
2761 gcaccggcgg acgccatcgg atggggcgct ggggcagcgg gggccgcccg agcccgcggg
2821 ccatggcccct ggccctcgtg accttctgga cttccccgc ctgccgacc cccaggccct
2881 gttcccagcc cgccgccggc cccctgagtt ccaggccgc cccaaccacc tgacctttgc
2941 cccgagacct cggccggctg ccagtcgccc cgcttggac ccctggaaac tggtctcctt
3001 cggccggaca ctcaccatct cgcctcccag caggccagac actccggaga gccctgggcc
3061 cccagcgtg cagcccacac tgctggacat ggacatggag gggcagaacc aagacagcac
3121 agtgcccctg tgcggggccc acggctccca ctaaggcctg cccaccaccg cccgcctggg
3181 cagccatgaa tgtagcgccc caggccctgc cccagcccgc catgccacaa ggtggggag
3241 gccctgggca ggatgttcac tctatttatt ggggaaggag ggaggggggg gacacttaac
3301 ttattccttt gtacccagg gggtggagcc ctgtgcccac cctgcactgg ggggaggggtg
3361 ggcagggata ctcagggaca gggcatcatg ggggatttgg cacaaaatgg agcattaaag
3421 gtaacccctg ccccc SEQ ID NO:87
   1 gggcccgccc ctggtcacag ccagactgac tcagtttccc tgggaggtcc cgctcgagcc
  61 cgtccttccc ctccctctgc ccgcccccag ccctcgcccc accctcggcg cccgcacatc
 121 tgcctgctca gctccagacg gcgcccggac ccccgggcgc gggatccagc caggtgggag
 181 ccccgcagat gaggtctctg aaggtgtgcc tgaaccagtg ccagcctgcc ctgtctgcag
 241 catcggcctg atggggtggt gactgatccc tcaggctcc ggagccatgt ggcccaacgg
 301 cagttccctg gggccctgtt tccggcccac aaacattacc ctggaggaga gacggctgat
 361 cgcctcgccc tggttcgccc cctccttctg cgtggtgggc ctggcctcca acctgctggc
 421 cctgagcgtg ctggcgggcg cgcggcaggg gggttcgcac acgcgctcct ccttcctcac
 481 cttcctctgc ggcctcgtcc tcaccgactt cctggggctg ctggtgaccg gtaccatcgt
 541 ggtgtcccag cacgccgcgc tcttcgagtg gcacgccgtg gaccctggct gccgtctctg
 601 tcgcttcatg ggcgtcgtca tgatcttctt cggcctgtcc ccgctgctgc tggggccgc
 661 catggcctca gagcgctacc tgggtatcac ccggcccttc tcgcgcccgg cggtcgcctc
 721 gcagcgccgc gcctgggcca ccgtgggggct ggtgtgggcg gccgcgctgg cgctgggcct
 781 gctgcccctg ctgggcgtgg gtcgctacac cgtgcaatac ccggggtcct ggtgcttcct
 841 gacgctgggc gccgagtccg gggacgtggc cttcggggctg ctcttctcca tgctgggcgg
 901 cctctcggtc gggctgtcct tcctgctgaa cacggtcagc gtggccaccc tgtgccacgt
 961 ctaccacggg caggaggcgg cccagcagcg tccccgggac tccgaggtgg agatgatggc
1021 tcagctcctg gggatcatgg tggtggccag cgtgtgttgg ctgccccttc tggtcttcat
1081 cgcccagaca gtgctgcgaa acccgcctgc catgagcccc gccgggcagc tgtcccgcac
1141 cacggagaag gagctgctca tctacttgcg cgtggccacc tggaaccaga tcctgaccc
1201 ctgggtgtat atcctgttcc gccgcgccgt gctccggcgt ctccagcctc gcctcagcac
1261 ccggcccagg tcgctgtccc tcagcccca gctcacgcag cgctccgggc tgcagtagga
1321 agtggacaga gcgcccctcc cgcgcctttc cgcggagccc ttggcccctc ggacagccca
1381 tctgcctgtt ctgaggattc aggggctggg ggtgctggat ggacagtggg catcagcagc
1441 agggttttgg gttgacccca atccaacccg gggaccccca actcctccct gatccttta
1501 ccaagcactc tcccttcctc ggccccttt tcccatccag agctcccacc ccttctctgc
1561 gtccctccca accccaggaa gggcatgcag acattggaag agggtcttgc attgctattt
1621 ttttttttag acggagtctt gctctgtccc ccaggctgga gtgcagtggc gcaatctcag
1681 ctcactgcaa cctccacctc ccgggttcaa gcgattctcc tgcctcagcc tcctgagtag
1741 ctgggactat aggcgcgcgc caccacgccc ggctaatttt tgtattttta gtagagacgg
1801 ggtttcaccg tgttggccag gctggtcttg aactcctgac ctcaggtgat tcaccagcct
1861 cagcctccca aagtgctggg atcacaggca tgaaccacca cacctggcca tttttttttt
1921 tttttttaga cggagtctca ctctgtggcc cagcctggag tacagtggca cgatctcggc
```

FIG. 10 A-78

```
1981 tcactgcaac ctccgcctcc cgggttcaag cgattctcgt gcctcagcct cccgagcagc
2041 tgggattaca ggcgtaagcc actgcgcccg gccttgcatg ctctttgacc ctgaatttga
2101 cctacttgct ggggtacagt tgcttccttt tgaacctcca acagggaagg ctctgtccag
2161 aaaggattga atgtgaacgg gggcaccccc ttttcttgcc aaaatatatc tctgcctttg
2221 gttttat
```

SEQ ID NO:88
```
   1 cccggacatg gccgccaaca tgtacagggt cggagactac gtctactttg agaactcctc
  61 cagcaaccca tacctgatcc ggagaatcga ggagctcaac aagacggcca atgggaacgt
 121 ggaggccaaa gtggtgtgct tctaccggag gcgggacatc tccagcaccc tcatcgccct
 181 ggccgacaag cacgcaaccc tgtcagtctg ctataaggcc ggaccggggg cggacaacgg
 241 cgaggaaggg gaaatagaag aggaaatgga gaatccggaa atggtggacc tgcccgagaa
 301 actaaagcac cagctgcggc atcgggagct gttcctctcc cggcagctgg agtctctgcc
 361 cgccacgcac atcaggggca agtgcagcgt caccctgctc aacgagaccg agtcgctcaa
 421 gtcctacctg gagcgggagg atttcttctt ctattctcta gtctacgacc cacagcagaa
 481 gaccctgctg gcagataaag gagagattcg agtaggaaac cggtaccagg cagacatcac
 541 cgacttgtta aaagaaggcg aggaggatgg ccgagaccag tccaggttgg agacccaggt
 601 gtgggaggcg cacaacccac tcacagacaa gcagatcgac cagttcctgg tggtggcccg
 661 ctctgtgggc accttcgcac gggccctgga ctgcagcaga tccgtccgac agcccagcct
 721 gcacatgagc gccgcagctg cctcccgaga catcaccctg ttccacgcca tggatactct
 781 ccacaagaac atctaccaca tctccaaggc catctcggcg ctggtgccgc agggcgggcc
 841 cgtgctctgc agggacgaga tggaggagtg gtctgcatca gaggccaacc ttttcgagga
 901 agccctggaa aaatatggga aggatttcac ggacattcag caagattttc tcccgtggaa
 961 gtcgtcgacc agcatcattg agtactacta catgtggaag accaccgaca gatacgtgca
1021 gcagaaacgc ttgaaagcag ctgaagctga gagcaagtta aagcaagttt atattcccaa
1081 ctataacaag ccaaatccga accaaatcag cgtcaacaac gtcaaggccg tgtggtgaa
1141 cggcacgggg gcgccgggcc agagccctgg ggctggccgg gcctgcgaga gctgttacac
1201 cacacagtct taccagtggt attcttgggg tcccccctaac atgcagtgtc gtctctgcgc
1261 atcttgttgg acatattgga agaaatatgg tggcttgaaa atgccaaccc ggttagatgg
1321 agagaggcca ggaccaaacc gcagtaacat gagtccccac ggcctcccag cccggagcag
1381 cgggagcccc aagtttgcca tgaagaccag gcaggctttc tatctgcaca cgacgaagct
1441 gacgcggatc gccggcgcc tgtgccgtga gatcctgcgc cgtggcacg ctgcgcggaa
1501 ccccctacctg cccatcaaca gcgcggccat caaggccgag tgcacggcgc ggctgcccga
1561 agcctcccag agcccgctgg tgctgaagca ggcggtacgc aagccgctgc aagccgtgct
1621 tcggtatctt gagacccacc ccgcccccc caagcctgac cccgtgaaaa gcgtgtccag
1681 cgtgctcagc agcctgacgc ccgccaaggt ggcccccgtc atcaacaacg gctcccccac
1741 catcctgggc aagcgcagct acgagcagca caacggggtg gacggcaaca tgaagaagcg
1801 cctcttgatg cccagtaggg gtctggcaaa ccacggacag accaggcaca tgggaccaag
1861 ccggaacctc ctgctcaacg ggaagtccta ccccaccaaa gtgcgcctga tccgggggg
1921 ctccctgccc ccagtcaagc ggcggcggat gaactggatc gacgccccgg gtgacgtgtt
1981 ctacatgccc aaagaggaga ccaggaagat ccgcaagctg ctctcatcct cggaaaccaa
2041 gcgtgctgcc cgccggccct acaagcccat cgcctgcgc cagagccagg ccctgccgcc
2101 gcggccaccg ccacctgcgc ccgtcaacga cgagcccatc gtcatcgagg actaggggcc
2161 gccccccacct gcggccgccc ccgccccctc gcccagcagc
2221 ccgccgcccg cccctcagtt tggtagtgcc ccacctcccg ccctcacctg aagagaaacg
2281 cgctccttgg cggacactgg gggaggagag gaagaagcgc ggctaactta ttccgagaat
2341 gccgaggagt tgtcgttttt agctttgtgt ttacttttg gctggagcgg agatgagggg
2401 ccacccgtg ccctgtgct gcggggcctt tgcccggag gcgggcct aaggttttgt
2461 tgtgttctgt tgaaggtgcc attttaaatt ttattttat tacttttttt gtagatgaac
2521 ttgagctctg taacttacac ctggaatgtt aggatcgtgc ggccgcggcc ggccgagctg
```

FIG. 10 A-79

```
2581 cctggcgggg ttggcccttg tcttttcaag taattttcat attaaacaaa aacaaagaaa
2641 aaaaatctta taaaaaggaa aa
```

SEQ ID NO:89
```
   1 atgagagagt acaaagtggt ggtgctgggc tcgggcggcg tgggcaagtc cgcgctcacc
  61 gtgcagttcg tgacgggctc cttcatcgag aagtacgacc cgaccatcga agacttttac
 121 cgcaaggaga ttgaggtgga ctcgtcgccg tcggtgctgg agatcctgga tacggcgggc
 181 accgagcagt tcgcgtccat gcgggacctg tacatcaaga acggccaggg cttcatcctg
 241 gtctacagcc tcgtcaacca gcagagcttc caggacatca gcccatgcg ggaccagatc
 301 atccgcgtga agcggtacga gcgcgtgccc atgatcctgg tgggcaacaa ggtggacctg
 361 gagggtgagc gcgaggtctc gtacggggag ggcaaggccc tggctgagga gtggagctgc
 421 cccttcatgg agacgtcggc caaaaacaaa gcctcggtag acgagctatt tgccgagatc
 481 gtgcggcaga tgaactacgc ggcgcagtcc aacggcgatg agggctgctg ctcggcctgc
 541 gtgatcctct ga
```

SEQ ID NO:90
```
   1 gagctgcggg cgctgctgct gtggggccgc cgcctgcggc ctttgctgcg ggcgccggcg
  61 ctggcggccg tgccgggagg aaaaccaatt ctgtgtcctc ggaggaccac agcccagttg
 121 ggcccccagc gaaacccagc ctggagcttg caggcaggac gactgttcag cacgcagacc
 181 gccgaggaca aggaggaacc cctgcactcg attatcagca gcacagagag cgtgcagggt
 241 tccacttcca aacatgagtt ccaggccgag acaaagaagc ttttggacat tgttgcccgg
 301 tccctgtact cagaaaaaga ggtgtttata cgggagctga tctccaatgc cagcgatgcc
 361 ttggaaaaac tgcgtcacaa actggtgtct gacgccaag cactgccaga aatggagatt
 421 cacttgcaga ccaatgccga gaaaggcacc atcaccatcc aggatactgg tatcgggatg
 481 acacaggaag agctggtgtc caacctgggg acgattgcca gatcggggtc aaaggccttc
 541 ctggatgctc tgcagaacca ggctgaggcc agcagcaaga tcatcggcca gtttggagtg
 601 ggtttctact cagctttcat ggtggctgac agagtggagg tctattcccg ctcggcagcc
 661 ccggggagcc tgggttacca gtggctttca gatggttctg gagtgtttga aatcgccgaa
 721 gcttcgggag ttagaaccgg gacaaaaatc atcatccacc tgaaatccga ctgcaaggag
 781 ttttccagcg aggcccgggt gcgagatgtg gtaacgaagt acagcaactt cgtcagcttc
 841 cccttgtact tgaatggaag gcggatgaac accttgcagg ccatctggat gatggaccc
 901 aaggatgtcc gtgagtggca acatgaggag ttctaccgct acgtcgcgca ggctcacgac
 961 aagcccgct acacctgca ctataagacg gacgcaccgc tcaacatccg cagcatcttc
1021 tacgtgcccg acatgaaacc gtccatgttt gatgtgagcc gggagctggg ctccagcgtt
1081 gcactgtaca gccgcaaagt cctcatccag accaaggcca cggacatcct gcccaagtgg
1141 ctgcgcttca tccgaggtgt ggtggacagt gaggacattc ccctgaacct cagccgggag
1201 ctcgctgcag gagcgcact catcaggaaa ctccggacag ttttacagca gggctgatc
1261 aaattcttca ttgaccagag taaaaaagat gctgagaagt atgcaaagtt ttttgaagat
1321 tacggcctgt tcatgcggga gggcattgtg accgccaccg agcaggaggt caaggaggac
1381 atagcaaagc tgctgcgcta cgagtcctcg gcgctgccct ccgggcagct aaccagcctc
1441 tcagaatacg ccagccgcat gcgggccggc acccgcaaca tctactacct gtgcgccccc
1501 aaccgtcacc tggcagagca ctcaccctac tatgaggcca tgaagaagaa agacacagag
1561 gttctcttct gctttgagca gtttgatgag ctcaccctgc tgcaccttcg tgagtttgac
1621 aagaagaagc tgatctctgt ggagacggaa atagtcgtgg atcactacaa ggaggagaag
1681 tttgaggaca ggtcccagc cgccagtgc ctatcagaga aggagacgga ggagctcatg
1741 gcctggatga aaatgtgct ggggtcgcgt gtcaccaacg tgaaggtgac cctccgactg
1801 gacacccacc ctgccatggt caccgtgctg gagatggggg ctgcccgcca cttcctgcgc
1861 atgcagcagc tggccaagac ccaggaggag cgcgcacagc tcctgcagcc cacgctggag
1921 atcaacccca ggcacgcgct catcaagaag ctgaatcagc tgcgcgcaag cgagcctggc
```

FIG. 10 A-80

```
1981 ctggctcagc tgctggtgga tcagatatac gagaacgcca tgattgctgc tggacttgtt
2041 gacgaccct a gggccatggt gggccgcttg aatgagctgc ttgtcaaggc cctggagcga
2101 cactgacagc caggggggcca gaaggactga caccacagat gacagcccca cctccttgag
2161 ctttatttac ctaaatttaa aggtatttct taacccga
```

SEQ ID NO:91
```
   1 agtgatgtcc ttgcattgcc cattttaag caagaagagt cgagtttgcc tcctgataat
  61 gagaataaaa tcctgccttt tcaatatgtg ctttgtgctg ctacctctcc agcagtgaaa
 121 ctccatgatg aaaccctaac gtatctcaat caaggacagt cttatgaaat cgaatgcta
 181 gacaatagga aacttggaga acttccagaa attaatggca aattggtgaa gagtatattc
 241 cgtgtggtgt tccatgacag aaggcttcag tacactgagc atcagcagct agagggctgg
 301 aggtggaacc gacctggaga cagaattctt gacatagata tcccgatgtc tgtgggtata
 361 atcgatccta gggctaatcc aactcaacta aatacagtgg agttcctgtg ggaccctgca
 421 aagaggacat ctgtgtttat tcaggtgcac tgtattagca cagagttcac tatgaggaaa
 481 catggtggag aaaagggggt gccattccga gtacaaatag ataccttcaa ggagaatgaa
 541 aacggggaat atactgagca cttacactcg gccagctgcc agatcaaagt tttcaagcca
 601 aagtgcaga cagaaagcaa aaaacggata gggaaaaat ggagaaacga acacctcatg
 661 aaaaggagaa atatcagcct tcctatgaga caaccatact cacagagtgt tctccatggc
 721 ccgagatcac gtatgtcaat aactccccat cacctggctt caacagttcc catagcagtt
 781 tttctcttgg ggaaggaaat ggttcaccaa accaccagcc agagccaccc cctccagtca
 841 cagataacct cttaccaaca accacacctc aggaagctca gcagtggttg catcgaaatc
 901 gttttctac attcacaagg cttttcacaa acttctcagg ggcagattta ttgaaattaa
 961 ctagagatga tgtgatccaa atctgtggcc ctgcagatgg aatcagactt tttaatgcat
1021 taaaagccg gatggtgcgt ccaagttaa ccatttatgt ttgtcaggaa tcactgcagt
1081 tgagggagca gcaacaacag cagcagcaac agcagcagaa gcatgaggat ggagactcaa
1141 atggtacttt cttcgtttac catgctatct atctagaaga actaacagct gttgaattga
1201 cagaaaaaat tgctcagctt ttcagcattt cccttgcca gatcagccag atttacaagc
1261 aggggccaac aggaattcat gtgctcatca gtgatgagat gatacagaac tttcaggaag
1321 aagcatgttt tattctggac acaatgaaag cagaaaccaa tgatagctat catatcatac
1381 tgaagtagga gtgcggcgtt tcgtgcccag tggctgctcc ttccttcacc tctgaaaacg
1441 gccctcttga aggggggatat gaatggagat ttgaaggtct gcaagaacct gactcgtctg
1501 actgtgtgtg gaggagtcca ggccatggag gcagaatcct ggccctctgt gttggcccaa
1561 gctcttgtgg tacacacaga ttactgccca atatgcagtt ctgcagctgt tttagttaaa
1621 tttctggacc ttgttgttgt taaatatcag tagaaactct acataattta gagtgtatgt
1681 agggcataat gatgatggga attgtgtgat gtttaacagg aagatcttaa attttgtgat
1741 atggagccct gtaattttt tcttatataa aaatgggtat ctatattcat
```

SEQ ID NO:92
```
   1 aggtctgttc cgcatgaaac tcctgctggg gaaggacttc cctgcctccc cacccaaggg
  61 ctacttcctg accaagatct tccacccgaa cttgggcgcc aatggcgaga tgtgcgtcaa
 121 cgtgctcaag agggactgga cggctgagct gggcatccga cacgtactgc tgaccatcaa
 181 gtgcctgctg atccacccta accccgagtc tgcactcaac gaggaggcgg gccgcctgct
 241 cttggagaac tacgaggagt atgcggctcg ggcccgtctg ctcacagaga tccacgggggg
 301 cgccggcggg cccagcggca gggcaaagc cgggcgggcc ctggccagtg gcactgcagc
 361 ttcctccacc gactctgggg ccccaggggg cttgggaggg ctgagggtc ccatggccaa
 421 gaagcatgct ggcgagcgcg ataagaagct ggcggccaag aaaaagacgg acaagaagcg
 481 ggcgctacgg cggctgtagt gggctctctt cctccttcca ccgtgacccc aacctctcct
 541 gtccctccc tccaactctg tctctaagtt atttaaatta tggctgggggt cggggagggt
 601 acagggggca ctgagacctg gatttgtttt tttaaataaa gttggaaaag ca
```

FIG. 10 A-81

```
SEQ ID NO:93
     1 gtcgtgttct ccgagttcct gtctctctgc caacgccgcc cggatggctt cccaaaaccg
    61 cgacccagcc gccactagcg tcgccgccgc ccgtaaagga gctgagccga gcggggcgc
   121 cgcccgggt ccggtgggca aaaggctaca gcaggagctg atgaccctca tgatgtctgg
   181 cgataaaggg atttctgcct tccctgaatc agacaacctt ttcaaatggg tagggaccat
   241 ccatggagca gctggaacag tatatgaaga cctgaggtat aagctctcgc tagagttccc
   301 cagtggctac ccttacaatg cgcccacagt gaagttcctc acgccctgct atcaccccaa
   361 cgtggacacc cagggtaaca tatgcctgga catcctgaag gaaaagtggt ctgccctgta
   421 tgatgtcagg accattctgc tctccatcca gagccttcta ggagaaccca acattgatag
   481 tcccttgaac acacatgctg ccgagctctg gaaaaacccc acagcttta agaagtacct
   541 gcaagaaacc tactcaaagc aggtcaccag ccaggagccc tgaccaggc tgcccagcct
   601 gtccttgtgt cgtctttta atttttcctt agatggtctg tccttttgt gatttctgta
   661 taggactctt tatcttgagc tgtggtattt ttgtttgtt tttgtcttt aaattaagcc
   721 tcggttgagc ccttgtatat taaataaatg cattttgtc cttttttaga c SEQ ID NO:94
     1 ctccagcagc acccgagagg gtcaggagaa aagcggagga agctgggtag gccctgaggg
    61 gcctcggtaa gccatcatga ccacccggca agccacgaag gatcccctcc tccgggtgt
   121 atctcctacc cctagcaaga ttccgtacg ctctcagaaa cgcacgcctt tccccactgt
   181 tacatcgtgc gccgtggacc aggagaacca agatcaagg agatgggtgc agaaaccacc
   241 gctcaatatt caacgccccc tcgttgattc agcaggcccc aggccgaaag ccaggcacca
   301 ggcagagaca tcacaaagat tggtggggat cagtcagcct cggaacccct tggaagagct
   361 caggcctagc cctaggggtc aaaatgtggg gcctgggccc ctgcccaga cagaggctcc
   421 agggaccata gagtttgtgg ctgaccctgc agccctggcc accatcctgt caggtgaggg
   481 tgtgaagagc tgtcacctgg ggcgccagcc tagtctggct aaaagagtac tggttcgagg
   541 aagtcaggga ggcaccaccc agagggtcca gggtgttcgg gcctctgcat atttggcccc
   601 cagaaccccc acccaccgac tggaccctgc cagggcttcc tgcttctcta ggctggaggg
   661 accaggacct cgaggccgga cattgtgtcc ccagaggcta caggctctga tttcaccttc
   721 aggaccttcc tttcacccttc ccactcgacc cagtttccag gagctaagaa gggagacagc
   781 tggcagcagc cggacttcag tgagccaggc ctcaggattg ctcctggaga ccccagtcca
   841 gcctgctttc tctcttccta aggagaacg cgaggttgtc actcactcag atgaaggagg
   901 tgtggcctct cttggtctgg cccagcgagt accattaaga gaaaaccgag aaatgtcaca
   961 taccagggac agccatgact cccccacctgat ccctccccct gccccgtgg ccagccctt
  1021 gcctggccat gtggtgccat gtccatcacc ctttggacgg gctcagcgtg taccctcccc
  1081 aggccctcca actctgacct catattcagt gttgcggcgt ctcaccgttc aacctaaaac
  1141 ccggttcaca cccatgccat caaccccag agttcagcag gcccagtggc tgcgtggtgt
  1201 ctccctcag tcctgctctg aagatcctgc cctgccctgg gagcaggttg ccgtccggtt
  1261 gtttgaccag gagagttgta taaggtcact gggaaaccac gggaaaccac
  1321 tccttctgga ccccactcta acagaacccc cagcctccag gaggtgaaga ttcaacgcat
  1381 cggtatcctg caaacagcgt tgagacagga agtagaggg ctggtagggg gccagtgtgt
  1441 ccctcttaat ggaggctctt ctctggatat ggttgaactt cagcccctgc tgactgagat
  1501 ttctagaact ctgaatgcca cagagcataa ctctcaccttc tcccaccttc ctgactgtt
  1561 aaaacactca gggctgccaa agccctgtct tccagaggag tgcggggaac cacagccctg
  1621 ccctccggca gagcctgggc cccagaggc cttctgtagg agtgagcctg agataccaga
  1681 gcctccctc caggaacagc ttgaagtacc agagccctac cctccagcag aacccaggcc
  1741 cctagagtcc tgctgtagga gtgagcctga gataccggag tcctctcgcc aggaacagct
  1801 tgaggtacct gagccctgcc ctccagcaga acccaggcc ctagagtcct actgtaggat
  1861 tgagcctgag ataccggagt cctctcgcca ggaacagctt gaggtacctg agccctgccc
  1921 tccagcagaa cccgggcccc ttcagcccag cacccagggg cagtctggac ccccagggcc
  1981 ctgccctagg gtagagctgg gggcatcaga gccctgcacc ctggaacata gaagtctaga
```

FIG. 10 A-82

```
2041 gtccagtcta ccaccctgct gcagtcagtg ggctccagca accaccagcc tgatcttctc
2101 ttcccaacac ccgctttgtg ccagccccc tatctgctca ctccagtctt tgagaccccc
2161 agcaggccag gcaggcctca gcaatctggc ccctcgaacc ctagccctga gggagcgcct
2221 caaatcgtgt ttaaccgcca tccactgctt ccacgaggct cgtctggacg atgagtgtgc
2281 cttttacacc agccgagccc ctccctcagg ccccacccgg gtctgcacca accctgtggc
2341 tacattactc gaatggcagg atgccctgtg tttcattcca gttggttctg ctgcccccca
2401 gggctctcca tgatgagaca accactcctg ccctgccgta cttcttcctt ttagcccctta
2461 tttattgtcg gtctgcccat gggactggga gccgcccact tttgtcctca ataaagtttc
2521 taaagta
```

SEQ ID NO:95

```
   1 agaataatca tgggccagac tgggaagaaa tctgagaagg gaccagtttg ttggcggaag
  61 cgtgtaaaat cagagtacat gcgactgaga cagctcaaga ggttcagacg agctgatgaa
 121 gtaaaggtat gtttagttcc aatcgtcaga aaattttgga aagaacggaa atcttaaacc
 181 aagaatggaa acagcgaagg atacagcctg tgcacatcct gacttctgtg agctcattgc
 241 gcgggactag ggagtgttcg gtgaccagtg acttggattt tccaacacaa gtcatcccat
 301 taaagactct gaatgcagtt gcttcagtac ccataatgta ttcttggtct ccctacagc
 361 agaattttat ggtggaagat gaaactgttt tacataacat tccttatatg ggagatgaag
 421 ttttagatca ggatggtact ttcattgaag aactaataaa aaattatgat gggaaagtac
 481 acggggatag agaatgtggg tttataaatg atgaaatttt tgtggagttg gtgaatgccc
 541 ttggtcaata taatgatgat gacgatgatg atgatggaga cgatcctgaa gaaagagaag
 601 aaaagcagaa agatctggag gatcaccgag atgataaaga aagccgccca cctcggaaat
 661 ttccttctga taaaattttt gaagccattt cctcaatgtt tccagataag ggcacagcag
 721 aagaactaaa ggaaaaatat aaagaactca ccgaacagca gctcccaggc gcacttcctc
 781 ctgaatgtac ccccaacata gatggaccaa atgctaaatc tgttcagaga gagcaaagct
 841 tacactcctt tcatacgctt ttctgtaggc gatgttttaa atatgactgc ttcctacatc
 901 cttttcatgc aacacccaac acttataagc ggaagaacac agaaacagct ctagacaaca
 961 aaccttgtgg accacagtgt taccagcatt tggagggagc aaaggagttt gctgctgctc
1021 tcaccgctga gcggataaag accccaccaa aacgtccagg aggccgcaga agaggacggc
1081 ttcccaataa cagtagcagg cccagcaccc ccaccattaa tgtgctggaa tcaaaggata
1141 cagacagtga tagggaagca gggactgaaa cgggggagga gaacaatgat aaagaagaag
1201 aagagaagaa agatgaaact tcgagctcct ctgaagcaa ttctcggtgt caaacaccaa
1261 taaagatgaa gccaaatatt gaacctcctg agaatgtgga gtggagtggt gctgaagcct
1321 caatgtttag agtcctcatt ggcacttact atgacaattt ctgtgccatt gctaggttaa
1381 ttgggaccaa aacatgtaga caggtgtatg agtttagagt caaagaatct agcatcatag
1441 ctccagctcc cgctgaggat gtggatactc ctccaaggaa aaagaagagg aaacaccggt
1501 tgtgggctgc acactgcaga aagatacagc tgaaaaagga cggctcctct aaccatgttt
1561 acaactatca accctgtgat catccacggc agccttgtga cagttcgtgc ccttgtgtga
1621 tagcacaaaa ttttttgtgaa aagttttgtc aatgtagttc agagtgtcaa aaccgctttc
1681 cgggatgccg ctgcaagca cagtgcaaca ccaaagctg cccgtgctac ctggctgtcc
1741 gagagtgtga ccctgacctc tgtcttactt gtggagccgc tgaccattgg gacagtaaaa
1801 atgtgtcctg caagaactgc agtattcagc ggggctccaa aaagcatcta ttgctggcac
1861 catctgacgt ggcaggctgg gggattttta tcaaagatcc tgtgcagaaa aatgaattca
1921 tctcagaata ctgtggagag attatttctc aagatgaagc tgacagaaga gggaaagtgt
1981 atgataaata catgtgcagc tttctgttca acttgaacaa tgattttgtg gtggatgcaa
2041 cccgcaaggg taacaaaatt cgttttgcaa atcattcggt aaatccaaac tgctatgcaa
2101 aagttatgat ggttaacggt gatcacagga taggtatttt tgccaagaga gccatccaga
2161 ctggcgaaga gctgttttt gattacagat acagccaggc tgatgccctg aagtatgtcg
2221 gcatcgaaag agaaatggaa atcccttgac atctgctacc tcctccccc tcctctgaaa
2281 cagctgcctt agcttcagga acctcgagta ctgtgggcaa tttagaaaaa gaacatgcag
```

FIG. 10 A-83

```
2341 tttgaaattc tgaatttgca aagtactgta agaataattt atagtaatga gtttaaaaat
2401 caactttta ttgccttctc accagctgca aagtgttttg taccagtgaa ttttgcaat
2461 aatgcagtat ggtacatttt tcaactttga ataaagaata cttgaacttg tc
```

SEQ ID NO: 96

```
   1 caggtctgag gcgaagctag gtgagccgtg ggaagaaaag agggagcagc tagggcgcgg
  61 gtctccctcc tcccggagtt tggaacggct gaagttcacc ttccagcccc tagcgccgtt
 121 cgcgccgcta ggcctggctt ctgaggcggt tgcggtgctc ggtcgccgcc taagcggggc
 181 agggtgcgaa caggggcttc gggccacgct tctcttggcg acaggatttt gctgtgaagt
 241 ccgtccggga aacggaggaa aaaagagtt gcgggaggct gtctgctaat aacggttctt
 301 gatacatatt tgccagactt caagatttca gaaaagggt gaaagagaag attgcaactt
 361 tgagtcagac ctgtaggcct gatagactga ttaaaccaca gaaggtgacc tgctgagaaa
 421 agtggtacaa atactgggaa aaacctgctc ttctgcgtta agtgggagac aatgtcacaa
 481 gttaaaagct cttattccta tgatgccccc tcggatttca tcaattttc atccttggat
 541 gatgaaggag atactcaaaa catagattca tggtttgagg agaaggccaa tttggagaat
 601 aagttactgg ggaagaatgg aactggaggg cttttcagg gcaaaactcc tttgagaaag
 661 gctaatcttc agcaagctat tgtcacacct tgaaaccag ttgacaacac ttactacaaa
 721 gaggcagaaa aagaaaatct tgtggaacaa tccattccgt caatgcttg ttcttccctg
 781 gaagttgagg cagccatatc aagaaaaact ccagcccagc ctcagagaag atctcttagg
 841 cttttctgtc agaaaggatt ggaacagaaa gaaaagcatc atgtaaaaat gaaagccaag
 901 agatgtgcca ctcctgtaat catcgatgaa attctaccct ctaagaaaat gaaagtttct
 961 aacaacaaaa agaagccaga ggaagaaggc agtgctcatc aagatactgc tgaaaacaat
1021 gcatcttccc cagagaaagc caagggtaga catactgtgc cttgtatgcc acctgcaaag
1081 cagaagtttc taaaaagtac tgaggagcaa gagctggaga agagtatgaa aatgcagcaa
1141 gaggtggtgg agatgcggaa aaagaatgaa gaattcaaga aacttgctct ggctggaata
1201 gggcaacctg tgaagaaatc agtgagccag gtcaccaaat cagttgactt ccacttccgc
1261 acagatgagc gaatcaaaca acatcctaag aaccaggagg aatataagga agtgaacttt
1321 acatctgaac tacgaaagca tccttcatct cctgcccgag tgactaaggg atgtaccatt
1381 gttaagcctt tcaacctgtc ccaaggaaag aaagaacat ttgatgaaac agtttctaca
1441 tatgtgcccc ttgcacagca agttgaagac ttccataaac gaaccctaa cagatatcat
1501 ttgaggagca agaaggatga tattaacctg ttaccctcca aatcttctgt gaccaagatt
1561 tgcagagacc cacagactcc tgtactgcaa accaaacacc gtgcacgggc tgtgacctgc
1621 aaaagtacag cagagctgga ggctgaggag ctcgagaaat tgcaacaata caaattcaaa
1681 gcacgtgaac ttgatcccag aatacttgaa ggtgggccca tcttgcccaa gaaaccacct
1741 gtgaaaccac ccaccgagcc tattggcttt gatttggaaa ttgagaaaag aatccaggag
1801 cgagaatcaa agaagaaaac agaggatgaa cactttgaat tcattccag accttgccct
1861 actaagattt tggaagatgt tgtgggtgtt cctgaaaaga aggtacttcc aatcaccgtc
1921 cccaagtcac cagcctttgc attgaagaac agaattcgaa tgcccaccaa agaagatgag
1981 gaaggggacg aaccggtagt gataaaagct caacctgtgc cacattatgg ggtgcctttt
2041 aagccccaaa tcccagaggc aagaactgtg gaaatatgcc ctttctcgtt tgattctcga
2101 gacaaagaac gtcagttaca gaaggagaag aaaataaaag aactgcagaa aggggaggtg
2161 cccaagttca aggcacttcc cttgcctcat tttgacacca ttaacctgcc agagaagaag
2221 gtaaagaatg tgacccagat tgaaccttc tgcttggaga ctgacagaag aggtgctctg
2281 aaggcacaga cttggaagca ccagctggaa gagaactga gacagcagaa agaagcagct
2341 tgtttcaagg ctcgtccaaa caccgtcatc tctcaggagc cctttgttcc caagaaagag
2401 aagaaatcag ttgctgaggg cctttctggt tctctagttc aggaacctt tcagctggct
2461 actgagaaga gagccaaaga gcggcaggag ctggagaaga gaatggctga ggtagaagcc
2521 cagaaagccc agcagttgga ggaggccaga ctacaggagg aagagcagaa aaagaggag
2581 ctggccaggc tacggagaga actggtgcat aaggcaaatc caatacgcaa gtaccagggt
2641 ctggagataa agtcaagtga ccagcctctg actgtgcctg tatctcccaa attctccact
```

FIG. 10 A-84

```
2701 cgattccact gctaaactca gctgtgagct gcggataccg cccggcaatg ggacctgctc
2761 ttaacctcaa acctaggacc gtcttgcttt gtcattgggc atggagagaa cccatttctc
2821 cagactttta cctacccgtg cctgagaaag catacttgac aactgtggac tccagttttg
2881 ttgagaattg ttttcttaca ttactaaggc taataatgag atgtaactca tgaatgtctc
2941 gattagactc catgtagtta cttcctttaa accatcagcc ggccttttat atgggtcttc
3001 actctgacta gaatttagtc tctgtgtcag cacagtgtaa tctctattgc tattgcccct
3061 tacgactctc accctctccc cactttttt aaaaatttta accagaaaat aaagatagtt
3121 aaatcctaag atagagatta agtcatggtt taaatgagga acaatcagta aatcagattc
3181 tgtcctcttc tctgcatacc gtgaatttat agttaaggat cccttgctg tgagggtaga
3241 aaacctcacc aactgcacca gtgaggaaga agactgcgtg gattcatggg gagcctcaca
3301 gcagccacgc agcaggctct gggtggggct gccgttaagg cacagttctt tccttactgg
3361 tgctgataac aacagggaac cgtgcagtgt gcattttaag acc
```

SEQ ID NO:97

```
   1 cttcaacccg cgccggcggc gactgcagtt cctgcgagcg aggagcgcgg gacctgctga
  61 cacgctgacg ccttcgagcg cggccggggg cccggagcgg ccggagcagc ccgggtcctg
 121 accccggccc ggctcccgct ccgggctctg ccggcgggcg ggcgagcgcg gcgcggtccg
 181 ggccgggggg atgtctcggc ggacgcgctg cgaggatctg gatgagctgc actaccagga
 241 cacagattca gatgtgccgg agcagaggga tagcaagtgc aaggtcaaat ggaccatga
 301 ggaggacgag cagctgaggg ccctggtgag gcagtttgga cagcaggact ggaagttcct
 361 ggccagccac ttccctaacc gcactgacca gcaatgccag tacaggtggc tgagagtttt
 421 gaatccagac cttgtcaagg ggccatggac caaagaggaa gaccaaaaag tcatcgagct
 481 ggttaagaag tatggcacaa agcagtggac actgattgcc aagcacctga agggccggct
 541 ggggaagcag tgccgtgaac gctggcacaa ccacctcaac cctgaggtga agaagtcttg
 601 ctggaccgag gaggaggacc gcatcatctg cgaggccac aaggtgctgg gcaaccgctg
 661 ggccgagatc gccaagatgt tgccagggag gacagacaat gctgtgaaga tcactggaa
 721 ctctaccatc aaaaggaagg tggacacagg aggcttcttg agcgagtcca agactgcaa
 781 gcccccagtg tacttgctgc tgggagctcga ggacaaggac ggcctccaga gtgcccagcc
 841 cacggaaggc cagggaagtc ttctgaccaa ctggccctcc gtccctccta ccataaagga
 901 ggaggaaaac agtgaggagg aacttgcagc agccaccaca tcgaaggaac aggagcccat
 961 cggtacagat ctggacgcag tgcgaacacc agagcccttg gaggaattcc gaagcgtga
1021 ggaccaggaa ggctccccac cagaaacgag cctgccttac aagtgggtgg tggaggcagc
1081 taacctcctc atccctgctg tgggttctag cctctctgaa gccctggact tgatcgagtc
1141 ggaccctgat gcttggtgtg acctgagtaa atttgacctc cctgaggaac catctgcaga
1201 ggacagtatc aacaacagcc tagtcagctt gcaagcgtca catcagcagc aagtcctgcc
1261 accccgccag ccttccgccc tggtgcccag tgtgaccgag taccgcctgg atggccacac
1321 catctcagac ctgagccgga gcagccgggg cgagctgatc cccatctccc cagcactgga
1381 agtcggggc tctggcattg gcacaccgcc ctctgtgctc aagcggcaga ggaagaggcg
1441 tgtggctctg tcccctgtca ctgagaatag caccagtctg tccttcctgg attcctgtaa
1501 cagcctcacg cccaagagca cacctgttaa gaccctgccc ttctcgccct cccagtttct
1561 gaacttctgg aacaaacagg acacattgga gctggagagc ccctcgctga catccacccc
1621 agtgtgcagc cagaaggtgg tggtcaccac accactgcac cgggacaaga caccccctgca
1681 ccagaaacat gctgcgtttg taaccccaga tcagaagtac tccatggaca acactcccca
1741 cacgccaacc ccgttcaaga acgccctgga gaagtacgga cccctgaagc cctgccaca
1801 gaccccgcac ctggaggagg acttgaagga ggtgctgcgt tctgaggctg catcgaact
1861 catcatcgag gacgacatca ggcccgagaa gcagaagagg aagcctgggc tgcggcggag
1921 ccccatcaag aaagtccgga gtctctggc tcttgacatt gtggatgagg atgtgaagct
1981 gatgatgtcc acactgccca gtctctatc cttgccgaca actgcccctt caaactcttc
2041 cagcctcacc ctgtcaggta tcaaagaaga aacagcttg ctcaaccagg cttcttgca
2101 ggccaagccc gagaaggcag cagtggccca gaagcccga agccacttca cgacacctgc
```

FIG. 10 A-85

```
2161 ccctatgtcc agtgcctgga agacggtggc ctgcgggggg accagggacc agcttttcat
2221 gcaggagaaa gcccggcagc tcctgggccg cctgaagccc agccacacat ctcggaccct
2281 catcttgtcc tgaggtgttg agggtgtcac gagcccattc tcatgtttac aggggttgtg
2341 ggggcagagg gggtctgtga atctgagagt cattcaggtg acctcctgca gggagccttc
2401 tgccaccagc ccctccccag actctcaggt ggaggcaaca gggccatgtg ctgccctgtt
2461 gccgagccca gctgtgggcg gctcctggtg ctaacaacaa agttccactt ccaggtctgc
2521 ctggttccct ccccaaggcc acaggagct ccgtcagctt ctcccaagcc cacgtcaggc
2581 ctggcctcat ctcagaccct gcttaggatg ggggatgtgg ccaggggtgc tcctgtgctc
2641 accctctctt ggtgcatttt tttggaagaa taaaattgcc tctctctt
```

SEQ ID NO:98

```
   1 atgaggttga cgctactttg ttgcacctgg agggaagaac gtatgggaga ggaaggaagc
  61 gagttgcccg tgtgtgcaag ctgcggccag aggatctatg atggccagta cctccaggcc
 121 ctgaacgcgg actggcacgc agactgcttc aggtgttgtg actgcagtgc ctccctgtcg
 181 caccagtact atgagaagga tggcagctc ttctgcaaga aggactactg ggcccgctat
 241 ggcgagtcct gccatgggtg ctctgagcaa atcaccaagg gactggttat ggtggctggg
 301 gagctgaagt accacccga gtgtttcatc tgcctcacgt gtgggacctt tatcggtgac
 361 ggggacacct acacgctggt ggagcactcc aagctgtact gcggcactg ctactaccag
 421 actgtggtga ccccgtcat cgagcagatc ctgcctgact cccctggctc ccacctgccc
 481 cacaccgtca cctggtgtc catcccagcc tcatctcatg gcaagcgtgg actttcagtc
 541 tccattgacc ccccgcacg cccaccgggc tgtggcaccg agcactcaca caccgtccgc
 601 gtccagggag tggatccggg ctgcatgagc ccagatgtga agaattccat ccacgtcgga
 661 gaccggatct tggaaatcaa tggcacgccc atccgaaatg tgccctgga cgagattgac
 721 ctgctgattc aggaaaccag ccgcctgctc cagctgaccc tcgagcatga ccctcacgat
 781 acactggggcc acgggctggg gcctgagacc agcccctga gctctccggc ttatactccc
 841 agcgggagg cgggcagctc tgcccggcag aaacctgtct tcgcaaggac ctggtcgct
 901 ctgagtccct ccgcgtagtc tgccggccac accgcatctt ccggccgtcg gacctcatcc
 961 acggggaggt gctgggcaag gctgcttcg gccaggctat caaggtgaca caccgtgaga
1021 caggtgaggt gatggtgatg aaggagctga tccggttcga cgaggagacc cagaggacgt
1081 tcctcaagga ggtgaaggtc atgcgatgcc tggaacaccc caacgtgctc aagttcatcg
1141 gggtgctcta caaggacaag aggctcaact tcatcactga gtacatcaag gcggcacgc
1201 tccgggcat catcaagagc atggacagcc agtacccatg gagccagaga gtgagctttg
1261 ccaaggacat cgcatcaggg atggcctacc tccactccat gaacatcatc caccgagacc
1321 tcaactccca caactgcctg gtccgcgaga caagaatgt ggtggtggct gacttcgggc
1381 tggcgcgtct catggtggac gagaagactc agcctgaggg cctgcggagc ctcaagaagc
1441 cagaccgcaa gaagcgctac accgtggtgg gcaaccccta ctggatggca cctgagatga
1501 tcaacgcccg cagctatgat gagaaggtgg atgtgttctc ctttgggatc gtcctgtgcg
1561 agatcatcgg gcgggtgaac gcagaccctg actaccgtgcc ccgcaccatg gactttggcc
1621 tcaacgtgcg aggattcctg gaccgctact gccccccaaa ctgccccccg agcttcttcc
1681 ccatcaccgt gcgctgttgc gatctggacc ccgagaagag gccatccttt gtgaagctgg
1741 aacactggct ggagaccctc cgcatgcacc tggccggcca cctgccactg ggcccacagc
1801 tggagcagct ggacagaggt ttctgggaga cctaccggcg cggcgagagc ggactgcctg
1861 cccacccctga ggtccccgac tga
```

SEQ ID NO:99

```
   1 atgcctggct tcgactacaa gttcctggag aagcccaagc gacggctgct gtgcccactg
  61 tgcgggaagc ccatgcgcga gcctgtgcag gtttccacct gcggccaccg tttctgcgat
 121 acctgcctgc aggagttcct cagtgaagga gtcttcaagt gccctgagga ccagcttcct
 181 ctggactatg ccaagatcta cccagaccgg agctggaag tacaagtatt gggcctgcct
 241 atccgctgca tccacagtga ggagggctgc cgctggagtg ggccactacg tcatctacag
```

FIG. 10 A-86

```
301 ggccacctga atacctgcag cttcaatgtc attccctgcc ctaatcgctg ccccatgaag
361 ctgagccgcc gtgatctacc tgcacacttg cagcatgact gcccaagcg gcgcctcaag
421 tgcgagtttt gtggctgtga cttcagtggg gaggcctatg aggtggatga gagttctctg
481 ggctttggtt atcccaagtt catctcccac caggacattc gaaagcgaaa ctatgtgcgg
541 gatgatgcag tcttcatccg tgctgctgtt gaactgcccc ggaagatcct cagctga
```

SEQ ID NO:104
```
   1 ttgcaggctg ctgggctggg gctaagggct gctcagtttc cttcagcggg gcactgggaa
  61 gcgccatggc actgcagggc atctcggtcg tggagctgtc cggcctggcc ccgggcccgt
 121 tctgtgctat ggtcctggct gacttcgggg cgcgtgtggt acgcgtggac cggcccggct
 181 cccgctacga cgtgagccgc ttgggccggg gcaagcgctc gctagtgctg gacctgaagc
 241 agccgcgggg agccgccgtg ctgcggcgtc tgtgcaagcg gtcggatgtg ctgctggagc
 301 ccttccgccg cggtgtcatg gagaaactcc agctggcccc agagattctg cagcgggaaa
 361 atccaaggct tatttatgcc aggctgaagtg gatttggcca gtcaggaagc ttctgccggt
 421 tagctggcca cgatatcaac tatttggctt tgtcaggtgt tctctcaaaa attggcagaa
 481 gtggtgagaa tccgtatgcc ccgctgaatc tcctggctga ctttgctggt ggtggcctta
 541 tgtgtgcact gggcattata atggctcttt tgaccgcac acgcactggc aagggtcagg
 601 tcattgatgc aaatatggtg gaaggaacag catatttaag ttcttttctg tggaaaactc
 661 agaaatcgag tctgtgggaa gcacctcgag gacagaacct gttggatggt ggagcacctt
 721 tctatacgac ttacaggaca gcagatgggg aattcatggc tgttggagca atagaacccc
 781 agttctacga gctgctgatc aaaggacttg gactaaagtc tgatgaactt cccaatcaga
 841 tgagcatgga tgattggcca gaaatgaaga agaagtttgc agatgtattt gcaaagaaga
 901 cgaaggcaga gtggtgtcaa atctttgacg gcacagatgc ctgtgtgact ccggttctga
 961 cttttgagga ggttgttcat catgatcaca acaaggaacg gggtcgtttt atcaccagtg
1021 aggagcagga cgtgagcccc cgccctgcac ctctgctgtt aaacacccca gccatccctt
1081 ctttcaaaag ggatcctttc ataggagaac acactgagga gatacttgaa gaatttggat
1141 tcagccgcga agagattat cagcttaact cagataaaat cattgaaagt aataaggtaa
1201 aagctagtct ctaacttcca ggcccacggc tcaagtgaat ttgaatactg catttacagt
1261 gtagagtaac ataacatt gtatgcatgg aaacatggag gaacagtatt acagtgtcct
1321 accactctaa tcaagaaaag aattacagac tctgattcta cagtgatgat tgaattctaa
1381 aaatggttat cattagggct tttgatttat aaaactttgg gtacttatac taaattatgg
1441 tagttattct gccttccagt ttgcttgata tatttgttga tattaagatt cttgacttat
1501 attttgaatg ggttctagtg aaaaaggaat gatatattct tgaagacatc gatatacatt
1561 tatttacact cttgattcta caatgtagaa aatgaggaaa tgccacaaat tgtatggtga
1621 taaaagtcac gtgaaacaga gtgattggtt gcatccaggc cttttgtctt ggtgttcatg
1681 atctccctct aagcacattc caaactttag caacagttat cacactttgt aatttgcaaa
1741 gaaaagtttc acctgtattg aatcagaatg ccttcaactg aaaaaaacat atccaaaata
1801 atgaggaaat gtgttggctc actacgtaga gtccagaggg acagtcagtt ttagggttgc
1861 ctgtatccag taactcgggg cctgtttccc cgtgggctc tgggctgtca gcttttccttt
1921 ctccatgtgt ttgatttctc ctcaggctgg tagcaagttc tggatcttat acccaacaca
1981 cagcaacatc cagaaataaa gatct
```

SEQ ID NO:114
```
   1 cggaggcgct gggcgcacgg cgcggagccg gccggagctc gaggccggcg gcggcgggag
  61 agcgacccgg gcggcctcgt agcggggccc cggatcccg agtggccggcc ggagcctcga
 121 aaagagattc tcagcgctga ttttgagatg atgggcttgg gaaacgggcg tcgcagcatg
 181 aagtcgccgc ccctcgtgct ggccgccctg gtggcctgca tcatcgtctt gggcttcaac
 241 tactggattg cgagctcccg gagcgtggac ctccagacac ggatcatgga gctggaaggc
 301 agggtccgca gggcggctgc agagagaggc gccgtggagc tgaagaagaa cgagttccag
 361 ggagagctgg agaagcagcg ggagcagctt gacaaaatcc agtccagcca caacttccag
 421 ctggagagcg tcaacaagct gtaccaggac gaaaaggcgg ttttggtgaa taacatcacc
```

FIG. 10 A-87

```
 481 acaggtgaga ggctcatccg agtgctgcaa gaccagttaa agaccctgca gaggaattac
 541 ggcaggctgc agcaggatgt cctccagttt cagaagaacc agaccaacct ggagaggaag
 601 ttctcctacg acctgagcca gtgcatcaat cagatgaagg aggtgaagga acagtgtgag
 661 gagcgaatag aagaggtcac caaaaagggg aatgaagctg tagcttccag agacctgagt
 721 gaaaacaacg accagagaca gcagctccaa gccctcagtg agcctcagcc caggctgcag
 781 gcagcaggcc tgccacacac agaggtgcca caagggaagg gaaacgtgct tggtaacagc
 841 aagtcccaga caccagcccc cagttccgaa gtggttttgg attcaaagag acaagttgag
 901 aaagaggaaa ccaatgagat ccaggtggtg aatgaggagc ctcagaggga caggctgccg
 961 caggagccag gccgggagca ggtggtggaa gacagacctg taggtggaag aggcttcggg
1021 ggagccggag aactgggcca gacccacag gtgcaggctg ccctgtcagt gagccaggaa
1081 aatccagaga tggagggccc tgagcgagac cagcttgtca tccccgacgg acaggaggag
1141 gagcaggaag ctgccgggga agggagaaac cagcagaaac tgagaggaga agatgactac
1201 aacatggatg aaaatgaagc agaatctgag acagacaagc aagcagccct ggcagggaat
1261 gacagaaaca tagatgtttt taatgttgaa gatcagaaaa gagacaccat aaatttactt
1321 gatcagcgtg aaaagcggaa tcatacactc tgaattgaac tggaatcaca tatttcacaa
1381 cagggccgaa gagatgacta taaaatgttc atgagggact gaatactgaa aactgtgaaa
1441 tgtactaaat aaaatgtaca tctgaagatg attattgtga aattttagta tgcactttgt
1501 gtaggaaaaa atggaatggt cttttaaaca gcttttgggg gggtactttg gaagtgtcta
1561 ataaggtgtc acaattttg gtagtaggta tttcgtgaga agttcaacac caaaactgga
1621 acatagttct ccttcaagtg ttggcgacag cgggcttcc tgattctgga atataacttt
1681 gtgtaaatta acagccacct ataaaagagt ccatctgctg tgaaggagag acagagaact
1741 ctgggttccg tcgtcctgtc cacgtgctgt accaagtgct ggtgccagcc tgttacctgt
1801 tctcactgaa aagtctggct aatgctcttg tgtagtcact tctgattctg acaatcaatc
1861 aatcaatggc ctagagcact gactgttaac acaaacgtca ctagcaaagt agcaacagct
1921 ttaagtctaa atacaaagct gttctgtgtg agaattttt aaaaggctac ttgtataata
1981 acccttgtca ttttaatgt acaaaacgct attaagtggc ttagaatttg aacatttgtg
2041 gtctttattt actttgcttc gtgtgtgggc aaagcaacat cttccctaaa tatatattac
2101 caagaaaagc aagaagcaga ttaggttttt gacaaaacaa acaggccaaa aggggctga
2161 cctggagcag agcatggtga gaggcaaggc atgagagggc aagtttgttg tggacagatc
2221 tgtgcctact ttattactgg agtaaaagaa aacaaagttc attgatgtcg aaggatatat
2281 acagtgttag aaattaggac tgtttagaaa aacaggaata caatggttgt ttttatcata
2341 gtgtacacat ttagcttgtg gtaaatgact cacaaaactg attttaaaat caagttaatg
2401 tgaattttga aaattactac ttaatcctaa ttcacaataa caatggcatt aaggtttgac
2461 ttgagttggt tcttagtatt attttatggta aataggctct taccacttgc aaataactgg
2521 ccacatcatt aatgactgac ttcccagtaa ggctctctaa ggggtaagta ggaggatcca
2581 caggatttga gatgctaagg ccccagagat cgtttgatcc aaccctctta ttttcagagg
2641 ggaaaatggg gcctagaagt tacagagcat ctagctggtg cgctggcacc cctggcctca
2701 cacagactcc cgagtagctg ggactacagg cacacagtca ctgaagcagg ccctgtttgc
2761 aattcacgtt gccacctcca acttaaacat tcttcatatg tgatgtcctt agtcactaag
2821 gttaaacttt cccacccaga aaaggcaact tagataaaat cttagagtac tttcatactc
2881 ttctaagtcc tcttccagcc tcactttgag tcctccttgg ggttgatagg aatttttctct
2941 tgctttctca ataaagtctc tattcatctc atgtttaatt tgtacgcata gaattgctga
3001 gaaataaaat gttctgttca acttaaaaaa aaaaaaaaa aa
```

SEQ ID NO:115

```
  1 cgggcgatgc cgcgctgcgg gggggccgca cagccgccgc caccgccacc gccgccgggt
 61 ggggtgggag gggcgggaac gcgcgccgcc gcctccaggg tgggcgcctt tcgccgtgga
121 cgccgaccgt ccgggacgag ggtttcatca ccttaaatgg ttttgaacca atgaaggtgt
```

FIG. 10 A-88

```
 181 attcccttaa aaagacggac agcccatcgt gtgaactata gagtttgtgg acagatttat
 241 attgggttca tagtggcgtc atgcacgcag actcctgcaa gttcccctaa gttcttagag
 301 gactgctttg ccttttgatc tgagagttgc aaagttccat aaagaatggc ccttgtggat
 361 aagcacaaag tcaagagaca gcgattggac agaatttgtg aaggtatccg cccccagatc
 421 atgaacggcc ccctgcaccc ccgcccctg gtggcgctgc tggacggccg cgactgcact
 481 gtggagatgc ccatcctgaa ggacctggcc actgtggcct tctgtgacgc gcagtcgacg
 541 caggaaatcc acgagaaggt tctaaacgaa gccgtgggcg ccatgatgta ccacaccatc
 601 accctcacca gggaggacct ggagaagttc aaggccctga gagtgatcgt gcggataggc
 661 agtggctatg acaacgtgga catcaaggct gccggcgagc tcggaattgc cgtgtgcaac
 721 atcccgtctg cagccgtgga agagacagcg gactctacca tctgccacat cctcaacctg
 781 taccggagga acacgtggct gtaccaggca ctgcgggaag gcacgcgggt tcagagcgtg
 841 gagcagatcc gcgaggtggc ctcgggagcg gcccgcatcc gtggggagac gctgggcctc
 901 attggctttg gtcgcacggg gcaggcggtt gcagttcgag ccaaggcctt tggattcagc
 961 gtcatatttt atgacccta cttgcaggat gggatcgagc ggtccctggg cgtgcagagg
1021 gtctacaccc tgcaggattt gctgtatcag agcgactgcg tctccttgca ctgcaatctc
1081 aacgaacata accaccacct catcaatgac tttaccataa agcagatgag gcagggagca
1141 ttccttgtga acgcagcccg tggcggcctg gtggacgaga aagccttagc acaagccctc
1201 aaggagggca ggatacgagg ggcagccctc gacgtgcatg agtcagagcc cttcagcttt
1261 gctcagggtc cgttgaaaga tgccccgaat ctcatctgca ctcctcacac tgcctggtac
1321 agtgagcagg cgtcactgga gatgagggag gcagctgcca ccgagatccg ccgagccatc
1381 acaggtcgca tcccagaaag cttaagaaat tgtgtgaaca aggaattctt tgtcacatca
1441 gcgccttggt cagtaataga ccagcaagca attcatcctg agctcaatgg tgccacatac
1501 agatatccgc caggcatcgt gggtgtggct ccaggaggac ttcctgcagc catggaaggg
1561 atcatccctg gaggcatccc agtgactcac aacctcccga cagtggcaca tccttcccaa
1621 gcgccctctc ccaaccagcc cacaaaacac ggggacaatc gagagcaccc caacgagcaa
1681 tagcagagaa tgccagaagg taatcactca gatacacttg ggaccaagag acagtgaaaa
1741 atagatgaac taagagaaaa agaatcggat ggtctttgta actgattctg gacatatgca
1801 tcattgatgt tgcagtgttg aaactacaag agctagaaaa ctgaagatgt cgtctgctta
1861 cggaagcgct gaaagactag gatgtgattt attaacgacc aacttctgtt attgtgtgtt
1921 aagtttttca tctgtgcatc aaatcacaaa agaataaat agagcttttt cctttatcag
1981 tcccttgggc acagcaggtc ctgaacaccc tgctctacaa tgttgcatca agagttcaaa
2041 caacaaaata aaaaatatta agaggaaatc cccatcctgt gacttgagtc ccttaagtct
2101 acaggggctg gtgacctctt tttgctaata ggaaaatcac attactacaa aatggggaga
2161 aaactgtttg cctgtggtag acacctgcac gcataggatt gaagacagta caggctgctg
2221 tacagagaag cgcctctcac atctgaactg catactgagc gggcaagtcg gttgtaagtt
2281 cagtaaaacc ctctgatgat gcaaaaaaaa aaaaaagta ttaagtttca caagctgttt
2341 gtactcaaat atatttctc agtttcag
```

SEQ ID NO:116

```
   1 catttgggga cgctctcagc tctcggcgca cggcccagct tccttcaaaa tgtctactgt
  61 tcacgaaatc ctgtgcaagc tcagcttgga gggtgatcac tctacacccc caagtgcata
 121 tgggtctgtc aaagcctata ctaactttga tgctgagcgg gatgctttga acattgaaac
 181 agccatcaag accaaaggtg tggatgaggt caccattgtc aacatttga ccaaccgcag
 241 caatgcacag agacaggata ttgccttcgc ctaccagaga aggaccaaaa aggaacttgc
 301 atcagcactg aagtcagcct tatctggcca cctggagacg gtgattttgg gcctattgaa
 361 gacacctgct cagtatgacg cttctgagct aaaagcttcc atgaagggc tgggaaccga
 421 cgaggactct ctcattgaga tcatctgctc cagaaccaac caggagctgc aggaaattaa
 481 cagagtctac aaggaaatgt acaagactga tctggagaag gacattattt cggacacatc
 541 tggtgacttc cgcaagctga tggttgccct ggcaaagggt agaagagcag aggatggctc
```

FIG. 10 A-89

```
 601 tgtcattgat tatgaactga ttgaccaaga tgctcgggat ctctatgacg ctggagtgaa
 661 gaggaaagga actgatgttc ccaagtggat cagcatcatg accgagcgga gcgtgcccca
 721 cctccagaaa gtatttgata ggtacaagag ttacagccct tatgacatgt tggaaagcat
 781 caggaaagag gttaaaggag acctggaaaa tgctttcctg aacctggttc agtgcattca
 841 gaacaagccc ctgtattttg ctgatcggct gtatgactcc atgaagggca aggggacgcg
 901 agataaggtc ctgatcagaa tcatggtctc ccgcagtgaa gtggacatgt tgaaaattag
 961 gtctgaattc aagagaaagt acggcaagtc cctgtactat tatatccagc aagacactaa
1021 gggcgactac cagaaagcgc tgctgtacct gtgtggtgga gatgactgaa gcccgacacg
1081 gcctgagcgt ccagaaatgg tgctcaccat gcttccagct aacaggtcta gaaaaccagc
1141 ttgcgaataa cagtccccgt ggccatccct gtgagggtga cgttagcatt accccccaacc
1201 tcattttagt tgcctaagca ttgcctggcc ttcctgtcta gtctctcctg taagccaaag
1261 aaatgaacat tccaaggagt tggaagtgaa gtctatgatg tgaaacactt tgcctcctgt
1321 gtactgtgtc ataaacagat gaataaactg aatttgtact tt
```

SEQ ID NO:117

```
   1 gccccaggtg cgcttcccct agagagggat tttccggtct cgtgggcaga ggaacaacca
  61 ggaacttggg ctcagtctcc accccacagt ggggcggatc cgtcccggat aagacccgct
 121 gtctggccct gagtagggtg tgacctccgc agccgcagag gaggagcgca gcccggcctc
 181 gaagaacttc tgcttgggtg gctgaactct gatcttgacc tagagtcatg gccatggcaa
 241 ccaaaggagg tactgtcaaa gctgcttcag gattcaatgc catggaagat gcccagaccc
 301 tgaggaaggc catgaaaggg ctcggcaccg atgaagacgc cattattagc gtccttgcct
 361 accgcaacac cgcccagcgc caggagatca ggacagccta caagagcacc atcggcaggg
 421 acttgataga cgacctgaag tcagaactga gtggcaactt cgagcaggtg attgtgggga
 481 tgatgacgcc cacggtgctg tatgacgtgc aagagctgcg aagggccatg aagggagccg
 541 gcactgatga gggctgccta attgagatcc tggcctcccg gacccctgag gagatccggc
 601 gcataagcca aacctaccag cagcaatatg gacggagcct tgaagatgac attcgctctg
 661 acacatcgtt catgttccag cgagtgctgg tgtctctgtc agctggtggg agggatgaag
 721 gaaattatct ggacgatgct ctcgtgagac aggatgccca ggacctgtat gaggctggag
 781 agaagaaatg ggggacagat gaggtgaaat ttctaactgt tctctgttcc cggaaccgaa
 841 atcacctgtt gcatgtgttt gatgaataca aaggatatc acagaaggat attgaacaga
 901 gtattaaatc tgaaacatct ggtagcttg aagatgctct gctggctata gtaaagtgca
 961 tgaggaacaa atctgcatat tttgctgaaa agctctataa atcgatgaag ggcttgggca
1021 ccgatgataa caccctcatc agagtgatgg tttctcgagc agaaattgac atgttggata
1081 tccgggcaca cttcaagaga ctctatggaa agtctctgta ctcgttcatc aagggtgaca
1141 catctggaga ctacaggaaa gtactgcttg ttctctgtgg aggagatgat aaaataaaa
1201 atcccagaag gacaggagga ttctcaacac tttgaatttt tttaacttca tttttctaca
1261 ctgctattat cattatctca gaatgcttat ttccaattaa acgcctaca gctgcctcct
1321 agaatataga ctgtctgtat tattattcac ctataattag tcattatgat gctttaaagc
1381 tgtacttgca tttcaaagct tataagatat aaatggagat tttaaagtag aaataaatat
1441 gtattccatg ttttaaaag attactttct actttgtgtt tcacagacat tgaatatatt
1501 aaattattcc atatttctt ttcagtgaaa aatttttaa atggaagact gttctaaaat
1561 cacttttttc cctaatccaa tttttagagt ggctagtagt ttcttcattt gaaattgtaa
1621 gcatccggtc agtaagaatg cccatccagt tttctatatt tcatagtcaa agccttgaaa
1681 gcatctacaa atctcttttt ttaggttttg tccatagcat cagttgatcc ttactaagtt
1741 tttcatggga gacttccttc atcacatctt atgttgaaat cactttctgt agtcaaagta
1801 taccaaaacc aatttatctg aactaaattc taaagtatgg ttatacaaac catatacatc
1861 tggttaccaa acataaatgc tgaacattcc atattattat agttaatgtc ttaatccagc
```

FIG. 10 A-90

```
1921 ttgcaagtga atggaaaaaa aaataagctt caaactaggt attctgggaa tgatgtaatg
1981 ctctgaattt agtatgatat aaagaaaact tttttgtgct aaaaatactt tttaaaatca
2041 attttgttga ttgtagtaat ttctatttgc actgtgcctt tcaactccag aaacattctg
2101 aagatgtact tggatttaat taaaaagttc actttgt
```

SEQ ID NO:118

```
   1 gctgctgcgc ccgcggctcc ccagtgcccc gagtgccccg cgggccccgc gagcgggagt
  61 gggacccagc cctaggcaga acccaggcgc cgcgcccggg acgcccgcgg agagagccac
 121 tcccgcccac gtcccatttc gcccctcgcg tcggagtcc ccgtggccag atctaaccat
 181 gagctaccct ggctatcccc cgcccccagg tggctaccca ccagctgcac caggtggtgg
 241 tccctgggga ggtgctgcct accctcctcc gcccagcatg cccccatcg ggctggataa
 301 cgtggccacc tatgcggggc agttcaacca ggactatctc tcgggaatgg cggccaacat
 361 gtctgggaca tttggaggag ccaacatgcc caacctgtac cctgggccc ctggggctgg
 421 ctacccacca gtgcccctg gcggctttgg gcagccccc tctgcccagc agcctgttcc
 481 tccctatggg atgtatccac cccaggagg aaaccaccc tccaggatgc cctcatatcc
 541 gccatacca ggggcccctg tgccgggcca gccatgcca cccccggac agcagccccc
 601 aggggcctac cctgggcagc caccagtgac ctaccctggt cagcctccag tgccactccc
 661 tgggcagcag cagccagtgc cgagctaccc aggatacccg gggtctggga ctgtcacccc
 721 cgctgtgccc ccaacccagt ttggaagccg aggcaccatc actgatgctc ccggctttga
 781 cccccctgcga gatgccgagg tcctgcggaa ggccatgaaa gcttcgggga cggatgagca
 841 ggccatcatt gactgcctgg ggagtcgctc caacaagcag cggcagcaga tcctactttc
 901 cttcaagacg gcttacggca aggatttgat caaagatctg aaatctgaac tgtcaggaaa
 961 ctttgagaag acaatcttgg ctctgatgaa gacccagtc ctctttgaca tttatgagat
1021 aaaggaagcc atcaagggg ttggcactga tgaagcctgc ctgattgaga tcctcgcttc
1081 ccgcagcaat gagcacatcc gagaattaaa cagagcctac aaagcagaat caaaaagac
1141 cctggaagag gccattcgaa gcgacacatc agggcacttc cagcggctcc tcatctctct
1201 ctctcaggga aaccgtgatg aaagcacaaa cgtggacatg tcactcgccc agagagatgc
1261 ccaggagctg tatgcggccg gggagaaccg cctgggaaca gacgagtcca agttcaatgc
1321 ggttctgtgc tcccggagcc gggcccacct ggtagcagtt ttcaatgagt accagagaat
1381 gacaggccgg gacattgaga gagcctctg ccgggagatg tccggggacc tggaggaggg
1441 catgctggcc gtggtgaaat gtctcaagaa tacccagcc ttctttgcgg agaggctcaa
1501 caaggccatg ggggggcag gaacaaagga ccggaccctg attcgcatca tggtgtctcg
1561 cagcgagacc gacctcctgg acatcagatc agagtataag cggatgtacg gcaagtcgct
1621 gtaccacgac atctcgggag atacttcagg ggattaccgg aagattctgc tgaagatctg
1681 tggtggcaat gactgaacag tgactggtgg ctcacttctg cccacctgcc ggcaacacca
1741 gtgccaggaa aaggccaaaa gaatgtctgt ttctaacaaa tccacaaata gccccgagat
1801 tcaccgtcct agagcttagg cctgtcttcc accctcctg acccgtatag tgtgccacag
1861 gacctgggtc ggtctagaac tctctcagga tgccttttct accccatccc tcacagcctc
1921 ttgctgctaa aatagatgtt tcattttct gaaaaaaa
```

SEQ ID NO:119

```
   1 ggctcatgct cgggagcgtg gttgagcggc tggcgcggtt gtcctggagc aggggcgcag
  61 gaattctgat gtgaaactaa cagtctgtga gccctggaac ctccactcag agaagatgaa
 121 ggatatcgac ataggaaaag agtatatcat ccccagtcct gggtatagaa gtgtgaggga
 181 gagaaccagc acttctggga cgcacagaga ccgtgaagat tccaagttca ggagaactcg
 241 accgttgaa tgccaagatg ccttggaaac agcagcccga gccgagggcc tctctcttga
 301 tgcctccatg cattctcagc tcagaatcct ggatgaggag catcccaagg gaaagtacca
 361 tcatggcttg agtgctctga gcccatccg gactacttcc aaacaccagc acccagtgga
```

FIG. 10 A-91

```
 421 caatgctggg ctttttcct gtatgactt ttcgtggctt tcttctctgg cccgtgtggc
 481 ccacaagaag ggggagctct caatggaaga cgtgtggtct ctgtccaagc acgagtcttc
 541 tgacgtgaac tgcagaagac tagagagact gtggcaagaa gagctgaatg aagttgggcc
 601 agacgctgct tccctgcgaa gggttgtgtg gatcttctgc cgcaccaggc tcatcctgtc
 661 catcgtgtgc ctgatgatca cgcagctggc tggcttcagt ggaccagcct tcatggtgaa
 721 acacctcttg gagtatacc aggcaacaga gtctaacctg cagtacagct tgttgttagt
 781 gctgggcctc ctcctgacgg aaatcgtgcg gtcttggtcg cttgcactga cttgggcatt
 841 gaattaccga accggtgtcc gcttgcgggg gccatccta accatggcat ttaagaagat
 901 ccttaagtta aagaacatta aagagaaatc cctgggtgag ctcatcaaca tttgctccaa
 961 cgatgggcag agaatgtttg aggcagcagc cgttggcagc ctgctggctg gaggacccgt
1021 tgttgccatc ttaggcatga tttataatgt aattattctg ggaccaacag gcttcctggg
1081 atcagctgtt tttatcctct tttacccagc aatgatgttt gcatcacggc tcacagcata
1141 tttcaggaga aaatgcgtgg ccgccacgga tgaacgtgtc cagaagatga atgaagttct
1201 tacttacatt aaatttatca aaatgtatgc ctgggtcaaa gcattttctc agagtgttca
1261 aaaaatccgc gaggaggagc gtcggatatt ggaaaaagct gggtacttcc agagcatcac
1321 tgtgggtgtg gctcccattg tggtggtgat tgccagcgtg gtgaccttct ctgttcatat
1381 gaccctgggc ttcgatctga cagcagcaca ggctttcaca gtggtgacag tcttcaattc
1441 catgactttt gctttgaaag taacaccgtt ttcagtaaag tccctctcag aagcctcagt
1501 ggctgttgac agatttaaga gtttgtttct aatggaagag gttcacatga taaagaacaa
1561 accagccagt cctcacatca agatagagat gaaaaatgcc accttggcat gggactcctc
1621 ccactccagt atccagaact cgcccaagct gacccccaaa atgaaaaaag acaagagggc
1681 ttccagggc aagaaagaga aggtgaggca gctgcagcgc actgagcatc aggcggtgct
1741 ggcagagcag aaaggccacc tcctcctgga cagtgacgag cggcccagtc cgaagagga
1801 agaaggcaag cacatccacc tgggccacct gcgcttacag aggacactgc acagcatcga
1861 tctggagatc aagagggta aactggttgg aatctgtggc agtgtgggaa gtggaaaaac
1921 ctctctcatt tcagccattt taggccagat gacgcttcta gagggcagca ttgcaatcag
1981 tggaaccttc gcttatgtgg cccagcaggc ctggatcctc aatgctactc tgagagacaa
2041 catcctgttt gggaaggaat atgatgaaga aagatacaac tctgtgctga acagctgctg
2101 cctgaggcct gacctggcca ttcttcccag cagcgacctg acggagattg gagagcgagg
2161 agccaacctg agcggtgggc agcgccagag gatcagcctt gcccgggcct tgtatagtga
2221 caggagcatc tacatcctgg acgacccct cagtgcctta gatgcccatg tgggcaacca
2281 catcttcaat agtgctatcc ggaaacatct caagtccaag acagttctgt tgttaccca
2341 ccagttacag tacctggttg actgtgatga agtgatcttc atgaaagagg gctgtattac
2401 ggaaagaggc acccatgagg aactgatgaa tttaaatggt gactatgcta ccatttttaa
2461 taacctgttg ctgggagaga caccgccagt tgagatcaat tcaaaaaagg aaaccagtgg
2521 ttcacagaag aagtcacaag acaagggtcc taaaacagga tcagtaaaga aggaaaaagc
2581 agtaaagcca gaggaaggc agcttgtgca gctggaagag aaagggcagg gttcagtgcc
2641 ctggtcagta tatggtgtct acatccaggc tgctgggggc cccttggcat tcctggttat
2701 tatggccctt tcatgctga atgtaggcag caccgccttc agcacctggt ggttgagtta
2761 ctggatcaag caaggaagcg ggaacaccac tgtgactcga ggaacgaga cctcggtgag
2821 tgacagcatg aaggacaatc ctcatatgca gtactatgcc agcatctacg ccctctccat
2881 ggcagtcatg ctgatcctga agccattcg aggagttgtc tttgtcaagg gcacgctgcg
2941 agcttcctcc cggctgcatg acgagctttt ccgaaggatc cttcgaagcc ctatgaagtt
3001 ttttgacacg accccacag ggaggattct caacaggttt tccaaagaca tggatgaagt
3061 tgacgtgcgg ctgccgttcc aggccagat gttcatccag aacgttatcc tggtgttctt
3121 ctgtgtggga atgatcgcag gagtcttccc gtggttcctt gtggcagtgg ggccccttgt
3181 catcctcttt tcagtcctgc acattgtctc cagggtcctg attcgggagc tgaagcgtct
3241 ggacaatatc acgcagtcac ctttcctctc ccacatcacg tccagcatac agggccttgc
3301 caccatccac gcctacaata aagggcagga gtttctgcac agataccagg agctgctgga
3361 tgacaaccaa gctcctttt ttttgtttac gtgtgcgatg cggtggctgg ctgtgcggct
```

FIG. 10 A-92

```
3421 ggacctcatc agcatcgccc tcatcaccac cacggggctg atgatcgttc ttatgcacgg
3481 gcagattccc ccagcctatg cgggtctcgc catctcttat gctgtccagt taacggggct
3541 gttccagttt acggtcagac tggcatctga gacagaagct cgattcacct cggtggagag
3601 gatcaatcac tacattaaga ctctgtcctt ggaagcacct gccagaatta agaacaaggc
3661 tccctcccct gactggcccc aggagggaga ggtgaccttt gagaacgcag agatgaggta
3721 ccgagaaaac ctccctctcg tcctaaagaa agtatccttc acgatcaaac ctaaagagaa
3781 gattggcatt gtggggcgga caggatcagg gaagtcctcg ctggggatgg ccctcttccg
3841 tctggtggag ttatctggag gctgcatcaa gattgatgga gtgagaatca gtgatattgg
3901 ccttgccgac ctccgaagca aactctctat cattcctcaa gagccggtgc tgttcagtgg
3961 cactgtcaga tcaaatttgg accccttcaa ccagtacact gaagaccaga tttgggatgc
4021 cctggagagg acacacatga aagaatgtat tgctcagcta cctctgaaac ttgaatctga
4081 agtgatggag aatggggata acttctcagt gggggaacgg cagctcttgt gcatagctag
4141 agccctgctc cgccactgta agattctgat tttagatgaa gccacagctg ccatggacac
4201 agagacagac ttattgattc aagagaccat ccgagaagca tttgcagact gtaccatgct
4261 gaccattgcc catcgcctgc acacggttct aggctccgat aggattatgg tgctggccca
4321 gggacaggtg gtggagtttg acaccccatc ggtccttctg tccaacgaca gttcccgatt
4381 ctatgccatg tttgctgctg cagagaacaa ggtcgctgtc aagggctgac tcctccctgt
4441 tgacgaagtc tcttttcttt agagcattgc cattccctgc ctggggcggg cccctcatcg
4501 cgtcctccta ccgaaacctt gcctttctcg attttatctt tcgcacagca gttccggatt
4561 ggcttgtgtg tttcactttt agggagagtc atattttgat tatttgtattt attccatatt
4621 catgtaaaca aaatttagtt tttgttctta attgcactct aaaaggttca gggaaccgtt
4681 attataattg tatcagaggc ctataatgaa gctttatacg tgtagctata tctatatata
4741 attctgtaca tagcctatat ttacagtgaa aatgtaagct gtttatttta tattaaaata
4801 agcactgtgc taataacagt gcatattcct ttctatcatt tttgtacagt ttgctgtact
4861 agagatctgt ttttgctatt agactgtagg aagagtagca tttcattctt ctctagctgg
4921 tggtttcacg gtgccaggtt tctgggtgt ccaaaggaag acgtgtggca atagtgggcc
4981 ctccgacagc cccctctgcc gcctccccac ggccgctcca ggggtggctg gagacgggtg
5041 ggcggctgga gaccatgcag agcgccgtga gttctcaggg ctcctgcctt ctgtcctggt
5101 gtcacttact gtttctgtca ggagagcagc ggggcgaagc ccaggcccct tttcactccc
5161 tccatcaaga atggggatca cagagacatt cctccgagcc ggggagtttc tttcctgcct
5221 tcttcttttt gctgttgttt ctaaacaaga atcagtctat ccacagagag tcccactgcc
5281 tcaggttcct atggctggcc actgcacaga gctctccagc tccaagacct gttggttcca
5341 agccctggag ccaactgctg cttttgagg tggcactttt tcatttgcct attcccacac
5401 ctccacagtt cagtggcagg gctcaggatt tcgtgggtct gttttccttt ctcaccgcag
5461 tcgtcgcaca gtctctctct ctctctcccc tcaaagtctg caacttttaag cagctcttgc
5521 taatcagtgt ctcacactgt cgtagaagtt tttgtactgt aaaagagacct acctcaggtt
5581 gctggttgct gtgtggtttg gtgtgttccc gcaaaccccc tttgtgctgt ggggctggta
5641 gctcaggtgg gcgtggtcac tgctgtcatc aattgaatgg tcagcgttgc atgtcgtgac
5701 caactagaca ttctgtcgcc ttagcatgtt tgctgaacac cttgtggaag caaaaatctg
5761 aaaatgtgaa taaaattatt ttggattttg t SEQ ID NO:120
   1 aaacttcccg cacgcgttac aggagccagg tcggtataag cgccacgcct cgccgcccgt
  61 caagctgtcc acatccctgg cctcagcccg ccacatcacc ctgacctgct tacgcccaga
 121 ttttcttcaa tcacatctga ataaatcact tgaagaaagc ttatagcttc attgcaccat
 181 gtgtggcatt tgggcgctgt ttggcagtga tgattgcctt tctgttcagt gtctgagtgc
 241 tatgaagatt gcacacagag gtccagatgc attccgtttt gagaatgtca atggatacac
 301 caactgctgc tttggatttc accggttggc ggtagttgac ccgctgtttg gaatgcagcc
 361 aattcgagtg aagaaatatc cgtatttgtg gctctgttac aatggtgaaa tctacaacca
 421 taagaagatg caacagcatt ttgaatttga ataccagacc aaagtggatg tgagataat
```

FIG. 10 A-93

```
 481 ccttcatctt tatgacaaag gaggaattga gcaaacaatt tgtatgttgg atggtgtgtt
 541 tgcatttgtt ttactggata ctgccaataa gaaagtgttc ctgggtagag atacatatgg
 601 agtcagacct ttgtttaaag caatgacaga agatggattt ttggctgtat gttcagaagc
 661 taaaggtctt gttacattga agcactccgc gactcccttt ttaaaagtgg agcctttcct
 721 tcctggacac tatgaagttt tggatttaaa gccaaatggc aaagttgcat ccgtggaaat
 781 ggttaaatat catcactgtc gggatgtacc cctgcacgcc ctctatgaca atgtggagaa
 841 actctttcca ggttttgaga tagaaactgt gaagaacaac ctcaggatcc ttttttaataa
 901 tgctgtaaag aaacgtttga tgacagacag aaggattggc tgccttttat caggggcctt
 961 ggactccagc ttggttgctg ccactctgtt gaagcagctg aaagaagccc aagtacagta
1021 tcctctccag acatttgcaa ttggcatgga agacagcccc gatttactgg ctgctagaaa
1081 ggtggcagat catattggaa gtgaacatta tgaagtcctt tttaactctg aggaaggcat
1141 tcaggctctg gatgaagtca tattttcctt ggaaacttat gacattacaa cagttcgtgc
1201 ttcagtaggt atgtatttaa tttccaagta tattcggaag aacacagata gcgtggtgat
1261 cttctctgga gaaggatcag atgaacttac gcagggttac atatattttc acaaggctcc
1321 ttctcctgaa aaagccgagg aggagagtga gaggcttctg agggaactct atttgtttga
1381 tgttctccgc gcagatcgaa ctactgctgc ccatggtctt gaactgagag tcccatttct
1441 agatcatcga tttttttcct attacttgtc tctgccacca gaaatgagaa ttccaaagaa
1501 tgggataaga aaacatctcc tgagagagac gtttgaggat tccaatctga tacccaaaga
1561 gattctctgt cgaccaaaag aagccttcag tgatggaata acttcagtta agaattcctg
1621 gtttaagatt ttacaggaat acgttgaaca tcaggttgat gatgcaatga tggcaaatgc
1681 agcccagaaa tttcccttca atactcctaa aaccaaagaa ggatattact accgtcaagt
1741 ctttgaacgc cattacccag gccgggctga ctggctgagc cattactgga tgcccaagtg
1801 gatcaatgcc actgaccctt ctgcccgcac gctgacccac tacaagtcag ctgtcaaagc
1861 ttaggtggtc tttatgctgt aatgtgaaag caaatatttc ttcgtgttgg atggggactg
1921 tgggtagata ggggaacaat gagagtcaac tcaggctaac ttgggtttga aaaaaataaa
1981 attcctaaat tt
```

SEQ ID NO:121

```
   1 aggttcaagt ggagctctcc taaccgacgc gcgtctgtgg agaagcggct tggtcggggg
  61 tggtctcgtg gggtcctgcc tgtttagtcg ctttcagggt tcttgagccc cttcacgacc
 121 gtcaccatgg aagtgtcacc attgcagcct gtaaatgaaa atatgcaagt caacaaaata
 181 aagaaaaatg aagatgctaa gaaaaagactg tctgttgaaa gaatctatca aaagaaaaca
 241 caattggaac atattttgct ccgcccagac acctacattg gttctgtgga attagtgacc
 301 cagcaaatgt gggtttacga tgaagatgtt ggcattaact ataggggaagt cacttttgtt
 361 cctggttttgt acaaaatctt tgatgagatt ctagttaatg ctgcggacaa caaacaaagg
 421 gacccaaaaa tgtcttgtat tagagtcaca attgatccgg aaaacaattt aattagtata
 481 tggaataatg gaaaaggtat tcctgttgtt gaacacaaag ttgaaagat gtatgtccca
 541 gctctcatat ttggacagct cctaacttct agtaactatg atgatgatga aaagaaagtg
 601 acaggtggtc gaaatggcta tggagccaaa ttgtgtaaca tattcagtac caaatttact
 661 gtggaaacag ccagtagaga atacaagaaa atgttcaaac agacatggat ggataatatg
 721 ggaagagctg gtgagatgga actcaagccc ttcaatggag aagattatac atgtatcacc
 781 tttcagcctg atttgtctaa gttaaaatg caaagcctgg acaagatat tgttgcacta
 841 atggtcagaa gagcatatga tattgctgga tccaccaaag atgtcaaagt ctttcttaat
 901 ggaaataaac tgccagtaaa aggatttcgt agttatgtgg acatgtattt gaaggacaag
 961 ttggatgaaa ctggtaactc cttgaaagta atacatgaac aagtaaacca caggtgggaa
1021 gtgtgtttaa ctatgagtga aaaaggcttt cagcaaatta gctttgtcaa cagcattgct
1081 acatccaagg gtggcagaca tgttgattat gtagctgatc agattgtgac taaacttgtt
1141 gatgttgtga agaagaagaa caagggtggt gttgcagtaa aagcacatca ggtgaaaaat
```

FIG. 10 A-94

```
1201 cacatgtgga tttttgtaaa tgccttaatt gaaacccaa cctttgactc tcagacaaaa
1261 gaaaacatga ctttacaacc caagagcttt ggatcaacat gccaattgag tgaaaaattt
1321 atcaaagctg ccattggctg tggtattgta gaaagcatac taaactgggt gaagtttaag
1381 gcccaagtcc agtaaaacaa gaagtgttca gctgtaaaac ataatagaat caagggaatt
1441 cccaaactcg atgatgccaa tgatgcaggg ggccgaaact ccactgagtg tacgcttatc
1501 ctgactgagg gagattcagc caaaactttg gctgtttcag gccttggtgt ggttgggaga
1561 gacaaatatg gggtttccc tcttagagga aaaatactca atgttcgaga agcttctcat
1621 aagcagatca tggaaaatgc tgagattaac aatatcatca agattgtggg tcttcagtac
1681 aagaaaaact atgaagatga agattcattg aagacgcttc gttatgggaa gataatgatt
1741 atgacagatc aggaccaaga tggttcccac atcaaaggct tgctgattaa ttttatccat
1801 cacaactggc cctctcttct gcgacatcgt tttctggagg aatttatcac tcccattgta
1861 aaggtatcta aaaacaagca agaaatggca ttttacagcc ttcctgaatt tgaagagtgg
1921 aagagttcta ctccaaatca taaaaatgg aaagtcaaat attacaaagg tttgggcacc
1981 agcacatcaa aggaagctaa agaatacttt gcagatatga aaagacatcg tatccagttc
2041 aaatattctg gtcctgaaga tgatgctgct atcagcctgg cctttagcaa aaaacagata
2101 gatgatcgaa aggaatggtt aactaatttc atggaggata gaagacaacg aaagttactt
2161 gggcttcctg aggattactt gtatggacaa actaccacat atctgacata taatgacttc
2221 atcaacaagg aacttatctt gttctcaaat tctgataacg agagatctat cccttctatg
2281 gtggatggtt tgaaaccagg tcagagaaag gttttgttta cttgcttcaa acggaatgac
2341 aagcgagaag taaaggttgc ccaattagct ggatcagtgg ctgaaatgtc ttcttatcat
2401 catggtgaga tgtcactaat gatgaccatt atcaatttgg ctcagaattt tgtgggtagc
2461 aataatctaa acctcttgca gcccattggt cagtttggta ccaggctaca tggtggcaag
2521 gattctgcta gtccacgata catctttaca atgctcagct ctttggctcg attgttattt
2581 ccaccaaaag atgatcacac gttgaagttt ttatatgatg acaaccagcg tgttgagcct
2641 gaatggtaca ttcctattat tcccatggtg ctgataaatg gtgctgaagg aatcggtact
2701 gggtggtcct gcaaaatccc caactttgat gtgcgtgaaa ttgtaaataa catcaggcgt
2761 ttgatggatg gagaagaacc tttgccaatg cttccaagtt acaagaactt caagggtact
2821 attgaagaac tggctccaaa tcaatatgtg attagtggtg aagtagctat tcttaattct
2881 acaaccattg aaatctcaga gcttcccgtc agaactggat cccagacata caaagaacaa
2941 gttctagaac ccatgttgaa tggcaccgag aagacacctc ctctcataac agactatagg
3001 gaataccata cagataccac tgtgaaattt gttgtgaaga tgactgaaga aaaactggca
3061 gaggcagaga gagttggact acacaaagtc ttcaaactcc aaactagtct cacatgcaac
3121 tctatggtgc ttttgacca cgtaggctgt ttaagaaaat atgacacggt gttggatatt
3181 ctaagagact ttttgaact cagacttaaa tattatggat taagaaaga atggctccta
3241 ggaatgcttg gtgctgaatc tgctaaactg aataatcagg ctcgcttat cttagagaaa
3301 atagatggca aaataatcat tgaaaataag cctaagaaca aattaattaa agttctgatt
3361 cagaggggat atgattcgga tcctgtgaag gcctgaaaag aagcccagca aaaggttcca
3421 gatgaagaag aaaatgaaga gagtgacaac gaaaaggaaa ctgaaaagag tgactccgta
3481 acagattctg gaccaacctt caactatctt cttgatatgc cccttggta tttaaccaag
3541 gaaaagaaag atgaactctg caggctaaga atgaaaaag aacaagagct ggacacatta
3601 aaaagaaaga gtccatcaga tttgtggaaa gaagacttgg ctacatttat tgaagaattg
3661 gaggctgttg aagccaagga aaaacaagat gaacaagtcg gacttcctgg gaagggggg
3721 aaggccaagg ggaaaaaaac acaaatggct gaagttttgc cttctccgcg tggtcaaaga
3781 gtcattccac gaataaccat agaaatgaaa gcagaggcag aaaagaaaaa taaaagaaa
3841 attaagaatg aaaatactga aggaagccct caagaagatg gtgtggaact agaaggccta
3901 aaacaaagat tagaaagaa acagaaaaga gaaccaggta caaagacaaa gaaacaaact
3961 acattggcat ttaagccaat caaaaaagga aagaagagaa atccctggtc tgattcagaa
4021 tcagatagga gcagtgacga aagtaatttt gatgtccctc cacgagaaac agagccacgg
4081 agagcagcaa caaaaacaaa attcacaatg gatttggatt cagatgaaga tttctcagat
4141 tttgatgaaa aaactgatga tgaagatttt gtcccatcag atgctagtcc acctaagacc
```

FIG. 10 A-95

```
4201 aaaacttccc caaaacttag taacaaagaa ctgaaaccac agaaaagtgt cgtgtcagac
4261 cttgaagctg atgatgttaa gggcagtgta ccactgtctt caagccctcc tgctacacat
4321 ttcccagatg aaactgaaat tacaaaccca gttcctaaaa agaatgtgac agtgaagaag
4381 acagcagcaa aaagtcagtc ttccacctcc actaccggtg ccaaaaaaag ggctgcccca
4441 aaaggaacta aaagggatcc agctttgaat tctggtgtct ctcaaaagcc tgatcctgcc
4501 aaaaccaaga atcgccgcaa aaggaagcca tccacttctg atgattctga ctctaatttt
4561 gagaaaattg tttcgaaagc agtcacaagc aagaaatcca aggggagag tgatgacttc
4621 catatggact ttgactcagc tgtggctcct cgggcaaaat ctgtacgggc aaagaaacct
4681 ataaagtacc tggaagagtc agatgaagat gatctgtttt aaaatgtgag gcgattattt
4741 taagtaatta tcttaccaag cccaagactg gttttaaagt tacctgaagc tcttaacttc
4801 ctcccctctg aatttagttt ggggaaggtg ttttagtac aagacatcaa agtgaagtaa
4861 agcccaagtg ttctttagct ttttataata ctgtctaaat agtgaccatc tcatgggcat
4921 tgtttcttc tctgctttgt ctgtgttttg agtctgcttt cttttgtctt taaaacctga
4981 tttttaagtt cttctgaact gtagaaatag ctatctgatc acttcagcgt aaagcagtgt
5041 gtttattaac catccactaa gctaaaacta gagcagtttg atttaaaagt gtcactcttc
5101 ctcctttct actttcagta gatatgagat agagcataat tatctgtttt atcttagttt
5161 tatacataat ttaccatcag atagaacttt atggttctag tacagatact ctactacact
5221 cagcctctta tgtgccaagt tttttctttaa gcaatgagaa attgctcatg ttcttcatct
5281 tctcaaatca tcagaggcca agaaaaaca ctttggctgt gtctataact tgacacagtc
5341 aatagaatga agaaaattag agtagttatg tgattatttc agctcttgac ctgtcccctc
5401 tggctgcctc tgagtctgaa tctcccaaag agagaaacca atttctaaga ggactggatt
5461 gcagaagact cggggacaac atttgatcca agatcttaaa tgttatattg ataaccatgc
5521 tcagcaatga gctattagat tcattttggg aaatctccat aatttcaatt tgtaaacttt
5581 gttaagacct gtctacattg ttatatgtgt gtgacttgag taatgttatc aacgttttg
5641 taaatattta ctatgttttt ctattagcta aattccaaca attttgtact ttaataaa
```

SEQ ID NO:122

```
   1 gcgccatgga gcagtggcgg cagtgcggcc gctggctcat cgattgcaag gtcctgccgc
  61 ccaaccaccg ggtggtgtgg ccctcggccg tggtcttcga cctggcgcag gcgctgcgcg
 121 acgggtcct tctgtgccag ctgctgcaca acctctcccc cggctccatc gacctcaagg
 181 acatcaactt ccggccgcag atgtcccagt ttctgtgttt gaagaacata cgcaccttcc
 241 tgaaagtctg ccacgataaa tttggattaa ggaacagcga gctgtttgac cccttttgacc
 301 tcttcgatgt gcgagacttt ggaaaggtca tctccgcggt gtcgaggctc tccctgcaca
 361 gcatcgcgca gaacaaaggg atcaggcctt ttccctcaga ggagaccaca gagaatgacg
 421 atgacgtcta ccgcagcctg gaggagctgg ccgacgagca tgacctgggg gaggacatct
 481 acgactgcgt cccgtgtgag gatggagggg acgacatcta cgaggacatc atcaaggtgg
 541 aggtgcagca gcccatgatt agatacatgc agaaaatgga catgactgaa gatgacaaga
 601 ggaactgctg cctgctggag atccaggaga ccgaggccaa gtactaccgc accctggagg
 661 acattgagaa gaactacatg agcccctgc ggctggtgct gagcccggcg gacatggcag
 721 ctgtcttcat taacctggag gacctgatca aggtgcatca cagcttcctg agggccatcg
 781 acgtgtccgt gatggtgggg ggcagcacgc tggccaaggt cttcctcgat ttcaaggaaa
 841 ggcttctgat ctacggggag acatgcagaa cgcccagaac aactgaacc
 901 agctcctggc cagccgggag gacttcaggc agaaagtcga ggagtgcaca ctgaaggtcc
 961 aggatggaaa atttaagctg caagacctgc tggtggtccc catgcagagg gtgctcaaat
1021 accacctgct cttgaaggag cttctgagcc attctgcgga acggcctgag aggcagcagc
1081 tcaaagaagc actgaagcc atgcaggact tggcgatgta catcaatgaa gttaaacggg
1141 acaaggagac cttgaggaaa atcagcgaat ttcagagttc tatagaaaat ttgcaagtga
1201 aactggagga atttggaaga ccaaagattg acggggaact gaaagtccgg tccatagtca
1261 accacaccaa gcaggacagg tacttgttcc tgtttgacaa ggtggtcatc gtctgcaagc
1321 ggaagggcta cagctacgag ctcaaggaga tcatcgagct gctgttccac aagatgaccg
```

FIG. 10 A-96

```
1381 acgaccccat gaacaacaag gacgtcaaga agtctcacgg gaaaatgtgg tcctacggct
1441 tctacctaat tcaccttcaa ggaaagcagg gcttccagtt tttctgcaaa acagaagata
1501 tgaagaggaa gtggatggag cagtttgaga tggccatgtc aaacatcaag ccagacaaag
1561 ccaatgccaa ccaccacagt ttccagatgt acacgtttga caagaccacc aactgcaaag
1621 cctgcaaaat gttcctcagg ggcaccttct accagggata catgtgtacc aagtgtggcg
1681 tcgggcaca caaggagtgc ctggaagtga tacctccctg caagttcact tctcctgcag
1741 atctggacgc ctccggagcg ggaccaggtc caagatggt ggccatgcag aattaccatg
1801 gcaacccagc ccctcccggg aagcctgtgc tgaccttcca gacgggcgac gtgcttgagc
1861 tgctgagggg cgaccctgag tctccgtggt gggagggtcg tctggtacaa accaggaagt
1921 cagggtattt ccccagctca tctgtgaagc cctgccctgt ggatggaagg ccgcccatca
1981 gccggccgcc atcccgggag atcgactaca ctgcataccc ctggtttgca ggtaacatgg
2041 agaggcagca gacggacaac ctgctcaagt cccacgccag cgggacctac ctgatcaggg
2101 agcggcctgc cgaggctgag cgctttgcaa taagcatcaa gttcaatgat gaggtgaagc
2161 acatcaaggt ggtggagaag gacaactgga tccacatcac agaggccaag aaattcgaca
2221 gcctcctgga gttggtggag tactaccagt gccactcact gaaggagagc ttcaagcagc
2281 tggacaccac actcaagtac ccctacaagt cccgggaacg ttcggcctcc agggcctcca
2341 gccggtcccc agcttcctgt gcttcctaca actttttcttt tctcagtcct cagggcctca
2401 gctttgcttc tcagggcccc tccgctccct tctggtcagt gttcacgccc cgcgtcatcg
2461 gcacagctgt ggccaggtat aactttgccg cccgagatat gagggagctt tcgctgcggg
2521 agggtgacgt ggtgaggatc tacagccgca tcggcggaga ccagggctgg tggaagggcg
2581 agaccaacgg acggattggc tggtttcctt caacgtacgt agaagaggag ggcatccagt
2641 gacggcagga acgtggacaa gactcgcaga ttttcttggg agagtcactc cagccctgaa
2701 gtctgtctct agctcctctg tgactcagag gggaaatacc aacctcccag tct
```

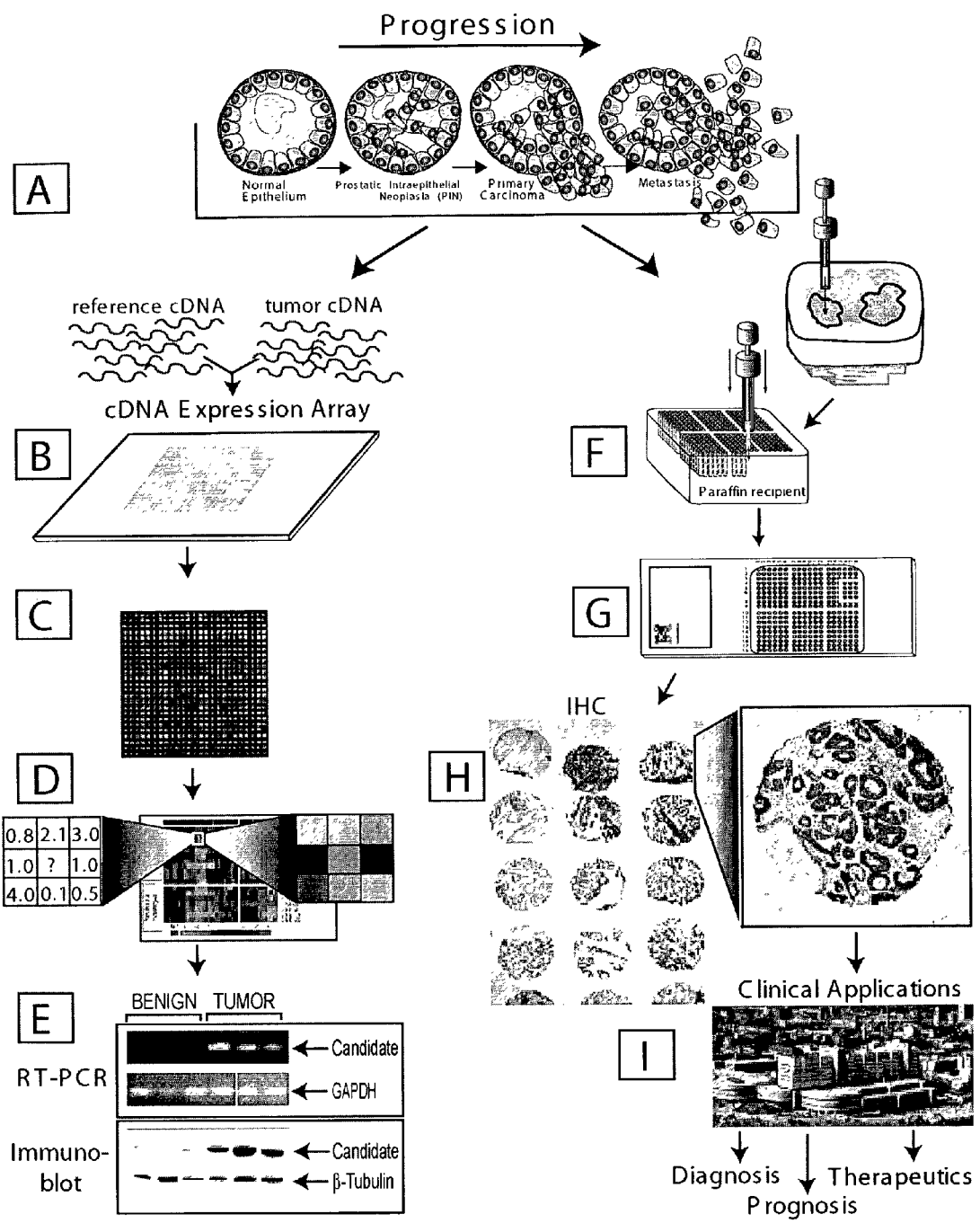

AMACR IN PCA CELL LINES

Immunoblot Analysis for AMACR in Prostate Cancer and Normal Sera

IMMUNOBLOT ANALYSIS
OF URINE SAMPLES FOR AMACR

U1-U10 : FEMALES WITH BLADDER CANCER
U11-U20 : MALES WITH BLADDER CANCER
AND INC PROSTATE

Figure 32
a) 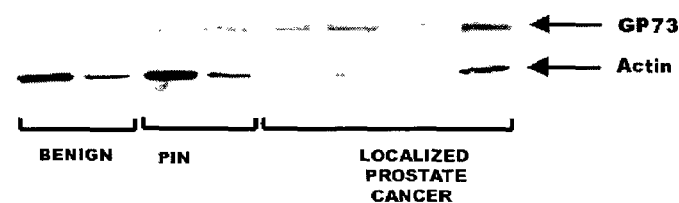
b) 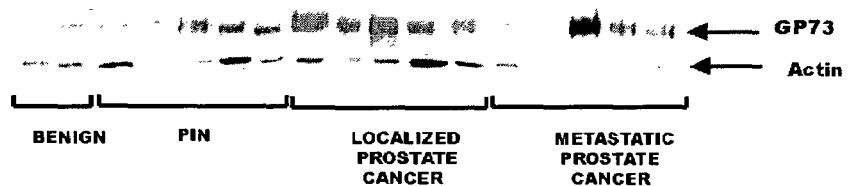

Figure 34

EXPRESSION PROFILE OF PROSTATE CANCER

This application claims priority to U.S. Provisional Application Ser. No. 60/309,581 filed Aug. 2, 2001 and U.S. Provisional Application Ser. No. 60/334,468 filed Nov. 15, 2001.

This invention was made with government support under Grant No. 5 P50 CA69568 awarded by the National Institutes of Health. The Government has certain rights in the invention.

Filed herewith as Tables 3, 4, 5, 6, and 7, and expressly incorporated by reference is an appendix contained on one compact disc, submitted in two identical sets labeled "Copy 1" and "Copy 2," for a total of two compact discs. Each compact disc was prepared in IBM-PC machine format and is compatible with the MS-Windows operating system. The set of two compact discs contains the following 5 files, in ASCII format:

Disc 1

| File Name | Creation Date | Size (bytes) |
|---|---|---|
| table3.txt | Aug. 01, 2002 | 1,964,212 |
| table4.txt | Aug. 01, 2002 | 1,498,092 |
| table5.txt | Aug. 01, 2002 | 3,374,515 |
| table6.txt | Aug. 01, 2002 | 82,030 |
| table7.txt | Aug. 01, 2002 | 18,882 |

FIELD OF THE INVENTION

The present invention relates to compositions and methods for cancer diagnostics, including but not limited to, cancer markers. In particular, the present invention provides gene expression profiles associated with prostate cancers. The present invention further provides novel markers useful for the diagnosis, characterization, and treatment of prostate cancers.

BACKGROUND OF THE INVENTION

Afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 184,500 American men will be diagnosed with prostate cancer and 39,200 will die in 2001.

Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

When PSA or digital tests indicate a strong likelihood that cancer is present, a transrectal ultrasound (TRUS) is used to map the prostate and show any suspicious areas. Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals.

The advent of prostate specific antigen (PSA) screening has led to earlier detection of PCA and significantly reduced PCA-associated fatalities. However, the impact of PSA screening on cancer-specific mortality is still unknown pending the results of prospective randomized screening studies (Etzioni et al., J. Natl. Cancer Inst., 91:1033 [1999]; Maattanen et al., Br. J. Cancer 79:1210 [1999]; Schroder et al., J. Natl. Cancer Inst., 90:1817 [1998]). A major limitation of the serum PSA test is a lack of prostate cancer sensitivity and specificity especially in the intermediate range of PSA detection (4–10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., JAMA 274:1445 [1995]). This has resulted in a surge of equivocal prostate needle biopsies (Epstein and Potter J. Urol., 166: 402 [2001]). Thus, development of additional serum and tissue biomarkers to supplement PSA screening is needed.

SUMMARY OF THE INVENTION

The present invention relates to compositions and methods for cancer diagnostics, including but not limited to, cancer markers. In particular, the present invention provides gene expression profiles associated with prostate cancers. The present invention further provides novel markers useful for the diagnosis, characterization, and treatment of prostate cancers.

In some embodiments, the present invention provides a method for characterizing prostate tissue in a subject, comprising: providing a prostate tissue sample from a subject; and detecting the presence or absence of expression of hepsin in the sample, thereby characterizing the prostate tissue sample. In some embodiments, detecting the presence of expression of hepsin comprises detecting the presence of hepsin mRNA. In other embodiments, detecting the presence of expression of hepsin mRNA comprises exposing the hepsin mRNA to a nucleic acid probe complementary to the hepsin mRNA. In yet other embodiments, detecting the presence of expression of hepsin comprises detecting the presence of a hepsin polypeptide. In some embodiments, detecting the presence of a hepsin polypeptide comprises exposing the hepsin polypeptide to an antibody specific to the hepsin polypeptide and detecting the binding of the antibody to the hepsin polypeptide. In some embodiments, the subject comprises a human subject. In some embodiments, the sample comprises tumor tissue. In some embodiments, the tumor tissue sample is a post-surgical tumor tissue sample and the method further comprises the step of c) identifying a risk of prostate specific antigen failure based on detecting the presence or absence of expression of hepsin. In some embodiments, characterizing prostate tissue comprises identifying a stage of prostate cancer in the tissue. In some embodiments, the stage includes but is not limited to, high-grade prostatic intraepithelial neoplasia, benign prostatic hyperplasia, prostate carcinoma, and metastatic prostate carcinoma. In some embodiments, the method further comprising the step of c) providing a prognosis to the subject. In some embodiments, the prognosis comprises a risk of developing prostate specific antigen failure. In other embodiments, the prognosis comprises a risk of developing prostate cancer.

The present invention also provides a method for characterizing prostate tissue in a subject, comprising: providing a prostate tissue sample from a subject; and detecting the presence or absence of expression of pim-1 in the sample, thereby characterizing the prostate tissue sample. In some embodiments, detecting the presence of expression of pim-1 comprises detecting the presence of pim-1 mRNA. In other embodiments, detecting the presence of expression of pim-1 mRNA comprises exposing the pim-1 mRNA to a nucleic acid probe complementary to the pim-1 mRNA. In yet other embodiments, detecting the presence of expression of pim-1 comprises detecting the presence of a pim-1 polypeptide. In some embodiments, detecting the presence of a pim-1 polypeptide comprises exposing the pim-1 polypeptide to an antibody specific to the pim-1 polypeptide and detecting the binding of the antibody to the pim-1 polypeptide. In some embodiments, the subject comprises a human subject. In some embodiments, the sample comprises tumor tissue. In some embodiments, the tumor tissue sample is a post-surgical tumor tissue sample and the method further comprises the step of c) identifying a risk of prostate specific antigen failure based on detecting the presence or absence of expression of pim-1. In some embodiments, characterizing prostate tissue comprises identifying a stage of prostate cancer in the tissue. In some embodiments, the stage includes but is not limited to, high-grade prostatic intraepithelial neoplasia, benign prostatic hyperplasia, prostate carcinoma, and metastatic prostate carcinoma. In some embodiments, the method further comprising the step of c) providing a prognosis to the subject. In some embodiments, the prognosis comprises a risk of developing prostate specific antigen failure. In other embodiments, the prognosis comprises a risk of developing prostate cancer.

The present invention further provides a method for characterizing prostate tissue in a subject, comprising: providing a prostate tissue sample; and detecting a decreased or increased expression relative to a non-cancerous prostate tissue control of two or more markers selected from the group consisting of HEPSIN, FKBP5, FASN, FOLH1, TNFSF10, PCM1, S100A11, IGFBP3, SLUG, GSTM3, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, C1S, C4BPA, COL3A1, FAT, MMECD10, CLUSTERIN, PLA2G2A, thereby characterizing the prostate tissue sample. In some embodiments, the detecting comprises detecting three or more markers. In other embodiments, the detecting comprises detecting five or more markers. In still further embodiments, the detecting comprises detecting ten or more markers.

The present invention additionally provides a method for characterizing prostate cancer in a subject, comprising: providing a tumor sample from a subject diagnosed with prostate cancer; and detecting decreased expression relative to a non-cancerous prostate tissue control of two or more cancer markers selected from the group consisting of IGFBP5, MADH4, NBL1, SEPP1, RAB2, FAT, PP1CB, MPDZ, PRKCL2, ATF2, RAB5A, and Cathepsin H, wherein decreased expression is diagnostic of metastatic prostate cancer. In some embodiments, the detecting comprises detecting three or more markers. In other embodiments, the detecting comprises detecting five or more markers. In still further embodiments, the detecting comprises detecting ten or more markers.

The present invention further provides a method for characterizing prostate cancer in a subject, comprising providing a tumor sample from a subject diagnosed with prostate cancer; and detecting increased expression relative to a non-cancerous prostate tissue of two or more cancer markers selected from the group consisting of CTBP1, MAP3K10, TBXA2R, MTA1, RAP2, TRAP1, TFCP2, E2-EPF, UBCH10, TASTIN, EZH2, FLS353, MYBL2, LIMK1, TRAF4, wherein increased expression is diagnostic of metastatic prostate cancer. In some embodiments, the detecting comprises detecting three or more markers. In other embodiments, the detecting comprises detecting five or more markers. In still further embodiments, the detecting comprises detecting ten or more markers.

In some embodiments, the present invention provides a kit for characterizing prostate cancer in a subject, comprising: a reagent capable of specifically detecting the presence of absence of expression of hepsin; and instructions for using the kit for characterizing cancer in the subject. In some embodiments, the reagent comprises a nucleic acid probe complementary to a hepsin mRNA. In other embodiments, the reagent comprises an antibody that specifically binds to a hepsin polypeptide. In some embodiments, the instructions comprise instructions required by the United States Food and Drug Administration for use in in vitro diagnostic products.

In other embodiments, the present invention provides a kit for characterizing prostate cancer in a subject, comprising: a reagent capable of specifically detecting the presence of absence of expression of pim-1; and instructions for using the kit for characterizing cancer in the subject. In some embodiments, the reagent comprises a nucleic acid probe complementary to a pim-1 mRNA. In other embodiments, the reagent comprises an antibody that specifically binds to a pim-1 polypeptide. In some embodiments, the instructions comprise instructions required by the United States Food and Drug Administration for use in in vitro diagnostic products.

In still further embodiments, the present invention provides a kit for characterizing prostate cancer in a subject, comprising: two or more reagents capable of specifically detecting expression levels of two or more markers selected from the group consisting of FKBP5, FASN, FOLH1, TNFS10, PCM1, S100A11, IGFBP3, SLUG, GSTM3, ATF2, RAB5A, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, CATHEPSIN H, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, C1S, C4BPA, COL3A1, FAT, MMECD10, CLUSTERIN, PLA2G2A, MADh4, SEPP1, RAB2, PP1CB, MPDZ, PRKCL2, CTBP1, CTBP2, MAP3K10, TBXA2F, MTA1, RAP2, TRAP1, TFCP2, E2EPF, UBCH10, TASTIN, EZH2, FLS353, MYBL2, LIMK1, GP73, VAV2, TOP2A, ASNS, CTBP, AMACR, ABCC5 (MDR5), and TRAF4; and instructions for using the kit for characterizing cancer in the subject. In some embodiments, the kit comprises reagents capable of specifically detecting expression levels of three or more of the markers. In other embodiments, the kit comprises reagents capable of specifically detecting expression levels of five or more of the markers. In still further embodiments, the kit comprises reagents capable of specifically detecting expression levels of ten or more of the markers. In some embodiments, the instructions comprise instructions required by the United States Food and Drug Administration for use in in vitro diagnostic products.

In yet other embodiments, the present invention provides a kit for characterizing prostate cancer in a subject, comprising: two or more reagents capable of specifically detecting decreased expression levels of two or more markers selected from the group consisting of IGFBP5, MADH4, NBL1, SEPP1, RAB2, FAT, PP1CB, MPDZ, PRKCL2, ATF2, RAB5A, and Cathepsin H; and instructions for using the kit for characterizing cancer in the subject. In some embodiments, the kit comprises reagents capable of specifically detecting decreased expression levels of three or more of the markers. In other embodiments, the kit comprises reagents capable of specifically detecting decreased expression levels of five or more of the markers. In still further embodiments, the kit comprises reagents capable of specifically detecting decreased expression levels of ten or more of the markers. In some embodiments, the instructions comprise instructions required by the United States Food and Drug Administration for use in in vitro diagnostic products.

In an additional embodiment, the present invention provides a kit for characterizing prostate cancer in a subject, comprising: two or more reagents capable of specifically detecting increased expression levels of two or more markers selected from the group consisting of CTBP1, MAP3K10, TBXA2R, MTA1, RAP2, TRAP1, TFCP2, E2-EPF, UBCH10, TASTIN, EZH2, FLS353, MYBL2, LIMK1, TRAF4; and instructions for using the kit for characterizing cancer in the subject. In some embodiments, the kit comprises reagents capable of specifically detecting decreased expression levels of three or more of the markers. In other embodiments, the kit comprises reagents capable of specifically detecting decreased expression levels of five or more of the markers. In still further embodiments, the kit comprises reagents capable of specifically detecting decreased expression levels of ten or more of the markers. In some embodiments, the instructions comprise instructions required by the United States Food and Drug Administration for use in in vitro diagnostic products.

The present invention also provides a method of screening compounds, comprising providing a prostate cell sample; and one or more test compounds; and contacting the prostate cell sample with the test compound; and detecting a change in hepsin expression in the prostate cell sample in the presence of the test compound relative to the absence of the test compound. In some embodiments, the detecting comprises detecting hepsin mRNA. In other embodiments, the detecting comprises detecting hepsin polypeptide. In some embodiments, the cell is in vitro. In other embodiments, the cell is in vivo. In some embodiments, the test compound comprises an antisense compound. In other embodiments, the test compound comprises a drug.

The present invention further provides a method of screening compounds, comprising providing a prostate cell sample; and one or more test compounds; and contacting the prostate cell sample with the test compound; and detecting a change in pim-1 expression in the prostate cell sample in the presence of the test compound relative to the absence of the test compound. In some embodiments, the detecting comprises detecting pim-1 mRNA. In other embodiments, the detecting comprises detecting pim-1 polypeptide. In some embodiments, the cell is in vitro. In other embodiments, the cell is in vivo. In some embodiments, the test compound comprises an antisense compound. In other embodiments, the test compound comprises a drug.

The present invention provides a prostate cancer expression profile map comprising gene expression level information for two or more markers selected from the group consisting of: FKBP5, FASN, FOLH1, TNFSF10, PCM1, S100A11, IGFBP3, SLUG, GSTM3, ATF2, RAB5A, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, CATHEPSIN H, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, C1S, C4BPA, COL3A1, FAT, MMECD10, CLUSTERIN, PLA2G2A, MADh4, SEPP1, RAB2, PP1CB, MPDZ, PRKCL2, CTBP1, CTBP2, MAP3K10, TBXA2F, MTA1, RAP2, TRAP1, TFCP2, E2EPF, UBCH10, TASTIN, EZH2, FLS353, MYBL2, LIMK1, GP73, VAV2, TOP2A, ASNS, CTBP, AMACR, ABCC5 (MDR5), and TRAF4. In some embodiments, the map is digital information stored in computer memory. In some embodiments, the map comprises information for three or more markers. In other embodiments, the map comprises information for five or more markers. In still further embodiments, the map comprises information for ten or more markers.

The present invention also provides a prostate cancer expression profile map comprising gene expression level information for two or more markers selected from the group consisting of: IGFBP5, MADH4, NBL1, SEPP1, RAB2, FAT, PP1CB, MPDZ, PRKCL2, ATF2, RAB5A, and Cathepsin H. In some embodiments, the map is digital information stored in computer memory. In some embodiments, the map comprises information for three or more markers. In other embodiments, the map comprises information for five or more markers. In still further embodiments, the map comprises information for ten or more markers. In some embodiments, the prostate cancer is metastatic.

The present invention further provides a prostate cancer expression profile map comprising gene expression level information for two or more markers selected from the group consisting of: CTBP1, MAP3K10, TBXA2R, MTA1, RAP2, TRAP1, TFCP2, E2EPF, UBCH10, TASTIN, EZH2, FLS353, MYBL2, LIMK1, TRAF4. In some embodiments, the map is digital information stored in computer memory. In some embodiments, the map comprises information for three or more markers. In other embodiments, the map comprises information for five or more markers. In still further embodiments, the map comprises information for ten or more markers. In some embodiments, the prostate cancer is metastatic.

In some embodiments, the present invention provides a method for characterizing prostate tissue in a subject, comprising providing a prostate tissue sample from a subject; and detecting the presence or absence of expression of EZH2 in the sample, thereby characterizing the prostate tissue sample. In some embodiments, detecting the presence of expression of EZH2 comprises detecting the presence of EZH2 mRNA (e.g., including, but not limited to, by exposing the hepsin mRNA to a nucleic acid probe complementary to the hepsin mRNA). In other embodiments, detecting the presence of expression of EZH2 comprises detecting the presence of a EZH2 polypeptide (e.g., including, but not limited to, by exposing the EZH2 polypeptide to an antibody specific to the EZH2 polypeptide and detecting the binding of the antibody to the EZH2 polypeptide). In some embodiments, the subject comprises a human subject. In some embodiments, the sample comprises tumor tissue. In some embodiments, characterizing the prostate tissue comprises identifying a stage of prostate cancer in the prostate tissue. In certain embodiments, the stage is selected from the group including, but not limited to, high-grade prostatic intraepithelial neoplasia, benign prostatic hyperplasia, prostate carcinoma, and metastatic prostate carcinoma. In some embodiments, the method further comprises the step of providing a prognosis to the subject (e.g., a risk of developing metastatic prostate cancer).

In further embodiments, the present invention provides a kit for characterizing prostate cancer in a subject, comprising a reagent capable of specifically detecting the presence of absence of expression of EZH2; and instructions for using the kit for characterizing cancer in the subject. In some embodiments, the reagent comprises a nucleic acid probe complementary to a EZH2 mRNA. In other embodiments, the reagent comprises an antibody that specifically binds to a EZH2 polypeptide. In certain embodiments, the instructions comprise instructions required by the United States Food and Drug Administration for use in in vitro diagnostic products.

In still other embodiments, the present invention provides a method of screening compounds, comprising providing a prostate cell sample; and one or more test compounds; and contacting the prostate cell sample with the test compound; and detecting a change in EZH2 expression in the prostate cell sample in the presence of the test compound relative to the absence of the test compound. In some embodiments, wherein the detecting comprises detecting EZH2 mRNA. In other embodiments, the detecting comprises detecting EZH2 polypeptide. In some embodiments, the cell is in vitro; while in other embodiments, the cell is in vivo. In some embodiments, the test compound comprises an antisense compound. In certain embodiments, the test compound comprises a drug.

In yet other embodiments, the present invention provides a method for characterizing inconclusive prostate biopsy tissue in a subject, comprising providing an inconclusive prostate biopsy tissue sample from a subject; and detecting the presence of expression of AMACR in the sample, thereby characterizing the inconclusive prostate biopsy tissue sample. In some embodiments, detecting the presence of expression of AMACR comprises detecting the presence of AMACR mRNA (e.g., by exposing the AMACR mRNA to a nucleic acid probe complementary to at least a portion of the AMACR mRNA). In other embodiments, detecting the presence of expression of AMACR comprises detecting the presence of a AMACR polypeptide (e.g., by exposing the AMACR polypeptide to an antibody specific to the AMACR polypeptide and detecting the binding of the antibody to the AMACR polypeptide). In some embodiments, the subject comprises a human subject. In some embodiments, the presence of AMACR expression in the inconclusive biopsy tissue is indicative of prostate cancer in the subject. In certain embodiments, the method further comprises the step of detecting expression of a basal cell marker selected from the group consisting of 34βBE12 and p63 and the absence of a basal cell marker expression and the presence of AMACR expression is indicative of prostate cancer in the subject.

The present invention further provides a method of detecting AMACR expression in a bodily fluid, comprising providing a bodily fluid from a subject; and a reagent for detecting AMACR expression in the biological fluid; and contacting the bodily fluid with the reagent under conditions such that the reagent detects AMACR expression in the bodily fluid. In some embodiments, the bodily fluid is selected from the group consisting of serum, urine, whole blood, lymph fluid, and mucus. In certain embodiments, the presence of AMACR in the bodily fluid is indicative of cancer (e.g., prostate cancer).

The present invention additionally provides a kit for characterizing inconclusive prostate biopsy tissue in a subject, comprising a reagent capable of specifically detecting the presence or absence of expression of AMACR; and instructions for using the kit for characterizing inconclusive biopsy tissue in the subject. In some embodiments, the reagent comprises a nucleic acid probe complementary to at least a portion of an AMACR mRNA. In other embodiments, the reagent comprises an antibody that specifically binds to a AMACR polypeptide. In still other embodiments, the kit further comprises a second reagent, the second reagent capable of specifically detecting the expression of a basal cell marker selected from the group consisting of 34βE12 and p63. In some embodiments, the instructions further comprise instructions for using the second reagent and the reagent for characterizing inconclusive biopsy tissue in the subject. In some embodiments, the instructions comprise instructions required by the United States Food and Drug Administration for use in in vitro diagnostic products.

The present invention further provides a method of characterizing tissue in a subject, comprising providing a tissue sample from a subject, the tissue sample selected from the group consisting of breast tissue, ovarian tissue, lymph tissue, and melanoma tissue; and detecting the presence or absence of expression of AMACR in the sample, thereby characterizing the breast tissue sample.

The present invention also provides a method of diagnosing cancer in a subject, comprising providing a tissue sample from a subject, the tissue sample selected from the group consisting of breast tissue, ovarian tissue, lymph tissue, and melanoma tissue; and wherein the subject is suspected of having cancer; and detecting the presence of expression of AMACR in the sample, thereby diagnosing cancer in the tissue sample of the subject.

The present invention provides a method of diagnosing cancer in a subject, comprising providing a blood sample from a subject suspected of having cancer; and detecting an immune response to AMACR in the blood sample, thereby diagnosing cancer in the subject. In some embodiments, the cancer is prostate cancer. In certain embodiments, detecting an immune response comprises detecting an antibody against the AMACR in the blood sample.

The present invention additionally provides a method of inhibiting the growth of cells, comprising providing a cell that expresses EZH2; and a reagent for inhibiting EZH2 expression in the cell; and contacting the cell with the reagent under conditions such that the expression of EZH2 in the cell is inhibited. In some embodiments, the reagent is an antisense oligonucleotide. In other embodiments, the reagent is a RNA duplex. In some embodiments, the reagent is a drug. In some embodiments, the cell is a prostate cancer cell. In some embodiments, the cell is in vitro; while in other embodiments, the cell is in vivo. In some embodiments, the contacting further results in a decrease in proliferation of the cell.

In certain embodiments, the present invention provides a method for characterizing prostate cancer in a subject, comprising providing a prostate tissue sample from a subject suspected of having prostate cancer; and detecting a decrease in expression of an annexin in the sample, thereby characterizing the prostate tissue sample. In some embodiments, the decrease in expression of an annexin is indicative of the presence of metastatic prostate cancer in the subject. In certain embodiments, the annexin is selected from the group including, but not limited to, Annexin 1, Annexin 2, Annexin 4, Annexin 6, Annexin 7, and Annexin 11.

In other embodiments, the present invention provides a method for characterizing prostate cancer in a subject, comprising providing a prostate tissue sample from a subject suspected of having prostate cancer; and detecting an increase in expression of a c-terminal binding protein in the sample, thereby characterizing the prostate tissue sample. In some embodiments, the c-terminal binding protein is selected from the group consisting of c-terminal binding protein 1 and c-terminal binding protein 2. In certain embodiments, the increase in expression of a c-terminal binding protein is indicative of the presence of metastatic prostate cancer in the subject. In some embodiments, the expression of a c-terminal binding protein is indicative of an increased risk of PSA failure.

In other embodiments, the present invention provides a method for characterizing prostate cancer in a subject, comprising providing a prostate tissue sample from a subject suspected of having prostate cancer; and detecting an increase or decrease in expression of GP73, thereby characterizing the prostate tissue sample. In some embodiments, an increase in expression of gp73 is indicative of localized prostate cancer. In other embodiments, the prostate tissue sample is prostate cancer and a decrease in the expression of gp73 is indicative of metastatic prostate cancer.

DESCRIPTION OF THE FIGURES

The patent file contains at least one drawing executed in color. Copies of this patent publication with color drawings will be provided by the U.S. Patent and Trademark Office upon request and payment of the necessary fee.

FIG. 1A shows a dendrogram describing the relatedness of the samples. FIG. 1B shows a cluster diagram of the samples groups compared against normal adjacent prostate pool as a reference. FIG. 1C shows a cluster diagram of the samples groups compared against commercial prostate pool reference.

FIG. 3A shows Northern blot analysis of human hepsin (top) and normalization with GAPDH (bottom). NAT indicates normal adjacent prostate tissue and PCA indicates prostate cancer. FIG. 3B shows tissue microarrays used for hepsin analysis. FIG. 3C shows a histogram of hepsin protein expression by tissue type. Benign prostate hyperplasia (BPH). High-grade intraepithelial neoplasia (HG-PIN). Localized prostate cancer (PCA). Hormone-refractory prostate cancer (MET). FIG. 3D shows Kaplan Meier Analysis.

FIG. 4 shows the expression of pim-1 in prostate cancer samples as determined by Northern blot analysis and immunohistochemistry. FIG. 4A shows a histogram of pim-1 protein expression by tissue type as assessed from 810 tissue microarray elements. High-grade intraepithelial neoplasia (HG-PIN). Localized prostate cancer (PCA). FIG. 4B shows a Kaplan-Meier analysis. The tope line represents patients with strong Pim-1 staining. The bottom line represents patients with absent/weak Pim-1 expression.

FIG. 9 describes exemplary accession numbers and sequence ID Numbers for exemplary genes of the present invention.

FIG. 10 provides exemplary sequences of some genes of the present invention.

FIG. 11 an overview of the discovery and characterization of AMACR in prostate cancer utilized in some embodiments of the present invention.

FIG. 19A shows AMACR protein expression in localized hormone naive PCA. FIG. 19B shows strong AMACR expression in a naive lymph node metastasis. Error bars represent the 95% CI of the mean expression of the primary naive prostate cancer and corresponding lymph node metastases.

FIG. 17A shows PCA demonstrating strong hormonal effect due to anti-androgen treatment. FIG. 17B shows Western Blot analysis representing the baseline AMACR expression in different prostate cell lines (Left) and Western Blot analysis of LNCaP cells for AMACR and PSA expression after treatment with an androgen or an anti-androgen for 24 h and 48 hours (right).

FIG. 20A shows a cluster diagram depicting genes that molecularly distinguish metastatic prostate cancer (MET) from clinically localized prostate cancer (PCA). FIG. 20B shows a DNA microarray analysis of prostate cancer that reveals upregulation of EZH2 in metastatic prostate cancer. FIG. 20C shows RT-PCR analysis of the EZH2 transcript in prostate tissue and cell lines. FIG. 20D shows increased expression of EZH2 protein in prostate cancer.

FIG. 21A shows tissue microarray analysis of EZH2 expression. The mean EZH2 protein expression for the indicated prostate tissues is summarized using error bars with 95% confidence intervals. FIG. 21B shows a Kaplan-Meier analysis demonstrating that patients with clinically localized prostate cancers that have high EZH2 expression (Moderate/Strong staining) have a greater risk for prostate cancer recurrence after prostatectomy (log rank test, p=0.03).

FIG. 22A shows an immunoblot analysis of RNA interference using siRNA duplexes targeting the EZH2 sequence in prostate cells. FIG. 22B shows that RNA interference of EZH2 decreases cell proliferation as assessed by cell counting assay. FIG. 22C shows that RNA interference of EZH2 inhibits cell proliferation as assessed by WST assay. FIG. 22D shows that RNA interference of EZH2 induces G2/M arrest of prostate cells.

FIG. 23A shows a schematic diagram of EZH2 constructs used in transfection/transcriptome analysis. ER, modified ligand binding domain of estrogen receptor. H-1 and H-2, homology domains 1 and 2 which share similarity between EZH2 and E(z). CYS, cysteine-rich domain. SET, SET domain. TAG, myc-epitope tag. NLS, nuclear localization signal. FIG. 23B shows confirmation of expression of EZH2 constructs used in A. An anti-myc antibody was used. FIG. 23C shows a cluster diagram of genes that are significantly repressed by EZH2 overexpression. FIG. 23D shows SAM analysis of gene expression profiles of EZH2 transfected cells compared against EZH2 . SET transfected cells. FIG. 23E shows a model for potential functional interactions of EZH2 as elucidated by transcriptome analysis and placed in the context of previously reported interactions. +, induction. −, repression.

FIG. 29A shows an immunoblot analysis of the humoral response to AMACR. FIG. 29B shows a control experiment where the humoral response was blocked.

FIG. 30A shows the level of GP73 in individual samples after microarray analysis. FIG. 30B shows the result of GP73 transcripts determined by DNA microarray analysis from 76 prostate samples grouped according to sample type and averaged.

FIG. 31A shows Western blot analysis of GP73 protein in prostate cancer. FIG. 31B shows an immunoblot analysis of the Golgi resident protein Golgin 97.

FIG. 32 shows immunoblot analysis of normal and prostate cancer epithelial cells.

FIG. 34 shows a heat map representation of annexin family gene expression across four prostate cancer profiling studies. Over and under expression at the transcript level are represented by shades of red and green, respectively. Gray shading indicates that insufficient data was available. Each square represents an individual tissue sample.

GENERAL DESCRIPTION

Figure 1:
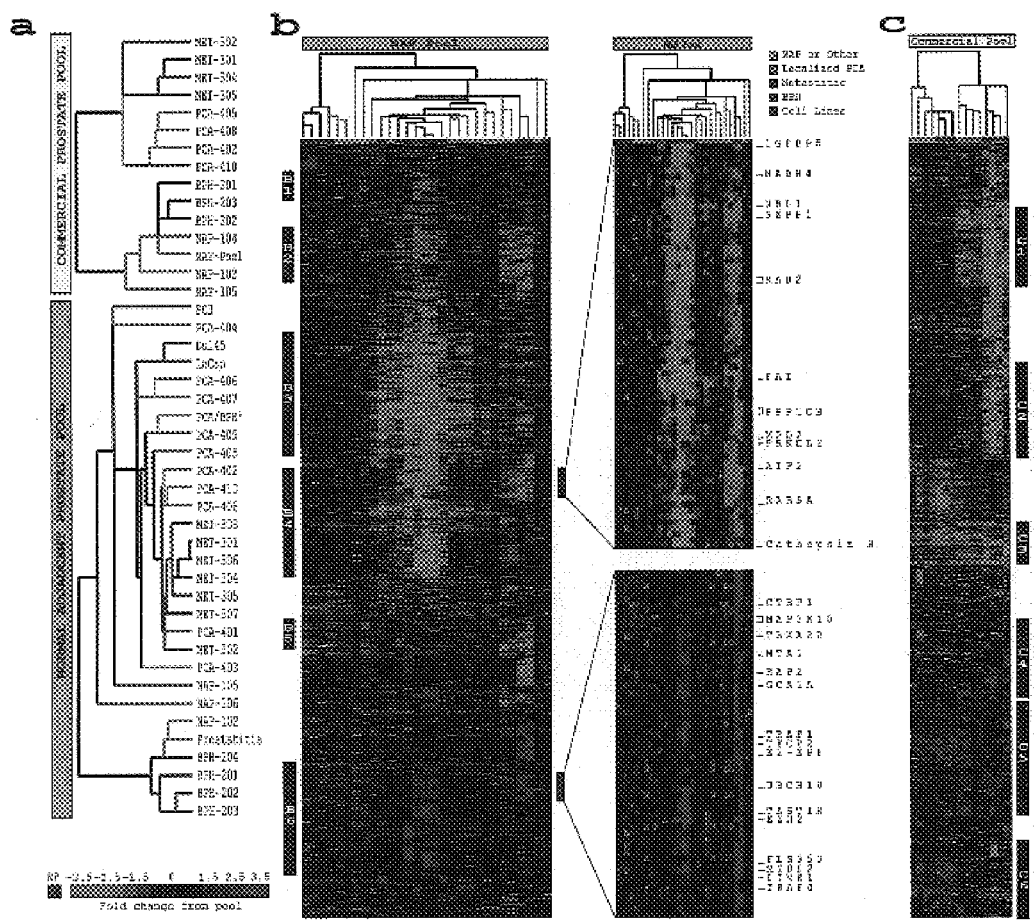
FIG. 1 shows a gene expression profile of prostate cancer samples.

Exploring the molecular circuitry that differentiates indolent PCA from aggressive PCA has the potential to lead to the discovery of prognostic markers and novel therapeutic targets. Insight into the mechanisms of prostate carcinogenesis is also gleaned by such a global molecular approach. Similar to breast cancer (Lopez-Otin and Diamandis, Endor. Rev., 19:365 [1998]), PCA develops in a complex milieu of genetic and environmental factors in which steroid hormone signaling plays a central role. The primary precursor lesion of PCA, high-grade prostatic intraepithelial neoplasia (HG-PIN), has several characteristics similar to other early invasive carcinomas (i.e., chromosomal abnormalities and cytologic features). Loss of specific chromosomal regions (e.g., 8p21, 10q, 13q, 17p) along with losses and mutations of tumor suppressor genes such as Nkx3.1, PTEN, Rb, and p53 have been implicated in the initiation and progression of prostate cancer (Abate-Shen and Shen, supra). With the emergence of global profiling strategies, a systematic analysis of genes involved in PCA is now possible. DNA microarray technology is revolutionizing the way fundamental biological questions are addressed in the post-genomic era. Rather than the traditional approach of focusing on one gene at a time, genomic-scale methodologies allow for a global perspective to be achieved. The power of this approach lies in its ability to comparatively analyze genome-wide patterns of mRNA expression (Brown and Botstein, Nat. Gent., 21:33 [1999]). Obtaining large-scale gene expression profiles of tumors allows for the identification of subsets of genes that function as prognostic disease markers or biologic predictors of therapeutic response (Emmert-Buck et al., Am. J. Pathol., 156:1109 [2000]). Golub et al. used DNA arrays in the molecular classification of acute leukemias (Golub et al., Science 286:531 [1999], demonstrating the feasibility of using microarrays for identifying new cancer classes (class discovery) and for assigning tumors to known classes (class prediction). Using a similar approach, Alizadeh et al. showed that diffuse large B-cell lymphoma could be dissected into two prognostic categories by gene expression profiling (Alizadeh et al., Nature 403:503 [2000]). They provided evidence that lymphomas possessing a gene expression signature characteristic of germinal center B cells had a more favorable prognosis than those expressing genes characteristic of activated peripheral B-cells. Similar large-scale classifications of breast cancer and melanoma have been undertaken, and as with the other studies, molecular classification was the primary focus (Alizadeh et al., supra).

Accordingly, the present invention provides an analysis of gene expression profiles in benign and malignant prostate tissue. Three candidate genes, AMACR, hepsin and pim-1, identified by DNA microarray analysis of PCA, were characterized at the protein level using PCA tissue microarrays. Analysis of the differential gene expression profiles of normal and neoplastic prostate has led to the identification of a select set of genes that define a molecular signature for PCA. The expression profiling experiments of the present invention demonstrate a role for multiple, collaborative gene expression alterations which ultimately manifest as the neoplastic phenotype. By making direct comparative hybridizations of normal and neoplastic tissues, genes that molecularly distinguish benign tissue from malignant are identified.

α-Methylacyl-CoA Racemase (AMACR) is an enzyme that plays an important role in bile acid biosynthesis and β-oxidation of branched-chain fatty acids (Ferdinandusse et al., J. Lipid Res., 41:1890 [2000]; Kotti et al., J. Biol. Chem., 275:20887 [2000]). Mutations of the AMACR gene have been shown to cause adult-onset sensory motor neuropathy (Ferdinandusse et al., Nat. Genet., 24:188 [2000]). In diagnostically challenging prostate biopsy cases, pathologists often employ the basal cell markers 34βE12 or p63, which stain the basal cell layer of benign glands that is not present in malignant glands. Thus, in many biopsy specimens, the pathologist must rely on absence of staining to make the final diagnosis of prostate cancer. Experiments conducted during the development of the present invention identified AMACR as a marker expressed in cancerous biopsy tissue. Thus, the clinical utility of AMACR in prostate needle biopsies is large. For example, at the University of Michigan Medical Center, approximately 400 prostate needle biopsies are performed per year and approximately 20% require the use of a basal-cell specific marker to evaluate difficult lesions, characterized by a small amount of atypical glands. Accordingly, it is contemplated that in combination with basal cell specific markers, such as 34βE12 or p63, screening for AMACR expression by the methods of the present invention results in fewer cases diagnosed as "atypical without a definitive diagnosis."

Identification of the over-expression of AMACR in prostate cancer has clinical utility beyond diagnostic uses. Experiments conducted during the development of the present invention revealed that the only non-cancerous tissue to expresses significant levels of AMACR protein is the human liver. The present invention is not limited to a particular mechanism. Indeed, an understanding of the mechanism in not necessary to practice the present invention. Nonetheless, it is contemplated that AMACR activity is required for prostate cancer growth and by virtue of its specificity serves as a therapeutic target.

Additional experiments conducted during the course of development of the present invention investigated AMACR expression in different groups of prostate cancer, including the aspect of neo-adjuvant hormonal withdrawal in localized disease. AMACR expression was found to be hormone independent in cell culture experiments. PSA, a gene known to be regulated by androgens, demonstrated hormone related alterations in expression under the same conditions. The present invention is not limited to a particular mechanism. Indeed, an understanding of the mechanism is not necessary to practice the present invention. Nonetheless, it is contemplated that these findings provide evidence that AMACR is not regulated by the androgen pathway. It is further contemplated that the decreased AMACR expression in hormone refractory tissue allows the use of AMACR as a biomarker for hormone resistance. It is also contemplated that, given the fact that hormone treatment in the mean of hormonal withdrawal did not affect AMACR expression in the cell culture, that some other mechanism than the androgen pathway is responsible for AMACR downregulation in the integrity of cancer tissue.

The present invention is not limited to a particular mechanism. Indeed, an understanding of the mechanism is not necessary to practice the present invention. Nonetheless, it is contemplated that, alternatively, AMACR is over expressed in the development of cancer, perhaps playing an important role in providing energy for the neoplastic cells. However, as the tumors become de-differentiated, they no longer require these sources of energy. It is contemplated that poorly differentiated tumors may take over other pathways to accomplish this same activity of branched fatty acid oxidation. There is no association with the proliferative rate of the tumor cells and AMACR expression.

AMACR expression was also examined in other cancers. Examination of other tumors demonstrated that colon cancer has the highest AMACR expression. As colorectal cancers are not known to be hormonally regulated, the fact that de-differentiation and decreased AMACR expression were correlated in PCA further supports the hypothesis that de-differentiation leads to decreased AMACR expression in the hormone refractory metastatic PCA. Hormone treatment is also a front line therapy in metastatic prostate cancer but is known to loose efficacy, selecting out hormone insensitive clones. The present invention is not limited to a particular mechanism. Indeed, an understanding of the mechanism is not necessary to practice the present invention. Nonetheless, it is contemplated that this phenomenon explains the observation that strong hormone treatment effect is consistent with decreased AMACR expression due to selection of potentially more de-differentiated cells.

The AMACR gene product is an enzyme, which plays an important role in bile acid biosynthesis and beta-oxidation of branched-chain fatty acids (Kotti et al., J. Biol. Chem. 275:20887 [2000]; Ferdinandusse et al., J Lipid Res 42:137 [2001]). AMACR over expression occurs in tumors with a high percentage of lipids such as PCA and colorectal cancer.

The relationship between fatty acid consumption and cancer is a controversial subject in the development of PCA and colorectal cancer (Moyad, Curr Opin Urol 11:457 [2001]; Willett, Oncologist 5:393 [2000]). An essential role for AMACR in the oxidation of bile acid intermediates has been demonstrated. AMACR encodes an enzyme which catalyzes the racemization of alpha-methyl branched carboxylic coenzyme A thioesters and is localized in peroxisomes and mitochondria (Schmitz et al., Eur J Biochem 231:815 [1995]). The present invention is not limited to a particular mechanism. Indeed, an understanding of the mechanism is not necessary to practice the present invention. Nonetheless, it is contemplated that, as AMACR is involved in the metabolism of lipids, that this leads to alterations in the oxidant balance of a cell. It is further contemplated that these changes are associated with DNA damage, malignant transformation, and other parameters of cell disturbance.

Additional experiments conducted during the course of development of the present invention demonstrated that AMACR mRNA and protein product are over expressed in a number of adenocarcinomas, including colorectal, prostate, breast, and ovarian and melanoma. Adenocarcinoma from the colorectum and prostate demonstrated consistent AMACR over expression (92% and 83% of tumor, respectively). Thus, AMACR is of use in the diagnosis of colonic neoplasia. For example, in some embodiments of the present invention, AMACR is used in the diagnosis of dysplasia. Specifically, in the setting of inflammatory bowel disease (IBD), where the identification of dysplasia may be diagnostically challenging, one evaluates putative lesions for their AMACR protein expression intensity. In some embodiments, this is performed in conjunction with the analysis of the adenomatous polyposis coli gene, since mutations in this gene are also believed to occur early in the development of colorectal neoplasia (Kinzler and Vogelstein, Cell 87:159 [1996]; Tsao and Shibata, Am J Pathol 145: 531 [1994]).

Colonic adenomas (Kinzler and Vogelstein, supra; Tsao and Shibata, supra) and high-grade PIN (McNeal and Bostwick, Hum Pathol 17:64 [1986]; McNeal et al., Lancet 1:60 [1986]) are well know precursors of invasive colonic and prostate cancer, respectively. Experiments conducted during the course of development of the present invention demonstrated that AMACR is over expressed in colorectal adenomas (75%) and high-grade PIN (64%). Further supporting AMACR expression in early neoplastic lesions was the presence of focal AMACR expression in some atrophic prostate lesions. Some atrophic lesions (i.e., proliferative inflammatory atrophy and postatrophic hyperplasia) have recently been recognized as proliferative in nature with molecular alterations suggestive of early neoplastic changes (De Marzo et al., Am J Pathol 155:1985 [1999]; Shah et al., Am J Pathol 158:1767 [2001]). Some morphologically benign prostate glands were also observed to have focal moderate AMACR staining. The present invention is not limited to a particular mechanism. Indeed, an understanding of the mechanism is not necessary to practice the present invention. Nonetheless, it is contemplated that AMACR may have a role in the early steps of cancer development.

Several cancers that are associated with AMACR over expression, including colorectal, prostate and breast cancer, have been linked to high-fat diet. The exact mechanism how high-fat diet contributes to tumorigenesis in these organ systems is unknown, but emerging evidence suggest that peroxisome proliferator activated receptor (PPAR) mediated pathway plays a critical role (Debril et al., J. Mol. Med. 79:30 [2001]). Diet fatty acids have been shown to function as peroxisome proliferators and bind to and activate PPARs (Zomer et al., J. Lipid Res. 41:1801 [2000]), a family of nuclear receptor transcriptional factors. Activation of PPAR mediated pathways in turn control cell proliferation and differentiation. In addition, it can also alter the cellular oxidant balance (Yeldandi et al., Mutat. Res. 448:159 [2000]). The present invention is not limited to a particular mechanism. Indeed, an understanding of the mechanism is not necessary to practice the present invention. Nonetheless, it is contemplated that these effects act in concert to contribute to the tumorigenesis of several cancers. This hypothesis is supported by the findings that peroxisome proliferators, when given to mice, enhance the development colon adenomatous polyps in mice (Saez et al., Nat. Med. 4:1058 [1998]). In addition, PPARs are expressed in several prostate cancer cell lines and their ligands, and peroxisome proliferators, when added to culture, affect the growth of these cell lines (Shappell et al., Cancer Res. 61:497 [2001]; Mueller et al., PNAS 97:10990 [2000]). A phase II clinical trial also showed that troglitazone, a PPARγ activator, could stabilize PSA level in patients with prostate cancer (Kubota et al., Cancer Res. 58:3344 [1998]; Hisatake et al., Cancer Res. 60:5494 [2000]).

AMACR is an involved in the β-oxidation of pristanic acid (Ferdinandusse et al., J. Lipid. Res. 41:1890 [2000]). Pristanic acid can function as a PPAR α activator and promote cell growth (Zomer et al., J. Lipid Res. 41:1801 [2000]). The present invention is not limited to a particular mechanism. Indeed, an understanding of the mechanism is not necessary to practice the present invention. Nonetheless, it is contemplated that hyperfunctioning of β-oxidation pathway leads to exhaustion of reducing molecules and alters the cellular oxidant status (Yeldandi et al., Mutat. Res. 448:159 [2000]).

The present invention further provides methods of targeting AMACR as a therapeutic target in cancer treatment. Over expressed in high percentage of colorectal, prostate, breast and melanoma, but not in adjacent normal tissues, AMACR is targeted using antibody or enzyme inhibitors. Toxicity is expected not to be a major concern because individuals with congenital absence of this enzyme have no or insignificant clinical manifestations (Clayton et al., Biochem. Soc. Trans. 29:298 [2001]).

Experiments conducted during the course of development of the present invention further demonstrated that AMACR is present in the serum of prostate cancer patients. In addition, a humoral response to AMACR was identified based on the presence of antibodies to AMACR in the serum of prostate cancer patients.

Annexins are a group of structurally related calcium-binding proteins, which have a domain that binds to phospholipids and an amino terminal domain that determines specificity (Smith et al., Trends. Genet. 10:241 [1994]; Mailliard et al., J Biol. Chem. 271:719 [1996]). The annexins are involved in regulation of membrane trafficking, cellular adhesion and possible tumorigenesis. Experiments conducted during the course of development of the present invention used cDNA microarrays to study the expression patterns of multiple annexin family members in a wide range of prostate tissue samples in order to determine their role in PCA progression. Meta-analysis of gene expression data was employed to help further validate the cDNA expression array findings. Finally, high-density tissue microarrays were used to assess annexin protein expression levels by immunohistochemistry.

Eight annexins were evaluated for their mRNA expression levels in benign prostatic tissue, localized hormone naïve PCA and metastatic hormone refractory PCA samples. Five annexins (1,2,4,7, and 11) demonstrated a progressive down regulation at the transcript level going from benign prostatic tissue to localized PCA to hormone refractory PCA. In order to validate the cDNA expression array finding of these 5 annexin family members, a meta-analysis was performed, which confirmed that when looking across 4 studies where at least two studies reported results, annexin 1,2,4, and 6 were significantly down regulated in localized PCA samples when compared to benign prostatic tissue. Therefore the meta-analysis confirmed results on annexin 1, 2, and 4. In these examples, summary statistics across all datasets found these annexins to be significantly down regulated at the cDNA level. However, not all of the 4 studies had significant down-regulation. Annexin 4, for example, was significantly down regulated in two of four studies but the resultant summary statistic, which also takes into account the number of samples evaluated, was statistically significant. Annexins 7,8, and 13 were not found to be significantly under expressed. As demonstrated in FIG. 1, annexin 7 does decrease significantly when comparing localized PCA and metastatic PCA.

The protein expression levels of all above five annexins tested were statistically significantly decreased in hormone refractory PCA samples when compared to either localized PCA or benign prostate tissue. Four of 5 annexins also demonstrated a decrease in protein expression in clinically localized PCA as compared to benign prostate tissue. However, in none of these cases was the protein expression found to be significantly decreased. This second validation method at the protein level confirmed the cDNA expression array data for annexin 1,2,4, 7, and 11.

Based on gene expression array data described herein, localized PCA cells down regulate their mRNA levels of annexins but maintained the corresponding protein expression levels. The present invention is not limited to a particular mechanism. Indeed, an understanding of the mechanism is not necessary to practice the present invention. Nonetheless, it is contemplated that post-translational alteration may compensate for decrease mRNA, producing enough protein to maintain levels seen with benign samples. Since annexins play an important role in maintaining cellular adhesion, once the cells eventually lose this ability, tumor progression may occur. Therefore, as one might anticipate, annexin expression levels decreased significantly in the advanced hormone refractory PCA samples. This was confirmed at the protein level by significant decreases as demonstrated by immunohistochemistry.

A sequential down-regulation of annexins in both transcriptional and translational levels in metastatic PCA samples was observed. Annexin I, also called lipocortin, has been described as a phospholipase A2 inhibitor, and served as a substrate of epidermal growth factor receptor (Pepinsky et al., Nature 321:81 [1986]; Wallner et al., Nature 320:77 [1986]). The significant reduction of protein level has been shown in esophageal and prostate tumor cells (Paweletz et al., Cancer Res. 60:6293 [2000]). Annexin 2, also called p36, appears an efficient substrate of protein kinase C and Src pp60 (Hubaishy et al., Biochemistry 34:14527 [1995]). Annexin 4, called endonexin, regulates Cl-flux by mediating calmodulin kinase II (CaMKII) activity (Chan et al., J. Biol. Chem. 269:32464 [1994]). Annexin 7, synexin, is involved in Duchenne's muscular dystrophy (Selbert et al. Exp. Cell. Res. 222:199 [1996]). Its gene is located on human chromosome 10q21 and its protein expression was decreased in hormone refractory tumor cells. In conclusion, the results of experiments conducted during the course of development of the present invention suggest that down regulation of several annexin family members may play a role in the development of the lethal PCA phenotype.

Additional experiments conducted during the course of development of the present invention identified additional markers that exhibited altered (e.g., increased or decreased) expression in prostate cancer. Additional markers include, but are not limited to, EZH2, Annexins 1, 2, 4, 7, and 11, CTBP 1 and 2, GP73, ABCC5 (MDR5), ASNS, TOP2A, and Vav2. In particular, EZH2 was identified as a marker that was overexpressed in prostate cancer, and in particular, in metastatic prostate cancer. EZH2 was further identified as being correlated with clinical failure (e.g., increased PSA levels). In addition, siRNA inhibition of EZH2 resulted in a decrease in cell proliferation of a prostate cancer cell line.

The present invention thus identifies markers and targets for diagnostic and therapeutic agents in a variety of cancers.

DEFINITIONS

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass or increased PSA level) but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "characterizing prostate tissue in a subject" refers to the identification of one or more properties of a prostate tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. Cancer marker expression may be characterized using any suitable method, including but not limited to, those described in illustrative Examples 1–15 below.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous prostate control" refers to measuring the level of expression of a gene (e.g., the level of mRNA or protein) relative to the level in a non-cancerous prostate control sample. Gene expression can be measured using any suitable method, including but not limited to, those described herein.

As used herein, the term "detecting a change in gene expression (e.g., hepsin, pim-1, EZH2, or AMACR) in said prostate cell sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described in Examples 1–15 below.

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

As used herein, the term "prostate cancer expression profile map" refers to a presentation of expression levels of genes in a particular type of prostate tissue (e.g., primary, metastatic, and pre-cancerous prostate tissues). The map may be presented as a graphical representation (e.g., on paper or on a computer screen), a physical representation (e.g., a gel or array) or a digital representation stored in computer memory. Each map corresponds to a particular type of prostate tissue (e.g., primary, metastatic, and pre-cancerous) and thus provides a template for comparison to a patient sample. In preferred embodiments, maps are generated from pooled samples comprising tissue samples from a plurality of patients with the same type of tissue.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "prostate specific antigen failure" refers to the development of high prostate specific antigen levels in a patient following prostate cancer therapy (e.g., surgery). See Examples 3 and 4 for examples of how prostate specific antigen failure is determined. As used herein, the term "risk of developing prostate specific antigen failure" refers to a subject's relative risk (e.g., the percent chance or a relative score) of developing prostate specific antigen failure following prostate cancer therapy.

As used herein, the term "post surgical tumor tissue" refers to cancerous tissue (e.g., prostate tissue) that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to results of initial cancer diagnosis (e.g. the presence or absence of cancerous cells). An initial diagnosis does not include information about the stage of the cancer of the risk of prostate specific antigen failure.

As used herein, the term "biopsy tissue" refers to a sample of tissue (e.g., prostate tissue) that is removed from a subject for the purpose of determining if the sample contains cancerous tissue. In some embodiment, biopsy tissue is obtained because a subject is suspected of having cancer. The biopsy tissue is then examined (e.g., by microscopy) for the presence or absence of cancer.

As used herein, the term "inconclusive biopsy tissue" refers to biopsy tissue for which histological examination has not determined the presence or absence of cancer.

As used herein, the term "basal cell marker" refers to a marker (e.g., an antibody) that binds to proteins present in the basal cell layer of benign prostate glands. Exemplary basal cell markers include, but are not limited to, 34βE12 and p63 (See e.g., O'Malley et al., Virchows Arch. Pathol. Anat. Histopathol., 417:191 [1990]; Wojno et al., Am. J. Surg. Pathol., 19:251 [1995]; Googe et al., Am. J. Clin. Pathol., 107:219 [1997]; Parsons et al., Urology 58:619; and Signoretti et al., Am. J. Pathol., 157:1769 [2000]).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% G+C)$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50–90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9–16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer diagnostics, including but not limited to, cancer markers. In particular, the present invention provides gene expression profiles associated with prostate cancers. Accordingly, the present invention provides method of characterizing prostate tissues, kits for the detection of markers, as well as drug screening and therapeutic applications.

I. Markers for Prostate Cancer

The present invention provides markers whose expression is specifically altered in cancerous prostate tissues. Such markers find use in the diagnosis and characterization of prostate cancer.

A. Identification of Markers

Experiments conducted during the development of the present invention resulted in the identification of genes whose expression level was altered (e.g., increased or decreased) in PCA. The methods utilized glass slide cDNA microarrays that included approximately 5000 known, named genes, 4400 ESTs, and 500 control elements, as well as normal and cancerous prostate tissue. Differentially expressed genes were divided into functional clusters. The expression of relevant genes was confirmed using Western blot analysis. Protein expression in prostate tissues was measured for several genes of interest.

The methods of the present invention (See e.g., Example 2) were used to identify clusters of genes that were up or down regulated in PCA, benign prostate tissue, pre-cancerous tissue, and normal prostate. From these clusters, two genes, hepsin and pim-1 were identified as genes that were of particular relevance. Immunohistochemistry (See e.g., Example 4) was used to characterize the presence of hepsin and pim-1 proteins in prostate tissue. Hepsin was found to stain strongly in pre-cancerous tissue (HG-PIN). In addition, hepsin was found to stain less strongly in PCA tissues of men found to have an increased risk of metastasis as measured by PSA failure (increased PSA following surgery), thus confirming the diagnostic utility of hepsin. In addition, deceased expression of pim-1 in PCA tissue was also found to be associated with increased risk of PSA failure. Accordingly, in some embodiments, the present invention provides methods of detecting and characterizing prostate tissues.

The methods of the present invention identified a further gene, alpha-methyl-CoA racemase (AMACR), that was found to be expressed in PCA, but not benign prostate tissue (See e.g., Example 5). AMACR was found to be present in the serum and urine of prostate or bladder cancer patients. In addition, a humoral response to AMACR was identified. In still further embodiments, the methods of the present invention were used to characterize the EZH2 gene. EZH2 was found to be up-regulated in metastatic prostate cancer. The inhibition of EZH2 expression in prostate cells inhibited cell proliferation in vitro, as well as inducing transcriptional repression of a variety of genes. The methods of the present invention further identified CtBP1 and CTBP2, as well as that GP73 as being over-expressed in metastatic prostate cancer relative to localized prostate cancer and benign tissue.

In still further embodiments, the methods of the present invention identified annexins 1, 2, 4, 7 and 11 as being significantly decreased in hormone refractory PCA when compared to localized hormone naïve Pca. Tissue microarray analysis revealed a significant decrease in protein expression for annexins 1, 2, 4, 7 and 11 in hormone refractory PCA as compared to localized Pca. No significant differences were detected between the clinically localized PCA and non-cancerous prostate tissues.

B. Detection of Markers

In some embodiments, the present invention provides methods for detection of expression of cancer markers (e.g., prostate cancer markers). In preferred embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In preferred embodiments, the presence of a cancer marker is used to provide a prognosis to a subject. For example, the detection of hepsin or pim-1 in prostate tissues is indicative of a cancer that is likely to metastasize and the expression of hepsin is indicative of a pre-cancerous tissue that is likely to become cancerous. In addition, the expression of AMACR is indicative of cancerous tissue. The information provided is also used to direct the course of treatment. For example, if a subject is found to have a marker indicative of a highly metastasizing tumor, additional therapies (e.g., hormonal or radiation therapies) can be started at a earlier point when they are more likely to be effective (e.g., before metastasis). In addition, if a subject is found to have a tumor that is not responsive to hormonal therapy, the expense and inconvenience of such therapies can be avoided.

The present invention is not limited to the markers described above. Any suitable marker that correlates with cancer or the progression of cancer may be utilized, including but not limited to, those described in the illustrative examples below (e.g., FKBP5, FASN, FOLH1, TNFSF10, PCM1, S100A11, IGFBP3, SLUG, GSTM3, ATF2, RAB5A, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, CATHEPSIN H, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, C1S, C4BPA, COL3A1, FAT, MMECD10, CLUSTERIN, PLA2G2A, MADh4, SEPP1, RAB2, PP1CB, MPDZ, PRKCL2, CTBP1, CTBP2, MAP3K10, TBXA2F, MTA1, RAP2, TRAP1, TFCP2, E2EPF, UBCH10, TASTIN, EZH2, FLS353, MYBL2, LIMK1, GP73, VAV2, TOP2A, ASNS, CTBP, AMACR, ABCC5 (MDR5), and TRAF4. Additional markers are also contemplated to be within the scope of the present invention. Any suitable method may be utilized to identify and characterize cancer markers suitable for use in the methods of the present invention, including but not limited to, those described in illustrative Examples 1–15 below. For example, in some embodiments, markers identified as being up or down-regulated in PCA using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with carcinogenesis and/or metastasis. For example, a panel may include markers identified as correlating with cancerous tissue, metastatic cancer, localized cancer that is likely to metastasize, pre-cancerous tissue that is likely to become cancerous, and pre-cancerous tissue that is not likely to become cancerous. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In other embodiments, the present invention provides an expression profile map comprising expression profiles of cancers of various stages or prognoses (e.g., likelihood of future metastasis). Such maps can be used for comparison with patient samples. In some embodiments comparisons are made using the method described in Example 2. However, the present invention is not limited to the method described in Example 2. Any suitable method may be utilized, including but not limited to, by computer comparison of digitized data. The comparison data is used to provide diagnoses and/or prognoses to patients.

1. Detection of RNA

In some preferred embodiments, detection of prostate cancer markers (e.g., including but not limited to, those disclosed herein) is detected by measuring the expression of corresponding mRNA in a tissue sample (e.g., prostate tissue). mRNA expression may be measured by any suitable method, including but not limited to, those disclosed below.

In some embodiments, RNA is detection by Northern blot analysis. Northern blot analysis involves the separation of RNA and hybridization of a complementary labeled probe. An exemplary method for Northern blot analysis is provided in Example 3.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of cancer markers is detected by measuring the expression of the corresponding protein or polypeptide. Protein expression may be detected by any suitable method. In some embodiments, proteins are detected by the immunohistochemistry method of Example 4. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of metastasis or PSA failure) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

4. Kits

In yet other embodiments, the present invention provides kits for the detection and characterization of prostate cancer. In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

5. In vivo Imaging

In some embodiments, in vivo imaging techniques are used to visualize the expression of cancer markers in an animal (e.g., a human or non-human mammal). For example, in some embodiments, cancer marker mRNA or protein is labeled using an labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention (e.g., prostate cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247–254 [1990] have described an optimized antibody-chelator for the radioimmunoscintographic imaging of tumors using Indium-111 as the label. Griffin et al., (J Clin Onc 9:631–640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339–342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxy-carbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

II. Antibodies

The present invention provides isolated antibodies. In preferred embodiments, the present invention provides monoclonal antibodies that specifically bind to an isolated polypeptide comprised of at least five amino acid residues of the cancer markers described herein (e.g., hepsin, pim-1, AMACR, EZH2, CTBP). These antibodies find use in the diagnostic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Drug Screening

In some embodiments, the present invention provides drug screening assays (e.g., to screen for anticancer drugs). The screening methods of the present invention utilize cancer markers identified using the methods of the present invention (e.g., including but not limited to, hepsin, pim-1, AMACR, EZH2, and CTBP). For example, in some embodiments, the present invention provides methods of screening for compound that alter (e.g., increase or decrease) the expression of cancer marker genes. In some embodiments, candidate compounds are antisense agents (e.g., oligonucleotides) directed against cancer markers. See Section IV below for a discussion of antisense therapy. In other embodiments, candidate compounds are antibodies that specifically bind to a cancer marker of the present invention.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer markers activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic (e.g., androgen independent) prostate cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678–85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412–421 [1992]), or on beads (Lam, Nature 354:82–84 [1991]), chips (Fodor, Nature 364:555–556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386–390 [1990]; Devlin Science 249:404–406 [1990]; Cwirla et al., Proc. Natl. Acad. Sci. 87:6378–6382 [1990]; Felici, J. Mol. Biol. 222:301 [1991]).

In one embodiment, an assay is a cell-based assay in which a cell that expresses a cancer marker protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity. The cell, for example, can be of mammalian origin.

The ability of the test compound to modulate cancer marker binding to a compound, e.g., a cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer markers substrate in a complex. For example, compounds (e.g., substrates) can be labeled with $^{125}$I, $^{35}$S $^{14}$C or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiometer can be used to detect the interaction of a compound with a cancer marker without the labeling of either the compound or the cancer marker (McConnell et al. Science 257:1906–1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the cancer marker protein or biologically active portion thereof is evaluated. Preferred biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the cancer markers protein to bind to a target molecule can be accomplished using real-time Biomolecular Interaction Analysis (BIA) (see, e.g., Sjolander and Urbaniczky, Anal. Chem. 63:2338–2345 [1991] and Szabo et al. Curr. Opin. Struct. Biol. 5:699–705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284–7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11: 141–8 [1998]; Hageand Tweed J. Chromatogr. Biomed. Sci. Appl 699:499–525 [1997]). Further, fluorescence energy transfer may also be conveniently utilized, as described herein, to detect binding without further purification of the complex from solution.

The assay can include contacting the cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223–232 [1993]; Madura et al., J. Biol. Chem. 268.12046–12054 [1993]; Bartel et al., Biotechniques 14:920–924 [1993]; Iwabuchi et al., Oncogene 8:1693–1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

IV. Cancer Therapies

In some embodiments, the present invention provides therapies for cancer (e.g., prostate cancer). In some embodiments, therapies target cancer markers (e.g., including but not limited to, hepsin, pim-1, AMACR, EZH2, and CTBP).

A. Antisense Therapies

In some embodiments, the present invention targets the expression of cancer markers. For example, in some embodiments, the present invention employs compositions comprising oligomeric antisense compounds, particularly oligonucleotides (e.g., those identified in the drug screening methods described above), for use in modulating the function of nucleic acid molecules encoding cancer markers of the present invention, ultimately modulating the amount of cancer marker expressed. This is accomplished by providing antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Pat. No. WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_3$)$_2$.

Other preferred modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisensce oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of cancer markers of the present invention. Examples of genetic manipulation include, but are not limited to, gene knockout (e.g., removing the cancer marker gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target prostate tumors that express a cancer marker of the present invention (e.g., hepsin, pim-1, EZH2, Annexin, CTBP, GP73, and AMACR). Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a cancer marker of the present invention (e.g., hepsin, pim-1, EZH2, Annexin, CTBP, GP73, and AMACR), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a cancer marker of the present invention (e.g., hepsin, pim-1, EZH2, Annexin, CTBP, GP73, and AMACR). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Pharmaceutical Compositions

The present invention further provides pharmaceutical compositions (e.g., comprising the antisense or antibody compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

V. Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

EXAMPLE 1

Preparation of Total RNA and Reference Pools

The prostate surgical specimens were obtained from The University of Michigan Specialized Research Program in Prostate Cancer (S.P.O.R.E.) Tumor Bank with Institutional Review Board approval. Tumors samples were derived from patients with clinically localized and advanced hormone refractory prostate cancer. Table 1 shows the samples used in the present studies. All patients were operated on between 1993 and 1998 for clinically localized prostate cancer as determined by preoperative PSA, digital-rectal examination, and prostate needle biopsy. In addition, a subset of patients received bone and CAT scans to evaluate the possibility of metastatic spread. All patients received radical prostatectomy as a monotherapy (i.e., no hormonal or radiation therapy). The advanced prostate tumors were collected from a series of 12 rapid autopsies performed at the University of Michigan on men who died of hormone refractory prostate cancer. In brief, the majority of these patients had either widely metastatic prostate cancer which was treated with hormonal therapy followed by chemotherapy, or patients who presented with clinically localized disease which progressed and were then treated with both hormonal and chemotherapy. The majority of cases had multiple metastatic lesions to numerous sites. All autopsies were performed within 4–6 hours after death. The clinical and pathologic findings of these cases have recently been reported (Rubin et al., Clin. Cancer Res., 6:1038 [2000]). All samples used for the tissue microarray study were fixed in 10% formalin.

Tissues were homogenized using a polytron homogenizer (Brinkman Instruments) in Trizol (Gibco BRL) and the total RNA was isolated according to the standard Trizol protocol. The total RNA obtained was further subjected to an additional round of phenol chloroform extraction, precipitated and resuspended in RNAse free water. Total RNA was quantitated by spectrophotmetric (260/280 nm) absorbance and integrity judged by denaturing-formaldehyde agarose gel electrophoresis. Total RNA from four normal tissues was combined in equal concentrations to obtain the reference pool. The human prostate total RNA used in the commercial reference pool was obtained from Clontech, Inc.

TABLE 1

Prostate Samples

| ID | PSA level | Tissue | Gleason Score |
|---|---|---|---|
| BPH-201 | 6.2 | Prostate | NA |
| BPH-202 | 3.9 | Prostate | NA |
| BPH-203 | 3.9 | Prostate | NA |
| BPH-204 | 4.6 | Prostate | NA |
| BPH-205 | 4.6 | Prostate | NA |
| BPH-206 | 4.6 | Prostate | NA |
| BPH-207 | 4.8 | Prostate | NA |
| BPH-208 | 13.6 | Prostate | NA |
| BPH-209 | 9.8 | Prostate | NA |
| BPH-210 | 4.6 | Prostate | NA |
| BPH-211 | 2.6 | Prostate | NA |
| BPH-212 | 7.1 | Prostate | NA |
| BPH-214 |  | Prostate | NA |
| BPH-215 | 5.4 | Prostate | NA |
| Prostatitis | 9.8 | Prostate | NA |
| NAP-101 | 4.6 | Prostate | NA |
| NAP-102 | 9.8 | Prostate | NA |
| NAP-104 | 7 | Prostate | NA |
| NAP-105 | 0.09 | Prostate | NA |
| NAP-107 | 4.7 | Prostate | NA |
| PCA-401 | 5.2 | Prostate | 4 + 4 |
| PCA-402 | 22 | Prostate | 4 + 3 |
| PCA-403 | 4.7 | Prostate | 3 + 3 |
| PCA-404 | 8.5 | Prostate | 3 + 3 |
| PCA-405 | 4.6 | Prostate | 3 + 3 |
| PCA-406 | 7.8 | Prostate | 3 + 3 |
| PCA-407 | 7.8 | Prostate | 3 + 3 |
| PCA-408 | 5.4 | Prostate | 3 + 3 |
| PCA-409 | 7 | Prostate | 3 + 3 |
| PCA-410 | 44.6 | Prostate | 4 + 4 |
| PCA-414 |  | Prostate | 3 + 4 |
| PCA-416 | 24.1 | Prostate | 4 + 4 |
| PCA-417 | 12.4 | Prostate | 4 + 4 |
| PCA-420 |  | Prostate | 3 + 3 |
| PCA-421 | 13.6 | Prostate | 3 + 4 |
| MET-301 |  | Lung | NA |
| MET-302 |  | Liver | NA |
| MET-303 |  | Liver | NA |
| MET-304 |  | Stomach | NA |
| MET-305 |  | Adrenal | NA |
| MET-306 |  | Prostate | NA |
| MET-307 |  | Lymph Node | NA |
| MET-308 |  | Lymph Node | NA |
| MET-309 |  | Lymph Node | NA |
| MET-310 |  | Liver | NA |
| MET-311 |  | Soft tissue | NA |
| MET-312 |  | Liver | NA |
| MET-313 |  | Soft tissue | NA |
| MET-314 |  | Soft tissue | NA |
| MET-315 |  | Soft tissue | NA |
| MET-316 |  | Soft tissue | NA |
| MET-317 |  | Liver | NA |
| MET-318 |  | bone | NA |
| MET-319 |  | bone | NA |
| MET-320 |  | bone | NA |

Table 1. Samples employed in the study. Designating PSA level in ng/mL, Organ sources and Gleason scores. Normal adjacent prostate (NAP), Benign prostatic hyperplasia (BPH), Localized prostate cancer (PCA) and Hormone refractory metastatic prostate cancer (MET).
NA refers to "not applicable".

EXAMPLE 2

Microarray Analysis

This example describes the use of microarray analysis to identify genes that demonstrate an altered level of expression in cancerous or benign prostate tissues.

A. Experimental Methods

Microarray analysis of gene expression was conducted essentially as described by the Brown and Derisi Labs (available at the Internet site www.microarrays.org). The sequence-verified cDNA clones on the human cDNA microarray are available from the web site of Research Genetics. Based on the latest Unigene build, the 10K human cDNA microarray used covers approximately 5520 known, named genes and 4464 ESTs. All chips have various control elements that include human, rat, and yeast genomic DNAs, SSC, yeast genes and "housekeeping genes," among others. In addition, 500 cancer- and apoptosis-related cDNAs from Research Genetics were used to serve as independent controls for clone tracking and function as duplicates for quality control. Three metastatic prostate cancer cell lines: DU-145, LnCAP, and PC3 were also profiled for gene expression.

Fluorescently labeled (Cy5) cDNA was prepared from total RNA from each experimental sample. The two reference samples used in this study were labeled using a second distinguishable fluorescent dye (Cy3) and included a pool of normal adjacent prostate tissue (NAP) from four patients (distinct from those used in the experimental samples) and a commercial pool of normal prostate tissues (CP). In addition to minimizing patient-to-patient variation, comparisons against pools of normal prostate tissue facilitate the discovery of genes that molecularly distinguish prostate neoplasms. The two reference pools are different in that one is comprised of normal adjacent prostate tissue, which may be influenced by paracrine effects mediated by PCA, and furthermore is exposed to the same environmental and genetic factors as the adjacent PCA. By contrast, the CP pool is derived from 19 individuals with no known prostate pathology and also represents a renewable commercially available reference resource.

Purified PCR products, generated using the clone inserts as template, were spotted onto poly-L-lysine coated microscope slides using an Omnigrid robotic arrayer (GeneMachines, CA) equipped with quill-type pins (Majer Scientific, AZ). One full print run generated approximately 100 DNA microarrays. Protocols for printing and post-processing of arrays are well known in the art.

B. Data analysis

Primary analysis was done using the Genepix software package. Images of scanned microarrays were gridded and linked to a gene print list. Initially, data was viewed as a scatter plot of Cy3 versus Cy5 intensities. Cy3 to Cy5 ratios were determined for the individual genes along with various other quality control parameters (e.g., intensity over local background). The Genepix software analysis package flags spots as absent based on spot characteristics (refer to the web site of Axon Instruments, Inc.). Bad spots or areas of the array with obvious defects were manually flagged. Spots with small diameters (<50 microns) and spots with low signal strengths <350 fluorescence intensity units over local background in the more intense channel were discarded. Flagged spots were not included in subsequent analyses. Data were scaled such that the average median ratio value for all spots was normalized to 1.0 per array.

These files were then imported into a Microsoft Access database. The data for the required experiments were extracted from the database in a single table format with each row representing an array element, each column a hybridization and each cell the observed normalized median of ratios for the array element of the appropriate hybridization. Prior to clustering, the normalized median of ratio values of the genes were log base 2 transformed and filtered for presence across arrays and selected for expression levels and patterns depending on the experimental set as stated. Average linkage hierarchial clustering of an uncentered Pearson correlation similarity matrix was applied using the program Cluster (Eisen et al., PNAS 95:14863 [1998]), and the results were analyzed and figures generated with the program TreeView. TreeView and Cluster are available from Michael Eisen's lab at the Lawrence Berkeley National Lab.

C. Results

Over forty 10K human cDNA microarrays were used to assess gene expression in four clinical states of prostate-derived tissues in relation to two distinct reference pools of normal specimens. FIG. 1 provides an overview of the variation in gene expression across the different tissue specimens analyzed. A hierarchical clustering algorithm was employed to group genes and experimental samples based on similarities of gene expression patterns over all the genes and samples tested, respectively.

1. Expression Dendrograms

Relationships between the experimental samples are summarized as dendrograms (FIG. 1a), in which the pattern and length of the branches reflect the relatedness of the samples. FIG. 1a shows dendrograms that reveal the variation in gene expression pattern between experimental samples with the two references employed. Individual samples in each group are indicated by the branches of the same color whereby METs are in dark blue, localized PCAs in orange, NAPs in light blue, BPHs in gray, and cell lines in pink. Asterisk (*) indicates a sample that was initially documented as BPH, but was later confirmed to have 5% cancer tissue. The details of metastatic samples used in this study are as follows: MET 301, from Lung; MET 302 and 303 from liver; MET 304, from stomach; MET 305 from adrenal gland; MET 306 from prostate; and MET 307 was from lymph node. Hierarchical clustering of the data identified distinct patterns of gene expression between the various groups analyzed. Each row represents a single gene with 1520 genes depicted in b, and 1006 genes depicted in c. The results represent the ratio of hybridization of fluorescent cDNA probes prepared from each experimental mRNA to the respective reference pools. These ratios are a measure of relative gene expression in each experimental sample and are depicted according to the color scale at the bottom left. Red and green colors in the matrix represent genes that are up- and down-regulated, respectively, relative to the reference pool employed. Black lines in the matrix represent transcript levels that are unchanged, while gray lines signify technically inadequate or missing data (NP, not present). Color saturation reflects the magnitude of the ratio relative to the median for each set of samples.

FIG. 1b shows a cluster diagram of the various sample groups compared against normal adjacent prostate pool as reference. Table 3 shows the associated data included in the normal adjacent prostate pool. Table 3 contains a CBCR-t Index number, Clone, ID, Unigene Cluster Ids, Accession ID, NID, gene symbol, and name fields for each gene used in the array. The name field contains genes having partial or complete homology based on homology searches. In addition, the table contains the numerical difference in expression levels compared to the reference pool for each gene. Prior to hierarchical average-linkage clustering, the data was filtered for at least a 2-fold change in expression ratio and ratio measurements present in 50% of the samples. By this method, 1520 genes were selected from the NAP reference data set. Indicated by vertical bars on the left (b1 to b6) of FIG. 1b are regions identified with characteristic gene expression signatures. Clusters b1 and b5 show genes up-regulated in localized PCA but not in metastatic PCA. Clusters b2 and b4 highlight genes down-regulated in metastatic PCA and the cell lines DU145 and LnCAP. Cluster b3 identifies genes down-regulated in both localized PCA and metastatic PCA. Cluster b6 highlights genes that are primarily up-regulated in metastatic PCA alone. Portions of Clusters b4 and b6 are shown enlarged with selected genes shown using Human genome organization (HUGO) gene nomenclature.

FIG. 1c shows a cluster diagram of the various sample groups compared against the commercial prostate pool reference. Table 4 shows the associated data included in the commercial prostate pool (See description of Table 3). Prior to hierarchical average-linkage clustering, the data was filtered for at least a 3-fold change in expression ratio and ratio measurements present in 75% of the samples resulting in a total of 1006 genes. Regions with distinct patterns (c1–c6) are indicated by vertical bars to the right of FIG. 1c. Cluster c1 depicts genes down-regulated in both localized PCA and metastatic PCA. Cluster c2 represents genes down-regulated only in metastatic PCA. Cluster c3 shows genes that are highly represented in the commercial pool. Cluster c4 highlights genes that are up-regulated in localized PCA and in metastatic PCA. Cluster c5 represent genes with a low representation in the commercial pool. Cluster c6, represents genes that are down-regulated in metastatic PCA but are up-regulated in all other samples used.

Benign conditions of the prostate such as BPH and NAP cluster separately from malignant PCA cell lines or tissues, regardless of the reference pool used. Within the PCA cluster, it is also evident that metastatic PCA and clinically localized PCA formed distinct subgroups. Similarly, in the "benign" grouping, BPH tended to distinguish itself from NAP. Interestingly, one of the "BPH" samples initially clustered with the localized PCA group. Upon further histopathologic review, however, it was discovered that this sample contained a small focus of neoplastic tissue (~5%), thus accounting for its initial misclassification (now designated PCA+BPH in FIG. 1a).

Eisen matrix formats (Eisen et al., supra) of the variation in gene expression are also presented (FIGS. 1b and 1c). With a global perspective of the data, it is apparent that metastatic PCA dominates the analysis and has the greatest variation in gene expression of the samples tested. Bars on the left or right of each matrix represent clusters of coordinately expressed genes highlighting interrelationships between specimens. For example, Clusters b3 and c1 represent genes down-regulated in both localized and metastatic PCA (FIGS. 1b and 1c). By contrast, Clusters b6 and b4 highlight genes that are specifically up- and down-regulated in metastatic PCA, respectively (FIG. 1b). IGFBP-5, DAN1, FAT tumor suppressor and RAB5A are examples of genes that are down-regulated specifically in metastatic PCA and also have a proposed role in oncogenesis ("magnified" regions, FIG. 1b). Similarly, cancer-related genes that are up-regulated in metastatic PCA include MTA-1 (metastasis-associated 1), MYBL2, and FLS353 (preferentially expressed in colorectal cancer). Many genes in this "met-specific" cluster are shared by both the metastatic PCA tissue and the two PCA cell lines DU145 and LnCAP.

Table 5 shows data from the expression profiling of additional prostate tissue specimens profiled against a commercial prostate reference pool (CPP) (See description of Table 3). A total of 53 prostate specimens were profiled against the commercial pool. They include 4 normal adjacent prostate tissue (NAP), 14 benign prostatic hyperplasia (BPH), 1 prostatitis, 14 localized prostate cancer (PCA) and 20 hormone refractory metastatic PCA (MET). Prior to hierarchial average-linkage clustering, the data was filtered for at least 3-fold change in Cy5/Cy3 ratios and measurements present in 75% of the samples. By this method 1325 genes were selected. The data expands on FIG. 1c with an additional 40 samples, which include all from FIG. 1b, and also includes 28 additional prostate specimens.

2. Focused Clusters

Figure 6:
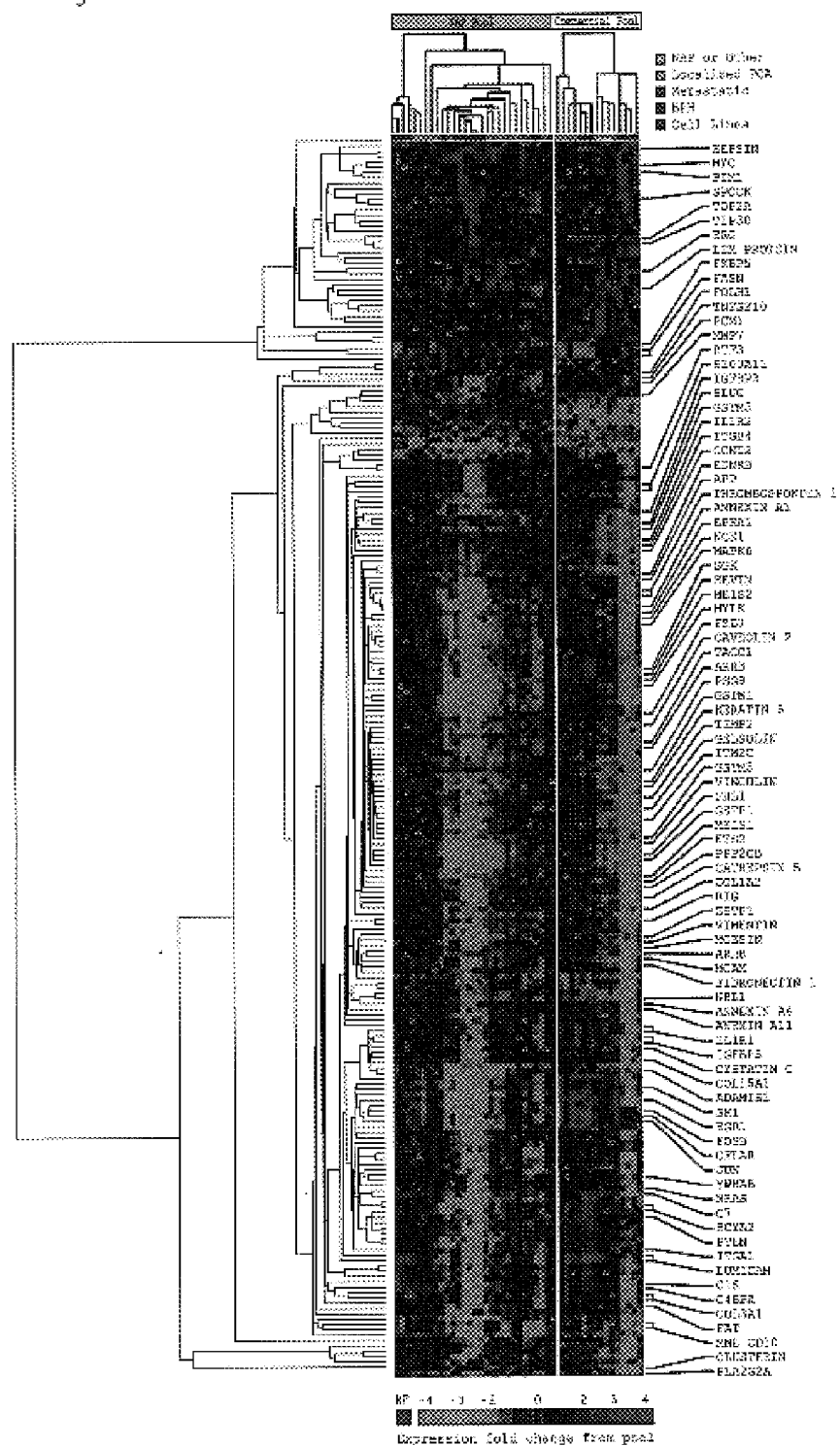
FIG. 6 shows a focused cluster of prostate cancer related genes.

Data was next assessed by examining functional groups of known, named genes. Cancer-related functional clusters were arbitrarily defined including cell growth/cell death, cell adhesion, anti-protease/protease, free radical scavengers, inflammation/immunity, phosphatase/kinase, transcription, and miscellaneous (FIGS. 2 and 6).

Figure 7:
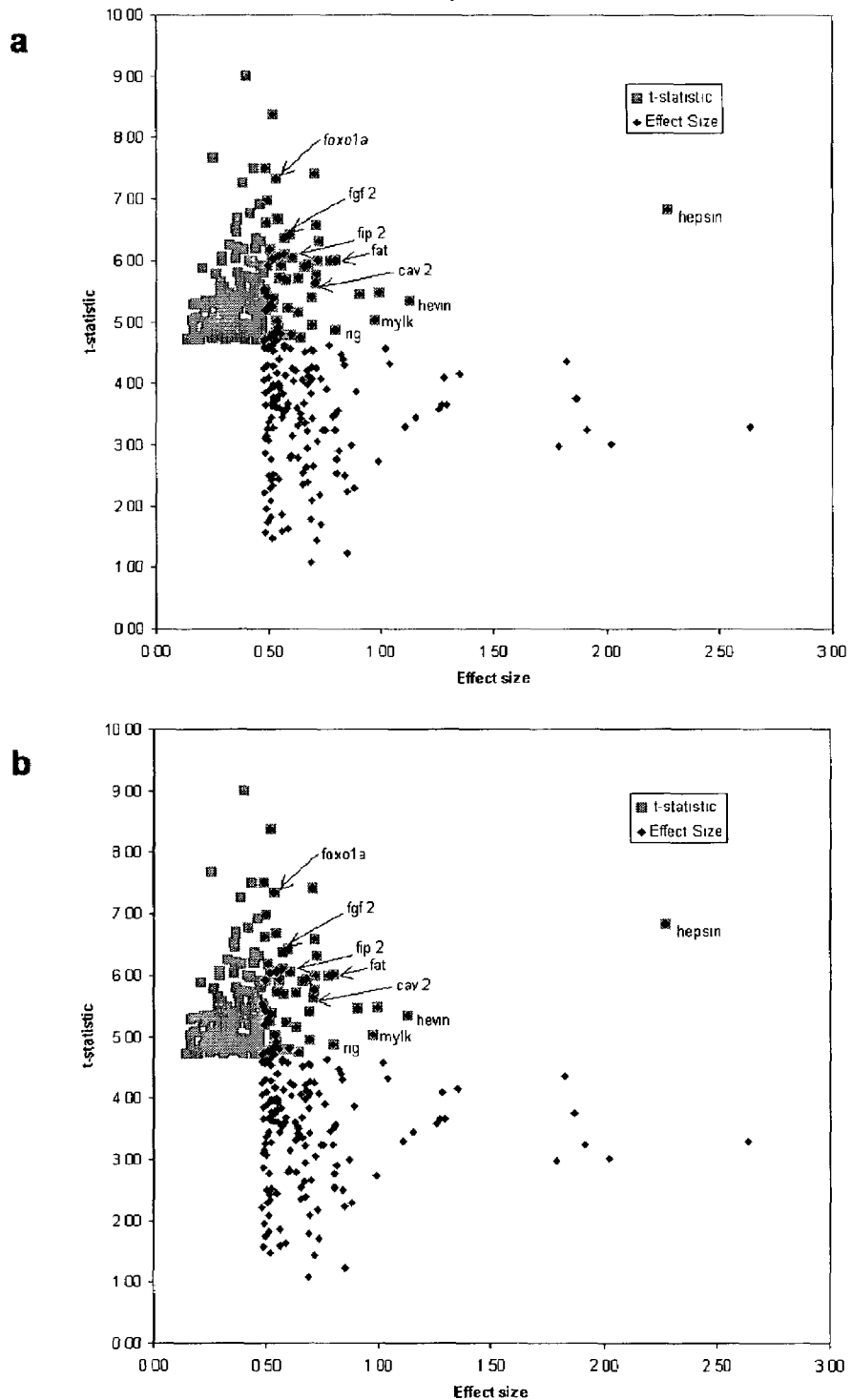
FIG. 7 shows data for gene selection based on computed t-statistics for the NAP and CP pools.

One of several available methods of gene selection was used to create a more limited set of genes for future exploration. In one method, t-statistics (based on MET/PCA vs. benign) were computed for each gene. The cell line samples were excluded from the analysis. Also, genes and ESTs that had data missing from 20% of samples were excluded from analysis. The t-statistics were ranked in two ways. First, they were ranked by absolute magnitude, which takes into account the inter-sample variability in expression ratios. Second, they were ranked by the magnitude of the numerator of the test statistic, which is based on the biological difference in expression ratios and designated as "effect size" (for MET/PCA vs. benign). A scatterplot of the genes with the 200 largest effect sizes and 200 largest t-statistics was then plotted (See FIG. 7). FIG. 7 shows gene selection based on computed t-statistics for each gene. Two groups were used in the analysis: PCA/MET and benign (NAP/BPH). FIG. 7a shows analysis of NAP pool data. FIG. 7b shows analysis of CP pool data. Selected genes are named and 200 genes for each data set are shown. Gene selection based on each method is shown. Selected gene names or symbols (as specified by Human genome organization (HUGO) gene nomenclature) are shown.

Genes that made both lists were also looked at separately in order to identify potential candidate genes. Implementing this methodology on both reference pool data sets (NAP and CP) yielded genes that included hepsin, pim-1, IM/ENIGMA, TIMP2, hevin, rig, and thrombospondin-1, among others. Several genes identified using gene selection methods are described in more detail in the context of "functional" clusters described in FIG. 2.

Figure 2:
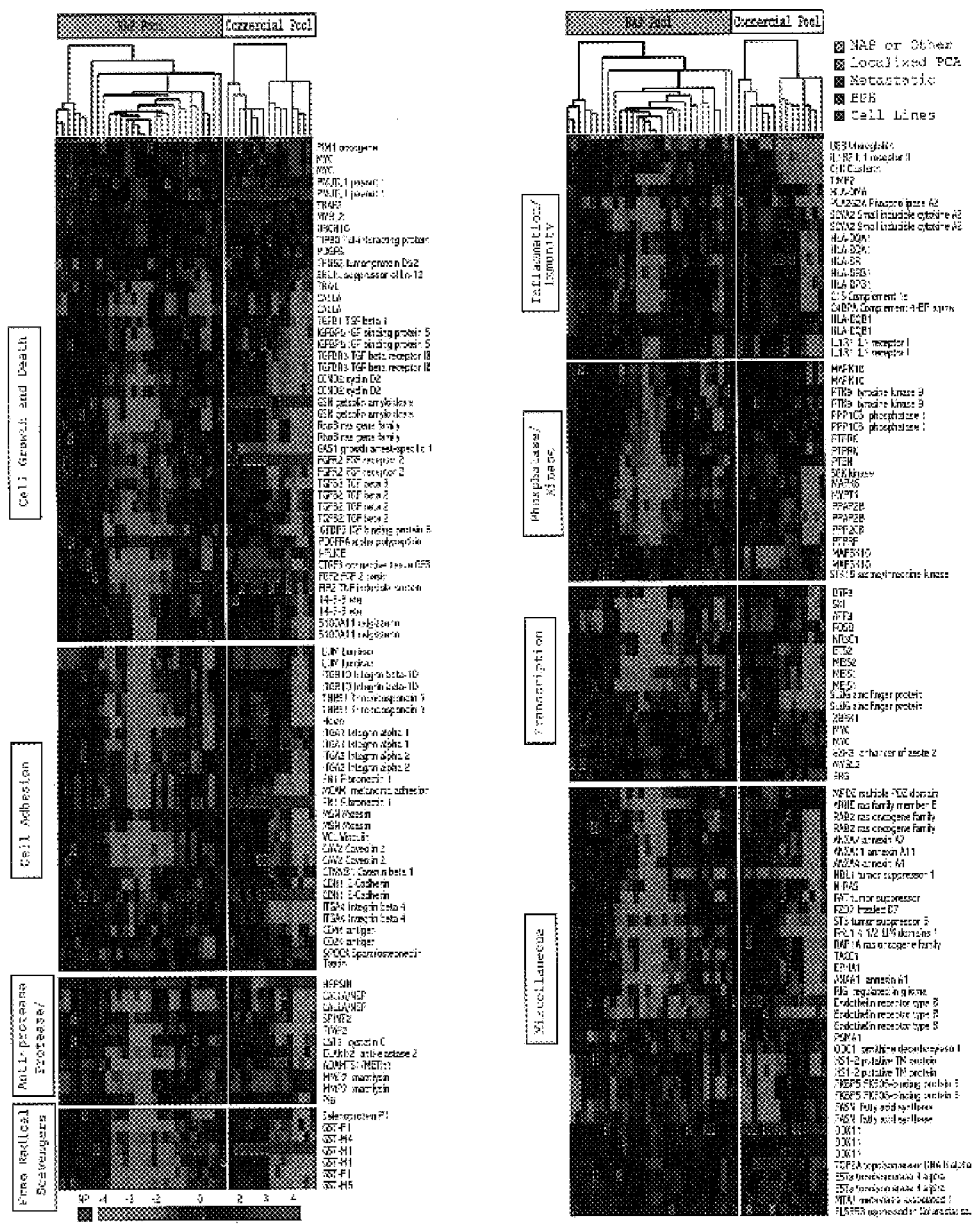
FIG. 2 shows functional clusters of genes differentially expressed in prostate cancer.

FIG. 2 shows the differential expression of functional clusters of select genes in prostate cancer. Gene names or symbols (as specified by Human genome organization (HUGO) gene nomenclature) are shown. The same convention for representing changes in transcript levels was used as in FIG. 1. The sample order from FIG. 1 was preserved for clarity.

Figure 8:
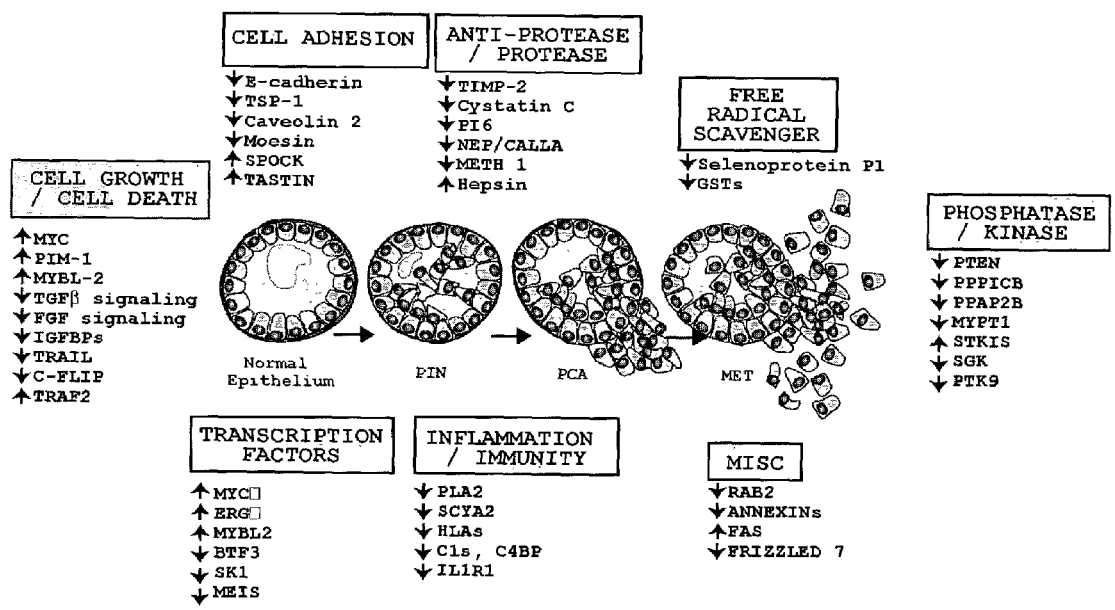
FIG. 8 shows an overview of genes differentially expressed in prostate cancer.

FIG. 8 shows a focused cluster of PCA-related genes. Table 6 shows the associated data (See description of Table 3). The same convention for representing changes in transcript levels was used as in FIG. 1. This cluster of 231 genes was generated by selecting for a 3.5-fold variation in at least 2 of any class, and ratio measurements present in 75% of the samples. Classes included: PCA vs. NAP, MET vs. NAP, PCA vs. CP and MET vs. CP.

The reliability of the hierarchical clustering results was assessed using three separate methods: that of Calinski and Harabasz (1974), Hartigan (1975) and Krzanowski and Lai (1985). The number of "stable" clusters estimated by all these methods is two. In the CP pool data set, that would elicit a valid benign cluster (NAP and BPH) and a malignant cluster (PCA and MET).

Many of the genes identified in these "focused" clusters have been implicated directly or indirectly as cancer biomarkers or mediators of carcinogenesis. Several have been shown to be dysregulated in PCA. For example, the tumor suppressor gene PTEN was down-regulated, while the proto-oncogene myc was up-regulated in the microarray analysis of PCA (FIG. 2) (Abate-Shen and Shen, supra). Likewise, decreased expression of E-cadherin and increased expression of fatty acid synthase, both of which have been shown to be dysregulated in PCA were observed (Tomita et al., Cancer Res., 60:3650 [2000] and Shurbaji et al., Hum. Pathol., 27:917 [1996]). In addition to uncharacterized expressed sequence tags (ESTs), there are numerous genes that were identified by the screen but not previously known to be associated with PCA. It is contemplated that they find use as cancer markers.

Exemplary nucleic acid sequences for some of the genes identified in focused clusters are shown in FIGS. 9 and 10. The present invention is not limited to the particular nucleic acid sequences described in FIGS. 9 and 10. One skilled in the art recognizes that additional variants, homologs, and mutants of the described sequences find use in the practice of the present invention.

3. Comparison Between NAP and CP Pools

Figure 5:
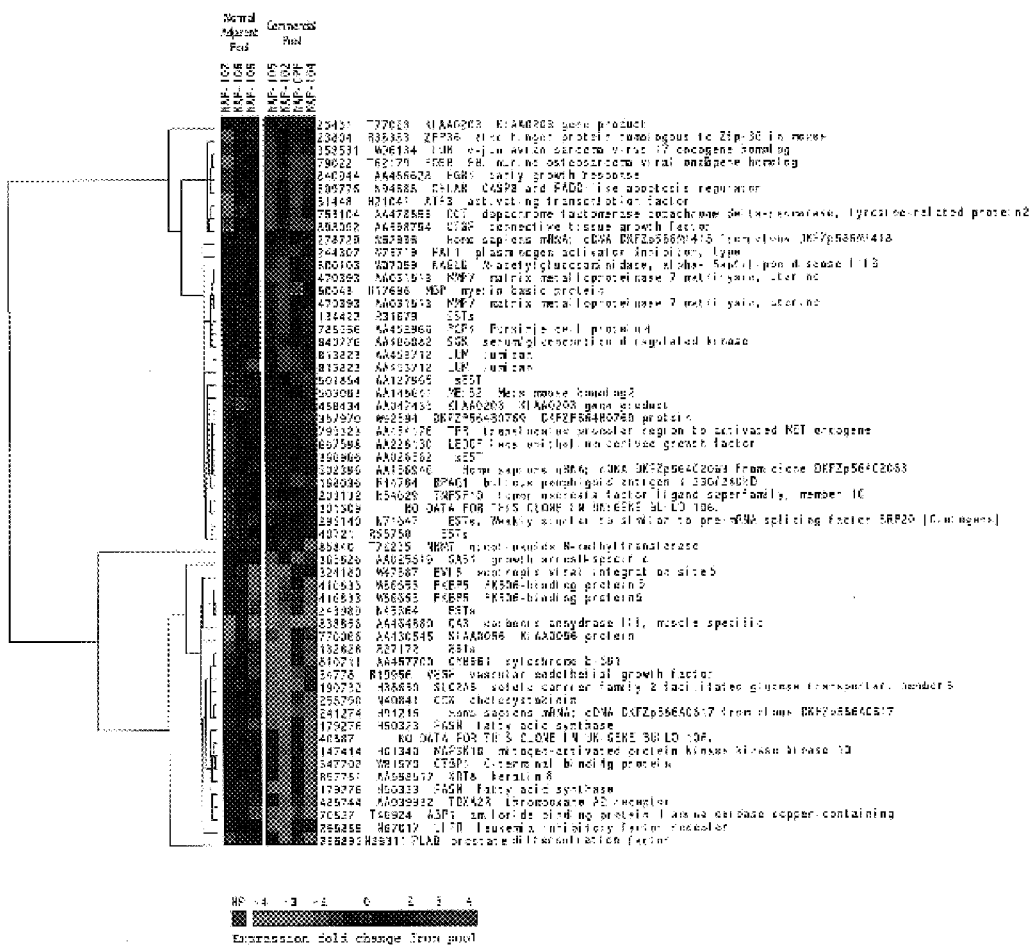
FIG. 5 shows a comparison of gene expression profiles for normal adjacent prostate tissue and normal prostate tissue reference.

A direct comparison between the NAP and CP pool was also made and notable gene expression differences were readily apparent. FIG. 5 shows a comparison between the NAP and CP pools. Table 7 shows a table of the associated data for FIG. 5 (See description of Table 3). The same convention for representing changes in transcript levels was used as in FIG. 1. The cluster was obtained by selecting for genes with at least a 2.5-fold variation in any two of the samples of each class, namely the normal tissues versus the NAP pool and normal tissue versus the CP pool at a 50% filter. Of the genes analyzed 59 were selected with this criteria. Genes that were found to be up-regulated in the NAP pool in comparison with CP pool included connective tissue growth factor, EGR-1 (Early Growth Response 1), matrilysin (MMP7), CFLAR/I-FLICE (caspase 8 and FADD-like apoptosis regulator), lumican, serum glucocorticoid regulated kinase, lens epithelium derived growth factor, PAI1 (plasminogen activator inhibitor type I), JUN and FOS B, among others. Vascular endothelial growth factor (VEGF), growth arrest specific (GAS1), cholecystokinin (CCK), amiloride binding protein (ABP1) were among the down-regulated genes in the normal adjacent prostate pool when compared to the commercial pool. The present invention is not limited to a particular mechanism. Indeed, an understanding of the mechanism is not necessary to practice the present invention. Nonetheless, it is contemplated that the gene expression differences between normal prostate adjacent to PCA (NAP) and normal prostate tissue from individuals without prostate pathology (CP) may be attributable to a "field effect" induced by PCA itself.

EXAMPLE 3

Northern Blot Analysis

Thirty micrograms of total RNA was resolved by denaturing formaldehyde agarose gel and transferred onto Hybond membrane (Amersham) by a capillary transfer set up. Hybridizations were performed by the method described by Church and Gilbert, 1984. Signal was visualized and quantitated by phosphorimager. For relative fold estimation, the ratio between the signals obtained from hepsin and GAPDH probes was calculated.

Selected genes identified by microarray analysis were corroborated by Northern analysis. For example, hevin, 4

1/2 LIM domain protein and gelsolin were shown to be 3.2-, 3.2- and 1.9-fold down-regulated, respectively by microarray and 8.8-, 4.5-, and 3.5-fold down-regulated by Northern analysis. Similarly, hepsin was 4.3-fold up-regulated by microarray and 11.3-fold up-regulated by Northern analysis (FIG. 3a). As bepsin is a cell-surface serine protease with transcript expression precisely restricted to localized and metastatic PCA, its expression was examined in more detail at the protein level (See Example 4 below).

EXAMPLE 4

Tissue Analysis

This example describes the analysis of protein expression in normal and cancerous prostate tissues.

A. Tissue Microarray Construction.

Kononen et al. have described a method for evaluating tumor tissues in large numbers on a single glass slide (Kononen et al., Nat. Med., 4:844 [1998]). These high-density tissue microarrays allow for analysis of up to 1,000 tissue samples on a single slide. These slides can be evaluated by routine light microscopy on hematoxylin and eosin (H&E) prepared and immunohistochemically stained slides. Thus, candidate cancer biomarkers, identified by gene expression methodologies, can be evaluated at the protein level over a large number of clinically stratified tumor specimens.

Prostate tissues used in microarray analysis included 4 BPH, 8 NAP, 1 commercial pool of normal prostate tissue (from 19 individuals), 1 prostatitis, 11 localized PCA, and 7 metastatic PCA specimens. High-density tissue microarrays (TMA) were assembled using a manual tissue puncher/array (Beecher Instruments, Silver Springs, Md.) as previously described (Kononen et al., Nat. Med., 4:844 [1998]; Perrone et al., J. Natl. Cancer Inst., 92:937 [2000]). The instrument consists of thin-walled stainless steel needles with an inner diameter of approximately 600 µm and stylet used to transfer and empty the needle contents. The assembly is held in an X-Y position guide that is manually adjusted by digital micrometers. Small biopsies are retrieved from selected regions of donor tissue and are precisely arrayed in a new paraffin block. Tissue cores were 0.6 mm in diameter and ranged in length from 1.0 mm to 3.0 mm depending on the depth of tissue in the donor block. Multiple replicate core samples of normal, HGPIN, and PCA were acquired from each tissue block of each case. Cores were inserted into a 45×20×12 mm recipient bock and spaced at a distance of 0.8 mm apart. Prostate tumor grading was performed using the system described by Gleason (Gleason, Cancer Chemother Rep., 50:125 [1966]). Pathologic stages for the radical prostatectomies were determined using the TNM staging system (Schroder et al., Prostate Suppl., 4:129 [1992]). Surgical margins were assessed separately and are not included in tumor staging.

B. Immunohistochemistry

TMA sections were cut at five-micron thick intervals for immunohistochemistry. Initial sections were stained for hematoxylin and eosin to verify histology. TMA slides prepared from formalin-fixed paraffin embedded tissue were heated for 0.5–1 hours at 60° centigrade. All slides were placed in 10 millimolar citrate buffer (pH 6.0) and microwaved for 5 minutes. Standard biotin-avidin complex immunohistochemistry was performed. The affinity purified polyclonal Rabbit antibody against hHepsin was used at a 1:40 dilution (original concentration 0.2 mg/ml) for this study. Immunostaining intensity was scored by a dedicated genitourinary pathologist as absent, weak, moderate, or strong. Scoring was performed using a telepathology system in a blinded fashion without knowledge of overall Gleason score (e.g., tumor grade), tumor size, or clinical outcome (Perrone et al., supra). A total of 738 tissue samples from benign (n=205), high-grade PIN (n=38), localized prostate cancer (n=335) and hormone refractory prostate cancer (n=160) were examined.

Similarly, pim-1 was analyzed using two TMA blocks from a total of 810 PCA samples from 135 patients. Six PCA samples were evaluated from each case and a median score was calculated. In addition, a small number of samples with benign prostatic tissues (e.g., benign epithelium and atrophy) and HG-PIN were examined. Immunohistochemistry was performed as above, using a rabbit polyclonal antibody against the N-terminus of pim-1 (Santa Cruz Biotechnology) at a 1:100 dilution. Pim-1 demonstrated cytoplasmic staining and was graded as either negative, weak, moderate, or strong. All samples were reviewed blinded with respect to all related pathology and clinical data.

C. Statistical Methods

A nonparametric ANOVA test (Mann-Whitney [two categories]) was employed to evaluate whether the prostate samples expressed hepsin and pim-1 at different levels based on various parameters (tissue type, Gleason score, and tumor size). Kaplan-Meier analysis was used to estimate the cumulative percentage of PSA free progression ("survival"). The log-rank test was employed to assess the differences in disease free progression hepsin immunostaining. Cox proportional-hazard regression was used for multivariate analysis. Commercial software from SPSS (Chicago, Ill.) was used for this study.

D. Results

1. Hepsin

Figure 3:
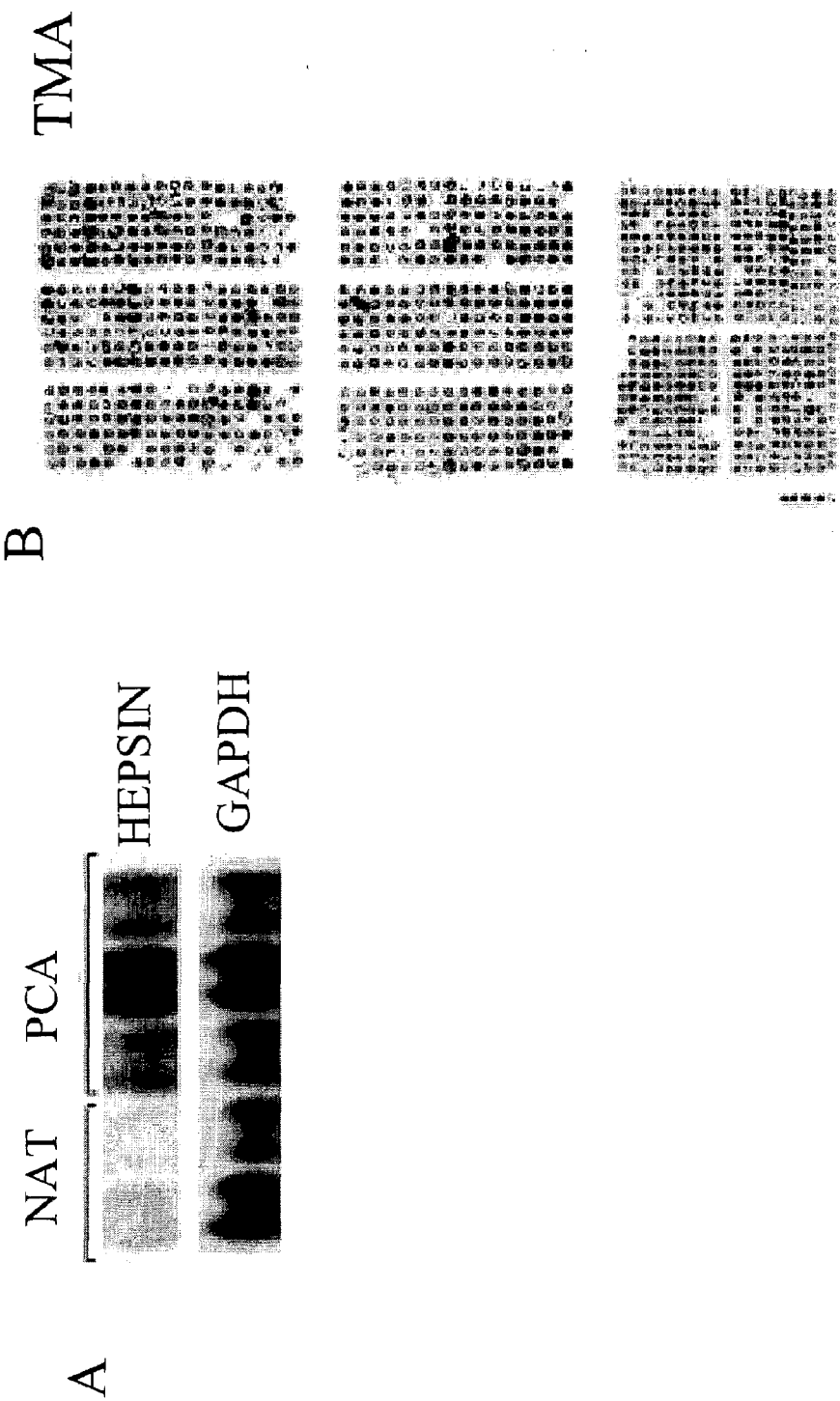
FIG. 3 shows the expression of hepsin in prostate cancer samples as determined by Northern blot analysis and immunohistochemistry.
Figure 3:
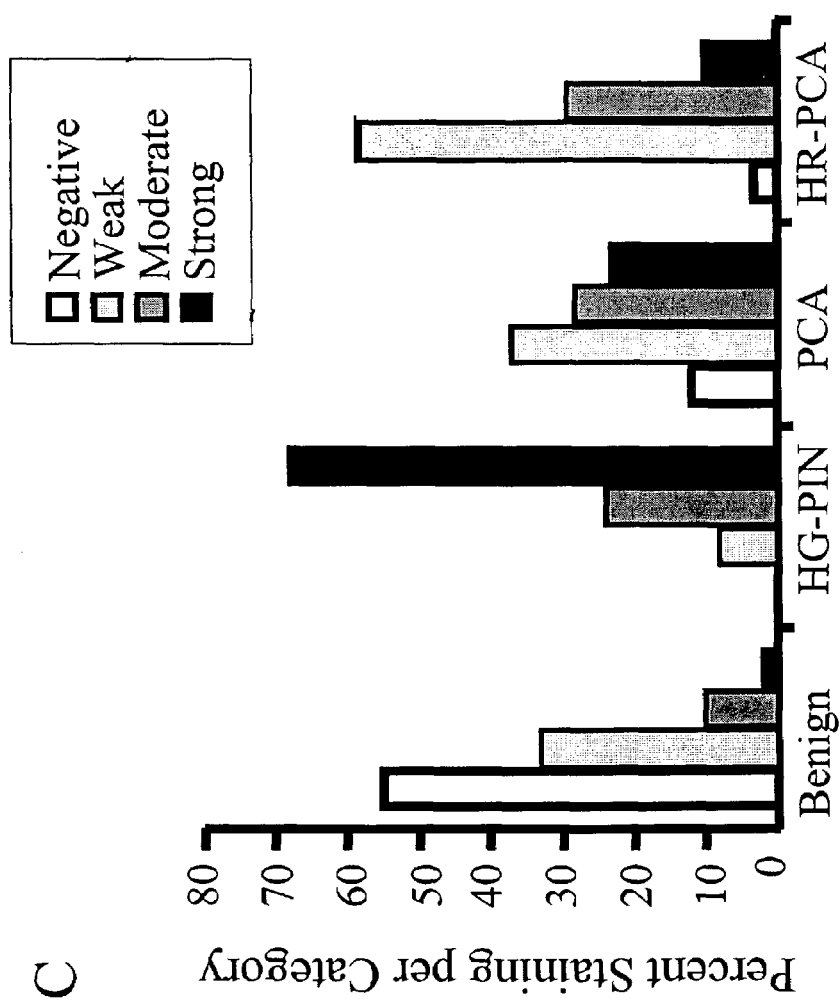
Figure 3:
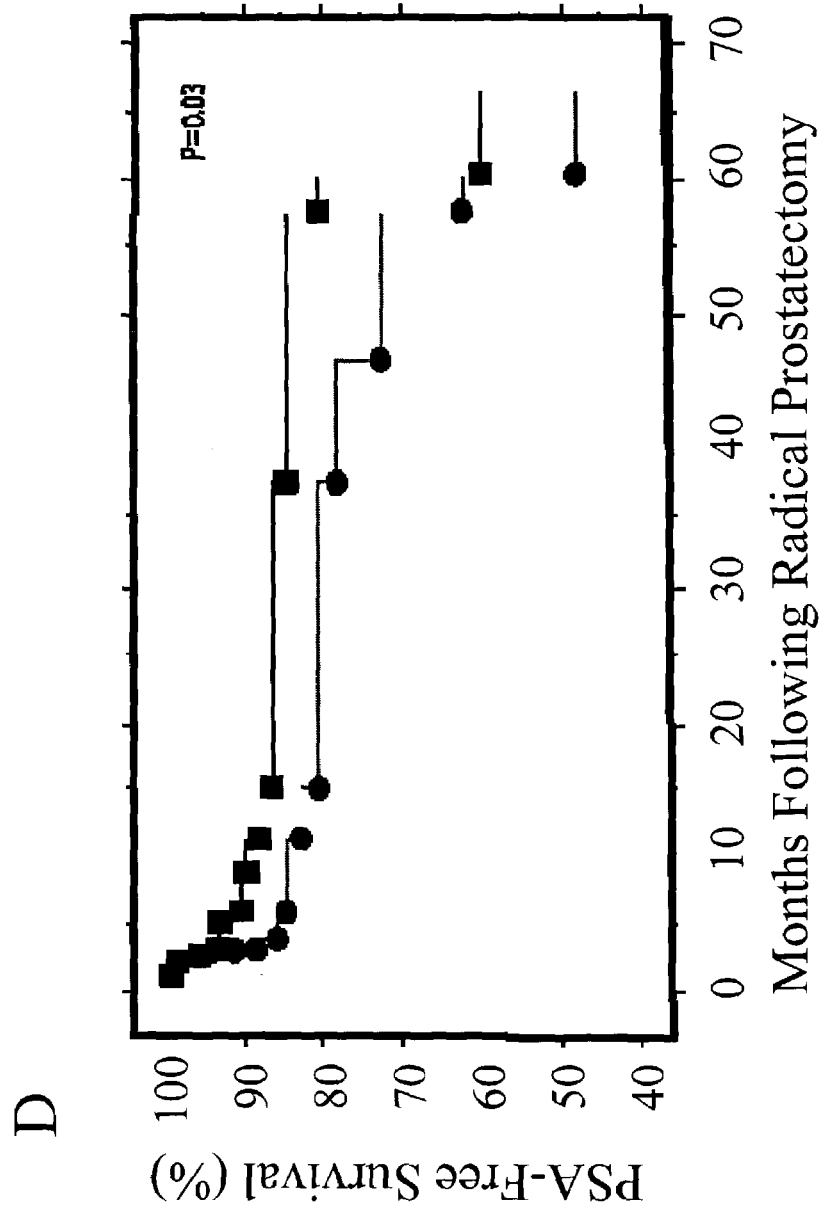

Microarrays used in this study are shown in FIG. 3b. Over 700 benign and malignant prostate tissues were immunohistochemically profiled on tissue microarrays (FIGS. 3c–e) using an affinity-purified hepsin-peptide antibody (Tsuji et al., J. Biol. Chem., 266:16948 [1991]). FIG. 3 shows the overexpression of Hepsin, a transmembrane serine protease, in prostate cancer. FIG. 3a shows a Northern blot analysis of human hepsin (top) and normalization with GAPDH (bottom). NAT indicates normal adjacent prostate tissue and PCA indicates prostate cancer. FIG. 3b shows tissue microarrays used for hepsin analysis. Staining was done with hemotoxylin and eosin to verify histology.

Immunohistochemical stains demonstrated absent or weak staining of benign prostate (c1), strong staining in localized prostate cancer (c2–6), and strong staining in a high-grade prostate tumor (magnification 100× was used for all images, samples measure 0.6 mm in diameter). Benign prostate glands demonstrate weak expression in the secretory, luminal cells and strong basal cell staining. In areas where prostate cancer and benign prostate glands are seen, significant hepsin staining differences are observed. Infiltrating prostate cancers (d3–4) demonstrate strong hepsin protein expression. Magnification for all images was 400×. FIG. 3c shows a histogram of hepsin protein expression by tissue type. Benign prostate hyperplasia (BPH). High-grade intraepithelial neoplasia (HG-PIN). Localized prostate cancer (PCA). Hormone-refractory prostate cancer (MET). Relative strength of hepsin staining was qualitatively assessed and categorized. Percentage of hepsin staining per category is shown on the y-axis. FIG. 3d shows Kaplan Meier Analysis. PSA-free survival was stratified by level of hepsin protein expression into two categories absent/low expression (circles) versus moderate/strong expression (squares).

Internal controls showed that liver tissue, as previously described, stained strongly for hepsin. Overall, hepsin exhibited predominantly membrane staining and was preferentially expressed in neoplastic prostate over benign prostate (Mann-Whitney test, p<0.0001). Importantly, the precursor lesion of PCA, HG-PIN, had the strongest expression of hepsin, and almost never had absent staining (Mann-Whitney, p<0.0001). Most cases of low or absent hepsin staining were seen in benign prostate specimens. In addition, hormone refractory metastatic cancers were intermediate in staining intensity between localized prostate tumors and benign prostate.

Men who develop elevated PSA levels following radical prostatectomy are at a high risk to develop distant metastases and die due to prostate cancer (Pound et al., JAMA, 281:1591 [1999]. Therefore, to assess the usefulness of hepsin as a potential PCA biomarker, PSA failure was defined as a PSA elevation of greater than 0.2 ng/ml following radical prostatectomy. Analysis was performed on 334 localized prostate cancer samples treating each as an independent sample. PSA elevation following radical prostatectomy was significantly associated with absent and low hepsin immunostaining with a 28% (46/119 samples) PSA failure rate, in contrast to 17% (28/141 samples) PSA failure rate for tumors with moderate to strong hepsin expression (FIG. 3d, Log Rank test P=0.03). Multivariate analysis was performed to examine if these results were independent of Gleason score, a well-established histologic grading system for PCA (Gleason, Hum. Pathol., 23:273 [1992]). Based on the results from fitting a Cox proportional hazards model, there is an association of weak or absent hepsin protein expression in PCA with increased risk of PSA elevation following prostatectomy, similar to high Gleason score (corresponding risk ratios were 2.9 (p=0.0004) and 1.65 (p=0.037), respectively). Weak or absent hepsin expression was also associated with large prostate cancers; the median tumor dimension for prostate tumors with moderate to strong expression was 1.3 cm but 1.5 cm for tumors with absent or weak staining (Mann-Whitney Rank test, P=0.043). Taken together, hepsin protein expression in PCA correlated inversely with measures of patient prognosis.

Hepsin is a 51 kDa transmembrane protein with highest expression in the liver, and like PSA, is a serine protease (Kurachi et al., Methods Enzymol., 244:100 [1994]). The protease domain of hepsin has access to the extracellular space and can potentially activate other proteases or degrade components of extracellular matrix. The function of hepsin is poorly understood. It has been proposed to have a role in controlling cell growth (Torres-Rosado et al., PNAS, 90:7181 [1993], cell morphology, and activating the extrinsic coagulation pathway on the cell surface, leading to thrombin formation (Kazama et al., J. Biol. Chem., 270:66 [1995]). Additionally, hepsin mRNA levels have been shown to be elevated in ovarian carcinomas (Tanimoto et al., Cancer Res., 57:2884 [1997]). The present invention is not limited to a particular mechanism. Indeed, an understanding of the mechanism is not necessary to practice the present invention. Nonetheless, it is contemplated that the high expression of hepsin in HG-PIN, and not benign prostate, suggests that hepsin plays a role in the establishment of PIN or in the transition from HG-PIN to carcinoma. Subsequent decreases in hepsin expression seen in large localized cancers and hormone-refractory cancers suggest a decreased requirement of this protease in later stages of PCA. Alternatively, patients with advanced PCA often develop disseminated intravascular coagulation (DIC) (Riddell et al., J. Nucl. Med., 37:401 [1996]) whereby hepsin may play an important role.

2. pim-1

Tumorigenic growth of the prostate depends on the evasion of normal homeostatic control mechanisms, where cell proliferation exceeds cell death (Bruckheimer and Kyprianou, Cell Tissue Res., 301: 153 [2000]). While it is well known that the oncogene myc is overexpressed in many PCAs (Buttyan et al., prostate 11:327–37 [1987]; Abate-Shen and Shen, supra), the present invention demonstrates that the proto-oncogene pim-1 kinase is similarly up-regulated (cell growth/cell death cluster, FIG. 2). Previous studies suggest that the cooperative interaction between pim-1 and myc may induce lymphoid cell transformation by promoting cell cycle progression and blocking apoptosis (Shirogane, et al., Immunity 11:709 [1999]). The present analysis supports a similar co-transcriptional regulation (or gene amplification) of pim-1 and myc possibly mediating a synergistic oncogenic effect in PCA.

Pim-1 kinase protein expression in PCA was also explored using high-denisty TMAs. FIG. 4 shows the overexpression of pim-1 in prostate cancer. Immunohistochemical stains demonstrated absent or weak staining of benign prostate, and strong cytoplasmic staining in localized prostate cancer. Benign prostate glands demonstrated absent or weak expression in the secretory, luminal cells. Infiltrating prostate cancers demonstrated strong pim-1 protein expression. Magnification for all images 1000×. FIG. 4a shows a histogram of pim-1 protein expression by tissue type as assessed from 810 tissue microarray elements. High-grade intraepithelial neoplasia (HG-PIN). Localized prostate cancer (PCA). Relative strength of pim-1 staining is represented in the included legend. The percentage of pim-1 staining per category shown on y-axis. FIG. 4b shows Kaplan-Meier analysis demonstrating that patients with PCA that have negative to weak pim-1 expression (bottom line) are at a greater risk of developing PSA-failure following prostatectomy (log rank p=0.04). PSA-free survival was stratified by level of pim-1 protein expression into two categories absent/ weak expression (bottom line) versus moderate/strong expression (top line).

Pim-1 protein was found to be markedly overexpressed in PCA (FIG. 4). Negative to weak pim-1 protein expression was observed in the majority of benign prostatic epithelial (97%), prostatic atrophy (73%), and high-grade PIN (82%) samples (FIG. 4a). In contrast, moderate to strong pim-1 expression was observed in approximately half of the PCA samples (51%) (FIG. 4a). Kaplan-Meier analysis for PSA-free survival demonstrated positive extraprostatic extension, seminal vesicle invasion, Gleason score greater than 7 and decreased pim-1 expression to be associated with a higher cumulative rate of PSA failure (FIG. 4b). By univariate Cox models, it was found that Pim-1 expression is a strong predictor of PSA recurrence (hazard ratio (HR)=2.1 (95% CI 1.2–3.8, p=0.01)).

Among the variables examined, significant predictors of PSA recurrence were Gleason score (HR=1.8 (95% CI 1.1–3.0), p=0.03), Gleason pattern 4/5 PCA (HR=3.9(95% CI 1.8–8.3), p<0.001), extraprostatic extension status (HR=2.6 (95% CI 1.6–4.2), p<0.0001), surgical margin status (HR=2.6 (95% CI 1.2–5.6), p=0.01), seminal vesicle status (HR=3.5 (95% CI 2.0–6.2), p<0.0001), the natural log of pre-operative PSA level (HR=2.5 (95% CI 1.6–3.8), p<0.001), HR=2.4, p<0.001), and maximum tumor dimension (HR=2.7 (95% CI 1.6–4.7), p<0.0001). Presence of Gleason pattern 4/5 PCA (HR=3.8 (95% CI 1.4–10.0), p<0.01), Ln(PSA) (HR=2.1 (95% CI 1.1–3.9), p=0.02), and decreased pim-1 protein expression (HR=4.5 (95% CI 1.6–15.2), p=0.01) were both found to be significant predictors of PSA recurrence by a multivariate Cox model. Thus, even more so than hepsin, decreased expression of pim-1 kinase in PCA correlated significantly with measures of poor patient outcome.

Pim-1 kinase is a proto-oncogene that is regulated by cytokine receptors (Matikainen et al., Blood 93:1980 [1999]). It was first described as a common site of proviral integration in murine retrovirus-induced T cell lymphomas (Cuypers et al., Cell 37:141 [1984]), and was previously thought to be involved exclusively in hematopoietic malignancies (Breuer et al., Nature 340:61 [1989]). Co-transcriptional regulation of pim-1 and myc was observed in the experiments described herein (FIG. 2 cell growth/cell death cluster). Chronic overexpression of myc in the ventral prostate of transgenic mice induced epithelial abnormalities similar to low-grade PIN, but progression to adenocarcinoma in this model was never observed (Zhang et al., Prostate 43:278 [2000]). The present invention is not limited to any one mechanism. Indeed, an understanding of the mechanism is not necessary to practice the present invention. Nonetheless, it is contemplated that pim-1 overexpression may potentiate myc-induced prostate carcinogenesis.

FIG. 8 provides a schematic overview of representative genes differentially expressed in PCA identified by DNA microarray analysis. Genes are grouped functionally and arrows represent up- or down-regulation in metastatic hormone-refractory PCA (MET) and/or localized PCA (PCA) relative to normal prostate epithelium. See FIG. 2 for gene expression levels.

EXAMPLE 5

AMACR Expression Analysis

The Example describes the analysis of the gene expression data described in Examples 1–4 above to identify AMACR as being consistently over-expressed in prostate cancer.

A. Tissue Samples

In order to examine the widest range of prostate cancer specimens, clinical samples were taken from the radical prostatectomy series at the University of Michigan and from the Rapid Autopsy Program. Both programs are part of the University of Michigan Prostate Cancer Specialized Program of Research Excellence (S.P.O.R.E.) Tissue Core.

Prostatectomy cases for the tissue microarray (TMA) outcomes array were selected from a cohort of 632 patients, who underwent radical retropubic prostatectomy at the University of Michigan as a monotherapy (i.e., no hormonal or radiation therapy) for clinically localized prostate cancer between the years of 1994 and 1998. Clinical and pathology data for all patients was acquired with approval from the Institutional Review Board at the University of Michigan. Detailed clinical, pathology, and TMA data is maintained on a secure relational database (Manley et al., Am. J. Pathol., 159:837 [2001]).

Processing of the prostate specimens began within approximately 15–20 minutes after surgical resection. The prostates were partially sampled and approximately 50% of the tissue was used for research. This protocol has been evaluated in a formal study to assure that partial sampling does not impair accurate staging and evaluation of the surgical margins (Hollenbeck et al., J. Urol., 164:1583 [2000]). Briefly, alternate sections of the prostate gland were submitted for histologic review. The remaining sections were frozen and stored in the SPORE Tissue Core. These samples were collected only from patients who had signed an IRB-approved informed consent. The samples were snap-frozen in OCT embedding media at −80° C. and stored in a holding area until the pathology report was finalized. These frozen samples were not available to researchers until adequate diagnosis and staging had been performed. The samples used for cDNA expression array analysis and RT-PCR were all evaluated by the study pathologists. All samples were grossly trimmed such that greater than 95% of the sample represented the desired lesion (e.g., prostate cancer, BPH, or benign prostate). Samples with prostate cancer were also assigned a Gleason score based on the sample used for molecular analysis.

In order to study hormone refractory prostate cancer, a Rapid Autopsy Protocol was used, which represents a valuable source of metastatic prostate tumors. Modeled after protocols developed at the University of Washington (Seattle, Wash.) and Johns Hopkins University (Baltimore, Md.), this program allows men with advanced prostate cancer to consent to an autopsy immediately after death. To date, 23 complete autopsies have been performed with a median time of 2 hours from death to autopsy. This procedure has previously been described in detail (Rubin et al., Clin. Cancer Res., 6:1038 [2000]). In brief, patients diagnosed with hormone refractory prostate cancer were asked to take part in a posthumous tissue donor program. The objectives and procedures for tissue donation were explained to the patient. Having agreed to participate in this IRB-approved tumor donor program, permission for autopsy is obtained before the death, with consent provided by the patient, or by next of kin. Hormone refractory primary and metastatic prostate cancer samples were collected using liquid nitrogen. Mirrored samples from the same lesion were placed in 10% buffered formalin. The fixed samples were embedded in paraffin and used for the development of TMAs. As with the prostatectomy samples, the study pathologist reviewed the glass slides, circled areas of viable prostate cancer, while avoiding areas of necrosis, and used these slides as a template for TMA construction.

B. Pathology and Evaluation

Prostates were inked before the assessment of surgical margins. Surgical margins from the apex and base were cut perpendicular to the prostatic urethral axis. The seminal vesicles were cut perpendicular to their entry into the prostate gland and submitted as the seminal vesicle margin. The prostates for this study were all partially embedded, taking alternate full sections from the apex, mid, and base. Detailed prostatectomy pathology reports included the presence or absence of surgical margin involvement by tumor (surgical margin status), the presence of extraprostatic extension, and seminal vesicle invasion. Tumors were staged using the TNM system, which includes extraprostatic extension and seminal vesicle invasion but does not take into account surgical margin status (Bostwick et al., Simin. Urol. Oncol., 17:222 [1999]). Tumors were graded using the Gleason grading system (Gleason, Cancer Chemother. Rep., 50:125 [1966]; Gleason, The Veterans Administration Cooperative Urological Research Group. Histologic Grading and Clinical Staging of Prostate Carcinoma. In: Tannenbaum M, editor. Urologic Pathology: The Prostate. Philadelphia: Lea & Febiger; 1977. p. 171–98).

As preparation for the construction of the TMAs, all glass slides were re-reviewed to identify areas of benign prostate, prostatic atrophy, high-grade prostatic intraepithelial neoplasia, and prostate cancer. To optimize the transfer of these designated tissues to the arrays, area of tumor involvement was encircled on the glass slide template as tightly around each lesion as possible. Areas with infiltrating tumor adjacent to benign glands were avoided.

C. RT-PCR

Total RNA integrity was judged by denaturing-formaldehyde agarose gel electrophoresis. cDNA was prepared using 1 μg of total RNA isolated from prostate tissue specimens. Primers used to amplify specific gene products were: AMACR sense, 5' CGTATGCCCCGCTGAATCTCGTG-3' (SEQ ID NO:100); AMACR antisense, 5'-TGGCCAAT-CATCCGTGCTCATCTG-3' (SEQ ID NO:101); GAPDH sense, 5'-CGGAGTCAACGGATTTGGTCGTAT-3' (SEQ ID NO:102); and GAPDH antisense, 5'-AGCCTTCTC-CATGGTGGTGAAGAC-3' (SEQ ID NO:103). PCR conditions for AMACR and GAPDH comprised 94° C. for 5 min, 28 cycles of 95° C. for 1 min, 60° C. for 1 min (annealing), and 72° C. for min, and a final elongation step of 72° C. for 7 min. PCR reactions used a volume of 50 μl, with 1 unit of Taq DNA polymerase (Gibco BRL). Amplification products (5 μl) were separated by 2% agarose gel electrophoresis and visualized by ultraviolet light.

D. Immunoblot Analysis

Representative prostate tissue specimens were used for Western blot analysis. Tissues were homogenized in NP-40 lysis buffer containing 50 mmol/L Tris-HCl, pH 7.4, 1% Nonidet P-40 (Sigma, St. Louis. Mo.) and complete proteinase inhibitor cocktail (Roche, Ind., USA). Fifteen μg of protein extracts were mixed with SDS sample buffer and electrophoresed onto a 10% SDS-polyacrylamide gel under reducing conditions. The separated proteins were transferred onto nitrocellulose membranes (Amersham Pharmacia Biotech, Piscataway, N.J.). The membrane was incubated for 1 hour in blocking buffer (Tris-buffered saline with 0.1% Tween (TBS-T) and 5% nonfat dry milk). The AMACR antibody (Obtained from Dr. R Wanders, University of Amsterdam) was applied at 1:10,000 diluted in blocking buffer overnight at 4° C. After washing three times with TBS-T buffer, the membrane was incubated with horseradish peroxidase-linked donkey anti-rabbit IgG antibody (Amersham Pharmacia Biotech, Piscataway, N.J.) at 1:5000 for 1 hour at room temperature. The signals were visualized with the ECL detection system (Amersham Pharmacia biotech, Piscataway, N.J.) and autoradiography.

For β-tubulin western blots, the AMACR antibody probed membrane was stripped with Western Re-Probe buffer (Geno-tech, St. Louis, Mo.) and blocked in Tris-buffered saline with 0.1% Tween (TBS-T) with 5% nonfat dry milk and incubated with rabbit anti β-tubulin antibodies (Santa Cruz Biotechnologies, Santa Cruz, Calif.) at 1:500 for two hours. The western blot was then processed as described above.

E. Immunohistochemistry

Standard indirect immunohistochemistry (IHC) was performed to evaluate AMACR protein expression using a polyclonal anti-AMACR antibody. Protein expression was scored as negative (score=1), weak (score 2), moderate (3) and strong (4). In order to evaluate whether AMACR protein expression was associated with prostate cancer proliferation, a subset of samples were evaluated using the monoclonal mouse IgG Mib-1 antibody for Ki-67 (1:150 dilution, Coulter-Immunotech, Miami, Fla.). Microwave pretreatment (30 minutes at 100 C. in Tris EDTA Buffer) for antigen retrieval was performed using 3,3' diaminobenzidine tetrahydrocloride as a chromogen. Lymph node tissue with known high Ki-67 positivity was used as a control.

F. Tissue Microarray Construction, Digital Image Capture, and Analysis

Five TMAs were used for this study. Three contained tissue from the prostatectomy series and two contained hormone refractory prostate cancer from the Rapid Autopsy Program. The TMAs were assembled using the manual tissue arrayer (Beecher Instruments, Silver Spring, Md.) as previously described (Kononen et al., Nat. Med., 4:844 [1998]; Perrone et al., J. Natl. Cancer Inst., 92:937 [2000]). Tissue cores from the circled areas (as described above) were targeted for transfer to the recipient array blocks. Five replicate tissue cores were sampled from each of the selected tissue types. The 0.6 mm diameter TMA cores were each spaced at 0.8 mm from core-center to core-center. After construction, 4 μm sections were cut and H&E staining was performed on the initial slide to verify the histology.

TMA H&E images were acquired using the BLISS Imaging System (Bacus Labs, Lombard, Ill.). AMACR protein expression was evaluated in a blinded manner. All images were scored for AMACR protein expression intensity. In addition, all TMA samples were assigned a diagnosis (i.e., benign, atrophy, high-grade prostatic intraepithelial neoplasia, and prostate cancer). This is recommended because the targeted tissues may not be what were actually transferred. Therefore, verification was performed at each step. TMA slides were evaluated for proliferation index using a CAS200 Cell Analysis System (Bacus Labs). Selected areas were evaluated under the 40× objective. Measurements were recorded as the percentage of total nuclear area that was positively stained. All positive nuclear staining, regardless of the intensity, was measured. Sites for analysis were selected to minimize the presence of stromal and basal cells; only tumor epithelium was evaluated. Specimens were evaluated for Ki-67 expression as previously described (Perrone et al., J. Natl. Cancer Inst. 92:937 [2000]). Each measurement was based on approximately 50–100 epithelial nuclei. Due to the fixed size of TMA samples, 5 repeat non-overlapping measurement was the maximum attainable.

G. Analysis of Prostate Needle Biopsies

In order to evaluate the usefulness of AMACR expression in diagnostic 18 gauge needle biopsies, 100 consecutive biopsies with prostate cancer or atypia that required further work-up were tested for AMACR expression. All cases were immunostained using two basal cell specific markers (34βE12 and p63) and AMACR. Cases were evaluated for cancer sensitivity and specificity. Twenty-six of these cases were seen in consultation with a pathologist and were considered diagnostically difficult, requiring expert review and additional characterization.

H. Results

FIG. 11 shows a schematic of the DNA and tissue microarray paradigm that lead to the discovery and characterization of AMACR in prostate cancer. A) Prostate cancer progression as adapted from Abate-Shen and Shen, (Genes Dev., 14:2410 [2000]). Distinct molecular changes occur at each stage of prostate cancer progression that can be studied using DNA microarray or "chip" technology. B) cDNA generated from tumor (prostate cancer) and reference (benign prostate tissue) samples is labeled with distinguishable fluorescent dyes and interrogated with a DNA microarray that can monitor thousands of genes in one experiment. C) After hybridization, the DNA microarray is analyzed using a scanner and fluorescence ratios determined for each gene (in this case prostate cancer/ benign tissue). D) The ratios are deposited into a computer database and subsequently analyzed using various statistical algorithms. One exemplary method of surveying the data (Eisen et al., PNAS 95:14863 [1998]) assigns color intensity to the ratios of gene expression. In this case, shades of red represent genes that are up-regulated in prostate cancer (e.g., a ratio of 4.0) and shades of green represent genes that a down-regulated (e.g., ratio of 0.1). Genes that are unchanged between tumor and benign tissues are represented by a black color and missing elements by a gray color. E) Genes that are identified by DNA microarray can then be validated at the transcript level (e.g., Northern blot, RT-PCR) or at the protein level (e.g., immunoblot). F) Construction of prostate cancer tissue microarrays facilitates the study of hundreds of patients (rather than hundreds of genes). G) Each tissue microarray slide contains hundreds of clinically stratified prostate cancer specimens linked to clinical and pathology databases (not shown). H) Tissue microarray slides can then be analyzed using various molecular or biochemical methods (in this case immunohistochemistry). I) Both DNA and tissue microarray data have clinical applications. Examples include, but are not limited to: 1. using gene expression profiles to predict patient prognosis, 2. identification of clinical markers and 3. development of novel therapeutic targets.

Figure 12:
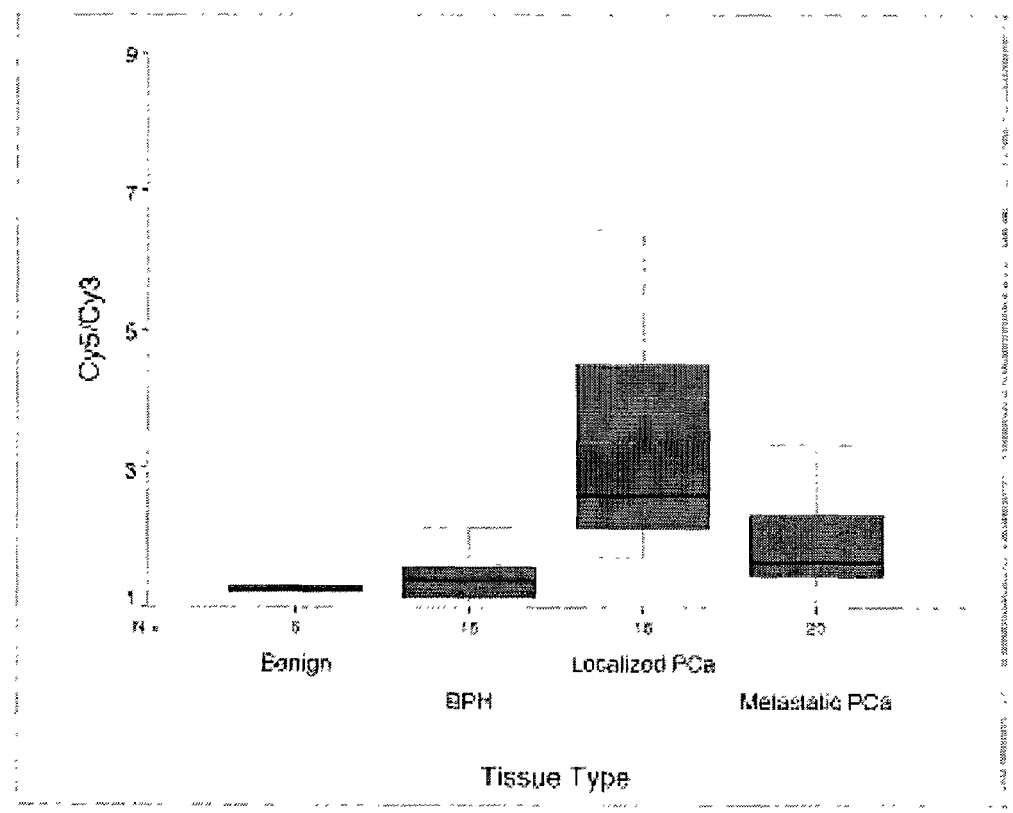
FIG. 12 describes a DNA microanalysis of AMACR expression in prostate cancer.

FIG. 12 summarizes AMACR transcript levels as determined by DNA microarray analysis over 57 prostate cancer specimens. Samples (Dhanasekaran et al., Nature 412: 822 [2001]) were grouped according to tissue type and averaged. The experimental sample was labeled in the Cy5 channel while the reference sample (pool of benign prostate tissue) was labeled in the Cy3 channel. The box-plot demonstrates the range of AMACR expression within each group. Tissues were grouped into the following classes benign (normal adjacent prostate tissue), benign prostatic hyperplasia (BPH), clinically localized prostate cancer, and metastatic prostate cancer. In relation to benign prostate tissues, localized prostate cancer and metastatic prostate cancer were 3.1 (Mann-Whitney test, p<0.0001)and 1.67 (Mann-Whitney test, p<0.004) fold up-regulated, respectively (represented as Cy5/Cy3 ratios).

Figure 13:
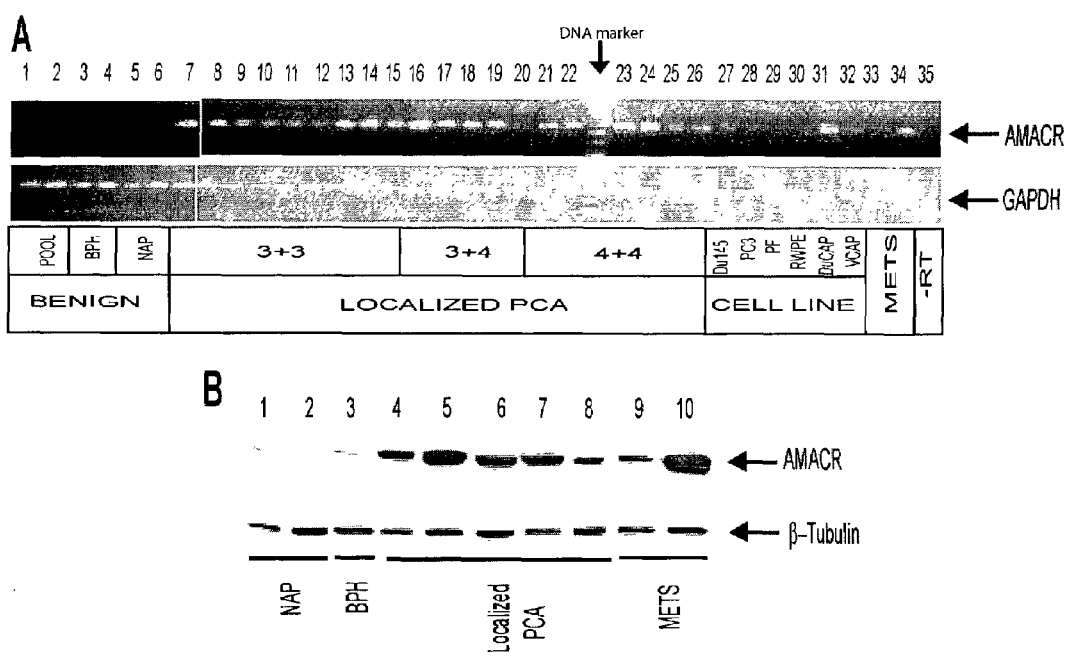
FIG. 13 describes an analysis of AMACR transcript and protein levels in prostate cancer.

DNA microarray results of AMACR mRNA levels were validated using an independent experimental methodology. AMACR-specific primers were generated and RT-PCR performed on the various RNA samples from 28 prostate tissue specimens and 6 prostate cell lines (FIG. 13A). GAPDH served as the loading control. Pool, refers to RNA from normal prostate tissues obtained from a commercial source. NAP, normal adjacent prostate tissue from a patient who has prostate cancer. 3+3, 3+4, 4+4, refers to the major and minor Gleason patterns of the clinically localized prostate cancer (PCA) examined. MET, metastatic prostate cancer. Various prostate cell lines are also examined. RT-PCR without enzyme served as a negative control. An RT-PCR product was clearly observed in the 20 localized prostate cancer samples but not in the benign samples examined. Metastatic prostate cancer and prostate cell lines displayed varying levels of AMACR transcript as compared to localized prostate cancer.

In order to gauge AMACR protein levels, immunoblot analysis was performed on selected prostate tissue extracts (FIG. 13B), β-tubulin served as a control for sample loading. Similar to AMACR transcript, over-expression of AMACR protein was observed in malignant prostate tissue relative to benign prostate tissue.

In order to validate protein expression of AMACR in situ, a separate cohort of prostate samples from those used in the cDNA expression array analysis was used. These prostate samples were taken from the University of Michigan Prostate SPORE Tissue Core and were assembled onto high-density tissue microarrays (schematically illustrated in FIGS. 11F–H). Moderate to strong AMACR protein expression was seen in clinically localized prostate cancer samples with predominately cytoplasmic localization. A large contrast in levels of AMACR in malignant epithelia relative to adjacent benign epithelia was seen. Prostatic intraepithelial neoplasia (PIN) and some atrophic lesions, which are thought to be potentially pre-cancerous lesions (Putzi et al., Urology 56:828 [2000]; Shah et al., Am. J. Pathol., 158:1767 [2001]), demonstrated cytoplasmic staining of AMACR. High-grade prostate cancer also demonstrated strong cytoplasmic staining. However, no association was identified with AMACR staining intensity and Gleason (tumor) score. Many of the metastatic prostate cancer samples demonstrated only weak AMACR expression. The metastatic samples showed uniform PSA immunostaining, confirming the immunogenicity of these autopsy samples.

Figure 14:
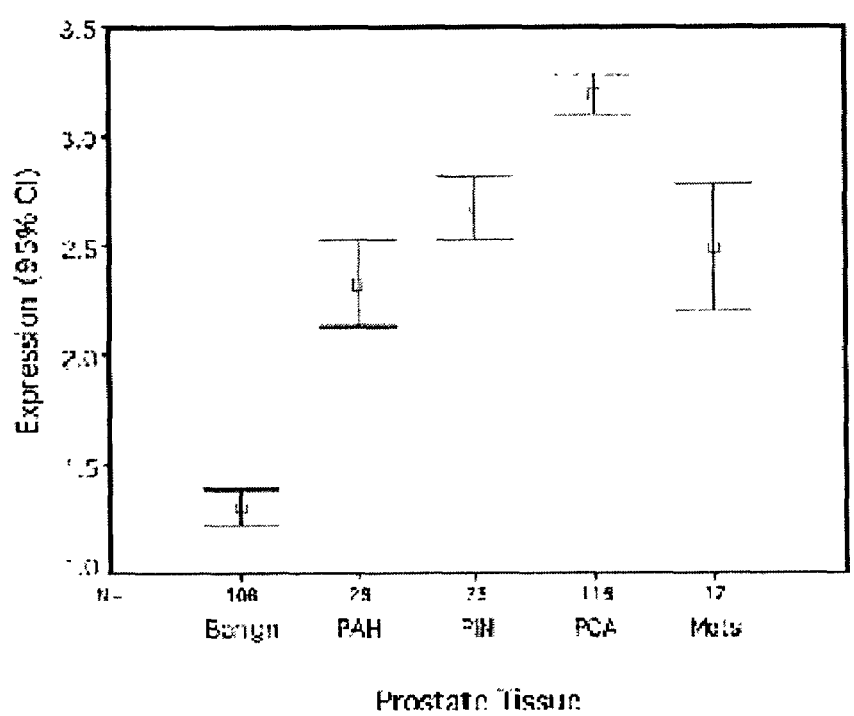
FIG. 14 describes an analysis of AMACR protein expression using prostate cancer tissue microarrays.

In order to assess AMACR protein expression over hundreds of prostate specimens, the tissue microarray data was quantitated. Benign prostate, atrophic prostate, PIN, localized prostate cancer, and metastatic prostate cancer demonstrated mean AMACR protein staining intensity of 1.0 (SE 0), 2.0 (SE 0.1), 2.5 (SE 0.1), 3.0 (SE 0), and 2.5 (SE 0.1), respectively (ANOVA p-value<0.0001). This data is graphically summarized using error bars representing the 95% confidence interval for each tissue category (FIG. 14).

The correlation of AMACR levels with tumor proliferation was next investigated using Ki-67 (Perrone et al., supra). There was no significant association between AMACR expression and Ki-67 expression with a correlation coefficient of 0.13 (p-value=0.22). In addition, no significant associations were identified between AMACR protein expression and pathology parameters such as radical prostatectomy, Gleason score, tumor stage, tumor size (cm), or surgical margin status. AMACR protein levels were next evaluated for association with PSA recurrence following surgery in 120 prostatectomy cases with a median follow-up time of 3 years. No statistically significant association was identified. AMACR demonstrated uniform moderate to strong expression in clinically localized prostate cancer with a high sensitivity for tumor and an equally high specificity. In addition, a preliminary survey of normal tissues including ovary, liver, lymph nodes, spleen, testis, stomach, thyroid, colon, pancreas, cerebrum, and striated muscle revealed significant AMACR protein expression in only normal liver.

The large difference in AMACR protein levels between normal secretory epithelial cells and malignant cells provides a clinical use for testing AMACR expression in prostate needle biopsy specimens. In diagnostically challenging cases, pathologists often employ the basal cell markers 34βE12 (O'Malley et al., Virchows Arch A Patho. Anat. Histopathol., 417:191 [1990]; Wojno et al., Am. J. Surg. Pathol., 19:251 [1995]; Googe et al., Am. J. Clin. Pathol., 107:219 [1997] or p63 (Parson et al., Urology 58:619 [2001]; Signoretti et al., Am. J. Pathol., 157:1769 [2000]), which stain the basal cell layer of benign glands. This second basal cell layer is absent in malignant glands. In many equivocal biopsy specimens, the surgical pathologist must rely on absence of staining to make the final diagnosis of prostate cancer. The clinical utility of AMACR immunostaining on 94 prostate needle biopsies was evaluated. The results are shown in Table 2. The sensitivity and specificity were calculated as 97% and 100%, respectively. These results included 26 cases where the final diagnosis required the use of a basal cell specific immunohistochemical marker (i.e., 34βE12 or p63).

This example demonstrated that AMACR is associated with PCA and that AMACR expression in prostate biopsies is useful for the diagnosis of cancer in inconclusive biopsy samples.

TABLE 2

Clinical utility of Assessing AMACR Protein in Prostate Needle Biopsies (n = 94)

| Sensitivity (TP/(TP + FN)) | Specificity (TN/(TN + FP)) | Positive Predictive Value (TP/(TP + FP)) | Negative Predictive Value (TN/(TN + FN)) |
|---|---|---|---|
| 97% ((68/(2 + 68)) | 100% ((24/(24 + 0)) | 100% ((68/(68 + 0)) | 92% ((24/24 + 2)) |

EXAMPLE 6

Hormone Regulation of AMACR

This example describes studies that indicate that AMACR expression is hormone independent.

A. Sample Collection, cDNA Array and TMA Construction and Evaluation

Clinical samples were taken from the radical prostatectomy series and from the Rapid Autopsy Program at the University of Michigan. Both are part of the University of Michigan Prostate Cancer Specialized Program of Research Excellence (S.P.O.R.E.). Primary PCA of metastatic cases as well as lymph node metastases were contributed in collaboration from the University of Ulm, Germany. Detailed clinical and expression analysis as well as TMA data was acquired and maintained on a secure relational database according to the Institutional Review Board protocol of both institutions. Tissue procurement for expression analysis on the RNA level is described in the above examples. For the development of TMA, samples were embedded in paraffin. The study pathologist reviewed slides of all cases and circled areas of interest. These slides were used as a template for construction of the six TMAs used in this study. All TMAs were assembled using a manual tissue arrayer (Beecher Instruments, Silver Spring, Md.). At least three tissue cores were sampled from each donor block. Histologic diagnosis of the tissue cores was verified by standard haematoxylin and eosin (H&E) staining of the initial TMA slide. Standard biotin-avidin complex immunohistochemistry (IHC) was performed using a polyclonal anti-AMACR antibody (Ronald Wanders, University of Amsterdam). Digital images were acquired using the BLISS Imaging System (Bacus Lab, Lombard, Ill.). Staining intensity was scored as negative (score=1), weak (score 2), moderate (3) and strong (4). For exploration of the treatment effect by the means of hormonal withdrawal before radical prostatectomy, standard slides were used for regular H&E staining and consecutive sections for detection of AMACR expression. In order to test AMACR expression in poorly differentiated colon cancers, cases were used from a cohort of well-described colon tumors. In addition to well-differentiated colon cancers, a recently described subset of poorly differentiated colon carcinomas with a distinctive histopathological appearance, termed large cell minimally differentiated carcinomas, was used. These poorly differentiated colon carcinomas had a high frequency of the microsatellite instability phenotype.

B. Cell Culture and Immunoblot Analysis

Prostate cell lines (RWPE-1, LNCaP, PC3 and DU145) were obtained from the American Tissue Culture Collection. Cells were maintained in RPMI-1640 with 8% decomplemented fetal bovine serum, 0.1% glutamine and 0.1% penicillin and streptomycin (BioWhittaker, Walkersville, Md.). Cells were grown to 75% confluence and then treated for 24 and 48 with the antiandrogen bicalutamide (CASODEX, Zeneca Pharmaceuticals, Plankstadt, Germany) at a final concentration of 20 μM or with methyltrienolone (synthetic androgen (R1881); NEN, Life Science Products, Boston, Mass.) at a final concentration of 1 nM. Cells were harvested and lysed in NP-40 lysis buffer containing 50 mmol/L Tris-HCl, pH 7.4, 1% Nonidet P-40 (Sigma, St. Louis, Mo.) and complete proteinase inhibitor cocktail (Roche, Ind., USA). 15 μg of protein extracts were mixed with SDS sample buffer and electrophoresed onto a 10% SDS-polyacrylamide gel under reducing conditions. After transferring, the membranes (Amersham Pharmacia Biotech, Piscataway, N.J.) were incubated for 1 hour in blocking buffer (Tris-buffered saline with 0.1% Tween and 5% nonfat dry milk). The AMACR antibody was applied at 1:10.000 diluted blocking buffer overnight at 4° C. After three washes with TBS-T buffer, the membrane was incubated with horseradish peroxidase-linked donkey anti-rabbit IgG antibody (Amersham Pharmacia Biotech, Piscataway, N.J.) at 1:5000 for 1 hour at room temperature. The signals were visualized with the ECL detection system (Amersham Pharmacia biotech, Piscataway, N.J.). For β-tubulin blots, membranes were stripped with Western Re-Probe buffer (Geno-tech, St. Louis, Mo.) and blocked in Tris-buffered saline with 0.1% Tween with 5% nonfat dry milk and incubated with rabbit anti β-tubulin antibodies (Santa Cruz Biotechnologies, Santa Cruz, Calif.) at 1:500 for two hours. For PSA expression the membranes were reprobed in the described manner with PSA antibody (rabbit polyclonal; DAKO Corporation, Carpinteria, Calif.) at 1:1000 dilution and further processed.

C. Statistical Analysis

Primary analysis of the cDNA expression data was done with the Genepix software. Cluster analysis with the program Cluster and generation of figures with TreeView was performed as described above. AMACR protein expression was statistically evaluated using the mean score result for each prostate tissue type (i.e., benign prostate, naive localized or advanced prostate cancer, hormone treated and hormone refractory prostate cancer). To test for significant differences in AMACR protein expression between all tissue types, a one-way ANOVA test was performed. To determine differences between all pairs, a post-hoc analysis using the Scheffé method was applied as described above. For comparison of naive primaries to their corresponding lymph node metastases with respect to AMACR protein expression, a non parametric analysis (Mann Whitney test) was performed. To compare AMACR expression intensity to the scored hormonal effect of the pretreated localized prostate cancer cases the Mantel-Haenszel Chi-Square test was applied. AMACR expression scores are presented in a graphical format using error-bars with 95% confidence intervals. P-values <0.05 were considered statistically significant.

D. Results

Figure 15:
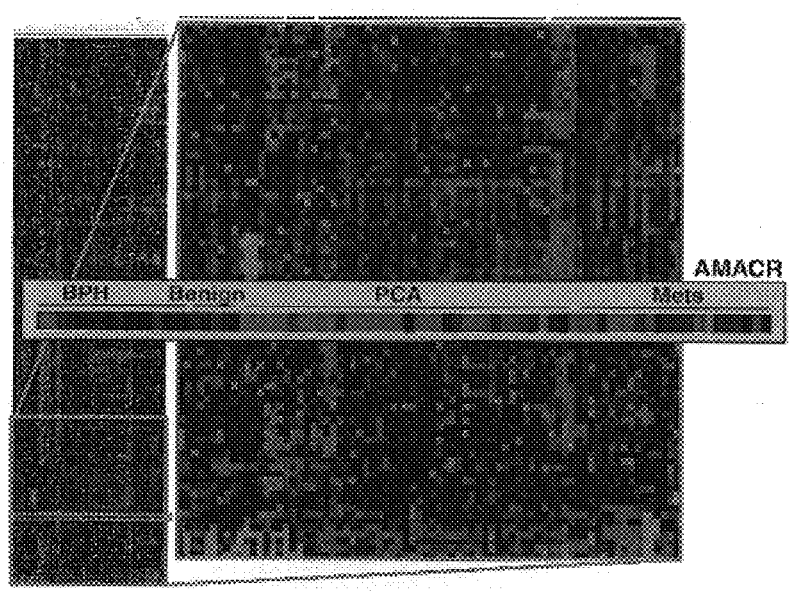
FIG. 15 shows relative gene expression of AMACR in several samples.

Hierarchical clustering of 76 prostate tissues including benign, BPH, localized PCA and metastatic PCA and filtering for only those genes with a 1.5 fold expression difference or greater, clustered the samples into histologically distinct groups as described above. As demonstrated by a TreeView presentation of this data (FIG. 15), AMACR was one of several genes that demonstrated over expression at the cDNA level of PCA samples with respect to benign pooled prostate tissue. The highest level of over expression by cDNA analysis was in the clinically localized PCA cases.

Figure 16:
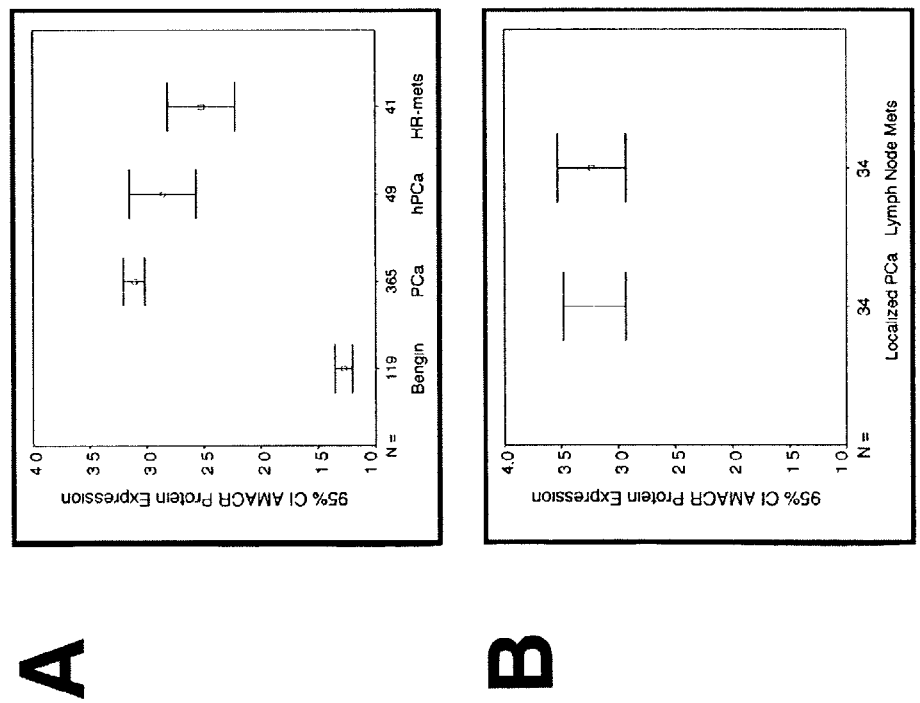
FIG. 16 shows AMACR protein expression PCA.

In order to further investigate the role of AMACR protein expression in samples with variable differentiation and exposure to anti-androgen treatment, several TMAs with a wide range of PCA were constructed: a total of 119 benign prostate samples, 365 primary hormone naive PCA samples, 37 naive prostate cancer lymph node metastases, and 41 hormone refractory metastatic PCA samples were evaluated. An additional 49 hormone treated primary prostate cancers (including 22 on standard slides) were examined for histologic changes associated with anti-androgen treatment and AMACR protein expression. The mean AMACR protein expression levels for each tissue category is presented in FIG. 16. Benign prostate, naive primary prostate cancer, hormone treated primary cancer, and hormone refractory metastatic tissue had a mean staining intensity of 1.28 (Standard Error SE 0.038, 95% Confidence Intervals CI 1.20–1.35), 3.11(SE 0.046, CI 3.02–3.20), 2.86 (SE 0.15, CI 2.56–3.15) and 2.52 (SE 0.15, CI 2.22–2.28), respectively). One-way ANOVA analysis revealed a p-value of <0.0001. To specifically examine the difference between different tissue types, a post-hoc pair-wise comparison was performed. Clinically localized PCA demonstrated a significantly stronger AMACR protein expression as compared to benign prostate tissue (post-hoc analysis using Scheffé method, mean difference=1.83, p<0.0001, CI 1.53–2.13). A significant decrease in AMACR protein expression was observed in the metastatic hormone refractory PCA samples with respect to clinically localized PCA (0.59, p=0.002, CI 0.15–1.03). Hormone treated primaries had a mean AMACR expression of 2.86, which was between the expression levels of naive primaries (3.11) and hormone refractory cases (2.52) (post-hoc analysis using Scheffé method, p=0.51, CI −0.66–0.16 and p=0.56, CI −0.23–0.91). There was no significant difference in AMACR expression in the 37 naive primary prostate samples and lymph node metastases derived from the same patient (Mann Whitney test, p=0.8). In other words, matched primaries and lymph node metastases showed similar AMACR expression pattern.

Figure 17:
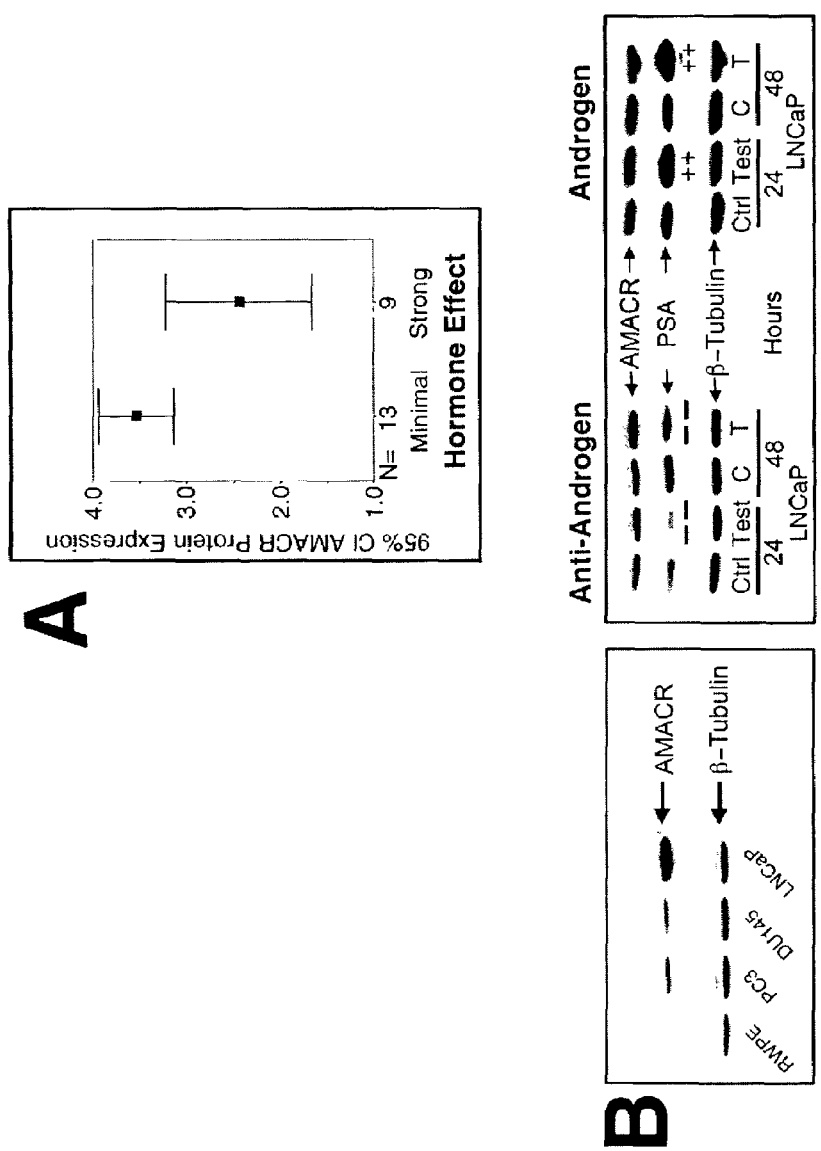
FIG. 17 shows the hormonal effect on AMACR expression.

A subset of 22 PCA cases in which the patients received variable amount and types of anti-androgen treatment prior to surgery was examined. These cases were evaluated blindly with respect to treatment protocol for histological evidence of hormone treatment (H&E slide) and AMACR protein expression. The hormonal effect visible on the H&E slides was classified from 1 to 4 with 1 representing "no effect" and 4 showing a "very strong effect". 13 cases demonstrated either no or moderate hormonal effect, and 9 cases had a very strong hormonal effect. Statistical analysis revealed a significant difference between these two groups with respect to AMACR expression intensity (FIG. 17, Mantel-Haenszel Chi-Square, p=0.009). FIG. 17 presents an example of a PCA case treated prior to surgery with anti-androgens that has a strong hormonal effect appreciated on H&E and decreased AMACR protein expression (FIG. 17A). In this dataset there was neither a correlation between treatment duration nor treatment type (monotherapy or complete hormonal withdrawal for hormone deprivation) and AMACR expression.

For further exploration of the hormonal effect on AMACR expression, primary cell culture experiments and Western blot analysis were performed. As demonstrated in FIG. 17 Panel B, LNCaP cells, derived from a metastatic lesion but considered hormone responsive, showed a higher baseline AMACR expression as compared to PC3 and DU-145 cells, which are both hormone independent cell lines derived from metastatic lesions. A benign cell line, RWPE-1 (Bello et al., Carcinogenesis 18:1215 [1997]), showed near absent AMACR expression, which is consistent with the in situ protein expression data. To simulate an anti-androgen treatment, the hormone responsive cell line LNCaP was treated with bicalutamide in a final concentration of 20 µM for a time period of 24 and 48 hours. AMACR expression in cell lysates of LNCaP cells did not change at either time point when exposed to anti-androgen therapy. Under the same conditions, PSA, a gene known to be regulated by the androgen receptor, showed decreased protein expression. In addition, when LNCaP cells were exposed to a synthetic androgen R1881, no increase in AMACR expression was observed (FIG. 17, Panel B). Therefore, these cell culture experiments provide evidence that AMACR expression is not regulated by the androgen pathway.

The present invention is not limited to a particular mechanism. Indeed, an understanding of the mechanism is not necessary to practice the present invention. Nonetheless, it is contemplated that another explanation for these observations was that AMACR over expression occurred in PCA, but as these tumors became poorly differentiated, as in the hormone refractory PCA, AMACR expression was down regulated either directly or indirectly due to the process of de-differentiation. To elucidate this potential correlation colon cancer samples were examined for AMACR expression (See Example 7). AMACR protein expression is also observed in some other tumor types, with the highest overall expression in colorectal cancers. Colorectal cancers are not known to be regulated by androgens and were therefore used as a control to test this hypothesis. Four well differentiated and seven anaplastic colon cancer samples were chosen. The poorly differentiated tumors have distinct molecular alterations distinguishing them from the common well to moderately differentiated colorectal tumors (Hinoi et al., Am. J. Pathol. 159:2239 [2001]). Strong AMACR protein expression in a moderately differentiated colon cancer was observed. This tumor still forms well defined glandular structures. The surrounding benign colonic tissue does not express AMACR. The anaplastic colon cancers demonstrated weak AMACR protein expression. Primarily data revealed positive AMACR expression in 4/4 well differentiated cases but only 4/7 anaplastic colonic cancers. Three of the anaplastic colon cancers had weak to moderate expression. Metastatic hormone refractory PCA demonstrated weak AMACR protein expression in tissue microarrays.

EXAMPLE 7

AMACR Expression in a Variety of Cancers

A. Analysis of Online EST and SAGE Database

The National Cancer Institute Cancer Genome Anatomy Project (CGAP) has several gene expression databases available online for comparing gene expression across multiple samples (See the Internet Web site of the National Cancer Institute). Both EST and SAGE databases offer Virtual Northern blots, which allow users to visualize and compare the expression level of a particular gene among multiple samples. The SAGE database includes over 5 million tags from 112 libraries of multiple benign and malignant tissues.

B. Selection of Study Cases

A total of 96 cases of cancers from different sites were selected for construction of a multi-tumor tissue microarray. The tissue microarray was constructed to perform a wide survey of multiple common tumor types. A minimum of three tissue cores (0.6 mm in diameter) was taken for each case. Tumors surveyed included colorectal adenocarcinoma (n=15 cases), renal cell carcinoma (6), prostatic adenocarcinoma (6), urothelial carcinoma (4), cervical squamous cell carcinoma (6), lung non-small cell carcinoma (4), lymphoma (15), melanoma (9) and several other cancer types. Normal adjacent tissue was taken when available. The prostate tissue microarray was constructed from selected patients who underwent radical prostatectomies as monotherapy for clinically localized prostate cancer. This tissue microarray contained a spectrum of prostatic tissue including prostatic atrophy, high-grade prostatic intraepithelial neoplasia (PIN), and clinically localized prostate cancer. In addition, standard slides were used to confirm results for colon cancer. Twenty-four cases of colorectal adenocarcinoma (16 well to moderately differentiated carcinoma and 8 large cell minimally differentiated carcinoma) and 8 endoscopically derived colorectal adenomas were selected for immunostaining for AMACR. For breast carcinoma, a TMA of 52 cases of invasive ductal carcinoma was used. Specimens were collected and analyzed in accordance with the Institutional Review Board guidelines.

C. Immunohistochemistry

Standard avidin-biotin complex immunohistochemistry was used. Pre-treatment was performed by steaming the slides for 10 minutes in sodium citrate buffer in a microwave oven. The slides were then incubated sequentially with primary antibody (1:2000 dilution, polyclonal rabbit anti-AMACR antibody), biotinylated secondary antibody, avidin-biotin complex and chromogenic substrate 3,3'-diaminobenzidine. Slides were evaluated for adequacy using a standard bright field microscope. Digital images were then acquired using the BLISS Imaging System (Bacus Lab, Lombard, Ill.) and evaluated by two pathologists. Protein expression was scored as negative, weak stain (faint cytoplasmic stain or granular apical staining), moderate (diffuse granular cytoplasmic stain) and strong (diffuse intense cytoplasmic stain). Only moderate and strong staining was considered as positive staining.

D. Laser Capture Microdissection

Sections of 2 radical prostatectomy samples were frozen in OCT in accordance with an Institutional Review Board protocol. Frozen sections (5 μm thick) were fixed in 70% alcohol for 10 minutes and then stained in hemotoxylin and eosin. Prostate cancer and benign prostate glands were dissected on a μCUT laser capture microdissector (MMI GmbH, Heidelberg, Germany). Approximately 6000 cells were harvested. Total RNA was isolated using Qiagen micro-isolation kit (Qiagen, San Diego, Calif.). Reverse transcription was performed using both oligo dT and random hexamer primers. Primers used to amplify specific gene products were: AMACR sense, 5'-CGTATGCCCCGCTGAATCTCGTG-3' (SEQ ID NO:123); AMACR antisense, 5'-TGGCCAATCATCCGTGCTCATCTG-3' (SEQ ID NO:105); GAPDH sense, 5'AGCCTTCTCCATGGTGGT-GAAGAC-3' (SEQ ID NO:106); and GALPDH antisense, 5'-AGCCTTCTCCATGGTGGTGAAGAC-3' (SEQ ID NO:107). PCR conditions for AMACR and GAPDH were: heat denaturation at 94° C. for 5 min, cycles of 94° C. for 1 min, 60° C. for 1 min, and 72° C. for 1 min (32 cycles for GAPDH, 40 cycles for AMACR), and a final extension step at 72° C. for 5 min PCR products were then separated on 2% agarose gel and visualized by UV illumination.

E. Results

Using the Virtual Northern tool from the online CGAP program, AMACR expression was surveyed in two databases, EST and SAGE libraries. AMACR was found to be expressed in a wide range of tissues, including central and peripheral nervous system, colon, kidney, breast, pancreas, prostate and blood. Compared to their normal counterparts, a number of cancers have elevated AMACR expression, including tumors arising in bone marrow, breast, colon, genitourinary system, lung, lymph node, nervous system, pancreas, prostate, soft tissue and uterus.

Figure 18:
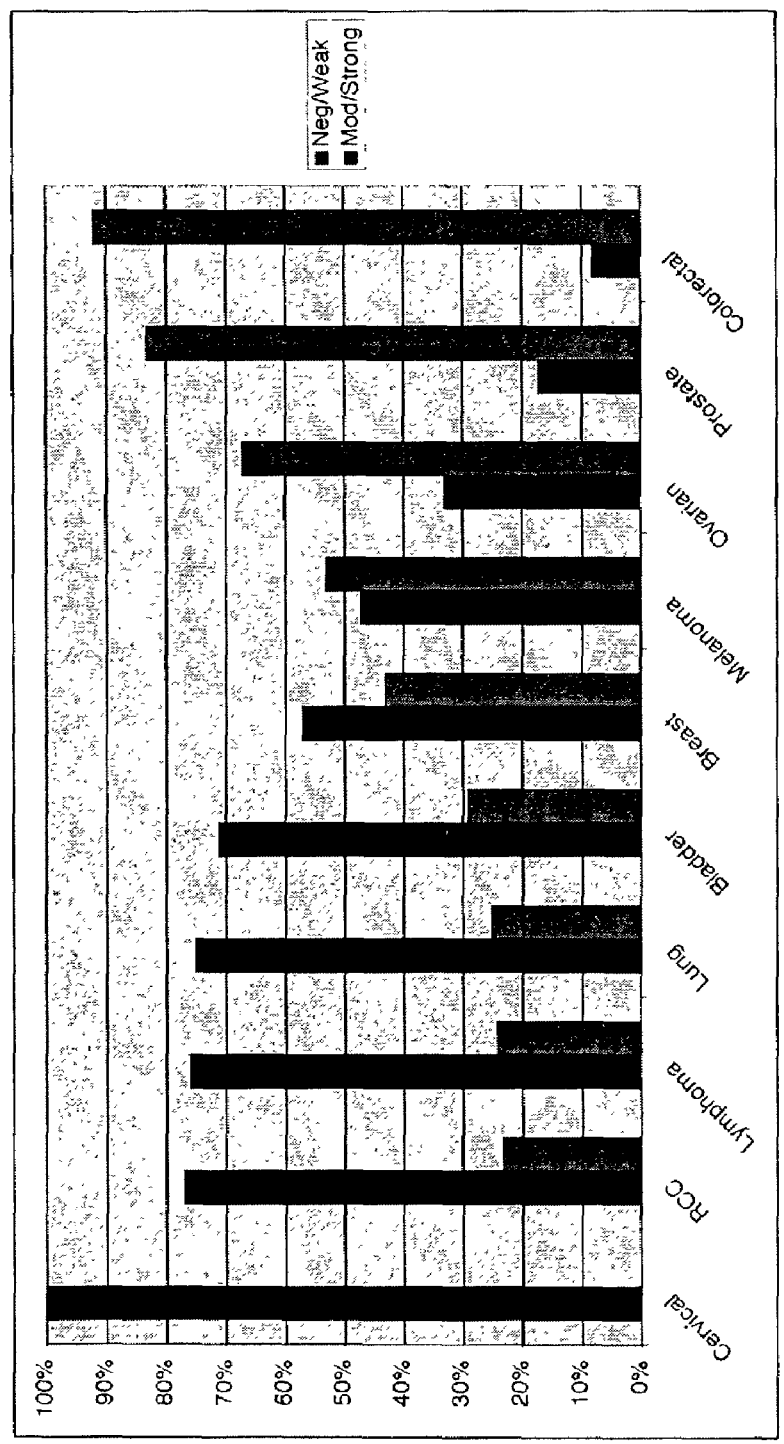
FIG. 18 shows AMACR over-expression in multiple tumors. AMACR protein expression was evaluated by immunohistochemistry on a multi-tumor and a breast cancer tissue microarray. Percentage of cases with positive staining (moderate and strong staining intensity) is summarized on the Y-axis. The left bar represents negative or weak staining and the right bar represents moderate or strong staining.

To confirm the gene expression data, AMACR immunohistochemistry was performed on a multi-tumor tissue array that included some of the most common cancers from multiple sites. AMACR protein level was increased in many cancers, including colorectal, prostate, ovarian, lung cancers, lymphoma and melanoma (FIG. 18). In particular, AMACR over-expression was observed in 92% and 83% of colorectal and prostate cancer, respectively. Using a breast cancer tissue microarray, it was found that AMACR overexpression was present in 44% of invasive ductal carcinomas. AMACR over expression was not observed in female cervical squamous cell carcinoma (6 cases).

Figure 19:
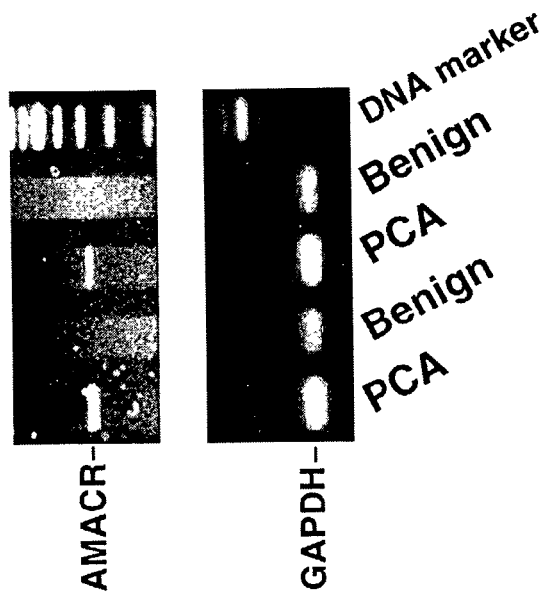
FIG. 19 shows the results of laser capture microdissection (LCM) and RT-PCR amplification of AMACR in prostate cancer. LCM was used to isolate pure prostate cancer and benign glands and AMACR gene expression was characterized by RT-PCR in 2 radical prostatectomies. A constitutively expressed gene, GAPDH, was used as quantitative control of input mRNA. AMACR expression is barely detectable in benign glands, and is elevated in prostate cancer.

To further characterize AMACR expression in a spectrum of proliferative prostate lesions, a prostate tissue microarray, which included prostate cancer, high grade PIN and atrophic glands, was utilized. Positive AMACR staining (moderate and strong staining) was observed in 83% and 64% of clinically localized prostate cancer and high-grade PIN, respectively. Focal AMACR expression was observed in 36% of the atrophic lesions and in rare morphologically benign glands. To confirm that AMACR protein over-expression was the result of increased gene transcription, laser capture microdissection was used to isolate cancerous and benign prostatic glands. RT-PCR was performed to assess the AMACR mRNA expression. Benign glands had very low baseline expression (FIG. 19). In contrast, prostate cancer had much higher mRNA level, confirming that increased AMACR gene transcription leads to elevated protein over expression in prostate cancer.

AMACR expression was studied in 24 colorectal adenocarcinomas, including 16 well to moderately differentiated, and 8 poorly differentiated large cell adenocarcinomas. Overall, 83% (20/24) demonstrated positive AMACR protein expression. All (16/16, 100%) cases of well to moderately differentiated carcinoma had positive staining, compared to 64% (5/8) of poorly differentiated carcinoma. AMACR expression was examined in 8 colorectal adenoma biopsies obtained by colonoscopy. Moderate staining was present in 6 (75%) cases. Compared with well-differentiated adenocarcinomas, adenomas usually showed more focal (10–60% of cells) and less intense staining.

EXAMPLE 8

Characterization of EZH2 Expression in Prostate Cancer

A. SAM Analysis

SAM analysis was performed by comparing gene expression profiles of 7 metastatic prostate cancer samples against 10 clinically localized prostate cancer samples. Data was normalized per array by multiplication by a factor to adjust the aggregate ratio of medians to one, then log base 2 transformed and median centered. This normalized data was divided into two groups for comparison using a two-class, unpaired t-test. Critical values for the analysis include: Iterations=500, Random Number Seed 1234567, a fold change cutoff of 1.5 and a delta cutoff of 0.985, resulting in a final largest median False Discovery Rate of 0.898% for the 535 genes selected as significant (55 relatively up and 480 relatively down regulated between MET and PCA). These 535 genes were analyzed using Cluster (Eisen et al., PNAS 95:14863 [1998]) implementing average linkage hierarchical clustering of genes. The output was visualized by Treeview (Eisen et al., [1998], supra).

B. RT-PCR

Reverse transcription and PCR amplification were performed with 1 µg total RNA isolated from the indicated prostate tissues and cell lines. Human EZH2 forward (5'-GCCAGACTGGGAAGAAATCTG-3' (SEQ ID NO:108)), reverse (5'-TGTGCTGGAAAATCCAAGTCA-3' (SEQ ID NO:109)) and GAPDH sense (5'-CGGAGTCAACG-GATTTGGTCGTAT-3' (SEQ ID NO:110)), antisense 5'-AGCCTTCTCCATGGTGGTGAAGAC-3' (SEQ ID NO:111)) primers were used. The amplified DNA was resolved on agarose gels and visualized with ethidium bromide.

C. Immunoblot Analysis

Prostate tissue extracts were separated by SDS-PAGE and blotted onto nitrocellulose membranes. Anti-EZH2 (Sewalt et al., Mol. Cell. Biol. 18:3586 [1998]), anti-EED (Sewalt et al., supra), and polyclonal anti-tubulin (Santa Cruz biotechnology) antibodies were used at 1:1000 dilution for immunoblot analysis. The primary antibodies were detected using horseradish peroxidase-conjugated secondary antibodies and visualized by enhanced chemiluminescence as described by the manufacturer (Amersham-Pharmacia).

D. Tissue Microarray Analysis

Clinically stratified prostate cancer tissue microarrays used in this study have been described previously (See above examples). Tissues utilized were from the radical prostatectomy series at the University of Michigan and from the Rapid Autopsy Program, which are both part of University of Michigan Prostate Cancer Specialized Program of Research Excellence (S.P.O.R.E.) Tissue Core. Institutional Review Board approval was obtained to procure and analyze the tissues used in this study.

EZH-2 protein expression was evaluated on a wide range of prostate tissue to determine the intensity and extent in situ. Immunohistochemistry was performed on three tissue microarrays (TMA) containing samples of benign prostate, prostatic atrophy, high-grade prostatic intraepithelial neoplasia (PIN), clinically localized prostate cancer (PCA), and metastatic hormone refractory prostate cancer (HR-METSs). Standard biotin-avidin complex immunohistochemistry (IHC) was performed to evaluate EZH2 protein expression using a polyclonal anti-EZH2 antibody. Protein expression was scored as negative (score=1), weak (score 2), moderate (3) and strong (4).

Approximately 700 TMA samples (0.6 mm diameter) were evaluated for this study (3–4 tissue cores per case). The TMAs were assembled using a manual tissue arrayer (Beecher Instruments, Silver Spring, Md.) as previously described (See above examples). Four replicate tissue cores were sampled from each of the selected tissue types. After construction, 4 µm sections were cut and hematoxylin and eosin staining was performed on the initial slide to verify the histologic diagnosis. TMA hematoxylin and eosin images were acquired using the BLISS Imaging System (Bacus Lab, Lombard, Ill.). EZH2 protein expression was evaluated in a blinded manner by the study pathologist using a validated web-based tool (Manley et al., Am. J. Pathol. 159:837 [2001]; Bova et al., Hum. Pathol. 32:417 [2001]) and the median value of all measurements from a single patient were used for subsequent analysis.

E. Clinical Outcomes Analysis

To assess individual variables for risk of recurrence, Kaplan-Meier survival analysis was performed and a univariate Cox proportional hazards model was generated. PSA-recurrence was defined as 0.2 ng/ml following radical prostatectomy. Covariates included Gleason sum, preoperative PSA, maximum tumor dimension, tumor stage, and surgical margin status. To assess the influence of several variables simultaneously including EZH2 protein expression, a final multivariate Cox proportional hazards model of statistically significant covariates was generated. Statistical significance in univariate and multivariate Cox models were determined by Wald's test. A p-value <0.05 was considered statistically significant.

F. EZH2 Constructs

Myc-tagged EZH2-pCMV was used. The Myc-EZH2 fragment was released with BamHI/XhoI double digest and was sub-cloned into the mammalian expression vector pCDNA3 (Invitrogen). An EZH2-ER in-frame fusion expression construct was generated by replacing the FADD fragment released by Kpn I/Not I double digest of the FADD-ER construct (originally derived from Myc-ER (Littlewood et al., Nuc. Acids. Res. 23:1686 [1995]) with the PCR amplified human EZH2 devoid of its stop codon. The EZH2 .SET mutant DNA was amplified using the primers 5'GGGGTACCATGGGCGGCCGCGAA-CAAAAGTTGATT 3' (SEQ ID NO:112) and 5'GGGGAAT-TCTCATGCCAGCAATAGATGCTTTTT3' (SEQ ID NO:113) and subsequently sub-cloned into pCDNA3 utilizing the in built KpnI/EcoRI sites. Expression of these constructs was verified by immunoblot analysis of the expressed proteins using either anti-Myc HRP (Roche, Inc) or anti-EZH2 antibodies.

G. RNA Interference 21-nucleotide sense and antisense RNA oligonucleotides were chemically synthesized (Dharmacon Research Inc.) and annealed to form duplexes. The siRNA employed in the study were targeted to the region corresponding from 85 to 106 of the reported human EZH2 (NM004456). Control siRNA duplexes targeted luciferase, lamin and AMACR (NM014324). The human transformed prostate cell line RWPE (Webber et al., Carcinogenesis 18:1225 [1997]) and PC3 were plated at $2\times10^5$ cells per well in a 12 well plate (for immunoblot analysis, cell counts, and fluorescence activated cell sorting (FACS) analysis) and $1.5\times10^4$ cell per well in a 96 well plate (for WST-1 proliferation assays). Twelve hours after plating, the cells were transfected with 60 picomoles of siRNA duplex, sense or antisense oligonucleotides (targeting EZH2) using oligofectamine (Invitrogen). A second identical transfection was performed 24 hours later. Forty-eight hours after the first transfection, the cells were lysed for immunoblot analysis and trypsinized for cell number estimation or FACS analysis. Cell viability was assessed 60 hours after the initial transfection.

H. Cell Proliferation Assays

Cell proliferation was determined with the colorimetric assay of cell viability, based on the cleavage of tetrazolium salt WST-1 by mitochondrial dehydrogenases as per manufacturers instructions (Roche, Inc.). The absorbance of the formazan dye formed, which directly correlates with the number of metabolically active cells in the culture, was measured at 450 nm (Bio-Tek instruments), an hour after the addition of the reagent. Cell counts were estimated by trypsinizing cells and analysis by coulter cell counter.

I. Flow Cytometric Analysis

Trypsinized cells were washed with phosphate buffered saline (PBS) and cell number was determined by using a coulter cell counter. For FACS analysis, the washed cells were fixed in 70% ethanol overnight. Before staining with propidium iodide, the cells were washed again with PBS and analyzed by flow cytometry (Becton Dickinson).

J. Microarray Analysis of EZH2 Transfected Cells

Initial testing of this transient transfection/transcriptome analysis system demonstrated that transient overexpression of TNFR1 (p55), a receptor for tumor necrosis factor, induced similar expression profiles as was observed with incubation of cells with TNF (Kumar-Smith et al., J. Biol. Chem. 24:24 [2001]). Other molecules have been similarly tested with this approach. Cells were transfected with different EZH2 constructs and transfection efficiency was monitored by beta-galactosidase assay and was approximately 30–50%. EZH2 .SET mutant expressing samples were compared to EZH2 expressing samples using the SAM analysis package (Tusher et al., PNAS 98:5116 [2001]). Data was pre-processed by multiplication by a normalization factor to adjust the aggregate ratio of medians to one, log base 2 transformed and median centered each array, individually. This pre-processed data was divided into 2 groups for comparison using a two-class, unpaired t-test. Critical values for the analysis include: iterations=5000, (720 at convergence) random Number Seed 1234567, a fold change of 1.5 and a delta cutoff of 0.45205, resulting in a final largest median False Discovery Rate of 0.45% for the 161 genes selected as significant. These 161 genes were supplemented by the values for EZH2 and then analyzed using Cluster implementing average linkage hierarchical clustering of genes. The output was visualized in Treeview. Selected genes identified as being repressed by EZH2 (e.g., EPC and cdc27) were re-sequenced to confirm identity.

The molecular identity of a cell is determined by the genes it expresses (and represses). Embryogenesis and cell differentiation intimately depend upon keeping certain genes "on" and other genes "off". When the transcriptional "memory" of a cell is perturbed this can lead to severe developmental defects (Jacobs et al., Semin. Cell Dev. Biol. 10:227 [1999]; Francis et al., Nat. Rev. Mol. Cell. Biol. 2:409 [2001]). Lack of differentiation, or anaplasia, is a hallmark of cancer, which results from normal cells "forgetting" their cellular identity. Thus, it is not surprising that dysregulation of the transcriptional maintenance system can lead to malignancy (Francis et al., supra; Jabobs et al., Nature 397:164 [1999]; Beuchle et al., Development 128:993 [2001]).

Studies in *Drosophila melanogaster* have been instrumental in the understanding of the proteins involved in transcriptional maintenance (Beuchle et al., [[2001], supra; Strutt et al., Mol. Cell. Biol. 17:6773 [1997]; Tie et al., Development 128:275 [2001]). Two groups of proteins have been implicated in the maintenance of homeotic gene expression and include polycomb (PcG) and trithorax (trxG) group proteins (Mahmoudi et al., Oncogene 20:3055 [2001]; Lajeunesse et al., Development 122:2189 [1996]). PcG proteins act in large complexes and are thought to repress gene expression, while trxG proteins are operationally defined as antagonists of PcG proteins and thus activate gene expression (Francis et al., Nat. Rev. Mol. Cell. Biol. 2:409 [2001]; Mahmoudi et al., supra). There are at least twenty PcG and trxG proteins in *Drosophila*, and many have mammalian counterparts. In human malignancies, PcG and trxG proteins have primarily been found to be dysregulated in cells of hematopoietic origin (Yu et al., Nature 378:505 [1995]; Raaphorst et al., Am. J. Pathol., 157:709 [2000]; van Lohuizzen et al., Cell 65:737 [1991]). EZH2 is the human homolog of the *Drosophila* protein Enhancer of Zeste (E(z)) ((Laible et al., Embo. J. 16:3219 [1997]), for which genetic data defines as a PcG protein with additional trxG properties (LaJeunesse et al., supra). E(z) and EZH2 share homology in four regions including domain I, domain II, a cysteine-rich amino acid stretch, and a C-terminal SET domain (Laible et al., supra). The SET domain is a highly conserved domain found in chromatin-associated regulators of gene expression often modulating cell growth pathways (Jenuwein et al., Cell. Mol. Life Sci. 54:80 [1998]). EZH2 is thought to function in a PcG protein complex made up of EED, YY1 and HDAC2 (Satijn et al., Biochim. Biophys. Acta. 1447:1 [1999]). Disruption of the EZH2 gene in mice causes embryonic lethality suggesting a crucial role in development (O'Carroll et al., Mol. Cell. Biol. 21:4330 [2001]).

Figure 20:
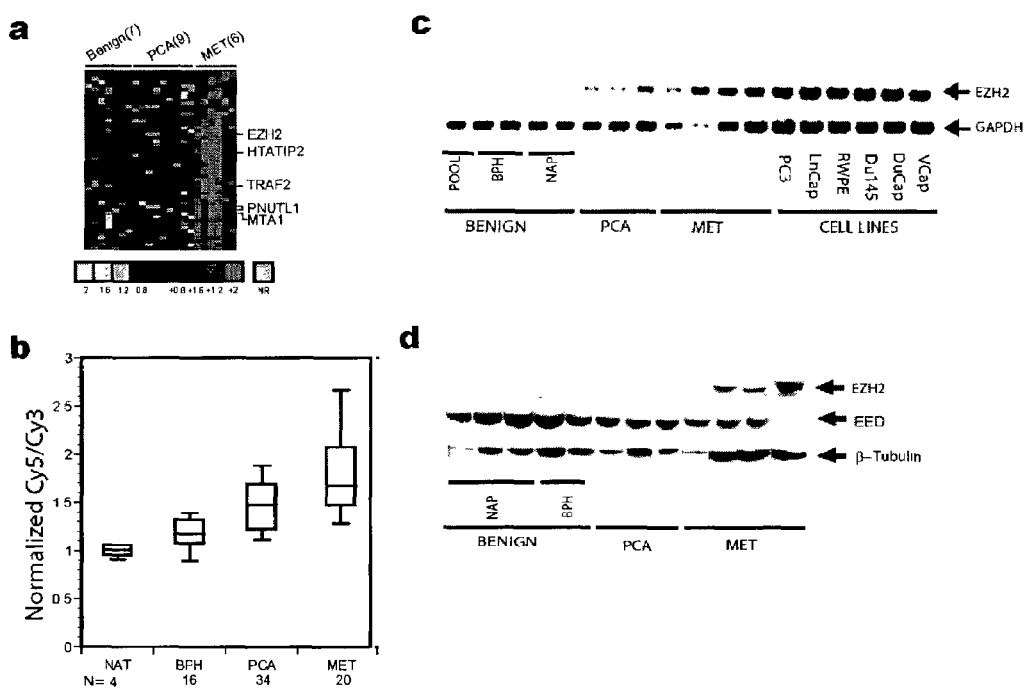
FIG. 20 describes the identification and validation of EZH2 over-expression in metastatic prostate cancer.

In previous studies (See e.g., Example 1), the gene at the top of the "list" of genes significantly up-regulated in metastatic prostate cancer was EZH2, which had a d-score (Tusher et al. PNAS 98:5116 [2001]) of 4.58 and a gene-specific FDR of 0.0012 (also called a "q-value" which is analogous to p-values, but adapted to multiple inference scenarios. FIG. 20a displays the 55 up-regulated genes identified by this approach. FIG. 20b summarizes the gene expression of EZH2 in 74 prostate tissue specimens analyzed on DNA microarrays made up of 10 K elements. The EZH2 transcript was significantly increased in metastatic prostate cancer with respect to clinically localized prostate cancer (Mann-Whitney test, p=0.001) and benign prostate (p=0.0001).

As independent experimental validation of DNA microarray results, RT-PCR was performed on 18 prostate samples and cell lines. As expected, EZH2 mRNA transcript levels were elevated in malignant prostate samples relative to benign (FIG. 20c). To determine whether EZH2 is up-regulated at the protein level in metastatic prostate cancer, tissue extracts were examined by immunoblotting. In the samples examined by immunoblot analysis, EZH2 protein was markedly elevated in metastatic prostate cancer relative to localized prostate cancer or benign prostate (FIG. 20d).

Figure 21:
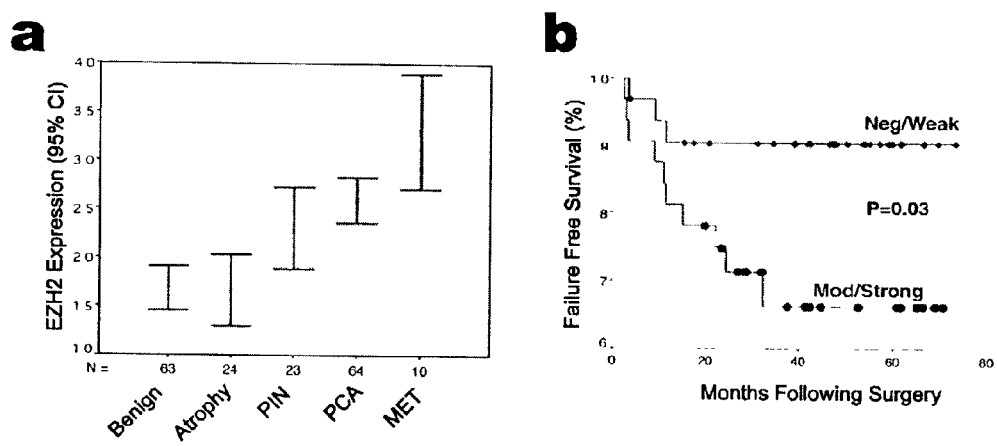
FIG. 21 shows that EZH2 protein levels correlate with the lethal progression and aggressiveness of prostate cancer.

Importantly, EED, a PcG protein that forms a complex with EZH2 (vanLohuizen et al., supra; Sewalt et al., supra), along with an un-related protein, β-tubulin, did not exhibit similar protein dysregulation. EZH2 protein expression was evaluated on a wide range of prostate tissues (over 700 tissue microarray elements) to determine the intensity and extent of expression in situ (FIGS. 21a,b). When highly expressed, EZH2 expression was primarily observed in the nucleus as suggested previously (Raaphorst et al., supra). The staining intensity was increased from benign, prostatic atrophy, prostatic intraepithelial neoplasia (PIN), to clinically localized prostate cancer with median staining intensity of 1.7 (standard error [SE], 0.1; 95% confidence interval [CI], 1.5–1.9), 1.7 (SE, 0.2; 95% CI, 1.3–2.0), 2.3 (SE, 0.2.; 95% CI, 1.9–2.7), and 2.6 (SE, 0.1; 95% CI, 2.4–2.8), respectively (FIG. 24b). The strongest EZH2 protein expression was observed in hormone-refractory metastatic prostate cancer with a median staining intensity of 3.3 (SE, 0.3; 95% CI, 2.7–3.9). There was a statistically significant difference in EZH2 staining intensity between benign prostate tissue and localized prostate cancer (ANOVA post-hoc analysis mean difference 0.9, p<0.0001). Although metastatic prostate cancer had a higher mean expression level than localized prostate cancer, the difference did not reach statistical significance (ANOVA post-hoc analysis mean difference 0.7, p=0.3). These findings suggest that as prostate neoplasia progresses there was a trend towards increased EZH2 protein expression, mimicking that seen by DNA expression array analysis. The present invention is not limited to a particular mechanism. Indeed, an understanding of the mechanism is not necessary to practice the present invention. Nonetheless, it is contemplated that this observation suggests that EZH2 levels may indicate how aggressive an individual's prostate cancer is given that the highest level of expression was observed in hormone-refractory, metastatic prostate cancer. Therefore, to test this hypothesis, the utility of EZH2 protein levels to predict clinical outcome in men treated with surgery for clinically localized prostate cancer was examined.

Two hundred and twenty-five (225) specimens from sixty-four patients (3–4 replicate samples per patient) with clinical follow up were interrogated on a single tissue microarray. These men had a median age of 61 years (range 43–76 years) and a 7.3 ng/ml median pre-operative serum prostate specific antigen (PSA) (range 0.8–21.0 ng/ml). Pathologic examination of their prostatectomy specimens indicated that 77% had organ-confined disease (pT2 stage) and 72% had negative surgical margins. The patient demographics and tumor stages were representative of the over 1500 radical prostatectomy patients. In order to test the utility of EZH2 as a potential tissue biomarker for prostate cancer, the clinical outcome of these 64 cases was examined, taking into account clinical and pathological parameters. Clinical failure was defined as either a 0.2 ng/ml PSA elevation or disease recurrence following prostatectomy (e.g., development of metastatic disease). By Kaplan-Meier analysis (FIG. 21c), EZH2 staining intensity of 3 and greater was significantly associated with clinical failure in 31% (10/32) of patients in contrast to 9% (3/32) of patients with an EZH2 protein levels below 3 (log rank p=0.03). There was no significant correlation between EZH2 levels and Gleason score (<7 versus=7), tumor stage (pT2 versus pT3), or surgical margin status (negative versus positive). There was a significant (p=0.048) albeit weak (Pearson coefficient=0.33) correlation between EZH2 protein levels and proliferation index in situ as assessed by Ki-67 labeling index. Multivariable Cox-Hazards regression analysis revealed that EZH2 protein expression (=3 versus <3) was the best predictor of clinical outcome with a recurrence ratio of 4.6 (95% CI 1.2–17.1, p=0.02), which was significantly better than surgical margin status, maximum tumor dimension, Gleason score, and pre-operative PSA. Thus, monitoring EZH2 protein levels in prostate specimens may provide additional prognostic information not discernible with current clinical and pathology parameters alone.

Figure 22:
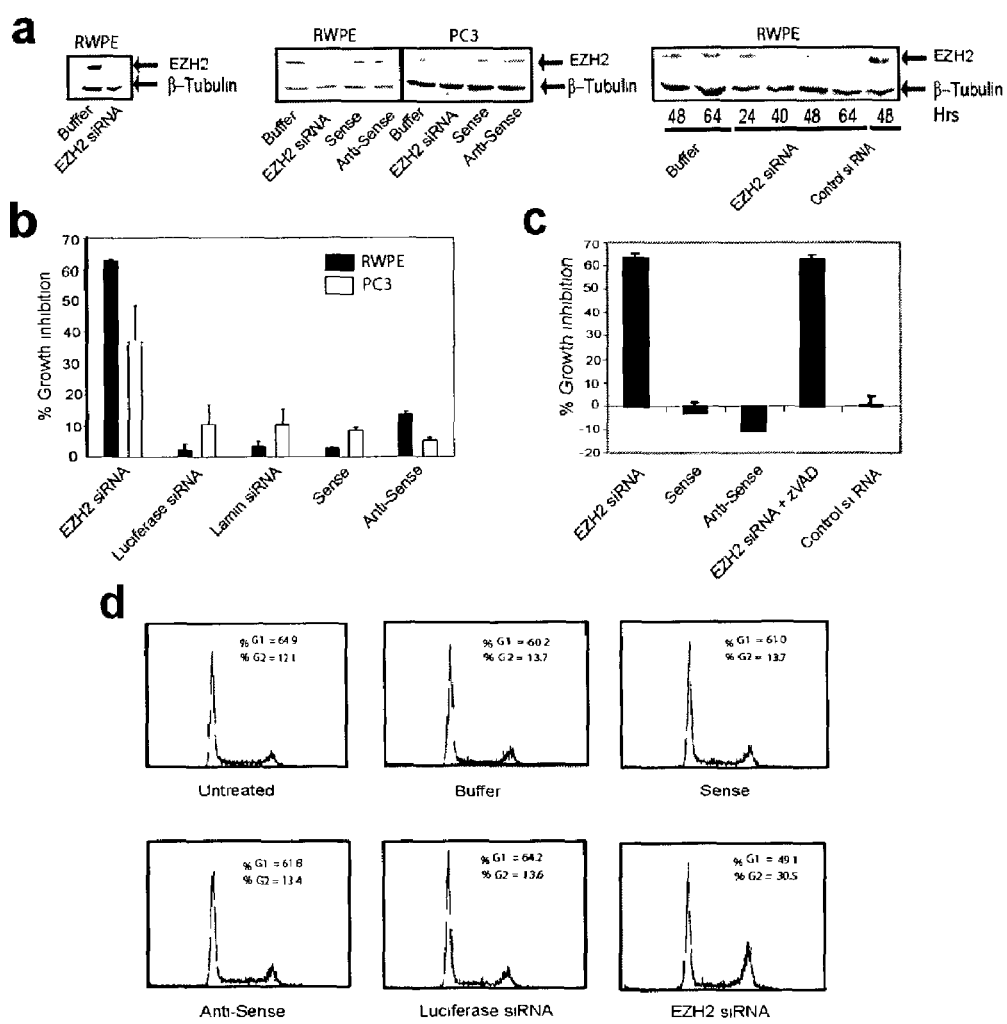
FIG. 22 shows the role of EZH2 in prostate cell proliferation.

To shed light into the functional role of EZH2 in prostate cancer progression, EZH2 expression in transformed prostate cells in vitro was disrupted using RNA interference. T. Tuschl and colleagues recently reported that duplexes of 21-nucleotide RNA (siRNAs) mediate RNA interference in cultured mammalian cells in a gene-specific fashion (Elbashir et al., Nature 411:494 [2001]). RNA interference has been used effectively in insect cell lines to "knock-down" the expression of specific proteins, owing to sequence-specific, double stranded-RNA mediated RNA degradation (Hammond et al., Nature 404:293 [2000]). siRNAs are potent mediators of gene silencing, several orders of magnitude more potent than conventional antisense or ribozyme approaches (Macejak et al., Hepatology 31:769 [2000]). Thus, a 21-nucleotide stretch of the EZH2 molecule was targeted using criteria provided by Elbashir et al. (supra), and RNA oligonucleotides were synthesized commercially. After the RNA oligos were annealed to form siRNA duplexes, they were tested on the transformed androgen-responsive prostate cell line RWPE (Webber et al., Carcinogenesis 18:1225 [1997]; Bello et al., Carcinogenesis 18:1215 [1997]) as well as the metastatic prostate cancer cell line PC3. Forty-eight hours after transfection with siRNA duplexes, the levels of endogenous EZH2 protein were quntitated. When EZH2 protein was specifically down-regulated in prostate cell lines, the levels of the un-related control protein, β-tubulin, remained unchanged (FIG. 22a). The sense or anti-sense oligonucleotides comprising the EZH2 duplex, as well as un-related siRNA duplexes, did not affect EZH2 protein levels (FIG. 22a, middle and right panels), verifying the specificity of the siRNA approach in both prostate cell lines.

The phenotype of EZH2 "knock-down" prostate cells was next examined. By phase contrast microscopy, it was observed that siRNA directed against EZH2 markedly inhibited cell number/confluency relative to buffer control. Cell counts taken 48 hrs after transfection with siRNA showed a 62% inhibition of RWPE cell growth mediated by the EZH2 siRNA duplex, which is in contrast to the corresponding sense and anti-sense EZH2 oligonucleotides or control duplexes (targeting luciferase and lamin) which exhibited minimal inhibition (FIG. 22b). The prostate cancer cell line, PC3, demonstrated a similar growth inhibition mediated by EZH2 siRNA, suggesting that the findings are not a peculiarity of the RWPE cell line (FIG. 22b). Using a commercially available cell proliferation reagent WST-1, which measures mitochondrial dehydrogenase activity, a decrease in cell proliferation mediated by the EZH2 siRNA duplex, but not by un-related duplexes, was observed (FIG. 22c). In the time frame considered (48 hrs), RNA interference of EZH2 did not induce apoptosis as assessed by propidium idodide staining of nuclei or PARP cleavage. Consistent with this, the broad-spectrum caspase inhibitor, z-VAD-fmk, failed to attenuate EZH2 siRNA induced inhibition of cell proliferation (FIG. 22c). Thus, activation of the apoptosis pathway does not account for the decreases in cell number observed by RNA interference of EZH2.

Various PcG Group proteins have been suggested to play a role in cell cycle progression (Jacobs et al., Nature 397:164 [1999]; Visser et al., Br. J. Hematol. 112:950 [2001]; Borck et al. Curr. Opin. Genet. Dev. 11:175 [2001]). Flow cytometric analysis of EZH2 siRNA-treated prostate cells demonstrated cell cycle arrest in the G2/M phase (FIG. 22d). Un-related control siRNA duplexes failed to induce a similar cell cycle dysregulation. Few apoptotic cells (sub-G1 cells) were present in any of the experimental samples tested as assessed by flow cytometry (FIG. 22d). The present invention is not limited to a particular mechanism. Indeed, an understanding of the mechanism is not necessary to practice the present invention. Nonetheless, it is contemplated that these observations suggest that EZH2 plays a role in prostate cell proliferation by mitigating the G2/M transition.

To further understand the functional role of EZH2 in prostate cells, an epitope-tagged version of wild-type EZH2 and a deletion mutant of EZH2 missing the conserved SET domain in the eukaryotic expression vector pcDNA3 were generated (FIG. 23a). An "inducible"-version of EZH2 was also generated by creating a fusion protein with a modified murine estrogen receptor (ER) (FIG. 26a) (Littlewood et al., Nuc. Acid. Res. 23:1686 [1995]; Juin et al., Genes Dev. 13:1367 [1999]). EZH2-ER fusion was expressed in cells (FIG. 26b) and is inactivated, presumably by sequestration/ binding to hsp90 and other proteins (Littlewood et al., supra). Upon treatment of cells with 4-hydroxytamoxifen, hsp90 dissociates from the ER fusion and liberates its activity. Expression of the epitope-tagged EZH2 constructs was confirmed by transfection in 293 (FIG. 23b), RWPE and in other mammalian cell lines.

PcG proteins have been proposed to mediate their functions by repression of target genes (Laible et al., supra; Jacobs et al., Semin Cell Dev. Biol. 10:227 [1999]). To begin to test this hypothesis, RWPE prostate cells were transiently transfected with wild-type EZH2 and global gene expression alterations were monitored using DNA microarrays. While RNA from the experimental (transfected) cell line was labeled with one fluorescent dye, the paired reference sample was labeled with a second distinguishable fluorescent dye. By making direct comparisons between "gene"-transfected cell lines and control vector-transfected cell lines the molecular differences between the samples were observed. When EZH2 was over-expressed in RWPE cells or SUM149 breast carcinoma cells, there was a consistent repression of a cohort of genes (FIGS. 23c, d). This exclusive repression of genes was unique compared to other molecules tested in this system including c-myc and TNFR1, among others. When compared to vector-transfected cells the only gene that was significantly up-regulated in EZH2-transfected cells was EZH2 itself (FIG. 23c).

EZH2-mediated transcriptional repression was dependent on an intact SET domain (FIG. 23c), as deletion of this domain did not produce a repressive phenotype and in some cases "de-repressed" genes. EZH2 has been shown to interact with histone deacetylase 2 (HDAC2) via the EED protein (van der Vlag et al., Nat. Genet. 23:474 [1999]). In the experiments described above, EZH2-mediated gene silencing was dependent on HDAC activity, as the commonly used HDAC inhibitor, trichostatin A (TSA) completely abrogated the effects of EZH2 (FIG. 23c). Thus, EZH2 function requires both an intact SET domain as well as endogenous HDAC activity.

To identify genes that are significantly repressed by EZH2, wild-type EZH2-transfected cells were compared with EZH2 .SET-transfected cells. Using this approach, 163 genes were consistently repressed while no genes were activated at an FDR of 0.0045 (FIG. 23d). Examination of the significant gene list identified the PcG group protein EPC, which is the human homolog of the *drosophila* protein Enhancer of Polycomb (E(Pc)) as being consistently repressed by EZH2 (FIG. 23c). Of the *Drosophila* PcG proteins, E(Pc) and E(z) are related in that they both act as suppressors of variegation (Su(var)) (Sinclair et al., Genetics 148:211 [1998]) and are the only PcG proteins to have yeast homologs, emphasizing the evolutionary conservation of this PcG pair. In addition to EPC, a host of other transcriptional regulators/activators were transcriptionally silenced by EZH2 including MDNA, RNF5, RNF15, ZNF42, ZNF262, ZNFN1A1, RBM5, SPIB, and FOXF2, among others (FIG. 23c). MDNA, also known as myeloid cell nuclear differentiation antigen, mediates transcriptional repression by interacting with the transcription factor YY1, which is a PcG homolog of *Drosophila* Pho and shown to be part of the EZH2/EED complex of proteins (Satijin et al., Mol. Cell. Biol. 21:1360 [2001]).

Figure 23:
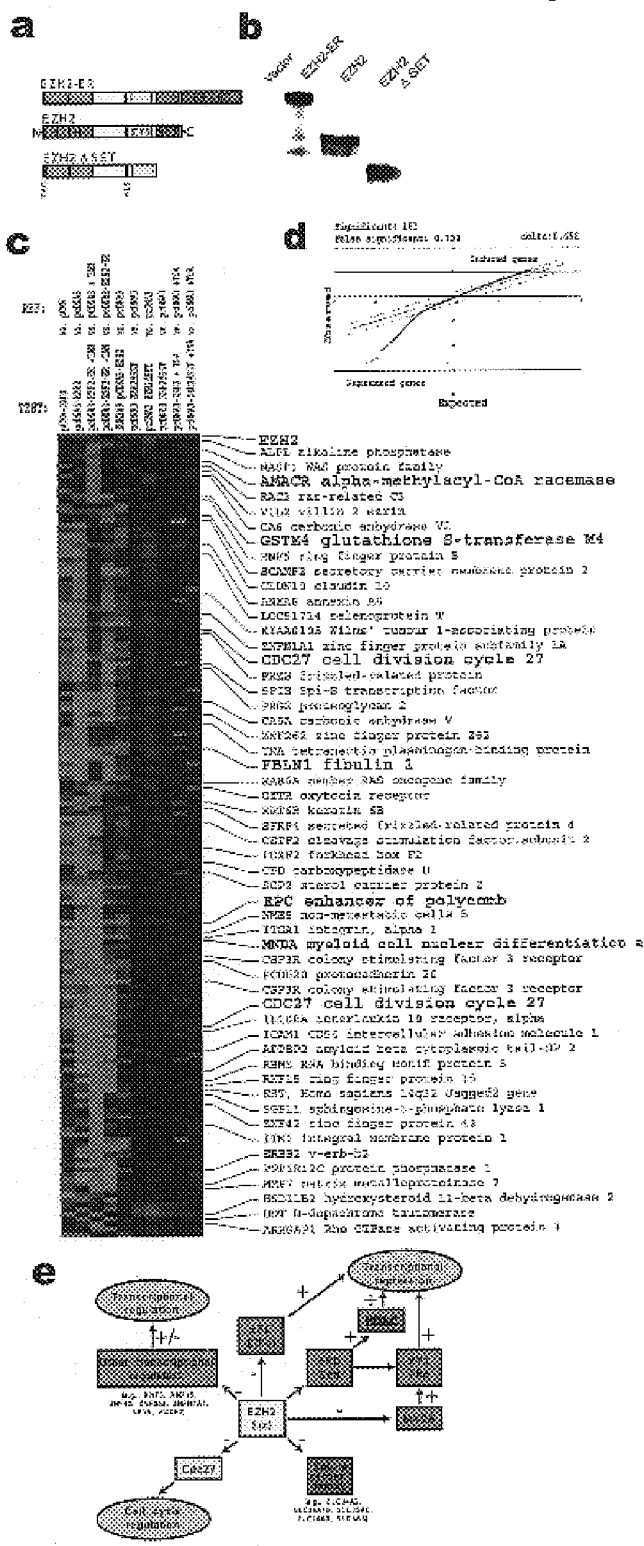
FIG. 23 shows that EZH2 functions as a transcriptional repressor in prostate cells.

In addition to transcriptional repression in prostate cells, the results also support a role for EZH2 in regulating cell growth (FIG. 23). Transcriptional repression of cdc27 (two independent Unigene clones) was also observed. Cdc27 is part of the anaphase-promoting complex (APC) which mediates ubiquitination of cyclin B1, resulting in cyclinB/cdk complex degradation (Jorgensen et al., Mol. Cell. Biol. 18:468 [1998]). Another family of proteins that was repressed when EZH2 was targeted was the solute carriers. At least 5 distinct members were shown to be repressed (i.e., SSLC34A2, SLC25A16, SLC25A6, SLC16A2, and SLC4A3).

EXAMPLE 9

Expression of AMACR in Serum and Urine

Figure 24:
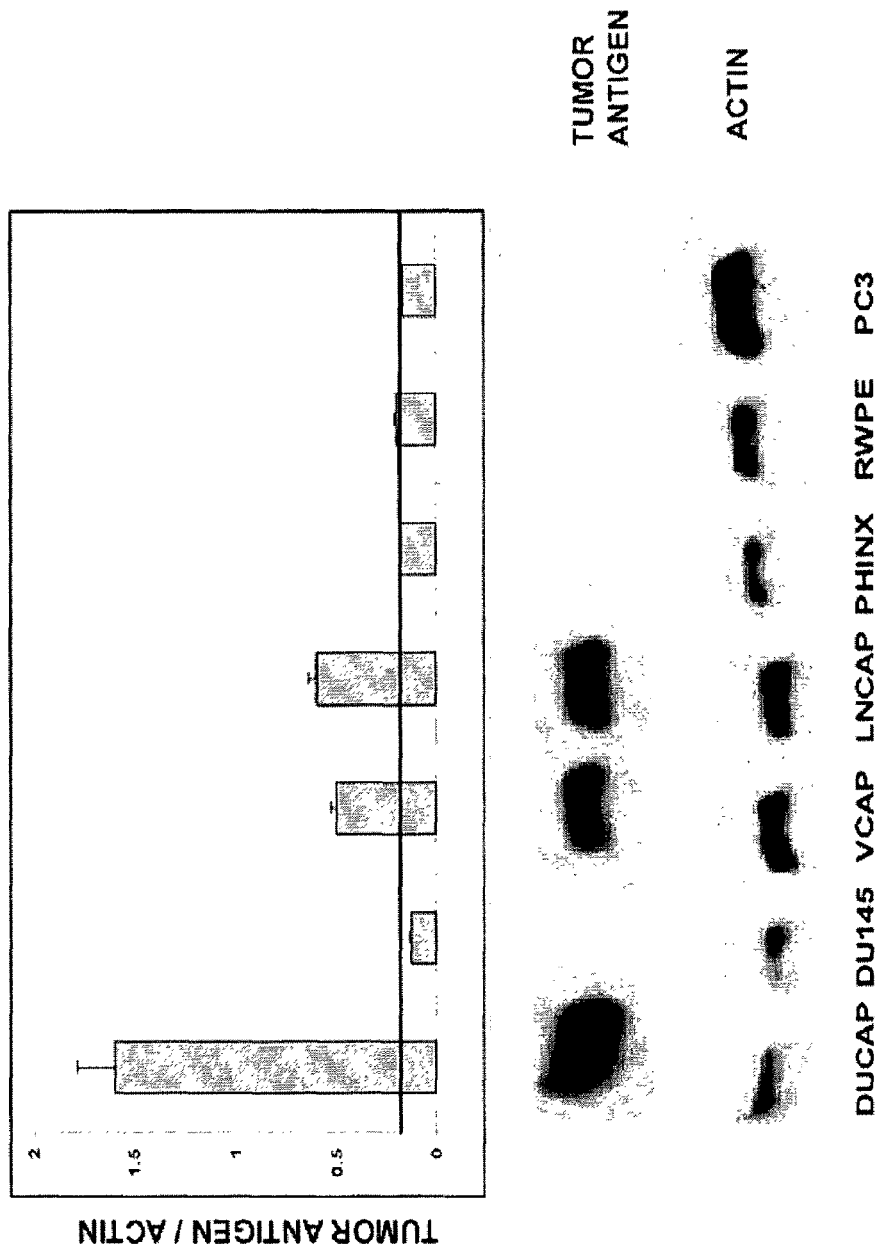
FIG. 24 shows the detection of AMACR in PCA cell lines.

This example describes the expression of AMACR in serum and urine. AMACR was detected by standard immunoblotting and by protein microarray using a polyclonal rabbit anti-AMACR antibody. The results are shown in FIGS. 24–27. FIG. 24 shows the detection of AMACR protein in PCA cell lines by quantitation of microarray data. DUCAP, DU145, and VCAP are prostate cancer cell lines. RWPE is a benign prostate cell line. PHINX is a human embryonic kidney cell line.

Figure 25:
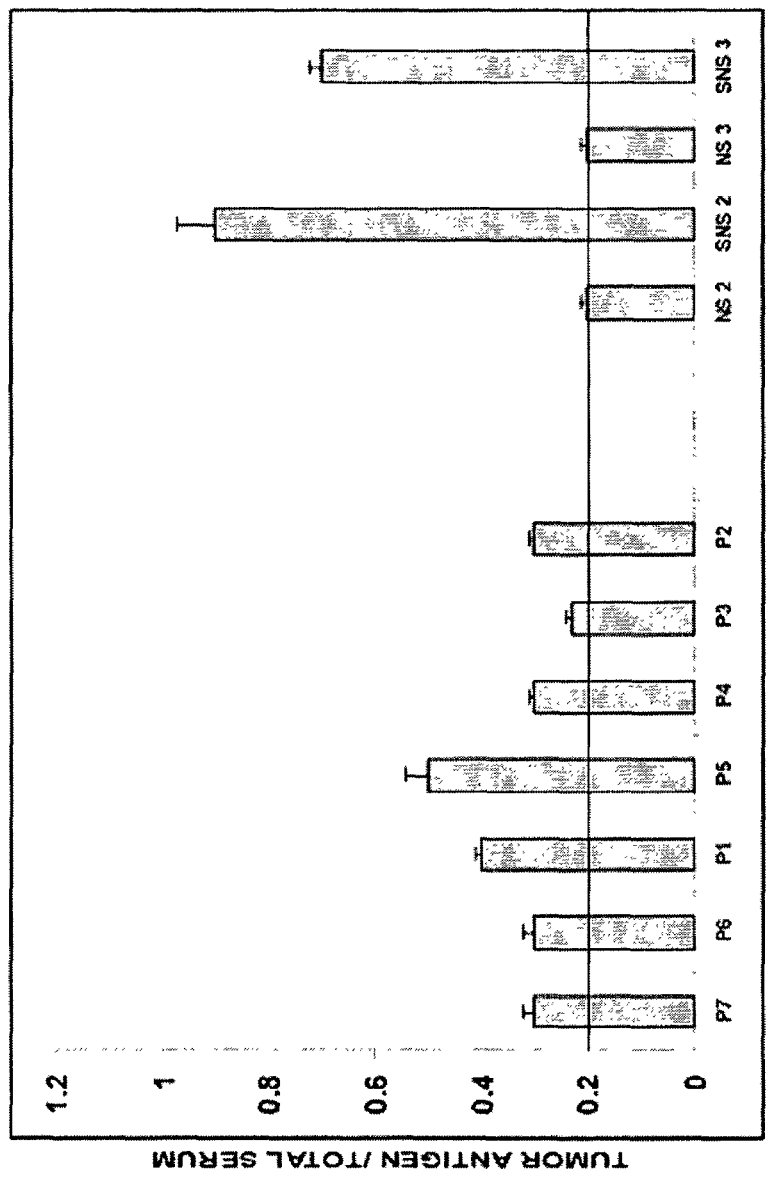
FIG. 25 shows the detection of AMACR protein in serum by quantitation of microarray data.
Figure 26:
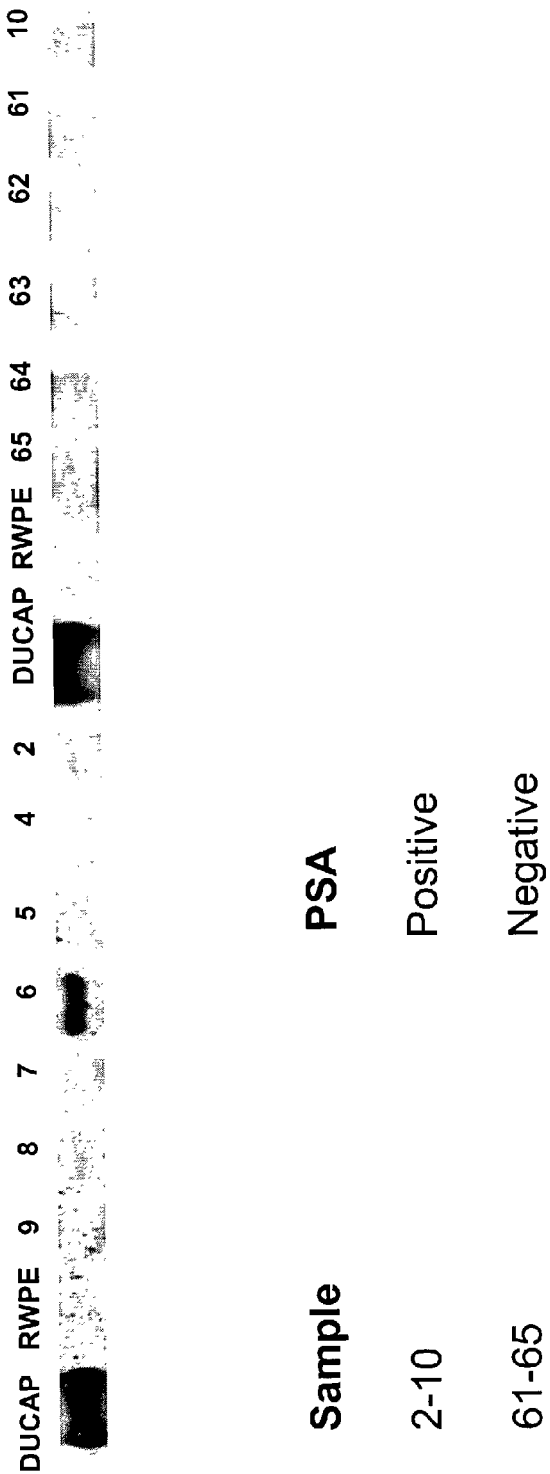
FIG. 26 shows an immunoblot analysis of serum from patients with either negative or positive PSA antigen.
Figure 27:
FIG. 27 shows an immunoblot analysis of the presence of AMACR in urine samples from patients with bladder cancer (females) or bladder cancer and increased PSA (males).

FIG. 25 shows the detection of AMACR protein in serum by quantitation of microarray data. P1–P7 represent serum from patients with prostate cancer. NS2 and NS3 represent serum from patients that do not have PCA. SNS2 and SNS3 represent serum from patients that do not have PCA that has been spiked with AMACR protein. FIG. 26 shows an immunoblot analysis of serum from patients with either negative or positive PSA antigen. FIG. 27 shows an immunoblot analysis of the presence of AMACR in urine samples from patients with bladder cancer (females) or bladder cancer and incidental prostate cancer (males). The results demonstrate that AMACR can be detected in the serum and urine of patients with bladder cancer or bladder cancer and prostate cancer.

EXAMPLE 10

AMACR as a Tumor Antigen

Figure 28:
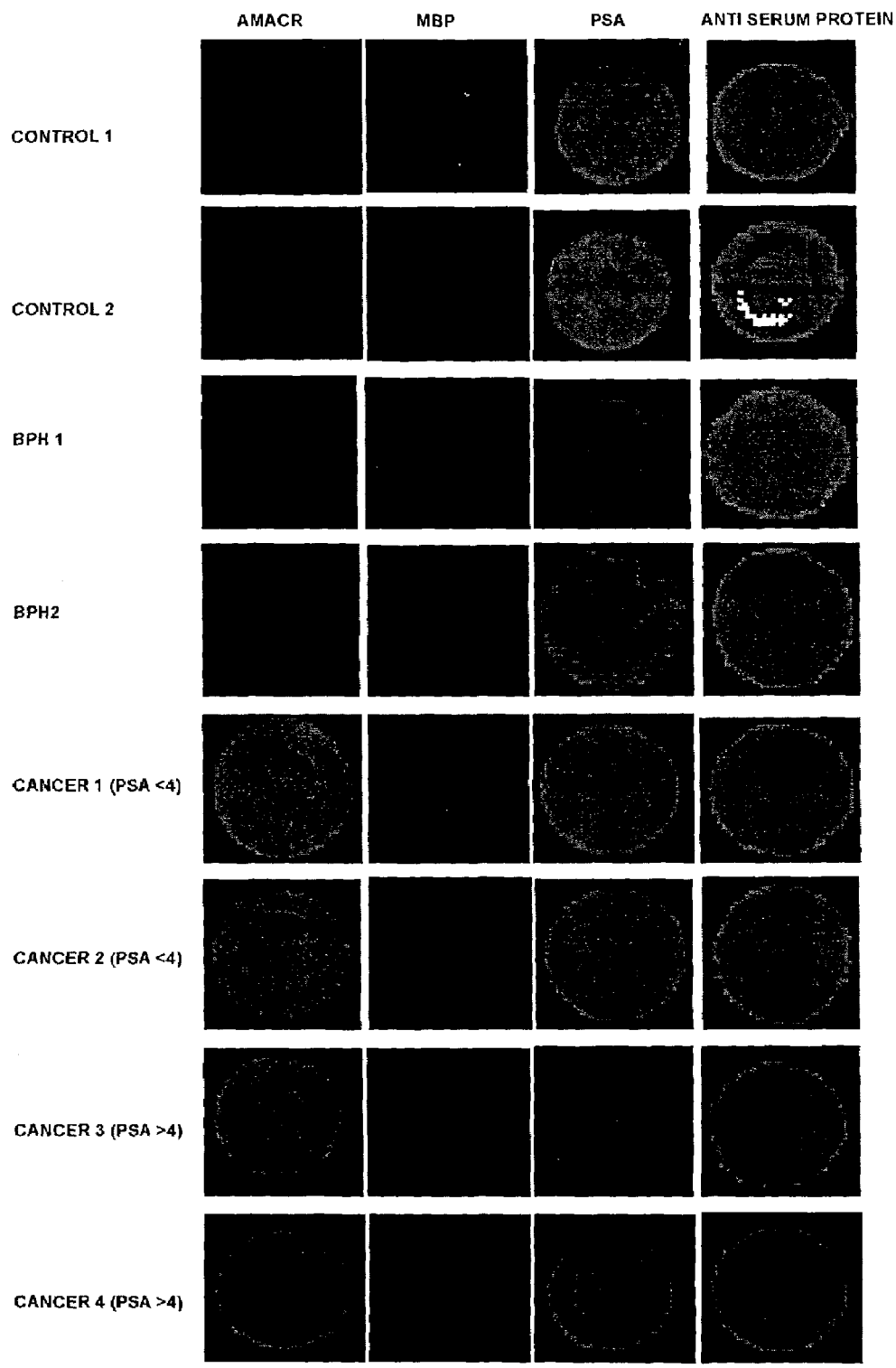
FIG. 28 shows representative data of a humoral response by protein microarray analysis.

This example describes the presence of an immune response against AMACR in serum. FIG. 28 shows representative data of a humoral response by protein microarray analysis. Tumor antigens including AMACR, PSA, CEA, HSPs were spotted onto nitrocellulose coated slides. The slides were incubated with sera from different patients to detect a humoral response. The microarray was then washed. A Cy5 labeled goat anti-human IgG was used to detect the humoral response. The slide was then scanned using a microarray scanner (Axon). After data normalization, intensity of spots reflects the presence, absence or strength of humoral response to specific tumor antigen. A specific humoral response to AMACR was detected in cancer patients but not in controls. Cancer refers to sera from prostate cancer patients. BPH refers to sera from patients with benign prostate hyperplasia.

Figure 29:
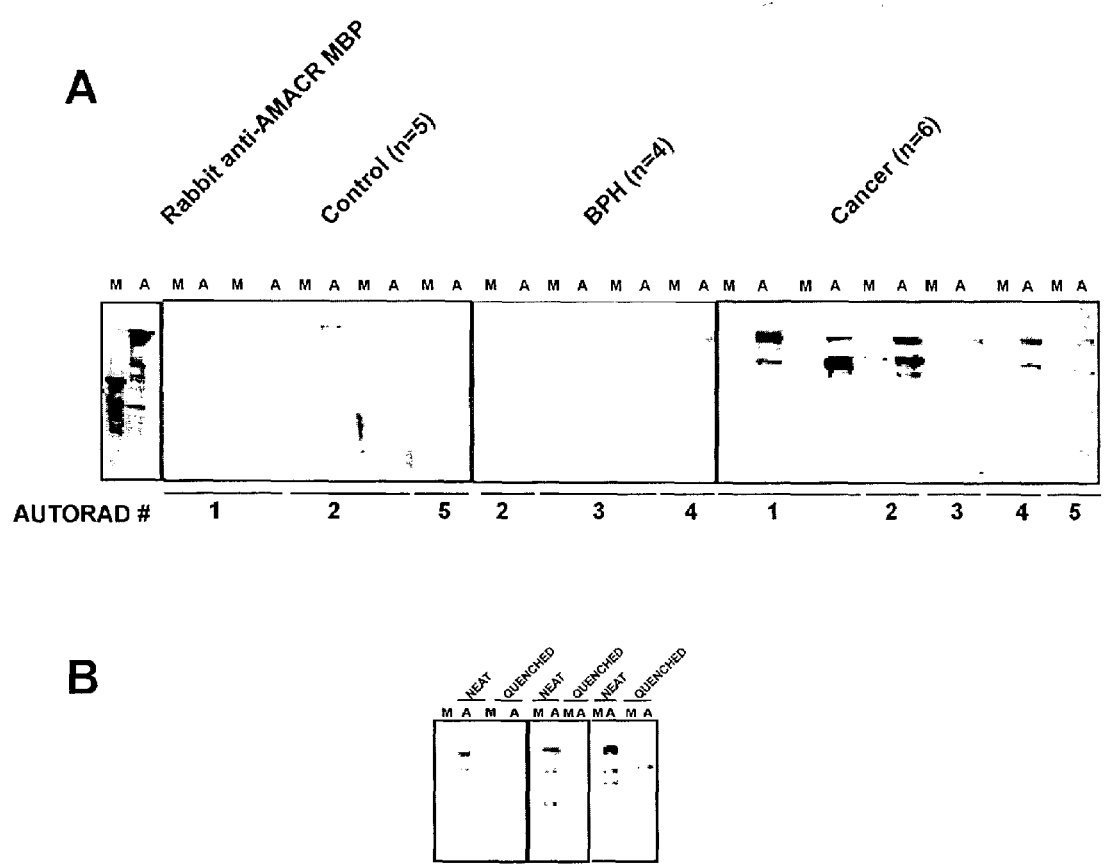
FIG. 29 shows immunoblot analysis of the humoral response of AMACR.

FIG. 29 shows immunoblot analysis of the humoral response to AMACR. FIG. 29A shows an SDS-PAGE gel containing recombinant MBP (control protein=M) and recombinant AMACR-MBP (A) that was run and transferred to nitrocellulose paper. Each strip blot was then incubated with human sera. A humoral response to the AMACR was detected using an HRP-conjugated anti-human antibody. Only AMACR and fragments of AMACR were detected in sera from prostate cancer patients and not in controls. FIG. 29B shows a control experiment whereby the humoral response is blocked with recombinant AMACR (quenched) and thus shows the specificity of the response.

This example demonstrates that AMACR functions as a tumor antigen in human serum of prostate cancer patients. A specific immune response was generated to AMACR in the serum of PCA patients, but not in controls.

EXAMPLE 11

Expression of GP73 in Prostate Cancer

This example describes the association of GP73 with prostate cancer.

A. Methods

Microarray analysis, RT-PCR, Western blotting, and immunohistochemistry were performed as described in the above examples.

B. Results

Figure 30:
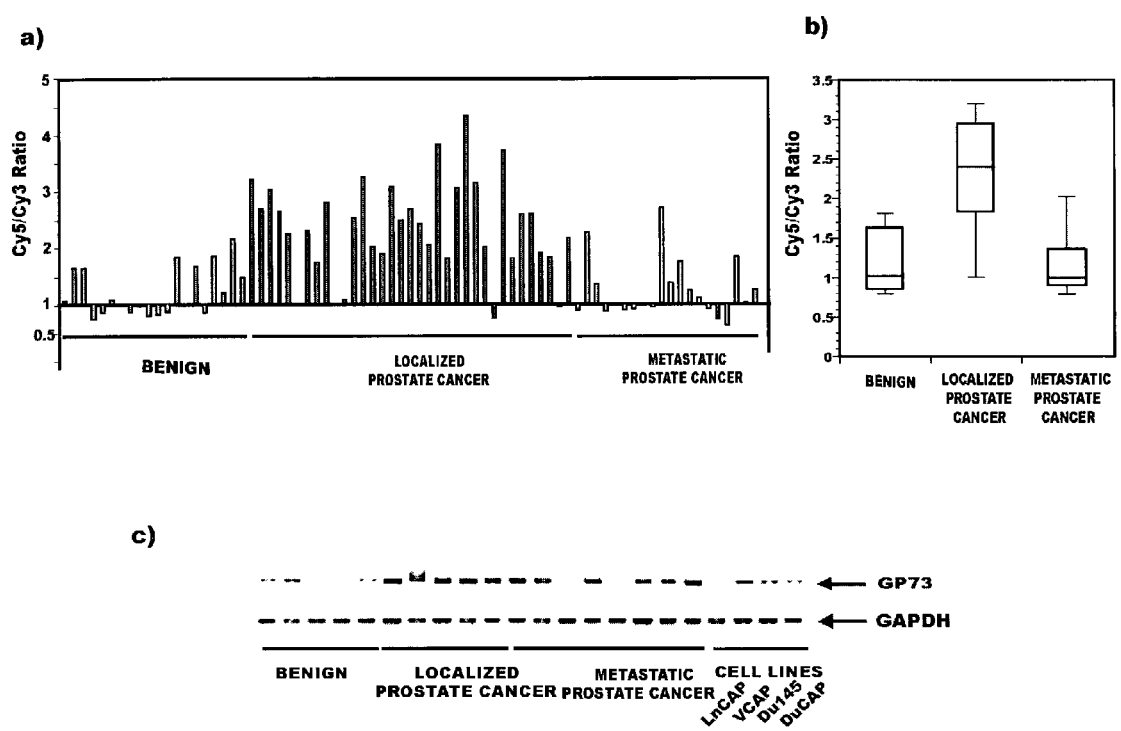
FIG. 30 shows GP73 Transcript levels in prostate cancer.

FIG. 30 shows GP73 Transcript levels in prostate cancer. FIG. 30a shows the level of GP73 in individual samples after microarray analysis. The graph shows the values of Cy5 versus Cy3 ratio wherein the prostate cancer tissue sample RNA were labeled with Cy5 fluorescent dye, while the reference sample (pool of benign tissue RNA) sample was labeled with Cy3 fluorescent dye. A total of 76 individual experiments from different prostate tissue are plotted and they are classified as benign, prostate cancer and metastatic cancer types. FIG. 30b shows the result of GP73 transcripts determined by DNA microarray analysis from 76 prostate samples grouped according to sample type and averaged. The experimental samples were labeled with Cy5 fluorescent dye, whereas the reference sample (pool of benign tissue sample) was labeled with Cy3 fluorescent dye. The box plot demonstrates the range of GP73 expression within each group. The middle horizontal bar indicates median values; the upper and lower limits of the boxes, interquartile ranges; and the error bars, 95% confidence intervals. FIG. 30c demonstrates that GP73 transcript levels are elevated in prostate cancer. RT-PCR was used to detect GP73 transcript levels in RNA preparations from prostate tissue extracts. GAPDH served as the loading control.

Figure 31:
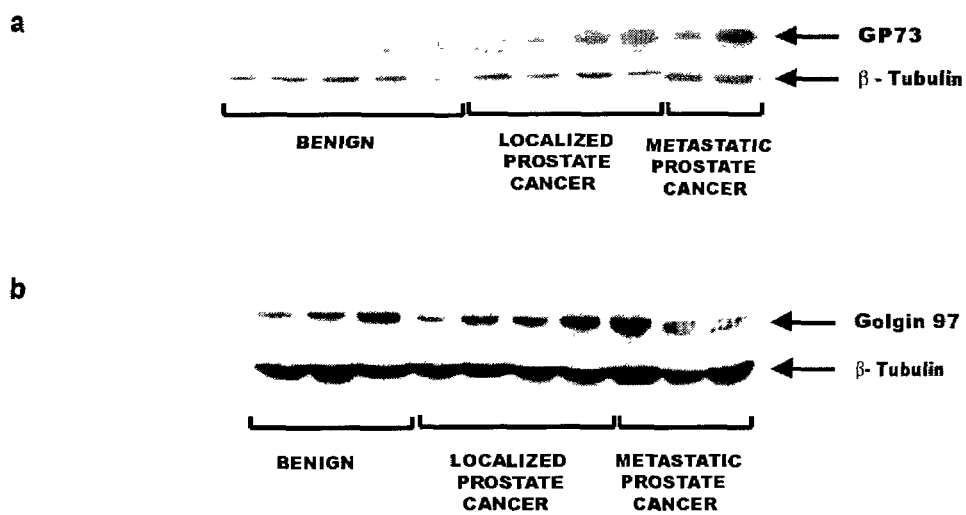
FIG. 31 shows that GP73 protein is upregulated in prostate cancer.

FIG. 31 shows that GP73 protein is upregulated in prostate cancer. FIG. 31a shows Western blot analysis of GP73 protein in prostate cancer. Total tissue proteins from benign, cancer and metastatic tissues (10 μg) were analyzed using anti-GP73 antiserum. β-Tubulin serves as control for sample loading. FIG. 31b shows an immunoblot analysis of the Golgi resident protein Golgin 97. The Golgin 97 protein levels were analyzed in the prostate tissue sample to indicate the level of Golgi structure in normal and cancerous prostate tissue. β-Tubulin serves as control for sample loading.

Tissue microarray analysis of GP73 protein in normal and cancerous prostate tissue was also performed. GP73 protein expression was analyzed by standard biotin-avidin immunohistochemical analysis using a polyclonal mouse antibody to GP73. Protein expression was evaluated on a wide range of prostate tissue using high-density tissue microarrays. High levels of staining were observed in prostate cancer tissue. Some normal epithelial cells did not stain for GP73 in a sub region of prostate cancer tissue.

FIG. 32 shows immunoblot analysis of normal and prostate cancer epithelial cells. The epithelial cells were isolated from normal prostate tissue and cancer tissue to specifically isolate the protein from epithelial cell for GP73 immunoblot analysis. For this purpose, laser capture microdissected samples were used. Actin western serves as control.

EXAMPLE 12

Lethal Markers and Targets

This example describes the identification of lethal markers. The markers serve as potential therapeutic targets. Markers were identified by correlating the number of samples with clinical parameters and gene expression. Specifically, the present study identified markers that have an expression profile similar to EZH2, which serves as a prototypic lethal biomarker of prostate cancer. These genes were identified by a scoring system that takes into account whether localized prostate cancer has recurred or not recurred. In addition, genes that have highly correlated expression with EZH2 were identified that may serve as markers to supplement EZH2.

| mean | dev | Total High | 16 bph_count | 13 pca_count | 16 pcau_count | 6 pcar_count | 20 met_count | score | UNIQID | NAME |
|---|---|---|---|---|---|---|---|---|---|---|
| −0.024 | 0.3725 | 0.7206 | 0 | 4 | 5 | 6 | 16 | 18 | 5814 | NULL ESTs Hs.30237 |
| −0.306 | 0.1707 | 0.0351 | 0 | 0 | 3 | 3 | 14 | 17 | 2506 | HN1 |
| −0.348 | 0.2394 | 0.1312 | 0 | 2 | 1 | 4 | 14 | 16 | 5112 | CSF2 |
| 0.0623 | 0.1578 | 0.3779 | 0 | 1 | 2 | 3 | 13 | 15 | 6053 | ASNS |
| −0.246 | 0.1689 | 0.0921 | 0 | 2 | 0 | 2 | 15 | 15 | 1520 | NULL ESTs Hs.16304 |
| −0.212 | 0.1386 | 0.0648 | 0 | 2 | 0 | 2 | 15 | 15 | 8273 | PRC1 |
| −0.352 | 0.1458 | −0.06 | 0 | 3 | 7 | 3 | 14 | 14 | 34 | GPAA1 |
| −0.292 | 0.2538 | 0.2153 | 0 | 0 | 1 | 3 | 10 | 13 | 5239 | KIAA1691 |
| −0.141 | 0.1572 | 0.1729 | 0 | 2 | 5 | 3 | 12 | 13 | 8562 | NULL Human clone 23614 |
| −0.21 | 0.1083 | 0.0067 | 0 | 4 | 4 | 2 | 15 | 13 | 3351 | FLJ11715 hypothetical protein |
| −0.22 | 0.1846 | 0.1495 | 0 | 5 | 4 | 5 | 13 | 13 | 2715 | NULL ESTs |
| −0.638 | 0.2696 | −0.099 | 1 | 5 | 4 | 3 | 15 | 13 | 9556 | FLJ12443 hypothetical protein |
| −0.142 | 0.1396 | 0.1371 | 0 | 0 | 2 | 2 | 10 | 12 | 1158 | TGFBI |
| −0.124 | 0.1606 | 0.1967 | 0 | 1 | 1 | 3 | 10 | 12 | 5292 | NULL ESTs |
| −0.444 | 0.2474 | 0.0504 | 0 | 1 | 2 | 2 | 11 | 12 | 3689 | NUF2R hypothetical protein |
| −0.205 | 0.2362 | 0.2674 | 0 | 2 | 1 | 2 | 12 | 12 | 1219 | ABCC5 |
| −0.09 | 0.2214 | 0.3526 | 0 | 4 | 2 | 4 | 12 | 12 | 1360 | MEN1 |
| −0.241 | 0.1541 | 0.0673 | 0 | 5 | 3 | 2 | 15 | 12 | 8476 | SARM and HEAT/Armadillo motif |
| −0.874 | 0.3367 | −0.201 | 0 | 1 | 4 | 2 | 10 | 11 | 3747 | H2BFB |
| −0.196 | 0.254 | 0.3122 | 0 | 2 | 1 | 3 | 10 | 11 | 4941 | VAV2 |

-continued

| mean | dev | Total High | 16 bph_count | 13 pca_count | 16 pcau_count | 6 pcar_count | 20 met_count | score | UNIQID | NAME |
|---|---|---|---|---|---|---|---|---|---|---|
| −0.166 | 0.1486 | 0.1307 | 0 | 2 | 4 | 2 | 11 | 11 | 8636 | NULL ESTs Hs.23268 |
| 0.0255 | 0.1542 | 0.3338 | 0 | 3 | 3 | 3 | 11 | 11 | 280 | TOP2A |
| −0.226 | 0.2536 | 0.2812 | 0 | 4 | 3 | 4 | 11 | 11 | 2156 | EZH2 |
| −0.031 | 0.1826 | 0.3346 | 0 | 4 | 4 | 2 | 13 | 11 | 1979 | NULL ESTs Hs.268921 |
| −0.48 | 0.2967 | 0.1131 | 0 | 2 | 0 | 2 | 10 | 10 | 906 | MGC5627 hypothetical protein |
| −0.243 | 0.1421 | 0.0411 | 0 | 2 | 8 | 2 | 10 | 10 | 3728 | NULL ESTs |
| −0.133 | 0.1806 | 0.2279 | 0 | 2 | 2 | 2 | 10 | 10 | 8759 | RAB24 |
| −0.192 | 0.1782 | 0.1645 | 0 | 3 | 2 | 2 | 11 | 10 | 2029 | FLJ12876 hypothetical protein |
| −0.617 | 0 | −0.617 | 0 | 3 | 2 | 2 | 10 | 9 | 3928 | DGKD |
| 0.1079 | 0.1132 | 0.3343 | 0 | 3 | 2 | 2 | 10 | 9 | 5372 | ODF2 |
| −0.288 | 0.1221 | −0.043 | 0 | 4 | 3 | 3 | 10 | 9 | 7193 | KIAA0602 |
| −0.167 | 0.2278 | 0.2883 | 0 | 4 | 2 | 2 | 11 | 9 | 8535 | EHM2 |
| −0.95 | 0.3504 | −0.249 | 0 | 4 | 2 | 2 | 11 | 9 | 9824 | SLC19A1 |
| −0.314 | 0.187 | 0.06 | 1 | 4 | 2 | 2 | 11 | 9 | 9447 | LIG1 |
| 0.1366 | 0.1883 | 0.5132 | 1 | 4 | 3 | 2 | 10 | 8 | 327 | NULL ESTs |
| −0.586 | 0.2952 | 0.0044 | 0 | 5 | 2 | 2 | 11 | 8 | 1269 | DGKZ | mean: mean expression in BPH
Dev: standard deviation in BPH
High: 2 SD's above the mean (threshold)
Bph: # of BPH samples > thresh
PCA: # of PCA samples > thresh (>1 yr no recur)
Pcau: # of PCA samples > thresh (<1 yr followup)
Pcar: # of PCA samples > thresh (recur)
Met: # of metastatic samples > thresh
Score: = met + pcar − pca
Total: # of samples in category Exemplary lethal markers identified using the above methods include ABCC5 (MDR5). This multi-drug resistance gene actively pumps cyclic nucleotides and other small molecules out of cells. An unrelated study found that this enzyme is potently Inhibited by phosphodiesterase inhibitors, including sildenafil (viagra). The present invention is not limited to a particular mechanism. Indeed, an understanding of the mechanism is not required to practice the present invention. Nonetheless, it is contemplated that sildenafil may be useful in the treatment of aggressive PCA.

Another lethal marker identified is asparagine synthetase (ASNS). Current therapeutics for the inhibition of ASNS include asparaginase, an enzyme that destroys asparagine in the body. It has been shown that cancers expressing the synthetase are resistant. Analogs are being developed to inhibit the synthetase.

Top2A (topoisomerase 2) and the Vav2 Oncogene were also identified using the methods of the present invention. Vav2 is required for cell spreading, but is dependent on src. The present invention is not limited to a particular mechanism. Indeed, an understanding of the mechanism is not required to practice the present invention. Nonetheless, it is contemplated src inhibitors can stop vav2 mediated cell spreading This example describes the identification of cancer markers overexpressed in prostate cancers. The present invention is not limited to a particular mechanism. Indeed, an understanding of the mechanism is not necessary to practice the present invention. Nonetheless, it is contemplated that therapeutic compounds that inhibit these lethal markers are useful in the treatment of prostate cancer.

EXAMPLE 13

Characterization of Annexin Expression in Prostate Cancer

This Example describes the expression of Annexins in prostate cancer.

A. Materials and Methods

Prostate Sample Collection

Prostate tissues were taken from the radical prostatectomy series and the rapid autopsy program available through the University of Michigan Prostate Cancer Specialized Program of Research Excellence (S.P.O.R.E.) Tissue Core. This program is approved by Institutional Review Board at the University of Michigan.

Hormone naïve, clinically localized PCA samples used for this study were taken from a cohort of men who underwent radical retropubic prostatectomy as a monotherapy (i.e., no hormonal or radiation therapy) for clinically localized PCA between the years 1994 and 1998. Processing of the prostatic tissues started within 20 minutes after surgical resection. The prostates were partially sampled and approximately 50% of the tissue was used for research. This protocol has been evaluated in a formal study to assure that partial sampling does not impair accurate staging and evaluation of the surgical margins (Hollenbeck et al., J. Urol. 164:1583 [2000]). The snap frozen samples used for cDNA expression array analysis were all evaluated by one of the study pathologists. All samples were grossly trimmed to ensure greater than 95% of the sample represented the desired lesion.

Hormone refractory PCA samples were collected from the rapid autopsy program (Rubin et al., [2000], supra). Snap frozen samples were used for cDNA expression array analysis. Mirrored samples from the same lesion were placed in 10% buffered formalin. The fixed samples are embedded in paraffin. As with the prostatectomy samples, the study pathologist reviewed the glass slides, circled areas of viable prostate cancer, avoiding areas of necrosis, and used these slides as a template for tissue microarray construction. In this study, twenty (20) hormone refractory metastatic PCAs were extracted from 15 rapid autopsy cases performed from 1997 to 2000. The patients' ages ranged from 53 to 84 and time from diagnosis to death ranged from 21 to 193 months.

All 15 patients died with widely metastatic PCA after extensive treatment, which included antiandrogens and chemotherapy.

Prostatectomy samples were evaluated for the presence or absence of surgical margin involvement by tumor (surgical margin status), the presence of extraprostatic extension, and seminal vesicle invasion. Tumors were staged using the TNM system, which includes extraprostatic extension and seminal vesicle invasion but does not take into account surgical margin status (Bostwick et al., Semin. Urol. Oncol. 17:222 [1999]). Tumors were graded using the Gleason grading system (Gleason, [1966], supra).

Immunohistochemistry

After paraffin removal and hydration, the tissue microarray slides were immersed in 10 mM citrate buffer placed in a pressure cooker chamber and microwaved for 10 minutes for optimal antigen retrieval. Immunostaining was performed using a Dako autostainer (DAKO, Carpinteria, Calif.). The primary antibody was incubated for 45 minutes at room temperature and a secondary biotin-labeled antibody for 30 minutes. Streptavidin-LSA amplification method (DAKO K0679) was carried out for 30 minutes followed by peroxidase/diaminobenzidine substrate/Chromagen. The slides were counterstained with hematoxylin. Polyclonal antibodies directed against the N-terminus of annexin 1(dilution 1:50), annexin 2 (dilution 1:100), annexin 4 (dilution 1:100), annexin 7 (dilution 1:500), and annexin 11 (dilution 1:100) were obtained from a signal source (Santa Cruz Biotechnology, Santa Cruz, Calif.). Protein expression as determined by two pathologists immunohistochemistry was scored as negative (score=1), weak (score 2), moderate (3) or strong (4), using the system described above.

Tissue Microarray Construction, Digital Image Capture, and Analysis

Tissue microarrays were constructed as previously described to evaluate protein expression in a wide range of samples ranging from benign prostate tissue taken from the prostatectomy samples to hormone refractory PCA. Three tissue microarrays were used for this study consisting of benign prostate, localized PCAs, and hormone refractory PCA. The tissue microarrays were assembled using the manual tissue arrayer (Beecher Instruments, Silver Spring, Md.) as previously described (Kononen et al., [1998], supra; Perrone et al., [2000], supra). Tissue cores from the circled areas of interest were targeted for transfer to the recipient array blocks. The 0.6 mm diameter tissue microarray cores were each spaced at 0.8 mm from core-center to core-center. Tissue microarray images were acquired using the BLISS Imaging System (Bacus Lab, Lombard, Ill.).

Statistical Analyses

To investigate the statistical significance associated with the differential expression of annexins across 4 independent gene expression studies, standard methods (Hedges et al., Statistical Methods for Meta-analysis meta-analysis. Orlando, Academic Press 1985, pp xxii, 369) were used to combine the results. For each of the studies, a t-statistic was computed (with the two groups being benign tissue compared against localized prostate cancer) and the associated p-values were transformed using a negative logarithmic transformation. These numbers were then doubled and added together to arrive at a summary measure of differential gene expression across the three studies. To assess the statistical significance associated with this summary measure, a permutation-based approach was adopted (Hedges et al., supra). Namely, the tissue types were permuted within studies, and the summary measure was computed for the permutated data. A p-value was computed using the permutation distribution of the summary measure. The issue then arises of whether or not the t-statistics from the three studies are comparable.

Annexin protein expression was statistically evaluated using the mean score results from each tissue microarray sample for each prostate tissue type (i.e., benign, localized PCA, and hormone refractory PCA). To determine differences between all pairs (e.g., localized prostate cancer versus benign), an ANOVA with a post-hoc analysis was performed using the Scheffé method (Scheffae et al., supra). The mean expression scores for all examined cases were presented in a graphical format by using error-bars with 95% confidence intervals.

B. Results

Figure 33:
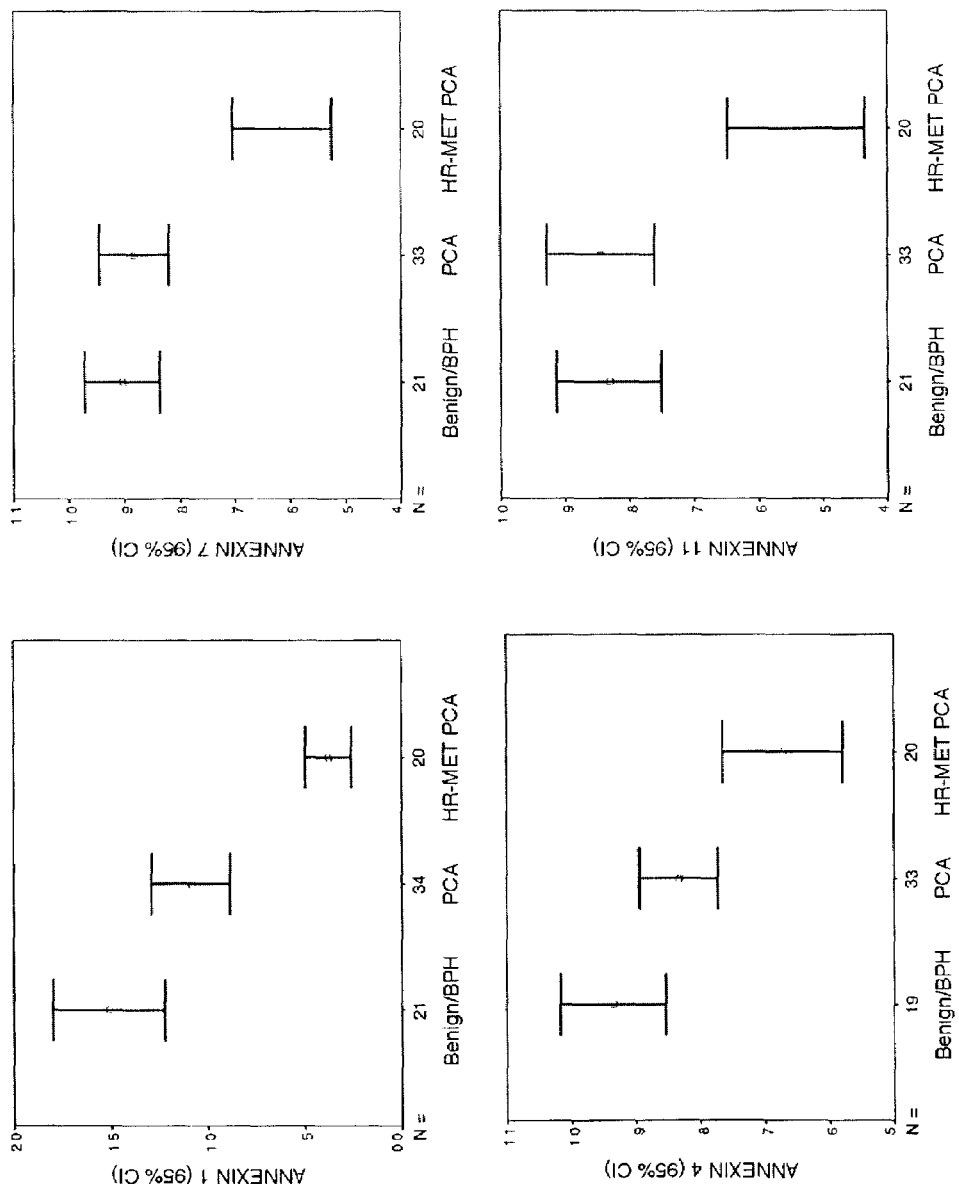
FIG. 33 shows the cDNA expression of select annexin gene family members.

Expression array analysis revealed a significant dysregulation of annexin family members with PCA progression. The cDNA expression of annexins 1, 2, 4, 7 and 11 were significantly decreased in the hormone refractory PCA samples as compared to localized hormone sensitive PCA samples with 2.2, 1.5, 1.3, 1.4 and 1.8 fold decrease, respectively (all p-values<0.01) (Table 8 and FIG. 33). Annexins 1 and 4 showed significant decreases of mRNA expression in localized PCA samples as compared to the benign samples. There were no significant differences between localized hormone naive PCA and the benign samples for annexin 2, 7, and 11. No cDNA dysregulation between the tested prostate samples and annexins 8 and 13 was observed. Annexin 6 demonstrated a slight decrease in cDNA expression between localized PCA and benign samples, which was not statistically significant (Table 8).

Figure 34:
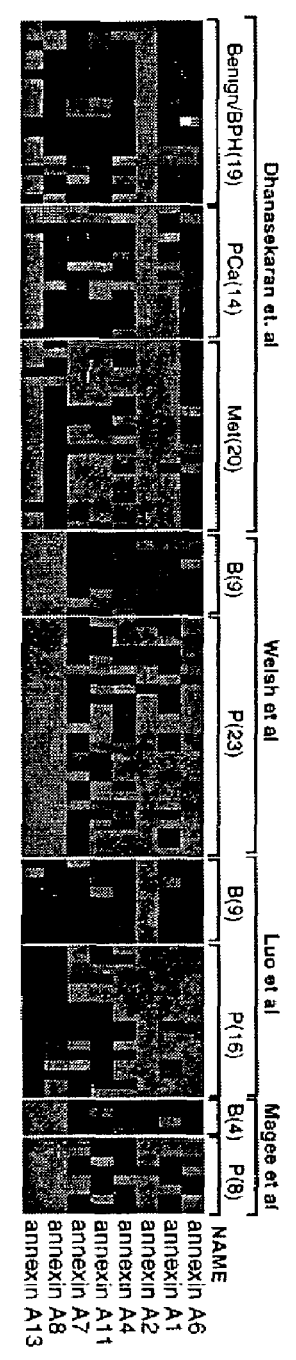

In order to cross validate the cDNA expression results for these annexin family members, a meta-analysis of gene expression was performed. Annexin family members cDNA expression results were evaluated using a series of data sets (Welsh et al., Cancer Res. 61:5974 [2001]; Luo et al., Cancer Res. 61:4683 [2001]; Magee et al., Cancer Res. 61:5692 [2001]). The analysis evaluated annexins for each of the individual studies as well as performing a summary statistic, taking into account the significance of the gene expression across the 4 studies. The meta-analysis compared differences between clinically localized PCA and benign prostate tissue as not all of the studies had hormone refractory metastatic PCA. The meta-analysis (Table 9 and FIG. 34) demonstrated that annexins 1, 2, 4, and 6 were significantly down regulated across independent studies. Annexin 6 was down regulated to a significant level in 4 of 4 studies. Annexin 1 demonstrated down regulation in 3 of 4 studies. Annexins 2 and 4 were down regulated in 2 studies and overall considered to be significantly under expressed by the meta-analysis. Annexin 7 was not found to be significantly under expressed in any of the 4 studies at the transcript level.

Immunohistochemistry was performed to confirm these results at the protein level (Table 10). By immunohistochemistry, a significant decrease in protein expression for annexins 1, 2, 4, 7 and 11 in hormone refractory PCA samples as compared to localized PCA samples was identified with 2.5 (3.8 vs. 1.5 median expression), 2.4 (4 vs. 1.7 median expression), 3.6 (4 vs. 1.1 median expression) and 3.3 (4 vs. 1.2 median expression) fold decreases, respectively (Kruskal Wallis test, all p-values p<0.05). No statistically significant differences were seen between benign and localized PCA samples in any of the annexins tested.

TABLE 8

Gene Expression of Select Annexins.

| Annexin | Benign Count | Benign Median | BPH[1] Count | BPH[1] Median | Loc-PCA[2] Count | Loc-PCA[2] Median | Met-PCA[3] Count | Met-PCA[3] Median | Ratio PCA/Met | p Value* |
|---|---|---|---|---|---|---|---|---|---|---|
| 1 | 5 | 1.56 | 16 | 1.35 | 16 | 0.69 | 20 | 0.31 | 2.23 | <0.001 |
| 2 | 5 | 0.79 | 16 | 0.69 | 16 | 0.74 | 20 | 0.49 | 1.51 | 0.009 |
| 4 | 5 | 0.91 | 16 | 0.97 | 16 | 0.9 | 20 | 0.69 | 1.30 | 0.001 |
| 6 | 5 | 1.2 | 16 | 1.29 | 16 | 1.05 | 20 | 1.15 | 0.91 | 0.377 |
| 7 | 5 | 0.8 | 16 | 0.88 | 16 | 0.88 | 20 | 0.62 | 1.42 | <0.001 |
| 8 | 5 | 1.14 | 16 | 1.06 | 16 | 0.99 | 20 | 1.19 | 0.83 | 0.156 |
| 11 | 5 | 0.99 | 16 | 0.76 | 16 | 0.94 | 20 | 0.52 | 1.81 | <0.001 |
| 13 | 5 | 1.08 | 16 | 1.35 | 16 | 1.03 | 20 | 0.94 | 1.10 | 0.393 |

*Kruskal Wallis Test.
[1]BPH, benign prostatic hyperplasia.
[2]Loc-PCA, localized prostate cancer.
[3]Met-PCA, metastatic hormone refractory prostatic cancer. Ratio PCA/Met, ratio of expression of localized PCA over hormone refractory PCA.

TABLE 9

Meta-Analysis of cDNA Prostate Gene Expression Studies for Annexin Family Members

| Annexin | Present study | Welsh et al. | Luo et al. | Magee et al. | Summary p-Value |
|---|---|---|---|---|---|
| 6 | 0.024 | 0.0001 | 0.0001 | 0.026 | 0.0001 |
| 1 | 0.0001 | 0.031 | 0.0007 | 0.23 | 0.0001 |
| 2 | NA | 0.0001 | NA | 0.002 | 0.0001 |
| 11 | NA | 0.010 | NA | 0.6 | 0.17 |
| 7 | 0.25 | 0.48 | 0.38 | 0.088 | 0.20 |
| 4 | 0.33 | 0.023 | 0.0093 | 0.58 | 0.011 |
| 13 | 0.177 | NA | 1.00 | NA | 0.48 |
| 8 | 0.79 | NA | 0.104 | NA | 0.29 |

TABLE 10

Tissue Microarray Protein Expression for Annexins by Tissue Type

| Annexin | Benign Count | Benign Median | Loc-PCA[2] Count | Loc-PCA[2] Median | Met-PCA[3] Count | Met-PCA[3] Median | PCA/MET | p-value* |
|---|---|---|---|---|---|---|---|---|
| 1 | 37 | 2.59 | 360 | 2.45 | 162 | 1.46 | 1.68 | <0.001 |
| 2 | 57 | 3.95 | 82 | 3.62 | 214 | 1.47 | 2.46 | <0.001 |
| 4 | 23 | 3.65 | 357 | 3.96 | 141 | 1.57 | 2.52 | <0.001 |
| 7 | 26 | 3.77 | 350 | 3.97 | 126 | 1.32 | 3.01 | <0.001 |
| 11 | 23 | 4.00 | 360 | 3.99 | 163 | 1.30 | 3.01 | <0.001 |

*Kruskal Wallis Test.
1 BPH, benign prostatic hyperplasia.
[2]Loc-PCA, localized prostate cancer.
[3]Met-PCA, metastatic hormone refractory prostatic cancer.

EXAMPLE 14

Association of CtBP with Prostate Cancer

This example describes the expression of C-terminal binding proteins 1 and 2 (CtBP1 and CtBP2) in prostate cancer. Microarray analysis, Western Blots, immunohistochemistry, and statistical analysis were performed as described in the above examples.

Figure 35:
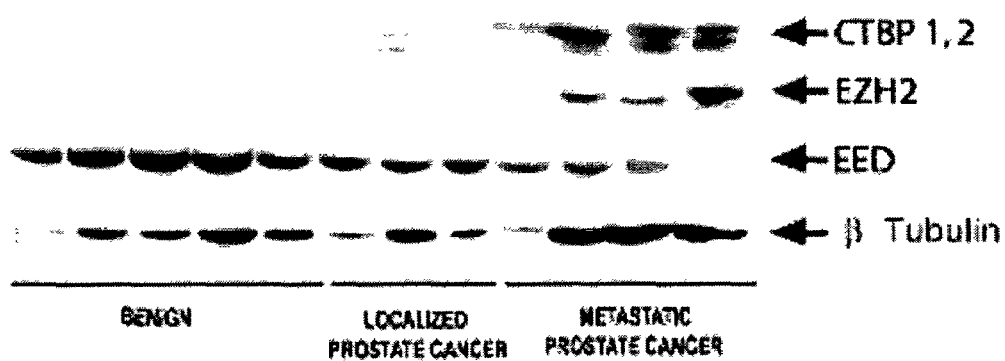
FIG. 35 shows the expression of CtBP proteins in PCA specimens.
Figure 38:
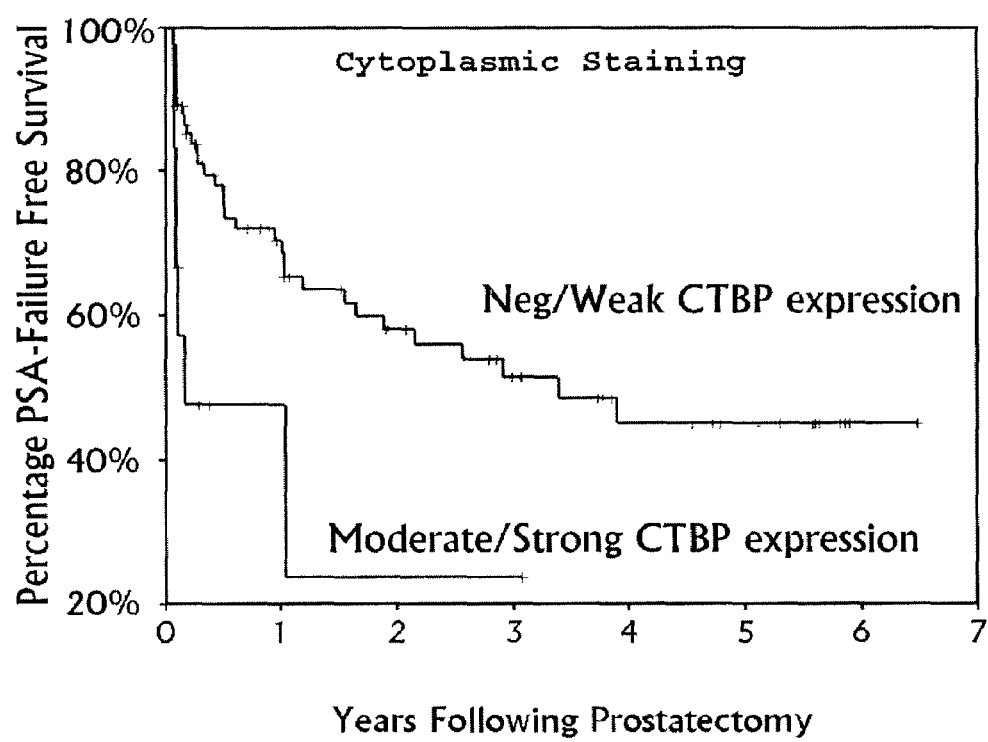
FIG. 38 shows a Kaplan-Meier Analysis of prostate cancer tissue microarray data.

The CtBP transcript was found to be up-regulated in metastatic prostate cancer (FIG. 38). Tissue extracts were used to validate this finding at the protein level using an antibody that recognizes CtBP1 and CtBP2 (Sewalt et al., Mol. Cell. Biol. 19:777 [1999]. The results are shown in FIG. 35. FIG. 35 shows the Expression of CtBP proteins in PCA specimens. Extracts from selected prostate specimens were assessed for expression of CtBP and PcG proteins by immunoblot analysis. Protein level was equalized in each extract before loading and blots were stained with Ponceau S to confirm equal loading. β-tubulin was used as a control protein.

Both CtBPs were over-expressed in metastatic prostate cancer relative to localized prostate cancer and benign tissue. EZH2 protein was also elevated in metastatic prostate cancer relative to localized prostate cancer or benign prostate (FIG. 35). EED, a PcG protein that forms a complex with EZH2, along with an un-related protein, β-tubulin, did not exhibit similar protein dysregulation. Thus, both transcriptional repressors (CtBP and EZH2) are mis-expressed in metastatic prostate cancer.

To determine in situ expression of CtBP, immunohistochemistry of prostate tissue sections were performed using prostate tissue microarrays. Benign prostatic epithelia exhibited exclusively nuclear staining consistent with CtBP's role as a transcriptional repressor. Both clinically localized and metastatic prostate cancer exhibited nuclear staining as well. Most of the metastatic prostate cancer cases and a fraction of the localized prostate cancer cases exhibited distinct cytoplasmic staining of CtBP.

Figure 36:
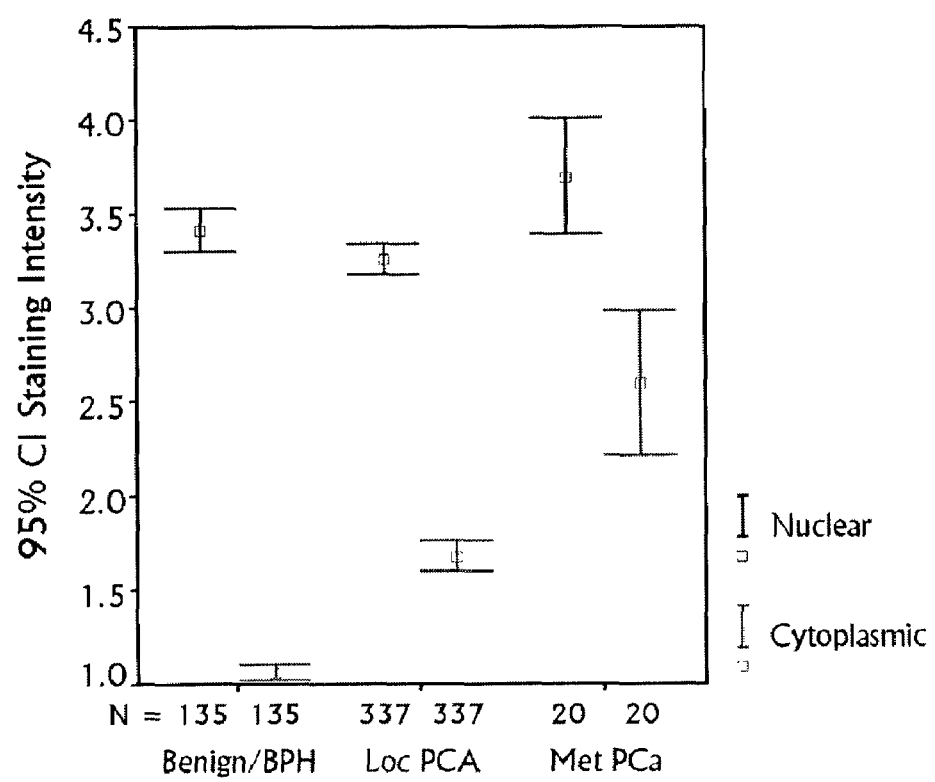
FIG. 36 shows tissue microarray analysis of CtBP in prostate cancer that suggests mis-localization during prostate cancer progression.
Figure 37:
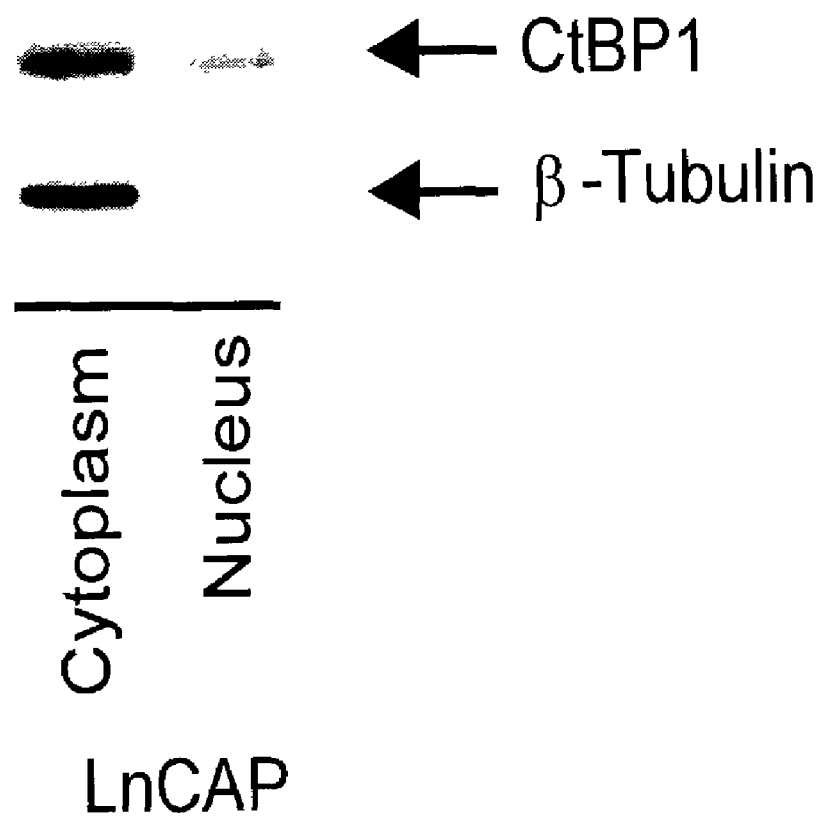
FIG. 37 shows the sub-cellular fractionation of LNCaP cells.

FIG. 36 shows tissue microarray analysis of CtBP in prostate cancer that suggests mis-localization during prostate cancer progression. The mean CtBP protein expression for the indicated prostate tissues and sub-cellular compartment is summarized using error bars with 95% confidence intervals. FIG. 37 shows the sub-cellular fractionation of LNCaP cells. The results show an increased level of CtBP1 in the cytoplasm relative to the nucleus. CtBP2 is weakly expressed in the cell lines and is not easily apparent. β-tubulin, which is not expressed in the nucleus, is provided as a control. FIG. 38 shows a Kaplan-Meier Analysis of prostate cancer tissue microarray data. The results demonstrate that the presence of cytoplasmic CtBP may be associated with a poorer clinical outcome. The median follow up time for all patients was 1 year (range 2 month to 6.5 years). Over this follow up time, 38% of the patients developed a recurrence or PSA elevation greater than 0.2 ng/ml. Prostate tumors from 97 patients demonstrated near uniform nuclear protein expression for CTBP. Cytoplasmic expression was variable with 85 of 97 cases (88%) demonstrating weak cytoplasmic staining and 12 (12%) with moderate to strong CTBP expression. There was a significant association with increased CTBP cytoplasmic staining intensity and PSA recurrence or presence of recurrent disease following prostatectomy with a relative risk of 1.7 (Cox regression analysis $p=0.034$). The data presented demonstrates a Kaplan-Meier Analysis of outcome stratified by negative/weak cytoplasmic CTBP staining and moderate/strong staining. CTBP cytoplasmic expression predicted recurrence even when Gleason score was taken into account in a multivariable model, suggesting that CTBP is a prognostic predictor of poor outcome [Gleason relative risk 1.4 ($p=0.005$) and cCTBP rr 1.6 ($p=0.042$)].

CtBP has been shown to bind nitric oxide synthase (NOS), which is thought to shift the localization of CtBP from the nuclear compartment to the cytoplasmic compartment (Riefler et al., J. Biol. Chem. 276:48262 [2001]). Weigert and colleagues have proposed a cytoplasmic role for CtBP in the induction of Golgi membrane fission (Weigart et al., Nature 402:429 [1999]). To further support the preliminary immunohistochemical findings, LNCaP (metastatic) prostate cancer cells were fractionated and it was found that CtBP levels were higher in the cytosol relative to the nucleus (FIG. 38).

EXAMPLE 15

Methods of Characterizing Cancer Markers

This example describes exemplary methods for the characterization of new cancer markers of the present invention. These methods, in combination with the methods described in the above examples, are used to characterized new cancer markers and identify new diagnostic and therapeutic targets.

A. Determination of Quantitative mRNA Transcript Levels of Cancer Markers in Prostate Cancer Specimens In some embodiments, markers revealed to be over or under expressed in cancer microarrays (See e.g., Example 1 for a description of microarrays) are quantitated using real-time PCR (Wurmbach et al., J. Biol. Chem. 276:47195 [2001]).

In preferred embodiments, cDNA from over 100 prostate samples for archived cDNA samples and associated clinical data are available (See Example 1). The level of expression in the microarray is compared to those obtained by real-time PCR. To identify genes with dysregulation of expression, real-time PCR analysis of cDNA generated from laser-capture microdissected prostate cancer epithelia and benign epithelia is performed.

B. Detection of Mis-localized Transcripts

In some embodiments, in order to determine if a cancer marker normally present in the nucleus of a cell (e.g., a transcriptional repressor) is mis-localized to the cytoplasm (or other mis-locations) in cancer, the expression of the marker is examined in tissue extracts from preferably at least 20 benign prostate samples, 20 prostate cancer specimens, and 20 metastatic prostate specimens. Expression of the marker in benign prostate cell lines (RWPE), primary prostatic epithelial cells (Clonetics, Inc.) and a panel of prostate cancer cells including LNCaP, DU145, PC3, DUCaP, and VCaP cells is also examined. Once overall expression of prostate cell lines and tissues is established, the cellular localization of the marker is determined by 2 methods. In the first method, the cell and tissue extracts are fractionated into a nuclear fraction and a cytosolic fraction (NE-PER, Pierce-Endogen; Orth et al., J. Biol. Chem. 271:16443 [1996]). Quantitated protein is then analyzed by immunoblotting. Relative levels of cytosolic and nuclear cancer marker are determined by densitometry. To verify clean fractionation, antibodies to β-tubulin and PCNA (or lamin A) are used to assess cytosolic and nuclear fractions, respectively.

In the second method, cells are immunostained with antibodies to the cancer marker followed by detection using anti-rabbit FITC secondary antibody. Confocal microscopy (U of M Anatomy and Cell Biology Core Facility) is used to examine in situ localization of the cancer markers.

In some embodiments, mis-localization is further investigated by sequencing the gene in cells containing the mis-located transcript (e.g., metastatic cases) for mutations.

C. Correlation of Cancer Markers with Clinical Outcome

In some preferred embodiments, the association of expression or mis-localization of a cancer marker with clinical outcome is investigated. The ratio of total cancer marker to β-tubulin by immunoblot analysis of prostate cancer tissue extracts is first determined and associated with clinical outcome parameters. For markers suspected of being mis-localized in cancer (e.g., CtBP), the ratio of cytoplasmic marker to nuclear marker is next determined by immunoblot analysis of prostate cancer tissue extracts and associated with clinical outcome parameters. For example, it is contemplated that a high cytoplasmic/nuclear cancer marker ratio may portend a poor clinical outcome. In some embodiments (e.g., where a cancer marker is suspected of being mis-localized), immunohistochemistry of prostate cancer tissue microarrays is used to determine whether the presence of cytoplasmic marker correlates with poor clinical outcome. Tissue microarrays are prepared and performed as described in the above examples.

Briefly, high-density tissue microarrays (TMA) are constructed as previously described (Perrone et al., supra; Kononen et al., supra). Immunostaining intensity is scored by a genitourinary pathologist as absent, weak, moderate, or strong (or alternatively analyzed separately as for cytoplasmic and nuclear staining). Scoring is performed using a telepathology system in a blinded fashion without knowledge of overall Gleason score (e.g., tumor grade), tumor size, or clinical outcome (Perrone et al., supra). Tumor samples are derived from patients with clinically localized, advanced hormone refractory prostate cancer and naïve metastatic PCA. Cases of clinically localized prostate cancer are identified from the University of Michigan Prostate S.P.O.R.E. Tumor Bank. All patients were operated on between 1993 and 1998 for clinically localized prostate cancer as determined by preoperative PSA, digital-rectal examination, and prostate needle biopsy. All tissues used are collected with institutional review board approval. The advanced prostate tumors are collected from a series of 23 rapid autopsies performed at the University of Michigan on men who died of hormone refractory prostate cancer. The clinical and pathologic findings of these cases have been reported (Rubin et al., [2000], supra).

Statistical analysis of the array data is used to correlate the cancer marker protein measurements on the TMA with clinical outcomes, such as time to PSA recurrence and survival time. This analysis involves survival analysis methods for correlating the measurements with these censored response times. Kaplan-Meier curves are plotted for descriptive purposes. Univariate analyses is performed using the Cox model associating the biomarker with the survival time. In addition, multivariate Cox regression analysis is performed to test whether the biomarker adds any prognostic information over and above that available from known prognostic markers (i.e., Gleason score, tumor stage, margin status, PSA level before surgery).

D. RNA Interference

In some embodiments, RNA interference of cancer markers is used to investigate the role of the cancer marker in cell culture and well as for application as a therapeutic cancer treatment (See e.g., Example 8 for an example of RNA interference). 21-nucleotide RNAs (siACE-RNAi) are synthesized through a commercial vendor (Dharmacon Research, Inc.). RNA interference has been used in mammalian cells (Elbashir et al., Nature 411:494 [2001]). Several siRNA duplexes and controls are designed for each marker. The design of the siRNA duplexes uses criteria provided by Elbashir et al. (Elbashir et al., supra) and Dharmacon Research which include: starting approximately 75 bases downstream of the start codon, locating an adenine-adenine dimer, maintaining G/C content around 50%, and performing a BLAST-search against EST databases to ensure that only one gene is targeted. Multiple (e.g., two) siRNA duplexes are designed for each molecule of interest since whether the siRNA duplex is functional is a relatively empirical process. In addition, it is contemplated that using two siRNA duplexes may provide a combined "knockdown" effect. As a control, a "scrambled" siRNA, in which the order of nucleotides is randomized, is designed for each molecule of interest. Oligonucleotides are purchased deprotected and desalted. Upon arrival, the oligonucleotides are annealed to form a duplex using the manufacturer's provided protocol.

To test the efficacy of each siRNA duplex, prostate cell lines (RWPE, DU145, LnCAP, and PC3) are transfected with the OLIGOFECTAMINE reagent as described (Elbashir et al., supra). The cells are assayed for gene silencing 48 hrs post-transfection by immunoblotting with respective antibodies. A number of controls are included: buffer controls, sense siRNA oligo alone, anti-sense siRNA oligo alone, scrambled siRNA duplex, and siRNA duplexes directed against unrelated proteins. If significant silencing is not appreciated after single transfection, sequential transfection is performed and inhibition is monitored at later time points (i.e., 8 days later) as suggested by others (Breiling et al, Nature. 412: 51 [2001]). This may be necessary with proteins that have a long half-life.

In addition to the transient expression of siRNAs, a method for stable expression of siRNAs in mammalian cells is used (Brummelkamp et al., Science 296:550 [2002]). Prostate cancer cell lines are generated that express siRNA targeting cancer markers using the pSUPER system. Scrambled siRNA is used as a control. The cell lines facilitate downstream characterization of cancer markers that may be cumbersome using duplexes transiently. If inhibition of a specific cancer marker is found to be toxic to cells, the pSUPER cassette containing siRNA to the marker is cloned into an inducible vector system (e.g., Tet on/off).

E. Generation of Mutants.

To study the function of cancer markers of the present invention, mutants of cancer markers are generated in eukaryotic expression vectors. myc-epitope tagged versions of cancer marker mutants are generated in both pcDNA3 and pcDNA3-ER (a modified estrogen receptor ligand binding domain). In the case of the ER constructs, the vectors produce an in-frame fusion protein with modified ER, thus generating a post-transcriptionally inducible vector (Littlewood et al., Nucleic Acids Res. 23: 686 [1995]). The ER-ligand domain is mutated and fails to bind endogenous estrogen, yet can be activated by 4-hydroxytamoxifen (Littlewood et al., supra). The ER-fusion proteins are inactivated in the absence of ligand presumably due to binding of proteins such as hsp90. In the presence of exogenously added 4-hydroxytamoxifen, ER-fusions become liberated. By using an inducible vector system, cell lines expressing a "toxic" or growth inhibitory version of a cancer marker can still be isolated.

Various N-terminal and C-terminal deletion mutants are generated that encompass function domains of the cancer marker (e.g., the PXDLS, dehydrogenase, and PDZ binding domains of CtBP; Chinnadurai, Mol Cell. 9: 213 [2002]). It is contemplated that some of the mutant versions of the cancer markers of the present invention act as dominant negative inhibitors of endogenous cancer marker function. Expression of epitope-tagged cancer markers and mutants is assessed by transient transfection of human embryonic kidney cells (using FUGENE) and subsequent Western blotting.

F. Establishing Stable Cell Lines Expressing Cancer Markers and Mutants

In some embodiments, cell lines stably expressing cancer markers of the present invention are generated for use in downstream analysis. FUGENE is used to transiently transfect prostate cell lines (RWPE, DU145, LnCAP, and PC3) with cancer markers and fusions or mutants using the above mentioned vectors and appropriate G418 selection. Prostate cell lines with varied expression levels of endogenous cancer marker protein are used. Both individual clones and pooled populations are derived and expression of cancer markers and mutants assessed by immunoblotting for the epitope tag. By also using an inducible system, clones expressing toxic versions of cancer markers or mutants can be isolated.

G. Cell Proliferation and Apoptosis Studies

In some embodiments, the role of cancer marker expression in prostate cell proliferation is investigated using a multi-faceted approach that includes 1. RNA interference, 2. transient transfection of cancer markers and potential dominant negative mutants, and 3. comparing stable transfectants of cancer markers and mutants. The following predictions are tested using these methods: 1. whether inhibition of cancer markers will block cell growth and 2. whether overexpression of cancer markers will enhance cell proliferation.

Cell proliferation is assessed by cell counting (Coulter counter) over a time course in culture by using the WST-1 reagent (Roche, Inc.), which is a non-radioactive alternative to [$^3$H]-thymidine incorporation and analogous to the MTT assay. The rate of incorporation of the DNA labeling dye bromodeoxyuridine (BrdU) will also be measured as described previously (Jacobs et al., Nature. 397:164 [1999]). Potential cell cycle arrest induced by siRNA or dominant negative inhibitors of is determined by conventional flow cytometric methods. By using stable cell lines that "activate" cancer markers and mutants in a 4-hydroxytamoxifen-dependent fashion, cell proliferation and cell cycle alterations are monitored in a highly controlled in vitro system. To confirm that overexpression or inhibition of cancer markers does not activate the apoptosis pathway, several assays are used including propidium iodide staining of nuclei, TUNEL assay and caspase activation.

If a cancer marker is found to be a regulator of cell proliferation in prostate cells, studies are designed to address how components of cell cycle machinery are modulated by the cancer marker. Thus, in order to study cancer marker mediated effects on the cell cycle machinery of prostate cells, cancer marker functions are modulated with the above mentioned tools (i.e., siRNA, dominant negative inhibition, etc.) and the expression levels (transcript and protein) of cyclins (cyclin D1,E,A), cyclins-dependent kinases (cdk2, cdk4, cdk6) and cyclin-dependent kinase inhibitors (p21CIP1, p27KIP1, p45SKP2, p16INK4) are monitored.

H. Cell Adhesion and Invasion Assays

If a cancer marker is suspected of altering cell adhesion (e.g., the transcriptional repression of an epithelial gene program such as E-cadherin), the methods described above are used to investigate whether over-expression of the cancer marker causes increased or decreased cell adhesion. Adhesion to extracellular matrix components, human bone marrow endothelium (HBME) as well as to human umbilical vein endothelial cells (HUVEC) is tested. Cancer markers are further tested for their ability to modulate invasion of PCA.

Known methods are used in these studies (Cooper et al., Clin. Cancer Res. 6:4839 [2000]). Briefly, snap-apart 96-well tissue culture plates are coated with crude bone and kidney matrices. Plates are incubated overnight at room temperature under sterile conditions and stored at 4° C. until needed. Assay plates are also coated with extracellular matrix components (e.g., human collagen I, human fibronectin, mouse laminin I) and human transferrin at various concentrations according to the manufacturer's instruction (Collaborative Biomedical Products, Bedford, Mass.). Endothelial cells (HBME or HUVEC) are seeded onto bone matrices or plastic substrata at a concentration of 900 cells/µl and grown to confluence. Tumor cells are removed from the flask by a 15–20 minute treatment with 0.5 mM EDTA in Hank's balanced salt solution. Once the EDTA solution is removed, the cells are resuspended in adhesion medium (e.g., minimum essential medium (MEM) with 1% bovine serum albumin (BSA) supplemented with 10 uCi $^{51}$Cr sodium salt (NEN, Boston, Mass.)) for 1 hour at 37° C. Cells are then washed three times in isotope free media and 1×10$^5$ radio-labeled tumor cells are resuspended in adhesion media and layered upon a confluent layer of endothelial cells for 30 min at 37° C. In addition, radiolabeled tumor cells are applied to crude bone matrices. Again, plates are washed three times in phosphate buffered saline and adhesion is determined by counting individual wells on a gamma counter. Cell adhesion is reported relative to the adhesion of controls (PC-3 cells on plastic), which are set to 100.

Cell invasion assays are performed using a classic Boyden chamber assay. Both strategies to inhibit and overexpress cancer markers are evaluated. Previous reports have correlated increased cell migration in a Boyden Chamber system with increased invasive properties in vivo (Klemke et al., J Cell Biol. 140:61 [1998]. Commercially available 24-well invasion chambers are used (e.g., BD biosciences, Chemicon International).

I. Transcriptional Suppression in Prostate Cancer Cells

In some embodiments, the effect of cancer markers on gene silencing in prostate cells is assessed. Gene silencing is assayed in several ways. First, gene expression alterations induced by transient transfection of cancer markers and mutants in prostate cell lines (RWPE, DU145, LnCAP, and PC3) is assayed using FUGENE. Twelve to 48 hours after transfection, cells are harvested and a portion is processed to confirm expression of the transfectants by immunoblotting. Using vector-transfected cells as a reference sample, total RNA from transfected cells is then assessed on 20K cDNA microarrays.

In addition to transient transfections, stable cell lines overexpressing cancer markers and cancer marker mutants are generated. Patterns of gene expression from cancer marker and cancer marker mutant expressing cell lines are compared to vector-matched controls in order to identify a gene or group genes that is repressed by a given cancer marker. The present invention is not limited to a particular mechanism. Indeed, and understanding of the mechanism is not necessary to practice the present invention. Nonetheless, it is contemplated that genes identified as repressed by a given cancer marker will be increased (de-repressed) upon knock-down of the cancer marker (e.g., by siRNA inhibition).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for characterizing prostate tumor tissue in a subject, comprising:
   a) providing a prostate tumor tissue sample from a subject; and
   b) detecting the presence or absence of an increased level of expression of enhancer of zeste homolog 2 in said sample relative to the level of expression in a normal prostate tissue sample, thereby characterizing said prostate tissue sample.

2. The method of claim 1, wherein said detecting the presence of expression of enhancer of zeste homolog 2 comprises detecting the presence of a enhancer of zeste homolog 2 polypeptide.

3. The method of claim 2, wherein said detecting the presence of a enhancer of zeste homolog 2 polypeptide comprises exposing said enhancer of zeste homolog 2 polypeptide to an antibody specific to said enhancer of zeste homolog 2 polypeptide and detecting the binding of said antibody to said enhancer of zeste homolog 2 polypeptide.

4. The method of claim 1, wherein said subject comprises a human subject.

5. The method of claim 1, wherein said characterizing said prostate tumor tissue comprises identifying a stage of prostate cancer in said prostate tissue.

6. The method of claim 5, wherein said stage is selected from the group consisting of high-grade prostatic intraepithelial neoplasia, benign prostatic hyperplasia, prostate carcinoma, and metastatic prostate carcinoma.

7. The method of claim 1, further comprising the step of c) providing a prognosis to said subject.

8. The method of claim 7, wherein said prognosis comprises a risk of developing metastatic prostate cancer.

9. The method of claim 7, wherein said prognosis comprises the risk of prostate cancer recurrence after prostatectomy.

10. The method of claim 1, further comprising the step of measuring the level of expression of said enhancer of zeste homolog 2 polypeptide.

* * * * *

SEQUENCE LISTING

<160> NUMBER OF SEQ ID NOS: 123

<210> SEQ ID NO 1
<211> LENGTH: 1783
<212> TYPE: DNA
<213> ORGANISM: Homo sapiens

<400> SEQUENCE: 1

```
tcgagcccgc tttccaggga ccctacctga gggcccacag gtgaggcagc ctggcctagc      60
aggccccacg ccaccgcctc tgcctccagg ccgcccgctg ctgcggggcc accatgctcc     120
tgcccaggcc tggagactga cccgaccccg gcactacctc gaggctccgc ccccacctgc     180
tggaccccag gtcccaccc tggcccagga ggtcagccag ggaatcatta acaagaggca     240
gtgacatggc gcagaaggag ggtggccgga ctgtgccatg ctgctccaga cccaaggtgg     300
cagctctcac tgcggggacc ctgctacttc tgacagccat cggggcggca tcctgggcca     360
ttgtggctgt tctcctcagg agtgaccagg agccgctgta cccagtgcag gtcagctctg     420
cggacgctcg gctcatggtc tttgacaaga cggaagggac gtggcggctg ctgtgctcct     480
cgcgctccaa cgccagggta gccggactca gctgcgagga gatgggcttc ctcagggcac     540
tgacccactc cgagctggac gtgcgaacgg cgggcgccaa tggcacgtcg ggcttcttct     600
gtgtggacga ggggaggctg ccccacaccc agaggctgct ggaggtcatc tccgtgtgtg     660
attgccccag aggccgtttc ttggccgcca tctgccaaga ctgtggccgc aggaagctgc     720
ccgtggacca tcgtggga ggccgggaca ccagcttggg ccgtggccg tggcaagtca     780
gccttcgcta tgatggagca cacctctgtg ggggatccct gctctccggg gactgggtgc     840
tgacagccgc ccactgcttc ccggagcgga accgggtcct gtcccgatgg cgagtgtttg     900
ccggtgccgt ggcccaggcc tctccccacg gtctgcagct gggggtgcag gctgtggtct     960
accacgggg ctatcttccc tttcgggacc caacagcga ggagaacagc aacgatattg    1020
ccctggtcca cctctccagt cccctgcccc tcacagaata catccagcct gtgtgcctcc    1080
cagctgccgg ccaggccctg gtggatggca agatctgtac cgtgacgggc tggggcaaca    1140
cgcagtacta tggccaacag gccggggtac tccaggaggc tcgagtcccc ataatcagca    1200
atgatgtctg caatggcgct gacttctatg gaaaccagat caagcccaag atgttctgtg    1260
ctggctaccc cgagggtggc attgatgcct gccagggcga cagcggtggt ccctttgtgt    1320
gtgaggacag catctctcgg acgccacgtt ggcggctgtg tggcattgtg agttggggca    1380
ctggctgtgc cctggcccag aagccaggcg tctacaccaa agtcagtgac ttccgggagt    1440
ggatcttcca ggccataaag actcactccg aagccagcgg catggtgacc cagtctgac    1500
cggtggcttc tcgctgcgca gcctccaggg cccgaggtga tcccggtggt gggatccacg    1560
ctgggccgag gatgggacgt ttttcttctt gggcccggtc cacaggtcca aggacacccct    1620
ccctccaggg tcctctcttc cacagtggcg ggccactca gccccgagac cacccaacct    1680
caccctcctg accccatgt aaatattgtt ctgctgtctg ggactcctgt ctaggtgccc    1740
ctgatgatgg gatgctcttt aaataataaa gatggttttg att                     1783
```

<210> SEQ ID NO 2
<211> LENGTH: 2623
<212> TYPE: DNA
<213> ORGANISM: Homo sapiens

<400> SEQUENCE: 2

```
gaggaggccc gagaggagtc ggtggcagcg gcggcggcgg gaccggcagc agcagcagca      60
gcagcagcag caaccactag cctcctgccc cgcggcgttg cgacgagccc cacgagccgc     120
tcaccccgcc gttctcagcg ctgcccgacc ccgctggcgc gcctcccgcc gcagtcccgg     180
cagcgcctca gttgtcctcc gactcgccct cggccttcgc gcagcgcagc acagccgcac     240
gcaccgcagc acagcacagc acagcccagg catagcttcg gcacagcccc ggctccggct     300
```

-continued

```
cctgcggcag ctcctctggc acgtccctgc gccgacattc tggaggttgg atgctcttgt    360
ccaaaatcaa ctcgcttgcc cacctgcgcg ccgcgccctg caacgacctg cacgccacca    420
agctggcgcc cggcaaggag aaggagcccc tggagtcgca gtaccaggtg ggcccgctac    480
tgggcagcgg cggcttcggc tcggtctact caggcatccg cgtctccgac aacttgccgg    540
tggccatcaa acacgtggag aaggaccgga tttccgactg gggagagctg cctaatggca    600
ctcgagtgcc catggaagtg gtcctgctga agaaggtgag ctcgggtttc tccggcgtca    660
ttaggctcct ggactggttc gagaggcccg acagtttcgt cctgatcctg gagaggcccg    720
agccggtgca agatctcttc gacttcatca cggaaagggg agccctgcaa gaggagctgg    780
cccgcagctt cttctggcag gtgctggagg ccgtgcggca ctgccacaac tgcggggtgc    840
tacaccgcga catcaaggac gaaaacatcc ttatcgacct caatcgcggc gagctcaagc    900
tcatcgactt cgggtcgggg gcgctgctca aggacaccgt ctacacggac ttcgatggga    960
cccgagtgta tagccctcca gagtggatcc gctaccatcg ctaccatggc aggtcggcgg   1020
cagtctggtc cctggggatc ctgctgtatg atatggtgtg tggagatatt cctttcgagc   1080
atgacgaaga gatcatcagg ggccaggttt cttcaggca gaggtctct tcagaatgtc    1140 agcatctcat tagatggtgc ttggccctga gaccatcaga taggccaacc ttcgaagaaa   1200
tccagaacca tccatggatg caagatgttc tcctgcccca ggaaactgct gagatccacc   1260
tccacagcct gtcgccgggg cccagcaaat agcagccttt ctggcaggtc ctcccctctc   1320
ttgtcagatg cccgagggag gggaagcttc tgtctccagc ttcccgagta ccagtgacac   1380
gtctcgccaa gcaggacagt gcttgataca ggaacaacat ttacaactca ttccagatcc   1440
caggcccctg gaggctgcct cccaacagtg gggaagagtg actctccagg ggtcctaggc   1500
ctcaactcct cccatagata ctctcttctt ctcataggtg tccagcattg ctggactctg   1560
aaatatcccg ggggtggggg gtggggtgg cagaaccct gccaatggaa ctctttcttc    1620
atcatgagtt ctgctgaatg ccgcgatggg tcaggtaggg gggaaacagg ttgggatggg   1680
ataggactag cacattttaa gtccctgtca cctcttccga ctctttctga gtgccttctg   1740
tggggactcc ggctgtgctg ggagaaatac ttgaacttgc ctcttttacc tgctgcttct   1800
ccaaaaatct gcctgggttt tgttccctat ttttctctcc tgtcctccct caccccctcc   1860
ttcatatgaa aggtgccatg gaagaggcta cagggccaaa cgctgagcca cctgcccttt   1920
tttctgcctc ctttagtaaa actccgagtg aactggtctt ccttttttggt ttttacttaa   1980 ctgtttcaaa gccaagacct cacacacaca aaaaaatgca caaccaagc aatcaacaga    2040 aaagctgtaa atgtgtgtac agttggcatg gtagtataca aaaagattgt agtgatcta    2100 atttttaaga aattttgcct ttaagttatt ttacctgttt ttgtttcttg ttttgaaaga   2160
tgcgcattct aacctggagg tcaatgttat gtatttattt atttatttat ttggttccct   2220
tcctattcca agcttccata gctgctgccc tagttttctt tcctcctttc ctcctctgac   2280
ttggggacct tttgggggag ggctgcgacg cttgctctgt tgtggggtg acgggactca   2340 ggcgggacag tgctgcagct ccctggcttc tgtggggccc ctcacctact tacccaggtg   2400
ggtcccggct ctgtgggtga tgggaggggc cattgctgac tgtgtatata ggataattat   2460
gaaacacagt tctggatggt gtgccttcca gatcctctct ggggctgtgt tttgagcagc   2520
aggtagcctg ctggttttat ctgagtgaaa tactgtacag gggaataaaa gagatcttat   2580 tttttttta tacttgcgtt tggaataaaa accctttggc ttt                       2623
```

```
<210> SEQ ID NO 3
<211> LENGTH: 2226
<212> TYPE: DNA
<213> ORGANISM: Homo sapiens

<400> SEQUENCE: 3
gaacaatgaa gaaagcccca cagccactgt tgctgagcag ggagaggata ttacctccaa      60
aaaagacagg ggagtattaa agattgtcaa aagagtgggg aatggtgagg aaacgccgat     120
gattggagac aaagtttatg tccattacaa aggaaaattg tcaaatggaa agaagtttga     180
ttccagtcat gatagaaatg aaccatttgt ctttagtctt ggcaaaggcc aagtcatcaa     240
ggcatgggac attggggtgg ctaccatgaa gaaaggagag atatgccatt tactgtgcaa     300
accagaatat gcatatggct cggctggcag tctccctaaa attccctcga atgcaactct     360
cttttttgag attgagctcc ttgatttcaa aggagaggat ttatttgaag atggaggcat     420
tatccggaga accaaacgga aaggagaggg atattcaaat ccaaacgaag gagcaacagt     480
agaaatccac ctggaaggcc gctgtggtgg aaggatgttt gactgcagag atgtggcatt     540
cactgtgggc gaaggagaag accacgacat tccaattgga attgacaaag ctctggagaa     600
aatgcagcgg gaagaacaat gtattttata tcttggacca agatatggtt ttggagaggc     660
agggaagcct aaatttggca ttgaacctaa tgctgagctt atatatgaag ttacacttaa     720
gagcttcgaa aaggccaaag aatcctggga gatggatacc aaagaaaaat tggagcaggc     780
tgccattgtc aaagagaagg gaaccgtata cttcaaggga ggcaaataca tgcaggcggt     840
gattcagtat gggaagatag tgtcctggtt agagatggaa tatggtttat cagaaaagga     900
atcgaaagct tctgaatcat ttctccttgc tgcctttctg aacctggcca tgtgctacct     960
gaagcttaga gaatacacca agctgttga atgctgtgac aaggcccttg actggacag    1020 tgccaatgag aaaggcttgt ataggagggg tgaagcccag ctgctcatga acgagtttga    1080
gtcagccaag ggtgactttg agaaagtgct ggaagtaaac ccccagaata aggctgcaag    1140
actgcagatc tccatgtgcc agaaaaaggc caaggagcac aacgagcggg accgcaggat    1200
atacgccaac atgttcaaga gtttgcaga gcaggatgcc aaggaagagg ccaataaagc    1260
aatgggcaag aagacttcag aagggtcac taatgaaaaa ggaacagaca gtcaagcaat    1320
ggaagaagag aaacctgagg gccacgtatg acgccacgcc aaggagggaa gagtcccagt    1380
gaactcggcc cctcctcaat gggctttccc ccaactcagg acagaacagt gtttaatgta    1440
aagtttgtta tagtctatgt gattctggaa gcaaatggca aaaccagtag cttcccaaaa    1500
acagcccccc tgctgctgcc cggagggttc actgaggggt ggcacgggac cactccaggt    1560
ggaacaaaca gaaatgactg tggtgtggag ggagtgagcc agcagcttaa gtccagctca    1620
tttcagtttc tatcaacctt caagtatcca attcagggtc cctggagatc atcctaacaa    1680 tgtgggggctg ttaggttta cctttgaact ttcatagcac tgcagaaacc tttaaaaaaa    1740
aaatgcttca tgaatttctc cttttcctaca gttgggtagg gtaggggaag gaggataagc    1800
ttttgttttt taaatgactg aagtgctata aatgtagtct gttgcatttt taaccaacag    1860
aacccacagt agagggtct catgtctccc cagttccaca gcagtgtcac agacgtgaaa    1920
gccagaacct cagaggccac ttgcttgctg acttagcctc ctcccaaagt cccctcctc    1980 agccagcctc cttgtgagag tggctttcta ccacacacag cctgtccctg ggggagtaat    2040
tctgtcattc ctaaaacacc cttcagcaat gataatgagc agatgagagt ttctggatta    2100
gcttttccta ttttcgatga agttctgaga tactgaaatg tgaaagagc aatcagaatt    2160
```

| | |
|---|---|
| gtgcttttc tcccctcctc tattccttt agggaataat attcaataca cagtacttcc | 2220 |
| tcccag | 2226 |

<210> SEQ ID NO 4
<211> LENGTH: 7515
<212> TYPE: DNA
<213> ORGANISM: Homo sapiens

<400> SEQUENCE: 4

| | |
|---|---|
| atggaggagg tggtgattgc cggcatgttc gggaagctgc cagagtcgga gaacttgcag | 60 |
| gagttctggg acaacctcat cggcggtgtg gacatggtca cggacgatga ccgtcgctgg | 120 |
| aaggctgggc tctacggcct gccccggcgg tccggcaagc tgaaggacct gtctaggttt | 180 |
| gatgcctcct tcttcggagt ccaccccaag caggcacaca cgatggaccc tcagctgcgg | 240 |
| ctgctgctgg aagctaccta tgaagccatc gtggacggag gcatcaaccc agattcactc | 300 |
| cgaggaacac acactggcgt ctgggtgggc gtgagcggct ctgagacctc ggaggccctg | 360 |
| agccgagacc ccgagacact cgtgggctac agcatggtgg gctgccagcg agcgatgatg | 420 |
| gccaaccggc tctccttctt cttcgacttc agagggccca gcatcgcact ggacacagcc | 480 |
| tgctcctcca gcctgatggc cctgcagaac gcctaccagg ccatccacag cgggcagtgc | 540 |
| cctgccgcca tcgtgggggg catcaacgtc tgctgaagc ccaacacctc cgtgcagttc | 600 |
| ttgaggctgg ggatgctcag ccccgagggc acctgcaagg ccttcgacac agcggggaat | 660 |
| gggtactgcc gctcggaggg tgtggtggct gtcctgctga ccaagaagtc cctggcccgg | 720 |
| aaggtctaca ccaccatcct gaacaaaggc accaatacag atggcttcaa ggagcaaggc | 780 |
| gtgaccttcc ctcaggatat ccaggagcag cctatccgct cgttgtacca gtcggccgga | 840 |
| gtggcccctg agtcatttga atacatcgaa gcccacggac aggcaccaa ggtgggcgac | 900 |
| ccccaggagc gtaatggcat cacccgagcc tgtgcgcca cccgccagga gccgctgctc | 960 |
| atcggctcca ccaagtccaa catggggcac ccggagccag cctcggggct cgacgccctg | 1020 |
| gccaaggtgc tgctgtccct ggagcacggg ctctgggccc caacctgca cttccatagc | 1080 |
| cccaaccctg agatcccagc gctgttggat ggcggctgc aggtggtgga ccagcccctg | 1140 |
| cccgtccgtg gcggcaacgt gggcatcaac tcctttggct cgggggctc aacatgcac | 1200 |
| atcatcctga ggcccaacac gcagtccgcc cccgcacccg cccacatgc cacccctgccc | 1260 |
| cgtctgctgc gggccagcgg acgcacccct gaggccgtgc agaagctgct ggagcagggc | 1320 |
| ctccggcaca gccagggcct ggcttcctg agcatgctga cgacatcgc ggctgtcccc | 1380 |
| gccaccgcca tgcccttccg tggctacgct gtgctgggtg gtgagacgcg gtggcccaga | 1440 |
| gtgcagcagg tgcccgctgg cgagcgcccg ctctggttca tctgctctgg gatgggcaca | 1500 |
| cagtggcgtg gaatggggct gagccttatg cgcctggacc gcttccgaga ttccatccta | 1560 |
| cgctccgatg aggctgtgaa ccgattcggc ctgaaggtgt cacagctgct gctgagcaca | 1620 |
| gacgagagca cctttgatga catcgtccat cgtttgtga gcctgactgc catccagata | 1680 |
| ggcctcatag acctgctgag ctgcatggga cctgaggcag atggcatcgt cggccactcc | 1740 |
| ctggggggagt ggctgtcggt acgcgacggc tgcctgtccc aggaggaggc cgtcctcgct | 1800 |
| gcctactgga ggggacagtg catcaaagaa gccccacttc cgccggcgc catggcagcc | 1860 |
| gtgggcttgt cctgggagga gtgtaaacag cgctgccccc tgcggtggt gccgcctgc | 1920 |
| cacaactcca aggacacagt caccatctcg ggacctcagg ccccgtgtt tgagttcgtg | 1980 |
| gagcagctga ggaaggaggg tgtgtttgcc aaggaggtgc ggaccggcgg tatggccttc | 2040 |

-continued

```
cactcctact tcatggaggc catcgcaccc ccactgctgc aggagctcaa gaaggtgatc    2100
cgggagccga agccacgttc agcccgctgg ctcagcacct ctatcccga ggcccagtgg     2160 cacagcagcc tggcacgcac gtcttccgcc gagtacaatg tcaacaacct ggtgagccct    2220
gtgctgttcc aggaggccct gtggcacgtg cctgagcacg cggtggtgct ggagatcgcc    2280
ccgaccccgt gccctcaggc tgtcctgaag cgggtccgta agccgagctg caccatcatc    2340
ccccgtatga agaaggatca cagggacaac ctggagttct tcctggccgg catcggcagg    2400
ctgcacctct caggcatcga cgccaacccc aatgccttgt tcccacctgt ggagtcccca    2460
gctccccgag gaactcccct catctcccca ctcatcaagt gggaccacag cctggcctgg    2520
gacgcgccgg ccgccgagga cttccccaac ggttcaggtt ccccctcagc caccatctac    2580
acatgcacac caagctccga gtctcctgac cgctacctgg tggaccacac catcgacggt    2640
cgcgtcctct cccccgccac tggctacctg agcatagtgt ggaagacgct ggcccgcgcc    2700
tgggctgggc tcgagcagct gcctgtggtg tttgaggatg tggtgcagca ccaggccacc    2760
atcctgccca agactgggac agtgtccttg gaggtacggc tcctggaggc caccggtgcc    2820
ttcgaggtgt cagagaacgg caacctggta gtgagtggga aggtgtacca gtgggatgac    2880
cctgacccca ggctcttcga ccacccggaa agtccccacc ccaattcccc acggagtccc    2940
ctcttcctgg cccaggcaga agtttacaag gagctgcgtc tgcgtggcta cgactacggc    3000
cctcatttcc agggcatcct ggaggccagc ctggaaggtg actcggggag gctgctgtgg    3060
aaggataact gggtgagctt catggacacc atgctgcaga tgtccatcct gggctcggcc    3120
aagcacggcc tgtacctacc cacccgtgtc accgccatcc acatcgaccc tgccacccac    3180
aggcagaagc tgtacacact gcaggacaag gcccaagtgg ctgacgtggt ggtgagcagg    3240
tggccgaggg tcacagtggc gggaggcgtc cacatctccg ggctccacac tgagtcggcc    3300
ccgcggcggc acgaggagca gcaggtgccc atcctggaga agttttgctt cactccccac    3360
acggaggagg ggtgcctgtc tgagcacgct gccctcgagg aggagctgca actgtgcaag    3420
gggctggtcg aggcactcga gaccaaggtg acccagcagg ggctgaagat ggtggtgccg    3480
gactggacgg ggcccagatc cccccgggac ccctcacagc aggaactgcc ccggctgttg    3540
tcggctgcct gcaggcttca gctcaacggg aacctgcagc tggagctggc gcaggtgctg    3600
gcccaggaga ggcccaagct gccagaggac cctctgctca gcggcctcct ggactccccg    3660
gcactcaagg cctgcctgga cactgccgtg gagaacatgc ccagcctgaa gatgaaggtg    3720
gtggaggtgc tggccggcca cggtcacctg tattcccgca tcccaggcct gctcagcccc    3780
catcccctgc tgcagctgag ctacacggcc accgaccgcc accccaggcc cctgaggct    3840 gcccaggccg agctgcagca gcacgacgtt gcccagggcc agtgggatcc cgcagaccct    3900 gccccccagcg ccctgggcag cgcggacctc ctggtgtgca actgtgctgt ggctgccctc    3960
ggggacccgg cctcagctct cagcaacatg gtggctgccc tgagagaagg gggctttctg    4020
ctcctgcaca cactgctccg gggcaccct cgggacatcg tggccttcct cacctccact    4080
gagccgcagt atggccaggg catcctgagc caggacgcgt gggagagcct cttctccagg    4140
gtgtcgctgc gcctggtggg cctgaagaag tccttctacg cgccacgct cttcctgtgc    4200 cgccggccca ccccgcagga cagccccatc ttcctgccgg tggacgatac cagcttccgc    4260
tgggtggagt ctctgaaggg catcctggct gacgaagact cttcccggcc tgtgtggctg    4320
aaggccatca actgtgccac ctcgggcgtg gtgggcttgg tgaactgtct ccgccgagag    4380
```

```
cccggcggaa ccgtccggtg tgtgctgctc tccaacctca gcagcacctc ccacgtcccg    4440
gaggtggacc cgggctccgc agaactgcag aaggtgttgc agggagacct ggtgatgaac    4500
gtctaccgcg acgggccctg gggggttttc cgccacttcc tgctggagga caagcctgag    4560
gagccgacgg cacatgcctt tgtgagcacc ctcacccggg gggacctgtc ctccatccgc    4620
tgggtctgct cctcgctgcg ccatgccagc cccacctgcc ctggcgccca gctctgcacg    4680
gtctactacg cctccctcaa cttccgcgac atcatgctgg ccactggcaa gctgtcccct    4740
gatgccatcc cagggaagtg gacctcccag gacagcctgc taggtatgga gttctcgggc    4800
cgagacgcca gcggcaagcg tgtgatggga ctggtgcctg ccaagggcct ggccacctct    4860
gtcctgctgt caccggactt cctctgggat gtgccttcca actggacgct ggaggaggcg    4920
gcctcggtgc ctgtcgtcta cagcacggcc tactacgcgc tggtggtgcg tgggcgggtg    4980
cgccccgggg agacgctgct catccactcg ggctcgggcg cgtgggcca ggccgccatc    5040 gccatcgccc tcagtctggg ctgccgcgtc ttcaccaccg tggggtcggc tgagaagcgg    5100
gcgtacctcc aggccaggtt cccccagctc gacagcacca gcttcgccaa ctcccgggac    5160
acatccttcg agcagcatgt gctgtggcac acgggcggga agggcgttga cctggtcttg    5220
aactccttgg cggaagagaa gctgcaggcc agcgtgaggt gcttcggtac gcacggtcgc    5280
ttcctggaaa ttggcaaatt cgaccttcct cagaaccacc cgctcggcat ggctatcttc    5340
ctgaagaacg tgacattcca cggggtccta ctggatgcgt tcttcaacga gagcagtgct    5400
gactggcggg aggtgtgggc gcttgtcgag gccgccatcc gggatggggt ggtacggccc    5460
ctcaagtgca cggtgttcca tggggcccag gtggaggacg ccttccgcta catggcccaa    5520
gggaagcaca ttggcaaagt cgtcgtgcag gtgcttgcgg aggagccggc agtgctgaag    5580
ggggccaaac ccaagctgat gtcggccatc tccaagacct tctgcccggc ccacaagagc    5640
tacatcatcg ctggtggtct gggtggcttc ggcctggagt tggcgcagtg gctgatacag    5700
cgtggggtgc agaagctcgt gttgacttct cgctccggga tccggacagg ctaccaggcc    5760
aagcaggtcc gccggtggag cgccaggggg ctacaggtgc aggtgtccac cagcaacatc    5820
agctcactgg aggggcccg ggcctcatt gccgaggcgg cgcagcttgg gcccgtgggg    5880
ggcgtcttca acctgccgt ggtcttgaga gatggcttgc tggagaacca gaccccagag    5940
ttcttccagg acgtctgcaa gcccaagtac agcggcaccc tgaacctgga cagggtgacc    6000
cgagaggcgt gccctgagct ggactacttt gtggtcttct cctctgtgag ctgcgggcgt    6060
ggcaatgcgg acagagcaa ctacggctt gccaattccg ccatggagcg tatctgtgag    6120
aaacgccggc acgaaggcct cccaggcctg gccgtgcagt ggggcgccat cggcaccgtg    6180 ggcatttttgg tggagacgat gagcaccaac gacacgatcg tcagtggcac gctgcccacg    6240
cgcattggcg tccttggcct ggaggtgctg gacctcttcc tgaaccagcc ccacatggtc    6300
ctgagcagct ttgtgctggc tgagaaggct gcggcctata gggacaggga cagccagcgg    6360
gacctggtgg aggccgtggc acacatcctg gcatccgcg acttggctgc tgtcaacctg    6420
ggcggctcac tggcggacct gggcctggac tcgctcatga gcgcgccggt gcgccagacg    6480
ctggagcgtg agctcaacct ggtgctgtcc gtgcgcgagg tgcggcaact cacgctccgg    6540
aaactgcagg agctgtcctc aaaggcggat gaagccagcg agctggcatg ccccacgccc    6600
aaggaggatg gtctggccca gcagcagact cagctgaacc tgcgctccct gctggtgaaa    6660
ccggagggcc ccaccctgat gcggctcaac tccgtgcaga gctcggagcg gccctgttc    6720 ctggtgcacc caatcgaggc taccaccgtg ttccacagcc tcggtcccgg tctcagcatc    6780
```

-continued

| | |
|---|---|
| cccacctatg gcctgcagtg caccccggct gcgccccttg acagcatcca cagcctggct | 6840 |
| gcctactaca tcgactgcat caggcaggtg cagcccgagg gccccstaccg cgtggccggc | 6900 |
| tactcctacg gggcctgcgt ggcctttgaa atgtgctccc agctgcaggc ccagcagagc | 6960 |
| ccagccccca cccacaacag cctcttcctg ttcgacggct cgcccaccta cgtactggcc | 7020 |
| tacacccaga gctaccgggc aaagctgacc ccaggctgta aggctgaggc tgagacggag | 7080 |
| gccatatgct tcttcgtgca gcagttcacg gacatggagc acaacagggt gctggaggcg | 7140 |
| ctgctgccgc tgaagggcct agaggagcgt gtggcagccg ccgtggacct gatcatcaag | 7200 |
| agccaccagg gcctggaccg ccaggagctg agctttgcgg cccggtcctt ctactacagg | 7260 |
| ctgcgtgccg ctgaccagta tacccccaag gccaagtaca gtggcaacgt gatgctactg | 7320 |
| cgggccaaga cgggtggccg ctacggcgag gacctgggcg cggactacaa cctctcccag | 7380 |
| gtatgcgacg ggaaagtatc cgtccatatc atcgagggtg accaccgcac gctgctggag | 7440 |
| ggcagcggcc tggagtccat catcagcatc atccacagct ccctggctga gccacgtgtg | 7500 |
| agtcgggagg gctag | 7515 |

<210> SEQ ID NO 5
<211> LENGTH: 2653
<212> TYPE: DNA
<213> ORGANISM: Homo sapiens

<400> SEQUENCE: 5

| | |
|---|---|
| ctcaaaaggg gccggatttc cttctcctgg aggcagatgt tgcctctctc tctcgctcgg | 60 |
| attggttcag tgcactctag aaacactgct gtggtggaga aactggaccc caggtctgga | 120 |
| gcgaattcca gcctgcaggg ctgataagcg aggcattagt gagattgaga gagacttttac | 180 |
| cccgccgtgg tggttggagg gcgcgcagta gagcagcagc acaggcgcgg gtcccgggag | 240 |
| gccggctctg ctcgcgccga gatgtggaat ctccttcacg aaaccgactc ggctgtggcc | 300 |
| accgcgcgcc gcccgcgctg gctgtgcgct ggggcgctgg tgctggcggg tggcttcttt | 360 |
| ctcctcggct tcctcttcgg gtggttttata aaatcctcca atgaagctac taacattact | 420 |
| ccaaagcata atatgaaagc attttttggat gaattgaaag ctgagaacat caagaagttc | 480 |
| ttatataatt ttacacagat accacatttta gcaggaacag aacaaaactt tcagcttgca | 540 |
| aagcaaattc aatcccagtg gaaagaattt ggcctggatt ctgttgagct agcacattat | 600 |
| gatgtcctgt tgtcctaccc aaataagact catcccaact acatctcaat aattaatgaa | 660 |
| gatggaaatg agattttcaa cacatcatta tttgaaccac ctcctccagg atatgaaaat | 720 |
| gtttcggata ttgtaccacc tttcagtgct ttctctcctc aaggaatgcc agaggcgat | 780 |
| ctagtgtatg ttaactatgc acgaactgaa gacttcttta aattggaacg ggacatgaaa | 840 |
| atcaattgct ctgggaaaat tgtaattgcc agatatgggg aagttttcag aggaaataag | 900 |
| gttaaaaatg cccagctggc aggggccaaa ggagtcattc tctactccga ccctgctgac | 960 |
| tactttgctc ctgggtgaa gtcctatcca gatggttgga tcttcctgg aggtggtgtc | 1020 |
| cagcgtggaa atatcctaaa tctgaatggt gcaggagacc ctctcacacc aggttaccca | 1080 |
| gcaaatgaat atgcttatag gcgtggaatt gcagaggctg ttggtcttcc aagtattcct | 1140 |
| gttcatccaa ttggatacta tgatgcacag aagctcctag aaaaaatggg tggctcagca | 1200 |
| ccaccagata gcagctggag aggaagtctc aagtgccct acaatgttgg acctggcttt | 1260 |
| actggaaact tttctacaca aaaagtcaag atgcacatcc actctaccaa tgaagtgaca | 1320 |

-continued

| | |
|---|---|
| agaatttaca atgtgatagg tactctcaga ggagcagtgg aaccagacag atatgtcatt | 1380 |
| ctgggaggtc accgggactc atgggtgttt ggtggtattg accctcagag tggagcagct | 1440 |
| gttgttcatg aaattgtgag gagctttgga acactgaaaa aggaagggtg agacctaga | 1500 |
| agaacaattt tgtttgcaag ctgggatgca gaagaatttg gtcttcttgg ttctactgag | 1560 |
| tgggcagagg agaattcaag actccttcaa gagcgtggcg tggcttatat taatgctgac | 1620 |
| tcatctatag aaggaaacta cactctgaga gttgattgta caccgctgat gtacagcttg | 1680 |
| gtacacaacc taacaaaaga gctgaaaagc cctgatgaag ctttgaaggc aaatctctt | 1740 |
| tatgaaagtt ggactaaaaa aagtccttcc ccagagttca gtggcatgcc caggataagc | 1800 |
| aaattgggat ctggaaatga ttttgaggtg ttcttccaac gacttggaat tgcttcaggc | 1860 |
| agagcacggt atactaaaaa ttgggaaaca aacaaattca gcggctatcc actgtatcac | 1920 |
| agtgtctatg aaacatatga gttggtggaa aagtttatg atccaatgtt taaatatcac | 1980 |
| ctcactgtgg cccaggttcg aggagggatg gtgtttgagc tagccaattc catagtgctc | 2040 |
| ccttttgatt gtcgagatta tgctgtagtt ttaagaaagt atgctgacaa atctacagt | 2100 |
| atttctatga acatccaca ggaaatgaag acatacagtg tatcatttga ttcacttttt | 2160 |
| tctgcagtaa agaatttac agaaattgct tccaagttca gtgagagact ccaggacttt | 2220 |
| gacaaaagca acccaatagt attaagaatg atgaatgatc aactcatgtt tctggaaaga | 2280 |
| gcatttattg atccattagg gttaccagac aggccttttt ataggcatgt catctatgct | 2340 |
| ccaagcagcc acaacaagta tgcaggggag tcattcccag gaatttatga tgctctgttt | 2400 |
| gatattgaaa gcaaagtgga cccttccaag gcctggggag aagtgaagag acagatttat | 2460 |
| gttgcagcct tcacagtgca ggcagctgca gagactttga gtgaagtagc ctaagaggat | 2520 |
| tctttagaga atccgtattg aatttgtgtg gtatgtcact cagaaagaat cgtaatgggt | 2580 |
| atattgataa attttaaaat tggtatattt gaaataaagt tgaatattat atataaaaaa | 2640 |
| aaaaaaaaaa aaa | 2653 |

<210> SEQ ID NO 6
<211> LENGTH: 1750
<212> TYPE: DNA
<213> ORGANISM: Homo sapiens

<400> SEQUENCE: 6

| | |
|---|---|
| cctcactgac tataaaagaa tagagaagga agggcttcag tgaccggctg cctggctgac | 60 |
| ttacagcagt cagactctga caggatcatg gctatgatga aggtccaggg gggacccagc | 120 |
| ctgggacaga cctgcgtgct gatcgtgatc ttcacagtgc tcctgcagtc tctctgtgtg | 180 |
| gctgtaactt acgtgtactt taccaacgag ctgaagcaga tgcaggacaa gtactccaaa | 240 |
| agtggcattg cttgtttctt aaaagaagat gacagttatt gggaccccaa tgacgaagag | 300 |
| agtatgaaca gcccctgctg gcaagtcaag tggcaactcc gtcagctcgt tagaaagatg | 360 |
| attttgagaa cctctgagga aaccatttct acagttcaag aaaagcaaca aaatatttct | 420 |
| ccctagtga gagaaagagg tcctcagaga gtagcagctc acataactgg gaccagagga | 480 |
| agaagcaaca cattgtcttc tccaaactcc aagaatgaaa aggctctggg ccgcaaaata | 540 |
| aactcctggg aatcatcaag gagtgggcat tcattcctga gcaacttgca cttgaggaat | 600 |
| ggtgaactgg tcatccatga aaagggtttt tactacatct attcccaaac atactttcga | 660 |
| tttcaggaga aaataaaaga aaacacaaag aacgacaaac aaatggtcca atatatttac | 720 |
| aaatacacaa gttatcctga ccctatattg ttgatgaaaa gtgctagaaa tagttgttgg | 780 |

-continued

| | |
|---|---|
| tctaaagatg cagaatatgg actctattcc atctatcaag ggggaatatt tgagcttaag | 840 |
| gaaaatgaca gaattttttgt ttctgtaaca aatgagcact tgatagacat ggaccatgaa | 900 |
| gccagttttt ttggggcctt tttagttggc taactgacct ggaaagaaaa agcaataacc | 960 |
| tcaaagtgac tattcagttt tcaggatgat acactatgaa gatgtttcaa aaaatctgac | 1020 |
| caaaacaaac aaacagaaaa cagaaaacaa aaaaacctct atgcaatctg agtagagcag | 1080 |
| ccacaaccaa aaaattctac aacacacact gttctgaaag tgactcactt atcccaagag | 1140 |
| aatgaaattg ctgaaagatc tttcaggact ctacctcata tcagtttgct agcagaaatc | 1200 |
| tagaagactg tcagcttcca aacattaatg caatggttaa catcttctgt ctttataatc | 1260 |
| tactccttgt aaagactgta gaagaaagag caacaatcca tctctcaagt agtgtatcac | 1320 |
| agtagtagcc tccaggtttc cttaagggac aacatcctta agtcaaaaga gagaagaggc | 1380 |
| accactaaaa gatcgcagtt tgcctggtgc agtggctcac acctgtaatc ccaacatttt | 1440 |
| gggaacccaa ggtgggtaga tcacgagatc aagagatcaa gaccatagtg accaacatag | 1500 |
| tgaaacccca tctctactga aagtacaaaa attagctggg tgtgttggca catgcctgta | 1560 |
| gtcccagcta cttgagaggc tgaggcaaga gaattgtttg aacccgggag gcagaggttg | 1620 |
| cagtgtggtg agatcatgcc actacactcc agcctggcga cagagcgaga cttggtttca | 1680 |
| aaaaaaaaa aaaaaaaaac ttcagtaagt acgtgttatt tttttcaata aaattctatt | 1740 |
| acagtatgtc | 1750 |

<210> SEQ ID NO 7
<211> LENGTH: 6597
<212> TYPE: DNA
<213> ORGANISM: Homo sapiens

<400> SEQUENCE: 7

| | |
|---|---|
| ggtcacatga ctccagtcta gctcgcattg cggctcccgc ccgggcgagt tctcgccccc | 60 |
| gcgcggccgt tgccgaggag acggcgcatg tcccgccgcg cgttgccccc tctgcagtac | 120 |
| ccccgcccct cttctcccac cacaatgaga tcctaagatg gcggtggctg cggcggttgg | 180 |
| cgctgcgtag ctgaggtcga aaaggcggcc actgggccg aggcagccag gaaacgtgtg | 240 |
| ggcctctctg ctgcggtctc cgagggccga ccgctgccgg cggcgggtcg tgggggctga | 300 |
| ctgtcgctct gcctttgaca ggagaggctg cttcttgtag aggaaacagc tttgaagtgt | 360 |
| ggagcgggaa aggagcagtt tctgagctgc aaaaactagt ttctaaacag agagttaatt | 420 |
| gttaaatcca gtatggccac aggaggaggt ccctttgaag atggcatgaa tgatcaggat | 480 |
| ttaccaaact ggagtaatga gaatgttgat gacaggctca acaatatgga ttggggtgcc | 540 |
| caacagaaga aagcaaatag atcatcagaa aagaataaga aaaagtttgg tgtagaaagt | 600 |
| gataaaagag taaccaatga tatttctccg gagtcgtcac caggagttgg aaggcgaaga | 660 |
| acaaagactc cacatacgtt cccacacagt agatacatga gtcagatgtc tgtcccagag | 720 |
| caggcagaat tagagaaact gaaacagcgg ataaacttca gtgatttaga tcagagaagc | 780 |
| attggaagtg attcccaagg tagagcaaca gctgctaaca acaaacgtca gcttagtgaa | 840 |
| aaccgaaagc ccttcaactt tttgcctatg cagattaata ctaacaagag caaagatgca | 900 |
| tctacaagtc ccccaaacag agaaacgatt ggatcagcac agtgtaaaga gttgtttgct | 960 |
| tctgctttaa gtaatgacct cttgcaaaac tgtcaggtgt ctgaagaaga tgggagggga | 1020 |
| gaacctgcaa tggagagcag ccagattgta agcaggcttg ttcaaattcg cgattatatt | 1080 |

```
actaaagcta gttccatgcg ggaagatctt gtagagaaaa atgagagatc tgctaatgtt    1140
gagcgcctta ctcatctaat agatcacctt aaagaacaag agaagtcata tatgaaattt    1200
cttaaaaaaa tccttgccag agatcctcag caggagccta tggaagagat agaaaatttg    1260
aagaaacaac atgatttatt aaaaagaatg ttacaacagc aggagcaact aagagctcta    1320
cagggacggc aggctgcact tctagctctg caacataaag cagagcaagc tattgcagtg    1380
atggatgatt ctgttgttgc agaaactgca ggtagcttat ctggcgtcag tatcacatct    1440
gaactaaatg aagaattgaa tgacttaatt cagcgttttc ataatcagct tcgtgattct    1500
cagcctccag ctgttccaga caatagaaga caggcagaaa gtctttcatt aactagggag    1560
gtttcccaga gcaggaaacc atcagcttca gaacgtttac ctgatgagaa agtcgaactt    1620
tttagcaaaa tgagagtgct acaggaaaag aaacaaaaaa tggacaaatt gcttggagaa    1680
cttcatacac ttcgagatca gcatcttaac aattcatcat cctctccaca aaggagtgtc    1740
gatcagagaa gtacttcagc tccctctgct tctgtaggct tggcaccggt tgtcaatgga    1800
gaatccaata gcctcacatc atctgttcct tatcctactg cttctctagt atctcagaat    1860
gagagtgaaa acgaaggcca cctcaatcca tctgaaaaac tccagaagtt aaatgaagtt    1920
cgaaagagat tgaatgagct aagagaatta gttcattatt atgaacaaac gtcagacatg    1980
atgacagatg ctgtgaatga aaacaggaaa gatgaagaaa ctgaagagtc agaatatgat    2040
tctgagcatg aaaattccga gcctgttact aacattcgaa atccacaagt agcttccact    2100
tggaatgaag taaatagtca tagtaatgca cagtgtgttt ctaataatag agatgggcga    2160
acagttaatt ctaattgtga aattaacaac agatctgctg ccaacataag ggctctaaac    2220
gtgcctcctt ctttagattg tcgatataat agagaagggg aacaggagat tcatgttgca    2280
caaggtgaag atgatgagga ggaggaggaa gaagcagaag aggagggagt cagtggagct    2340
tcattatcta gtcacaggag cagtctggtt gatgagcatc cagaagatgc tgaatttgaa    2400
cagaagatca accgacttat ggctgcaaaa cagaaactta gacagttaca agatcttgtt    2460
gctatggtac aggatgatga tgcagctcaa ggagttatct ctgccagtgc atcaaatttg    2520
gatgatttct acccagcaga agaagacacc aagcaaaatt caaataacac tagaggaaat    2580
gccaataaaa cacagaaaga tactggagta aatgaaaagg caagagagaa attttatgag    2640
gctaaactac agcagcaaca gagagagcta aaacaattgc aggaagaaag aaagaaactg    2700
attgacattc aggagaaaat tcaagcattg caaacggcat gccctgactt acagctgtca    2760
gctgctagtg tgggtaactg tcccaccaaa aaatatatgc cagctgttac ttcaaccccca    2820 actgttaatc aacacgagac cagtacaagc aaatctgttt ttgagcctga agattcttca    2880
atagtagata atgagttgtg gtcagaaatg agaagacatg aaatgttgag ggaggagctg    2940
cgacagagaa gaaagcagct tgaagctctg atggctgaac atcagaggag gcaaggtcta    3000
gctgaaactg catctccagt ggctgtgtca ttgagaagtg atggatctga gacctatgt    3060 actcctcagc aaagtagaac agaaaaaacg atggcaactt ggggagggtc tacccagtgt    3120
gcactagatg aagaaggaga tgaagacggt tacctttctg aaggaattgt tcggacagat    3180
gaagaggagg aagaagagca agatgccagt tccaatgata acttttctgt gtgtccttct    3240
racagtgtga atcataactc ctacaatgga aaggaaacta aaaataggtg gaagaacaat    3300 tgccccttttt cggcagatga aaattatcgt cctttagcca agacaaggca acagaatatc    3360
agcatgcaac ggcaagaaaa ccttcgttgg gtgtcagagc tctcttacgt agaagagaaa    3420
gaacaatggc aagaacaaat caatcagcta aagaaacagc ttgatttag tgtcagtatt    3480
```

```
tgtcagactt tgatgcaaga ccagcagact ctatcttgtc tgctacaaac tcttctcacg   3540
ggtccttaca gtgttatgcc cagcaatgtt gcatctcctc aagtacactt cataatgcac   3600
cagttgaacc agtgctatac tcagctaaca tggcaacaga ataatgttca gaggttgaaa   3660
caaatgctaa atgaacttat gcgccagcaa aatcagcatc cagaaaaacc tggaggcaag   3720
gaaagaggca gtagtgcatc gcaccctcct tctcccagtt tattttgtcc tttcagcttt   3780
ccaacacagc ctgtaaatct cttcaatata cctggattta ctaacttttc atcatttgca   3840
ccaggtatga atttcagccc tttatttcct tctaattttg gagattttc tcagaatatc    3900 tctacaccca gtgaacagca gcaacccta gcccagaatt cttcaggaaa aacagaatat   3960
atggcttttc caaaaccttt tgaaagcagt tcctctattg gagcagagaa accaaggaat   4020
aaaaaactgc ctgaagagga ggtggaaagc agtaggacac catggttata tgaacaagaa   4080
ggtgaagtag agaaaccatt tatcaagact ggattttcag tgtctgtaga aaatctaca    4140 agtagtaacc gcaaaaatca attagataca aacggaagaa gacgccagtt tgatgaagaa   4200
tcactggaaa gctttagcag tatgcctgat ccagtagatc aacaacagt gactaaaaca    4260 ttcaagacaa gaaaagcgtc tgcacaggcc agcctggcat ctaaagataa aactcccaag   4320
tcaaaaagta agaagaggaa ttctactcag ctgaaaagca gagttaaaaa catcaggtat   4380
gaaagtgcca gtatgtctag cacatgtgaa ccttgcaaaa gtaggaacag acattcagcc   4440
cagactgaag agcctgttca agcaaaagta ttcagcagaa agaatcatga gcaactggaa   4500
aaaataataa aatgtaatag gtctacagaa atatcttcag aaactgggag tgattttccc   4560
atgtttgaag ctttgcgaga tactatttat tctgaagtag ctacattaat ttctcaaaat   4620
gaatctcgtc cacattttct tattgaactc ttccatgagc tgcagctact aaacacagac   4680
tacttgagac agagggcttt atatgcattg caggacatag tatccagaca tatttctgag   4740
agccatgaaa aaggagaaaa tgtaaagtca gtaaactctg gtacttggat agcatcaaac   4800
tcagaactta ctcctagtga gagccttgct actactgatg atgaaacttt tgagaagaac   4860
tttgaaagag aaacccataa aataagtgag caaaatgatg ctgataatgc tagtgtcctg   4920
tctgtatcat caaattttga gccttttgca acagatgatc taggtaacac cgtgattcac   4980
ttagatcaag cattagccag aatgagagaa tatgagcgta tgaagactga ggctgaaagt   5040
aactcaaata tgagatgcat ctgcaggatt attgaggatg gagatggtgc tggtgcaggt   5100
actacagtta ataatttaga agaaactccc gttattgaaa atcgtagttc acaacaacct   5160
gtaagtgaag tttctaccat cccatgtcct agaattgata ctcagcagct ggaccggcaa   5220
attaaagcaa ttatgaaaga agtcattcct ttttttgaagg agcacatgga tgaagtatgc   5280
tcctcgcagc ttctaacttc agtaaggcgc atggttttga cccttaccca gcaaaatgat   5340
gagagcaaag agtttgtaaa gttctttcat aaacaacttg aagtatatt acaggattca    5400 ctggcaaaat tgctggcag aaaactgaaa gactgtggag aagatcttct tgtagagata    5460
tctgaagtgt tgttcaatga attggctttc tttaagctta tgcaagattt ggataataat   5520
agtataactg ttaaacagag atgcaaaagg aaaatagaag caactggagt gatacaatct   5580
tgtgccaaag agctaaaagg attcttgaag atcatggctc acctgctgga gagattgatg   5640
atgaagacaa agacaaggat gaaactgaaa cagttaagca gactcaaaca tctgaggtgt   5700
atgatggtcc caaaaatgta agatctgata tttctgatca agaggaagat gaagaaagtg   5760
aaggatgtcc agtgtctatt aatttgtcta aagctgaaac tcaggctta actaattatg     5820
```

```
gaagtggaga agatgaaaat gaggatgaag aaatggaaga atttgaagaa ggccctgtgg      5880
atgtccagac ttccctccag gctaacactg aagctactga agaaaatgaa catgatgaac      5940
aggtcctaca acgtgacttt aaaaagacag cagaaagcaa aaatgtccca ttggaacgag      6000
aagccactag taaaaatgac caaaataact gtcctgtgaa accctgttac ctcaatatct      6060
tggaagatga gcaacctttta aatagtgctg cccataagga gtcacctcct actgttgatt      6120
caactcaaca gcctaaccct ttgccgttac gtttacctga aatggaaccc ttagtgccta      6180
gagtcaaaga agttaaatct gctcaggaaa ctcctgaaag ctctctggct ggaagtcctg      6240
atactgaatc tccagtgtta gtgaatgact atgaagcaga atctggtaat ataagtcaaa      6300
agtctgatga agaagatttt gtaaaagttg aagatttacc actgaaactg acaatatatt      6360
cagaggcaga tctaagaaag aaaatggtag aagaagaaca gaaaaaccat ttatctggtg      6420
aaatatgtga aatgcagacc gaagaattag ctggaaattc tgagacacta aaagaacctg      6480
aaacggtggg agcccagagt atatgagatg tcttcagagg ctcatctaac tctgtccttta     6540 catactcaat gcatatatga aaacaatact aaataaacat ctgatctgta taaaaat         6597

<210> SEQ ID NO 8
<211> LENGTH: 479
<212> TYPE: DNA
<213> ORGANISM: Homo sapiens

<400> SEQUENCE: 8
ctccaaaggc aaaaatctcc agccctacag agactgagcg gtgcatcgag tccctgattg       60
ctgtcttcca gaagtatgct ggaaaggatg gttataacta cactctctcc aagacagagt      120
tcgtaagctt catgaataca gaactagctg ccttcacaaa gaaccagaag gaccctggtg      180
tccttgaccg catgatgaag aaactggaca ccaacagtga tggtcagcta gatttctcag      240
aatttcttaa tctgattggt ggcctagcta tggcttgcca tgactccttc ctcaaggctg      300
tcccttccca gaagcggacc tgaggacccc ttggccctgg ccttcaaacc caccccttt      360 ccttccagcc tttctgtcat catctccaca gcccacccat cccctgagca cactaaccac      420
ctcatgcagg ccccacctgc caatagtaat aaagcaatgt cactttttta aaacatgaa      479

<210> SEQ ID NO 9
<211> LENGTH: 2465
<212> TYPE: DNA
<213> ORGANISM: Homo sapiens

<400> SEQUENCE: 9
gccgcttcct gcctggattc cacagcttcg cgccgtgtac tgtcgcccca tccctgcgcg       60
cccagcctgc caagcagcgt gccccggttg caggcgtcat gcagcgggcg cgacccacgc      120
tctgggccgc tgcgctgact ctgctggtgc tgctccgcgg gccgccggtg gcgcgggctg      180
gcgcgagctc ggcgggcttg ggtcccgtgg tgcgctgcga gccgtgcgac gcgcgtgcac      240
tggcccagtg cgcgcctccg cccgccgtgt gcgcggagct ggtgcgcgag ccgggctgcg      300
gctgctgcct gacgtgcgca ctgagcgagg gccagccgtg cggcatctac accgagcgct      360
gtggctccgg ccttcgctgc cagccgtcgc ccgacgaggc gcgaccgctg caggcgctgc      420
tggacggccg cggggctctgc gtcaacgcta gtgccgtcag ccgcctgcgc gcctacctgc      480
tgccagcgcc gccagctcca ggaaatgcta gtgagtcgga ggaagaccgc agcgccggca      540
gtgtggagag cccgtccgtc tccagcacgc accgggtgtc tgatcccaag ttccaccccc      600
tccattcaaa gataatcatc atcaagaaag ggcatgctaa agacagccag cgctacaaag      660
```

-continued

```
ttgactacga gtctcagagc acagataccc agaacttctc ctccgagtcc aagcgggaga      720
cagaatatgg tccctgccgt agagaaatgg aagacacact gaatcacctg aagttcctca      780
atgtgctgag tcccagggt gtacacattc ccaactgtga caagaaggga ttttataaga      840
aaaagcagtg tcgcccttcc aaaggcagga agcggggctt ctgctggtgt gtggataagt      900
atgggcagcc tctcccaggc tacaccacca aggggaagga ggacgtgcac tgctacagca      960
tgcagagcaa gtagacgcct gccgcaaggt taatgtggag ctcaaatatg ccttattttg     1020
cacaaaagac tgccaaggac atgaccagca gctggctaca gcctcgattt atatttctgt     1080
ttgtggtgaa ctgattttttt ttaaaccaaa gtttagaaaa aggttttttga aatgcctatg     1140 gtttctttga atggtaaact tgagcatctt ttcactttcc agtagtcagc aaagagcagt     1200
ttgaattttc ttgtcgcttc ctatcaaaat attcagagac tcgagcacag cacccagact     1260
tcatgcgccc gtggaatgct caccacatgt tggtcgaagc ggccgaccac tgactttgtg     1320
acttaggcgg ctgtgttgcc tatgtagaga acacgcttca cccccactcc cgtacagtg      1380 cgcacaggct ttatcgagaa taggaaaacc tttaaacccc ggtcatccgg acatcccaac     1440
gcatgctcct ggagctcaca gccttctgtg gtgtcatttc tgaaacaagg gcgtggatcc     1500
ctcaaccaag aagaatgttt atgtcttcaa gtgacctgta ctgcttgggg actattggag     1560
aaaataaggt ggagtcctac ttgtttaaaa aatatgtatc taagaatgtt ctagggcact     1620
ctgggaacct ataaaggcag gtatttcggg ccctcctctt caggaatctt cctgaagaca     1680
tggcccagtc gaaggcccag gatggctttt gctgcggccc cgtggggtag gagggacaga     1740
gagacaggga gagtcagcct ccacattcag aggcatcaca agtaatggca caattcttcg     1800
gatgactgca gaaaatagtg ttttgtagtt caacaactca agacgaagct tatttctgag     1860
gataagctct ttaaaggcaa agctttattt tcatctctca tcttttgtcc tccttagcac     1920
aatgtaaaaa agaatagtaa tatcagaaca ggaaggagga atggcttgct ggggagccca     1980
tccaggacac tgggagcaca tagagattca cccatgtttg ttgaacttag agtcattctc     2040
atgcttttct ttataattca cacatatatg cagagaagat atgttcttgt taacattgta     2100
tacaacatag ccccaaatat agtaagatct atactagata atcctagatg aaatgttaga     2160
gatgctattt gatacaactg tggccatgac tgaggaaagg agctcacgcc cagagactgg     2220
gctgctctcc cggaggccaa acccaagaag gtctggcaaa gtcaggctca gggagactct     2280
gccctgctgc agacctcggt gtggacacac gctgcataga gctctccttg aaaacagagg     2340
ggtctcaaga cattctgcct acctattagc ttttcttat ttttttaact ttttgggggg     2400
aaaagtattt ttgagaagtt tgtcttgcaa tgtatttata aatagtaaat aaagtttta     2460 ccatt                                                                 2465
```

<210> SEQ ID NO 10
<211> LENGTH: 807
<212> TYPE: DNA
<213> ORGANISM: Homo sapiens

<400> SEQUENCE: 10

```
atgccgcgct ccttcctggt caagaagcat ttcaacgcct ccaaaaagcc aaactacagc       60
gaactggaca cacatacagt gattatttcc ccgtatctct atgagagtta ctccatgcct      120
gtcataccac aaccagagat cctcagctca ggagcataca gccccatcac tgtgtggact      180
accgctgctc cattccacgc ccagctaccc aatggcctct ctcctctttc cggatactcc      240
```

-continued

| | |
|---|---|
| tcatctttgg ggcgagtgag tcccctcct ccatctgaca cctcctccaa ggaccacagt | 300 |
| ggctcagaaa gccccattag tgatgaagag gaaagactac agtccaagct ttcagacccc | 360 |
| catgccattg aagctgaaaa gtttcagtgc aatttatgca ataagaccta ttcaacttt | 420 |
| tctgggctgg ccaaacataa gcagctgcac tgcgatgccc agtctagaaa atctttcagc | 480 |
| tgtaaatact gtgacaagga atatgtgagc ctgggcgccc tgaagatgca tattcggacc | 540 |
| cacacattac cttgtgtttg caagatctgc ggcaaggcgt tttccagacc ctggttgctt | 600 |
| caaggacaca ttagaactca cacggggag aagccttttt cttgccctca ctgcaacaga | 660 |
| gcatttgcag acaggtcaaa tctgagggct catctgcaga cccattctga tgtaaagaaa | 720 |
| taccagtgca aaaactgctc caaaaccttc tccagaatgt ctctcctgca caaacatgag | 780 |
| gaatctggct gctgtgtagc acactga | 807 |

<210> SEQ ID NO 11
<211> LENGTH: 1266
<212> TYPE: DNA
<213> ORGANISM: Homo sapiens

<400> SEQUENCE: 11

| | |
|---|---|
| ctcggaagcc cgtcaccatg tcgtgcgagt cgtctatggt tctcgggtac tgggatattc | 60 |
| gtgggctggc gcacgccatc cgcctgctcc tggagttcac ggatacctct tatgaggaga | 120 |
| aacggtacac gtgcggggaa gctcctgact atgatcgaag ccaatggctg gatgtgaaat | 180 |
| tcaagctaga cctggacttt cctaatctgc cctacctcct ggatgggaag aacaagatca | 240 |
| cccagagcaa tgccatcttg cgctacatcg ctcgcaagca acatgtgt ggtgagactg | 300 |
| aagaagaaaa gattcgagtg gacatcatag agaaccaagt aatggatttc cgcacacaac | 360 |
| tgataaggct ctgttacagc tctgaccacg aaaaactgaa gcctcagtac ttggaagagc | 420 |
| tacctggaca actgaaacaa ttctccatgt ttctgtggaa attctcatgg tttgccgggg | 480 |
| aaaagctcac ctttgtggat tttctcacct atgatatctt ggatcagaac cgtatatttg | 540 |
| accccaagtg cctggatgag ttcccaaaacc tgaaggcttt catgtgccgt tttgaggctt | 600 |
| tggagaaaat cgctgcctac ttacagtctg atcagttctg caagatgccc atcaacaaca | 660 |
| agatggccca gtgggcaac aagcctgtat gctgagcagg aggcagactt gcagagcttg | 720 |
| ttttgtttca tcctgtccgt aaggggtcag cgctcttgct ttgctctttt caatgaatag | 780 |
| cacttatgtt actggtgtcc agctgagttt ctcttgggta taaaggctaa aagggaaaaa | 840 |
| ggatatgtgg agaatcatca agatatgaat tgaatcgctg cgatactgtg gcatttccct | 900 |
| actccccaac tgagttcaag ggctgtaggt tcatgcccaa gccctgagag tgggtactag | 960 |
| aaaaaacgag attgcacagt tggagagagc aggtgtgtta aatggactgg agtccctgtg | 1020 |
| aagactgggt gaggataaca caagtaaaac tgtggtactg atggacttaa ccggagttcg | 1080 |
| gaaaccgtcc tgtgtacaca tgggagttta gtgtgataaa ggcagtattt cagactggtg | 1140 |
| ggctagccaa tagagttggc aattgcttat tgaaactcat taaaaataat agagccccac | 1200 |
| ttgacactat tcactaaaat taatctggaa tttaaggccc aacattaaac acaaagctgt | 1260 |
| attgat | 1266 |

<210> SEQ ID NO 12
<211> LENGTH: 1308
<212> TYPE: DNA
<213> ORGANISM: Homo sapiens -continued

<400> SEQUENCE: 12

```
gccacgtgct gctgggtctc agtcctccac ttcccgtgtc ctctggaagt tgtcaggagc      60
aatgttgcgc ttgtacgtgt tggtaatggg agtttctgcc ttcacccttc agcctgcggc     120
acacacaggg gctgccagaa gctgccggtt tcgtgggagg cattacaagc gggagttcag     180
gctggaaggg gagcctgtag ccctgaggtg cccccaggtg ccctactggt tgtgggcctc     240
tgtcagcccc cgcatcaacc tgacatggca taaaaatgac tctgctagga cggtcccagg     300
agaagaagag acacggatgt gggcccagga cggtgctctg tggcttctgc agccttgca     360
ggaggactct ggcacctacg tctgcactac tagaaatgct tcttactgtg acaaaatgtc     420
cattgagctc agagttttttg agaatacaga tgctttcctg ccgttcatct catacccgca     480
aattttaacc ttgtcaacct ctggggtatt agtatgccct gacctgagtg aattcacccg     540
tgacaaaact gacgtgaaga ttcaatggta caaggattct cttctttttgg ataaagacaa     600
tgagaaattt ctaagtgtga gggggaccac tcacttactc gtacacgatg tggccctgga     660
agatgctggc tattaccgct gtgtcctgac atttgcccat gaaggccagc aatacaacat     720
cactaggagt attgagctac gcatcaagaa aaaaaaagaa gagaccattc ctgtgatcat     780
ttccccccctc aagaccatat cagcttctct ggggtcaaga ctgacaatcc cgtgtaaggt     840
gtttctggga accggcacac ccttaaccac catgctgtgg tggacggcca atgacaccca     900
catagagagc gcctacccgg gaggccgcgt gaccgagggg ccacgccagg aatattcaga     960
aaataatgag aactacattg aagtgccatt gattttttgat cctgtcacaa gagaggattt    1020
gcacatggat tttaaatgtg ttgtccataa taccctgagt tttcagacac tacgcaccac    1080
agtcaaggaa gcctcctcca cgttctcctg gggcattgtg ctggcccac tttcactggc     1140
cttcttggtt ttgggggggaa tatggatgca cagacggtgc aaacacagaa ctggaaaagc    1200
agatggtctg actgtgctat ggcctcatca tcaagacttt caatcctatc ccaagtgaaa    1260
taaatggaat gaaataattc aaacacaaaa aaaaaaaaa aaaaaaaa                  1308
```

<210> SEQ ID NO 13
<211> LENGTH: 5994
<212> TYPE: DNA
<213> ORGANISM: Homo sapiens

<400> SEQUENCE: 13

```
gcgctgcccg cctcgtcccc accccccaac ccccgcgcc cgccctcgga cagtccctgc      60
tcgcccgcgc gctgcagccc catctcctag cggcagccca ggcgcggagg gagcgagtcc     120
gccccgaggt aggtccagga cgggcgcaca gcagcagccg aggctggccg ggagagggag     180
gaagaggatg gcagggccac gccccagccc atgggccagg ctgctcctgg cagccttgat     240
cagcgtcagc ctctctggga ccttggcaaa ccgctgcaag aaggcccag tgaagagctg     300
cacggagtgt gtccgtgtgg ataaggactg cgcctactgc acagacgaga tgttcaggga     360
ccggcgctgc aacacccagg cggagctgct ggccgcgggc tgccagcggg agagcatcgt     420
ggtcatggag agcagcttcc aaatcacaga ggagacccag attgacacca ccctgcggcg     480
cagccagatg tccccccaag gcctgcgggt ccgtctgcgg cccggtgagg agcggcattt     540
tgagctggag gtgtttgagc cactggagag ccccgtggac ctgtacatcc tcatggactt     600
ctccaactcc atgtccgatg atctggacaa cctcaagaag atggggcaga acctggctcg     660
ggtcctgagc cagctcacca gcgactacac tattggatttt ggcaagtttg tggacaaagt     720
cagcgtcccg cagacggaca tgaggcctga gaagctgaag gagccctggc caacagtga     780
```

-continued

```
ccccccttc tccttcaaga acgtcatcag cctgacagaa gatgtggatg agttccggaa    840
taaactgcag ggagagcgga tctcaggcaa cctggatgct cctgagggcg gcttcgatgc    900
catcctgcag acagctgtgt gcacgaggga cattggctgg cgcccggaca gcacccacct    960
gctggtcttc tccaccgagt cagccttcca ctatgaggct gatggcgcca acgtgctggc   1020
tggcatcatg agccgcaacg atgaacggtg ccacctggac accacgggca cctacaccca   1080
gtacaggaca caggactacc cgtcggtgcc caccctggtg cgcctgctcg ccaagcacaa   1140
catcatcccc atctttgctg tcaccaacta ctcctatagc tactacgaga agcttcacac   1200
ctatttccct gtctcctcac tgggggtgct gcaggaggac tcgtccaaca tcgtggagct   1260
gctggaggag gccttcaatc ggatccgctc caacctggac atccgggccc tagacagccc   1320
ccgaggcctt cggacagagg tcacctccaa gatgttccag aagacgagga ctgggtcctt   1380
tcacatccgg cgggggaag tgggtatata ccaggtgcag ctgcgggccc ttgagcacgt   1440
ggatgggacg cacgtgtgcc agctgccgga ggaccagaag gcaacatcc atctgaaacc   1500
ttccttctcc gacggcctca agatggacgc gggcatcatc tgtgatgtgt gcacctgcga   1560
gctgcaaaaa gaggtgcggt cagctcgctg cagcttcaac ggagacttcg tgtgcggaca   1620
gtgtgtgtgc agcgagggct ggagtggcca gacctgcaac tgctccaccg gctctctgag   1680
tgacattcag ccctgcctgc gggagggcga ggacaagccg tgctccggcc gtggggagtg   1740
ccagtgcggg cactgtgtgt gctacggcga aggccgctac gagggtcagt tctgcgagta   1800
tgacaacttc cagtgtcccc gcacttccgg gttcctgtgc aatgaccgag acgctgctc   1860
catgggccag tgtgtgtgtg agcctggttg gacaggccca agctgtgact gtccctcag   1920
caatgccacc tgcatcgaca gcaatggggg catctgtaat ggacgtggcc actgtgagtg   1980
tggccgctgc cactgccacc agcagtcgct ctacacggac accatctgcg agatcaacta   2040
ctcggcgatc caccgggcc tctgcgagga cctacgctcc tgcgtgcagt gccaggcgtg   2100
gggcaccggc gagaagaagg gcgcacgtg tgaggaatgc aacttcaagg tcaagatggt   2160
ggacgagctt aagagagccg aggaggtggt ggtgcgctgc tccttccggg acgaggatga   2220
cgactgcacc tacagctaca ccatggaagg tgacggcgcc cctgggccca acagcactgt   2280
cctggtgcac aagaagaagg actgccctcc gggctccttc tggtggctca tcccctgct   2340
cctcctcctc ctgccgctcc tggccctgct actgctgcta tgctggaagt actgtgcctg   2400
ctgcaaggcc tgcctggcac ttctcccgtg ctgcaaccga ggtcacatgg tgggctttaa   2460
ggaagaccac tacatgctgc gggagaacct gatggcctct gaccacttgg acacgcccat   2520
gctgcgcagc gggaacctca agggccgtga cgtggtccgc tggaaggtca ccaacaacat   2580
gcagcggcct ggctttgcca ctcatgccgc cagcatcaac cccacagagc tggtgcccta   2640
cgggctgtcc ttgcgcctgg cccgcctttg caccgagaac ctgctgaagc ctgcactcg   2700
ggagtgcgcc cagctgcgcc aggaggtgga ggagaacctg aacaggtct acaggcagat   2760
ctccggtgta cacaagctcc agcagaccaa gttccggcag cagcccaatg ccgggaaaaa   2820
gcaagaccac accattgtgg acacagtgct gatggcgccc cgctcggcca agccggccct   2880
gctgaagctt acagagaagc aggtggaaca gagggccttc cacgacctca aggtggcccc   2940
cggctactac acctcactg cagaccagga cgcccgggc atggtggagt tccaggaggg   3000
cgtggagctg gtggacgtac gggtgcccct ctttatccgg cctgaggatg acgacgagaa   3060
gcagctgctg gtggaggcca tcgacgtgcc cgcaggcact gccacctcg ccgccgcct   3120
```

```
ggtaaacatc accatcatca aggagcaagc cagagacgtg gtgtcctttg agcagcctga   3180
gttctcggtc agccgcgggg accaggtggc ccgcatccct gtcatccggc gtgtcctgga   3240
cggcgggaag tcccaggtct cctaccgcac acaggatggc accgcgcagg caaccggga    3300 ctacatcccc gtggagggtg agctgctgtt ccagcctggg gaggcctgga aagagctgca   3360
ggtgaagctc ctggagctgc aagaagttga ctccctcctg cggggccgcc aggtccgccg   3420
tttccacgtc cagctcagca accctaagtt tggggcccac ctgggccagc cccactccac   3480
caccatcatc atcagggacc cagatgaact ggaccggagc ttcacgagtc agatgttgtc   3540
atcacagcca ccccctcacg cgacctgggc gccccgcag aacccccaatg ctaaggccgc   3600 tgggtccagg aagatccatt tcaactggct gccccttct ggcaagccaa tggggtacag   3660
ggtaaagtac tggattcagg cgactccga atccgaagcc cacctgctcg acagcaaggt   3720
gccctcagtg gagctcacca acctgtaccc gtattgcgac tatgagatga aggtgtgcgc   3780
ctacggggct cagggcgagg accctacag ctccctggtg tcctgccgca cccaccagga   3840
agtgcccagc gagccagggc gtctggcctt caatgtcgtc tcctccacgg tgacccagct   3900
gagctgggct gagccggctg agaccaacgg tgagatcaca gcctacgagg tctgctatgg   3960
cctggtcaac gatgacaacc gacctattgg gcccatgaag aaagtgctgg ttgacaaccc   4020
taagaaccgg atgctgctta ttgagaacct tcgggagtcc cagccctacc gctacacggt   4080
gaaggcgcgc aacggggccg gctgggggcc tgagcgggag gccatcatca acctggccac   4140
ccagcccaag aggcccatgt ccatccccat catccctgac atccctatcg tggacgccca   4200
gagcggggag gactacgaca gcttccttat gtacagcgat gacgttctac gctctccatc   4260
gggcagccag aggcccagcg tctccgatga cactggctgc ggctggaagt tcgagcccct   4320
gctgggggag gagctggacc tgcggcgcgt cacgtggcgg ctgccccgg agctcatccc   4380 gcgcctgtcg gccagcagcg ggcgctcctc cgacgccgag gccccacgg ccccccggac   4440 gacggcggcg cgggcgggaa gggcggcagc cgtgccccgc agtgcgacac ccgggccccc   4500
cggagagcac ctggtgaatg gccggatgga ctttgccttc ccgggcagca ccaactccct   4560
gcacaggatg accacgacca gtgctgctgc ctatggcacc cacctgagcc cacacgtgcc   4620
ccaccgcgtg ctaagcacat cctccaccct cacacgggac tacaactcac tgacccgctc   4680
agaacactca cactcgacca cactgcccag ggactactcc accctcacct ccgtctcctc   4740
ccacgactct cgcctgactg ctggtgtgcc cgacacgccc accgcctggg tgttctctgc   4800
cctggggccc acatctctca gagtgagctg gcaggagccg cggtgcgagc ggccgctgca   4860
gggctacagt gtggagtacc agctgctgaa cggcggtgag ctgcatcggc tcaacatccc   4920
caaccctgcc cagacctcgg tggtggtgga agacctcctg cccaaccact cctacgtgtt   4980
ccgcgtgcgg gcccagagcc aggaaggctg gggccgagag cgtgagggtg tcatcaccat   5040
tgaatcccag gtgcacccgc agagcccact gtgtcccctg ccaggctccg ccttcacttt   5100
gagcactccc agtgccccag gcccgctggt gttcactgcc ctgagccag actcgctgca   5160 gctgagctgg gagcggccac ggaggcccaa tggggatatc gtcggctacc tggtgacctg   5220
tgagatggcc caaggaggag ggccagccac cgcattccgg gtggatggag acagccccga   5280
gagccggctg accgtgccgg gcctcagcga gaacgtgccc tacaagttca aggtgcaggc   5340
caggaccact gagggcttcg ggccagagcg cgagggcatc atcaccatag agtcccagga   5400
tggaggaccc ttcccgcagc tgggcagccg tgccgggctc ttccagcacc cgctgcaaag   5460
cgagtacagc agcatcacca ccacccacac cagcgccacc gagcccttcc tagtggatgg   5520
```

-continued

| | |
|---|---|
| gctgaccctg ggggcccagc acctggaggc aggcggctcc ctcacccggc atgtgaccca | 5580 |
| ggagtttgtg agccggacac tgaccaccag cggaacccct tagcacccac atggaccaaca | 5640 |
| gttcttccaa acttgaccgc accctgcccc accccgcca tgtcccacta ggcgtcctcc | 5700 |
| cgactcctct cccggagcct cctcagctac tccatccttg caccctggg ggcccagccc | 5760 |
| acccgcatgc acagagcagg ggctaggtgt ctcctgggag gcatgaaggg ggcaaggtcc | 5820 |
| gtcctctgtg ggcccaaacc tatttgtaac caaagagctg ggagcagcac aaggacccag | 5880 |
| cctttgttct gcacttaata aatggttttg ctactgctaa aaaaaaaaaa aaaaaaaaa | 5940 |
| aaaaaaaaa aaaaaaaaa aaaaaaaaa aaaaaaaaa aaaaaaaaa aaaa | 5994 |

<210> SEQ ID NO 14
<211> LENGTH: 1898
<212> TYPE: DNA
<213> ORGANISM: Homo sapiens

<400> SEQUENCE: 14

| | |
|---|---|
| ccgccgggct ggccatggag ctgctgtgcc acgaggtgga cccggtccgc agggccgtgc | 60 |
| gggaccgcaa cctgctccga gacgaccgcg tcctgcagaa cctgctcacc atcgaggagc | 120 |
| gctaccttcc gcagtgctcc tacttcaagt gcgtgcagaa ggacatccaa ccctacatgc | 180 |
| gcagaatggt ggccacctgg atgctggagg tctgtgagga acagaagtgc gaagaagagg | 240 |
| tcttccctct ggccatgaat tacctggacc gtttcttggc tggggtcccg actccgaagt | 300 |
| cccatctgca actcctgggt gctgtctgca tgttcctggc ctccaaactc aaagagacca | 360 |
| gcccgctgac cgcggagaag ctgtgcattt acaccgacaa ctccatcaag cctcaggagc | 420 |
| tgctggagtg ggaactggtg gtgctgggga agttgaagtg gaacctggca gctgtcactc | 480 |
| ctcatgactt cattgagcac atcttgcgca agctgcccca gcagcgggag aagctgtctc | 540 |
| tgatccgcaa gcatgctcag accttcattg ctctgtgtgc caccgacttt aagtttgcca | 600 |
| tgtacccacc gtcgatgatc gcaactggaa gtgtgggagc agccatctgt gggctccagc | 660 |
| aggatgagga agtgagctcg ctcacttgtg atgccctgac tgagctgctg gctaagatca | 720 |
| ccaacacaga cgtggattgt ctcaaagctt gccaggagca gattgaggcg gtgctcctca | 780 |
| atagcctgca gcagtaccgt caggaccaac gtgacggatc caagtcggag gatgaactgg | 840 |
| accaagccag caccctaca gacgtgcggg atatcgacct gtgaggatgc cagttgggcc | 900 |
| gaaagagaga gacgcgtcca taatctggtc tcttcttctt tctggttgtt tttgttcttt | 960 |
| gtgttttagg gtgaaactta aaaaaaaaat tctgccccca cctagatcat atttaaagat | 1020 |
| cttttagaag tgagagaaaa aggtcctacg aaaacggaat aataaaaagc atttggtgcc | 1080 |
| tatttgaagt acagcataag ggaatccctt gtatatgcga acagttattg tttgattatg | 1140 |
| taaaagtaat agtaaaatgc ttacaggaaa acctgcagag tagttagaga atatgtatgc | 1200 |
| ctgcaatatg ggaacaaatt agaggagact ttttttttc atgttatgag ctagcacata | 1260 |
| caccccttg tagtataatt tcaaggaact gtgtacgcca tttatggcat gattagattg | 1320 |
| caaagcaatg aactcaagaa ggaattgaaa taaggaggga catgatgggg aaggagtaca | 1380 |
| aaacaatctc tcaacatgat tgaaccattt gggatggaga agcacctttg ctctcagcca | 1440 |
| cctgttacta agtcaggagt gtagttggat ctctacatta atgtcctctt gctgtctaca | 1500 |
| gtagctgcta cctaaaaaaa gatgttttat tttgccagtt ggacacaggt gattggctcc | 1560 |
| tgggtttcat gttctgtgac atcctgcttc ttcttccaaa tgcagttcat tgcagacacc | 1620 |

| | |
|---|---:|
| accatattgc tatctaatgg ggaaatgtag ctatgggcca taaccaaaac tcacatgaaa | 1680 |
| cggaggcaga tggagaccaa gggtgggatc cagaatggag tcttttctgt tattgtattt | 1740 |
| aaaagggtaa tgtggccttg gcatttcttc ttagaaaaaa actaattttt ggtgctgatt | 1800 |
| ggcatgtctg gttcacagtt tagcattgtt ataaaccatt ccattcgaaa agcactttga | 1860 |
| aaaattgttc ccgagcgata gatgggatgg tttatgca | 1898 |

<210> SEQ ID NO 15
<211> LENGTH: 4286
<212> TYPE: DNA
<213> ORGANISM: Homo sapiens

<400> SEQUENCE: 15

| | |
|---|---:|
| gagacattcc ggtgggggac tctggccagc ccgagcaacg tggatcctga gagcactccc | 60 |
| aggtaggcat ttgccccggt gggacgcctt gccagagcag tgtgtggcag gcccccgtgg | 120 |
| aggatcaaca cagtggctga acactgggaa ggaactggta cttggagtct ggacatctga | 180 |
| aacttggctc tgaaactgcg cagcggccac cggacgcctt ctggagcagg tagcagcatg | 240 |
| cagccgcctc caagtctgtg cggacgcgcc tggttgcgc tggttcttgc ctgcggcctg | 300 |
| tcgcggatct ggggagagga gagaggcttc ccgcctgaca gggccactcc gcttttgcaa | 360 |
| accgcagaga taatgacgcc acccactaag accttatggc ccaagggttc caacgccagt | 420 |
| ctggcgcggt cgttggcacc tgcggaggtg cctaaaggag acaggacggc aggatctccg | 480 |
| ccacgcacca tctcccctcc cccgtgccaa ggacccatcg agatcaagga gactttcaaa | 540 |
| tacatcaaca cggttgtgtc ctgccttgtg ttcgtgctgg ggatcatcgg gaactccaca | 600 |
| cttctgagaa ttatctacaa gaacaagtgc atgcgaaacg gtcccaatat cttgatcgcc | 660 |
| agcttggctc tgggagacct gctgcacatc gtcattgaca tccctatcaa tgtctacaag | 720 |
| ctgctggcag aggactggcc atttggagct gagatgtgta gctggtgcc tttcatacag | 780 |
| aaagcctccg tgggaatcac tgtgctgagt ctatgtgctc tgagtattga cagatatcga | 840 |
| gctgttgctt cttggagtag aattaaagga attggggttc caaaatggac agcagtagaa | 900 |
| attgttttga tttgggtggt ctctgtggtt ctggctgtcc ctgaagccat aggttttgat | 960 |
| ataattacga tggactacaa aggaagttat ctgcgaatct gcttgcttca tcccgttcag | 1020 |
| aagacagctt tcatgcagtt ttacaagaca gcaaaagatt ggtggctgtt cagtttctat | 1080 |
| ttctgcttgc cattggccat cactgcattt ttttatacac taatgacctg tgaaatgttg | 1140 |
| agaaagaaaa gtggcatgca gattgcttta aatgatcacc taaagcagag acgggaagtg | 1200 |
| gccaaaaccg tcttttgcct ggtccttgtc tttgccctct gctggcttcc ccttcacctc | 1260 |
| agcaggattc tgaagctcac tctttataat cagaatgatc ccaatagatg tgaacttttg | 1320 |
| agctttctgt tggtattgga ctatattggt atcaacatgg cttcactgaa ttcctgcatt | 1380 |
| aacccaattg ctctgtattt ggtgagcaaa agattcaaaa actgctttaa gtcatgctta | 1440 |
| tgctgctggt gccagtcatt tgaagaaaaa cagtccttgg aggaaaagca gtcgtgctta | 1500 |
| aagttcaaag ctaatgatca cggatatgac aacttccgtt ccagtaataa atacagctca | 1560 |
| tcttgaaaga gaactattc actgtatttc attttcttta tattggaccg aagtcattaa | 1620 |
| aacaaaatga acatttgcc aaaacaaaac aaaaaactat gtatttgcac agcacactat | 1680 |
| taaaatatta agtgtaatta ttttaacact cacagctaca tatgacattt tatgagctgt | 1740 |
| ttacggcatg gaaagaaaat cagtgggaat taagaaagcc tcgtcgtgaa agcacttaat | 1800 |
| tttttacagt tagcacttca acatagctct taacaacttc caggatattc acacaacact | 1860 |

```
taggcttaaa aatgagctca ctcagaattt ctattctttc taaaaagaga tttatttta    1920 aatcaatggg actctgatat aaaggaagaa taagtcactg taaaacagaa cttttaaatg    1980
aagcttaaat tactcaattt aaaattttaa aatcctttaa aacaactttt caattaatat    2040
tatcacacta ttatcagatt gtaattagat gcaaatgaga gagcagttta gttgttgcat    2100
ttttcggaca ctggaaacat ttaaatgatc aggagggagt aacagaaaga gcaaggctgt    2160
ttttgaaaat cattacactt tcactagaag cccaaacctc agcattctgc aatatgtaac    2220
caacatgtca caaacaagca gcatgtaaca gactggcaca tgtgccagct gaatttaaaa    2280
tataatactt ttaaaagaa aattattaca tcctttacat tcagttaaga tcaaacctca    2340
caaagagaaa tagaatgttt gaaaggctat cccaaaagac ttttttgaat ctgtcattca    2400 catccctgt gaagacaata ctatctacaa ttttttcagg attattaaaa tcttcttttt    2460
tcactatcgt agcttaaact ctgtttggtt ttgtcatctg taaatactta cctacataca    2520
ctgcatgtag atgattaaat gagggcaggc cctgtgctca tagctttacg atggagagat    2580
gccagtgacc tcataataaa gactgtgaac tgcctggtgc agtgtccaca tgacaaaggg    2640
gcaggtagca ccctctctca cccatgctgt ggttaaaatg gtttctagca tatgtataat    2700
gctatagtta aaatactatt tttcaaaatc atacagatta gtacatttaa cagctacctg    2760
taaagcttat tactaatttt tgtattattt ttgtaaatag ccaatagaaa gtttgcttg    2820 acatggtgct tttctttcat ctagaggcaa aactgctttt tgagaccgta agaacctctt    2880
agctttgtgc gttcctgcct aattttata tcttctaagc aaagtgcctt aggatagctt    2940
gggatgagat gtgtgtgaaa gtatgtacaa gagaaaacgg aagagagagg aaatgaggtg    3000
gggttggagg aaacccatgg ggacagattc ccattcttag cctaacgttc gtcattgcct    3060
cgtcacatca atgcaaaagg tcctgatttt gttccagcaa aacacagtgc aatgttctca    3120
gagtgacttt cgaaataaat tgggcccaag agctttaact cggtcttaaa atatgcccaa    3180 attttactt tgttttctt ttaataggct gggccacatg ttggaaataa gctagtaatg    3240
ttgttttctg tcaatattga atgtgatggt acagtaaacc aaaacccaac aatgtggcca    3300
gaaagaaaga gcaataataa ttaattcaca caccatatgg attctattta taaatcaccc    3360
acaaacttgt tctttaattt catcccaatc acttttcag aggcctgtta tcatagaagt    3420 catttagac tctcaattt aaattaattt tgaatcacta atattttcac agttattaa    3480 tatatttaat ttctatttaa attttagatt attttatta ccatgtactg aattttaca    3540 tcctgatacc ctttccttct ccatgtcagt atcatgttct ctaattatct tgccaaattt    3600
tgaaactaca cacaaaagc atacttgcat tatttataat aaaattgcat tcagtggctt    3660 tttaaaaaa atgtttgatt caaaacttta acatactgat aagtaagaaa caattataat    3720
ttctttacat actcaaaacc aagatagaaa aaggtgctat cgttcaactt caaaacatgt    3780
ttcctagtat taaggacttt aatatagcaa cagacaaaat tattgttaac atggatgtta    3840
cagctcaaaa gatttataaa agattttaac ctattttctc ccttattatc cactgctaat    3900
gtggatgtat gttcaaacac cttttagtat tgatagctta catatggcca aaggaataca    3960
gtttatagca aaacatgggt atgctgtagc taactttata aaagtgtaat ataacaatgt    4020
aaaaaattat atatctggga ggattttttg gttgcctaaa gtggctatag ttactgattt    4080
tttattatgt aagcaaaacc aataaaaatt taagttttt taacaactac cttatttttc    4140
actgtacaga cactaattca ttaaatacta attgattgtt taaaagaaat ataaatgtga    4200
```

-continued

| caagtggaca ttatttatgt taaatataca attatcaagc aagtatgaag ttattcaatt | 4260 |
| aaaatgccac atttctggtc tctggg | 4286 |

<210> SEQ ID NO 16
<211> LENGTH: 3148
<212> TYPE: DNA
<213> ORGANISM: Homo sapiens

<400> SEQUENCE: 16

| gaattcccgc ggagcagcgt gcgcggggcc ccgggagacg gcggcggtag cggcgcgggc | 60 |
| agagcaagga cgcggcggat cccactcgca cagcagcgca ctcggtgccc cgcgcagggt | 120 |
| cgcgatgctg cccggtttgg cactgctcct gctggccgcc tggacggctc gggcgctgga | 180 |
| ggtacccact gatggtaatg ctggcctgct ggctgaaccc cagattgcca tgttctgtgg | 240 |
| cagactgaac atgcacatga atgtccagaa tgggaagtgg gattcagatc catcagggac | 300 |
| caaaacctgc attgatacca aggaaggcat cctgcagtat tgccaagaag tctaccctga | 360 |
| actgcagatc accaatgtgg tagaagccaa ccaaccagtg accatccaga actggtgcaa | 420 |
| gcggggccgc aagcagtgca agacccatcc ccactttgtg attccctacc gctgcttagt | 480 |
| tggtgagttt gtaagtgatg cccttctcgt tcctgacaag tgcaaattct tacaccagga | 540 |
| gaggatggat gtttgcgaaa ctcatcttca ctggcacacc gtcgccaaag agacatgcag | 600 |
| tgagaagagt accaacttgc atgactacgg catgttgctg ccctgcggaa ttgacaagtt | 660 |
| ccgaggggta gagtttgtgt gttgcccact ggctgaagaa agtgacaatg tggattctgc | 720 |
| tgatgcggag gaggatgact cggatgtctg gtggggcgga gcagacacag actatgcaga | 780 |
| tgggagtgaa gacaaagtag tagaagtagc agaggaggaa gaagtggctg aggtggaaga | 840 |
| agaagaagcc gatgatgacg aggacgatga ggatggtgat gaggtagagg aagaggctga | 900 |
| ggaaccctac gaagaagcca cagagagaac caccagcatt gccaccacca ccaccaccac | 960 |
| cacagagtct gtggaagagg tggttcgaga ggtgtgctct gaacaagccg agacggggcc | 1020 |
| gtgccgagca atgatctccc gctggtactt tgatgtgact gaagggaagt gtgccccatt | 1080 |
| cttttacggc ggatgtggcg gcaaccggaa caactttgac acagaagagt actgcatggc | 1140 |
| cgtgtgtggc agcgccattc ctacaacagc agccagtacc cctgatgccg ttgacaagta | 1200 |
| tctcgagaca cctggggatg agaatgaaca tgcccatttc cagaaagcca agagaggct | 1260 |
| tgaggccaag caccgagaga aatgtccca ggtcatgaga aatgggaag aggcagaacg | 1320 |
| tcaagcaaag aacttgccta agctgataa gaaggcagtt atccagcatt tccaggagaa | 1380 |
| agtggaatct ttggaacagg aagcagccaa cgagagacag cagctggtgg agacacacat | 1440 |
| ggccagagtg gaagccatgc tcaatgaccg ccgccgcctg gccctggaga actacatcac | 1500 |
| cgctctgcag gctgttcctc ctcggcctcg tcacgtgttc aatatgctaa agaagtatgt | 1560 |
| ccgcgcagaa cagaaggaca gacagcacac cctaaagcat ttcgagcatg tgcgcatggt | 1620 |
| ggatcccaag aaagccgctc agatccggtc ccaggttatg acacacctcc gtgtgattta | 1680 |
| tgagcgcatg aatcagtctc tctccctgct ctacaacgtg cctgcagtgg ccgaggagat | 1740 |
| tcaggatgaa gttgatgagc tgcttcagaa agagcaaaac tattcagatg acgtcttggc | 1800 |
| caacatgatt agtgaaccaa ggatcagtta cggaaacgat gctctcatgc catctttgac | 1860 |
| cgaaacgaaa accaccgtgg agctccttcc cgtgaatgga gagttcagcc tggacgatct | 1920 |
| ccagccgtgg cattctttg gggctgactc tgtgccagcc aacacagaaa acgaagttga | 1980 |
| gcctgttgat gcccgccctg ctgccgaccg aggactgacc actcgaccag gttctgggtt | 2040 |

-continued

```
gacaaatatc aagacggagg agatctctga agtgaagatg gatgcagaat tccgacatga     2100
ctcaggatat gaagttcatc atcaaaaatt ggtgttcttt gcagaagatg tgggttcaaa     2160
caaaggtgca atcattggac tcatggtggg cggtgttgtc atagcgacag tgatcgtcat     2220
caccttggtg atgctgaaga agaaacagta cacatccatt catcatggtg tggtggaggt     2280
tgacgccgct gtcaccccag aggagcgcca cctgtccaag atgcagcaga acggctacga     2340
aaatccaacc tacaagttct tgagcagat gcagaactag acccccgcca cagcagcctc      2400
tgaagttgga cagcaaaacc attgcttcac tacccatcgg tgtccattta tagaataatg     2460
tgggaagaaa caaacccgtt ttatgattta ctcattatcg cctttgaca gctgtgctgt      2520 aacacaagta gatgcctgaa cttgaattaa tccacacatc agtaatgtat tctatctctc     2580
tttacatttt ggtctctata ctacattatt aatgggtttt gtgtactgta aagaatttag     2640
ctgtatcaaa ctagtgcatg aatagattct ctcctgatta tttatcacat agccccttag     2700
ccagttgtat attattcttg tggtttgtga cccaattaag tcctacttta catatgcttt     2760
aagaatcgat gggggatgct tcatgtgaac gtgggagttc agctgcttct cttgcctaag     2820
tattcctttc ctgatcacta tgcattttaa agttaaacat ttttaagtat ttcagatgct     2880
ttagagagat ttttttttcca tgactgcatt ttactgtaca gattgctgct tctgctatat    2940
ttgtgatata ggaattaaga ggatacacac gtttgtttct tcgtgcctgt tttatgtgca    3000
cacattaggc attgagactt caagcttttc ttttttttgtc cacgtatctt tgggtctttg   3060
ataaagaaaa gaatccctgt tcattgtaag cacttttacg gggcgggtgg ggagggggtgc  3120 tctgctggtc ttcaattacc aagaattc                                        3148
```

<210> SEQ ID NO 17
<211> LENGTH: 4434
<212> TYPE: DNA
<213> ORGANISM: Homo sapiens

<400> SEQUENCE: 17

```
gccgccctcg ccaccgctcc cggccgccgc gctccggtac acacaggatc cctgctgggc       60
accaacagct ccaccatggg gctggcctgg ggactaggcg tcctgttcct gatgcatgtg      120
tgtggcacca accgcattcc agagtctggc ggagacaaca gcgtgtttga catctttgaa      180
ctcaccgggg ccgcccgcaa ggggtctggg cgccgactgg tgaagggccc cgacccttcc     240
agcccagctt tccgcatcga ggatgccaac ctgatccccc ctgtgcctga tgacaagttc     300
caagacctgg tggatgctgt gcggacagaa aagggtttcc tccttctggc atccctgagg    360
cagatgaaga agacccgggg cacgctgctg gccctggagc ggaaagacca ctctggccag   420
gtcttcagcg tggtgtccaa tggcaaggcg ggcaccctgg acctcagcct gaccgtccaa   480
ggaaagcagc acgtggtgtc tgtggaagaa gctctcctgg caaccggcca gtggaagagc   540
atcaccctgt ttgtgcagga agacagggcc cagctgtaca tcgactgtga aaagatggag   600
aatgctgagt tggacgtccc catccaaagc gtcttcacca gagacctggc cagcatcgcc   660
agactccgca tcgcaagggg gggcgtcaat gacaatttcc aggggggtgct gcagaatgtg   720 aggtttgtct ttggaaccac accagaagac atcctcagga acaaaggctg ctccagctct   780
accagtgtcc tcctcaccct tgacaacaac gtggtgaatg gttccagccc tgccatccgc   840
actaactaca ttggccacaa gacaaaggac ttgcaagcca tctgcggcat ctcctgtgat   900
gagctgtcca gcatggtcct ggaactcagg ggcctgcgca ccattgtgac cacgctgcag   960
gacagcatcc gcaaagtgac tgaagagaac aaagagttgg ccaatgagct gaggcggcct   1020
```

```
cccctatgct atcacaacgg agttcagtac agaaataacg aggaatggac tgttgatagc    1080
tgcactgagt gtcactgtca gaactcagtt accatctgca aaaggtgtc  ctgccccatc    1140 atgccctgct ccaatgccac agttcctgat ggagaatgct gtcctcgctg ttggcccagc    1200
gactctgcgg acgatggctg gtctccatgg tccgagtgga cctcctgttc tacgagctgt    1260
ggcaatggaa ttcagcagcg cggccgctcc tgcgatagcc tcaacaaccg atgtgagggc    1320
tcctcggtcc agacacggac ctgccacatt caggagtgtg acaagagatt taaacaggat    1380
ggtggctgga gccactggtc cccgtggtca tcttgttctg tgacatgtgg tgatggtgtg    1440
atcacaagga tccggctctg caactctccc agccccaga tgaacgggaa accctgtgaa    1500
ggcgaagcgc gggagaccaa agcctgcaag aaagacgcct gccccatcaa tggaggctgg    1560
ggtccttggt caccatggga catctgttct gtcacctgtg gaggaggggt acagaaacgt    1620
agtcgtctct gcaacaaccc cacaccccag tttggaggca aggactgcgt tggtgatgta    1680
acagaaaacc agatctgcaa caagcaggac tgtccaattg atggatgcct gtccaatccc    1740
tgctttgccg gcgtgaagtg tactagctac cctgatggca gctggaaatg tggtgcttgt    1800 cccccctggtt acagtggaaa tggcatccag tgcacagatg ttgatgagtg caaagaagtg    1860
cctgatgcct gcttcaacca caatggagag caccggtgtg agaacacgga ccccggctac    1920
aactgcctgc cctgccccc  acgcttcacc ggctcacagc ccttcggcca gggtgtcgaa    1980
catgccacgg ccaacaaaca ggtgtgcaag ccccgtaacc cctgcacgga tgggacccac    2040
gactgcaaca agaacgccaa gtgcaactac ctgggccact atagcgaccc catgtaccgc    2100
tgcgagtgca agcctggcta cgctggcaat ggcatcatct gcggggagga cacagacctg    2160
gatggctggc ccaatgagaa cctggtgtgc gtggccaatg cgacttacca ctgcaaaaag    2220
gataattgcc ccaaccttcc caactcaggg caggaagact atgacaagga tggaattggt    2280
gatgcctgtg atgatgacga tgacaatgat aaaattccag atgacaggga caactgtcca    2340
ttccattaca acccagctca gtatgactat acagagatg atgtgggaga ccgctgtgac    2400
aactgtccct acaaccacaa cccagatcag gcagacacag acaacaatgg ggaaggagac    2460
gcctgtgctg cagacattga tggagacggt atcctcaatg aacgggacaa ctgccagtac    2520
gtctacaatg tggaccagag agacactgat atggatgggg ttggagatca gtgtgacaat    2580 tgcccccttgg aacacaatcc ggatcagctg gactctgact cagaccgcat tggagatacc    2640
tgtgacaaca atcaggatat tgatgaagat ggccaccaga acaatctgga caactgtccc    2700
tatgtgccca atgccaacca ggctgaccat gacaaagatg caagggaga tgcctgtgac    2760 cacgatgatg acaacgatgg cattcctgat gacaaggaca actgcagact cgtgcccaat    2820
cccgaccaga aggactctga cggcgatggt cgaggtgatg cctgcaaaga tgattttgac    2880
catgacagtg tgccagacat cgatgacatc tgtcctgaga atgttgacat cagtgagacc    2940
gatttccgcc gattccagat gattcctctg accccaaag ggacatccca aaatgaccct    3000
aactgggttg tacgccatca gggtaaagaa ctcgtccaga ctgtcaactg tgatcctgga    3060
ctcgctgtag ttatgatga  gtttaatgct gtggacttca gtggcacctt cttcatcaac    3120
accgaaaggg acgatgacta tgctggattt gtctttggct accagtccag cagccgcttt    3180
tatgttgtga tgtggaagca agtcacccag tcctactggg acaccaaccc cacgagggct    3240
cagggatact cgggcctttc tgtgaaagtt gtaaactcca ccacagggcc tggcgagcac    3300
ctgcggaacg ccctgtggca cacaggaaac accctggcc  aggtgcgcac cctgtggcat    3360
gaccctcgtc acataggctg gaaagatttc accgcctaca gatggcgtct cagccacagg    3420
```

-continued

| | |
|---|---|
| ccaaagacgg gtttcattag agtggtgatg tatgaaggga agaaaatcat ggctgactca | 3480 |
| ggacccatct atgataaaac ctatgctggt ggtagactag ggttgtttgt cttctctcaa | 3540 |
| gaaatggtgt tcttctctga cctgaaatac aatgtagag atccctaatc atcaaattgt | 3600 |
| tgattgaaag actgatcata aaccaatgct ggtattgcac cttctggaac tatgggcttg | 3660 |
| agaaaacccc caggatcact tctccttggc ttccttcttt tctgtgcttg catcagtgtg | 3720 |
| gactcctaga acgtgcgacc tgcctcaaga aaatgcagtt ttcaaaaaca gactcagcat | 3780 |
| tcagcctcca atgaataaga catcttccaa gcatataaac aattgctttg gtttcctttt | 3840 |
| gaaaaagcat ctacttgctt cagttgggaa ggtgcccatt ccactctgcc tttgtcacag | 3900 |
| agcagggtgc tattgtgagg ccatctctga gcagtggact caaaagcatt ttcaggcatg | 3960 |
| tcagagaagg gaggactcac tagaattagc aaacaaaacc ccctgacat cctccttcag | 4020 |
| gaacacgggg agcagaggcc aaagcactaa ggggagggcg catacccgag acgattgtat | 4080 |
| gaagaaaata tggaggaact gttacatgtt cggtactaag tcatttcag gggattgaaa | 4140 |
| gactattgct ggatttcatg atgctgactg gcgttagctg attaacccat gtaaataggc | 4200 |
| acttaaaatag aagcaggaaa gggagacaaa gactggcttc tggacttcct ccctgatccc | 4260 |
| caccccttact catcacctgc agtggccaga attagggaat cagaatcgaa accagtgtaa | 4320 |
| ggcagtgctg gctgccattg cctggtcaca ttgaaattgg tggcttcatt ctagatgtag | 4380 |
| cttgtgcaga tgtagcagga aaataggaaa acctaccatc tcagtgagca ccag | 4434 |

<210> SEQ ID NO 18
<211> LENGTH: 1377
<212> TYPE: DNA
<213> ORGANISM: Homo sapiens

<400> SEQUENCE: 18

| | |
|---|---|
| atttctcttt agttctttgc aagaaggtag agataaagac acttttcaa aaatggcaat | 60 |
| ggtatcagaa ttcctcaagc aggcctggtt tattgaaaat gaagagcagg aatatgttca | 120 |
| aactgtgaag tcatccaaag gtggtcccgg atcagcggtg agcccctatc ctaccttcaa | 180 |
| tccatcctcg gatgtcgctg ccttgcataa ggccataatg gttaaaggtg tggatgaagc | 240 |
| aaccatcatt gacattctaa ctaagcgaaa caatgcacag cgtcaacaga tcaaagcagc | 300 |
| atatctccag gaaacaggaa agcccctgga tgaaacactg aagaaagccc ttacaggtca | 360 |
| ccttgaggag gttgttttag ctctgctaaa aactccagcg caatttgatg ctgatgaact | 420 |
| tcgtgctgcc atgaagggcc ttggaactga tgaagatact ctaattgaga ttttggcatc | 480 |
| aagaactaac aaagaaatca gagacattaa caggtctac agagaggaac tgaagagaga | 540 |
| tctggccaaa gacataacct cagacacatc tggagatttt cggaacgctt tgctttctct | 600 |
| tgctaagggt gaccgatctg aggactttgg tgtgaatgaa gacttggctg attcagatgc | 660 |
| cagggccttg tatgaagcag gagaaggag aaagggaca gacgtaaacg tgttcaatac | 720 |
| catccttacc accagaagct atccacaact tcgcagagtg tttcagaaat acaccaagta | 780 |
| cagtaagcat gacatgaaca aagttctgga cctggagttg aaaggtgaca ttgagaaatg | 840 |
| cctcacagct atcgtgaagt gcgccacaag caaaccagct ttcctttgcag agaagcttca | 900 |
| tcaagccatg aaaggtgttg gaactcgcca taggcattg atcaggatta tggtttcccg | 960 |
| ttctgaaatt gacatgaatg atatcaaagc attctatcag aagatgtatg gtatctccct | 1020 |
| ttgccaagcc atcctggatg aaaccaaagg agattatgaa aaaatcctgg tggctctttg | 1080 |
| tggaggaaac taaacattcc cttgatggtc tcaagctatg atcagaagac tttaattata | 1140 |

-continued

| | |
|---|---|
| tattttcatc ctataagctt aaataggaaa gtttcttcaa caggattaca gtgtagctac | 1200 |
| ctacatgctg aaaaatatag cctttaaatc attttatat tataactctg tataatagag | 1260 |
| ataagtccat tttttaaaaa tgttttcccc aaaccataaa acctataca agttgttcta | 1320 |
| gtaacaatac atgagaaaga tgtctatgta gctgaaaata aaatgacgtc acaagac | 1377 |

<210> SEQ ID NO 19
<211> LENGTH: 3370
<212> TYPE: DNA
<213> ORGANISM: Homo sapiens

<400> SEQUENCE: 19

| | |
|---|---|
| gcccccgccc ggcccgcccc gctctcctag tcccttgcaa cctggcgctg catccgggcc | 60 |
| actgtcccag gtcccaggtc ccggcccgga gctatggagc ggcgctggcc cctgggcta | 120 |
| gggctggtgc tgctgctctg cgccccgctg ccccggggg cgcgcgccaa ggaagttact | 180 |
| ctgatggaca caagcaaggc acagggagag ctgggctggc tgctggatcc cccaaaagat | 240 |
| gggtggagtg aacagcaaca gatactgaat gggacacccc tctacatgta ccaggactgc | 300 |
| ccaatgcaag gacgcagaga cactgaccac tggcttcgct ccaattggat ctaccgcggg | 360 |
| gaggaggctt cccgcgtcca cgtggagctg cagttcaccg tgcgggactg caagagtttc | 420 |
| cctggggag ccgggcctct gggctgcaag agacccttca accttctgta catggagagt | 480 |
| gaccaggatg tgggcattca gctccgacgg cccttgttcc agaaggtaac cacggtggct | 540 |
| gcagaccaga gcttcaccat cgagaccctt cgtctggct ccgtgaagct gaatgtggag | 600 |
| cgctgctctc tgggccgcct gacccgccgt ggcctctacc tcgctttcca aacccgggt | 660 |
| gcctgtgtgg ccctggtgtc tgtccgggtc ttctaccagc gctgtcctga cccctgaat | 720 |
| ggcttggccc aattcccaga cactctgcct ggccccgctg ggttggtgga agtggcgggc | 780 |
| acctgcttgc cccacgcgcg ggccagcccc aggccctcag gtgcaccccg catgcactgc | 840 |
| agccctgatg gcgagtggct ggtgcctgta ggacggtgcc actgtgagcc tggctatgag | 900 |
| gaaggtggca gtggcgaagc atgtgttgcc tgcccagcg gctcctaccg gatgcacatg | 960 |
| gacacacccc attgtctcac gtgcccccag cagagcactg ctgagtctga gggggccacc | 1020 |
| atctgtacct gtgagagcgg ccattacaga gctcccgggg agggcccccca ggtggcatgc | 1080 |
| acaggtcccc cctcggcccc ccgaaacctg agcttctctg cctcagggac tcagctctcc | 1140 |
| ctgcgttggg aaccccagc agatacgggg ggacgccagg atgtcagata cagtgtgagg | 1200 |
| tgttcccagt gtcagggcac agcacaggac gggggccct gccagccctg tggggtgggc | 1260 |
| gtgcacttct cgccggggc ccgggcgctc accacacctg cagtgcatgt caatggcctt | 1320 |
| gaaccttatg ccaactacac ctttaatgtg aagcccaaa atggagtgtc agggctgggc | 1380 |
| agctctggcc atgccagcac ctcagtcagc atcagcatgg ggcatgcaga gtcactgtca | 1440 |
| ggcctgtctc tgagactggt gaagaaagaa ccgaggcaac tagagctgac ctgggcgggg | 1500 |
| tcccggcccc gaagccctgg ggcgaacctg acctatgagc tgcacgtgct gaaccaggat | 1560 |
| gaagaacggt accagatggt tctagaaccc agggtcttgc tgacagagct gcagcctgac | 1620 |
| accacataca tcgtcagagt ccgaatgctg accccactgg gtcctggccc tttctcccct | 1680 |
| gatcatgagt ttcggaccag cccaccagtg tccaggggcc tgactggagg agagattgta | 1740 |
| gccgtcatct ttgggctgct gcttggtgca gccttgctgc ttgggattct cgttttccgg | 1800 |
| tccaggagag cccagcggca gaggcagcag aggcacgtga ccgcgccacc gatgtggatc | 1860 |
| gagaggacaa gctgtgctga agccttatgt ggtacctcca ggcatacgag gaccctgcac | 1920 |

```
agggagcctt ggactttacc cggaggctgg tctaattttc cttcccggga gcttgatcca    1980
gcgtggctga tggtggacac tgtcatagga aaggagagt ttggggaagt gtatcgaggg    2040
accctcaggc tccccagcca ggactgcaag actgtggcca ttaagacctt aaaagacaca    2100
tccccaggtg gccagtggtg gaacttcctt cgagaggcaa ctatcatggg ccagtttagc    2160
cacccgcata ttctgcatct ggaaggcgtc gtcacaaagc gaaagccgat catgatcatc    2220
acagaattta tggagaatgc agccctggat gccttcctga gggagcggga ggaccagctg    2280
gtccctgggc agctagtggc catgctgcag ggcatagcat ctggcatgaa ctacctcagt    2340
aatcacaatt atgtccaccg ggacctggct gccagaaaca tcttggtgaa tcaaaacctg    2400
tgctgcaagt tgtctgactt tggcctgact cgcctcctgg atgactttga tggcacatac    2460
gaaacccagg gaggaaagat ccctatccgt tggacagccc ctgaagccat tgcccatcgg    2520
atcttcacca cagccagcga tgtgtggagc tttgggattg tgatgtggga ggtgctgagc    2580
tttgggggaca agccttatgg ggagatgagc aatcaggagg ttatgaagag cattgaggat    2640
gggtaccggt tgcccctcc tgtggactgc cctgccctc tgtatgagct catgaagaac    2700
tgctgggcat atgaccgtgc ccgccggcca cacttccaga agcttcaggc acatctggag    2760
caactgcttg ccaaccccca ctccctgcgg accattgcca actttgaccc cagggtgact    2820
cttcgcctgc ccagcctgag tggctcagat gggatcccgt atcgaaccgt ctctgagtgg    2880
ctcgagtcca tacgcatgaa acgctacatc ctgcacttcc actcggctgg gctggacacc    2940
atggagtgtg tgctggagct gaccgctgag gacctgacgc agatgggaat cacactgccc    3000
gggcaccaga gcgcattct ttgcagtatt cagggattca aggactgatc cctcctctca    3060
ccccatgccc aatcagggtg caaggagcaa ggacggggcc aaggtcgctc atggtcactc    3120
cctgcgcccc ttcccacaac ctgccagact aggctatcgg tgctgcttct gcccgcttta    3180
aggagaaccc tgctctgcac cccagaaaac ctctttgttt taaaagggag gtgggggtag    3240
aagtaaaagg atgatcatgg gagggagctc aggggttaat atatatacat acatacacat    3300
atatatattg ttgtaaataa acaggaaatg attttctgcc tccatcccac ccatcagggc    3360
tgcaggcact                                                          3370
```

<210> SEQ ID NO 20
<211> LENGTH: 1913
<212> TYPE: DNA
<213> ORGANISM: Homo sapiens

<400> SEQUENCE: 20

```
ccaagagcta cgcggcggcg gcggagcgca ggcctcgtgc cgttacggcc atcacggcgg     60
ccgcagtggc gtcctggagc cctcctcagt gctgaagctg ctgaaagatg gcagaagaag    120
tggtggtagt agccaaattt gattatgtgg cccaacaaga acaagagttg acatcaaga    180
agaatgagag attatggctt ctggatgatt ctaagtcctg gtggcgagtt cgaaattcca    240
tgaataaaac aggttttgtg ccttctaact atgtggaaag gaaaacagt gctcggaaag    300
catctattgt gaaaaaccta aaggatacct taggcattgg aaaagtgaaa agaaaaccta    360
gtgtgccaga ttctgcatct cctgctgatg atagttttgt tgacccaggg gaacgtctct    420
atgacctcaa catgcccgct tatgtgaaat ttaactacta ggctgagaga gaggatgaat    480
tatcattgat aaaggggaca aaggtgatcg tcatggagaa atgcagtgat gggtggtggc    540
gtggtagcta caatggacaa gttggatggt tcccttcaaa ctatgtaact gaagaaggtg    600
```

```
acagtccttt gggtgaccat gtgggttctc tgtcagagaa attagcagca gtcgtcaata    660
acctaaatac tgggcaagtg ttgcatgtgg tacaggctct ttacccattc agctcatcta    720
atgatgaaga acttaatttc gagaaaggag atgtaatgga tgttattgaa aaacctgaaa    780
atgacccaga gtggtggaaa tgcaggaaga tcaatggtat ggttggtcta gtaccaaaaa    840
actatgttac cgttatgcag aataatccat taacttcagg tttggaacca tcacctccac    900
agtgtgatta cattaggcct tcactcactg gaaagtttgc tggcaatcct tggtattatg    960
gcaaagtcac caggcatcaa gcagaaatgg cattaaatga agaggacat gaaggggatt    1020 tcctcattcg tgatagtgaa tcttcgccaa atgattctc agtatcacta aaagcacaag    1080
ggaaaaacaa gcattttaaa gtccaactaa aagagactgt ctactgcatt gggcagcgta    1140
aattcagcac catggaagaa cttgtagaac attacaaaaa ggcaccaatt tttacaagtg    1200
aacaaggaga aaaattatat cttgtcaagc atttatcatg atactgctga ccagaagtga    1260
ctgctgtgta gctgtaattt gtcatgtaat tgaagactga gaaatgttg ggtccagtcg    1320 tgcttgattg gaaattgttg tttctaaatc tatatgagaa ttgacaataa gtatttttat    1380
tataactcag cccatacata tatactatgt atgcagtgca tctgcataga acagttcctt    1440
atccttggcc ttctgtttta ttgtttttt ctttgctgtt ttcccttgc ttctaatatt    1500 acagttttgt attttgtaaa caaaaatcaa ataatgcata tcagaatctt tatatggaag    1560
aaatccttta ttgcctttcc tttgtttcct tgtaaaggca ccctgttctg ttatggtttt    1620
tcattatata aaattattat atctatatat gacatatgct aaaatttctt ggagagtgtt    1680
aatcttttct gtgactaaat agcaataata agtggaaaat tagaaattat ttccaggtat    1740
tatatttgtc acaggccatt gtaaatacca agtatattgt gtctgccata atttttaaaa    1800
atacattcat tgtcttcagt catacagcaa gacacatgag acatagatta gaaaacatgt    1860
tgtacaattt taatttacaa ctgttggaaa taaaaatcac ttaattttt tcc           1913

<210> SEQ ID NO 21
<211> LENGTH: 3257
<212> TYPE: DNA
<213> ORGANISM: Homo sapiens

<400> SEQUENCE: 21
catggcggcg actgcggcaa agcgagagcc tcggagacgc cgctgccgcc agcacagccg     60
gagacctgag ccgacactgg gggcagtccg cgagccccgc actctctcga tgagtcggag    120
aagtcccgtt gtatcagagt aagatggacg gtagctttga ttgtgattgt ggtgagctgg    180
agccacctga tcactaacaa aagacatctt ctgttaacca acagccgcca gggcttcctg    240
ttgaaataaa tatatagcaa caaaggaaaa aagaagcaa acggaaaata gtgcttacca    300
gcaccttaga atgatgctgc tcaggaccag tccaacactg aatgtatctg cactgtgagg    360
agaatgttca tagaagcctg ttgtgtgcat atttattcac attttttgtta aatgttaaat    420 cgtttagcac ggtaatctga gtgcacagta tgtcatttca ttccgtttga gtttcttgtt    480
ttcgttaaat gtctgcagag ttgctgcccc tttcttgaac tatgagtact gcaatctttt    540
taattctcaa tatgaataga gctttttgag ctttaaatct aaggggaact cgacaggcct    600
gtttggcata tgcaatgaac atcaagaaac catcttgctg tggaagcata attatttttc    660
ttctcccttt ttgaaagatc tttccttttg atgccagttt tcttccttgt ttacacaagt    720
tcaatttgaa aggaaaaggc aatagtaagg gtttcaaaat ggcagagaaa tttgaaagtc    780
tcatgaacat tcatggtttt gatctgggtt ctaggtatat ggacttaaaa ccattgggtt    840
```

-continued

```
gtggaggcaa tggcttggtt ttttctgctg tagacaatga ctgtgacaaa agagtagcca      900
tcaagaaaat tgtccttact gatccccaga gtgtcaaaca tgctctacgt gaaatcaaaa      960
ttattagaag acttgaccat gataacattg tgaaagtgtt tgagattctt ggtcccagtg     1020
gaagccaatt aacagacgat gtgggctctc ttacggaact gaacagtgtt tacattgttc     1080
aggagtacat ggagacagac ttggctaatg tgctggagca gggcccttta ctggaagagc     1140
atgccaggct tttcatgtat cagctgctac gggggctcaa gtatattcac tctgcaaatg     1200
tactgcacag agatctcaaa ccagctaatc ttttcattaa tacggaagac ttggtgctga     1260
agataggtga ctttggtctt gcacggatca tggatcctca ttattcccat aagggtcatc     1320
tttctgaagg attggttact aaatggtaca gatctccacg tcttttactt tctcctaata     1380
attatactaa agccattgac atgtgggctg caggctgcat ctttgctgaa atgctgactg     1440
gtaaaaccct ttttgcaggt gcacatgaac ttgaacagat gcagctgatt ttagaatcta     1500
ttcctgttgt acatgaggaa gatcgtcagg agcttctcag cgtaattcca gtttacatta     1560
gaaatgacat gactgagcca cacaaacctt taactcagct gcttccagga attagtcgag     1620
aagcactgga tttcctggaa caaattttga catttagccc catggatcgg ttaacagcag     1680
aagaagcact ctcccatcct tacatgagca tatattcttt tccaatggat gagccaattt     1740
caagccatcc ttttcatatt gaagatgaag ttgatgatat tttgcttatg gatgaaactc     1800
acagtcacat ttataactgg gaaaggtatc atgattgtca gttttcagag catgattggc     1860
ctgtacataa caactttgat attgatgaag ttcagcttga tccaagagct ctgtccgatg     1920
tcactgatga agaagaagta caagttgatc cccgaaaata tttggatgga gatcgggaaa     1980
agtatctgga ggatcctgct tttgatacca attactctac tgagccttgt tggcaatact     2040
cagatcatca tgaaaacaaa tattgtgatc tggagtgtag ccatacttgt aactacaaaa     2100
cgaggtcatc atcatattta gataacttag tttggagaga gagtgaagtt aaccattact     2160
atgaacccaa gcttattata gatctttcca attggaaaga acaaagcaaa gaaaaatctg     2220
ataagaaagg caaatcaaaa tgtgaaagga atggattggt taaagcccag atagcgctag     2280
aggaagcatc acagcaactg gctggaaaag aaagggaaaa gaatcaggga tttgatttttg    2340
attccttat tgcaggaact attcagctta gttcccagca tgagcctact gatgttgttg     2400
ataaattaaa tgacttgaat agctcagtgt cccaactaga attgaaaagt ttgatatcaa     2460
agtcagtaag ccaagaaaaa caggaaaaag gaatggcaaa tctggctcaa ttagaagcct     2520
tgtaccagtc ttcttgggac agccagtttg tgagtggtgg ggaggactgt tttttcataa     2580
atcagttttg tgaggtaagg aaggatgaac aagttgagaa ggaaaacact tacactagtt     2640
acttggacaa gttctttagc aggaaagaag atactgaaat gctagaaact gagccagtag     2700
aggatgggaa gcttggggag agaggacatg aggaaggatt tctgaacaac agtgggagt     2760
tcctctttaa caagcagctc gagtccatag gcatcccaca gtttcacagt ccagttgggt     2820
caccacttaa gtcaatacag gccacattaa caccttctgc tatgaaatct tcccctcaaa     2880
ttcctcatca aacatacagc agcattctga acatctgaa ctaaaacact cagcagacat     2940
ttatctttgt attcttcatg aaatgtgttt tgtctttttt tattactagt gtttaagtca     3000
ttttttactt gaatcagatg gtgtcattta gtaaggattt tatgagttct tgttttttaa     3060
aatccagact ttcttttttct acatgtgaga tagttttcat tttaactggc atgtcatttg     3120
cacacaaaaa taaagactag agcaaaataa tgcaacgcag gaggagaaaa gaaatgcact     3180
```

-continued

| | |
|---|---|
| aagacaagaa cattctctca tagaacattg atctgtttta caggaaacaa accttgcctt | 3240 |
| gaaatttaca cagtgag | 3257 |

<210> SEQ ID NO 22
<211> LENGTH: 2354
<212> TYPE: DNA
<213> ORGANISM: Homo sapiens

<400> SEQUENCE: 22

| | |
|---|---|
| ggtctttgag cgctaacgtc tttctgtctc cccgcggtgg tgatgacggt gaaaactgag | 60 |
| gctgctaagg gcaccctcac ttactccagg atgaggggca tggtggcaat tctcatcgct | 120 |
| ttcatgaagc agaggaggat gggtctgaac gactttattc agaagattgc caataactcc | 180 |
| tatgcatgca acaccctga agttcagtcc atcttgaaga tctcccaacc tcaggagcct | 240 |
| gagcttatga atgccaaccc ttctcctcca ccaagtcctt ctcagcaaat caaccttggc | 300 |
| ccgtcgtcca atcctcatgc taaaccatct gactttcact tcttgaaagt gatcggaaag | 360 |
| ggcagttttg gaaaggttct tctagcaaga cacaaggcag aagaagtgtt ctatgcagtc | 420 |
| aaagttttac agaagaaagc aatcctgaaa agaaagagg agaagcatat tatgtcggag | 480 |
| cggaatgttc tgttgaagaa tgtgaagcac cctttcctgg tgggccttca cttctctttc | 540 |
| cagactgctg acaaattgta ctttgtccta gactacatta atggtggaga gttgttctac | 600 |
| catctccaga gggaacgctg cttcctggaa ccacgggctc gtttctatgc tgctgaaata | 660 |
| gccagtgcct gggctacct gcattcactg aacatcgttt atagagactt aaaaccagag | 720 |
| aatattttgc tagattcaca gggacacatt gtccttactg acttcggact ctgcaaggag | 780 |
| aacattgaac acaacagcac aacatccacc ttctgtggca cgccggagta tctcgcacct | 840 |
| gaggtgcttc ataagcagcc ttatgacagg actgtggact ggtggtgcct gggagctgtc | 900 |
| ttgtatgaga tgctgtatgg cctgccgcct tttatagcc gaaacacagc tgaaatgtac | 960 |
| gacaacattc tgaacaagcc tctccagctg aaaccaaata ttacaaattc cgcaagacac | 1020 |
| ctcctggagg gcctcctgca gaaggacagg acaaagcggc tcggggccaa ggatgacttc | 1080 |
| atggagatta agagtcatgt cttcttctcc ttaattaact gggatgatct cattaataag | 1140 |
| aagattactc cccttttaa cccaaatgtg agtgggccca acgacctacg gcactttgac | 1200 |
| cccgagttta ccgaagagcc tgtccccaac tccattggca agtcccctga cagcgtcctc | 1260 |
| gtcacagcca gcgtcaagga agctgccgag gctttcctag gcttttccta tgcgcctccc | 1320 |
| acggactctt tcctctgaac cctgttaggg cttggttta aaggatttta tgtgtgtttc | 1380 |
| cgaatgtttt agttagcctt ttggtggagc cgccagctga caggacatct tacaagagaa | 1440 |
| tttgcacatc tctggaagct tagcaatctt attgcacact gttcgctgga agcttttga | 1500 |
| agagcacatt ctcctcagtg agctcatgag gttttcattt ttattcttcc ttccaacgtg | 1560 |
| gtgctatctc tgaaacgagc gttagagtgc cgccttagac ggaggcagga gtttcgttag | 1620 |
| aaagcggacg ctgttctaaa aaaggtctcc tgcagatctg tctgggctgt gatgacgaat | 1680 |
| attatgaaat gtgcctttc tgaagagatt gtgttagctc caaagctttt cctatcgcag | 1740 |
| tgtttcagtt cttttatttc ccttgtggat atgctgtgtg aaccgtcgtg tgagtgtggt | 1800 |
| atgcctgatc acagatggat tttgttataa gcatcaatgt gacacttgca ggacactaca | 1860 |
| acgtgggaca ttgtttgttt cttccatatt tggaagataa atttatgtgt agactttttt | 1920 |
| gtaagatacg gttaataact aaaatttatt gaaatggtct tgcaatgact cgtattcaga | 1980 |
| tgcttaaaga aagcattgct gctacaaata tttctatttt tagaaagggt ttttatggac | 2040 |

-continued

| | |
|---|---|
| caatgcccca gttgtcagtc agagccgttg gtgtttttca ttgtttaaaa tgtcacctgt | 2100 |
| aaaatgggca ttatttatgt tttttttttt gcattcctga taattgtatg tattgtataa | 2160 |
| agaacgtctg tacattgggt tataacacta gtatatttaa acttacaggc ttatttgtaa | 2220 |
| tgtaaaccac cattttaatg tactgtaatt aacatggtta taatacgtac aatccttccc | 2280 |
| tcatcccatc acacaacttt ttttgtgtgt gataaactga ttttggtttg caataaaacc | 2340 |
| ttgaaaaata ttta | 2354 |

<210> SEQ ID NO 23
<211> LENGTH: 1728
<212> TYPE: DNA
<213> ORGANISM: Homo sapiens

<400> SEQUENCE: 23

| | |
|---|---|
| gagcagcaga atttcaactc cagtagactt gaatatgcct ctgggcaaag aagcagagct | 60 |
| aacgaggaaa gggatttaaa gagttttttct tgggtgtttg tcaaactttt attccctgtc | 120 |
| tgtgtgcaga ggggattcaa cttcaatttt tctgcagtgg ctctgggtcc agccccttac | 180 |
| ttaaagatct ggaaagcatg aagactgggc ttttttttcct atgtctcttg ggaactgcag | 240 |
| ctgcaatccc gacaaatgca agattattat ctgatcattc caaccaact gctgaaacgg | 300 |
| tagcacctga caacactgca atccccagtt taagggctga agctgaagaa atgaaaaag | 360 |
| aaacagcagt atccacagaa gacgattccc accataaggc tgaaaaatca tcagtactaa | 420 |
| agtcaaaaga ggaaagccat gaacagtcag cagaacaggg caagagttct agccaagagc | 480 |
| tgggattgaa ggatcaagag gacagtgatg gtcacttaag tgtgaatttg gagtatgcac | 540 |
| caactgaagg tacattggac ataaagaag atatgagtga gcctcaggag aaaaaactct | 600 |
| cagagaacac tgattttttg gctcctggtg ttagttcctt cacagattct aaccaacaag | 660 |
| aaagtatcac aaagagagag gaaaaccaag aacaacctag aaattattca catcatcagt | 720 |
| tgaacaggag cagtaaacat agccaaggcc taagggatca aggaaaccaa gagcaggatc | 780 |
| caaatatttc caatggagaa gaggaagaag aaaaagagcc aggtgaagtt ggtacccaca | 840 |
| atgataacca agaaagaaag acagaattgc ccagggagca tgctaacagc aagcaggagg | 900 |
| aagacaatac ccaatctgat gatatttttgg aagagtctga tcaaccaact caagtaagca | 960 |
| agatgcagga ggatgaattt gatcagggta accaagaaca agaagataac tccaatgcag | 1020 |
| aaatggaaga ggaaaatgca tcgaacgtca ataagcacat tcaagaaact gaatggcaga | 1080 |
| gtcaagaggg taaaactggc ctagaagcta tcagcaacca caagagaca gaagaaaaga | 1140 |
| ctgtttctga ggctctgctc atggaaccta ctgatgatgg taataccacg cccagaaatc | 1200 |
| atggagttga tgatgatggc gatgatgatg gcgatgatgg cggcactgat ggccccaggc | 1260 |
| acagtgcaag tgatgactac ttcatcccaa gccaggcctt tctggaggcc gagagagctc | 1320 |
| aatccattgc ctatcacctc aaaattgagg agcaaagaga aaagtacat gaaaatgaaa | 1380 |
| ataggtac cactgagcct ggagagcacc aagaggccaa gaaagcagag aactcatcaa | 1440 |
| atgaggagga aacgtcaagt gaaggcaaca tgagggtgca tgctgtggat tcttgcatga | 1500 |
| gcttccagtg taaagaggc cacatctgta aggcagacca acaggaaaaa cctcactgtg | 1560 |
| tctgccagga tccagtgact tgtcctccaa caaaacccct tgatcaagtt tgtggcactg | 1620 |
| acaatcagac ctatgctagt tcctgtcatc tattcgctac taaatgcaga ctggaggga | 1680 |
| ccaaaaaggg gcatcaactc cagctggatt attttggagc ctgcaaat | 1728 |

```
<210> SEQ ID NO 24
<211> LENGTH: 1848
<212> TYPE: DNA
<213> ORGANISM: Homo sapiens

<400> SEQUENCE: 24
cggataagga caaaaaacgc cagaagaaaa gaggcatttt ccccaaagta gcaacaaata      60
tcatgagagc atggctcttc cagcatctca cacatccgta cccttccgaa gagcagaaga     120
aacagttagc gcaagacaca ggacttacaa ttctccaagt aaacaactgg tttattaatg     180
ccagaagaag aatagtacag cccatgattg accagtcaaa tcgagcagtg agccaaggag     240
cagcatatag tccagagggt cagcccatgg ggagctttgt gttggatggt cagcaacaca     300
tggggatccg gcctgcagga cctatgagtg gaatgggcat gaatatgggc atggatgggc     360
aatggcacta catgtaacct tcatcatgta agcaatcgc aaagcaaggg ggaagtttgc      420
agagcatgcc aggggactac gtttctcagg gtggtcctat gggaatgagt atggcacagc     480
caagttacac tcctccccag atgaccccac accctactca attaagacat ggaccccaa      540 tgcattcata tttgccaagc catccccacc acccagccat gatgatgcac ggaggacccc     600
ctacccaccc tggaatgact atgtcagcac agagccccac aatgttaaat tctgtagatc     660
ccaatgttgg cggacaggtt atggacattc atgcccaata gtataaggga actcaaggga     720
aaaggaaaca cacgcaaaaa ctattttaag actttctgaa ctttgaccag atgttgacac     780
ttaatatgaa attccagaca gctgtgatta ttttttactt ttgtcatttt tcatcaagca     840
acagaggacc aatgcaacaa gaacacaaat gtgaaatcat gggctgactg agacaattct     900
gtccatgtaa agatcctctg gaaaaagact ccgagagtta taactactgt agtataaata     960
taggaactaa gttaaacttg tacatttctg ttgatcacgc cgttatgttg cctcaaatag    1020
ttttagaaga gaaaaaaaaa tatatccttg ttttccacac tatgtgtgtt gttcccaaaa    1080
gaatgactgt tttggttcat cagtgaattc accatccagg agagactgtg gtatatattt    1140
taaacctgtt gggccaatga gaaaagaacc acactggaga tcatgatgaa ctttttggctg   1200 aacctcatca ctcgaactcc agcttcaaga atgtgttttc atgcccggcc tttgttcctc    1260
cataaatgtg tcctttagtt tcaaacagat ctttatagtt cgtgcttcat aagccaattc    1320
ttattattat ttttggggga ctcttcttca aagagcttgc caatgaagat ttaaagacag    1380
agcaggagct tcttccagga gttctgagcc ttggttgtgg acaaaacaat cttaagttgg    1440
gcagctttcc tcaacacaaa aaaagttat taatggtcat tgaaccataa ctaggacttt     1500
atcagaaact caaagcttgg gggataaaaa ggagcaagag aatactgtaa caaacttcgt    1560
acagagttcg gtctattaat tgtttcatgt tagatattct atgtgtttac ctcaattgaa    1620 aaaaaaaga atgttttttgc tagtatcaga tctgctgtgg aattggtatt gtatgtccat    1680
gaattcttct tttctcagca cgtgttcctc actagaagaa aatgctgtta cctttaagct    1740
ttgtcaaatt tacattaaaa tacttgtatg aggactgtga cgttatgtta aaaaaaaaa    1800 ggtgttaagt cacaaaaagc ggtaataaat atttcatttt tgattttt                 1848

<210> SEQ ID NO 25
<211> LENGTH: 3164
<212> TYPE: DNA
<213> ORGANISM: Homo sapiens

<400> SEQUENCE: 25
agcacactga ggaggcgatc cgccagcagg aggtggagca gctggacttc cgagacctcc      60
```

-continued

```
tggggaagaa ggtgagtaca agaccctat cggaagacga cctgaaggag atcccagccg    120
agcagatgga tttccgtgcc aacctgcagc ggcaagtgaa gccaaagact gtgtctgagg   180
aagagaggaa ggtgcacagc ccccagcagg tcgattttcg ctctgtcctg gccaagaagg   240
ggacttccaa gaccccgtg cctgagaagg tgccaccgcc aaaacctgcc accccggatt    300
ttcgctcagt gctgggtggc aagaagaaat taccagcaga gaatggcagc agcagtgccg   360
agaccctgaa tgccaaggca gtggagagtt ccaagcccct gagcaatgca cagccttcag   420
ggcccttgaa accgtgggc aacgccaagc ctgctgagac cctgaagcca atgggcaacg    480
ccaagcctgc cgagaccctg aagcccatgg gcaatgccaa gcctgatgag aacctgaaat   540
ccgctagcaa agaagaactc aagaaagacg ttaagaatga tgtgaactgc aagagaggcc   600
atgcagggac cacagataat gaaaagagat cagagagcca ggggacagcc ccagccttca   660
agcagaagct gcaagatgtt catgtggcag agggcaagaa gctgctgctc cagtgccagg   720
tgtcttctga ccccccagcc accatcatct ggacgctgaa cggaaagacc atcaagacca   780
ccaagttcat catcctctcc caggaaggct cactctgctc cgtctccatc gagaaggcac   840
tgcctgagga cagaggctta tacaagtgtg tagccaagaa tgacgctggc caggcggagt   900
gctcctgcca agtcaccgtg gatgatgctc cagccagtga gaacaccaag gccccagaga   960
tgaaatcccg gaggcccaag agctctcttc ctcccgtgct aggaactgag agtgatgcga  1020
ctgtgaaaaa gaaacctgcc cccaagacac ctccgaaggc agcaatgccc ctcagatca   1080 tccagttccc tgaggaccag aaggtacgcg caggagagtc agtggagctg tttggcaaag  1140
tgacaggcac tcagcccatc acctgtacct ggatgaagtt ccgaaagcag atccaggaaa  1200
gcgagcacat gaaggtggag aacagcgaga atggcagcaa gctcaccatc ctggccgcgc  1260
gccaggagca ctgcggctgc tacacactgc tggtggagaa caagctgggc agcaggcagg  1320
cccaggtcaa cctcactgtc gtggataagc cagaccccc agctggcaca ccttgtgcct   1380
ctgacattcg gagctcctca ctgaccctgt cctggtatgg ctcctcatat gatgggggca   1440
gtgctgtaca gtcctacagc atcgagatct gggactcagc caacaagacg tggaaggaac   1500
tagccacatg ccgcagcacc tctttcaacg tccaggacct gctgcctgac cacgaatata  1560
agttccgtgt acgtgcaatc aacgtgtatg gaaccagtga gccaagccag gagtctgaac  1620
tcacaacggt aggagagaaa cctgaagagc cgaaggatga agtggaggtg tcagacgatg  1680
atgagaagga gcccgaggtt gattaccgga cagtgacaat caatactgaa caaaaagtat  1740
ctgacttcta cgacattgag gagagattag gatctgggaa atttggacag gtctttcgac  1800
ttgtagaaaa gaaaactcga aaagtctggg cagggaagtt cttcaaggca tattcagcaa  1860
aagagaaaga gaatatccgg caggagatta gcatcatgaa ctgcctccac caccctaagc  1920
tggtccagtg tgtggatgcc tttgaagaaa aggccaacat cgtcatggtc ctggagatcg  1980
tgtcaggagg ggagctgttt gagcgcatca ttgacgagga ctttgagctg acggagcgtg  2040
agtgcatcaa gtacatgcgg cagatctcgg agggagtgga gtacatccac aagcagggca  2100
tcgtgcacct ggacctcaag ccggagaaca tcatgtgtgt caacaagacg ggcaccagga  2160
tcaagctcat cgactttggt ctggccagga ggctggagaa cgcggggtct ctgaaggtcc  2220
tctttggcac cccagaattt gtggctcctg aagtgatcaa ctatgagccc atcggctacg  2280
ccacagacat gtggagcatc ggggtcatct gctacatcct agtcagtggc cttttcccct  2340
tcatgggaga caacgataac gaaaccttgg ccaacgttac ctcagccacc tgggacttcg  2400
```

-continued

```
acgacgaggc attcgatgag atctccgacg atgccaagga tttcatcagc aatctgctga    2460
agaaagatat gaaaaaccgc ctggactgca cgcagtgcct tcagcatcca tggctaatga    2520
aagataccaa gaacatggag gccaagaaac tctccaagga ccggatgaag aagtacatgg    2580
caagaaggaa atggcagaaa acgggcaatg ctgtgagagc cattggaaga ctgtcctcta    2640
tggcaatgat ctcagggctc agtggcagga atcctcaac agggtcacca accagcccgc     2700
tcaatgcaga aaaactagaa tctgaagaag atgtgtccca agctttcctt gaggctgttg    2760
ctgaggaaaa gcctcatgta aaaccctatt tctctaagac cattcgcgat ttagaagttg    2820
tggagggaag tgctgctaga tttgactgca agattgaagg atacccagac cccgaggttg    2880
tctggttcaa agatgaccag tcaatcaggg agtcccgcca cttccagata gactacgatg    2940
aggacgggaa ctgctcttta attattagtg atgtttgcgg ggatgacgat gccaagtaca    3000
cctgcaaggc tgtcaacagt cttggagaag ccacctgcac agcagagctc attgtggaaa    3060
cgatggagga aggtgaaggg gaaggggaag aggaagaaga gtgaaacaaa gccagagaaa    3120
agcagtttct aagtcatatt aaaaggacta tttctctaaa actc                    3164
```

<210> SEQ ID NO 26
<211> LENGTH: 3851
<212> TYPE: DNA
<213> ORGANISM: Homo sapiens

<400> SEQUENCE: 26

```
ctctcccaac cgcctcgtcg cactcctcag gctgagagca ccgctgcact cgcggccggc      60
gatgcgggac cccggcgcgg ccgctccgct ttcgtccctg ggcctctgtg ccctggtgct     120
ggcgctgctg ggcgcactgt ccgcgggcgc cggggcgcag ccgtaccacg gagagaaggg     180
catctccgtg ccggaccacg gcttctgcca gcccatctcc atcccgctgt gcacggacat     240
cgcctacaac cagaccatcc tgcccaacct gctgggccac acgaaccaag aggacgcggg     300
cctcgaggtg caccagttct acccgctggt gaaggtgcag tgttctcccg aactccgctt     360
tttcttatgc tccatgtatg cgcccgtgtg caccgtgctc gatcaggcca tcccgccgtg     420
tcgttctctg tgcgagcgcg cccgccaggg ctgcgaggcg ctcatgaaca agttcggctt     480
ccagtggccc gagcggctgc gctgcgagaa cttcccggtg cacggtgcgg gcagatctg      540 cgtgggccag aacacgtcgg acggctccgg gggcccaggc ggcggcccca ctgcctaccc     600
taccgcgccc tacctgccgg acctgccctt caccgcgctg ccccggggg cctcagatgg      660 cagggggcgt ccccgccttcc ccttctcatg cccccgtcag ctcaaggtgc ccccgtacct    720
gggctaccgc ttcctggggtg agcgcgattg tggcgccccg tgcgaaccgg gccgtgccaa    780
cggcctgatg tactttaagg aggaggagag gcgcttcgcc cgcctctggg tgggcgtgtg     840
gtccgtgctg tgctgcgcct cgacgctctt taccgttctc acctacctgg tggacatgcg     900
gcgcttcagc tacccagagc ggcccatcat cttcctgtcg ggctgctact tcatggtggc     960
cgtggcgcac gtggccggct tccttctaga ggaccgcgcc gtgtgcgtgg agcgcttctc    1020
ggacgatggc taccgcacgg tggcgcaggg caccaagaag gagggctgca ccatcctctt    1080
catggtgctc tacttcttcg gcatggccag ctccatctgg tgggtcattc tgtctctcac    1140
ttggttcctg gcggccggca tgaagtgggg ccacgaggcc atcgaggcca actcgcagta    1200
cttccacctg gccgcgtggg ccgtgcccgc cgtcaagacc atcactatcc tggccatggg    1260
ccaggtagac gggaccctgc tgagcggggt gtgctacgtt ggcctctcca gtgtggacgc    1320 gctgcgggc ttcgtgctgg cgcctctgtt cgtctacctc ttcataggca cgtccttctt    1380
```

```
gctggccggc ttcgtgtccc tcttccgtat ccgcaccatc atgaaacacg acggcaccaa   1440
gaccgagaag ctggagaagc tcatggtgcg catcggcgtc ttcagcgtgc tctacacagt   1500
gcccgccacc atcgtcctgg cctgctactt ctacgagcag gccttccgcg agcactggga   1560
gcgcacctgg ctcctgcaga cgtgcaagag ctatgccgtg ccctgcccgc ccggccactt   1620
cccgcccatg agccccgact tcaccgtctt catgatcaag tacctgatga ccatgatcgt   1680
cggcatcacc actggcttct ggatctggtc gggcaagacc ctgcagtcgt ggcgccgctt   1740
ctaccacaga cttagccaca gcagcaaggg ggagactgcg gtatgagccc cggcccctcc   1800
ccacctttcc caccccagcc ctcttgcaag aggagaggca cggtagggaa agaactgct   1860 gggtggggc ctgtttctgt aactttctcc ccctctactg agaagtgacc tggaagtgag   1920
aagttctttg cagatttggg gcgaggggtg atttggaaaa aagacctgg gtggaaagcg   1980 gtttggatga aaagatttca ggcaaagact gcaggaaga tgatgataac ggcgatgtga   2040
atcgtcaaag gtacgggcca gcttgtgcct aatagaaggt tgagaccagc agagactgct   2100
gtgagtttct cccggctccg aggctgaacg gggactgtga gcgatccccc tgctgcaggg   2160
cgagtggcct gtccagaccc ctgtgaggcc ccggaaaagg tacagccctg tctgcggtgg   2220
ctgctttgtt ggaaagaggg agggcctcct gcggtgtgct tgtcaagcag tggtcaaacc   2280
ataatctctt ttcactgggg ccaaactgga gcccagatgg gttaatttcc agggtcagac   2340
attacggtct ctcctcccct gcccctccc gcctgttttt cctcccgtac tgctttcagg   2400
tcttgtaaaa taagcatttg gaagtcttgg gaggcctgcc tgctagaatc ctaatgtgag   2460
gatgcaaaag aaatgatgat aacattttga gataaggcca aggagacgtg gagtaggtat   2520
ttttgctact ttttcatttt ctggggaagg caggaggcag aaagacgggt gttttatttg   2580
gtctaatacc ctgaaaagaa gtgatgactt gttgcttttc aaaacaggaa tgcattttc   2640 cccttgtctt tgttgtaaga gacaaaagag gaaacaaaag tgtctccctg tggaaaggca   2700
taactgtgac gaaagcaact tttataggca aagcagcgca aatctgaggt ttcccgttgg   2760 ttgttaatt ggttgagata acattcctt tttaaggaaa agtgaagagc agtgtgctgt   2820
cacacaccgt taagccagag gttctgactt cgctaaagga aatgtaagag gttttgttgt   2880
ctgttttaaa taaatttaat tcggaacaca tgatccaaca gactatgtta aaatattcag   2940
ggaaatctct cccttcattt acttttcctt gctataagcc tatatttagg tttcttttct   3000
atttttttct cccatttgga tccttgagg taaaaaaca taatgtcttc agcctcataa   3060
taaaggaaag ttaattaaaa aaaaaagca agagccatt ttgtcctgtt tcttggttc   3120 catcaatctg tttattaaac atcatccata tgctgaccct gtctctgtgt ggttgggttg   3180
ggaggcgatc agcagatacc atagtgaacg aagaggaagg tttgaaccat gggccccatc   3240
tttaaagaaa gtcattaaaa gaaggtaaac ttcaaagtga ttctggagtt ctttgaaatg   3300
tgctggaaga cttaaattta ttaatcttaa atcatgtact ttttttctgt aatagaactc   3360
ggattctttt gcatgatggg gtaaagctta gcagagaatc atgggagcta accttttatcc  3420 cacctttgac actaccctcc aatcttgcaa cactatcctg tttctcagaa cagtttttaa   3480
atgccaatca tagagggtac tgtaaagtgt acaagttact ttatatatgt aatgttcact   3540
tgagtggaac tgcttttttac attaaagtta aaatcgatct tgtgtttctt caaccttcaa   3600
aactatctca tctgtcagat ttttaaaact ccaacacagg ttttggcatc ttttgtgctg   3660
tatcttttaa gtgcatgtga aatttgtaaa atagagataa gtacagtatg tatattttgt   3720
```

```
aaatctccca tttttgtaag aaaatatata ttgtatttat acattttac tttggatttt      3780 tgttttgttg gctttaaagg tctaccccac tttatcacat gtacagatca caaataaatt      3840
tttttaaata c                                                           3851
```

<210> SEQ ID NO 27
<211> LENGTH: 1476
<212> TYPE: DNA
<213> ORGANISM: Homo sapiens

<400> SEQUENCE: 27

```
ggggctcggg acggccgggc tgggagctgg agcccacagc gggaagcggc cgccgcccgg       60
gcctcgcagg gctaggcgag gcgagggggg gcggggccgg gcgctacggg aaggggaggc      120
cgcgcggacc gggagccgca ccgcgccagc cgggctgcag cggccgcgca ccaaggctgc      180 gatgggctg gagacggaga aggcggacgt acagctcttc atggacgacg actcctacag       240
ccaccacagc ggcctcgagt acgccgaccc cgagaagttc gcggactcgg accaggaccg      300
ggatccccac cggctcaact cgcatctcaa gctgggcttc gaggatgtga tcgcagagcc      360
ggtgactacg cactcctttg acaaagtgtg gatctgcagc catgccctct ttgaaatcag      420
caaatacgta atgtacaagt tcctgacggt gttcctggcc attcccctgg ccttcattgc      480
gggaattctc tttgccaccc tcagctgtct gcacatctgg atttaatgc cttttgtaaa       540 gacctgccta atggttctgc cttcagtgca gacaatatgg aagagtgtga cagatgttat      600
cattgctcca ttgtgtacga gcgtaggacg atgcttctct tctgtcagcc tgcaactgag      660
ccaggattga atacttggac cccaggtctg gagattggga tactgtaata cttctttgtt      720
attataacat aaaagcacca ctgttctgtt catttcctag ctgttctaat taagaaaact      780
attaagatga gcaaccacat ttagaaatgt ttattgacag gtcttttcaa ataatgcttt      840
tctaattaat agccaaagat tcatatctca actttgtaac cagaattata cagtaagttg      900
acaccactta gatttaaagg cagacagttt tgctttagta caatagtata cattttataa      960
tgatgaactt ataatgatta agggacattt ctataaaaat actacaatag ttttatgcac     1020
aacttcccat taaaaatgag atttcttatt tgtttgtctg tttttactct gggagtaata     1080 cttttaaat tacctttaca tatatagtca ctggcatact gagaatatac aatgatcctg     1140
gaaattgcag taacaaaagc acacaacgat tatagtaact ataagataca ataaaacaaa     1200
taaatatgaa agtagattca tgaaaatgta ttcctttaaa atattgtttt cctacaggcc     1260
tatttaacaa gatgtttcat tttactgtat attttgtagt taatataaat gttgctctaa     1320
tcagattgct taaaagcatt tttattatat ttatgttgtt gaactaatat atgaaataag     1380
taaatgtagc tcccacaagg taaacttcat tggtaagatt gcactgttct gattatgtaa     1440
gcatttgtac atcttctttg gaaataaaag ataaaa                                1476
```

<210> SEQ ID NO 28
<211> LENGTH: 4116
<212> TYPE: DNA
<213> ORGANISM: Homo sapiens

<400> SEQUENCE: 28

```
gtttagaaca gcctacagac ccagtggcac gagacgggcc tctctcccaa acatcttcca       60
agccagatcc tagtcagtgg gaaagcccca gcttcaaccc ctttgggagc cactctgttc      120
tgcagaactc cccaccctc tcttctgagg gctcctacca ctttgaccca gataactttg       180
acgaatccat ggatcccttt aaaccaacta cgaccttaac aagcagtgac ttttgttctc      240
```

-continued

```
ccactggtaa tcacgttaat gaaatcttag aatcacccaa gaaggcaaag tcgcgtttaa      300
taacgactac tgaacaagtg aaatttctct gttttctgtt gagtggctgt aaggtgaaga      360
agcatgaaac tcagtctctc gccctggatg catgttctcg ggatgaaggg gcagtgatct      420
cccagatttc agacatttct aatagggatg gccatgctac tgatgaggag aaactggcat      480
ccacgtcatg tggtcagaaa tcagctggtg ccgaggtgaa aggtgagcca gaggaagacc      540
tggagtactt tgaatgttcc aatgttcctg tgtctaccat aaatcatgcg ttttcatcct      600
cagaagcagg catagagaag gagacgtgcc agaagatgga agaagacggg tccactgtgc      660
ttgggctgct ggagtcctct gcagagaagg cccctgtgtc ggtgtcctgt ggaggtgaga      720
gcccctggga tgggatctgc ctcagcgaat cagacaagac agccgtgctc accttaataa      780
gagaagagat aattactaaa gagattgaag caaatgaatg gaagaagaaa tacgaagaga      840
cccggcaaga agttttggag atgaggaaaa ttgtagctga atatgaaaag actattgctc      900
aaatgattga tgaacaaagg acaagtatga cctctcagaa gagcttccag caactgacca      960
tggagaagga acaggccctg gctgacctta actctgtgga aggtcccctt tctgatctct     1020
tcaggagata tgagaacctg aaaggtgttc tggaagggtt caagaagaat gaagaagcct     1080
tgaagaaatg tgctcaggat tacttagcca gagttaaaca agaggagcag cgataccagg     1140
ccctgaaaat ccacgcagaa gagaaactgg acaaagccaa tgaagagatt gctcaggttc     1200
gaacaaaagc aaaggctgag agtgcagctc tccatgctgg actccgcaaa gagcagatga     1260
aggtggagtc cctggaaagg gccctgcagc agaagaacca agaaattgaa gaactgacaa     1320
aaatctgtga tgagctgatt gcaaagctgg gaaagactga ctgagacact ccccctgtta     1380
gctcaacaga tctgcatttg gctgcttctc ttgtgaccac aattatcttg ccttatccag     1440
gaataattgc ccctttgcag agaaaaaaaa aaacttaaaa aaagcacatg cctactgctg     1500
cctgtcccgc tttgctgcca atgcaacagc cctggaagaa accctagagg gttgcatagt     1560
ctagaaagga gtgtgacctg acagtgctgg agcctcctag tttcccccta tgaaggttcc     1620
cttaggctgc tgagtttggg tttgtgattt atctttagtt tgttttaaag tcatctttac     1680
tttcccaaat gtgttaaatt tgtaactcct cttttgggtc ttctccacca cctgtctgat     1740
ttttttgtga tctgtttaat cttttaattt tttagtatca gtggttttat ttaaggagac     1800
agtttggcct attgttactt ccaatttata atcaagaagg ggctctggat cccctttaaa     1860
attacacaca ctctcacaca catacatgta tgtttataga tgctgctgct cttttccctg     1920
aagcatagtc aagtaagaac tgctctacag aaggacatat ttccttggat gtgagaccct     1980
attttgaaat agagtcctga ctcagaacac caacttaaga attttggggga ttaaagatgt     2040
gaagaccaca gtcttgggtt ttcatatctg gagaagacta tttgccatga cgttttgttg     2100
ccctggtatt tggacactcc tcagctttaa tgggtgtggc ccctttaggg ttagtcctca     2160
gactaatgat agtgtctgct ttctgcatga acggcaatat gggactccct ccaagctagg     2220
gtttggcaag tctgccctag agtcatttac tctcctctgc ctccatttgt taatacagaa     2280
tcaacattta gtcttcatta tctttttttt tttttttgag acagagtttc gatctatttt     2340
aagtatgtga agaaaatcta cttgtaaaag gctcagatct taattaaaag gtaattgtag     2400
cacattacca attataaggt gaagaaatgt ttttttccca agtgtgatgc attgttcttc     2460
agatgttgaa aagaaagcaa aaaataccct ctaacttaag acagaatttt taacaaaatg     2520
agcagtaaaa gtcacatgaa ccactccaaa aatcagtgca ttttgcatat ttttaaacaa     2580
```

-continued

```
agacagcttg ttgaatactg agaagaggag tgcaaggaga aggtctgtac taacaaagcc   2640
aaattcctca agctcttact ggactcagtt cagagtggtg ggccattaac cccaacatgg   2700 aattttttcca tataaatctc aatgaattcc ctttcatttg aataggcaaa cccaaatcca   2760
tgcaagtgtt ttaaagcact gtcctgtctt aatcttacat gctgaaagtc ttcatggtga   2820
tatgcactat attcagtata cgtatgtttt cctacttctc ttgtaaaact gttgcatgat   2880
ccaacttcag caatgaattg tgcctagtgg agaacctcta tagatcttaa aaaatgaatt   2940
attctttagc agtgtattac tcacatgggt gcaatcttta gccccaggga ggtcaataat   3000
gtcttttaaa gccagaagtc acatttacc aatatgcatt tatcataatt ggtgcttagg    3060
ctgtatattc aagcctgttg tcttaacatt ttgtataaaa agaacaaca gaaattatct    3120 gtcatttgag aagtggcttg acaatcattt gagctttgaa agcagtcact gtggtgtaat   3180
atgaatgctg tcctagtggt catagtacca agggcacgtg tctccccttg gtataactga   3240
tttccttttt agtcctctac tgctaaataa gttaattttg cattttgcag aaagaaacat   3300
tgattgctaa atcttttttgc tgctgtgttt tggtgttttc atgtttactt gttttatatt   3360
gatctgtttt aagtatgaga ggcttatagt gccctccatt gtaaatccat agtcatcttt   3420
ttaagcttat tgtgtttaag aaagtagcta tgtgttaaac agaggtgatg gcagcccttc   3480
cctagcacac tggtggaaga gacccttaa gaacctgacc ccagtgaatg aagctgatgc     3540
acagggagca ccaaaggacc ttcgttaagt gataattgtc ctggcctctc agccatgacc   3600
gttatgagga aatatccccc attcgaactt aacagatgcc tcctctccaa agagaattaa   3660
aatcgtagct tgtacagatc aagagaatat actgggcaga atgaagtatg tttgtttatt   3720
tttctttaaa aataaaggat tttggaactc tggagagtaa gaatatagta tagagtttgc   3780
ctcaacacat gtgagggcca aataacctgc tagctaggca gtaataaact ctgttacaga   3840
agagaaaaag ggccgggcac agtggcttat tcctgtaatc ccaacactgt ggaaggccga   3900
ggcaggagga tcacttgagt ccaggagttt gaaacctacc taggcaacat ggtgaaacct   3960
tgtctctacc aaaataaaaa ttagctgggc atggtggcac gtgcctgtgg tcccagctac   4020
ttgggaggct gaggtgggag cctgggaggt caaggctgca gtgagccatg atcatgccac   4080
tgcactccat cctgggtgac agcaagatct tgtctc                             4116
```

<210> SEQ ID NO 29
<211> LENGTH: 540
<212> TYPE: DNA
<213> ORGANISM: Homo sapiens

<400> SEQUENCE: 29

```
cgagttcccc gaggtgtacg tgcccaccgt cttcgagaac tatgtggccg acattgaggt    60
ggacggcaag caggtggagc tggcgctgtg ggacacggcg ggccaggagg actacgaccg   120
cctgcggccc ctctcctacc cggacaccga cgtcattctc atgtgcttct cggtggacag   180
cccggactcg ctggagaaca tccccgagaa gtgggtcccc gaggtgaagc acttctgtcc   240
caatgtgccc atcatcctgg tggccaacaa aaaagacctg cgcagcgacg agcatgtccg   300
cacagagctg gcccgcatga agcaggaacc cgtgcgcacg gatgacggcc gcgccatggc   360
cgtgcgcatc caagcctacg actacctcga gtgctctgcc aagaccaagg aaggcgtgcg   420
cgaggtcttc gagacggcca cgcgcgccgc gctgcagaag cgctacggct cccagaacgg   480
ctgcatcaac tgctgcaagg tgctatgagg gccgcgcccg tcgcgcctgc ccctgccggc   540
```

<210> SEQ ID NO 30
<211> LENGTH: 1063
<212> TYPE: DNA
<213> ORGANISM: Homo sapiens

<400> SEQUENCE: 30

| | | | | | |
|---|---|---|---|---|---|
| cggggagacc | atggggcccc | tctcagcccc | ttcctgcaca | cacctcatca | cttggaaggg | 60 |
| ggtcctgctc | acagcatcac | tttaaactt | ctggaatccg | cccaccactg | ccgaagtcac | 120 |
| gattgaagcc | cagccaccca | aagtttctga | ggggaaggat | gttcttctac | ttgttcacaa | 180 |
| tttgccccag | aatcttcctg | gctacttctg | gtacaaaggg | gaaatgacgg | acctctacca | 240 |
| ttacattata | tcgtatatag | ttgatggtaa | aataattata | tatgggcctg | catacagtgg | 300 |
| aagagaaaca | gtatattcca | acgcatccct | gctgatccag | aatgtcaccc | ggaaggatgc | 360 |
| aggaacctac | accttacaca | tcataaagcg | aggtgatgag | actagagaag | aaattcgaca | 420 |
| tttcaccttc | accttatact | atggtccaga | cctccccaga | atttacccctt | cattcaccta | 480 |
| ttacggttca | ggagaaaacc | tcgacttgtc | ctgcttcacg | gaatctaacc | caccggcaga | 540 |
| gtattttttgg | acaattaatg | ggaagtttca | gcaatcagga | caaaagctct | ttatccccca | 600 |
| aattactaga | aatcatagcg | ggctctatgt | ttgctctgtt | cataactcag | ccactggcaa | 660 |
| ggaaatctcc | aaatccatga | cagtcaaagt | ctctggtccc | tgccatggag | acctgacaga | 720 |
| gtttcagtca | tgactgcaac | aactgagaca | ctgagaaaaa | gaacaggctg | ataccttcat | 780 |
| gaaattcaag | acaaagaaga | aaaaaactca | atgttattgg | actaaataat | caaaaggata | 840 |
| atgttttcat | aatttttat | tggaaaatgt | gctgattctt | tgaatgtttt | attctccaga | 900 |
| tttatgaact | tttttttcttc | agcaattggt | aaagtatact | tttgtaaaca | aaaattgaaa | 960 |
| tatttgcttt | tgctgtctat | ctgaatgccc | cagaattgtg | aaactactca | tgagtactca | 1020 |
| taggtttatg | gtaataaagt | tatttgcaca | tgttccgtag | ttt | | 1063 |

<210> SEQ ID NO 31
<211> LENGTH: 1117
<212> TYPE: DNA
<213> ORGANISM: Homo sapiens

<400> SEQUENCE: 31

| | | | | | |
|---|---|---|---|---|---|
| gcaccaacca | gcaccatgcc | catgatactg | gggtactggg | acatccgcgg | gctggcccac | 60 |
| gccatccgcc | tgctcctgga | atacacagac | tcaagctatg | aggaaaagaa | gtacacgatg | 120 |
| ggggacgctc | ctgattatga | cagaagccag | tggctgaatg | aaaaattcaa | gctgggcctg | 180 |
| gactttccca | atctgcccta | cttgattgat | ggggctcaca | agatcaccca | gagcaacgcc | 240 |
| atcttgtgct | acattgcccg | caagcacaac | ctgtgtgggg | agacagaaga | ggagaagatt | 300 |
| cgtgtggaca | ttttggagaa | ccagaccatg | gacaaccata | tgcagctggg | catgatctgc | 360 |
| tacaatccag | aatttgagaa | actgaagcca | aagtacttgg | aggaactccc | tgaaaagcta | 420 |
| aagctctact | cagagtttct | ggggaagcgg | ccatggtttg | caggaaacaa | gatcactttt | 480 |
| gtagattttc | tcgtctatga | tgtccttgac | ctccaccgta | tatttgagcc | caactgcttg | 540 |
| gacgccttcc | caaatctgaa | ggacttcatc | tcccgctttg | agggcttgga | gaagatctct | 600 |
| gcctacatga | gtccagccg | cttcctccca | agacctgtgt | tctcaaagat | ggctgtctgg | 660 |
| ggcaacaagt | agggccttga | aggcaggagg | tgggagtgag | gagcccatac | tcagcctgct | 720 |
| gcccaggctg | tgcagcgcag | ctggactctg | catcccagca | cctgcctcct | cgttcctttc | 780 |
| tcctgtttat | tcccatcttt | actcccaaga | cttcattgtc | cctcttcact | ccccctaaac | 840 |

```
ccctgtccca tgcaggccct ttgaagcctc agctacccac tatccttcgt gaacatcccc      900
tcccatcatt acccttccct gcactaaagc cagcctgacc ttccttcctg ttagtggttg      960
tgtctgcttt aaagcctgcc tggccctcg cctgtggagc tcagcccga gctgtccccg     1020 tgttgcatga aggagcagca ttgactggtt tacaggccct gctcctgcag catggtccct     1080
gcctaggcct acctgatgga agtaaagcct caaccac                              1117

<210> SEQ ID NO 32
<211> LENGTH: 1869
<212> TYPE: DNA
<213> ORGANISM: Homo sapiens

<400> SEQUENCE: 32
ttcaggaacc ggtttggtgc tggtgctgga ggcggctatg ctttggagg tggtgccggt       60 agtggatttg gtttcggcgg tggagctggt ggtggctttg ggctcggtgg cggagctggc     120 tttgaggtg gcttcggtgg ccctggcttt cctgtctgcc ctcctggagg tatccaagag      180
gtcactgtca accagagtct cctgactccc ctcaacctgc aaatcgaccc cagcatccag     240
agggtgagga ccgaggagcg cgagcagatc aagaccctca caataagtt tgcctccttc     300 atcgacaagg tgcggttcct ggagcagcag aacaaggttc tggacaccaa gtggaccctg     360
ctgcaggagc agggcaccaa gactgtgagg cagaacctgg agccgttgtt cgagcagtac     420
atcaacaacc tcaggaggca gctggacagc atcgtggggg aacggggccg cctggactca     480
gagctgagaa acatgcagga cctggtggaa gacttcaaga acaagtatga ggatgaaatc     540
aacaagcgta ccactgctga gaatgagttt gtgatgctga agaaggatgt agatgctgcc     600
tacatgaaca aggtggagct ggaggccaag gttgatgcac tgatggatga gattaacttc     660
atgaagatgt tctttgatgc ggagctgtcc cagatgcaga cgcatgtctc tgacacctca     720
gtggtcctct ccatggacaa caaccgcaac ctggacctgg atagcatcat cgctgaggtc     780
aaggcccagt atgaggagat tgccaaccgc agccggacag aagccgagtc ctggtatcag     840
accaagtatg aggagctgca gcagacagct ggccggcatg gcgatgacct ccgcaacacc     900
aagcatgaga tctctgagat gaaccggatg atccagaggc tgagagccga gattgacaat     960
gtcaagaaac agtgcgccaa tctgcagaac gccattgcgg atgccgagca gcgtggggag    1020
ctggccctca aggatgccag gaacaagctg gccgagctgg aggaggccct gcagaaggcc    1080
aagcaggaca tggcccggct gctgcgtgag taccaggagc tcatgaacac caagctggcc    1140
ctggacgtgg agatcgccac ttaccgcaag ctgctggagg cgaggaatg cagactcagt    1200 ggagaaggag ttggaccagt caacatctct gttgtcacaa gcagtgtttc ctctggatat    1260
ggcagtggca gtggctatgg cggtggcctc ggtggaggtc ttggcggcgg cctcggtgga    1320
ggtcttgccg gaggtagcag tggaagctac tactccagca gcagtgggg tgtcggccta    1380 ggtggtgggc tcagtgtggg gggctctggc ttcagtgcaa gcagtggccg agggctgggg    1440
gtgggctttg gcagtggcgg gggtagcagc tccagcgtca aatttgtctc caccacctcc    1500
tcctcccgga gagcttcaa gagctaagaa cctgctgcaa gtcactgcct tccaagtgca    1560
gcaacccagc ccatggagat tgcctcttct aggcagttgc tcaagccatg ttttatcctt    1620
ttctggagag tagtctagac caagccaatt gcagaaccac attctttggt tcccaggaga    1680
gccccattcc cagcccctgg tctcccgtgc cgcagttcta tattctgctt caaatcagcc    1740
ttcaggtttc ccacagcatg gcccctgctg acacagaaac ccaagttttt cccaaatcta    1800
aatcatcaaa acagaatccc cacccccaatc ccaaatttg ttttggttct aactacctcc    1860
```

<210> SEQ ID NO 33
<211> LENGTH: 664
<212> TYPE: DNA
<213> ORGANISM: Homo sapiens

<400> SEQUENCE: 33

```
agtgatcagg gccaaagcgg tcagtgagaa ggaagtggac tctggaaacg acatttatgg      60
caaccctatc aagaggatcc agtatgagat caagcagata aagatgttca aagggcctga     120
gaaggatata gagtttatct acacggcccc ctcctcggca gtgtgtgggg tctcgctgga     180
cgttggagga aagaaggaat atctcattgc aggaaaggcc gagggggacg gcaagatgca     240
catcaccctc tgtgacttca tcgtgccctg ggacaccctg agcaccaccc agaagaagag     300
cctgaaccac aggtaccaga tgggctgcga gtgcaagatc acgcgctgcc ccatgatccc     360
gtgctacatc tcctccccgg acgagtgcct ctggatggac tgggtcacag agaagaacat     420
caacgggcac caggccaagt tcttcgcctg catcaagaga agtgacggct cctgtgcgtg     480
gtaccgcggc gcggcgcccc ccaagcagga gtttctcgac atcgaggacc cataagcagg     540
cctccaacgc ccctgtggcc aactgcaaaa aaagcctcca agggtttcga ctggtccagc     600
tctgacatcc cttcctggaa acagcatgaa taaaacactc atcccatggg tccaaattaa     660
tatg                                                                  664
```

<210> SEQ ID NO 34
<211> LENGTH: 2598
<212> TYPE: DNA
<213> ORGANISM: Homo sapiens

<400> SEQUENCE: 34

```
tgtcgccacc atggctccgc accgccccgc gcccgcgctg ctttgcgcgc tgtccctggc      60
gctgtgcgcg ctgtcgctgc ccgtccgcgc ggccactgcg tcgcgggggg cgtcccaggc     120
ggggcgcccc caggggcggg tgcccgaggc gcggcccaac agcatggtgg tggaacaccc     180
cgagttcctc aaggcaggga aggagcctgg cctgcagatc tggcgtgtgg agaagttcga     240
tctggtgccc gtgcccacca acctttatgg agacttcttc acgggcgacg cctacgtcat     300
cctgaagaca gtgcagctga ggaacggaaa tctgcagtat gacctccact actggctggg     360
caatgagtgc agccaggatg agagcggggc ggccgccatc tttaccgtgc agctggatga     420
ctacctgaac ggccgggccg tgcagcaccg tgaggtccag gcttcgagt cggccacctt     480
cctaggctac ttcaagtctg gcctgaagta caagaaagga ggtgtggcat caggattcaa     540
gcacgtggta cccaacgagg tggtggtgca gagactcttc caggtcaaag gcggcgtgt     600
ggtccgtgcc accgaggtac ctgtgtcctg ggagagcttc aacaatggcg actgcttcat     660
cctggacctg gcaacaaca tccaccagtg tgtgtggttcc aacagcaatc ggtatgaaag     720
actgaaggcc acacaggtgt ccaagggcat ccgggacaac gagcggagtg gccgggcccg     780
agtgcacgtg tctgaggagg gcactgagcc cgaggcgatg ctccaggtgc tgggccccaa     840
gccggctctg cctgcaggta ccgaggacac cgccaaggag gatgcggcca accgcaagct     900
ggccaagctc tacaaggtct ccaatggtgc agggaccatg tccgtctccc tcgtggctga     960
tgagaacccc ttcgcccagg ggcctgaa gtcagaggac tgcttcatcc tggaccacgg    1020
caaagatggg aaaatctttg tctggaaagg caagcaggca aacacggagg agaggaaggc    1080
```

```
tgccctcaaa acagcctctg acttcatcac caagatggac tacccccaagc agactcaggt    1140 ctcggtcctt cctgagggcg gtgagacccc actgttcaag cagttcttca agaactggcg    1200
ggacccagac cagacagatg gcctgggctt gtcctacctt tccagccata tcgccaacgt    1260
ggagcgggtg cccttcgacg ccgccaccct gcacacctcc actgccatgg ccgcccagca    1320
cggcatggat gacgatggca caggccagaa acagatctgg agaatcgaag gttccaacaa    1380
ggtgcccgtg gaccctgcca catatggaca gttctatgga ggcgacagct acatcattct    1440
gtacaactac cgccatggtg gccgccaggg gcagataatc tataactggc agggtgccca    1500
gtctacccag gatgaggtcg ctgcatctgc catcctgact gctcagctgg atgaggagct    1560
gggaggtacc cctgtccaga gccgtgtggt ccaaggcaag gagcccgccc acctcatgag    1620
cctgtttggt gggaagccca tgatcatcta caagggcggc acctcccgcg agggcgggca    1680
gacagcccct gccagcaccc gcctcttcca ggtccgcgcc aacagcgctg agccacccg    1740 ggctgttgag gtattgccta aggctggtgc actgaactcc aacgatgcct ttgttctgaa    1800
aaccccctca gccgcctacc tgtgggtggg tacaggagcc agcgaggcag agaagacggg    1860
ggcccaggag ctgctcaggg tgctgcgggc ccaacctgtg caggtggcag aaggcagcga    1920
gccagatggc ttctgggagg ccctgggcgg gaaggctgcc taccgcacat ccccacggct    1980
gaaggacaag aagatggatg cccatcctcc tcgcctcttt gcctgctcca acaagattgg    2040
acgttttgtg atcgaagagg ttcctggtga gctcatgcag gaagacctgg caacggatga    2100
cgtcatgctt ctggacacct gggaccaggt ctttgtctgg gttggaaagg attctcaaga    2160
agaagaaaag acagaagcct tgacttctgc taagcggtac atcgagacgg acccagccaa    2220
tcgggatcgg cggacgccca tcaccgtggt gaagcaaggc tttgagcctc cctcctttgt    2280
gggctggttc cttggctggg atgatgatta ctggtctgtg gaccccttgg acagggccat    2340
ggctgagctg gctgcctgag gaggggcagg gcccacccat gtcaccggtc agtgcctttt    2400
ggaactgtcc ttccctcaaa gaggccttag agcgagcaga gcagctctgc tatgagtgtg    2460
tgtgtgtgtg tgtgttgttt cttttttttt tttttacagt atccaaaaat agccctgcaa    2520
aaattcagag tccttgcaaa attgtctaaa atgtcagtgt ttgggaaatt aaatccaata    2580
aaaacatttt gaagtgtg                                                  2598
```

<210> SEQ ID NO 35
<211> LENGTH: 329
<212> TYPE: DNA
<213> ORGANISM: Homo sapiens
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t

<400> SEQUENCE: 35

```
gaagtaaaag attttattg ttctatagac acttctgaaa agagatctaa ttgagaaaat      60
atacaaagca tttaagagtt tcatccccag agactgactg aaggcgttac agccctcctc    120
tccaaggctc agggctgaga acggttagca tatcgaatga tcagtaaaaa catgcaaaag    180
tgagaaggaa agggaaaaag gtgcattccc ctaagctgag ggggatggaa tttcagaaca    240
gaggangcag ggtggacaag taccaaggtg gctctccctt tccctctgtg tnatctttca    300
aaaccanttc caagcntgga tnaaagcaa                                       329
```

<210> SEQ ID NO 36
<211> LENGTH: 1555
<212> TYPE: DNA
<213> ORGANISM: Homo sapiens

<400> SEQUENCE: 36

```
caaagtctga gccccgctcc gctgatgcct gtctgcagaa tccgcaccaa ccagcaccat     60
gcccatgact ctggggtact gggacatccg tgggctggcc cacgccatcc gcttgctcct   120
ggaatacaca gactcaagct atgtggaaaa gaagtacacg ctgggggacg ctcctgacta   180
tgacagaagc cagtggctga tgaaaaaatt caagctgggc ctggactttc ccaatctgcc   240
ctacttgatt gatggggctc acaagatcac ccagagcaat gccatcctgc gctacattgc   300
ccgcaagcac aacctgtgtg gggagacaga agaggagaag attcgtgtgg acattttgga   360
gaaccaggtt atggataacc acatggagct ggtcagactg tgctatgacc agattttga    420 gaaactgaag ccaaaatact tggaggaact ccctgaaaag ctaaagctct actcagagtt   480
tctggggaag cggccatggt ttgcaggaga caagatcacc tttgtggatt tccttgccta   540
tgatgtcctt gacatgaagc gtatatttga gcccaagtgc ttggacgcct tcctaaactt   600
gaaggacttc atctcccgct ttgagggttt gaagaagatc tctgcctaca tgaagtccag   660
ccaattcctc cgaggtcttt tgtttggaaa gtcagctaca tggaacagca aatagggccc   720
agtgatgcca aagatgggga gggaggagcc aaccttgctg cctgcgaccc tggaggacag   780
cctgactccc tggacctgcc ttcttccttt tccttctttt ctactctctt ctcttcccca   840
aggcctcatt ggcttccttt cttctaacat catccctccc cgcatcgagg ctctttaaag   900
cttcagctcc ccactgtcct ccatcaaagt cccctccta acgtcttcct ttccctgcac    960
taacgccaac ctgactgctt ttcctgtcag tgcttttctc ttctttgaga agccagactg  1020
atctctgagc tccctagcac tgtcctcaaa gaccatctgt atgccctgct cccttttgctg 1080 ggtccctacc ccagctccgt gtgatgccca gtaaagcctg aaccatgcct gccatgtctt  1140
gtcttattcc ctgaggctcc cttgactcag gactgtgctc gaattgtggg tggttttttg  1200
tcttctgttg tccacagcca gagcttagtg gatgggtgtg tgtgtgtgtg tgttggggt    1260 ggtgatcagg caggttcata aatttccttg gtcatttctg ccctctagcc acatccctct   1320
gttcctcact gtggggatta ctacagaaag gtgctctgtg ccaagttcct cactcattcg   1380
cgctcctgta ggccgtctag aactggcatg gttcaaagag gggctaggct gatggggaag   1440
ggggctgagc agctcccagg cagactgcct tctttcaccc tgtcctgata gacttccctg  1500
atctagatat ccttcgtcat gacacttctc aataaaacgt atcccaccgt attgt         1555
```

<210> SEQ ID NO 37
<211> LENGTH: 4812
<212> TYPE: DNA
<213> ORGANISM: Homo sapiens
<220> FEATURE:

-continued

```
<221> NAME/KEY: misc_feature
<222> LOCATION: (784)..(1133)
<223> OTHER INFORMATION: n is a, c, g, or t

<400> SEQUENCE: 37
ggttgagaat gcttgcacca agcttgtcca ggcagctcag atgcttcagt cagacccta      60 ctcagtgcct gctcgagatt atctaattga tgggtcaagg ggcatcctct ctggaacatc    120
agacctgctc cttaccttcg atgaggctga ggtccgtaaa attattagag tttgcaaagg    180
aattttggaa tatcttacag tggcagaggt ggtggagact atggaagatt tggtcactta    240
cacaaagaat cttgggccag gaatgactaa gatggccaag atgattgacg agagacagca    300
ggagctcact caccaggagc accgagtgat gttggtgaac tcgatgaaca ccgtgaaaga    360
gttgctgcca gttctcattt cagctatgaa gatttttgta acaactaaaa actcaaaaaa    420
ccaaggcata gaggaagctt taaaaaatcg caattttact gtagaaaaaa tgagtgctga    480
aattaatgag ataattcgtg tgttacaact cacctcttgg gatgaagatg cctgggccag    540
caaggacact gaagccatga agagagcatt ggcctccata gactccaaac tgaaccaggc    600
caaaggttgg ctccgtgacc ctagtgcctc cccaggggat gctggtgagc aggccatcag    660
acagatctta gatgaagctg gaaaagttgg tgaactctgt gcaggcaaag aacgcaggga    720
gattctggga acttgcaaaa tgctagggca gatgactgat caagtggctg acctccgtgc    780
cagnnnnnnn nnnnnnnnn nnnnnnnnn nnnnnnnnn nnnnnnnnn nnnnnnnnn       840 nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnaggctcg   1140
agccttggcc aaacaggtgg ccacggccct gcagaacctg cagaccaaaa ccaaccgggc    1200
tgtggccaac agcagaccgg ccaaagcagc tgtacacctt gagggcaaga ttgagcaagc    1260
acagcggtgg attgataatc ccacagtgga tgaccgtgga gtcggtcagg ctgccatccg    1320
ggggcttgtg gccgaagggc atcgtctggc taatgttatg atggggcctt atcggcaaga    1380
tcttctcgcc aagtgtgacc gagtggacca gctgacagcc cagctggctg acctggctgc    1440
cagaggggaa gggagagtc ctcaggcacg agcacttgca tctcagctcc aagactcctt    1500
aaaggatcta aaagctcgga tgcaggaggc catgactcag gaagtgtcag atgttttcag    1560
cgataccaca actcccatca agctgttggc agtggcagcc acggcgcctc ctgatgcgcc    1620
taacagggaa gaggtatttg atgagagggc agctaacttt gaaaaccatt caggaaagct    1680
tggtgctacg gccgagaagg cggctgcggt tggtactgct aataaatcaa cagtggaagg    1740
cattcaggcc tcagtgaaga cggcccgaga actcacaccc caggtggtct cggctgctcg    1800
tatcttactt aggaaccctg gaaatcaagc tgcttatgaa catttgaga ccatgaagaa     1860 ccagtggatc gataatgttg aaaaaatgac agggctggtg gacgaagcca ttgataccaa    1920
atctctgttg gatgcttcag aagaagcaat taaaaaagac ctggacaagt gcaaggtagc    1980
tatggccaac attcagcctc agatgctggt tgctggggca accagtattg ctcgtcgggc    2040
caaccggatc ctgctggtgg ctaagaggga ggtggagaat tccgaggatc ccaagttccg    2100
tgaggctgtg aaagctgcct ctgatgaatt gagcaaaacc atctccccga tggtgatgga    2160
tgcaaaagct gtggctggaa acatttccga ccctggactg caaaagagct tcctggactc    2220
```

-continued

```
aggatatcgg atcctgggag ctgtggccaa ggtcagagaa gccttccaac ctcaggagcc    2280
tgacttcccg ccgcctccac cagaccttga caactccga ctaacagatg agcttgctcc     2340
tcccaaacca cctctgcctg aaggtgaggt ccctccacct aggcctccac caccagagga    2400
aaaggatgaa gagttccctg agcagaaggc cggggaggtg attaaccagc caatgatgat    2460
ggctgccaga cagctccatg atgaagctcg caaatggtcc agcaagggca atgacatcat    2520
tgcagcagcc aagcgcatgg ctctgctgat ggctgagatg tctcggctgg taagaggggg    2580
cagtggtacc aagcgggcac tcattcagtg tgccaaggac atcgccaagg cctcagatga    2640
ggtgactcgg ttggccaagg aggttgccaa gcagtgcaca gataaacgga ttagaaccaa    2700
cctcttacag gtatgtgagc gaatcccaac cataagcacc cagctcaaaa tcctgtccac    2760
agtgaaggcc accatgctgg gccggaccaa catcagtgat gaggagtctg agcaggccac    2820
agagatgctg gttcacaatg cccagaacct catgcagtct gtgaaggaga ctgtgcggga    2880
agctgaagct gcttcaatca aaattcgaac agatgctgga tttacactgc gctgggttag    2940
aaagactccc tggtaccagt aggcacctgg ctgagcctgg ctggcacaga aacctctact    3000
aaaaagaagg aaaatgatct gagtcccagg agctgcccag agttgctggg agctgaaaaa    3060
tcacatcctg gcctggcaca tcagaaagga atgggggcct cttcaaatta gaagacattt    3120
atactctttt ttcatggaca ctttgaaatg tgtttctgta taaagcctgt attctcaaac    3180
acagttacac ttgtgcaccc tctatcccaa taggcagact gggtttctag cccatggact    3240
tcacataagc tcagaatcca agtgaacact agccagacac tctgctctgc ccttgttccc    3300
taggggacac ttccctctgt ttctcttttcc ttggctccca ttcactcttc cagaatccca    3360
agacccaggg cccaggcaaa tcagttacta agaagaaaat tgctgtgcct cccaaaattg    3420
ttttgagctt tccatgttgc tgccaaccat accttccttc cctgggctgt gctacctggg    3480 tcctttttcag aagtgagctt tgctgctaca ggggaaggtg gcctctgtgg agccccagca    3540
tatgggggcc tggattcatt tcctgccctt cctcagttta atccttctag tttcccacaa    3600
tataaaactg tacttcactg tcaggaagaa atcacagaat catatgattc tgcttttacc    3660
atgcccctga gcaatgtctg tgctagggaa acttcccgtc ccatatcctg cctcagcccg    3720
ccaaggtagc catcccatga acacactgtg tcctggtgct ctctgccact ggaagggcag    3780
agtagccagg gtgtggccct gccatcttcc cagcagggcc actcccggca ctccatgctt    3840
agtcactgcc tgcagaggtc tgtgctgagg cctatcatt cattcttagc tcttaattgt     3900
tcattttgag ctgaaatgct gcattttaat tttaaccaaa acatgtctcc tatcctggtt    3960
tttgtagcct tcctccacat cctttctaaa caagatttta aagacatgta ggtgtttgtt    4020
catctgtaac tctaaaagat ccttttttaaa ttcagtccta agaaagagga gtgcttgtcc    4080
cctaagagtg tttaatggca aggcagccct gtctgaagga cacttcctgc ctaagggaga    4140
gtggtatttg cagactagaa ttctagtgct gctgaagatg aatcaatggg aaatactact    4200
cctgtaattc ctacctccct gcaaccaact acaaccaagc tctctgcatc tactcccaag    4260
tatggggttc aagagagtaa tgggtttcat atttcttatc accacagtaa gttcctacta    4320
ggcaaaatga gagggcagtg tttcctttttt ggtacttatt actgctaagt atttcccagc    4380
acatgaaacc ttatttttc ccaaagccag aaccagatga gtaaaggagt aagaaccttg     4440
cctgaacatc cttccttccc acccatcgct gtgtgttagt tcccaacatc gaatgtgtac    4500
aacttaagtt ggtcctttac actcaggctt tcactatttc ctttataatg aggatgatta    4560
```

-continued

| | | |
|---|---|---|
| ttttcaaggc cctcagcata tttgtatagt tgcttgcctg atataaatgc aatattaatg | 4620 | |
| cctttaaagt atgaatctat gccaaagatc acttgttgtt ttactaaaga aagattactt | 4680 | |
| agaggaaata agaaaaatca tgtttgctct cccggttctt ccagtggttt gagacactgg | 4740 | |
| tttacacttt atgccggatg tgcttttctc caatatcagt gctcgagaca cagtgaagca | 4800 | |
| aattaaaaaa aa | 4812 | |

<210> SEQ ID NO 38
<211> LENGTH: 2038
<212> TYPE: DNA
<213> ORGANISM: Homo sapiens

<400> SEQUENCE: 38

| | |
|---|---|
| atatccagcc tttgccgaat acatcctatc tgccacacat ccagcgtgag gtccctccag | 60 |
| ctacaaggtg ggcaccatgg cggagaagtt tgactgccac tactgcaggg atcccttgca | 120 |
| ggggaagaag tatgtgcaaa aggatggcca ccactgctgc ctgaaatgct ttgacaagtt | 180 |
| ctgtgccaac acctgtgtgg aatgccgcaa gcccatcggt gcggactcca aggaggtgca | 240 |
| ctataagaac cgcttctggc atgacacctg cttccgctgt gccaagtgcc ttcaccccct | 300 |
| ggccaatgag acctttgtgg ccaaggacaa caagatcctg tgcaacaagt gcaccactcg | 360 |
| ggaggactcc cccaagtgca aggggtgctt caaggccatt gtggcaggag atcaaaacgt | 420 |
| ggagtacaag gggaccgtct ggcacaaaga ctgcttcacc tgtagtaact gcaagcaagt | 480 |
| catcgggact ggaagcttct tccctaaagg ggaggacttc tactgcgtga cttgccatga | 540 |
| gaccaagttt gccaagcatt gcgtgaagtg caacaaggcc atcacatctg gaggaatcac | 600 |
| ttaccaggat cagccctggc atgccgattg ctttgtgtgt gttacctgct ctaagaagct | 660 |
| ggctgggcag cgtttcaccg ctgtggagga ccagtattac tgcgtggatt gctacaagaa | 720 |
| ctttgtggcc aagaagtgtg ctggatgcaa gaacccatc actgggaaaa ggactgtgtc | 780 |
| aagagtgagc cacccagtct ctaaagctag gaagccccca gtgtgccacg ggaaacgctt | 840 |
| gcctctcacc ctgtttccca cgccaaccct ccggggcagg catccgggtg gagagaggac | 900 |
| ttgtccctcg tgggtggtgg ttctttatag aaaaaatcga agcttagcag ctcctcgagg | 960 |
| cccgggtttg gtaaaggctc cagtgtggtg gcctatgaag acaatcctg gcacgactac | 1020 |
| tgcttccact gcaaaaaatg ctccgtgaat ctggccaaca gcgctttgt tttccaccag | 1080 |
| gagcaagtgt attgtcccga ctgtgccaaa aagctgtaaa ctgacagggg ctcctgtcct | 1140 |
| gtaaaatggc atttgaatct cgttctttgt gtccttactt tctgccctat accatcaata | 1200 |
| ggggaagagt ggtccttccc ttctttaaag ttctccttcc gtcttttctc ccattttaca | 1260 |
| gtattactca aataagggca cacagtgatc atattagcat ttagcaaaaa gcaaccctgc | 1320 |
| agcaaagtga atttctgtcc ggctgcaatt taaaaatgaa aacttaggta gattgactct | 1380 |
| tctgcatgtt tctcatagag cagaaaagtg ctaatcattt agccacttag tgatgtaagc | 1440 |
| aagaagcata ggagataaaa ccccccactga gatgcctctc atgcctcagc tgggacccac | 1500 |
| cgtgtagaca cacgacatgc aagagttgca gcggctgctc caactcactg ctcaccctct | 1560 |
| tctgtgagca ggaaaagaac cctactgaca tgcatggttt aacttcctca tcagaactct | 1620 |
| gcccttcctt ctgttctttt gtgctttcaa ataactaaca cgaacttcca gaaaattaac | 1680 |
| atttgaactt agctgtaatt ctaaactgac cttttccccgt actaacgttt ggtttccccg | 1740 |
| tgtggcatgt tttctgagcg ttcctacttt aaagcatgga acatgcaggt gatttgggaa | 1800 |
| gtgtagaaag acctgagaaa acgagcctgt ttcagaggaa catcgtcaca acgaatactt | 1860 |

-continued

```
ctggaagctt aacaaaacta accctgctgt cctttttatt gttttttaatt aatatttttg    1920 ttttaattga tagcaaaata gtttatgggt ttggaaactt gcatgaaaat attttagccc    1980
cctcagatgt tcctgcagtg ctgaaattca tcctacggaa gtaaccgcaa aactctag    2038

<210> SEQ ID NO 39
<211> LENGTH: 691
<212> TYPE: DNA
<213> ORGANISM: Homo sapiens
<220> FEATURE:
<221> NAME/KEY: misc_feature
<222> LOCATION: (37)..(238)
<223> OTHER INFORMATION: The n at this position can be a, c, t, or g.
<220> FEATURE:
<221> NAME/KEY: misc_feature
<222> LOCATION: (240)..(268)
<223> OTHER INFORMATION: The n at this position can be a, c, t, or g.

<400> SEQUENCE: 39
tgccgcccta caccgtggtc tatttcccag ttcgagnnnn nnnnnnnnn nnnnnnnnn      60 nnnnnnnnnn nnnnnnnngc tgctggcaga tcagggccag agctggaagg aggaggtggt   120
gaccgtggag acgtggcagg agggctcact caaagcctcc tgcctatacg ggcagctccc   180
caagttccag gacggagacc tcaccctgta ccagtccaat accatcctgc gtcacctggn   240
nnnnnnnnnn nnnnnnnnnn nnnnnnnngg ctctatggga aggaccagca ggaggcagcc   300
ctggtggaca tggtgaatga cggcgtggag gacctccgct gcaaatacat ctccctcatc   360
tacaccaact atgaggcggg caaggatgac tatgtgaagg cactgcccgg gcaactgaag   420
ccttttgaga ccctgctgtc ccagaaccag ggaggcaaga ccttcattgt gggagaccag   480
atctccttcg ctgactacaa cctgctggac ttgctgctga tccatgaggt cctagcccct   540
ggctgcctgg atgcgttccc cctgctctca gcatatgtgg ggcgcctcag tgcccggccc   600
aagctcaagg ccttcctggc ctcccctgag tacgtgaacc tccccatcaa tggcaacggg   660
aaacagtgag ggttgggggg actctgagcg g                                 691

<210> SEQ ID NO 40
<211> LENGTH: 2511
<212> TYPE: DNA
<213> ORGANISM: Homo sapiens
<220> FEATURE:
<221> NAME/KEY: misc_feature
<222> LOCATION: (799)..(953)
<223> OTHER INFORMATION: The n at this position can be a, c, t, or g.

<400> SEQUENCE: 40
cttttcacac tggccttaaa gaggatatat tagaagttga agtaggaagg gagccagaga    60
ggccgatggc gcaaaggtac gacgatctac cccattacgg gggcatggat ggagtaggca   120
tcccctccac gatgtatggg gacccgcatg cagccaggtc catgcagccg gtccaccacc   180
tgaaccacgg gcctcctctg cactcgcatc agtacccgca cacagctcat accaacgcca   240
tggcccccag catgggctcc tctgtcaatg acgctttaaa gagagataaa gatgccattt   300
atggacaccc cctcttccct ctcttagcac tgatttttga gaaatgtgaa ttagctactt   360 gtacccccg cgagccgggg gtggcgggcg gggacgtctg ctcgtcagag tcattcaatg   420
aagatatagc cgtgttcgcc aaacagattc gcgcagaaaa acctctattt tcttctaatc   480
cagaactgga taacttgatg attcaagcca tacaagtatt aaggtttcat ctattggaat   540
tagagaaggt acacgaatta tgtgacaatt tctgccaccg gtatattagc tgtttgaaag   600
```

```
ggaaaatgcc tatcgatttg gtgatagacg atagagaagg aggatcaaaa tcagacagtg    660
aagatataac aagatcagca aatctaactg accagccctc ttggaacaga gatcatgatg    720
acacggcatc tactcgttca ggaggaaccc caggcccttc cagcggtggc cacacgtcac    780
acagtgggga caacagcann nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnncaccctt    960
acccttctga agaacagaaa aagcagttgg cacaagacac gggactcacc atccttcaag   1020
tgaacaattg gtttattaat gcccggagaa gaatagtgca gcccatgata gaccagtcca   1080
accgagcagt aagtcaagga acaccttata atcctgatgg acagcccatg ggaggtttcg   1140
taatggacgg tcagcaacat atgggaatta gagcaccagg acctatgagt ggaatgggca   1200
tgaatatggg catggagggg cagtggcact acatgtaacc ttcatctagt taaccaatcg   1260
caaagcaagg gggaaggctg caaagtatgc caggggagta tgtagcccgg ggtggtccaa   1320
tgggtgtgag tatgggacag ccaagttata cccaaccoca gatgccccoc catcctgctc   1380 agctgcgtca tgggccccec atgcatacgt acattcctgg acaccctcac cacccaacag   1440
tgatgatgca tggaggaccg ccccaccctg gaatgccaat gtcagcatca agccccacag   1500
ttcttaatac aggagaccca acaatgagtg gacaagtcat ggacattcat gctcagtagc   1560
ttaagggaat atgcattgtc tgcaatggtg actgatttca aatcatgttt tttctgcaat   1620
gactgtggag ttccattctt ggcatctact ctggaccaag gagcatccct aattcttcat   1680
agggaccttt aaaaagcagg aaataccaac tgaagtcaat ttgggggaca tgctaaataa   1740
ctatataaga cattaagaga acaaagagtg aaatattgta aatgctatta tactgttatc   1800
catattacgt tgtttcttat agattttttta aaaaaaatgt gaaattttc cacactatgt   1860 gtgttgtttc catagctctt cacttcctcc agaagcctcc ttacattaaa aagccttaca   1920
gttatcctgc aagggacagg aaggtctgat ttgcaggatt tttagagcat taaaataact   1980
atcaggcaga agaatctttc ttctcgccta ggatttcagc catgcgcgcg ctctctctct   2040
ttctctctct tttcctctct ctccctcttt ctagcctggg gcttgaattt gcatgtctaa   2100
ttcatttact caccatattt gaattggcct gaacagatgt aaatcgggaa ggatgggaaa   2160
aactgcagtc atcaacaatg attaatcagc tgttgcaggc agtgtcttaa ggagactggt   2220
aggaggaggc atggaaacca aaaggccgtg tgtttagaag cctaattgtc acatcaagca   2280
tcattgtccc catgcaacaa ccaccacctt atacatcact tcctgtttta agcagctcta   2340
aaacatagac tgaagattta ttttttaatat gttgacttta tttctgagca aagcatcggt   2400
catgtgtgta ttttttcata gtcccacctt ggagcattta tgtagacatt gtaaataaat   2460
tttgtgcaaa aaggactgga aaaatgaact gtattattgc aatttttttt t            2511
```

<210> SEQ ID NO 41
<211> LENGTH: 441
<212> TYPE: DNA
<213> ORGANISM: Homo sapiens

<400> SEQUENCE: 41

```
ctcaataagc caaccatgtc tttcaaggat tacatccaag agaggagtga cccagtggag     60
caaggcaaac cagttatacc tgcagctgtg ctggccggct tcacaggaag tggacctatt    120
cagctgtgga gtttctcct ggagctgcta tcagacaaat cctgccagtc attcatcagc    180
tggactggag acggatggga gtttaagctc gccgaccccg atgaggtggc ccgccggtgg    240
```

```
ggaaagagga aaaataagcc caagatgaac tacgagaagc tgagccgggg cttacgctac      300
tattacgaca agaacatcat ccacaagacg tcggggaagc gctacgtgta ccgcttcgtg      360
tgcgacctcc agaacttgct ggggttcacg cccgaggaac tgcacgccat cctgggcgtc      420
cagcccgaca cggaggactg a                                                441

<210> SEQ ID NO 42
<211> LENGTH: 1531
<212> TYPE: DNA
<213> ORGANISM: Homo sapiens

<400> SEQUENCE: 42
ggacgacaag gcgttcacca aggagctgga ccagtgggtc gagcagctga acgagtgtaa       60
gcagctgaac gagaaccaag tgcggacgct gtgcgagaag gcaaaggaaa ttttaacaaa      120
agaatcaaat gtgcaagagg ttcgttgccc tgttactgtc tgtggagatg tgcatggtca      180
atttcatgat cttatggaac tctttagaat tggtggaaaa tcaccggata caaactactt      240
attcatgggt gactatgtag acagaggata ttattcagtg gagactgtga ctcttcttgt      300
agcattaaag gtgcgttatc cagaacgcat tacaatattg agaggaaatc acgaaagccg      360
acaaattacc caagtatatg gcttttatga tgaatgtctg cgaaagtatg ggaatgccaa      420
cgtttggaaa tattttacag atctctttga ttatcttcca cttacagctt tagtagatgg      480
acagatattc tgcctccatg gtggcctctc tccatccata gacacactgg atcatataag      540
agccctggat cgtttacagg aagttccaca tgagggccca atgtgtgatc tgttatggtc      600
agatccagat gatcgtggtg gatggggtat ttcaccacgt ggtgctggct acacatttgg      660
acaagacatt tctgaaacct ttaaccatgc caatggtctc acactggttt ctcgtgccca      720
ccagcttgta atggagggat acaattggtg tcatgatcgg aatgtggtta ccattttcag      780
tgcacccaat tactgttatc gttgtgggaa ccaggctgct atcatggaat tagatgacac      840 ttttaaaatat tccttccttc aatttgaccc agcgcctcgt cgtggtgagc ctcatgttac      900
acggcgcacc ccagactact tcctataaat ttctcctggg aaacctgcct ttgtatgtgg      960
aagtatacct ggcttttaa aatatatgta tttaaaaaca aaagcaaca gtaatctatg      1020 tgtttctgta acaaattggg atctgtcttg gcattaaacc acatcatgga ccaaatgtgc      1080
catactaatg atgagcattt agcacaattt gagactgaaa tttagtacac tatgttctag      1140
gtcagtctaa cagtttgcct gctgtattta tagtaaccat tttcctttgg actgttcaag      1200
caaaaaaggt aactaactgc ttcatctcct tttgcgctta tttggaaatt ttagttatag      1260
tgtttaactg gcatggatta atagagttgg agttttattt ttaagaaaaa ttcacaagct      1320
aacttccact aatccattat cctttatttt attgaaatgt ataattaact taactgaaga      1380
aaaggttctt cttgggagta tgttgtcata acatttaaag agatttccct tcatttaaac      1440
taaattactg ttttatgttg atctgcatat ttctgtatat ttgtcatgac agtgcttgca      1500
tcctatttgg tgtactcagc aaataaactt t                                    1531

<210> SEQ ID NO 43
<211> LENGTH: 1260
<212> TYPE: DNA
<213> ORGANISM: Homo sapiens

<400> SEQUENCE: 43
cctgtgagca ccacgtcaac ggctcccggc ccccatgcac gggggaggga gataccccca       60
```

| | |
|---|---|
| agtgtagcaa gatctgtgag cctggctaca gcccgaccta caaacaggac aagcactacg | 120 |
| gatacaattc ctacagcgtc tccaatagcg agaaggacat catggccgag atctacaaaa | 180 |
| acggccccgt ggagggagct ttctctgtgt attcggactt cctgctctac aagtcaggag | 240 |
| tgtaccaaca cgtcaccgga gagatgatgg gtggccatgc catccgcatc ctgggctggg | 300 |
| gagtggagaa tggcacaccc tactggctgg ttgccaactc ctggaacact gactggggtg | 360 |
| acaatggctt ctttaaaata ctcagaggac aggatcactg tggaatcgaa tcagaagtgg | 420 |
| tggctggaat tccacgcacc gatcagtact gggaaaagat ctaatctgcc gtgggcctgt | 480 |
| cgtgccagtc ctgggggcga gatgggggta gaaatgcatt ttattcttta agttcacgta | 540 |
| agatacaagt ttcagacagg gtctgaagga ctggattggc caaacatcag acctgtcttc | 600 |
| caaggagacc aagtcctggc tacatcccag cctgtggtta cagtgcagac aggccatgtg | 660 |
| agccaccgct gccagcacag agcgtccttc ccctgtaga ctagtgccgt agggagtacc | 720 |
| tgttgcccca gctgactgtg gcccctccg tgatccatcc atctccaggg agcaagacag | 780 |
| agacccagga atggaaagcg gagttcctaa caggatgaaa gttcccccat cagttccccc | 840 |
| agtacctcca gcaagtagc tttccacatt tgtcacagaa atcagaggag agatggtgtt | 900 |
| gggagccctt tggagaacgc cagtctccca ggcccctgc atctatcgag tttgcaatgt | 960 |
| cacaacctct ctgatcttgt gctcagcatg attctttaat agaagtttta ttttttcgtg | 1020 |
| cactctgcta atcatgtggg tgagccagtg gaacagcggg agacctgtgc tagttttaca | 1080 |
| gattgcctcc ttatgacgcg gctcaaaagg aaaccaagtg gtcaggagtt gtttctgacc | 1140 |
| cactgatctc tactaccaca aggagaatag tttaggagaa accagctttt actgtttttg | 1200 |
| aaaaattaca gcttcaccct gtcaagttaa caaggaatgc ctgtgccaat aaaaggtttc | 1260 |

<210> SEQ ID NO 44
<211> LENGTH: 5418
<212> TYPE: DNA
<213> ORGANISM: Homo sapiens
<220> FEATURE:
<221> NAME/KEY: misc_feature
<222> LOCATION: (1210)..(1219)
<223> OTHER INFORMATION: The "n" at this position can be either "a", "t", "g", or "c".

<400> SEQUENCE: 44

| | |
|---|---|
| gtgtcccata gtgtttccaa acttggaaag ggcgggggag ggcgggagga tgcggagggc | 60 |
| ggaggtatgc agacaacgag tcagagtttc cccttgaaag cctcaaaagt gtccacgtcc | 120 |
| tcaaaagaa tggaaccaat ttaagaagcc agcccgtgg ccacgtccct tcccccattc | 180 |
| gctccctcct ctgcgccccc gcaggctcct cccagctgtg gctgcccggg ccccagccc | 240 |
| cagccctccc attggtggag gcccttttgg aggcacccta gggccaggga aacttttgcc | 300 |
| gtataaatag ggcagatccg ggctttatta ttttagcacc acggcagcag gaggtttcgg | 360 |
| ctaagttgga ggtactggcc acgactgcat gcccgcgccc gccaggtgat acctccgccg | 420 |
| gtgacccagg ggctctgcga cacaaggagt ctgcatgtct aagtgctaga catgctcagc | 480 |
| tttgtggata cgcggacttt gttgctgctt gcagtaacct tatgcctagc aacatgccaa | 540 |
| tctttacaag aggaaactgt aagaaagggc ccagccggag atagaggacc acgtggagaa | 600 |
| agggtccac caggccccc aggcagagat ggtgaagatg gtcccacagg ccctcctggt | 660 |
| ccacctggtc ctcctggccc ccctggtctc gtgggaact tgctgctca gtatgatgga | 720 |
| aaaggagttg gacttggccc tggaccaatg ggcttaatgg gacctagagg cccacctggt | 780 |

-continued

```
gcagctggag ccccaggccc tcaaggtttc caaggacctg ctggtgagcc tggtgaacct    840
ggtcaaactg gtcctgcagg tgctcgtggt ccagctggcc ctcctggcaa ggctggtgaa    900
gatggtcacc ctggaaaacc cggacgacct ggtgagagag gagttgttgg accacaggt    960 gctcgtggtt tccctggaac tcctggactt cctggcttca aaggcattag gggacacaat   1020 ggtctgatg gattgaaggg acagcccggt gctcctggtg tgaagggtga acctggtgcc   1080
cctggtgaaa atggaactcc aggtcaaaca ggagcccgtg ggcttcctgg tgagagagga   1140
cgtgttggtg cccctggccc agctggtgcc cgtggcagtg atggaagtgt gggtcccgtg   1200
ggtcctgctn nnnnnnnng gtctgctggc cctccaggct tcccaggtgc ccctggcccc   1260
aagggtgaaa ttggagctat tggtaacgct ggtcctgctg gtcccgccgg tccccgtggt   1320
gaagtgggtc ttccaggcct ctccggcccc gttggacctc ctggtaatcc tggagcaaac   1380
ggccttactg gtgccaaggg tgctgctggc cttcccggcg ttgctggggc tcccggcctc   1440
cctggacccc gcggtattcc tggccctgtt ggtgctgccg tgctactgg tgccagagga   1500 cttgttggtg agcctggtcc agctggctcc aaaggagaga gcggtaacaa gggtgagccc   1560
ggctctgctg ggccccaagg tcctcctggt cccagtggtg aagaaggaaa gagaggccct   1620
aatggggaag ctggatctgc cggccctcca ggacctcctg ggctgagagg tagtcctggt   1680
tctcgtggtc ttcctggagc tgatggcaga gctggcgtca tgggccctcc tggtagtcgt   1740
ggtgcaagtg gccctgctgg agtccgagga cctaatggag atgctggtcg ccctggggag   1800
cctggtctca tgggacccag aggtcttcct ggttcccctg gaaatatcgg ccccgctgga   1860
aaagaaggtc ctgtcggcct ccctggcatc gacggcaggc ctggcccaat ggccccgtt   1920 ggagcaagag gagagcctgg caacattgga ttccctggac ccaaaggccc cactggtgac   1980
cctggcaaaa acggtgataa aggtcatgct ggtcttgctg gtgctcgggg tgctccaggt   2040
cctgatggaa acaatggtgc tcagggacct cctggaccac aggtgttca aggtggaaaa   2100 ggtgaacagg gtcccgctgg tcctccaggc ttccagggtc tgcctggccc ctcaggtccc   2160
gctggtgaag ttggcaaacc aggagaaagg ggtctccatg gtgagtttgg tctccctggt   2220
cctgctggtc aagagggga acgcggtccc ccaggtgaga gtggtgctgc cggtcctact   2280
ggtcctattg gaagccgagg tccttctgga ccccaggc ctgatggaaa caagggtgaa   2340
cctggtgtgg ttggtgctgt gggcactgct ggtccatctg gtcctagtgg actcccagga   2400 gagagggtg ctgctggcat acctggaggc aagggagaaa aggtgaacc tggtctcaga   2460 ggtgaaattg gtaaccctgg cagagatggt gctcgtggtg ctcatggtgc tgtaggtgcc   2520
cctggtcctg ctggagccac aggtgaccgg ggcgaagctg gggctgctgg tcctgctggt   2580
cctgctggtc ctcggggaag ccctggtgaa cgtggcgagg tcggtcctgc tggccccaac   2640
ggatttgctg gtccggctgg tgctgctggt caaccgggtg ctaaaggaga aagaggaggc   2700
aaagggccta aggtgaaaa cggtgttgtt ggtcccacag gccccgttgg agctgctggc   2760
ccagctggtc caaatggtcc cccggtcct gctggaagtc gtggtgatgg aggccccct   2820 ggtatgactg gtttccctgg tgctgctgga cggactggtc ccccaggacc ctctggtatt   2880
tctggccctc ctggtccccc tggtcctgct gggaagaag gcttcgtgg tcctcgtggt   2940 gaccaaggtc cagttggccg aactggagaa gtaggtgcag ttggtccccc tggcttcgct   3000
ggtgagaagg gtccctctgg agaggctggt actgctggac ctcctggcac tccaggtcct   3060
cagggtcttc ttggtgctcc tggtattctg ggtctccctg gctcgagagg tgaacgtggt   3120
ctacctggtg ttgctggtgc tgtgggtgaa cctggtcctc ttggcattgc cggccctcct   3180
```

-continued

```
ggggcccgtg gtcctcctgg tgctgtgggt agtcctggag tcaacggtgc tcctggtgaa   3240
gctggtcgtg atggcaaccc tgggaacgat ggtcccccag gtcgcgatgg tcaacccgga   3300
cacaagggag agcgcggtta ccctggcaat attggtcccg ttggtgctgc aggtgcacct   3360
ggtcctcatg gccccgtggg tcctgctggc aaacatggaa accgtggtga aactggtcct   3420
tctggtcctg ttggtcctgc tggtgctgtt ggcccaagag gtcctagtgg cccacaaggc   3480
attcgtggcg ataagggaga gcccggtgaa aagggcccca gaggtcttcc tggcttcaag   3540
ggacacaatg gattgcaagg tctgcctggt atcgctggtc accatggtga tcaaggtgct   3600
cctggctccg tgggtcctgc tggtcctagg ggccctgctg gtccttctgg ccctgctgga   3660
aaagatggtc gcactggaca tcctggtacg gttggacctg ctggcattcg aggccctcag   3720
ggtcaccaag gccctgctgg cccccctggt ccccctggcc ctcctggacc tccaggtgta   3780
agcggtggtg gttatgactt tggttacgat ggagacttct acagggctga ccagcctcgc   3840
tcagcacctt ctctcagacc caaggactat gaagttgatg ctactctgaa gtctctcaac   3900
aaccagattg agacccttct tactcctgaa ggctctagaa agaacccagc tcgcacatgc   3960
cgtgacttga gactcagcca cccagagtgg agcagtggtt actactggat tgaccccaac   4020
caaggatgca ctatggaagc catcaaagta tactgtgatt ccctaccggc gaaacctgt    4080 atccgggccc aacctgaaaa catcccagcc aagaactggt ataggagctc caaggacaag   4140
aaacacgtct ggctaggaga aactatcaat gctggcagcc agtttgaata taatgttgaa   4200
ggagtgactt ccaaggaaat ggctacccaa cttgccttca tgcgcctgct ggccaactat   4260
gcctctcaga acatcaccta ccactgcaag aacagcattg catacatgga tgaggagact   4320
ggcaacctga aaaaggctgt cattctacag ggctctaatg atgttgaact tgttgctgag   4380
ggcaacagca ggttcactta cactgttctt gtagatggct gctctaaaaa gacaaatgaa   4440
tggggaaaga caatcattga atacaaaaca aataagccat cacgcctgcc cttccttgat   4500
attgcacctt tggacatcgg tggtgctgac catgaattct tgtggacat tggcccagtc    4560 tgtttcaaat aaatgaactc aatctaaatt aaaaagaaa gaatttgaa aaactttct     4620 ctttgccatt tcttcttctt cttttttaac tgaaagctga atccttccat ttcttctgca   4680
catctacttg cttaaattgt gggcaaaaga gaaaagaag gattgatcag agcattgtgc   4740
aatacagttt cattaactcc ttcccccgct ccccccaaaaa tttgaattttt tttttcaaca   4800 ctcttacacc tgttatggaa aatgtcaacc tttgtaagaa aaccaaaata aaaattgaaa   4860
aataaaaacc ataaacattt gcaccacttg tggcttttga atatcttcca cagagggaag   4920
tttaaaaccc aaacttccaa aggtttaaac taccctcaaaa cactttccca tgagtgtgat   4980
ccacattgtt aggtgctgac ctagacagag atgaactgag gtccttgttt tgttttgttc   5040
ataatacaaa ggtgctaatt aatagtattt cagatacttg aagaatgttg atggtgctag   5100
aagaatttga gaagaaatac tcctgtattg agttgtatcg tgtggtgtat ttttttaaaaa   5160 atttgattta gcattcatat tttccatctt attcccaatt aaaagtatgc agattatttg    5220
cccaaagttg tcctcttctt cagattcagc atttgttctt tgccagtctc attttcatct   5280
tcttccatgg ttccacagaa gctttgtttc ttgggcaagc agaaaaatta aattgtacct   5340 atttttgtata tgtgagatgt ttaaataaat tgtgaaaaaa atgaaataaa gcatgtttgg   5400
ttttccaaaa gaacatat                                                  5418
```

<210> SEQ ID NO 45

<211> LENGTH: 2566
<212> TYPE: DNA
<213> ORGANISM: Homo sapiens

<400> SEQUENCE: 45

```
cagaccacag gaatacctaa tgcctttttt ctcttcctgt ctttgtccct cacactacag     60
caggcccctc ccttccctct tcaacctcat cctccctccc cacaggccca gagaaccagt    120
tgggctttgt tctcctgcag gctatggttc atcatgcaaa tagctcctgt gtcagaaatg    180
cttttttggct tcaaataaca gaaaagctaa caccagcttt atcaataata atatcggtgg    240
tttacttaag gtgtccagag atggtggaga acaggattgg tttcctcctc aatgtcaagg    300
actcaaagac tctttctgtg gtagggccac atcctaaacc ctgtatcctg tgattattta    360
cctgacaggg caaagagat tttgcagatg caattaaggt taaggacctt gacgtgggaa    420
gattgtgatt atttacctga cagggcaaaa gagattttgc agatgcaatt aaggttaagg    480
accttgacgt gggaagatta ttctggatta tctaggtggg cgcaatttga tcacatgggt    540
ccccagaagt ggagaacctt tcccacctgt agaaagccag agagctggca cctgagaagg    600
acagaactgt cactgcagga tttgaagatg aaggggccca tgagccaagg aatgccagtg    660
acctatagag gctaaaaaac agcaaggaaa tggactctcc ccagagcctc cagaggaatg    720
cagccctgtt gatcacatga tcaccagatg gctgccccag agccaaatgt cgcttcctga    780
gcaccatact caaaggcagg ggaagtggat ggagggcagg agctccattc ttgtttgcca    840
ctctcctttt gtcaattggg aaaaaattcc agaaactctg ggagccctcc ccttacattt    900
cctgggtcat ggggccagcc ctagctgctg gagggactga gaactgctgt tgagcagttt    960
acctgacggc atctgccatg gcttggcagg aactctggct ttgggagaga gcagcagcaa   1020
ggtattcaag caccacctcc acccagcccc tcccacattt cactcaggac tgagtaaagg   1080
agacactcag atgctactca gatgctggct tcagctaagt attttgcaaa gcctctcgtg   1140
ttcttacaag tttgtggcta tcatgacaaa atggagcagc ctactatatc tacatataca   1200
actatggggg acctagtttt atctcattta ccacaatgtt ttcaatcatt ttttggatga   1260
cataattttt agcctcttct ctaaatgctt cctcaagctt ccttgccttt ccagccactg   1320
caaatgactt gcagtttccc ctacatggca cctgacccttt gtgcctccct ccctctgccc   1380
atggcccaga aagcccttc ctgtgccctc tggcttcctg ataaactcct atcatcttca   1440
agagccagtt cccatgccag ctctccccaa gtgctccact gaggcttccg taacacctct   1500
gttcccacat cgggttgact gtctttgttt tgtcattgct tgctctggct gtgtctccct   1560
cattagactg ggatgccttc aaggtaggga ccctatctgg gtcagcttgg cacccccaaag   1620
cgtaccacag cacctgattc tgaggaggct ctcagtagat atctgttgag taaccagaat   1680
gtagggtggt cctgatggtt tctgacattg aatagaaaac agctccctat ttgatcttaa   1740
aataatcact ataacctgga catactgtac tagatgctgt ttttgtctga cttctactct   1800
gtcaatctct ttgcacctcc atttgttcat ctgtgaaatg aagaaaatgc tcatggagtt   1860
cagtgaagat taaatgaatg aatataggta gactgcctaa tctggcactt gccacgcagc   1920
tgacttcaat atagtagctc taatattatg gtccttgagg atcttactgt cttatggccc   1980
agaactgcat ttgattaaag aaggctcccc taaaaaaaga gtcatacata ttccatttgt   2040
cctttcagaa ggccgtgaag catttacact ctttaagaca aattcccatc caaaaatagt   2100
taagatttct aaaatatttt gatgctgaaa gaggtgtgct tcagtgggt ggcaaatttg   2160
cttctatgga agattttaa tacaggttgt ttctatttta cttttctgg ctgaaaggat   2220
```

```
tttacattta ttcaaagtca aaagggaaaa gaaatccaag aactacagaa gagcagttga    2280
agtgatttat gcttgatttc taaatgcaac ttatgtttat acataattta aaactcaaag    2340
aaagcatgct tatacaatca tgtgcaactt taaactttaa gaactctgga tgaatacatg    2400
gtggcaacag tccatgacac ctgaaaacat catttgtgga gtggcgtaga gttcagtgtt    2460
cgcagtcgca tattacaacc atgtttcaca cagccctgct cggtttgatt ttctccacgt    2520
ggttgataat tgtcttcagt tgctgctaag tgattttgca aatttc                  2566
```

<210> SEQ ID NO 46
<211> LENGTH: 1847
<212> TYPE: DNA
<213> ORGANISM: Homo sapiens

<400> SEQUENCE: 46

```
gtccccgcgc cagagacgca gccgcgctcc caccacccac acccaccgcg ccctcgttcg      60
cctcttctcc gggagccagt ccgcgccacc gccgccgccc aggccatcgc caccctccgc     120
agccatgtcc accaggtccg tgtcctcgtc ctcctaccgc aggatgttcg gcggcccggg     180
caccgcgagc cggccgagct ccagccggag ctacgtgact acgtccaccc gcacctacag     240
cctgggcagc gcgctgcgcc ccagcaccag ccgcagcctc tacgcctcgt ccccgggcgg     300
cgtgtatgcc acgcgctcct ctgccgtgcg cctgcggagc agcgtgcccg gggtgcggct     360
cctgcaggac tcggtggact ctctcgctgg cgacgccatc aacaccgagt tcaagaacac     420
ccgcaccaac gagaaggtgg agctgcagga gctgaatgac cgcttcgcca actacatcga     480
caaggtgcgc ttcctggagc agcagaataa gatcctgctg ccgagctcg agcagctcaa     540 gggccaaggc aagtcgcgcc tgggggacct ctacgaggag gagatgcggg agctgcgccg     600
gcaggtggac cagctaacca acgacaaagc ccgcgtcgag gtggagcgcg acaacctggc     660
cgaggacatc atgcgcctcc gggagaaatt gcaggaggag atgcttcaga gagaggaagc     720
cgaaaacacc ctgcaatctt tcagacagga tgttgacaat gcgtctctgg cacgtcttga     780
ccttgaacgc aaagtggaat cttttgcaaga agagattgcc tttttgaaga aactccacga     840
agaggaaatc caggagctgc aggctcagat tcaggaacag catgtccaaa tcgatgtgga     900
tgtttccaag cctgacctca cggctgccct cgtgacgta cgtcagcaat atgaaagtgt     960
ggctgccaag aacctgcagg aggcagaaga atggtacaaa tccaagtttg ctgacctctc    1020
tgaggctgcc aaccggaaca atgacgccct gcgccaggca agcaggagt ccactgagta    1080 ccggagacag gtgcagtccc tcacctgtga agtggatgcc cttaaaggaa ccaatgagtc    1140 cctgaacgc cagatgcgtg aaatggaaga gaactttgcc gttgaagctg ctaactacca    1200
agacactatt ggccgcctgc aggatgagat tcagaatatg aaggaggaaa tggctcgtca    1260
ccttcgtgaa taccaagacc tgctcaatgt taagatggcc cttgacattg agattgccac    1320
ctacaggaag ctgctggaag gcgaggagag caggatttct ctgcctcttc caaactttc    1380 ctccctgaac ctgagggaaa ctaatctgga ttcactccct ctggttgata cccactcaaa    1440
aaggacactt ctgattaaga cggttgaaac tagagatgga caggttatca acgaaacttc    1500
tcagcatcac gatgaccttg aataaaaaatt gcacacactc agtgcagcaa tatattacca    1560
gcaagaataa aaaagaaatc catatcttaa agaaacagct ttcaagtgcc tttctgcagt    1620
ttttcaggag cgcaagatag atttggaata ggaataagct ctagttctta acaaccgaca    1680
ctcctacaag atttagaaaa aagtttacaa cataatctag tttacagaaa aatcttgtgc    1740
```

| | |
|---|---:|
| tagaatactt tttaaaaggt attttgaata ccattaaaac tgctttttt tttccagcaa | 1800 |
| gtatccaacc aacttggttc tgcttcaata aatctttgga aaaactc | 1847 |

<210> SEQ ID NO 47
<211> LENGTH: 3864
<212> TYPE: DNA
<213> ORGANISM: Homo sapiens

<400> SEQUENCE: 47

| | |
|---|---:|
| ggccagccga atccaagccg tgtgtactgc gtgctcagca ctgcccgaca gtcctagcta | 60 |
| aacttcgcca actccgctgc ctttgccgcc accatgccaa aaacgatcag tgtgcgtgtg | 120 |
| accaccatgg atgcagagct ggagtttgcc atccagccca acaccaccgg aagcagcta | 180 |
| tttgaccagt ggtgaaaac tattggcttg agggaagttt ggttctttgg tctgcagtac | 240 |
| caggacacta aaggtttctc cacctggctg aaactcaata agaaggtgac tgcccaggat | 300 |
| gtgcggaagg aaagcccct gctctttaag ttccgtgcca agttctaccc tgaggatgtg | 360 |
| tccgaggaat tgattcagga catcactcag cgcctgttct ttctgcaagt gaaagagggc | 420 |
| attctcaatg atgatattta ctgcccgcct gagaccgctg tgctgctggc ctcgtatgct | 480 |
| gtccagtcta agtatggcga cttcaataag gaagtgcata agtctggcta cctggccgga | 540 |
| gacaagttgc tcccgcagag agtcctggaa cagcacaaac tcaacaagga ccagtgggag | 600 |
| gagcggatcc aggtgtggca tgaggaacac cgtggcatgc tcagggagga tgctgtcctg | 660 |
| gaatatctga agattgctca agatctggag atgtatggtg tgaactactt cagcatcaag | 720 |
| aacaagaaag gctcagagct gtggctgggg gtggatgccc tgggtctcaa catctatgag | 780 |
| cagaatgaca gactaactcc caagataggc ttcccctgga gtgaaatcag gaacatctct | 840 |
| ttcaatgata agaaatttgt catcaagccc attgacaaaa agccccgga cttcgtcttc | 900 |
| tatgctcccc ggctgcggat taacaagcgg atccttggcct tgtgcatggg gaaccatgaa | 960 |
| ctatacatgc gccgtcgcaa gcctgatacc attgaggtgc agcagatgaa ggcacaggcc | 1020 |
| cgggaggaga agcaccagaa gcagatggag cgtgctatgc tggaaaatga aagaagaag | 1080 |
| cgtgaaatgg cagagaagga gaaagagaag attgaacggg agaaggagga gctgatggag | 1140 |
| aggctgaagc agatcgagga acagactaag aaggctcagc aagaactgga agaacagacc | 1200 |
| cgtagggctc tggaacttga gcaggaacgg aagcgtgccc agagcgaggc tgaaaagctg | 1260 |
| gccaaggagc gtcaagaagc tgaagaggcc aaggaggcct tgctgcaggc ctcccgggac | 1320 |
| cagaaaaaga ctcaggaaca gctggccttg gaaatggcag agctgacagc tcgaatctcc | 1380 |
| cagctggaga tggcccgaca agaagaggag agtgaggctg tggagtggca gcagaaggcc | 1440 |
| cagatggtac aggaagactt ggagaagacc cgtgctgagc tgaagactgc catgagtaca | 1500 |
| cctcatgtgg cagagcctgc tgagaatgag caggatgagc aggatgagaa tggggcagag | 1560 |
| gctagtgctg acctacgggc tgatgctatg gccaaggacc gcagtgagga ggaacgtacc | 1620 |
| actgaggcag agaagaatga gcgtgtgcag aagcacctga aggccctcac ttcggagctg | 1680 |
| gccaatgcca gagatgagtc caagaagact gccaatgaca tgatccatgc tgagaacatg | 1740 |
| cgactgggcc gagacaaata caagaccctg cgccagatcc ggcagggcaa caccaagcag | 1800 |
| cgcattgacg aatttgagtc tatgtaatgg cacccagcc tctagggacc cctcctccct | 1860 |
| ttttccttgt ccccacactc ctacacctaa ctcacctaac tcatactgtg ctggagccac | 1920 |
| taactagagc agccctggag tcatgccaag catttaatgt agccatggga ccaaacctag | 1980 |
| ccccttagcc cccacccact tccctgggca aatgaatggc tcactatggt gccaatggaa | 2040 |

-continued

```
cctcctttct cttctctgtt ccattgaatc tgtatggcta aatatcctca cttctccagc    2100
ctagaggtac tttccacttg attttgcaaa tgcccttaca cttactgttg tcctatggga    2160
gtcaagtgtg gagtaggttg gaagctagct cccctcctct cccctaccac tgtcttcttc    2220
agggtcctga gatttacacg gttggagtgt tatgcggtct agggaatgag acaggaccta    2280
ggatatcttc tccaggatgt caactgacct aaaatttgcc ctcccatccc gtttagagtt    2340
atttaggctt tgtaacgatt gggggataaa agatgttca gtcattttg tttctacctc      2400
ccagatcgga tctgttgcaa actcagcctc aataagcctt gtcgttgact ttagggactc    2460
aatttctccc cagggtggat gggggaaatg gtgccttcaa gaccttcacc aaacatacta    2520
gaagggcatt ggccattcta ttgtggcaag gctgagtaga agatcctacc ccaattcctt    2580
gtaggagtat aggccggtct aaagtgagct ctatgggcag atctacccct tacttattat    2640
tccagatctg cagtcacttc gtgggatctg ccctcctg cttcaatacc caaatcctct     2700
ccagctataa cagtagggat gagtacccaa aagctcagcc agccccatca ggactcttgt    2760
gaaaagagag gatatgttca cacctagcgt cagtattttc cctgctaggg gttttaggtc    2820
tcttcccctc tcagagctac ttgggccata gctcctgctc cacagccatc ccagccttgg    2880
catctagagc ttgatgccag taggctcaac tagggagtga gtgcaaaaag ctgagtatgg    2940
tgagagaagc ctgtgccctg atccaagttt actcaaccct ctcaggtgac caaaatcccc    3000
ttctcatcac tccctccaa agaggtgact gggccctgcc tctgtttgac aaacctctaa    3060
cccaggtctt gacaccagct gttctgtccc ttggagctgt aaaccagaga gctgctgggg    3120
attctggcct agtcccttcc acccccccac cccttgctct caacccagga gcatccacct    3180
ccttctctgt ctcatgtgtg ctcttcttct ttctacagta ttatgtactc tactgatatc    3240
taaatattga tttctgcctt ccttgctaat gcaccattag aagatattag tcttggggca    3300
ggatgatttt ggcctcatta cttaccacc cccacacctg gaaagcatat actatattac     3360
aaaatgacat tttgccaaaa ttattaatat aagaagcttt cagtattagt gatgtcatct    3420
gtcactatag gtcatacaat ccattcttaa agtacttgtt atttgttttt attattactg    3480
tttgtcttct ccccaggggtt cagtcctcaa ggggccatcc tgtcccacca tgcagtgccc   3540
ctagcttaga gcctccctca attcccctg gccaccaccc cccactctgt gcctgacctt     3600
gaggagtctt gtgtgcattg ctgtgaatta gctcacttgg tgatatgtcc tatattggct    3660
aaattgaaac ctggaattgt ggggcaatct attaatagct gccttaaagt cagtaactta    3720
cccttaggga ggctggggga aaaggttaga ttttgtattc agggttttt tgtgtacttt     3780
ttgggttttt taaaaattgt ttttggaggg gtttatgctc aatccatgtt ctatttcagt    3840
gccaataaaa tttaggaaga cttc                                          3864
```

<210> SEQ ID NO 48
<211> LENGTH: 2270
<212> TYPE: DNA
<213> ORGANISM: Homo sapiens

<400> SEQUENCE: 48

```
ggtgtgcccg agaggctga gcagcctgcg cctgagctgg tggaggtgga agtgggcagc     60
acagcccttc tgaagtgcgg cctctcccag tcccaaggca acctcagcca tgtcgactgg   120
tttctgtcc acaaggagaa gcggacgctc atcttccgtg tgcgccaggg ccagggccag   180
agcgaacctg gggagtacga gcagcggctc agcctccagg acagaggggc tactctggcc   240
```

| | |
|---|---|
| ctgactcaag tcaccccca agacgagcgc atcttcttgt gccagggcaa gcgccctcgg | 300 |
| tcccaggagt accgcatcca gctccgcgtc tacaaagctc cggaggagcc aaacatccag | 360 |
| gtcaaccccc tgggcatccc tgtgaacagt aaggagcctg aggaggtcgc tacctgtgta | 420 |
| gggaggaacg ggtaccccat tcctcaagtc atctggtaca agaatggccg gcctctgaag | 480 |
| gaggagaaga accgggtcca cattcagtcg tcccagactg tggagtcgag tggtttgtac | 540 |
| accttgcaga gtattctgaa ggcacagctg gttaaagaag acaaagatgc ccagttttac | 600 |
| tgtgagctca actaccggct gcccagtggg aaccacatga aggagtccag ggaagtcacc | 660 |
| gtccctgttt ctacccgac agaaaaagtg tggctgaaa tggagcccgt gggaatgctg | 720 |
| aaggaagggg accgcgtgga atcaggtgt ttggctgatg caaccctcc accacacttc | 780 |
| agcatcagca gcagaaccc cagcaccagg gaggcagagg aagagacaac caacgacaac | 840 |
| ggggtcctgg tgctggagcc tgcccggaag gaacacagtg ggcgctatga atgtcagggc | 900 |
| ctggacttgg acaccatgat atcgctgctg agtgaaccac aggaactact ggtgaactat | 960 |
| gtgtctgacg tccgagtgag tcccgcagca cactgagaga caggaaggca gcagcctcac | 1020 |
| cctgacctgt gaggcagaga gtagccagga cctcgagttc cagtggctga gagaagagac | 1080 |
| aggccaggtg ctggaaaggg ggcctgtgct tcagttgcat gacctgaaac gggaggcagg | 1140 |
| aggcggctat cgctgcgtgg cgtctgtgcc cagcataccc ggcctgaacc gcacacagct | 1200 |
| ggtcaacgtg gccatttttg gcccccttg gatggcattc aaggagagga aggtgtgggt | 1260 |
| gaaagagaat atggtgttga atctgtcttg tgaagcgtca gggcacccccc ggcccaccat | 1320 |
| ctcctggaac gtcaacggca cggcaagtga acaagaccaa gatccacagc gagtcctgag | 1380 |
| caccctgaat gtcctcgtga ccccggagct gttggagaca ggtgttgaat gcacggcctc | 1440 |
| caacgacctg ggcaaaaaca ccagcatcct cttcctggag ctggtcaatt taaccaccct | 1500 |
| cacaccagac tccaacacaa ccactggcct cagcacttcc actgccagtc ctcataccag | 1560 |
| agccaacagc acctccacag agagaaagct gccggagccg gagagccggg gcgtggtcat | 1620 |
| cgtggctgtg attgtgtgca tcctggtcct ggcggtgctg ggcgctgtcc tctatttcct | 1680 |
| ctataagaag ggcaagctgc cgtgcaggcg ctcagggaag caggagatca cgctgccccc | 1740 |
| gtctcgtaag agcgaacttg tagttgaagt taagtcagat aagctcccag aagagatggg | 1800 |
| cctcctgcag ggcagcagcg gtgacaagag ggctccggga gaccagggag agaaatacat | 1860 |
| cgatctgagg cattagcccc gaatcacttc agctcccttc cctgcctgga ccattcccag | 1920 |
| ctccctgctc actcttctct cagccaaagc ctccaagggg actagagaga gcctcctgc | 1980 |
| tcccctcgcc tgcacacccc ctttcagagg gccactgggt taggacctga ggacctcact | 2040 |
| tggccctgca aggcccgctt tcagggacc agtccaccac catctccacg ttgagtgaag | 2100 |
| ctcatcccaa gcaaggagcc ccagtctccc gagcgggtag gagagtttct tgtagaacgt | 2160 |
| gttttttctt tacacacatt atggctgtaa atacctggct cctgccagca gctgagctgg | 2220 |
| gtagcctctc tgagctggga ttacaggtgt gagccactgc gcccagccaa | 2270 |

<210> SEQ ID NO 49
<211> LENGTH: 2127
<212> TYPE: DNA
<213> ORGANISM: Homo sapiens

<400> SEQUENCE: 49

| | |
|---|---|
| caaacttggt ggcaacttgc ctcccggtgc gggcgtctct ccccaccgt ctcaacatgc | 60 |
| ttaggggtcc ggggcccggg ctgctgctgc tggccgtcct gtgcctgggg acagcggtgc | 120 |

-continued

```
cctccacggg agcctcgaag agcaagaggc aggctcagca aatggttcag ccccagtccc        180
cggtggctgt cagtcaaagc aagcccggtt gttatgacaa tggaaaacac tatcagataa        240
atcaacagtg ggagcggacc tacctaggca atgcgttggt ttgtacttgt tatggaggaa        300
gccgaggttt taactgcgag agtaaacctg aagctgaaga acttgctttt gacaagtaca        360
ctggaacac ttaccgagtg ggtgacactt atgagcgtcc taaagactcc atgatctggg         420
actgtacctg catcggggct gggcgaggga gaataagctg taccatcgca aaccgctgcc        480
atgaaggggg tcagtcctac aagattggtg acacctggag agaccacat gagactggtg         540
gttacatgtt agagtgtgtg tgtcttggta atggaaaagg agaatggacc tgcaagccca        600
tagctgagaa gtgttttgat catgctgctg ggacttccta tgtggtcgga gaaacgtggg        660
agaagcccta ccaaggctgg atgatggtag attgtacttg cctgggagaa ggcagcggac        720
gcatcacttg cacttctaga aatagatgca acgatcagga cacaaggaca tcctatagaa        780
ttggagacac ctggagcaag aaggataatc gaggaaacct gctccagtgc atctgcacag        840
gcaacggccg aggagagtgg aagtgtgaga ggcacacctc tgtgcagacc acatcgagcg        900
gatctggccc cttcaccgat gttcgtgcag ctgtttacca accgcagcct cacccccagc        960
ctcctcccta tggccactgt gtcacagaca gtggtgtggt ctactctgtg gggatgcagt       1020
ggctgaagac acaggaaat aagcaaatgc tttcacgtg cctgggcaac ggagtcagct         1080
gccaagagac agctgtaacc cagacttacg gtggcaactc aaatggagag ccatgtgtct       1140
taccattcac ctacaatggc aggacgtgca gcacaacttc gaattatgag caggaccaga      1200
aatactcttt ctgcacagac cacactgttt tggttcagac tcgaggagga aattccaatg       1260
gtgccttgtg ccacttcccc ttcctataca acaaccacaa ttacactgat tgcacttctg       1320
agggcagaag agacaacatg aagtggtgtg ggaccacaca gaactatgat gccgaccaga      1380
agtttgggtt ctgccccatg gctgcccacg aggaaatctg cacaaccaat gaaggggtca       1440
tgtaccgcat ggagatcag tgggataagc agcatgacat gggtcacatg atgaggtgca       1500
cgtgtgttgg gaatggtcgt ggggaatgga catgcattgc ctactcgcag cttcgagatc       1560
agtgcattgt tgatgacatc acttacaatg tgaacgacac attccacaag cgtcatgaag       1620
agggcacat gctgaactgt acatgcttcg gtcagggtcg gggcaggtgg aagtgtgatc       1680
ccgtcgacca atgccaggat tcagagactg ggacgtttta tcaaattgga gattcatggg       1740
agaagtatgt gcatggtgtc agataccagt gctactgcta tggccgtggc attggggagt       1800
ggcattgcca acctttacag acctatccaa gctcaagtgg tcctgtcgaa gtatttatca       1860
ctgagactcc gagtcagccc aactcccacc ccatccagtg gaatgcacca cagccatctc       1920
acatttccaa gtacattctc aggtggagac ctgtgagtat cccacccaga aaccttggat       1980
actgagtctc ctaatcttat caattctgat ggtttctttt tttcccagct tttgagccaa       2040
caactctgat taactattcc tatagcattt actatatttg tttagtgaac aaacaatatg       2100
tggtcaatta aattgacttg tagactg                                           2127
```

<210> SEQ ID NO 50
<211> LENGTH: 1918
<212> TYPE: DNA
<213> ORGANISM: Homo sapiens

<400> SEQUENCE: 50

```
accccccgcac ccagctccgc aggaccggcg ggcgcgcgcg ggctctggag gccacgggca       60
```

| | |
|---|---|
| tgatgcttcg ggtcctggtg ggggctgtcc tccctgccat gctactggct gccccaccac | 120 |
| ccatcaacaa gctggcactg ttcccagata agagtgcctg gtgcgaagcc aagaacatca | 180 |
| cccagatcgt gggccacagc ggctgtgagg ccaagtccat ccagaacagg gcgtgcctag | 240 |
| gacagtgctt cagctacagc gtccccaaca ccttcccaca gtccacagag tccctggttc | 300 |
| actgtgactc ctgcatgcca gcccagtcca tgtgggagat tgtgacgctg gagtgcccgg | 360 |
| gccacgagga ggtgcccagg gtggacaagc tggtggagaa gatcctgcac tgtagctgcc | 420 |
| aggcctgcgg caaggagcct agtcacgagg ggctgagcgt ctatgtgcag ggcgaggacg | 480 |
| ggccgggatc ccagcccggc acccaccctc accccatcc ccaccccat cctggcgggc | 540 |
| agacccctga gcccgaggac cccctgggg cccccacac agaggaagag ggggctgagg | 600 |
| actgaggccc cccaactct tcctcccctc tcatcccct gtggaatgtt gggtctcact | 660 |
| ctctggggaa gtcaggggag aagctgaagc ccccctttgg cactggatgg acttggcttc | 720 |
| agactcggac ttgaatgctg cccggttgcc atggagatct gaaggggcgg ggttagagcc | 780 |
| aagctgcaca atttaatata ttcaagagtg gggggaggaa gcagaggtct tcagggctct | 840 |
| ttttttgggg ggggtggtct cttcctgtct ggcttctaga gatgtgcctg tgggaggggg | 900 |
| aggaagttgg ctgagccatt gagtgctggg ggaggccatc caagatggca tgaatcgggc | 960 |
| taaggtccct gggggtgcag atggtactgc tgaggtcccg ggcttagtgt gagcatcttg | 1020 |
| ccagcctcag gcttgaggga gggctgggct agaaagacca ctggcagaaa caggaggctc | 1080 |
| cggcccacag gtttccccaa ggcctctcac cccacttccc atctccaggg aagcgtcgcc | 1140 |
| ccagtggcac tgaagtggcc ctccctcagc ggaggggttt gggagtcagg cctgggcagg | 1200 |
| accctgctga ctcgtggcgc gggagctggg agccaggctc tccgggcctt tctctggctt | 1260 |
| ccttggcttg cctggtgggg aaggggagg aggggaagaa ggaaagggaa gagtcttcca | 1320 |
| aggccagaag gaggggaca accccccaag accatccctg aagacgagca tccccctcct | 1380 |
| ctccctgtta gaaatgttag tgccccgcac tgtgccccaa gttctaggcc ccccagaaag | 1440 |
| ctgccagagc cggccgcctt ctcccctctc ccagggatgc tctttgtaaa tatcggatgg | 1500 |
| gtgtgggagt gagggttac ctccctcgcc ccaaggttcc agaggcccta ggcgggatgg | 1560 |
| gctcgctgaa cctcgaggaa ctccaggacg aggaggacat gggacttgcg tggacagtca | 1620 |
| gggttcactt gggctctctc tagctcccca attctgcctg cctcctccct cccagctgca | 1680 |
| ctttaacccct agaaggtggg gacctggggg gagggacagg gcaggcgggc ccatgaagaa | 1740 |
| agcccctcgt tgcccagcac tgtctgcgtc tgctcttctg tgcccaggt ggctgccagc | 1800 |
| ccactgcctc ctgcctgggg tggcctggcc ctcctggctg ttgcgacgcg ggcttctgga | 1860 |
| gcttgtcacc attggacagt ctccctgatg gaccctcagt cttctcatga ataaattc | 1918 |

<210> SEQ ID NO 51
<211> LENGTH: 1222
<212> TYPE: DNA
<213> ORGANISM: Homo sapiens

<400> SEQUENCE: 51

| | |
|---|---|
| atccgtcccg gataagaccc gctgtctggc cctgagtagg gtgtgacctc cgcagccgca | 60 |
| gaggaggagc gcagcccggc ctcgaagaac ttctgcttgg gtggctgaac tctgatcttg | 120 |
| acctagagtc atggccatgg caaccaaagg aggtactgtc aaagctgctt caggattcaa | 180 |
| tgccatggaa gatgcccaga ccctgaggaa ggccatgaaa gggctcggca ccgatgaaga | 240 |
| cgccattatt agcgtccttg cctaccgcaa caccgcccag cgccaggaga tcaggacagc | 300 |

```
ctacaagagc accatcggca gggacttgat agacgacctg aagtcagaac tgagtggcaa    360
cttcgagcag gtgattgtgg ggatgatgac gcccacggtg ctgtatgacg tgcaagagct    420
gcgaagggcc atgaagggag ccggcactga tgagggctgc ctaattgaga tcctggcctc    480 ccggaccct gaggagatcc ggcgcataag ccaaacctac cagcagcaat atggacggag    540
ccttgaagat gacattcgct ctgacacatc gttcatgttc cagcgagtgc tggtgtctct    600
gtcagctggt gggagggatg aaggaaatta tctggacgat gctctcgtga gacaggatgc    660
ccaggacctg tatgaggctg agagaagaa atggggggaca gatgaggtga aatttctaac    720
tgttctctgt tcccggaacc gaaatcacct gttgcatggt ttgatgaata caaaaggata    780
tcacagaagg atattgaaca gagtattaaa tctgaaacat ctggtagctt tgaagatgct    840
ctgctggcta tagtaaagtg catgaggaac aaatctgcat attttgctga aaagctctat    900
aaatcgatga agggcttggg caccgatgat aacacccctca tcagagtgat ggtttctcga    960
gcagaaattg acatgttgga tatccgggca cacttcaaga gactctatgg aaagtctctg    1020
tactcgttca tcaagggtga cacatctgga gactacagga agtactgct tgttctctgt   1080 ggaggagatg attaaaataa aaatcccaga aggacaggag gattctcaac actttgaatt    1140
ttttaacttt cattttctca cactgctatt atcattatct cagaatgctt atttccaatt    1200
aaaacgccta cagctgcctc ct                                              1222

<210> SEQ ID NO 52
<211> LENGTH: 2468
<212> TYPE: DNA
<213> ORGANISM: Homo sapiens

<400> SEQUENCE: 52
tggggcagcc gcgcccgcgg tgttttccgc ccggcgctgg cggctgctgc gcccgcggct      60
ccccagtgcc ccgagtgccc cgcgggcccc gcgagcggga gtgggaccca gcccctaggc     120
agaacccagg cgccgcgccc gggacgcccg cggagagagc cactcccgcc cacgtcccat     180
ttcgcccctc gcgtccggag tcctcgtggc cagatctaac catgagctac cctggctatc     240
ccccgccccc aggtggctac ccaccagctg caccaggtgg tggtccctgg ggaggtgctg     300
cctaccctcc tccgcccagc atgccccca tcgggctgga taacgtgcc acctatgcgg      360 ggcagttcaa ccaggactat ctctcgggaa tggcggccaa catgtctggg acatttggag     420
gagccaacat gccaacctg taccctgggg cccctgggcc tggctaccca ccagtgcccc      480
ctggcggctt tgggcagccc ccctctgccc agcagcctgt tcctccctat gggatgtatc     540
cacccccagg aggaaaccca ccctccagga tgccctcata tccgccatac ccaggggccc    600
ctgtgccggg ccagcccatg ccacccccg acagcagcc cccaggggcc tacctgggc      660 agccaccagt gacctaccct ggtcagcctc cagtgccact ccctgggcag cagcagccag    720
tgccgagcta cccaggatac ccggggtctg ggactgtcac cccgctgtg cccccaaccc    780 agttggaag ccgaggcacc atcactgatg ctccggcctt tgaccccctg cgagatgccg     840
aggtcctgcg gaaggccatg aaggctcg ggacggatga gcaggccatc attgactgcc     900
tggggagtcg ctccaacaag cagcggcagc agatcctact ttccttcaag acggcttacg    960
gcaaggattt gatcaaagat ctgaaatctg aactgtcagg aaactttgag aagacaatct    1020
tggctctgat gaagacccca gtcctctttg acatttatga gataaaggaa gccatcaagg    1080
gggttggcac tgatgaagcc tgcctgattg agatcctcgc ttcccgcagc aatgagcaca    1140
```

-continued

```
tccgagaatt aaacagagcc tacaaagcag aattcaaaaa gaccctggaa gaggccattc    1200
gaagcgacac atcagggcac ttccagcggc tcctcatctc tctctctcag ggaaaccgtg    1260
atgaaagcac aaacgtggac atgtcactcg cccagagaga tgcccaggag ctgtatgcgg    1320
ccggggagaa ccgcctggga acagacgagt ccaagttcaa tgcggttctg tgctcccgga    1380
gccgggccca cctggtagca gttttcaatg agtaccagag aatgacaggc cgggacattg    1440
agaagagcat ctgccgggag atgtccgggg acctggagga gggcatgctg gccgtggtga    1500
aatgtctcaa gaatacccca gccttctttg cggagaggct caacaaggcc atgagggggg    1560
caggaacaaa ggaccggacc ctgattcgca tcatggtgtc tcgcagcgag accgacctcc    1620
tggacatcag atcagagtat aagcggatgt acggcaagtc gctgtaccac gacatctcgg    1680
gagatacttc aggggattac cggaagattc tgctgaagat ctgtggtggc aatgactgaa    1740
cagtgactgg tggctcactt ctgcccacct gccggcaaca ccagtgccag gaaaaggcca    1800
aaagaatgtc tgtttctaac aaatccacaa atagccccga gattcaccgt cctagagctt    1860
aggcctgtct tccacccctc ctgacccgta tagtgtgcca caggacctgg gtcggtctag    1920
aactctctca ggatgccttt tctaccccat ccctcacagc ctcttgctgc taaaatagat    1980
gtttcatttt tctgactcat gcaatcattc ccctttgcct gtggctaaga cttggcttca    2040
tttcgtcatg taattgtata ttttttatttg gaggcatatt ttcttttctt acagtcattg    2100
ccagacagag gcatacaagt ctgtttgctg catacacatt tctggtgagg gcgactgggt    2160
gggtgaagca ccgtgtcctc gctgaggaga gaaagggagg cgtgcctgag aaggtagcct    2220
gtgcatctgg tgagtgtgtc acgagctttg ttactgccaa actcactcct ttttagaaaa    2280
aacaaaaaaa aagggccaga aagtcattcc ttccatcttc cttgcagaaa ccacgagaac    2340
aaagccagtt ccctgtcagt gacagggctt cttgtaattt gtggtatgtg ccttaaacct    2400
gaatgtctgt agccaaaact tgtttccaca ttaagagtca gccagctctg gaatggtctg    2460
gaaatgtc                                                             2468
```

<210> SEQ ID NO 53
<211> LENGTH: 4907
<212> TYPE: DNA
<213> ORGANISM: Homo sapiens

<400> SEQUENCE: 53

```
tagacgcacc ctctgaagat ggtgactccc tcctgagaag ctggacccct tggtaaaaga     60
caaggccttc tccaagaaga atatgaaagt gttactcaga cttatttgtt tcatagctct    120
actgatttct tctctggagg ctgataaatg caaggaacgt gaagaaaaaa taattttagt    180
gtcatctgca aatgaaattg atgttcgtcc ctgtcctctt aacccaaatg aacacaaagg    240
cactataact tggtataaag atgacagcaa gacacctgta tctacagaac aagcctccag    300
gattcatcaa cacaaagaga aactttggtt tgttcctgct aaggtggagg attcaggaca    360
ttactattgc gtggtaagaa attcatctta ctgcctcaga attaaaataa gtgcaaaatt    420
tgtggagaat gagcctaact tatgttataa tgcacaagcc atatttaagc agaaactacc    480
cgttgcagga gacggaggac ttgtgtgccc ttatatggag ttttttaaaa atgaaaataa    540
tgagttacct aaaattacagt ggtataagga ttgcaaccct ctacttcttg acaatataca    600
ctttagtgga gtcaaagata ggctcatcgt gatgaatgtg gctgaaaagc atagagggaa    660
ctatacttgt catgcatcct acacatactt gggcaagcaa tatcctatta cccgggtaat    720
agaaatttatt actctagagg aaaacaaacc cacaaggcct gtgattgtga gcccagctaa    780
```

-continued

| | | | | |
|---|---|---|---|---|
| tgagacaatg | gaagtagact | tgggatccca | gatacaattg atctgtaatg | tcaccggcca | 840 |
| gttgagtgac | attgcttact | ggaagtggaa | tgggtcagta attgatgaag | atgacccagt | 900 |
| gctaggggaa | gactattaca | gtgtggaaaa | tcctgcaaac aaaagaagga | gtaccctcat | 960 |
| cacagtgctt | aatatatcgg | aaattgaaag | tagattttat aaacatccat | ttacctgttt | 1020 |
| tgccaagaat | acacatggta | tagatgcagc | atatatccag ttaatatatc | cagtcactaa | 1080 |
| tttccagaag | cacatgattg | gtatatgtgt | cacgttgaca gtcataattg | tgtgttctgt | 1140 |
| tttcatctat | aaaatcttca | agattgacat | tgtgctttgg tacagggatt | cctgctatga | 1200 |
| ttttctccca | ataaaagctt | cagatggaaa | gacctatgac gcatatatac | tgtatccaaa | 1260 |
| gactgttggg | gaagggtcta | cctctgactg | tgatatttt gtgtttaaag | tcttgcctga | 1320 |
| ggtcttggaa | aaacagtgtg | gatataagct | gttcatttat ggaagggatg | actacgttgg | 1380 |
| ggaagacatt | gttgaggtca | ttaatgaaaa | cgtaaagaaa agcagaagac | tgattatcat | 1440 |
| tttagtcaga | gaaacatcag | gcttcagctg | gctgggtggt tcatctgaag | agcaaatagc | 1500 |
| catgtataat | gctcttgttc | aggatggaat | taaagttgtc ctgcttgagc | tggagaaaat | 1560 |
| ccaagactat | gagaaaatgc | cagaatcgat | taaattcatt aagcagaaac | atggggctat | 1620 |
| ccgctggtca | ggggactta | cagggacc | acagtctgca aagacaaggt | tctgaagaa | 1680 |
| tgtcaggtac | cacatgccag | tccagcgacg | gtccttca tctaaacacc | agttactgtc | 1740 |
| accagccact | aaggagaaac | tgcaaagaga | ggctcacgtg cctctcgggt | agcatggaga | 1800 |
| agttgccaag | agttcttag | gtgcctcctg | tcttatggcg ttgcaggcca | ggttatgcct | 1860 |
| catgctgact | tgcagagttc | atggaatgta | actatatcat cctttatccc | tgaggtcacc | 1920 |
| tggaatcaga | ttattaaggg | aataagccat | gacgtcaata gcagcccagg | gcacttcaga | 1980 |
| gtagagggct | tgggaagatc | ttttaaaaag | gcagtaggcc cggtgtggtg | gctcacgcct | 2040 |
| ataatcccag | cactttggga | ggctgaagtg | ggtggatcac cagaggtcag | gagttcgaga | 2100 |
| ccagcccagc | caacatggca | aaaccccatc | tctactaaaa atacaaaaat | gagctaggca | 2160 |
| tggtggcaca | cgcctgtaat | cccagctaca | cctgaggctg aggcaggaga | attgcttgaa | 2220 |
| ccggggagac | ggaggttgca | gtgagccgag | tttgggccac tgcactctag | cctggcaaca | 2280 |
| gagcaagact | ccgtctcaaa | aaagggcaa | taaatgccct ctctgaatgt | ttgaactgcc | 2340 |
| aagaaaggc | atggagacag | cgaactagaa | gaaagggcaa gaaggaaata | gccaccgtct | 2400 |
| acagatggct | tagttaagtc | atccacagcc | caagggcggg gctatgcctt | gtctggggac | 2460 |
| cctgtagagt | cactgacccct | ggagcggctc | tcctgagagg tgctgcaggc | aaagtgagac | 2520 |
| tgacacctca | ctgaggaagg | gagacatatt | cttggagaac tttccatctg | cttgtatttt | 2580 |
| ccatacacat | ccccagccag | aagttagtgt | ccgaagaccg aattttattt | tacagagctt | 2640 |
| gaaaactcac | ttcaatgaac | aaagggattc | tccaggattc caaagttttg | aagtcatctt | 2700 |
| agctttccac | aggagggaga | gaacttaaaa | aagcaacagt agcagggaat | tgatccactt | 2760 |
| cttaatgctt | tcctccctgg | catgaccatc | ctgtcctttg ttattatcct | gcatttacg | 2820 |
| tctttggagg | aacagctccc | tagtggcttc | ctccgtctgc aatgtcccctt | gcacagccca | 2880 |
| cacatgaacc | atccttccca | tgatgccgct | cttctgtcat cccgctcctg | ctgaaacacc | 2940 |
| tcccaggggc | tccacctgtt | caggagctga | agcccatgct ttcccaccag | catgtcactc | 3000 |
| ccagaccacc | tccctgccct | gtcctccagc | ttccccctcgc tgtcctgctg | tgtgaattcc | 3060 |
| caggttggcc | tggtggccat | gtcgcctgcc | cccagcactc ctctgtctct | gctcttgcct | 3120 |

-continued

```
gcacccttcc tcctcctttg cctaggaggc cttctcgcat tttctctagc tgatcagaat    3180
tttaccaaaa ttcagaacat cctccaattc cacagtctct gggagacttt ccctaagagg    3240
cgacttcctc tccagccttc tctctctggt caggcccact gcagagatgg tggtgagcac    3300
atctgggagg ctggtctccc tccagctgga attgctgctc tctgagggag aggctgtggt    3360
ggctgtctct gtccctcact gccttccagg agcaatttgc acatgtaaca tagatttatg    3420
taatgcttta tgtttaaaaa cattccccaa ttatcttatt taattttgc aattattcta     3480
attttatata tagagaaagt gacctatttt ttaaaaaaat cacactctaa gttctattga    3540
acctaggact tgagcctcca tttctggctt ctagtctggt gttctgagta cttgatttca    3600
ggtcaataac ggtccccccct cactccacac tggcacgttt gtgagaagaa atgacatttt   3660
gctaggaagt gaccgagtct aggaatgctt ttattcaaga caccaaattc caaacttcta    3720
aatgttggaa ttttcaaaaa ttgtgtttag atttttatgaa aaactcttct actttcatct   3780
attctttccc tagaggcaaa catttcttaa aatgtttcat tttcattaaa aatgaaagcc    3840
aaatttatat gccaccgatt gcaggacaca agcacagttt taagagttgt atgaacatgg    3900
agaggacttt tggttttat atttctcgta tttaatatgg gtgaacacca actttttattt   3960
ggaataataa ttttcctcct aaacaaaaac acattgagtt taagtctctg actcttgcct    4020
ttccacctgc tttctcctgg gcccgctttg cctgcttgaa ggaacagtgc tgttctggag    4080
ctgctgttcc aacagacagg gcctagcttt catttgacac acagactaca gccagaagcc    4140
catggagcag ggatgtcacg tcttgaaaag cctattagat gttttacaaa tttaattttg    4200
cagattattt tagtctgtca tccagaaaat gtgtcagcat gcatagtgct aagaaagcaa    4260
gccaatttgg aaacttaggt tagtgacaaa attggccaga gagtgggggt gatgatgacc    4320
aagaattaca agtagaatgg cagctggaat ttaaggaggg acaagaatca atggataagc    4380
gtgggtggag gaagatccaa acagaaaagt gcaaagttat tccccatctt ccaagggttg    4440
aattctggag gaagaagaca cattcctagt tccccgtgaa cttcctttga cttattgtcc    4500
ccactaaaac aaaacaaaaa acttttaatg ccttccacat taattagatt ttcttgcagt    4560
tttttttatgg catttttta aagatgccct aagtgttgaa gaagagtttg caaatgcaac   4620
aaaatattta attaccggtt gttaaaactg gtttagcaca atttatattt tccctctctt    4680
gcctttctta tttgcaataa aaggtattga gccattttt aaatgacatt tttgataaat    4740
tatgtttgta ctagttgatg aaggagtttt tttaacctg tttatataat tttgcagcag     4800
aagccaaatt ttttgtatat taaagcacca aattcatgta cagcatgcat cacggatcaa    4860
tagactgtac ttatttttcca ataaaatttt caaactttgt actgtta                4907
```

<210> SEQ ID NO 54
<211> LENGTH: 1004
<212> TYPE: DNA
<213> ORGANISM: Homo sapiens

<400> SEQUENCE: 54

```
ccctgcactc tcgctctcct gccccacccc gaggtaaagg gggcgactaa gagaagatgg     60
tgttgctcac cgcggtcctc ctgctgctgg ccgcctatgc ggggccggcc cagagcctgg    120
gctccttcgt gcactgcgag ccctgcgacg agaaagccct ctccatgtgc cccccagcc    180
ccctgggctg cgagctggtc aaggagccgg gctgcggctg ctgcatgacc tgcgccctgg    240
ccgaggggca gtcgtgcggc gtctacaccg agcgctgcgc ccaggggctg cgctgcctcc    300
cccggcagga cgaggagaag ccgctgcacg ccctgctgca cggccgcggg tttgcctca    360
```

```
acgaaaagag ctaccgcgag caagtcaaga tcgagagaga ctcccgtgag cacgaggagc      420
ccaccacctc tgagatggcc gaggagacct actcccccaa gatcttccgg cccaaacaca      480
cccgcatctc cgagctgaag gctgaagcag tgaagaagga ccgcagaaag aagctgaccc      540
agtccaagtt tgtcggggga gccgagaaca ctgcccaccc ccggatcatc tctgcacctg      600
agatgagaca ggagtctgag cagggcccct gccgcagaca catggaggct tccctgcagg      660
agctcaaagc cagcccacgc atggtgcccc gtgctgtgta cctgcccaat tgtgaccgca      720
aaggattcta caagagaaag cagtgcaaac cttcccgtgg ccgcaaacgt ggcatctgct      780
ggtgcgtgga caagtacggg atgaagctgc caggcatgga gtacgttgac ggggactttc      840
agtgccacac cttcgacagc agcaacgttg agtgatgcgt cccccccaa cctttccctc       900 accccctccc accccagcc ccgactccag ccagcgcctc cctccacccc aggacgccac        960
tcatttcatc tcatttaagg gaaaaatata tatctatcta tttg                       1004
```

<210> SEQ ID NO 55
<211> LENGTH: 772
<212> TYPE: DNA
<213> ORGANISM: Homo sapiens

<400> SEQUENCE: 55

```
cgcagcgggt cctctctatc tagctccagc ctctcgcctg cgccccactc ccgcgtccc        60 gcgtcctagc cgaccatggc cgggcccctg cgcgccccgc tgctcctgct ggccatcctg      120
gccgtggccc tggccgtgag ccccgcggcc ggctccagtc ccgcaagcc gccgcgccta       180 gtgggaggcc ccatggacgc cagcgtggag gaggagggtg tgcggcgtgc actggacttt      240
gccgtcggcg agtacaacaa agccagcaac gacatgtacc acagccgcgc gctgcaggtg      300
gtgcgcgccc gcaagcagat cgtagctggg gtgaactact tcttggacgt ggagctgggc      360
cgaaccacgt gtaccaagac ccagcccaac ttggacaact gccccttcca tgaccagcca      420
catctgaaaa ggaaagcatt ctgctctttc cagatctacg ctgtgccttg cagggcaca       480 atgaccttgt cgaaatccac ctgtcaggac gcctaggggt ctgtaccggg ctggcctgtg      540
cctatcacct cttatgcaca cctcccaccc cctgtattcc caccccttgga ctggtggccc     600 ctgccttggg gaaggtctcc ccatgtgcct gcaccaggag acagacagag aaggcagcag      660
gcggcctttg ttgctcagca aggggctctg ccctccctcc ttccttcttg cttctcatag      720
ccccggtgtg cggtgcatac accccccacct cctgcaataa aatagtagca tc             772
```

<210> SEQ ID NO 56
<211> LENGTH: 2128
<212> TYPE: DNA
<213> ORGANISM: Homo sapiens

<400> SEQUENCE: 56

```
gaaagatgga tcactccagc tcaaagagaa catgtgggaa tgaaaggaca ggctgggccc       60
aaaggagaaa agggtgatgc tggggaggag cttcctggcc ctcctgaacc ttctgggcct      120
gttggaccca cggcaggagc agaagcagag ggctctggcc taggctgggg ctcggacgtc      180
ggctctggct ctggtgacct ggtgggcagt gagcagctgc tgagaggtcc tccaggaccc      240
ccagggccac ctggcttacc tgggattcca ggaaaaccag gaactgatgt tttcatggga      300
ccccctggat ctcctggaga ggatggacct gctggtgaac ctgggccccc gggccctgag      360
ggacagcctg gagttgatgg agccaccggc cttcccggga tgaaagggga gaagggagca      420
```

| | |
|---|---:|
| agagggccta atggctcagt tggtgaaaag ggtgaccctg gcaacagagg cttacctgga | 480 |
| cccccgggga aaagggaca agctggccct cctgggtca tgggacccc agggcctcct | 540 |
| ggaccccctg gcccccagg ccctggatgc acaatgggac ttggattcga ggataccgaa | 600 |
| ggctctggaa gcacccagct attgaatgaa cccaaactct ccagaccaac ggctgcaatt | 660 |
| ggtctcaaag gagagaaagg agaccgggga cccaagggag aaaggggat ggatggagcc | 720 |
| agtattgtgg gaccccctgg gccgagaggg ccacctgggc acatcaaggt cttgtctaat | 780 |
| tccttgatca atatcaccca tggattcatg aatttctcgg acattcctga gctggtgggg | 840 |
| cctccggggc cggacgggtt gcctgggctg ccaggatttc caggtccta gaggaccaaa | 900 |
| aggtgacact ggtttacctg gctttccagg actaaaagga gaacagggcg agaagggaga | 960 |
| gccgggtgcc atcctgacag aggacattcc tctggaaagg ctgatgggga aaagggtga | 1020 |
| acctggaatg catggagccc caggaccaat ggggcccaaa ggaccaccag gacataaagg | 1080 |
| agaatttggc cttcccggc gacctggtcg cccaggactg aatggcctca agggtaccaa | 1140 |
| aggagatcca ggggtcatta tgcagggccc acctggctta cctggccctc caggcccccc | 1200 |
| tgggccacct ggagctgtga ttaacatcaa aggagccatt ttcccaatac ccgtccgacc | 1260 |
| acactgcaaa atgccagttg atactgctca tcctgggagt ccagagctca tcactttca | 1320 |
| cggtgttaaa ggagagaaag gatcctgggg tcttcctggc tcaaagggag aaaaaggcga | 1380 |
| ccagggagcc cagggaccac caggtcctcc acttgatcta gcttacctga gacactttct | 1440 |
| gaacaacttg aagggggaga atggagacaa ggggttcaaa ggtgaaaaag agaaaaagg | 1500 |
| agacattaat ggcagcttcc ttatgtctgg gcctccaggc ctgcccggaa atccaggccc | 1560 |
| ggctggccaa aaaggggaga cagtcgttgg gccccaagga ccccaggtg ctcctggtct | 1620 |
| gcctgggcca cctggctttg aagacctgg tgatcctggg ccaccggggc ccccgggggcc | 1680 |
| accaggacct ccagctatcc tgggagcagc tgtggccctt ccaggtcccc ctggccctcc | 1740 |
| aggacagcca gggcttcccg gatccagaaa cctggtcaca gcattcagca acatggatga | 1800 |
| catgctgcag aaagcgcatt tggttataga aggaacattc atctacctga gggacagcac | 1860 |
| tgagtttttc attcgtgtta gagatggctg gaaaaaatta cagctgggag aactgatccc | 1920 |
| cattcctgcc gacagccctc caccccctgc gctttccagc aacccacatc agcttctgcc | 1980 |
| tccaccaaac cctatttcaa gtgccaatta tgagaagcct gctctgcatt tggctgctct | 2040 |
| gaacatgcca ttttctgggg acattcgagc tgattttcag tgcttcaagc aggccagagc | 2100 |
| tgcaggactg ttgtccacct accgagca | 2128 |

<210> SEQ ID NO 57
<211> LENGTH: 4309
<212> TYPE: DNA
<213> ORGANISM: Homo sapiens

<400> SEQUENCE: 57

| | |
|---|---:|
| tagaaattgt taattttaac aatccagagc aggccaacga ggctttgctc tcccgacccg | 60 |
| aactaaaggt ccctcgctcc gtgcgctgct acgagcggtg tctcctgggg ctccaatgca | 120 |
| gcgagctgtg cccgagggt tcggaaggcg caagctgggc agcgacatgg ggaacgcgga | 180 |
| gcgggctccg ggtctcgga gctttgggcc agtacccacg ctgctgctgc tcgccgcggc | 240 |
| gctactggcc gtgtcggacg cactcgggcg cccctccgag gaggacgagg agctagtggt | 300 |
| gccggagctg gagcgcgccc cggacacgg gaccacgcgc ctccgcctgc acgcctttga | 360 |
| ccagcagctg gatctggagc tgcggcccga cagcagcttt ttggcgcccg gcttcacgct | 420 |

-continued

```
ccagaacgtg gggcgcaaat ccgggtccga gacgccgctt ccggaaaccg acctggcgca    480
ctgcttctac tccggcaccg tgaatggcga tcccagctcg gctgccgccc tcagcctctg    540
cgagggcgtg cgcggcgcct tctacctgct gggggaggcg tatttcatcc agccgctgcc    600
cgccgccagc gagcgcctcg ccaccgccgc cccaggggag aagccgccgg caccactaca    660
gttccacctc ctgcggcgga atcggcaggg cgacgtcggc ggcacgtgcg gggtcgtgga    720
cgacgagccc cggccgactg ggaaagcgga gaccgaagac gaggacgaag ggactgaggg    780
cgaggacgaa gggctcagt ggtcgccgca ggacccggca ctgcaaggcg taggacagcc    840
cacaggaact ggaagcataa gaaagaagcg atttgtgtcc agtcaccgct atgtggaaac    900
catgcttgtg gcagaccagt cgatggcaga attccacggc agtggtctaa agcattacct    960
tctcacgttg ttttcggtgg cagccagatt gtacaaacac cccagcattc gtaattcagt   1020
tagcctggtg gtggtgaaga tcttggtcat ccacgatgaa cagaaggggc cggaagtgac   1080
ctccaatgct gccctcactc tgcggaactt ttgcaactgg cagaagcagc acaacccacc   1140
cagtgaccgg gatgcagagc actatgacac agcaattctt ttcaccagac aggacttgtg   1200
tgggtcccag acatgtgata ctcttgggat ggctgatgtt ggaactgtgt gtgatccgag   1260
cagaagctgc tccgtcatag aagatgatgg tttacaagct gccttcacca cagcccatga   1320
attaggccac gtgtttaaca tgccacatga tgatgcaaag cagtgtgcca gccttaatgg   1380
tgtgaaccag gattcccaca tgatggcgtc aatgctttcc aacctggacc acagccagcc   1440
ttggtctcct tgcagtgcct acatgattac atcatttctg gataatggtc atggggaatg   1500
tttgatggac aagcctcaga atcccataca gctcccaggc gatctccctg gcacctcgta   1560
cgatgccaac cggcagtgcc agtttacatt tggggaggac tccaaacact gccccgatgc   1620
agccagcaca tgtagcacct tgtggtgtac cggcacctct ggtggggtgc tggtgtgtca   1680
aaccaaacac ttcccgtggg cggatggcac cagctgtgga aagggaaat ggtgtatcaa   1740
cggcaagtgt gtgaacaaaa ccgacagaaa gcattttgat acgccttttc atggaagctg   1800
gggaatgtgg gggccttggg gagactgttc gagaacgtgc ggtggaggag tccagtacac   1860
gatgagggaa tgtgacaacc cagtcccaaa gaatggaggg aagtactgtg aaggcaaacg   1920
agtgcgctac agatcctgta accttgagga ctgtccagac aataatggaa aaaccttag    1980
agaggaacaa tgtgaagcac acaacgagtt ttcaaaagct tcctttggga gtgggcctgc   2040
ggtggaatgg attcccaagt acgctggcgt ctcaccaaag gacaggtgca agctcatctg   2100
ccaagccaaa ggcattggct acttcttcgt tttgcagccc aaggttgtag atggtactcc   2160
atgtagccca gattccacct ctgtctgtgt gcaaggacga tgtgtaaaag ctggttgtga   2220
tcgcatcata gactccaaaa agaagtttga taaatgtggt gtttgcgggg gaaatggatc   2280
tacttgtaaa aaaatatcag gatcagttac tagtgcaaaa cctggatatc atgatatcat   2340
cacaattcca actggagcca ccaacatcga agtgaaacag cggaaccaga ggggatccag   2400
gaacaatggc agctttcttg ccatcaaagc tgctgatggc acatatattc ttaatggtga   2460
ctacactttg tccaccttag agcaagacat tatgtacaaa ggtgttgtct tgaggtacag   2520
cggctcctct gcggcattgg aaagaattcg cagctttagc cctctcaaag agcccttgac   2580
catccaggtt cttactgtgg gcaatgccct tcgacctaaa attaaataca cctacttcgt   2640
aaagaagaag aaggaatctt tcaatgctat ccccactttt tcagcatggg tcattgaaga   2700
gtggggcgaa tgttctaagt catgtgaatt gggttggcag agaagactgg tagaatgccg   2760
```

-continued

```
agacattaat ggacagcctg cttccgagtg tgcaaaggaa gtgaagccag ccagcaccag    2820
accttgtgca gaccatccct gcccccagtg gcagctgggg gagtggtcat catgttctaa    2880
gacctgtggg aagggttaca aaaaagaag cttgaagtgt ctgtcccatg atggagggggt   2940
gttatctcat gagagctgtg atcctttaaa gaaacctaaa catttcatag acttttgcac    3000
aatggcagaa tgcagttaag tggtttaagt ggtgttagct ttgagggcaa ggcaaagtga    3060
ggaagggctg gtgcagggaa agcaagaagg ctggagggat ccagcgtatc ttgccagtaa    3120
ccagtgaggt gtatcagtaa ggtgggatta tgggggtaga tagaaaagga gttgaatcat    3180
cagagtaaac tgccagttgc aaatttgata ggatagttag tgaggattat taacctctga    3240
gcagtgatat agcataataa agccccgggc attattatta ttatttcttt tgttacatct    3300
attacaagtt tagaaaaaac aaagcaattg tcaaaaaaag ttagaactat tacaaccct    3360
gtttcctggt acttatcaaa tacttagtat catgggggtt gggaaatgaa agtaggaga    3420
aaagtgagat tttactaaga cctgttttac tttacctcac taacaatggg gggagaaagg    3480
agtacaaata ggatctttga ccagcactgt ttatggctgc tatggtttca gagaatgttt    3540
atacattatt tctaccgaga attaaaactt cagattgttc aacatgagag aaaggctcag    3600
caacgtgaaa taacgcaaat ggcttcctct ttcctttttt ggaccatctc agtctttatt    3660
tgtgtaattc attttgagga aaaaacaact ccatgtattt attcaagtgc attaaagtct    3720
acaatggaaa aaaagcagtg aagcattaga tgctggtaaa agctagagga gacacaatga    3780
gcttagtacc tccaacttcc tttctttcct accatgtaac cctgctttgg gaatatggat    3840
gtaaagaagt aacttgtgtc tcatgaaaat cagtacaatc acacaaggag gatgaaacgc    3900
cggaacaaaa atgaggtgtg tagaacaggg tcccacaggt ttggggacat tgagatcact    3960
tgtcttgtgg tggggaggct gctgagggt agcaggtcca tctccagcag ctggtccaac    4020
agtcgtatcc tggtgaatgt ctgttcagct cttctgtgag aatatgattt tttccatatg    4080
tatatagtaa aatatgttac tataaattac atgtactttta taagtattgg tttgggtgtt    4140
ccttccaaga aggactatag ttagtaataa atgcctataa taacatattt atttttatac    4200
atttatttct aatgaaaaaa actttttaaat tatatcgctt ttgtggaagt gcatataaaa    4260
tagagtattt atacaatata tgttactaga aataaaagaa cacttttgg                4309
```

<210> SEQ ID NO 58
<211> LENGTH: 3488
<212> TYPE: DNA
<213> ORGANISM: Homo sapiens

<400> SEQUENCE: 58

```
gggcccgggc gcgcgggagc gggagcggcc ggggagccg gagcgcacca tggaggcggc      60
ggcaggcggc cgcggctgtt tccagccgca cccggggctg cagaagacgc tggagcagtt    120
ccacctgagc tccatgagct cgctgggcgg cccggccgct ttctcggcgc gctgggcgca    180
ggaggcctac aagaaggaga gcgccaagga ggcgggcgcg ccgcggtgc cggcgccggt    240
gcccgcagcc accgagccgc cgcccgtgct gcacctgccc gccatccagc cgccgccgcc    300
cgtgctgccc gggcccttct tcatgccgtc cgaccgctcc accgagcgct gcgagaccgt    360
actggaaggc gagaccatct cgtgcttcgt ggtgggaggc gagaagcgcc tgtgtctgcc    420
gcagattctc aactcggtgc tgcgcgactt ctcgctgcag cagatcaacg cggtgtgcga    480
cgagctccac atctactgct cgcgctgcac ggccgaccag ctggagatcc tcaaagtcat    540
gggcatcctg ccccttctcgg cgccctcgtg cgggctcatc accaagacgg acgccgagcg    600
```

-continued

```
cctgtgcaac gcgctgctct acggcggcgc ctacccgccg ccctgcaaga aggagctggc    660
cgccagcctg gcgctgggcc tggagctcag cgagcgcagc gtccgcgtgt accacgagtg    720
cttcggcaag tgtaagggc tgctggtgcc cgagctctac agcagcccga cgccgcctg    780 catccagtgc ctggactgcc gcctcatgta cccgccgcac aagttcgtgg tgcactcgca    840
caaggccctg gagaaccgga cctgccactg gggcttcgac tcggccaact ggcgggccta    900
catcctgctg agccaggatt acacgggcaa ggaggagcag gcgcgcctcg ccgctgcct    960 ggacgacgtg aaggagaaat cgactatgg caacaagtac aagcggcggg tgccccgggt   1020
ctcctctgag cctccggcct ccataagacc caaaacagat gacacctctt cccagtcccc   1080
cgcgccttcc gaaaaggaca agccgtccag ctggctgcgg accttggccg gctcttccaa   1140
taagagcctg ggctgtgttc accctcgcca gcgcctctct gctttccgac cctggtcccc   1200
cgcagtgtca gcgagtgaga aagagctctc cccacacctc ccggccctca tccgagacag   1260
cttctactcc tacaagagct ttgagacagc cgtggcgccc aacgtggccc tcgcaccgcc   1320
ggcccagcag aaggttgtga gcagccctcc gtgtgccgcc gccgtctccc gggccccga   1380 gcctctcgcc acttgcaccc agcctcggaa gcggaagctg actgtggaca ccccaggagc   1440
cccagagacg ctggcgcccg tggctgcccc agaggaggac aaggactcgg aggcggaggt   1500
ggaagttgaa agcaggagg aattcacctc ctccttgtcc tcgctctctt ccccgtcctt   1560
tacctcatcc agctccgcca aggacctggg ctccccgggt gcgcgtgccc tgccctcggc   1620
cgtccctgat gctgcggccc ctgccgacgc ccccagtggg ctggaggcgg agctggagca   1680
cctgcggcag gcactggagg gcggcctgga caccaaggaa gccaaagaga gttcctgca   1740 tgaggtggtc aagatgcgcg tgaagcagga ggagaagctc agcgcagccc tgcaggccaa   1800
gcgcagcctc caccaggagc tggagttcct acgcgtggcc aagaaggaga agctgcggga   1860
ggccacggag gccaagcgta acctgcggaa ggagatcgag cgtctccgcg ccgagaacga   1920
gaagaagatg aaagaggcca acagtcacg gctgcgcctg aagcgggagc tggagcaggc   1980
gcggcaggcc cgggtgtgcg acaagggctg cgaggcgggc cgcctgcgcg ccaagtactc   2040
ggcccagatc gaagacctgc aggtgaagct gcagcacgcg gaggcggacc gggagcagct   2100
gcgggccgac ctgctgcggg agcgcgaggc ccggagcac ctggagaagg tggtgaagga   2160
gctgcaggaa cagctgtggc cgcgggcccg ccccgaggct gcgggcagcg agggcgctgc   2220
ggagctggag ccgtagattc cgtgcctgcc gccgcagcgc cgccgacaac gcgggtgcag   2280
gggggcgcgg ctgggcggtg cagctccgcc cggctccgcc cctgcagccc acacagcaca   2340
acgtcttacc gtgcctatta ccaagcgagt gtttgtaacc atgtagttt ggaacccact   2400 gcaaaatttt ctactggcca agttcaagtg agtaagccgc gtcccccaac tacagctgga   2460
gacggggcca gctcggcggc ctgctggtcc tctgcttgct ggaacattct aacatttaca   2520
cttttgttat aagctattta aaaccagtaa ggagacttga aattcagaaa atcaacacat   2580
ttttaaatga ctaacttcta aaagcccaa cacatgacgc catctgaaga cccgcaacgg   2640
agtgggggtg gcggccgccc caccctcccc acccgggaa gccatcacag ctcatctgcc   2700
cgcggctgcg tgaggacagc aggggttttt cttcagagtc tattttttca gcgacaagga   2760
cccaggtctt cctgctgctg ccaggagag cagggacagt gccgcgtgcg agatgagctc   2820
gaacactgcc cgccttactg ccgcctaccc cgcccgccac gccgccgtcg atgccagcgc   2880
tgtccccacg ggtaccagga agtgcagagc cgcacaggag ctgccccgga gctgagggga   2940
```

| | |
|---|---:|
| cggtcttcgg ctcctctgca ccccgtgatt ctgcccacgc tcctccacca cgaggcactg | 3000 |
| acctgcgtcg ggtggtgacc gtggctggcg gtcacgccct cagcccctcc gggcacacgt | 3060 |
| gccgcctgac cgggcgaccc ttttcagttc ggcaaacgtc gctcccttca ttttgggact | 3120 |
| gaggctgcag cattggaaca aaagagcatt atttcaattt ttctttcttt ttttttgttc | 3180 |
| gttcatttaa acgtatattt agaactgcac tttgtccaca accttccctt ctctttctat | 3240 |
| tccccagtga actgaggttt ttaccgattt atagagcagt caaatccgaa gtgctcgagt | 3300 |
| gcttagaaac cccctctggt gcttggttga acaagggaat cacaagaaaa cgaaaatgca | 3360 |
| aaaactgaac ttcgggggtc gttctgtgcc ttccagcatc ttgtacagca aatcctgact | 3420 |
| cgtgtctttt taccccaag atatctgtct tcagtagcga ctgaatctgc cactctcaga | 3480 |
| ataagttc | 3488 |

<210> SEQ ID NO 59
<211> LENGTH: 3108
<212> TYPE: DNA
<213> ORGANISM: Homo sapiens

<400> SEQUENCE: 59

| | |
|---|---:|
| gccgccgccg ccatccgccg ccgcagccag cttccgccgc cgcaggaccg gcccctgccc | 60 |
| cagcctccgc agccgcggcg cgtccacgcc gcccgcgcc cagggcgagt cggggtcgcc | 120 |
| gcctgcacgc ttctcagtgt tccccgcgcc ccgcatgtaa cccggccagg ccccgcaac | 180 |
| tgtgtccct gcagctccag ccccgggctg catcccccg ccccgacacc agctctccag | 240 |
| cctgctcgtc caggatggcc gcggccaagg ccgagatgca gctgatgtcc ccgctgcaga | 300 |
| tctctgaccc gttcggatcc tttcctcact cgcccaccat ggacaactac cctaagctgg | 360 |
| aggagatgat gctgctgagc aacggggctc cccagttcct cggcgccgcc ggggcccag | 420 |
| agggcagcgg cagcaacagc agcagcagca gcagcggggg cggtggaggc ggcggggcg | 480 |
| gcagcaacag cagcagcagc agcagcacct tcaaccctca ggcggacacg ggcgagcagc | 540 |
| cctacgagca cctgaccgca gagtcttttc ctgacatctc tctgaacaac gagaaggtgc | 600 |
| tggtggagac cagttacccc agccaaacca ctcgactgcc cccatcacc tatactggcc | 660 |
| gcttttccct ggagcctgca cccaacagtg gcaacacctt gtggcccgag cccctcttca | 720 |
| gcttggtcag tggcctagtg agcatgacca acccaccggc ctcctcgtcc tcagcaccat | 780 |
| ctccagcggc ctcctccgcc tccgcctccc agagcccacc cctgagctgc cagtgccat | 840 |
| ccaacgacag cagtcccatt tactcagcgg cacccaccttccccacgccg aacactgaca | 900 |
| tttttccctga gccacaaagc caggccttcc cgggctcggc agggacagcg ctccagtacc | 960 |
| cgcctcctgc ctaccctgcc gccaagggtg gcttccaggt tccatgatc cccgactacc | 1020 |
| tgttccaca gcagcagggg gatctgggcc tgggcacccc agaccagaag cccttccagg | 1080 |
| gcctggagag ccgcacccag cagccttcgc taacccctct gtctactatt aaggcctttg | 1140 |
| ccactcagtc gggctcccag gacctgaagg ccctcaatac cagctaccag tcccagctca | 1200 |
| tcaaacccag ccgcatgcgc aagtacccca accggcccag caagacgccc cccacgaac | 1260 |
| gcccttacgc ttgcccagtg gagtcctgtg atcgccgctt ctcccgctcc gacgagctca | 1320 |
| cccgccacat ccgcatccac acaggccaga gccttccca gtgccgcatc tgcatgcgca | 1380 |
| acttcagccg cagcgaccac ctcaccaccc acatccgcac ccacacaggc gaaaagccct | 1440 |
| tcgcctgcga catctgtgga gaaagtttg ccaggagcgc tgaacgcaag aggcatacca | 1500 |
| agatccactt gcggcagaag gacaagaaag cagacaaaag tgttgtggcc tcttcggcca | 1560 |

```
cctcctctct ctcttcctac ccgtcccgg ttgctaccctc ttacccgtcc ccggttacta   1620
cctcttatcc atccccggcc accacctcat acccatcccc tgtgcccacc tccttctcct   1680
ctcccggctc ctcgacctac ccatcccctg tgcacagtgg cttcccctcc ccgtcggtgg   1740
ccaccacgta ctcctctgtt cccctgctt tcccggccca ggtcagcagc ttcccttcct    1800
cagctgtcac caactccttc agcgcctcca cagggctttc ggacatgaca gcaacctttt   1860
ctcccaggac aattgaaatt tgctaaaggg aaaggggaaa gaaagggaaa agggagaaaa   1920
agaaacacaa gagacttaaa ggacaggagg aggagatggc cataggagag gagggttcct   1980
cttaggtcag atggaggttc tcagagccaa gtcctccctc tctactggag tggaaggtct   2040
attggccaac aatcctttct gcccacttcc ccttccccaa ttactattcc ctttgacttc   2100
agctgcctga aacagccatg tccaagttct tcacctctat ccaaagaact tgatttgcat   2160
ggattttgga taaatcattt cagtatcatc tccatcatat gcctgacccc ttgctccctt   2220
caatgctaga aaatcgagtt ggcaaaatgg ggtttgggcc cctcagagcc ctgccctgca   2280
cccttgtaca gtgtctgtgc catggatttc gttttcttg gggtactctt gatgtgaaga   2340
taatttgcat attctattgt attatttgga gttaggtcct cacttggggg aaaaaaaaaa   2400
aagaaaagcc aagcaaacca atggtgatcc tctattttgt gatgatgctg tgacaataag   2460
tttgaacctt ttttttgaa acagcagtcc cagtattctc agagcatgtg tcagagtgtt   2520
gttccgttaa ccttttgta aatactgctt gaccgtactc tcacatgtgg caaaatatgg   2580 tttggtttt cttttttttt tttttgaaa gtgttttttc ttcgtccttt tggtttaaaa    2640
agtttcacgt cttggtgcct tttgtgtgat gcgccttgct gatggcttga catgtgcaat   2700
tgtgagggac atgctcacct ctagccttaa ggggggcagg gagtgatgat ttgggggagg   2760
ctttgggagc aaaataagga agagggctga gctgagcttc ggttctccag aatgtaagaa   2820
aacaaaatct aaaacaaaat ctgaactctc aaaagtctat ttttttaact gaaaatgtaa   2880
atttataaat atattcagga gttggaatgt tgtagttacc tactgagtag gcggcgattt   2940
ttgtatgtta tgaacatgca gttcattatt ttgtggttct attttacttt gtacttgtgt   3000
ttgcttaaac aaagtgactg tttggcttat aaacacattg aatgcgcttt attgcccatg   3060
ggatatgtgg tgtatatcct tccaaaaaat taaaacgaaa ataaagta                3108

<210> SEQ ID NO 60
<211> LENGTH: 3775
<212> TYPE: DNA
<213> ORGANISM: Homo sapiens

<400> SEQUENCE: 60
cattcataag actcagagct acggccacgg cagggacacg cggaaccaag acttggaaac   60
ttgattgttg tggttcttct tgggggttat gaaatttcat taatcttttt ttttttccggg   120 gagaaagttt ttggaaagat tcttccagat atttcttcat tttcttttgg aggaccgact   180
tacttttttt ggtcttcttt attactcccc tccccccgtg ggacccgccg gacgcgtgga   240
ggagaccgta gctgaagctg attctgtaca gcgggacagc gctttctgcc cctgggggag   300 caaccccctcc ctcgcccctg gtcctacgg agcctgcact tcaagaggt acagcggcat    360 cctgtggggg cctgggcacc gcaggaagac tgcacagaaa ctttgccatt gttggaacgg   420
gacgttgctc cttccccgag cttccccgga cagcgtactt tgaggactcg ctcagctcac   480
cggggactcc cacggctcac cccggacttg caccttactt ccccaacccg gccatagcct   540
```

-continued

```
tggcttcccg gcgacctcag cgtggtcaca ggggccccccc tgtgcccagg gaaatgtttc      600
aggctttccc cggagactac gactccggct cccggtgcag ctcctcaccc tctgccgagt      660
ctcaatatct gtcttcggtg gactccttcg gcagtccacc caccgccgcg gcctcccagg      720
agtgcgccgg tctcggggaa atgcccggtt ccttcgtgcc cacggtcacc gcgatcacaa      780
ccagccagga cctccagtgg cttgtgcaac ccaccctcat ctcttccatg gcccagtccc      840
aggggcagcc actggcctcc cagccccccgg tcgtcgaccc ctacgacatg ccgggaacca      900
gctactccac accaggcatg agtggctaca gcagtggcgg agcgagtggc agtggtgggc      960
cttccaccag cggaactacc agtgggcctg ggcctgcccg cccagcccga gcccggccta     1020
ggagaccccg agaggagacg ctcaccccag aggaagagga gaagcgaagg gtgcgccggg     1080
aacgaaataa actagcagca gctaaatgca ggaaccggcg gagggagctg accgaccgac     1140
tccaggcgga gacagatcag ttggaggaag aaaaagcaga gctggagtcg gagatcgccg     1200
agctccaaaa ggagaaggaa cgtctggagt ttgtgctggt ggcccacaaa ccgggctgca     1260
agatccccta cgaagagggg cccgggccgg gcccgctggc ggaggtgaga gatttgccgg     1320
gctcagcacc ggctaaggaa gatggcttca gctggctgct gccgcccccg ccaccaccgc     1380
ccctgccctt ccagaccagc caagacgcac cccccaacct gacggcttct ctctttacac     1440
acagtgaagt tcaagtcctc ggcgacccct tcccgttgt taacccttcg tacacttctt     1500
cgtttgtcct cacctgcccg gaggtctccg cgttcgccgg cgcccaacgc accagcggca     1560
gtgaccagcc ttccgatccc ctgaactcgc cctccctcct cgctcggtga actctttaga     1620
cacacaaaac aaacaaacac atgggggaga gagacttgga agaggaggag gaggaggaga     1680
aggaggagag agaggggaag agacaaagtg ggtgtgtggc ctccctggct cctccgtctg     1740
accctctgcg gccactgcgc cactgccatc ggacaggagg attccttgtg ttttgtcctg     1800
cctcttgttt ctgtgccccg gcgaggccgg agagctggtg actttgggga caggggtgg      1860 gaagggatg gacaccccca gctgactgtt ggctctctga cgtcaaccca agctctgggg     1920
atgggtgggg aggggggcgg gtgacgccca ccttcgggca gtcctgtgtg aggatgaagg     1980
gacgggggtg ggaggtaggc tgtggggtgg gctggagtcc tctccagaga ggctcaacaa     2040
ggaaaaatgc cactccctac ccaatgtctc ccacacccac ccttttttg gggtgcccag      2100 gttggtttcc cctgcactcc cgaccttagc ttattgatcc cacatttcca tggtgtgaga     2160
tcctctttac tctgggcaga agtgagcccc cccttaaagg gaattcgatg cccccctaga     2220
ataatctcat ccccccaccc gacttctttt gaaatgtgaa cgtccttcct tgactgtcta     2280
gccactccct cccagaaaaa ctggctctga ttggaatttc tggcctccta aggctcccca     2340
ccccgaaatc agccccagc cttgtttctg atgacagtgt tatcccaaga ccctgccccc      2400
tgccagccga ccctcctggc cttcctcgtt gggccgctct gatttcaggc agcaggggct     2460
gctgtgatgc cgtcctgctg gagtgattta tactgtgaaa tgagttggcc agattgtggg     2520
gtgcagctgg gtggggcagc acacctctgg ggggataatg tccccactcc cgaaagcctt     2580
tcctcggtct cccttccgtc catccccctt cttcctcccc tcaacagtga gttagactca     2640
agggggtgac agaaccgaga aggggtgac agtcctccat ccacgtggcc tctctctctc      2700
tcctcaggac cctcagccct ggcctttttc tttaaggtcc cccgaccaat ccccagccta     2760
ggacgccaac ttctcccacc ccttggcccc tcacatcctc tccaggaagg cagtgagggg     2820
ctgtgacatt tttccggaga agatttcaga gctgaggctt tggtaccccc aaaccccccaa    2880 tattttgga ctggcagact caaggggctg gaatctcatg attccatgcc cgagtccgcc      2940
```

```
catccctgac catggttttg gctctcccac cccgccgttc cctgcgcttc atctcatgag   3000
gatttcttta tgaggcaaat ttatattttt taatatcggg gggtggacca cgccgccctc   3060
catccgtgct gcatgaaaaa cattccacgt gccccttgtc gcgcgtctcc catcctgatc   3120
ccagacccat tccttagcta tttatccctt tcctggtttc cgaaaggcaa ttatatctat   3180
tatgtataag taaatatatt atatatggat gtgtgtgtgt gcgtgcgcgt gagtgtgtga   3240
gcgcttctgc agcctcggcc taggtcacgt tggccctcaa agcgagccgt tgaattggaa   3300
actgcttcta gaaactctgg ctcagcctgt ctcgggctga cccttttctg atcgtctcgg   3360
cccctctgat tgttcccgat ggtctctctc cctctgtctt ttctcctccg cctgtgtcca   3420
tctgaccgtt ttcacttgtc tcctttctga ctgtccctgc caatgctcca gctgtcgtct   3480
gactctgggt tcgttgggga catgagattt tattttttgt gagtgagact gagggatcgt   3540
agatttttac aatctgtatc tttgacaatt ctgggtgcga gtgtgagagt gtgagcaggg   3600
cttgctcctg ccaaccacaa ttcaatgaat ccccgacccc cctaccccat gctgtacttg   3660
tggttctctt tttgtatttt gcatctgacc ccggggggct gggacagatt ggcaatgggc   3720
cgtcccctct ccccttggtt ctgcactgtt gccaataaaa agctcttaaa aacgc        3775
```

<210> SEQ ID NO 61
<211> LENGTH: 2021
<212> TYPE: DNA
<213> ORGANISM: Homo sapiens

<400> SEQUENCE: 61

```
agcgagcttg cagcctcacc gacgagtctc aactaaaagg gactcccgga gctaggggtg     60
gggactcggc ctcacacagt gagtgccggc tattggactt ttgtccagtg acagctgaga    120
caacaaggac cacgggagga ggtgtaggag agaagcgccg cgaacagcga tcgcccagca    180
ccaagtccgc ttccaggctt tcggtttctt tgcctccatc ttgggtgcgc cttccggcg     240 tctaggggag cgaaggctga ggtggcagcg gcaggagagt ccggccgcga caggacgaac    300
tcccccactg gaaaggattc tgaaagaaat gaagtcagcc ctcagaaatg aagttgactg    360
cctgctggct ttctgttgac tggcccggag ctgtactgca agacccttgt gagcttccct    420
agtctaagag taggatgtct gctgaagtca tccatcaggt tgaagaagca cttgatacag    480
atgagaagga gatgctgctc tttttgtgcc gggatgttgc tatagatgtg gttccaccta    540
atgtcaggga ccttctggat attttacggg aaagaggtaa gctgtctgtc ggggacttgg    600
ctgaactgct ctacagagtg aggcgatttg acctgctcaa acgtatcttg aagatggaca    660
gaaaagctgt ggagacccac ctgctcagga accctcacct tgtttcggac tatagagtgc    720
tgatggcaga gattggtgag gatttggata atctgatgt gtcctcatta attttcctca    780
tgaaggatta catgggccga ggcaagataa gcaaggagaa ggtttcttgg accttgtggt    840
tgagttggag aaactaaatc tggttgcccc agatcaactg gatttattag aaaaatgcct    900
aaagaacatc cacagaatag acctgaagac aaaaatccag aagtacaagc agtctgttca    960
aggagcaggg acaagttaca ggaatgttct ccaagcagca atccaaaaga gtctcaagga   1020
tccttcaaat aacttcaggc tccataatgg gagaagtaaa gaacaaagac ttaaggaaca   1080
gcttggcgct caacaagaac cagtgaagaa atccattcag gaatcagaag cтттттттgcc   1140 tcagagcata cctgaagaga gatacaagat gaagagcaag cccctaggaa tctgcctgat   1200
aatcgattgc attggcaatg agacagagct tcttcgagac accttcactt ccctgggcta   1260
```

```
tgaagtccag aaattcttgc atctcagtat gcatggtata tcccagattc ttggccaatt    1320
tgcctgtatg cccgagcacc gagactacga cagctttgtg tgtgtcctgg tgagccgagg    1380
aggctcccag agtgtgtatg gtgtggatca gactcactca gggctccccc tgcatcacat    1440
caggaggatg ttcatgggag attcatgccc ttatctagca gggaagccaa agatgttttt    1500
tattcagaac tatgtggtgt cagagggcca gctggaggac agcagcctct tggaggtgga    1560
tgggccagcg atgaagaatg tggaattcaa ggctcagaag cgaggctgt gcacagttca    1620 ccgagaagct gacttcttct ggagcctgtg tactgcggac atgtccctgc tggagcagtc    1680
tcacagctca ccatccctgt acctgcagtg cctctcccag aaactgagac aagaaagaaa    1740
acgcccactc ctggatcttc acattgaact caatggctac atgtatgatt ggaacagcag    1800
agtttctgcc aaggagaaat attatgtctg gctgcagcac actctgagaa agaaacttat    1860
cctctcctac acataagaaa ccaaaaggct gggcgtagtg gctcacacct gtaatcccag    1920
cactttggga ggccaaggag ggcagatcac ttcaggtcag gagttcgaga ccagcctggc    1980
caacatggta aacgctgtcc ctagtaaaaa tacaaaaatt a                        2021
```

<210> SEQ ID NO 62
<211> LENGTH: 3254
<212> TYPE: DNA
<213> ORGANISM: Homo sapiens

<400> SEQUENCE: 62

```
agagttgcac tgagtgtggc tgaagcagcg aggcgggagt ggaggtgcgc ggagtcaggc      60
agacagacag acacagccag ccagccaggt cggcagtata gtccgaactg caaatcttat     120
tttcttttca ccttctctct aactgccag agctagcgcc tgtggctccc gggctggtgt      180
ttcgggagtg tccagagagc ctggtctcca gccgccccg ggaggagagc cctgctgccc      240
aggcgctgtt gacagcggcg gaaagcagcg gtacccacgc gcccgccggg ggaagtcggc     300
gagcggctgc agcagcaaag aactttcccg gctgggagga ccggagacaa gtggcagagt    360
cccggagcca acttttgcaa gcctttcctg cgtcttaggc ttctccacgg cggtaaagac    420
cagaaggcgg cggagagcca cgcaagagaa gaaggacgtg cgctcagctt cgctcgcacc    480
ggttgttgaa cttgggcgag cgcgagccgc ggctgccggg cgcccctcc ccctagcagc    540 ggaggagggg acaagtcgtc ggagtccggg cggccaagac ccgccgccgg ccggccactg    600
cagggtccgc actgatccgc tccgcgggga gagccgctgc tctgggaagt gagttcgcct    660
gcggactccg aggaaccgct gcgcacgaag agcgctcagt gagtgaccgc gacttttcaa    720
agccgggtag cgcgcgcgag tcgacaagta agagtgcggg aggcatctta attaaccctg    780
cgctccctgg agcgagctgg tgaggagggc gcagcgggga cgacagccag cgggtgcgtg    840
cgctcttaga gaaactttcc ctgtcaaagg ctccgggggg cgcgggtgtc cccgcttgc    900 cacagccctg ttgcggcccc gaaacttgtg cgcgcagccc aaactaacct cacgtgaagt   960
gacggactgt tctatgactg caaagatgga aacgaccttc tatgacgatg ccctcaacgc   1020
ctcgttcctc ccgtccgaga gcggacctta tggctacagt aaccccaaga tcctgaaaca   1080
gagcatgacc ctgaacctgg ccgacccagt ggggagcctg aagccgcacc tccgcgccaa   1140
gaactcggac ctcctcacct cgcccgacgt ggggctgctc aagctggcgt cgcccgagct   1200
ggagcgcctg ataatccagt ccagcaacgg gcacatcacc accacgccga ccccaccca   1260 gttcctgtgc cccaagaacg tgacagatga gcaggagggc ttcgccgagg cttcgtgcg   1320 cgccctggcc gaactgcaca gccagaacac gctgcccagc gtcacgtcgg cggcgcagcc   1380
```

-continued

```
ggtcaacggg gcaggcatgg tggctcccgc ggtagcctcg gtggcagggg gcagcggcag      1440
cggcggcttc agcgccagcc tgcacagcga ccgccggtc tacgcaaacc tcagcaactt       1500
caacccaggc gcgctgagca gcggcggcgg ggcgccctcc tacggcgcgg ccggcctggc      1560
ctttcccgcg caaccccagc agcagcagca gccgccgcac cacctgcccc agcagatgcc      1620
cgtgcagcac ccgcggctgc aggccctgaa ggaggagcct cagacagtgc ccgagatgcc      1680
cggcgagaca ccgcccctgt cccccatcga catggagtcc caggagcgga tcaaggcgga      1740
gaggaagcgc atgaggaacc gcatcgctgc ctccaagtgc cgaaaaagga agctggagag      1800
aatcgcccgg ctggaggaaa agtgaaaac cttgaaagct cagaactcgg agctggcgtc       1860
cacggccaac atgctcaggg aacaggtggc acagcttaaa cagaaagtca tgaaccacgt      1920
taacagtggg tgccaactca tgctaacgca gcagttgcaa acattttgaa gagagaccgt     1980
cgggggctga gggcaacga agaaaaaaaa taacacagag agacagactt gagaacttga      2040
caagttgcga cggagagaaa aagaagtgt ccgagaacta agccaaggg tatccaagtt       2100 ggactgggtt gcgtcctgac ggcgccccca gtgtgcacga gtgggaagga cttggcgcgc     2160
cctcccttgg cgtggagcca gggagcggcc gcctgcgggc tgccccgctt gcggacggg     2220 ctgtccccgc gcgaacgaa cgttggactt tcgttaaca ttgaccaaga actgcatgga       2280
cctaacattc gatctcattc agtattaaag ggggagggg gaggggtta caaactgcaa       2340 tagagactgt agattgcttc tgtagtactc cttaagaaca caaagcgggg ggagggttgg     2400
ggaggggcgg caggagggag gtttgtgaga gcgaggctga gcctacagat gaactctttc     2460
tggcctgcct tcgttaactg tgtatgtaca tatatatatt ttttaatttg atgaaagctg     2520
attactgtca ataaacagct tcatgccttt gtaagttatt tcttgtttgt ttgtttgggt     2580
atcctgccca gtgttgtttg taaataagag atttggagca ctctgagttt accatttgta    2640
ataaagtata taattttttt atgttttgtt tctgaaaatt ccagaaagga tatttaagaa    2700
aatacaataa actattggaa agtactcccc taacctcttt tctgcatcat ctgtagatac    2760
tagctatcta ggtggagttg aaagagttaa gaatgtcgat taaaatcact ctcagtgctt    2820
cttactatta agcagtaaaa actgttctct attagacttt agaaataaat gtacctgatg    2880
tacctgatgc tatggtcagg ttatactcct cctcccccag ctatctatat ggaattgctt    2940
accaaaggat agtgcgatgt ttcaggaggc tggaggaagg ggggttgcag tggagaggga    3000
cagcccactg agaagtcaaa catttcaaag tttggattgt atcaagtggc atgtgctgtg    3060
accatttata atgttagtag aaatttaca ataggtgctt attctcaaag caggaattgg      3120
tggcagattt tacaaaagat gtatccttcc aatttggaat cttctctttg acaattccta   3180
gataaaaaga tggcctttgc ttatgaatat ttataacagc attcttgtca cataaaatgt    3240
attcaaatac caat                                                      3254
```

<210> SEQ ID NO 63
<211> LENGTH: 3254
<212> TYPE: DNA
<213> ORGANISM: Homo sapiens

<400> SEQUENCE: 63

```
agagttgcac tgagtgtggc tgaagcagcg aggcgggagt ggaggtgcgc ggagtcaggc       60
agacagacag acacagccag ccagccaggt cggcagtata gtccgaactg caaatctttat     120 tttcttttca ccttctctct aactgcccag agctagcgcc tgtggctccc gggctggtgt      180
```

-continued

```
ttcgggagtg tccagagagc ctggtctcca gccgcccccg ggaggagagc cctgctgccc      240
aggcgctgtt gacagcggcg gaaagcagcg gtacccacgc gcccgccggg ggaagtcggc      300
gagcggctgc agcagcaaag aactttcccg gctgggagga ccggagacaa gtggcagagt      360
cccggagcca acttttgcaa gcctttcctg cgtcttaggc ttctccacgg cggtaaagac      420
cagaaggcgg cggagagcca cgcaagagaa gaaggacgtg cgctcagctt cgctcgcacc      480
ggttgttgaa cttgggcgag cgcgagccgc ggctgccggg cgcccctcc ccctagcagc       540 ggaggagggg acaagtcgtc ggagtccggg cggccaagac ccgccgccgg ccggccactg      600
cagggtccgc actgatccgc tccgcgggga gagccgctgc tctgggaagt gagttcgcct      660
gcggactccg aggaaccgct gcgcacgaag agcgctcagt gagtgaccgc gacttttcaa      720
agccgggtag cgcgcgcgag tcgacaagta agagtgcggg aggcatctta attaaccctg      780
cgctccctgg agcgagctgg tgaggagggc gcagcgggga cgacagccag cgggtgcgtg      840
cgctcttaga gaaactttcc ctgtcaaagg ctccgggggg cgcgggtgtc ccccgcttgc      900
cacagccctg ttgcggcccc gaaacttgtg cgcgcagccc aaactaacct cacgtgaagt      960
gacggactgt tctatgactg caaagatgga aacgaccttc tatgacgatg ccctcaacgc     1020
ctcgttcctc ccgtccgaga gcggaccttta tggctacagt aaccccaaga tcctgaaaca     1080
gagcatgacc ctgaacctgg ccgacccagt ggggagcctg aagccgcacc tccgcgccaa     1140
gaactcggac ctcctcacct cgcccgacgt ggggctgctc aagctggcgt cgcccgagct     1200
ggagcgcctg ataatccagt ccagcaacgg gcacatcacc accacgccga cccccaccca     1260
gttcctgtgc cccaagaacg tgacagatga gcaggagggc ttcgccgagg gcttcgtgcg     1320
cgccctggcc gaactgcaca gccagaacac gctgcccagc gtcacgtcgg cggcgcagcc     1380
ggtcaacggg gcaggcatgg tggctcccgc ggtagcctcg gtggcagggg gcagcggcag     1440
cggcggcttc agcgccagcc tgcacagcga gccgccggtc tacgcaaacc tcagcaactt     1500
caacccaggc gcgctgagca gcggcggcgg ggcgccctcc tacggcgcgg ccggcctggc     1560
ctttcccgcg caaccccagc agcagcagca gccgccgcac cacctgcccc agcagatgcc     1620
cgtgcagcac ccgcggctgc aggccctgaa ggaggagcct cagacagtgc ccgagatgcc     1680
cggcgagaca ccgccctgt ccccatcga catggagtcc caggagcgga tcaaggcgga      1740
gaggaagcgc atgaggaacc gcatcgctgc ctccaagtgc cgaaaaagga agctggagag     1800
aatcgcccgg ctggaggaaa aagtgaaaac cttgaaagct cagaactcgg agctggcgtc     1860
cacggccaac atgctcaggg aacaggtggc acagcttaaa cagaaagtca tgaaccacgt     1920
taacagtggg tgccaactca tgctaacgca gcagttgcaa acattttgaa gagagaccgt     1980 cggggctga gggcaacga agaaaaaaaa taacacagag agacagactt gagaacttga      2040
caagttgcga cggagagaaa aaagaagtgt ccgagaacta agccaagggg tatccaagtt     2100
ggactgggtt gcgtcctgac ggcgccccca gtgtgcacga gtgggaagga cttggcgcgc     2160
cctcccttgg cgtggagcca gggagcggcc gcctgcgggc tgccccgctt gcggacgggg    2220
ctgtccccgc gcgaacggaa cgttggactt ttcgttaaca ttgaccaaga actgcatgga    2280
cctaacattc gatctcattc agtattaaag gggggagggg gaggggggtta caaactgcaa    2340 tagagactgt agattgcttc tgtagtactc cttaagaaca caaagcgggg ggagggttgg    2400
ggaggggcgg caggagggag gtttgtgaga gcgaggctga gcctacagat gaactctttc    2460
tggcctgcct tcgttaactg tgtatgtaca tatatatatt ttttaatttg atgaaagctg    2520
attactgtca ataaacagct tcatgccttt gtaagttatt tcttgtttgt ttgtttgggt    2580
```

-continued

| | |
|---|---|
| atcctgccca gtgttgtttg taaataagag atttggagca ctctgagttt accatttgta | 2640 |
| ataaagtata taatttttt atgttttgtt tctgaaaatt ccagaaagga tatttaagaa | 2700 |
| aatacaataa actattggaa agtactcccc taacctcttt tctgcatcat ctgtagatac | 2760 |
| tagctatcta ggtggagttg aaagagttaa gaatgtcgat taaaatcact ctcagtgctt | 2820 |
| cttactatta agcagtaaaa actgttctct attagacttt agaaataaat gtacctgatg | 2880 |
| tacctgatgc tatggtcagg ttatactcct cctcccccag ctatctatat ggaattgctt | 2940 |
| accaaaggat agtgcgatgt ttcaggaggc tggaggaagg ggggttgcag tggagaggga | 3000 |
| cagcccactg agaagtcaaa catttcaaag tttggattgt atcaagtggc atgtgctgtg | 3060 |
| accatttata atgttagtag aaattttaca ataggtgctt attctcaaag caggaattgg | 3120 |
| tggcagattt tacaaaagat gtatccttcc aatttggaat cttctctttg acaattccta | 3180 |
| gataaaaaga tggcctttgc ttatgaatat ttataacagc attcttgtca cataaatgt | 3240 |
| attcaaatac caat | 3254 |

<210> SEQ ID NO 64
<211> LENGTH: 1832
<212> TYPE: DNA
<213> ORGANISM: Homo sapiens

<400> SEQUENCE: 64

| | |
|---|---|
| gtgccgctcc ttggtggggg ctgttcatgg cggttccggg gtctccaaca ttttcccgg | 60 |
| ctgtggtcct aaatctgtcc aaagcagagg cagtggagct tgaggttctt gctggtgtga | 120 |
| aatgactgag tacaaactgg tggtggttgg agcaggtggt gttgggaaaa gcgcactgac | 180 |
| aatccagcta atccagaacc actttgtaga tgaatatgat cccaccatag aggattctta | 240 |
| cagaaaacaa gtggttatag atggtgaaac ctgtttgttg gacatactgg atacagctgg | 300 |
| acaagaagag tacagtgcca tgagagacca atacatgagg acaggcgaag gcttcctctg | 360 |
| tgtatttgcc atcaataata gcaagtcatt tgcggatatt aacctctaca gggagcagat | 420 |
| taagcgagta aaagactcgg atgatgtacc tatggtgcta gtgggaaaca agtgtgattt | 480 |
| gccaacaagg acagttgata caaaacaagc ccacgaactg ccaagagtt acgggattcc | 540 |
| attcattgaa acctcagcca agaccagaca gggtgttgaa gatgcttttt acacactggt | 600 |
| aagagaaata cgccagtacc gaatgaaaaa actcaacagc agtgatgatg ggactcaggg | 660 |
| ttgtatggga ttgccatgtg tggtgatgta acaagatact tttaaagttt tgtcagaaaa | 720 |
| gagccacttt caagctgcac tgacaccctg gtcctgactt ccctggagga aagtattcc | 780 |
| tgttgctgtc ttcagtctca cagagaagct cctgctactt ccccagctct cagtagttta | 840 |
| gtacaataat ctctatttga gaagttctca gaataactac ctcctcactt ggctgtctga | 900 |
| ccagagaatg cacctcttgt tactccctgt tatttttctg ccctgggttc ttccacagca | 960 |
| caaacacacc tctgccaccc caggttttc atctgaaaag cagttcatgt ctgaaacaga | 1020 |
| gaaccaaacc gcaaacgtga aattctattg aaaacagtgt cttgagctct aaagtagcaa | 1080 |
| ctgctggtga tttttttt cttttactg ttgaacttag aactatgcta attttggag | 1140 |
| aaatgtcata aattactgtt ttgccaagaa tatagttatt attgctgttt ggtttgttta | 1200 |
| taatgttatc ggctctattc tctaaactgg catctgctct agattcataa atacaaaaat | 1260 |
| gaatactgaa ttttgagtct atcctagtct tcacaacttt gacgtaatta aatccaacttt | 1320 |
| tcacagtgaa gtgcctttt cctagaagtg gtttgtagac ttcctttata atatttcagt | 1380 |

-continued

```
ggaatagatg tctcaaaaat ccttatgcat gaaatgaatg tctgagatac gtctgtgact    1440
tatctaccat tgaaggaaag ctatatctat ttgagagcag atgccatttt gtacatgtat    1500
gaaattggtt ttccagaggc ctgttttggg gctttcccag gagaaagatg aaactgaaag    1560
cacatgaata atttcactta ataattttta cctaatctcc actttttca taggttacta    1620 cctatacaat gtatgtaatt tgtttcccct agcttactga taaacctaat attcaatgaa    1680
cttccatttg tattcaaatt tgtgtcatac cagaaagctc tacatttgca gatgttcaaa    1740
tattgtaaaa ctttggtgca ttgttattta atagctgtga tcagtgattt tcaaacctca    1800
aatatagtat attaacaaat tacattttca ct                                  1832
```

<210> SEQ ID NO 65
<211> LENGTH: 3890
<212> TYPE: DNA
<213> ORGANISM: Homo sapiens

<400> SEQUENCE: 65

```
atgaaggtga taagcttatt cattttggtg ggatttatag gagagttcca aagtttttca      60
agtgcctcct ctccagtcaa ctgccagtgg gacttctatg cccccttggtc agaatgcaat    120 ggctgtacca agactcagac tcgcaggcgg tcagttgctg tgtatgggca gtatggaggc    180
cagccttgtg ttggaaatgc ttttgaaaca cagtcctgtg aacctacaag aggatgtcca    240
acagaggagg gatgtggaga gcgtttcagg tgcttttcag gtcagtgcat cagcaaatca    300 ttggttttgca atgggattc tgactgtgat gaagacagtg ctgatgaaga cagatgtgag    360
gactcagaaa ggagaccttc ctgtgatatc gataaacctc ctcctaacat agaacttact    420
ggaaatggtt acaatgaact cactggccag tttaggaaca gagtcatcaa taccaaaagt    480
tttggtggtc aatgtagaaa ggtgtttagt ggggatggaa aagatttcta caggctgagt    540
ggaaatgtcc tgtcctatac attccaggtg aaaataaata atgattttaa ttatgaattt    600
tacaatagta cttggtctta tgtaaaacat acgtcgacag aacacacatc atctagtcgg    660
aagcgctcct tttttagatc ttcatcatct tcttcacgca gttatacttc acataccaat    720
gaaatccata aaggaaagag ttaccaactg ctggttgttg agaacactgt tgaagtggct    780
cagttcatta ataacaatcc agaatttttta caacttgctg agccattctg gaaggagctt    840
tcccacctcc cctctctgta tgactacagt gcctaccgaa gattaatcga ccagtacggg    900
acacattatc tgcaatctgg gtcgttagga ggagaataca gagttctatt ttatgtggac    960
tcagaaaaat taaacaaaaa tgattttaat tcagtcgaag aaaagaaatg taaatcctca   1020
ggttggcatt ttgtcgttaa attttcaagt catggatgca aggaactgga aaacgcttta   1080
aaagctgctt caggaaccca gaacaatgta ttgcgaggag aaccgttcat cagagggga   1140 ggtgcaggct tcatatctgg ccttagttac ctagagctgg acaatcctgc tggaaacaaa   1200
aggcgatatt ctgcctgggc agaatctgtg actaatcttc tcaagtcat aaaacaaaag   1260 ctgacacctt tatatgagct ggtaaaggaa gtaccttgtg cctctgtgaa aaaactatac   1320
ctgaaatggg ctcttgaaga gtatctggat gaatttgacc cctgtcattg ccggccttgt   1380
caaaatggtg gtttggctac tgttgagggg acccattgtc tgtgccattg caaaccgtac   1440
acatttggtg cggcgtgtga gcaaggagtc ctcgtaggga tcaagcagg agggggttgat   1500 ggaggttgga gttgctggtc ctcttggagc ccctgtgtcc aagggaagaa aacaagaagc   1560
cgtgaatgca ataacccccacc tcccagtggg ggtgggagat cctgcgttgg agaaacgaca   1620
gaaagcacac aatgcgaaga tgaggagctg gagcacttga ggttgcttga accacattgc   1680
```

-continued

```
tttcctttgt ctttggttcc aacagaattc tgtccatcac ctcctgcctt gaaagatgga    1740
tttgttcaag atgaaggtcc aatgtttcct gtggggaaaa atgtagtgta cacttgcaat    1800
gaaggatact ctcttattgg aaacccagtg gccagatgtg gagaagattt acggtggctt    1860
gttggggaaa tgcattgtca gaaaattgcc tgtgttctac ctgtactgat ggatggcata    1920
cagagtcacc cccaaaaacc tttctacaca gttggtgaga aggtgactgt ttcctgttca    1980
ggtggcatgt ccttagaagg tccttcagca tttctctgtg gctccagcct taagtggagt    2040
cctgagatga agaatgcccg ctgtgtacaa aaagaaaatc cgttaacaca ggcagtgcct    2100
aaatgtcagc gctgggagaa actgcagaat tcaagatgtg tttgtaaaat gccctacgaa    2160
tgtggacctt ccttggatgt atgtgctcaa gatgagagag caaaaggat actgcctctg     2220 acagtttgca agatgcatgt tctccactgt cagggtagaa attcacccct tactggtagg    2280
gacagctgta ctctgcctgc ctcagctgag aaagcttgtg gtgcctgccc actgtgggga    2340
aaatgtgatg ctgagagcag caaatgtgtc tgccgagaag catcggagtg cgaggaagaa    2400
gggtttagca tttgtgtgga agtgaacggc aaggagcaga cgatgtctga gtgtgaggcg    2460
ggcgctctga gatgcagagg gcagagcatc tctgtcacca gcataaggcc ttgtgctgcg    2520
gaaacccagt aggctcctgg aggccatggt cagcttgctt ggaatccagc aggcagctgg    2580
ggctgagtga aaacatctgc acaactgggc actggacagc ttttccttct tctccagtgt    2640
ctaccttcct cctcaactcc cagccatctg tataaacaca atcctttgtt ctcccaaatc    2700
tgaatcgaat tactcttttg cctccttttt aatgtcagta aggatatgag cctttgcaca    2760
ggctggctgc gtgttcttga ataggtgtt accttctctg ggccttggtt ttttaaaatc    2820
tgtaaaatta gaggattgca ctagagaaac ttgaatgctc cattcaggcc tatcatttta    2880
ttaagtatga ttgacacagc ccatgggcca gaacacactc tacaaaatga ctaggataac    2940
agaaagaacg tgatctcctg attagagagg gtggttttcc tcaatggaac caaatataaa    3000
gaggacttga acaaaaatga cagatacaaa ctatttctat cctgagtagt aatctcacac    3060
ttcatcctat agagtcaacc accacagata ggaattcctt attcttttt taatttttt     3120 aagacagagt ctcactttgt tgcccaggct ggagcgcagt ggggtgatct catctccctg    3180
caacctccgc ctcctgggtt gaagcgattc ttgtgcctca gcttcccaag cagctgggat    3240
tacaggtgcc cgccaccacg cccagctaat ttttgcattt ttagtagaga tgggtttcac    3300
catgttggcc atgctcgtct ccaactcctg acctcaggta atccgtctgc cttggcctcc    3360
caaatgctgg gattacagac atgaaccacc acgcctggct ggaatactta ctcttgtcgg    3420
gagattgaac cactaaaatg ttagagcaga attcattatg ctgtggtcac agggtgtct     3480 tgtctgagaa caaatacaat tcagtcttct ctttggggtt ttagtatgtg tcaaacatag    3540
gactggaagt ttgcccctgt tcttttttct tttgaaagaa catcagttca tgcctgaggc    3600
atgagtgact gtgcatttga gatagttttc cctattctgt ggatacagtc ccagagtttt    3660
cagggagtac acaggtagat tagtttgaag cattgacctt ttatttattc cttatttctc    3720
tttcatcaaa acaaaacagc agctgtggga ggagaaatga gagggcttaa atgaaattta    3780
aaataagcta tattatacaa atactatctc tgtattgttc tgaccctggt aaatatattt    3840
caaaacttca gatgacaagg attagaacac tcattaagat gctattcttc               3890
```

<210> SEQ ID NO 66
<211> LENGTH: 725
<212> TYPE: DNA

<213> ORGANISM: Homo sapiens

<400> SEQUENCE: 66

| ctaacccaga | aacatccaat | tctcaaactg | aagctcgcac | tctcgcctcc | agcatgaaag | 60 |
| tctctgccgc | ccttctgtgc | ctgctgctca | tagcagccac | cttcattccc | caagggctcg | 120 |
| ctcagccaga | tgcaatcaat | gccccagtca | cctgctgtta | taacttcacc | aataggaaga | 180 |
| tctcagtgca | gaggctcgcg | agctatagaa | gaatcaccag | cagcaagtgt | cccaaagaag | 240 |
| ctgtgatctt | caagaccatt | gtggccaagg | agatctgtgc | tgaccccaag | cagaagtggg | 300 |
| ttcaggattc | catggaccac | ctggacaagc | aaacccaaac | tccgaagact | tgaacactca | 360 |
| ctccacaacc | caagaatctg | cagctaactt | attttcccct | agctttcccc | agacaccctg | 420 |
| ttttatttta | ttataatgaa | ttttgtttgt | tgatgtgaaa | cattatgcct | taagtaatgt | 480 |
| taattcttat | ttaagttatt | gatgttttaa | gtttatcttt | catggtacta | gtgttttta | 540 |
| gatacagaga | cttggggaaa | ttgcttttcc | tcttgaacca | cagttctacc | cctgggatgt | 600 |
| tttgagggtc | tttgcaagaa | tcattaatac | aaagaatttt | ttttaacatt | ccaatgcatt | 660 |
| gctaaaatat | tattgtggaa | atgaatattt | tgtaactatt | acaccaaata | aatatatttt | 720 |
| tgtac | | | | | | 725 |

<210> SEQ ID NO 67
<211> LENGTH: 3451
<212> TYPE: DNA
<213> ORGANISM: Homo sapiens
<220> FEATURE:
<221> NAME/KEY: misc_feature
<222> LOCATION: (841)..(1225)
<223> OTHER INFORMATION: The "n" at this position can be either "a", "t",
      "g", or "c".

<400> SEQUENCE: 67

| ttcaatgttg | atgtgaaaaa | ttcaatgact | ttcagcggcc | cggtggaaga | catgtttgga | 60 |
| tatactgttc | aacaatatga | aaatgaagaa | ggaaaatggg | tgcttattgg | ttctccgtta | 120 |
| gttggccaac | ccaaaaacag | aactggagat | gtctataagt | gtccagttgg | gagaggtgaa | 180 |
| tcattacctt | gcgtaaagtt | ggatctacca | gttaatacat | caattcccaa | tgtcacagaa | 240 |
| gtaaaggaga | acatgacatt | tggatcaact | ttagtcacca | acccaaatgg | aggatttctg | 300 |
| gcttgtgggc | ccttatatgc | ctatagatgt | ggacatttgc | attacacaac | tggaatctgt | 360 |
| tctgacgtca | gccccacatt | tcaagtcgtg | aattccattg | ccctgtaca | gaatgcagc | 420 |
| actcaactgg | acatagtcat | agtgctggat | ggttccaaca | gtatttaccc | atgggacagt | 480 |
| gttacagctt | ttttaaatga | ccttcttgaa | agaatggata | ttggtcctaa | acagacacag | 540 |
| gttggaattg | tacagtatgg | agaaaacgtg | acccatgagt | tcaacctcaa | taagtattct | 600 |
| tccaccgaag | aggtacttgt | tgcagcaaag | aaaatagtcc | agagaggtgg | ccgccagact | 660 |
| atgacagctc | ttggaataga | cacagcaaga | aaggaggcat | tcacggaagc | ccggggtgcc | 720 |
| cgaagaggag | ttaaaaaagt | catggttatt | gtgacagatg | gagagtctca | tgacaatcat | 780 |
| cgactgaaga | aggtcatcca | agactgtgaa | gatgaaaaca | ttcaacggtt | ttccatagct | 840 |
| nnnnnnnnnn | nnnnnnnnnn | nnnnnnnnnn | nnnnnnnnnn | nnnnnnnnnn | nnnnnnnnnn | 900 |
| nnnnnnnnnn | nnnnnnnnnn | nnnnnnnnnn | nnnnnnnnnn | nnnnnnnnnn | nnnnnnnnnn | 960 |
| nnnnnnnnnn | nnnnnnnnnn | nnnnnnnnnn | nnnnnnnnnn | nnnnnnnnnn | nnnnnnnnnn | 1020 |
| nnnnnnnctt | catatgaaat | ggaaatgtct | cagactggct | tcagtgctca | ttattcacag | 1080 |

```
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnngttac actgtaaact ctgctactgc ttcttctgga    1260
gatgtgctct atattgctgg acagcctcgg tacaatcata caggccaggt cattatctac    1320
aggatggaag atggaaacat caaaattctc cagacgctca gtggagaaca gattggttcc    1380
tactttggca gtattttaac aacaactgac attgacaagg attctaatac tgacattctt    1440
ctagtcggag cccctatgta catgggaaca gagaaggagg agcaaggaaa agtgtatgtg    1500
tatgctctca atcagacaag gtttgaatat caaatgagcc tggaacctat taagcagacg    1560
tgctgttcat ctcggcagca caattcatgc acaacagaaa acaaaaatga gccatgcggg    1620
gctcgttttg gaactgcaat tgctgctgta aagacctca atcttgatgg atttaatgac    1680
atcgtgatag gagctccgct ggagatgatc acggggagc tgtgtacatt tatcatggaa    1740
gtggcaagac tataaggaaa gagtatgcac aacgtattcc atcaggtggg gatggtaaga    1800
cactgaaatt ttttggccag tctatccacg gagaaatgga tttaaatggt gacggtctga    1860
cagatgtgac tattggggc cttggtggtg ctgccctctt ctggtcccga gatgtggccg    1920
tagttaaagt gaccatgaat tttgagccaa ataaagtgaa tattcaaaag aaaaactgcc    1980
atatggaggg aaaggaaaca gtatgcataa atgctacagt gtgttttgat gtgaaattaa    2040
agtctaaaga agacacgatt tatgaagctg atttgcagta ccgtgtcacc ctagattcac    2100
taagacaaat atcacgaagt ttttctctg gaactcaaga gagaaaggtt caaaggaaca    2160
tcacagttcg aaaatcagaa tgcactaagc actccttcta catgttgaca agcatgactt    2220
tcaggactct gtgagaataa cgttggactt taatcttacc gatccagaaa atgggcctgt    2280
tcttgatgat tctctaccaa actcagtaca tgaatatatt cccttttgcca aagattgtgg    2340
aaataaggaa aaatgtatct cagacctcag cctgcatgtc gccaccactg aaaaggacct    2400
gctgattgtc cgatcccaga tgataagtt caacgttagc ctcacagtca aaaatacaaa    2460
ggacagtgcc tataacacca ggacaatagt gcattattct ccaaatctag tttttttcagg    2520
aattgaggct atccaaaaag acagttgtga atctaatcat aatatcacat gtaaagttgg    2580
atatcccttc ctgagaagag gagagatggt aactttcaaa atattgtttc agtttaacac    2640
atcctatctc atggaaaatg tgaccattta tttaagtgca acaagtgaca gcgaagaacc    2700
tcctgaaacc ctttctgata atgtagtaaa catttctatc ccggtaaaat atgaagttgg    2760
actacagttt tacagctctg caagtgaata ccacatttca attgctgcca atgagacagt    2820
ccctgaagtt attaattcta ctgaggacat tggaaatgaa attaatatct tctacttgat    2880
tagaaaaagt ggatctttc caatgccaga gcttaagctg tcaatttcat tcccaatat    2940
gacatcaaat ggttaccctg tgctgtaccc aactggattg tcatcttctg agaatgcaaa    3000
ctgcagaccc catatctttg aggatccttt cagtatcaac tctggaaaga aaatgactac    3060
atcaactgac catctcaaac gaggcacaat tctggactgc aatacatgta aatttgctac    3120
catcacatgt aatctcactt cttctgacat cagccaagtc aatgtttcgc ttatcttgtg    3180
gaaaccaact tttataaaat catatttttc cagcttaaat cttactataa ggggagaact    3240
tcggagtgaa aatgcatctc tggttttaag tagcagcaat caaaaaagag agcttgctat    3300
tcaaatatcc aaagatgggc taccgggcag agtgccatta tgggtcatcc tgctgagtgc    3360
ttttgccgga ttgttgctgt taatgctgct catttttagca ctgtggaaga ttggattctt    3420
caaaagacca ctgaaaaaga aaatggagaa a                                   3451
```

<210> SEQ ID NO 68
<211> LENGTH: 1772
<212> TYPE: DNA
<213> ORGANISM: Homo sapiens

<400> SEQUENCE: 68

| | | | | | |
|---|---|---|---|---|---|
| gtatcactca | gaatctggca | gccagttccg | tcctgacaga | gttcacagca | tatattggtg | 60 |
| gattcttgtc | catagtgcat | ctgctttaag | aattaacgaa | agcagtgtca | agacagtaag | 120 |
| gattcaaacc | atttgccaaa | aatgagtcta | agtgcattta | ctctcttcct | ggcattgatt | 180 |
| ggtggtacca | gtggccagta | ctatgattat | gattttcccc | tatcaattta | tgggcaatca | 240 |
| tcaccaaact | gtgcaccaga | atgtaactgc | cctgaaagct | acccaagtgc | catgtactgt | 300 |
| gatgagctga | aattgaaaag | tgtaccaatg | gtgcctcctg | gaatcaagta | tctttacctt | 360 |
| aggaataacc | agattgacca | tattgatgaa | aaggcctttg | agaatgtaac | tgatctgcag | 420 |
| tggctcattc | tagatcacaa | ccttctagaa | aactccaaga | taaagggag | agttttctct | 480 |
| aaattgaaac | aactgaagaa | gctgcatata | accacaaca | acctgacaga | gtctgtgggc | 540 |
| ccacttccca | atctctgga | ggatctgcag | cttactcata | caagatcac | aaagctgggc | 600 |
| tcttttgaag | gattggtaaa | cctgaccttc | atccatctcc | agcacaatcg | gctgaaagag | 660 |
| gatgctgttt | cagctgcttt | taaggtctt | aaatcactcg | aataccttga | cttgagcttc | 720 |
| aatcagatag | ccagactgcc | ttctggtctc | cctgtctctc | ttctaactct | ctacttagac | 780 |
| aacaataaga | tcagcaacat | ccctgatgag | tatttcaagc | gttttaatgc | attgcagtat | 840 |
| ctgcgtttat | ctcacaacga | actggctgat | agtggaatac | ctggaaattc | tttcaatgtg | 900 |
| tcatccctgg | ttgagctgga | tctgtcctat | aacaagctta | aaaacatacc | aactgtcaat | 960 |
| gaaaaccttg | aaaactatta | cctggaggtc | aatcaacttg | agaagtttga | cataaagagc | 1020 |
| ttctgcaaga | tcctggggcc | attatcctac | tccaagatca | agcatttgcg | tttggatggc | 1080 |
| aatcgcatct | cagaaaccag | tcttccaccg | gatatgtatg | aatgtctacg | tgttgctaac | 1140 |
| gaagtcactc | ttaattaata | tctgtatcct | ggaacaatat | tttatggtta | tgttttctg | 1200 |
| tgtgtcagtt | ttcatagtat | ccatatttta | ttactgttta | ttacttccat | gaattttaaa | 1260 |
| atctgaggga | aatgttttgt | aaacatttat | tttttttaaa | gaaagatga | aaggcaggcc | 1320 |
| tatttcatca | aagaacaca | cacatataca | cgaatagaca | tcaaactcaa | tgctttattt | 1380 |
| gtaaatttag | tgttttttta | tttctactgt | caaatgatgt | gcaaaacctt | ttactggttg | 1440 |
| catggaaatc | agccaagttt | tataatcctt | aaatcttaat | gttcctcaaa | gcttggatta | 1500 |
| aatacatatg | gatgttactc | tcttgcacca | aattatcttg | atacattcaa | atttgtctgg | 1560 |
| ttaaaaaata | ggtggtagat | attgaggcca | agaatattgc | aaaatacatg | aagcttcatg | 1620 |
| cacttaaaga | agtatttta | gaataagaat | ttgcatactt | acctagtgaa | acttttctag | 1680 |
| aattattttt | cactctaagt | catgtatgtt | tctctttgat | tatttgcatg | ttatgtttaa | 1740 |
| taagctacta | gcaaaataaa | acatagcaaa | tg | | | 1772 |

<210> SEQ ID NO 69
<211> LENGTH: 2198
<212> TYPE: DNA
<213> ORGANISM: Homo sapiens

<400> SEQUENCE: 69

| | | | | | |
|---|---|---|---|---|---|
| tggacagagg | agcagtaaca | atccccactc | tccaattgtg | gaagagttcc | aagtcccata | 60 |

```
caacaaactc caggtgatct ttaagtcaga cttttccaat gaagagcgtt ttacggggtt        120
tgctgcatac tatgttgcca cagacataaa tgaatgcaca gattttgtag atgtcccttg        180
tagccacttc tgcaacaatt tcattggtgg ttacttctgc tcctgccccc cggaatattt        240
cctccatgat gacatgaaga attgcggagt taattgcagt ggggatgtat tcactgcact        300
gattggggag attgcaagtc ccaattatcc caaaccatat ccagagaact caaggtgtga        360
ataccagatc cggttggaga aagggttcca agtggtggtg accttgcgga gagaagattt        420
tgatgtggaa gcagctgact cagcgggaaa ctgccttgac agtttagttt ttgttgcagg        480
agatcggcaa tttggtcctt actgtggtca tggattccct gggcctctaa atattgaaac        540
caagagtaat gctcttgata tcatcttcca aactgatcta acagggcaaa aaaagggctg        600
gaaacttcgc tatcatggag atccaatgcc ctgccctaag gaagacactc ccaattctgt        660
ttgggagcct gcgaaggcaa aatatgtctt tagagatgtg gtgcagataa cctgtctgga        720
tgggtttgaa gttgtggagg gacgtgttgg tgcaacatct ttctattcga cttgtcaaag        780
caatggaaag tggagtaatt ccaaactgaa atgtcaacct gtggactgtg gcattcctga        840
atccattgag aatggtaaag ttgaagaccc agagagcact ttgtttggtt ctgtcatccg        900
ctacacttgt gaggagccat attactacat ggaaaatgga ggaggtgggg agtatcactg        960
tgctggtaac gggagctggg tgaatgaggt gctgggcccg gagctgccga aatgtgttcc       1020
aggtctgtgg agtccccaga gaacccttyg aagaaaaaca gaggataatt ggaggatccg       1080
atgcagatat taaaaacttc ccctggcaag tcttctttga caacccatgg gctggtggag       1140
cgctcattaa tgagtactgg gtgctgacgg ctgctcatgt tgtggaggga acagggagc       1200 caacaatgta tgttgggtcc acctcagtgc agacctcacg gctggcaaaa tccaagatgc       1260
tcactcctga gcatgtgttt attcatccgg gatggaagct gctggaagtc ccagaaggac       1320
gaaccaattt tgataatgac attgcactgg tgcggctgaa agacccagtg aaaatgggac       1380
ccaccgtctc tcccatctgc ctaccaggca cctcttccga ctacaacctc atggatgggg       1440
acctgggact gatctcaggc tggggccgaa cagagaagag agatcgtgct gttcgcctca       1500
aggcggcaag gttacctgta gctccttttaa gaaaatgcaa agaagtgaaa gtggagaaac       1560
ccacagcaga tgcagaggcc tatgttttca ctcctaacat gatctgtgct ggaggagaga       1620
agggcatgga tagctgtaaa ggggacagtg gtgggccctt tgctgtacag gatcccaatg       1680
acaagaccaa attctacgca gctggcctgg tgtcctgggg gcccagtgt gggacctatg        1740 ggctctacac acgggtaaag aactatgttg actggataat gaagactatg caggaaaata       1800 gcacccccg tgaggactaa tccagataca tcccaccagc ctctccaagg gtggtgacca       1860
atgcattacc ttctgttcct tatgatattc tcattatttc atcatgactg aaagaagaca       1920
cgagcgaatg atttaaatag aacttgattg ttgagacgcc ttgctagagg tagagtttga       1980
tcatagaatt gtgctggtca tacatttgtg gtctgactcc ttggggtcct ttccccggag       2040
tacctattgt agataacact atgggtgggg cactcctttc ttgcactatt ccacagggat       2100 acctataattc tttgtttcct ctttacctgt tcaaaattcc atttacttga tcattctcag       2160
tatccactgt ctatgtacaa taaaggatgt ttataagc                               2198
```

<210> SEQ ID NO 70
<211> LENGTH: 2177
<212> TYPE: DNA
<213> ORGANISM: Homo sapiens

<400> SEQUENCE: 70

```
aaactctgat ctggggagga accaggacta catagatcaa ggcagttttc ttctttgaga     60
aactatccca gatatcatca tagagtcttc tgctcttcct caactaccaa agaaaaacat    120
cagcgaagca gcaggccatg cacccccccaa aaactccatc tggggctctt catagaaaaa   180
ggaaaatggc agcctggccc ttctccaggc tgtggaaagt ctctgatcca attctcttcc    240
aaatgacctt gatcgctgct ctgttgcctg ctgttcttgg caattgtggt cctccaccca    300
ctttatcatt tgctgccccg atggatatta cgttgactga gacacgcttc aaaactggaa    360
ctactctgaa atacacctgc ctccctggct acgtcagatc ccattcaact cagacgctta    420
cctgtaattc tgatggcgaa tgggtgtata acaccttctg tatctacaaa cgatgcagac    480
acccaggaga gttacgtaat gggcaagtag agattaagac agatttatct tttggatcac    540
aaatagaatt cagctgttca gaaggatttt tcttaattgg ctcaaccact agtcgttgtg    600
aagtccaaga tagaggagtt ggctggagtc atcctctccc acaatgtgaa attgtcaagt    660
gtaagcctcc tccagacatc aggaatggaa ggcacagcgg tgaagaaaat ttctacgcat    720
acggcttttc tgtcacctac agctgtgacc cccgcttctc actcttgggc catgcctcca    780
tttcttgcac tgtggagaat gaaacaatag gtgtttggag accaagccct cctacctgtg    840
aaaaaatcac ctgtcgcaag ccagatgttt cacatgggga aatggtctct ggatttggac    900
ccatctataa ttacaaagac actattgtgt ttaagtgcca aaaggtttt gttctcagag     960
gcagcagtgt aattcattgt gatgctgata gcaaatggaa tccttctcct cctgcttgtg   1020
agcccaatag ttgtattaat ttaccagaca ttccacatgc ttcctgggaa acatatccta   1080
ggccgacaaa agaggatgtg tatgttgttg ggactgtgtt aaggtaccgc tgtcatcctg   1140
gctacaaacc cactacagat gagcctacga ctgtgatttg tcagaaaaat ttgagatgga   1200
ccccatacca aggatgtgag gcgttatgtt gccctgaacc aaagctaaat aatggtgaaa   1260
tcactcaaca caggaaaagt cgtcctgcca atcactgtgt ttatttctat ggagatgaga   1320
tttcattttc atgtcatgag accagtaggt tttcagctat atgccaagga gatggcacgt   1380
ggagtccccg aacaccatca tgtggagaca tttgcaattt tcctcctaaa attgcccatg   1440
gcattataa acaatctagt tcatacagct ttttcaaaga agagattata tatgaatgtg    1500
ataaaggcta cattctggtc ggacaggcga aactcctg cagttattca cactggtcag     1560
ctccagcccc tcaatgtaaa gctctgtgtc ggaaaccaga attagtgaat ggaaggttgt   1620
ctgtggataa ggatcagtat gttgagcctg aaaatgtcac catccaatgt gattctggct   1680
atggtgtggt tggtccccaa agtatcactt gctctgggaa cagaacctgg tacccagagg   1740
tgcccaagtg tgagtgggag acccccgaag gctgtgaaca agtgctcaca ggcaaaagac   1800
tcatgcagtg tctcccaaac ccagaggatg tgaaaatggc cctggaggta tataagctgt   1860
ctctggaaat tgaacaactg gaactacaga gagacagcgc aagacaatcc actttggata   1920
agaactata attttctca aagaaggag gaaaggtgt cttgctggct tgcctcttgc       1980
aattcaatac agatcagttt agcaaatcta ctgtcaattt ggcagtgata ttcatcataa    2040
taaatatcta gaaatgataa tttgctaaag tttagtgctt tgagattgtg aaattattaa    2100
tcatcctctg tgtggctcat gttttttgctt ttcaacacac aaagcacaaa ttttttttcg    2160
attaaaaatg tatgtat                                                   2177
```

<210> SEQ ID NO 71
<211> LENGTH: 387
<212> TYPE: DNA

<213> ORGANISM: Homo sapiens
<220> FEATURE:
<221> NAME/KEY: misc_feature
<222> LOCATION: (27)..(53)
<223> OTHER INFORMATION: The "n" at this position can be either "a", "t", "g", or "c".

<400> SEQUENCE: 71

| | | | | | |
|---|---|---|---|---|---|
| gccctgctgg | ccctgctggt | gctcccnnnn | nnnnnnnnnn | nnnnnnnnnn | nnnggtcctc | 60 |
| aaggcccacg | tggtgacaaa | ggtgaaacag | gtgaacgtgg | agctgctggc | atcaaaggac | 120 |
| atcgaggatt | ccctggtaat | ccaggtgccc | caggttctcc | agggccctgc | tggtcagcag | 180 |
| ggtgcaatcg | gcagtccagg | acctgcaggc | cccagaggac | ctgttggacc | cagtggacct | 240 |
| cctggcaaag | atggaaccag | tggacatcca | ggtcccattg | gaccaccagg | gcctcgaggt | 300 |
| aacagaggtg | aaagaggatc | tgagggctcc | ccaggccacc | cagggcaacc | aggccctcct | 360 |
| ggacctcctg | gtgcccctgg | tccttgc | | | | 387 |

<210> SEQ ID NO 72
<211> LENGTH: 14749
<212> TYPE: DNA
<213> ORGANISM: Homo sapiens
<220> FEATURE:
<221> NAME/KEY: misc_feature
<222> LOCATION: (4989)..(4997)
<223> OTHER INFORMATION: n is a, c, g, or t
<220> FEATURE:
<221> NAME/KEY: misc_feature
<222> LOCATION: (10041)..(10537)
<223> OTHER INFORMATION: n is a, c, g, or t
<220> FEATURE:
<221> NAME/KEY: misc_feature
<222> LOCATION: (11852)..(11893)
<223> OTHER INFORMATION: n is a, c, g, or t

<400> SEQUENCE: 72

| | | | | | |
|---|---|---|---|---|---|
| gggcgcgggg | agagggcgcg | ggagcggctc | gcgcggcagg | taccatgcgg | acgcgcgagc | 60 |
| ccggcgaggg | ccccggcagg | cccggtccct | gctcggggc | gcgctgagac | ggcgggtgag | 120 |
| ctccacgaga | gcgccgtcgc | cacttcgggc | caactttgcg | attcccgaca | gttaagcaat | 180 |
| ggggagacat | ttggctttgc | tcctgcttct | gctccttctc | ttccaacatt | ttggagacag | 240 |
| tgatggcagc | caacgacttg | aacagactcc | tctgcagttt | acacacctcg | agtacaacgt | 300 |
| caccgtgcag | gagaactctg | cagctaagac | ttatgtgggg | catcctgtca | agatgggtgt | 360 |
| ttacattaca | catccagcgt | gggaagtaag | gtacaaaatt | gtttccggag | acagtgaaaa | 420 |
| cctgttcaaa | gctgaagagt | acattctcgg | agacttttgc | tttctaagaa | taaggaccaa | 480 |
| aggaggaaat | acagctattc | ttaatagaga | agtgaaggat | cactacacat | tgatagtgaa | 540 |
| agcacttgaa | aaaatacta | atgtggaggc | gcgaacaaag | gtcagggtgc | aggtgctgga | 600 |
| tacaaatgac | ttgagaccgt | tattctcacc | cacctcatac | agcgtttctt | tacctgaaaa | 660 |
| cacagctata | aggaccagta | tcgcaagagt | cagcgccacg | gatgcagaca | taggaaccaa | 720 |
| cgggggaattt | tactacagtt | ttaaagatcg | aacagatatg | tttgctattc | acccaaccag | 780 |
| tggtgtgata | gtgttaactg | gtagacttga | ttacctagag | accaagctct | atgagatgga | 840 |
| aatcctcgct | gcggaccgtg | gcatgaagtt | gtatgggagc | agtggcatca | gcagcatggc | 900 |
| caagctaacg | gtgcacatcg | aacaggccaa | tgaatgtgct | ccggtgataa | cagcagtgac | 960 |
| attgtcacca | tcagaactgg | acagggaccc | agcatatgca | attgtgacag | tggatgactg | 1020 |
| cgatcagggt | gccaatggtg | acatagcatc | tttaagcatc | gtggcaggtg | accttctcca | 1080 |

-continued

```
gcagtttaga acagtgaggt cctttccagg gagtaaggag tataaagtca aagccatcgg      1140
tggcattgat tgggacagtc atcctttcgg ctacaatctc acactacagg ctaaagataa      1200
aggaactccg ccccagttct cttctgttaa agtcattcac gtgacttctc cacagttcaa      1260
agccgggcca gtcaagtttg aaaaggatgt ttacagagca gaaataagtg aatttgctcc      1320
tcccaacaca cctgtggtca tggtaaaggc cattcctgct tattcccatt tgaggtatgt      1380
ttttaaaagt acacctggaa aagctaaatt cagtttaaat tacaacactg gtctcatttc      1440
tattttagaa ccagttaaaa gacagcaggc agcccatttt gaacttgaag taacaacaag      1500
tgacagaaaa gcgtccacca aggtcttggt gaaagtctta ggtgcaaata gcaatccccc      1560
tgaatttacc cagacagcgt acaaagctgc ttttgatgag aacgtgccca ttggtactac      1620
tgtcatgagc ctgagtgccg tagccctga tgagggtgag aacgggtacg tgacatacag      1680
tatcgcaaat ttaaatcatg tgccgtttgc gattgaccat ttcactggtg ccgtgagtac      1740
gtcagaaaac ctggactacg aactgatgcc tcgggtttat actctgagga ttcgtgcatc      1800
agactggggc ttgccgtacc gccgggaagt cgaagtcctt gctacaatta ctctcaataa      1860
cttgaatgac aacacacctt tgtttgagaa aataaattgt gaagggacaa ttcccagaga      1920
tctaggcgtg ggagagcaaa taaccactgt ttctgctatt gatgcagatg aacttcagtt      1980
ggtacagtat cagattgaag ctggaaatga actggatttc tttagtttaa accccaactc      2040
gggggtattg tcattaaagc gatcgctaat ggatggctta ggtgcaaagg tgtctttcac      2100
agtctgagaa tcacagctac agatggaaaa aattttgcca caccattata tatcaacata      2160
acagtggctg ccagtcacaa gctggtaaac ttgcagtgtg aagagactgg tgttgccaaa      2220
atgctggcag agaagctcct gcaggcaaat aaattacaca accagggaga ggtggaggat      2280
attttcttcg attctcactc tgtcaatgct cacataccgc agtttagaag cactcttccg      2340
actggtattc aggtaaagga aaaccagcct gtgggttcca gtgtaatttt catgaactcc      2400
actgaccttg acactggctt caatggaaaa ctggtctatg ctgtttctgg aggaaatgag      2460
gatagttgct tcatgattga tatggaaaca ggaatgctga aaattttatc tcctcttgac      2520
cgtgaaacaa cagacaaata caccctgaat attaccgtct atgaccttgg atacccccag      2580
aaggctgcgt ggcgtcttct acatgtcgtg gttgtcgatg ccaatgataa tcccaccgag      2640 ttttttacagg agagctattt tgtggaagtg agtgaagaca aggaggtaca tagtgaaatc      2700
atccaggttg aagccacaga taaagacctg gggcccaacg gacacgtgac gtactcaatt      2760
gttacagaca cagacacatt ttcaattgac agcgtgacgg gtgttgttaa catcgcacgc      2820
cctctggatc gagagctgca gcatgagcac tccttaaaga ttgaggccag ggaccaagcc      2880
agagaagagc ctcagctgtt ctccactgtc gttgtgaaag tatcactaga agatgttaat      2940
gacaacccac ctacatttat tccacctaat tatcgtgtga agtccgaga ggatcttcca       3000 gaaggaaccg tcatcatgtg gttagaagcc acgatcctg atttaggtca gtctggtcag       3060
gtcagcacac agccttctgg accacggaga aggaaacttc gatgtggata aactcagtgg      3120
agcagttagg atcgtccagc agttggactt tgagaagaag caagtgtata atctcactgt      3180
gagggccaaa gacaagggaa agccagtttc tctgtcttct acttgctatg ttgaagttga      3240
ggtggttgat gtgaatgaga acctgcaccc acccgtgttt tccagctttg tggaaaaggg      3300
gacagtgaaa gaagatgcac ctgttggttc attggtaatg acggtgtcgg ctcatgatga      3360
ggacgccaga agagatgggg agatccgata ctccattaga gatggctctg gcgttggtgt      3420
tttcaaaata ggtgaagaga caggtgtcat agagacgtca gatcgactgg accgtgaatc      3480
```

-continued

```
gacctcccat tattggctaa cagtctttgc aaccgatcag ggtgtcgtgc ctctttcatc    3540
gttcatagag atctacatag aggttgagga tgtcaatgac aatgcaccac agacatcaga    3600
gcctgtttat tacccagaaa tcatggaaaa ttctcctaaa gatgtatctg tggtccagat    3660
cgaggcattt gatccagatt cgagctctaa tgacaagctc atgtacaaaa ttacaagtgg    3720
aaatccacaa ggattctttt caatacatcc taaaacaggt ctcatcacaa ctacgtcaag    3780
gaagctagac cgagaacagc aagatgaaca catattagag gttactgtga cagacaatgg    3840 tagtccccc aaatcaacca ttgcaagagt cattgtgaaa atccttgatg aaaatgacaa     3900
caaacctcag tttctgcaaa agttctacaa aatcagactc cctgagcggg aaaagccaga    3960
ccgagaaaga aatgccagac gggagccgct ctatcgcgtc atagccaccg acaaggatga    4020 gggcccccaat gcagaaatct cctacagcat cgaagacggg aatgagcatg gcaaattttt   4080
catcgaaccg aaaactggag tggtttcgtc caagaggttt tcagcagctg agaatatga    4140 tattctttca attaaggcag ttgacaatgg tcgccctcaa aagtcatcaa ccaccagact    4200
ccatattgaa tggatctcca gcccaaaacc gtccctggag cccatttcat ttgaagaatc    4260
attttttacc tttactgtga tggaaagtga ccccgttgct cacatgattg gagtaatatc    4320
tgtggagcct cctggcatac cccttttggtt tgacatcact ggtggcaact acgacagtca    4380
cttcgatgtg gacaagggaa ctggaaccat cattgttgcc aaacctcttg atgcagaaca    4440
gaagtcaaac tacaacctca cagtcgaggc tacagatgga accaccacta tcctcactca    4500
ggtattcatc aaagtaatag acacaaatga ccatcgtcct cagttttcta catcaaagta    4560
tgaagttgtt attcctgaag atacagcgcc agaaacagaa attttgcaaa tcagtgctgt    4620
ggatcaggat gagaaaaaca aactaatcta cactctgcag agcagtagag atccactgag    4680
tctcaagaaa tttcgtcttg atcctgcaac cggctctctc tatacttctg agaaactgga    4740
tcatgaagct gttcaccagc acaccctcac ggtcatggta cgagatcaag atgtgcctgt    4800
aaaacgcaac tttgcaagga ttgtggtcaa tgtcagcgac acgaatgacc acgccccgtg    4860
gttcaccgct tcctcctaca aagggcgggt ttatgaatcg gcagccgttg gctcagttgt    4920
gttgcaggtg acggctctgg acaaggacaa agggaaaaat gctgaagtgc tgtactcgat    4980
cgagtcagnn nnnnnnngaa atattggaaa ttcttttatg attgatcctg tcttgggctc    5040
tattaaaact gccaaagaat tagatcgaag taaccaagcg gagtatgatt taatggtaaa    5100
agctacagat aagggcagtc caccaatgag tgaaataact tctgtgcgta tctttgtcac    5160
aattgctgac aacgcctctc cgaagtttac atcaaaagaa tattctgttg aacttagtga    5220
aactgtcagc attgggagtt tcgttgggat ggttacagcc catagtcaat catcagtggt    5280
gtatgaaata aaagatggaa atacaggtga tgcttttgat attaatccac attctggaac    5340
tatcatcact cagaaagccc tggactttga aactttgccc atttacacat tgataataca    5400
aggaactaac atggctggtt tgtccactaa tacaacggtt ctagttcact tgcaggatga    5460
gaatgacaac gcgccagttt ttatgcaggc agaatataca ggactcatta gtgaatcagc    5520
ctcaattaac agcgtggtcc taacagacag gaatgtccca ctggtgattc gagcagctga    5580
tgctgataaa gactcaaatg ctttgcttgt atatcacatt gttgaaccat ctgtacacac    5640
atattttgct attgattcta gcactggtgc tattcataca gtactaagtc tggactatga    5700
agaaacaagt atttttcact ttaccgtcca agtgcatgac atgggaaccc cacgtttatt    5760
tgctgagtat gcagcgaatg taacagtaca tgtaattgac attaatgact gccccccctgt    5820
```

-continued

```
gtttgccaag ccattatatg aagcatctct tttgttacca acatacaaag gagtaaaagt    5880
catcacagta aatgctacag atgctgattc aagtgcattc tcacagttga tttactccat    5940
caccgaaggc aacatcgggg agaagttttc tatggactac aagactggtg ctctcactgt    6000
ccaaaacaca actcagttaa gaagccgcta cgagctaacc gttagagctt ccgatggcag    6060
atttgccggc cttacctctg tcaaaattaa tgtgaaagaa agcaaagaaa gtcacctaaa    6120
gtttacccag gatgtctact ctgcggtagt gaaagagaat tccaccgagg ccgaaacatt    6180
agctgtcatt actgctattg ggaatccaat caatgagcct tgttttatc acatcctcaa     6240 cccagatcgc agatttaaaa taagccgcac ttcaggagtt ctgtcaacca ctggcacgcc    6300
cttcgatcgt gagcagcagg aggcgtttga tgtggttgta gaagtgacag aggaacataa    6360
gccttctgca gtggcccacg ttgtcgtgaa ggtcattgta aagaccaaa atgataatgc     6420 gccggtgttt gtcaaccttc cctactacgc cgttgttaaa gtggacactg aggtgggcca    6480
tgtcattcgc tatgtcactg ctgtagacag agacagtggc agaaacgggg aagtgcatta    6540
ctacctcaag gaacatcatg aacactttca aattggaccc ttgggtgaaa tttcactgaa    6600
aaagcaattt gagcttgaca ccttaaataa agaatatctt gttacagtgg ttgcaaaaga    6660
tggagggaac ccggcctttt cagcggaagt tatcgttccg atcactgtca tgaataaagc    6720
catgcctgtg tttgaaaaac cttttctacag tgcagagatt gcagagagca tccaggtgca   6780
cagccctgtg gtccacgtgc aggctaacag cccggaaggc ctgaaagtgt tctacagcat    6840
cacagacgga gacccttca gccagttcac tattaacttc aatactggag ttatcaatgt     6900
catagctcct ctggactttg aggcccaccc ggcatataag ctgagcatac gcgcaactga    6960
ctccttgacg ggcgctcatg ctgaagtatt tgtggacatc atagtagacg acatcaatga    7020
taaccctcct gtgtttgctc agcagtctta tgcggtgacc ctgtctgagg catctgtaat    7080
tggaacgtct gttgttcaag ttagagccac cgattctgat tcagaaccaa atagaggaat    7140
ctcataccag atgtttggga atcacagcaa gagtcatgat cattttcatg tagacagcag    7200
cactggcctc atctcactac tcagaaccct ggattacgag cagtcccggc agcacacgat    7260
ttttgtgagg gcagttgatg gtggtatgcc cacgctgagc agtgatgtga ttgtcacggt    7320
ggacgttacc gacctcaatg ataatccacc actctttgaa caacagattt atgaagccag    7380
aattagcgag cacgcccctc atgggcattt cgtgacctgt gtaaaagcct atgatgcaga    7440
cagttcagac atagacaagt tgcagtattc cattctgtct ggcaatgatc ataaacattt    7500
tgtcattgac agtgcaacag ggattatcac cctctcaaac ctgcaccggc acgccctgaa    7560
gccattttac agtcttaacc tgtcagtgtc tgatggagtt tttagaagtt ccacccaggt    7620
tcatgtaact gtaattggag gcaatttgca cagtcctgct ttccttcaga acgaaatga    7680 agtggaacta gctgaaaacg ctcccctaca taccctggtg atggaggtga aaactacgga    7740
tggggattct ggtatttatg gtcacgttac ttaccatatt gtaaatgact ttgccaaaga    7800
cagattttac ataaatgaga gaggacagat atttactttg gaaaaacttg atcgagaaac    7860
cccggcggag aaagtgatct cagtccgttt aatggctaag gatgctggag aaaagttgc    7920 tttctgcacc gtgaatgtca tccttacaga tgacaatgac aatgcaccac aatttcgagc    7980
aaccaaatac gaagtgaata tcgggtccag tgctgctaaa gggacttcag tcgttaaagt    8040
tcttgcaagt gatgccgatg agggctccaa tgccgacatc acctatgcca ttgaagcaga    8100
ctctgaaagt gtaaaagaga atttggaaat taacaaactg tccggcgtaa tcactacaaa    8160
ggagagcctc attggcttgg aaaatgaatt cttcacttc tttgttagag ctgtggataa     8220
```

```
tgggtctcca tcaaaagaat ctgttgttct tgtctatgtt aaaatccttc caccggaaat   8280
gcagcttcca aaattttcag aacctttcta tacctttaca gtgtcagagg acgtgcctat   8340
tggaacagag atagatctca tccgagcaga acatagtggg actgttcttt acagcctggt   8400
caaagggaat actccagaaa gcaatagggac tgagtccttt gtgattgaca gacagagcgg   8460
gagactgaag ttggagaaga gtcttgatca tgagacaact aagtggtatc agttttccat   8520
actggccagg tgcactcaag atgaccatga gatggtggct tctgtagatg ttagtatcca   8580
agtgaaagat gcaaatgaca acagcccggt ctttgaatct agtccatatg aggcattcat   8640
tgttgaaaac ctgccagggg gaagtagagt aattcagatc agggcatctg atgctgactc   8700
aggaaccaac ggccaagtta tgtatagcct ggatcagtca caaagtgtgg aagtcattga   8760
atcctttgcc attaacatgg aaacaggctg gattacaact ttaaaggaac ttgaccatga   8820
aaagagagac aattaccaga ttaaagtggt tgcatcagat catggtgaaa agatccagct   8880
atcctccaca gccattgtgg atgttaccgt caccgatgtc aacgatagtc caccacgatt   8940
cacggccgag atctataaag ggactgtgag tgaggatgac ccccaaggtg gggtgattgc   9000
catcttaagt accacggatg ctgattctga agagatcaac agacaagtta catatttcat   9060
aacaggaggg gatcctttag gacagtttgc cgttgaaact atacagaatg aatgaaggt    9120 atatgtgaag aaacctctag acagggaaaa aagggacaat taccttctta ctatcacggc   9180
aactgatggc accttctcat caaaagcgat agttgaagtg aaagttctgg atgcaaatga   9240
caacagtcca gtttgtgaaa agactttata ttcagacact attcctgaag acgtccttcc   9300
tggaaaattg atcatgcaga tctctgctac agacgcagac atccgctcta acgctgaaat   9360
tacttacacg ttattgggtt caggtgcaga aaaattcaaa ctaaatccag acacaggtga   9420
actgaaaacg tcaaccccccc ttgatcgtga ggagcaagct gtttatcatc ttctcgtcag   9480
ggccacagat ggaggaggaa gattctgcca agccagtatt gtgctcacgc tagaagatgt   9540
gaacgataac gccccccgaat tctctgccga tccttatgcc atcaccgtgt ttgaaaacac   9600
agagccggga acgctgctga caagagtgca ggccacagat gccgacgcag gattaaatcg   9660
gaagatttta tactcactga ttgactctgc tgatgggcag ttctccatta acgaattatc   9720
tggaattatt cagttagaaa aacctttgga cagagaactc caggcagtat acaccctctc   9780
tttgaaagct gtggatcaag gcttgccaag gaggctgact gccactggca ctgtgattgt   9840
atcagttctt gacataaatg acaaccccccc tgtgtttgag taccgtgaat atggtgccac   9900
cgtgtctgag gacattcttg ttggaactga agttcttcaa gtgtatgcag caagtcggga   9960
tattgaagca aatgcagaaa tcacctactc aataataagt ggaaatgaac atgggaaatt  10020
cagcatagat tctaaaacag nnnnnnnnnn nnnnnnnnnn nnnnnnnnnn nnnnnnnnnn  10080
nnnnnnnnnn nnnnnnnnnn nnnnnnnnnn nnnnnnnnnn nnnnnnnnnn nnnnnnnnnn  10140
nnnnnnnnnn nnnnnnnnnn nnnnnnnnnn nnnnnnnnnn nnnnnnnnnn nnnnnnnnnn  10200
nnnnnnnnnn nnnnnnnnnn nnnnnnnnnn nnnnnnnnnn nnnnnnnnnn nnnnnnnnnn  10260
nnnnnnnnnn nnnnnnnnnn nnnnnnnnnn nnnnnnnnnn nnnnnnnnnn nnnnnnnnnn  10320
nnnnnnnnnn nnnnnnnnnn nnnnnnnnnn nnnnnnnnnn nnnnnnnnnn nnnnnnnnnn  10380
nnnnnnnnnn nnnnnnnnnn nnnnnnnnnn nnnnnnnnnn nnnnnnnnnn nnnnnnnnnn  10440
nnnnnnnnnn nnnnnnnnnn nnnnnnnnnn nnnnnnnnnn nnnnnnnnnn nnnnnnnnnn  10500
nnnnnnnnnn nnnnnnnnnn nnnnnnnnnn nnnnnnngaa aataagccag tgggcttcag  10560
```

-continued

```
cgtgctgcag ctggtagtaa cagatgagga ttcttcccat aacgtccac ccttcttctt    10620 tactattgta actggaaatg atgagaaggc ttttgaagtt aacccgcaag gagtcctcct    10680
gacatcatct gccatcaaga ggaaggagaa agatcattac ttactgcagg tgaaggtggc    10740
agataatgga aagcctcagt tgtcatcttt gacatacatt gacattaggg taattgagga    10800
gagcatctat ccgcctgcga ttttgcccct ggagattttc atcacctctt ctggagaaga    10860
atactcaggt ggcgtcattg ggaagatcca tgccacagac caggacgtgt atgatactct    10920
aacctacagt ctcgaccctc agatggacaa cctgttctct gtttccagca caggggggcaa   10980 gctgatagca cacaaaaagc tagacatagg gcaatacctt ctcaatgtca gcgtaacaga    11040
tgggaagttc acgacggtgg ccgacatcac agtgcatatc agacaagtca cacaggagat    11100
gttgaaccac accatcgcga tccgctttgc caacctcact ccggaagaat tcgttggtga    11160
ctactggcgc aacttccagc gagctttacg gaacatcctg ggtgtgagga ggaacgacat    11220
acagattgtt agtttgcagt cctctgaacc tcacccacat ctggacgtct tactttttgt    11280
agagaaacca ggtagtgctc agatctcaac aaaacaactt ctgcacaaga ttaactcttc    11340
cgtgactgac attgaggaaa tcattggagt taggatactg aatgtattcc agaaactctg    11400
cgcgggactg gactgccct ggaagttctg cgatgaaaag gtgtctgtgg atgaaagtgt    11460
gatgtcaaca cacagcacag ccagactgag ttttgtgact ccccgccacc acagggcagc    11520
ggtgtgtctc tgcaaagagg gaaggtgccc acctgtccac catggctgtg aagatgatcc    11580
gtgccctgag ggatccgaat gtgtgtctga tccctgggag gagaaacaca cctgtgtctg    11640
tcccagcggc aggtttggtc agtgcccagg gagttcatct atgacactga ctggaaacag    11700
ctacgtgaaa taccgtctga cggaaaatga aaacaaatta gagatgaaac tgaccatgag    11760
gctcagaaca tattccacgc atgcggttgt catgtatgct cgaggaactg actatagcat    11820
cttggagatt catcatggaa ggtgcagtca annnnnnnnn nnnnnnnnnn nnnnnnnnnn    11880 nnnnnnnnn nnncattcag gtcaatgatg ggcagtggca cgcagtggcc ctggaagtga    11940
atggaaacta tgctcgcttg gttctagacc aagttcatac tgcatcgggc acagccccag    12000
ggactctgaa aaccctgaac ctggataact atgtgttttt tggtggccac atccgtcagc    12060
agggaacaag gcatggaaga agtcctcaag ttggtaatgg tttcagggggt tgtatggact   12120 ccatttattt gaatgggcag gagctcccctt taaacagcaa acccagaagc tatgcacaca    12180
tcgaagagtc ggtggatgta tctccaggct gcttcctgac ggccacgaaa gactgcgcca    12240
gcaacccttg ccagaatgga ggcgtttgca atccgtcacc tgctggaggt tattactgca    12300
aatgcagtgc cttgtacata gggacccact gtgagataag cgtcaatccg tgttcctcca    12360
agccatgcct ctatggggggc acgtgtgttg tcgacaacgg aggctttgtt tgccagtgta    12420
gaggattata tactggtcag aggtgtcagc ttagtccata ctgcaaagat gaaccctgta    12480
agaatggcgg aacatgcttt gacagtttgg atggcgccgt ttgtcagtgt gattcgggtt    12540 ttagggggaga aaggtgtcag agtgatatcg acgagtgctc tggaaaccct gcctgcacg    12600 gggcctctg tgagaacacg cacggctcct atcactgcaa ctgcagccac gagtacaggg    12660
gacgtcactg cgaggatgct gcgcccaacc agtatgtgtc cacgccgtgg aacattgggt    12720
tggcggaagt aattggaatc gttgtgtttg ttgcagggat atttttactg gtggtggtgt    12780
ttgttctctg ccgtaagatg attagtcgga aaaagaagca tcaggctgaa cctaaagaca    12840
agcacctggg acccgctacg gctttcttgc aaagaccgta ttttgattcc aagctaaata    12900
agaacattta ctcagacata ccacccagg tgcctgtccg gcctatttcc tacacccga    12960
```

-continued

```
gtattccaag tgactcaaga acaatctgg accgaaattc cttcgaagga tctgctatcc    13020
cagagcatcc cgaattcagc acttttaacc ccgagtctgt gcacgggcac cgaaaagcag    13080
tggcggtctg cagcgtggcg ccaaacctgc ctcccccacc cccttcaaac tccccttctg    13140
acagcgactc catccagaag cctagctggg actttgacta tgacacaaaa gtggtggatc    13200
ttgatccctg tctttccaag aagcctctag aggaaaagcc ttcccagcca tacagtgccc    13260
gggaaagcct gtctgaagtg cagtctctga gctccttcca gtccgaatcg tgcgatgaca    13320
atgggtatca ctgggataca tcagattgga tgccaagcgt tcctctgccg gacatacaag    13380
agttccccaa ctatgaggtg attgatgagc agacacccct gtactcagca gatccaaacg    13440
ccatcgatac ggactattac cctggaggct acgacatcga aagtgatttt cctccacccc    13500
cagaagactt ccccgcagct gatgagctac caccgttacc gcccgaattc agcaatcagt    13560
ttgaatccat ccaccctcct agagacatgc ctgccgcggg tagcttgggt tcttcatcaa    13620
gaaaccggca gaggttcaac ttgaatcagt atttgcccaa ttttatccc ctcgatatgt    13680 ctgaacctca acaaaaggc actggtgaga atagtacttg tagagaaccc catgccccctt   13740 acccgccagg gtatcaaaga cacttcgagg cgcccgctgt cgagagcatg cccatgtctg    13800
tgtacgcctc caccgcctcc tgctctgacg tgtcagcctg ctgcgaagtg gagtccgagg    13860
tcatgatgag tgactatgag agcggggacg acggccactt cgaagaggtg acgatcccgc    13920
ccctggattc ccagcagcac acggaagtct gactctcaac tccccccaaa gtgcctgact    13980
ttagtgaacc tagaggtgat gtgagtaatc cgcgctgttc tttgcagcag tgcttccaag    14040
ctttttttgg tgagccgaat gggcatggct gcgctggatc ctgcgcctct ggacgtgcta    14100
gccatttcca gtgtcccaac tactgtcatc gtgaggtttt catcggctgt gccatttccc    14160
aacgtctttt gggatttaca tctgtctgtg ttaaaataat caaacgaaaa atcagtcctg    14220
tgttgtcagc atgattcatg tatttatata gatttgatta ttttaatttt cctgtctctt    14280 tttttttgtaa attttatgta cagatttgat ttttcatagt tttaactaga tttccaagat    14340
attttgtgca tttgtttcaa ctgaatttg gtggtgtcag tgccattatc tagcaccctg    14400 atttttttt ttttactata accagggttt cattctgtct ttttccactg aagtgtgaca    14460
ttttgttagt acatttcagt gtagtcattc atttctagct gtacatagga tgaaggagag    14520
atcagataca tgaacatgtc ttacatgggt tgctgtattt agaattataa acatttttca    14580
ttattggaaa gtgtaacggg gaccttctgc atacctgttt agaaccaaaa ccaccatgac    14640
acagttttta tagtgtctgt atatttgtga tgcaatggtc ttgtaaaggt ttttaatgaa    14700
aactaccatt agccagtctt tcttactgac aataaattat taataaaat                14749
```

<210> SEQ ID NO 73
<211> LENGTH: 5508
<212> TYPE: DNA
<213> ORGANISM: Homo sapiens
<400> SEQUENCE: 73

```
gattttaggt gatgggcaag tcagaaagtc agatggatat aactgatatc aacactccaa      60
agccaaagaa gaaacagcga tggactccac tggagatcag cctctcggtc cttgtcctgc     120
tcctcaccat catagctgtg acaatgatcg cactctatgc aacctacgat gatggtattt     180
gcaagtcatc agactgcata aaatcagctg ctcgactgat ccaaacatg gatgccacca     240 ctgagccttg tacagacttt ttcaaatatg cttgcggagg ctggttgaaa cgtaatgtca     300
```

-continued

```
ttcccgagac cagctcccgt tacggcaact ttgacatttt aagagatgaa ctagaagtcg    360 tttttgaaaga tgtccttcaa gaacccaaaa ctgaagatat agtagcagtg cagaaagcaa    420
aagcattgta caggtcttgt ataaatgaat ctgctattga tagcagaggt ggagaacctc    480
tactcaaact gttaccagac atatatgggt ggccagtagc aacagaaaac tgggagcaaa    540 atatggtgc ttcttggaca gctgaaaaag ctattgcaca actgaattct aaatatggga    600 aaaagtcct tattaatttg tttgttggca ctgatgataa gaattctgtg aatcatgtaa    660
ttcatattga ccaacctcga cttggcctcc cttctagaga ttactatgaa tgcactggaa    720
tctataaaga ggcttgtaca gcatatgtgg attttatgat ttctgtggcc agattgattc    780
gtcaggaaga aagattgccc atcgatgaaa accagcttgc tttggaaatg aataaagtta    840
tggaattgga aaaagaaatt gccaatgcta cggctaaacc tgaagatcga aatgatccaa    900
tgcttctgta taacaagatg acattggccc agatccaaaa taacttttca ctagagatca    960
atgggaagcc attcagctgg ttgaatttca caaatgaaat catgtcaact gtgaatatta   1020
gtattacaaa tgaggaagat gtggttgttt atgctccaga atatttaacc aaacttaagc   1080
ccattcttac caaatattct gccagagatc ttcaaaattt aatgtcctgg agattcataa   1140
tggatcttgt aagcagcctc agccgaacct acaaggagtc cagaaatgct ttccgcaagg   1200 cccctttatgg tacaacctca gaaacagcaa cttggagacg ttgtgcaaac tatgtcaatg   1260
ggaatatgga aaatgctgtg gggaggcttt atgtggaagc agcatttgct ggagagagta   1320
aacatgtggt cgaggatttg attgcacaga tccgagaagt ttttattcag actttagatg   1380
acctcacttg gatggatgcc gagacaaaaa agagagctga agaaaaggcc ttagcaatta   1440
aagaaaggat cggctatcct gatgacattg tttcaaatga taacaaactg aataatgagt   1500
acctcgagtt gaactacaaa gaagatgaat acttcgagaa cataattcaa aatttgaaat   1560
tcagccaaag taaacaactg aagaagctcc gagaaaaggt ggacaaagat gagtggataa   1620
gtggagcagc tgtagtcaat gcattttact cttcaggaag aaatcagata gtcttcccag   1680
ccggcattct gcagcccccc ttctttagtg cccagcagtc caactcattg aactatgggg   1740
gcatcggcat ggtcatagga cacgaaatca cccatggctt cgatgacaat ggcagaaact   1800
ttaacaaaga tggagacctc gttgactggt ggactcaaca gtctgcaagt aactttaagg   1860
agcaatccca gtgcatggtg tatcagtatg aaacttttc ctgggacctg gcaggtggac   1920
agcaccttaa tggaattaat acactgggag aaaacattgc tgataatgga ggtcttggtc   1980
aagcatacag agcctatcag aattatatta aaaagaatgg cgaagaaaaa ttacttcctg   2040
gacttgacct aaatcacaaa caactatttt tcttgaactt tgcacaggtg tggtgtggaa   2100
cctataggcc agagtatgcg gttaactcca ttaaaacaga tgtgcacagt ccaggcaatt   2160
tcaggattat tgggactttg cagaactctg cagagttttc agaagccttt cactgccgca   2220
agaattcata catgaatcca gaaaagaagt gccgggtttg tgatcttca aaagaagcat   2280 tgcagccctt ggctagactt gccaacacca cagaaatggg gaattctcta atcgaaagaa   2340
aatgggccct agggtcact gtactgactt gagggtgatt aacagagagg gcaccatcac   2400
aatacagata acattaggtt gtcctagaaa gggtgtggag ggaggaaggg ggtctaaggt   2460
ctatcaagtc aatcatttct cactgtgtac ataatgctta atttctaaag ataatattac   2520 tgttttatttc tgtttctcat atggtctacc agtttgctga tgtccctaga aacaatgca    2580 aaaccttga ggtagaccag gatttctaat caaaagggaa aagaagatgt tgaagaatac   2640
agttaggcac cagaagaaca gtaggtgaca ctatagttta aaacacattg cctaactact   2700
```

```
agtttttact tttatttgca acatttacag tccttcaaaa tccttccaaa gaattcttat   2760
acacattggg gccttggagc ttacatagtt ttaaactcat ttttgccata catcagttat   2820
tcattctgtg atcatttatt ttaagcactc ttaaagcaaa aaatgaatgt ctaaaattgt   2880 ttttgttgt acctgctttg actgatgctg agattcttca ggcttcctgc aattttctaa   2940
gcaatttctt gctctatctc tcaaaacttg gtatttttca gagatttata taaatgtaaa   3000
aataataatt tttatattta attattaact acatttatga gtaactatta ttataggtaa   3060
tcaatgaata ttgaagtttc agcttaaaat aaacagttgt gaaccaagat ctataaagcg   3120
atatacagat gaaaatttga gactatttaa acttataaat catattgatg aaaagattta   3180
agcacaaact ttagggtaaa aattgccatt ggacagttgt ctagagatat atatacttgt   3240
ggttttcaaa ttggactttc aaaattaaat ctgtccctga gagtgtctct gataaaaggg   3300
caaatctgca cctatgtagc tctgcatctc ctgtcttttc aggtttgtca tcagatggaa   3360
atattttgat aataaattga aattgtgaac tcattgctcc ctaagactgt gacaactgtc   3420
taactttaga agtgcatttc tgaatagaaa tgggaggcct ctgatggacc ttctagaatt   3480
ataagtcaca aagagttctg gaaaagaact gtttactgct tgataggaat tcatcttttg   3540
aggcttctgt tcctctcttt tcctgttgta ttgactattt tcgttcatta cttgattaag   3600
attttacaaa agaggagcac ttccaaaatt cttatttttc ctaacaaaag atgaaagcag   3660
ggaatttcta tctaaatgat gagtattagt tccctgtctc ttgaaaaatg cccatttgcc   3720
tttaaaaaaa aagttacag aaatactata acatatgtac ataaattgca taaagcataa   3780
gtatacagtt caataaactt aactttaact gaacaatggc cctgtagcca gcacctgtaa   3840
gaaacagagc agtaccagcg ctctaaaagc acctccttgt cactttatta ctcccagaac   3900
aacaactatc ctgacttcta atatcattca ctagctttgc ctggttttgt cttttatgca   3960
gatagaatca atcagtatgt attcttttgt gcctggcttc tttctctcag ccttacattt   4020
gtgagattcc tctgtattgt gctgattgtg gatcttttca ttctcattgc agaataatgt   4080
tctattgtgg gacttattac aatttgttca tcctattgtt gatgggcact tgagaacttt   4140 ccatttggc gctattacaa atagtgcaac tatgaatgta ctgcatgtta ccatcttact   4200
tgagccttta atggacttat ttcttcaaat ccttccaaaa attattataa gcattgaaat   4260
tatagtttca agccaactgt ggatacccctt acccttccct cctttatcac aaccaccgtt   4320
acaagtatac ttatatttcc ctaaaataca tttaaaactt acctaagtga catttgtagt   4380
tggagtaata ggagcttcca gctctaataa aacagctgtc tctaacttat tttatttcca   4440
tcatgtcaga gcaggtgaag agccagaagt gaagagtgac tagtacaaat tataaaaagc   4500
cactagactc ttcactgtta gcttttttaaa acattaggct cccatcccta tggaggaaca   4560
actctccagt gcctggatcc cctctgtcta caaatataag attttctggg cctaaaggat   4620
agatcaaagt caaaaatagc aatgcctccc tatccctcac acatccagac atcatgaatt   4680
ttacatggta ctcttgttga gttctgtaga gccttctgat gtctctaaag cactaccgat   4740
tctttggagt tgtcacatca gataagacat atctctaatt ccatccataa atccagttct   4800
actatggctg agttctggtc aaagaaagaa agtttagaag ctgagacaca aagggttggg   4860
agctgatgaa actcacaaat gatggtagga agaagctctc gacaataccc gttggcaagg   4920
agtctgcctc catgctgcag tgttcgagtg gattgtaggt gcaagatgga aaggattgta   4980
ggtgcaagct gtccagagaa aagagtcctt gttccagccc tattctgcca ctcctgacag   5040
```

```
ggtgaccttg ggtatttgca atattccttt gggcctctgc ttctctcacc taaaaaaaga      5100
gaattagatt atattggtgg ttctcagcaa gagaaggagt atgtgtccaa tgctgccttc      5160
ccatgaatct gtctcccagt tatgaatcag tgggcaggat aaactgaaaa ctcccattta      5220
cgtgtctgaa tcgagtgaga caaaatttta gtccaaataa caagtaccaa agttttatca      5280
agtttgggtc tgtgctgctg ttactgttaa ccatttaagt ggggcaaaac cttgctaatt      5340
ttctcaaaag catttatcat tcttgttgcc acagctggag ctctcaaact aaaagacatt      5400
tgttattttg gaaagaagaa agactctatt ctcaaagttt cctaatcaga aatttttatc      5460
agtttccagt ctcaaaaata caaaataaaa acaaacgttt ttaatact                   5508

<210> SEQ ID NO 74
<211> LENGTH: 1495
<212> TYPE: DNA
<213> ORGANISM: Homo sapiens

<400> SEQUENCE: 74
atgtccaatc agggaagtaa gtacgtcaat aaggaaattc aaaatgctgt caacggggtg        60
aaacagataa agactctcat agaaaaaaca acgaagagc gcaagacact gctcagcaac       120
ctagaagaag ccaagaagaa gaaagaggat gccctaaatg agaccaggga atcagagaca       180
aagctgaagg agctcccagg agtgtgcaat gagaccatga tggccctctg ggaagagtgt       240
aagccctgcc tgaaacagac ctgcatgaag ttctacgcac gcgtctgcag aagtggctca       300
ggcctggttg ccgccagct tgaggagttc ctgaaccaga gctcgccctt ctacttctgg       360
atgaatggtg accgcatcga ctccctgctg agaacgacc ggcagcagac gcacatgctg       420
gatgtcatgc aggaccactt cagccgcgcg tccagcatca tagacgagct cttccaggac       480
aggttcttca cccgggagcc ccaggatacc taccactacc tgcccttcag cctgccccac       540
cggaggcctc acttcttctt tcccaagtcc cgcatcgtcc gcagcttgat gcccttctct       600
ccgtacgagc ccctgaactt ccacgccatg ttccagccct ccttgagat gatacacgag       660 gctcagcagg ccatggacat ccacttccat agcccggcct tccagcaccc gccaacagaa       720
ttcatacgag aaggcgacga tgaccggact gtgtgccggg agatccgcca caactccacg       780
ggctgcctgc ggatgaagga ccagtgtgac aagtgccggg agatcttgtc tgtggactgt       840
tccaccaaca cccctccca ggctaagctg cggcgggagc tcgacgaatc cctccaggtc       900
gctgagaggt tgaccaggaa atacaacgag ctgctaaagt cctaccagtg gaagatgctc       960
aacacctcct ccttgctgga gcagctgaac gagcagttta ctgggtgtc ccggctggca      1020 aacctcacgc aaggcgaaga ccagtactat ctgcgggtca ccacggtggc ttcccacact      1080
tctgactcgg acgttccttc cggtgtcact gaggtggtcg tgaagctctt tgactctgat      1140
cccatcactg tgacggtccc tgtagaagtc tccaggaaga accctaaatt tatgagacc      1200 gtggcggaga aagcgctgca ggaataccgc aaaaagcacc gggaggagtg agatgtggat      1260
gttgcttttg cacctacggg ggcatctgag tccagctccc ccaagatga gctgcagccc      1320 cccagagaga gctctgcacg tcaccaagta accaggcccc agcctccagg ccccaactc      1380 cgcccagcct ctccccgctc tggatcctgc actctaacac tcgactctgc tgctcatggg      1440
aagaacagaa ttgctcctgc atgcaactaa ttcaataaaa ctgtcttgtg agctg          1495

<210> SEQ ID NO 75
<211> LENGTH: 967
<212> TYPE: DNA
<213> ORGANISM: Homo sapiens
```

<400> SEQUENCE: 75

```
gaaggaaaaa gagcaacaga tccagggagc attcacctgc cctgtctcca acagccttg      60
tgcctcacct accccaacc tcccagaggg agcagctatt aaggggagc aggagtgcag      120
aacaaacaag acggcctggg gatacaactc tggagtcctc tgagagagcc accaaggagg    180
agcaggggag cgacggccgg ggcagaagtt gagaccaccc agcagaggag ctaggccagt    240
ccatctgcat ttgtcaccca agaactctta ccatgaagac cctcctactg ttggcagtga    300
tcatgatctt tggcctactg caggcccatg ggaatttggt gaatttccac agaatgatca    360
agttgacgac aggaaaggaa gccgcactca gttatggctt ctacggctgc cactgtggcg    420
tgggtggcag aggatccccc aaggatgcaa cggatcgctg ctgtgtcact catgactgtt    480
gctacaaacg tctggagaaa cgtggatgtg gcaccaaatt tctgagctac aagtttagca    540
actcggggag cagaatcacc tgtgcaaaac aggactcctg cagaagtcaa ctgtgtgagt    600
gtgataaggc tgctgccacc tgttttgcta gaaacaagac gacctacaat aaaaagtacc    660
agtactattc caataaacac tgcagaggga gcacccctcg ttgctgagtc ccctcttccc    720
tggaaacctt ccacccagtg ctgaatttcc ctctctcata ccctccctcc ctaccctaac    780
caagttcctt ggccatgcag aaagcatccc tcacccatcc tagaggccag gcaggagccc    840
ttctataccc acccagaatg agacatccag cagatttcca gccttctact gctctcctcc    900
acctcaactc cgtgcttaac caaagaagct gtactccggg gggtctcttc tgaataaagc    960
aattagc                                                               967
```

<210> SEQ ID NO 76
<211> LENGTH: 2515
<212> TYPE: DNA
<213> ORGANISM: Homo sapiens

<400> SEQUENCE: 76

```
gctccatcaa gtatgatggt gaaggatgaa tatgtgcatg actttgaggg acagccatcg    60
ttgtccactg aaggacattc aattcaaacc atccagcatc caccaagtaa tcgtgcatcg    120
acagagacat acagcacccc agctctgtta gccccatctg agtctaatgc taccagcact    180
gccaactttc ccaacattcc tgtggcttcc acaagtcagc ctgccagtat actgggggc    240
agccatagtg aaggactgtt gcagatagca tcagggcctc agccaggaca gcagcagaat    300
ggatttactg gtcagccagc tacttaccat cataacagca ctaccacctg gactggaagt    360
aggactgcac catacacacc taatttgcct caccaccaaa acggccatct tcagcaccac    420
ccgcctatgc cgccccatcc cggacattac tggcctgttc acaatgagct tgcattccag    480
cctcccattt ccaatcatcc tgctcctgag tattggtgtt ccattgctta ctttgaaatg    540
gatgttcagg taggagagac atttaaggtt ccttcaagct gccctattgt tactgttgat    600
ggatacgtgg acccttctgg aggagatcgc ttttgtttgg gtcaactctc caatgtccac    660
aggacagaag ccattgagag agcaaggttg cacataggca aaggtgtgca gttggaatgt    720
aaaggtgaag gtgatgtttg ggtcaggtgc cttagtgacc acgcggtctt tgtacagagt    780
tactacttag acagagaagc tgggcgtgca cctggagatg ctgttcataa gatctaccca    840
agtgcatata taaaggtctt tgatttgcgt cagtgtcatc gacagatgca gcagcaggcg    900
gctactgcac aagctgcagc agctgcccag gcagcagccg tggcaggaaa catccctggc    960
ccaggatcag taggtggaat agctccagct atcagtctgt cagctgctgc tggaattggt   1020
```

-continued

```
gttgatgacc ttcgtcgctt atgcatactc aggatgagtt ttgtgaaagg ctggggaccg    1080
gattacccaa gacagagcat caaagaaaca ccttgctgga ttgaaattca cttacaccgg    1140
gccctccagc tcctagacga agtacttcat accatgccga ttgcagaccc acaacctta    1200
gactgaggtc ttttaccgtt ggggccctta accttatcag gatggtggac tacaaaatac    1260
aatcctgttt ataatctgaa gatatatttc acttttgttc tgctttatct tttcataaag    1320
ggttgaaaat gtgtttgctg ccttgctcct agcagacaga aactggatta aaacaattt    1380
tttttttcctc ttcagaactt gtcaggcatg gctcagagct tgaagattag gagaaacaca    1440
ttcttattaa ttcttcacct gttatgtatg aaggaatcat tccagtgcta gaaaatttag    1500
cccttaaaaa cgtcttagag cctttttatct gcagaacatc gatatgtata tcattctaca    1560
gaataatcca gtattgctga ttttaaaggc agagaagttc tcaaagttaa ttcacctatg    1620
ttattttgtg tacaagttgt tattgttgaa catacttcaa aaataatgtg ccatgtgggt    1680
gagttaattt taccaagagt aactttactc tgtgtttaaa aagtaagtta ataatgtatt    1740
gtaatctttc atccaaaata ttttttgcaa gttatattag tgaagatggt ttcaattcag    1800
attgtcttgc aacttcagtt ttattttgc caaggcaaaa aactcttaat ctgtgtgtat    1860
attgagaatc ccttaaaatt accagacaaa aaatttaaa attacgtttg ttattcctag    1920
tggatgactg ttgatgaagt atacttttcc cctgttaaac agtagttgta ttcttctgta    1980
tttctaggca caaggttggt tgctaagaag cctataagag gaatttcttt tccttcattc    2040
atagggaaag gttttgtatt ttttaaaaca ctaaaagcag cgtcactcta cctaatgtct    2100
cactgttctg caaaggtggc aatgcttaaa ctaaataatg aataaactga atattttgga    2160
aactgctaaa ttctatgtta aatactgtgc agaataatgg aaacattaca gttcataata    2220
ggtagtttgg atatttttgt acttgatttg atgtgacttt ttttggtata atgtttaaat    2280
catgtatgtt atgatattgt ttaaaattca gttttttgtat cttggggcaa gactgcaaac    2340
tttttttatat cttttggtta ttctaagccc tttgccatca atgatcatat caattggcag    2400
tgactttgta tagagaattt aagtagaaaa gttgcagatg tattgactgt accacagaca    2460
caatatgtat gcttttacc tagctggtag cataaataaa actgaatctc aacat         2515
```

<210> SEQ ID NO 77
<211> LENGTH: 2017
<212> TYPE: DNA
<213> ORGANISM: Homo sapiens

<400> SEQUENCE: 77

```
gcaggcccgt tggaagtggt tgtgacaacc ccagcaatgt ggagaagcct ggggcttgcc      60
ctggctctct gtctcctccc atcgggagga acagagagcc aggaccaaag ctccttatgt     120
aagcaacccc cagcctggag cataagagat caagatccaa tgctaaactc caatggttca     180
gtgactgtgg ttgctcttct tcaagccagc tgatacctgt gcatactgca ggcatctaaa     240
ttagaagacc tgcgagtaaa actgaagaaa gaaggatatt ctaatatttc ttatattgtt     300
gttaatcatc aaggaatctc ttctcgatta aaatacacac atcttaagaa taaggtttca     360
gagcatattc ctgtttatca acaagaagaa aaccaaacag atgtctggac tcttttaaat     420
ggaagcaaag atgacttcct catatatgat agatgtggcc gtcttgtata tcatcttggt     480
ttgcctttt ccttcctaac tttcccatat gtagaagaag ccattaagat tgcttactgt     540
gaaaagaaat gtgaaactg ctctctcacg actctcaaag atgaagactt ttgtaaacgt     600
gtatctttgg ctactgtgga taaaacagtt gaaactccat cgcctcatta ccatcatgag     660
```

| | |
|---|---|
| catcatcaca atcatggaca tcagcacctt ggcagcagtg agctttcaga gaatcagcaa | 720 |
| ccaggagcac caaatgctcc tactcatcct gctcctccag gccttcatca ccaccataag | 780 |
| cacaagggtc agcataggca gggtcaccca gagaaccgag atatgccagc aagtgaagat | 840 |
| ttacaagatt tacaaagaa gctctgtcga aagagatgta taaatcaatt actctgtaaa | 900 |
| ttgcccacag attcagagtt ggctcctagg agctgatgct gccattgtcg acatctgata | 960 |
| tttgaaaaaa cagggtctgc aatcacctga cagtgtaaag aaaacctccc atctttatgt | 1020 |
| agctgacagg gacttcgggc agaggagaac ataactgaat cttgtcagtg acgtttgcct | 1080 |
| ccagctgcct gacaaataag tcagcagctt atacccacag aagccagtgc cagttgacgc | 1140 |
| tgaaagaatc aggcaaaaaa gtgagaatga ccttcaaact aaatatttaa ataggacat | 1200 |
| actccccaat ttagtctaga cacaatttca tttccagcat ttttataaac taccaaatta | 1260 |
| gtgaaccaaa aatagaaatt agatttgtgc aaacatggag aaatctactg aattggcttc | 1320 |
| cagattttaa attttatgtc atagaaatat tgactcaaac catatttttt atgatggagc | 1380 |
| aactgaaagg tgattgcagc ttttggttaa tatgtctttt tttttctttt tccagtgttc | 1440 |
| tatttgcttt aatgagaata gaaacgtaaa ctatgaccta ggggtttctg ttggataatt | 1500 |
| agcagtttag aatggaggaa gaacaacaaa gacatgcttt ccattttttt ctttacttat | 1560 |
| ctctcaaaac aatattactt tgtcttttca atcttctact tttaactaat aaaataagtg | 1620 |
| gattttgtat tttaagatcc agaaatactt aacacgtgaa tattttgcta aaaaagcata | 1680 |
| tataactatt ttaaatatcc atttatcttt tgtatatcta agactcatcc tgattttac | 1740 |
| tatcacacat gaataaagcc tttgtatctt tctttctcta atgttgtatc atactcttct | 1800 |
| aaaacttgag tggctgtctt aaaagatata aggggaaaga taatattgtc tgtctctata | 1860 |
| ttgcttagta agtatttcca tagtcaatga tggtttaata ggtaaaccaa accctataaa | 1920 |
| cctgacctcc tttatggtta atactattaa gcaagaatgc agtacagaat tggatacagt | 1980 |
| acggatttgt ccaaataaat tcaataaaaa ccttaaa | 2017 |

<210> SEQ ID NO 78
<211> LENGTH: 1468
<212> TYPE: DNA
<213> ORGANISM: Homo sapiens

<400> SEQUENCE: 78

| | |
|---|---|
| caaccacttg acaacctggt tagaagatgc ccgccagcat tccaattcca acatggtcat | 60 |
| tatgcttatt ggaaataaaa gtgatttaga atctagaaga gaagtaaaaa agaagaagg | 120 |
| tgaagctttt gcacgagaac atggactcat cttcatggaa acgtctgcta agactgcttc | 180 |
| caatgtagaa gaggcattta ttaatacagc aaaagaaatt tatgaaaaaa ttcaagaagg | 240 |
| agtctttgac attaataatg aggcaaatgg cattaaaatt ggccctcagc atgctgctac | 300 |
| caatgcaaca catgcaggca atcagggagg acagcaggct gggggcggct gctgttgagt | 360 |
| ctgttttttac tgtctagctg cccaacgggg cctactcact tattctttca cccctctcc | 420 |
| tcctgctcag ctgagacatg aaactatttg aaatggcttt atgtcacaga agactttaat | 480 |
| ccgtcaaatt cttgtataac tttgaataaa tggttaatgt tcacttaaaa gacagatttt | 540 |
| ggagattgta ttcatatcta tttgcatttg atttctaggt caattgatgt gattattttt | 600 |
| gttaaatgtt gtcttgtgcc cttaactacg aactgaattg tattaaacac tacaaagtca | 660 |
| tcttgagtat tttaaatcgg tttgtgtagt taggtttccc aacatctgtg gttacctaat | 720 |

```
gtttaatatt atagaactgt cctcagaaac tttgtcaatt ttcacggcta taaggaaaca    780
gaaggactct tttaattctg tatttatcat ttactttctg tatatatagt ttaataacct    840
gcttgggtgt aatttgccaa gcttgaattc tttaatgcat ttgcataaat tctatactgt    900
ttagagctta aagctacaga agcattgtta ggaattgctt ggacactgaa ttttaaactt    960
tttgacattg ttaacaagca tgttcatctt ttcttgtcac tagtccaaga aaaatatgct   1020
taatgtatat tacaaaggct ttgtatatgt taacctgttt taatgccaaa agtttgcttt   1080
gtccacaatt tccttaagac ctcttcagaa agggatttgt ttgccttaat gaatactgtt   1140
gggaaaaaac acagtataat gagtgaaaag ggcagaagca agaaatttct acatcttagc   1200
gactccaaga agaatgagta tccacattta gatggcacat tatgaggact ttaatctttc   1260
cttaaacaca ataatgtttt cttttttctt ttattcacat gatttctaag tatattttc    1320
atgcaggaca gttttttcaac cttgatgtac agtgactgtg taaaatttt ctttcagtgg    1380
caacctctat aatctttaaa atatggtgag catcttgtct gttttgaagg ggatatgaca   1440
ataaatctat cagatggaaa atcctgtt                                      1468
```

<210> SEQ ID NO 79
<211> LENGTH: 3590
<212> TYPE: DNA
<213> ORGANISM: Homo sapiens

<400> SEQUENCE: 79

```
cctgggtctg acgcggccct gttcgagggg gcctctcttg tttatttatt tattttccgt      60
gggtgcctcc gagtgtgcgc gcgctctcgc tacccggcgg ggagggggtg ggggagggc     120
ccgggaaaag ggggagttgg agccggggtc gaaacgccgc gtgacttgta ggtgagagaa    180
cgccgagccg tcgccgcagc ctccgccgcc gagaagccct tgttcccgct gctgggaagg    240
agagtctgtg ccgacaagat ggcggacggg gagctgaacg tggacagcct catcacccgg    300
ctgctggagg tacgaggatg tcgtccagga aagattgtgc agatgactga agcagaagtt    360
cgaggcttat gtatcaagtc tcgggagatc tttctcagcc agcctattct tttggaattg    420
gaagcaccgc tgaaaatttg tggagatatt catggacaat atacagattt actgagatta    480
tttgaatatg gaggtttccc accagaagcc aactatcttt tcttaggaga ttatgtggac    540
agaggaaagc agtctttgga aaccatttgt ttgctattgg cttataaaat caaatatcca    600
gagaacttct ttctcttaag aggaaaccat gagtgtgcta gcatcaatcg catttatgga    660
ttctatgatg aatgcaaacg aagatttaat attaaattgt ggaagacctt cactgattgt    720
tttaactgtc tgcctatagc agccattgtg gatgagaaga tcttctgttg tcatggagga    780
ttgtcaccag acctgcaatc tatggagcag attcggagaa ttatgagacc tactgatgtc    840
cctgatacag gtttgctctg tgatttgcta tggtctgatc cagataagga tgtgcaaggc    900
tggggagaaa atgatcgtgg tgtttccttt acttttggag ctgatgtagt cagtaaattt    960
ctgaatcgtc atgatttaga tttgatttgt cgagctcatc aggtggtgga agatggatat   1020
gaatttttg ctaaacgaca gttggtaacc ttattttcag cccaaatta ctgtggcgag    1080
tttgataatg ctggtggaat gatgagtgtg gatgaaactt tgatgtgttc atttcagata   1140
ttgaaaccat ctgaaaagaa agctaaatac cagtatggtg gactgaattc tggacgtcct   1200
gtcactccac ctcgaacagc taatccgccg aagaaaaggt gaagaaagga attctgtaaa   1260
gaaaccatca gatttgttaa ggacatactt cataatatat aagtgtgcac tgtaaaacca   1320
tccagccatt tgacacccct tatgatgtca cacctttaac ttaaggagac gggtaaagga   1380
```

```
tcttaaattt ttttctaata gaaagatgtg ctacactgta ttgtaataag tatactctgt   1440
tatagtcaac aaagttaaat ccaaattcaa aattatccat taaagttaca tcttcatgta   1500
tcacaatttt taaagttgaa aagcatccca gttaaactag atgtgatagt taaaccagat   1560
gaaagcatga tgatccatct gtgtaatgtg gttttagtgt tgcttggttg tttaattatt   1620
ttgagcttgt tttgtttttg tttgttttca ctagaataat ggcaaatact tctaattttt   1680
ttccctaaac attttttaaaa gtgaaatatg ggaagagctt tacagacatt caccaactat   1740
tattttccct tgtttatcta cttagatatc tgtttaatct tactaagaaa actttcgcct   1800
cattacatta aaaaggaatt ttagagattg attgttttaa aaaaaaatac gcacattgtc   1860
caatccagtg attttaatca tacagtttga ctgggcaaac tttacagctg atagtgaata   1920
ttttgcttta tacaggaatt gacactgatt tggatttgtg cactctaatt tttaacttat   1980
tgatgctcta ttgtgcagta gcatttcatt taagataagg ctcatatagt attacccaac   2040
tagttggtaa tgtgattatg tggtaccttg gctttaggtt ttcattcgca cggaacacct   2100
tttggcatgc ttaacttcct ggtaacacct tcacctgcat tggttttctt tttcttttt   2160 cttctttttt tttttttttt ttttttttga gttgttgttt gttttttagat ccacagtaca   2220 tgagaatcct tttttgacaa gccttggaaa gctgacactg tctcttttc ctccctctat   2280 acgaaggatg tatttaaatg aatgctggtc agtgggacat tttgtcaact atgggtattg   2340
ggtgcttaac tgtctaatat tgccatgtga atgttgtata cgattgtaag gcttatgtca   2400
ctaaagattt ttattctgat ttttttcataa tcaaaggtca tatgatactg tatagacaag   2460
ctttgtagtg aagtatagta gcaataattt ctgtacctga tcaagtttat tgcagccttt   2520
cttttcctat ttctttttt taagggttag tattaacaaa tggcaatgag tagaaaagtt   2580
aacatgaaga tttttagaagg agagaactta caggacacag atttgtgatt ctttgactgt   2640
gacactattg gatgtgattc taaaagcttt tattgagcat tgtcaaattt gtaagcttca   2700
tagggatgga catcatatct ataatgccct tctatatgtg ctaccataga tgtgacattt   2760
ttgaccttaa tatcgtcttt gaaaatgtta aattgagaaa cctgttaact tacattttat   2820
gaattggcac attgtattac ttactgcaag agatatttca ttttcagcac agtgcaaaag   2880
ttctttaaaa tgcatatgtc ttttttttcta attccgtttt gttttaaagc acattttaaa   2940
tgtagttttc tcatttagta aaagttgtct aattgatatg aagcctgact gattttttt   3000 ttccttacag tgagacattt aagcacacat tttattcaca tagatactat gtccttgaca   3060
tattgaaatg attcttttct gaaagtattc atgatctgca tatgatgtat taggttaggt   3120
cacaaaggtt ttatctgagg tgatttaaat aacttcctga ttggagtgtg taagctgagc   3180
gatttctaat aaaatttag ttgtacactt ttagtagtca tagtgaagca ggtctagaaa   3240
ataagccttt ggcagggaaa aagggcaatg ttgattaatc tcagtattaa accacattaa   3300
tctgtatccc attgtctggc ttttgtaaat tcatccaggt caagactaag tatgttggtt   3360
aataggaatc ctttttttt tttaaagact aaatgtgaaa aaataatcac tacttaagct   3420
aattaatatt ggtcattaaa tttaaaggat ggaaatttat catgtttaaa aattattcaa   3480
gcactcttaa aaccacttaa acagcctcca gtcataaaaa tgtgttcttt acaaatattt   3540
gcttggcaac acgacttgaa ataaataaaa ctttgtttct taggagaaaa              3590
```

<210> SEQ ID NO 80
<211> LENGTH: 1750
<212> TYPE: DNA

<213> ORGANISM: Homo sapiens

<400> SEQUENCE: 80

```
gcaacctgcc ccattatccc tggctgcgaa acaaccatcg agatttccaa agggcgaaca      60
gggctgggcc tgagcatcgt tggggttca  gacacgctgc tgggtgccat tattatccat    120
gaagtttatg aagaaggagc agcatgtaaa gatggaagac tctgggctgg agatcagatc    180
ttagaggtga atggaattga cttgagaaag gccacacatg atgaagcaat caatgtcctg    240
agacagacgc cacagagagt gcgcctgaca ctctacagag atgaggcccc atacaaagag    300
gaggaagtgt gtgacaccct cactattgag ctgcagaaga agccgggaaa aggcctagga    360
ttaagtattg ttggtaaaag aaacgatact ggagtatttg tgtcagacat tgtcaaagga    420
ggaattgcag atgccgatgg aagactgatg cagggagacc agatattaat ggtgaatggg    480
gaagacgttc gtaatgccac ccaagaagcg gttgccgctt tgctaaagtg ttccctaggc    540
acagtaacct ggaagttgg  aagaatcaaa gctggtccat tccattcaga gaggaggcca    600
tctcaaagca gccaggtgag tgaaggcagc ctgtcatctt tcacttttcc actctctgga    660
tccagtacat ctgagtcact ggaaagtagc tcaaagaaga atgcattggc atctgaaata    720
cagggattaa gaacagtcga atgaaaaag  ggccctactg actcactggg aatcagcatt    780
gctggaggag taggcagccc acttggtgat gtgcctatat ttattgcaat gatgcaccca    840
actggagttg cagcacagac ccaaaaactc agagttgggg ataggattgt caccatctgt    900
ggcacatcca ctgagggcat gactcacacc caagcagtta acctactgaa aaatgcatct    960
ggctccattg aaatgcaggt ggttgctgga ggagacgtga gtgtggtcac aggtcatcag   1020
caggagcctg caagttccag tctttctttc actgggctga cgtcaagcag tatatttcag   1080
gatgatttag gacctcctca atgtaagtct attacactag agcgaggacc agatggctta   1140
ggcttcagta tagttggagg atatggcagc cctcatggag acttaccat  ttatgttaaa   1200
acagtgtttg caagggagc  agcctctgaa gacggacgtc tgaaagggg  cgatcagatc   1260
attgctgtca atggcagag  tctagaagga gtcacccatg aagaagctgt tgccatcctt   1320
aaacggacaa aaggcactgt cactttgatg gttctctctt gaattggctg ccagaattga   1380
accaacccaa ccctagctc  acctcctact gtaaagagaa tgcactggtc ctgacaattt   1440
ttatgctgtg ttcagccggg tcttcaaaac tgtagggggg aaataacact taagtttctt   1500
tttctcatct agaaatgctt tccttactga caacctaaca tcattttct ttcttcttg    1560
cattttgtga acttaaagag aaggaatatt tgtgtaggtg aatctcgttt ttatttgtgg   1620
agatatctaa tgttttgtag tcacatgggc aagaattatt acatgctaag ctggttagta   1680
taaagaaaga taattctaaa gctaaccaaa gaaaatggct tcagtaaatt aggatgaaaa   1740
atgaaaatat                                                         1750
```

<210> SEQ ID NO 81
<211> LENGTH: 3254
<212> TYPE: DNA
<213> ORGANISM: Homo sapiens

<400> SEQUENCE: 81

```
ggagcgcaat ggcgtccaac cccgaacggg gggagattct gctcacggaa ctgcagggg      60
attcccgaag tcttccgttt tctgagaatg tgagtgctgt tcaaaaatta gacttttcag    120
atacaatggt gcagcagaaa ttggatgata tcaaggatcg aattaagaga gaaataagga    180
aagaactgaa aatcaaagaa ggagctgaaa atctgaggaa agtcacaaca gataaaaaaa    240
```

```
gtttggctta tgtagacaac attttgaaaa aatcaaataa aaaattagaa gaactacatc    300
acaagctgca ggaattaaat gcacatattg ttgtatcaga tccagaagat attacagatt    360
gcccaaggac tccagatact ccaaataatg accctcgttg ttctactagc aacaatagat    420
tgaaggcctt acaaaaacaa ttggatatag aacttaaagt aaaacaaggt gcagagaata    480
tgatacagat gtattcaaat ggatcttcaa aggatcggaa actccatggt acagctcagc    540
aactgctcca ggacagcaag acaaaaatag aagtcatacg aatgcagatt cttcaggcag    600
tccagactaa tgaattggct tttgataatg caaaacctgt gataagtcct cttgaacttc    660
ggatggaaga attaaggcat cattttagga tagagtttgc agtagcagaa ggtgcaaaga    720
atgtaatgaa attacttggc tcaggaaaag taacagacag aaaagcactt tcagaagctc    780
aagcaagatt taatgaatca agtcagaagt tggaccttTT aaagtattca ttagagcaaa    840
gattaaacga agtccccaag aatcatccca aaagcaggat tattattgaa gaactttcac    900
ttgttgctgc atcaccaaca ctaagtccac gtcaaagtat gatatctacg caaaatcaat    960
atagtacact atccaaacca gcagcactaa caggtacttt ggaagttcgt cttatgggct   1020
gccaagatat cctagagaat gtccctggac ggtcaaaagc aacatcagtt gcactgcctg   1080
gttggagtcc aagtgaaacc agatcatctt tcatgagcag aacgagtaaa agtaaaagcg   1140
gaagtagtcg aaatcttcta aaaccgatg acttgtccaa tgatgtctgt gctgttttga   1200
agctcgataa tactgtggtt ggccaaacta gctggaaacc catttccaat cagtcatggg   1260
accagaagtt tacactggaa ctggacaggt cacgtgaact ggaaatttca gtttattggc   1320
gtgattggcg gtctctgtgt gctgtaaaat ttctgaggtt agaagatttt ttagacaacc   1380
aacggcatgg catgtgtctc tatttggaac cacagggtac tttatttgca gaggttacct   1440
tttttaatcc agttattgaa agaagaccaa aacttcaaag acaaaagaaa attttttcaa   1500
agcaacaagg caaacatttt ctcagagctc ctcaaatgaa tattaatatt gccacttggg   1560
gaaggctagt aagaagagct attcctacag taaatcattc tggcaccttc agccctcaag   1620
ctcctgtgcc tactacagtg ccagtggttg atgtacgcat ccctcaacta gcacctccag   1680
ctagtgattc tacagtaacc aaattggact tgatcttga gcctgaacct cctccagccc   1740
caccacgagc ttcttctctt ggagaaatag atgaatcttc tgaattaaga gttttggata   1800
taccaggaca ggattcagag actgttttg atattcagaa tgacagaaat agtatacttc   1860
caaaatctca atctgaatac aagcctgata ctcctcagtc aggcctagaa tatagtggta   1920
ttcaagaact tgaggacaga gatctcagc aaaggtttca gtttaatcta caagatttca   1980
ggtgttgtgc tgtcttggga gaggacatt tggaaaggt gcttttagct gaatataaaa   2040
acacaaatga gatgtttgct ataaaagcct taaagaaagg agatattgtg gctcgagatg   2100
aagtagacag cctgatgtgt gaaaaaagaa ttttgaaac tgtgaatagt gtaaggcatc   2160
ccttttttgg gaaccttttt gcatgtttcc aaaccaaaga gcatgtttgc tttgtaatgg   2220
aatatgctgc cggtggggac ctaatgatgc acattcatac tgatgtcttt tctgaaccaa   2280
gagctgtatt ttatgctgct tgtgtagttc ttgggttgca gtatttacat gaacacaaaa   2340
ttgtttatag agatttgaaa ttggataact tattgctaga tacagagggc tttgtgaaaa   2400
ttgctgattt tggtctttgc aaagaaggaa tgggatatgg agatagaaca agcacattt   2460
gtggcactcc tgaatttctt gccccagaag tattaacaga aacttcttat acaagggctg   2520
tagattggtg gggccttggc gtgcttatat atgaaatgct tgttggtgag tctccctttc   2580
```

| | |
|---|---|
| ctggtgatga tgaagaggaa gttttttgaca gtattgtaaa tgatgaagta aggtatccaa | 2640 |
| ggttcttatc tacagaagcc atttctataa tgagaaggct gttaagaaga aatcctgaac | 2700 |
| ggcgccttgg ggctagcgag aaagatgcag aggatgtaaa aaagcaccca ttttccggc | 2760 |
| taattgattg gagcgctctg atggacaaaa aagtaaagcc accatttata cctaccataa | 2820 |
| gaggacgaga agatgttagt aattttgatg atgaatttac ctcagaagca cctattctga | 2880 |
| ctccacctcg agaaccaagg atactttcgg aagaggagca ggaaatgttc agagattttg | 2940 |
| actacattgc tgattggtgt taagttgcta gacactgcga aaccaagctg actcacaaga | 3000 |
| agacctctta aaaatagcaa cccttcattt gctctctgtg ccaccaatag cttctgagtt | 3060 |
| ttttgttgtt gttgttttta ttgaaacacg tgaagatttg tttaaaagta ccattctaat | 3120 |
| acttcttcaa aagtggctcc tcattgtact tcagcgtaaa tatgagcact ggaaacagtt | 3180 |
| tcatggagtt taagttgagt gaacatcggc catgaaaatc catcacgaat acttttggat | 3240 |
| caatagtcta tttt | 3254 |

<210> SEQ ID NO 82
<211> LENGTH: 509
<212> TYPE: DNA
<213> ORGANISM: Homo sapiens

<400> SEQUENCE: 82

| | |
|---|---|
| atgaaattca agttacatgt gaattctgcc aggcaataca aggacctgtg gaatatgagt | 60 |
| gatgacaaac cctttctatg tactgcgcct ggatgtggcc agagtgaagt cacccctgctg | 120 |
| agaaatgaag tggcacagct gaaacagctt cttctggctc ataaagattg ccctgtaacc | 180 |
| gccatgcaga agaaatctgg ctatcatact gctgataaag atgatagttc agaagacatt | 240 |
| tcagtgccga gtagtccaca tacagaagct atacagcata gttcggtcag cacatccaat | 300 |
| ggagtcagtt caacctccaa ggcagaagct gtagccactt cagtcctcac ccagatggcg | 360 |
| gaccagagta cagagcctgc tcttttcacag atcgttatgg ctccttcctc ccagtcacag | 420 |
| ccctcaggaa gttgattaaa aacctgcagt acaacagttt tagatactca ttagtgactt | 480 |
| caaagggaaa tcaaggaaag accagtttc | 509 |

<210> SEQ ID NO 83
<211> LENGTH: 719
<212> TYPE: DNA
<213> ORGANISM: Homo sapiens

<400> SEQUENCE: 83

| | |
|---|---|
| gaattctgga agttcattga agagtctgaa attagggact tatttcaaat ttggacatgg | 60 |
| ctagtcgagg cgcaacaaga cccaacggcc caaatactgg aaataaaata tgccagttca | 120 |
| aactagtact tctgggagag tccgctgttg gcaaatcaag cctagtgctt cgttttgtga | 180 |
| aaggccaatt tcatgaattt caagagagta ccattggggc tgcttttcta acccaaactg | 240 |
| tatgtcttga tgacactaca gtaaagtttg aaatctggga tacagctggt caagaaggat | 300 |
| accatagcct agcaccaatg tactacagag gagcacaagc agccatagtt gtatatgata | 360 |
| tcacaaatga ggagtccttt gcaagagcaa aaaattgggt taagaacttc agaggcaag | 420 |
| caagtcctaa cattgtaata gctttatcgg gaaacaaggc cgacctagca aataaaagag | 480 |
| cagtagattt ccaggaagca cagtcctatg cagatgacaa tagtttatta ttcatggaga | 540 |
| catccgctaa aacatcaatg aatgtaaatg aaatattcat ggcaatagct aaaaaattgc | 600 |
| caaagaatga accacaaaat ccaggagcaa attctgccag aggaggagga gtagacctta | 660 |

```
ccgaacccac acaaccaacc aggaatcagt gttgtagtaa ctaaacctct agtttgaac      719
```

<210> SEQ ID NO 84
<211> LENGTH: 1433
<212> TYPE: DNA
<213> ORGANISM: Homo sapiens

<400> SEQUENCE: 84

```
gacgctctgg gccgccacct ccgcggaccc tgagcgcaag agccaagccg ccagcgctgc       60
gatgtgggcc acgctgccgc tgctctgcgc cggggcctgg ctcctgggag tccccgtctg      120
cggtgccgcc gaactgtgcg tgaactcctt agagaagttt cacttcaagt catggatgtc      180
taagcaccgt aagacctaca gtacggagga gtaccaccac aggctgcaga cgtttgccag      240
caactggagg aagataaacg cccacaacaa tgggaaccac acatttaaaa tggcactgaa      300
ccaattttca gacatgagct tgctgaaat aaaacacaag tatctctggt cagagcctca      360
gaattgctca gccaccaaaa gtaactacct tcgaggtact ggtccctacc caccttccgt      420
ggactggcgg aaaaaaggaa attttgtctc acctgtgaaa aatcagggtg cctgcgcag       480
ttgctggact ttctccacca ctgggccct ggagtctgcg atcgccatcg caaccggaaa      540
gatgctgtcc ttggcggaac agcagctggt ggactgcgcc caggacttca ataatcacgg      600
ctgccaaggg ggtctcccca gccaggcttt cgagtatatc ctgtacaaca agggatcat     660
gggtgaagac acctacccct accagggcaa ggatggttat tgcaagttcc aacctggaaa      720
ggccatcggc tttgtcaagg atgtagccaa catcacaatc tatgacgagg aagcgatggt      780
ggaggctgtg gccctctaca accctgtgag ctttgccttt gaggtgactc aggacttcat      840
gatgtataga accggcatct actccagtac ttcctgccat aaaactccag ataaagtaaa      900
ccatgcagta ctggctgttg gtatggaga aaaaaatggg atcccttact ggatcgtgaa      960
aaactcttgg ggtccccagt ggggaatgaa cgggtacttc ctcatcgagc gcggaaagaa     1020
catgtgtggc ctgctgcct gcgcctccta ccccatccct ctggtgtgag ccgtggcagc     1080
cgcagcgcag actggcggag aaggagagga acgggcagcc tgggcctggg tggaaatcct     1140
gccctggagg aagttgtggg gagatccact gggaccccca acattctgcc ctcacctctg     1200
tgcccagcct ggaaacctac agacaaggag gagttccacc atgagctcac ccgtgtctat     1260
gacgcaaaga tcaccagcca tgtgccttag tgtccttctt aacagactca aaccacatgg     1320
accacgaata ttctttctgt ccagaagggc tactttccac atatagagct ccagggactg     1380
tcttttctgt attcgctgtt caataaacat tgagtgagca cctccccaga tgg            1433
```

<210> SEQ ID NO 85
<211> LENGTH: 2093
<212> TYPE: DNA
<213> ORGANISM: Homo sapiens

<400> SEQUENCE: 85

```
ggtcggggcc cgcggccgct cgcgcctctc gatgggcagc tcgcacttgc tcaacaaggg       60
cctgccgctt ggcgtccgac ctccgatcat gaacgggccc ctgcacccgc ggcccctggt      120
ggcattgctg gatggccggg actgcacagt ggagatgccc atcctgaagg acgtggccac      180
tgtggccttc tgcgacgcgc agtccacgca ggagatccat gagaaggtcc tgaacgaggc      240
tgtgggggcc ctgatgtacc acaccatcac tctcaccagg gaggacctgg agaagttcaa      300
agccctccgc atcatcgtcc ggattggcag tggttttgac aacatcgaca tcaagtcggc      360
```

```
cggggattta ggcattgccg tctgcaacgt gcccgcggcg tctgtggagg agacggccga    420
ctcgacgctg tgccacatcc tgaacctgta ccggcgggcc acctggctgc accaggcgct    480
gcgggagggc acacgagtcc agagcgtcga gcagatccgc gaggtggcgt ccggcgctgc    540
caggatccgc ggggagacct tgggcatcat cggacttgtc gcgtggggca ggcagtggcg    600
ctgcgggcca aggccttcgg cttcaacgtg ctcttctacg acccttactt gtcggatggc    660
gtggagcggc gctggggct gcagcgtgtc agcaccctgc aggacctgct cttccacagc    720
gactgcgtga ccctgcactg cggcctcaac gagcacaacc accacctcat caacgacttc    780
accgtcaagc agatgagaca aggggccttc ctggtgaaca cagcccgggg tggcctggtg    840
gatgagaagg cgctggccca ggccctgaag gagggccgga tccgcggcgc ggccctggat    900
gtgcacgagt cggaacccctt cagctttagc cagggccctc tgaaggatgc acccaacctc    960
atctgcaccc ccatgctgc atggtacagc gagcaggcat ccatcgagat gcgagaggag   1020
gcggcacggg agatccgcag agccatcaca ggccggatcc cagacagcct gaagaactgt   1080
gtcaacaagg accatctgac agccgccacc cactgggcca gcatggaccc cgccgtcgtg   1140
caccctgagc tcaatggggc tgcctatagg taccctccgg gcgtggtggg cgtggccccc   1200
actggcatcc cagctgctgt ggaaggtatc gtccccagcg ccatgtccct gtcccacggc   1260 ctgcccctg tggcccaccc gccccacgcc cttctcctg gccaaaccgt caagcccgag   1320
gcggatagag accacgccag tgaccagttg tagcccggga ggagctctcc agcctcggcg   1380
cctgggcaga gggcccggaa accctcggac cagagtgtgt ggaggaggca tctgtgtggt   1440
ggccctggca ctgcagagac tggtccgggc tgtcaggagg cgggaggggg cagcgctggg   1500
cctcgtgtcg cttgtcgtcg tccgtcctgt gggcgctctg ccctgtgtcc ttcgcgttcc   1560
tcgttaagca gaagaagtca gtagttattc tcccatgaac gttcttgtct gtgtacagtt   1620
tttagaacat tacaaaggat ctgttttgctt agctgtcaac aaaaagaaaa cctgaaggag   1680
catttggaag tcaatttgag gtttttttttt ttgttttttt tttttttgta tgttggaacg   1740
tgccccagaa tgaggcagtt ggcaaacttc tcaggacaat gaatccttcc cgttttttctt   1800 tttatgccac acagtgcatt gttttttcta cctgcttgtc ttattttag aataatttag   1860 aaaaacaaaa caaggctgt ttttcctaat ttttggcatga accccccctt gttccaaatg   1920
aagacggcat cacgaagcag ctccaaaagg aaaagcttgg gcggtgccca gcgtgcccgc   1980
tgcccatcga cgtctgtcct ggggacgtgg agggtggcag cgtccccgcc tgcaccagtg   2040
ccgtcctgct gatgtggtag gctagcaata ttttggttaa aatcatgttt gtg           2093

<210> SEQ ID NO 86
<211> LENGTH: 3435
<212> TYPE: DNA
<213> ORGANISM: Homo sapiens

<400> SEQUENCE: 86
cgcgcggcca ggccctctta gccctctgcc gtttgggggg cacgggtgaa cctgccgccc     60
cactcccacc ccgccccgcc ccgccgtac agccaaatcg gaagggacga gcctgccctt    120
tgaaagggtt tttttcttg ctcctgcgga gggcgcccca gccatggccc tcaggagctc    180
cctagacccc gcaggactg ccctccatcc cggccgccgg ggcccgccct ctgcatcccg    240
cgggcagcct gtgtgaagcg gcctcccgca gcccccggcc cctccccat ggaggaggag    300 gaggggcgtg tggccaagga gtggggcacg accccgcgg ggcccgtctg gaccgcggtg    360
ttcgactacg aggcggcggg cgacgaggag ctgaccctgc ggaggggcga tcgcgtccag    420
```

-continued

```
gtgctttccc aagactgtgc ggtgtccggc gacgagggct ggtggaccgg gcagctcccc        480
agcggccgcg tgggcgtctt ccccagcaac tacgtggccc ccggcgcccc cgctgcaccc        540
gcgggcctcc agctgcccca ggagatcccc ttccacgagc tgcagctaga ggagatcatc        600
ggtgtggggg gctttggcaa ggtctatcgg gccctgtggc gtggcgagga ggtggcagtc        660
aaggccgccc ggctggaccc tgagaaggac ccggcagtga cagcggagca ggtgtgccag        720
gaagcccggc tctttggagc cctgcagcac cccaacataa ttgcccttag ggcgcctgc         780 ctcaaccccc cacacctctg cctagtgatg gagtatgccc ggggtggtgc actgagcagg        840
gtgctggcag gtcgccgggt gccacctcac gtgctggtca actgggctgt gcaggtggcc        900
cggggcatga actacctaca caatgatgcc cctgtgccca tcatccaccg ggacctcaag        960
tccatcaaca tcctgatcct ggaggccatc gagaaccaca acctcgcaga cacggtgctc       1020
aagatcacgg acttcggcct cgcccgcgag tggcacaaga ccaccaagat gagcgctgcg       1080
gggacctacg cctggatggc gccggaggtt atccgtctct ccctcttctc caaaagcagt       1140
gatgtctgga gcttcggggt gctgctgtgg gagctgctga cggggggaggt cccctaccgt     1200 gagatcgacg ccttggccgt ggcgtatggc gtggctatga ataagctgac gctgcccatt      1260
ccctccacgt gccccgagcc ctttgcccgc ctcctggagg aatgctggga cccagacccc       1320
cacgggcggc cagatttcgg tagcatcttg aagcggcttg aagtcatcga acagtcagcc       1380
ctgttccaga tgccactgga gtccttccac tcgctgcagg aagactggaa gctggagatt       1440
cagcacatgt ttgatgacct tcggaccaag gagaaggagc ttcggagccg tgaggaggag       1500
ctgctgcggg cggcacagga gcagcgcttc caggaggagc agctgcggcg gcgggagcag       1560
gagctggcag aacgtgagat ggacatcgtg aacgggagc tgcacctgct catgtgccag       1620
ctgagccagg agaagccccg ggtccgcaag cgcaagggca acttcaagcg cagccgcctg       1680
ctcaagctgc gggaaggcgg cagccacatc agcctgccct ctggctttga gcataagatc       1740
acagtccagg cctctccaac tctggataag cggaaaggat ccgatggggc cagcccccct       1800
gcaagcccca gcatcatccc ccggctgagg gccattcgcc tgactcccgt ggactgtggt       1860
ggcagcagca gtggcagcag cagtggagga agtgggacat ggagccgcgg tgggccccca       1920
aagaaggaag aactggtcgg gggcaagaag aagggacgaa cgtgggggcc cagctccacc       1980
ctgcagaagg agcgggtggg aggagaggag aggctgaagg ggctggggga aggaagcaaa       2040
cagtggtcat caagtgcccc caacctgggc aagtccccca acacacacc cagtcgccgc      2100 tggcttcgcc agcctcaatg agatggagga gttcgcggag gcagaggatg gaggcagcag       2160 cgtgcccct tccccctact cgaccccgtc ctacctctca gtgccactgc ctgccgagcc       2220
ctccccgggg gcgcgggcgc cgtgggagcc gacgccgtcc gcgccccccg ctcggtgggg       2280
acacggcgcc cggcggcgct gcgacctggc gctgctaggc tgcgccacgc tgctggggc       2340 tgtgggcctg ggcgccgacg tggccgaggc gcgcgcggcc gacggtgagg agcagcggcg       2400
ctggctcgac ggcctcttct ttccccgcgc cggccgcttc ccgcggggcc tcagcccacc       2460
cgcgcgtccc cacggccgcc gcgaagacgt gggcccggc ctgggcctgg cgccctcggc       2520
caccctcgtg tcgctgtcgt ccgtgtccga ctgcaactcc acgcgttcac tgctgcgctc       2580
tgacagtgac gaggccgcac cggccgcgcc ctccccacca ccctcccgc ccgcgcccac       2640 acccacgccc tcgcccagca ccaacccccct ggtggacctg gagctggaga gcttcaagaa       2700
ggacccccgc cagtcgctca cgcccaccca cgtcacggct gcatgcgctg tgagccgcgg       2760
```

| | |
|---|---|
| gcaccggcgg acgccatcgg atggggcgct ggggcagcgg gggccgcccg agcccgcggg | 2820 |
| ccatggccct ggccctcgtg accttctgga cttcccccgc ctgcccgacc cccaggccct | 2880 |
| gttcccagcc cgccgccggc ccctgagtt cccaggccgc cccaccaccc tgacctttgc | 2940 |
| cccgagacct cggccggctg ccagtcgccc ccgcttggac ccctggaaac tggtctcctt | 3000 |
| cggccggaca ctcaccatct cgcctcccag caggccagac actccggaga gccctgggcc | 3060 |
| ccccagcgtg cagcccacac tgctggacat ggacatggag gggcagaacc aagacagcac | 3120 |
| agtgccctg tgcggggccc acggctccca ctaaggcctg cccaccaccg cccgcctggg | 3180 |
| cagccatgaa tgtagcgccc caggccctgc cccagcccgc catgccacaa ggtgggggag | 3240 |
| gccctgggca ggatgttcac tctatttatt ggggaaggag ggaggggggg gacacttaac | 3300 |
| ttattccttt gtaccccagg gggtggagcc ctgtgcccac cctgcactgg ggggagggtg | 3360 |
| ggcagggata ctcagggaca gggcatcatg ggggatttgg cacaaaatgg agcattaaag | 3420 |
| gtaaccctg ccccc | 3435 |

<210> SEQ ID NO 87
<211> LENGTH: 2227
<212> TYPE: DNA
<213> ORGANISM: Homo sapiens

<400> SEQUENCE: 87

| | |
|---|---|
| gggcccgccc ctggtcacag ccagactgac tcagtttccc tgggaggtcc cgctcgagcc | 60 |
| cgtccttccc ctccctctgc ccgccccag cctcgcccc accctcggcg cccgcacatc | 120 |
| tgcctgctca gctccagacg gcgcccggac ccccgggcgc gggatccagc caggtgggag | 180 |
| ccccgcagat gaggtctctg aaggtgtgcc tgaaccagtg ccagcctgcc ctgtctgcag | 240 |
| catcggcctg atggggtggt gactgatccc tcagggctcc ggagccatgt ggcccaacgg | 300 |
| cagttccctg gggcctgtt tccggcccac aaacattacc ctggaggaga acggctgat | 360 |
| cgcctcgccc tggttcgccg cctccttctg cgtggtgggc ctggcctcca acctgctggc | 420 |
| cctgagcgtg ctggcgggcg cgcggcaggg gggttcgcac acgcgctcct ccttcctcac | 480 |
| cttcctctgc ggcctcgtcc tcaccgactt cctggggctg ctggtgaccg gtaccatcgt | 540 |
| ggtgtcccag cacgccgcgc tcttcgagtg gcacgccgtg gacctggct gccgtctctg | 600 |
| tcgcttcatg ggcgtcgtca tgatcttctt cggcctgtcc ccgctgctgc tgggggccgc | 660 |
| catggcctca gagcgctacc tgggtatcac ccggccctc tcgcgcccgg cggtcgcctc | 720 |
| gcagcgccgc gcctgggcca ccgtgggggct ggtgtggggcg gccgcgctgg cgctgggcct | 780 |
| gctgcccctg ctgggcgtgg gtcgctacac cgtgcaatac ccggggtcct ggtgcttcct | 840 |
| gacgctgggc gccgagtccg gggacgtggc cttcgggctg ctcttctcca tgctgggcgg | 900 |
| cctctcggtc gggctgtcct tcctgctgaa cacggtcagc gtggccaccc tgtgccacgt | 960 |
| ctaccacggg caggaggcgg cccagcagcg tccccggac tccgaggtgg agatgatggc | 1020 |
| tcagctcctg gggatcatgg tggtggccag cgtgtgttgg ctgcccccttc tggtcttcat | 1080 |
| cgcccagaca gtgctgcgaa acccgcctgc catgagcccc gccgggcagc tgtcccgcac | 1140 |
| cacggagaag gagctgctca tctacttgcg cgtggccacc tggaaccaga tcctggaccc | 1200 |
| ctgggtgtat atcctgttcc gccgcgccgt gctccggcgt ctccagcctc gcctcagcac | 1260 |
| ccggcccagg tcgctgtccc tccagcccca gctcacgcag cgctccgggc tgcagtagga | 1320 |
| agtgacaga gcgcccctcc cgcgccttc cgcggagccc ttggcccctc ggacagccca | 1380 |
| tctgcctgtt ctgaggattc aggggctggg ggtgctggat ggacagtggg catcagcagc | 1440 |

```
agggttttgg gttgacccca atccaacccg gggaccccca actcctccct gatcctttta   1500
ccaagcactc tcccttcctc ggcccctttt tcccatccag agctcccacc ccttctctgc   1560
gtccctccca accccaggaa gggcatgcag acattggaag agggtcttgc attgctattt   1620 tttttttag acggagtctt gctctgtccc ccaggctgga gtgcagtggc gcaatctcag   1680
ctcactgcaa cctccacctc ccgggttcaa gcgattctcc tgcctcagcc tcctgagtag   1740
ctgggactat aggcgcgcgc caccacgccc ggctaatttt tgtattttta gtagagacgg   1800
ggtttcaccg tgttggccag gctggtcttg aactcctgac ctcaggtgat tcaccagcct   1860
cagcctccca aagtgctggg atcacaggca tgaaccacca cacctggcca tttttttttt   1920
tttttttaga cggagtctca ctctgtggcc cagcctggag tacagtggca cgatctcggc   1980
tcactgcaac ctccgcctcc cgggttcaag cgattctcgt gcctcagcct cccgagcagc   2040
tgggattaca ggcgtaagcc actgcgcccg gccttgcatg ctctttgacc ctgaatttga   2100
cctacttgct ggggtacagt tgcttccttt tgaacctcca acagggaagg ctctgtccag   2160
aaaggattga atgtgaacgg gggcaccccc ttttcttgcc aaaatatatc tctgcctttg   2220
gttttat                                                              2227

<210> SEQ ID NO 88
<211> LENGTH: 2662
<212> TYPE: DNA
<213> ORGANISM: Homo sapiens

<400> SEQUENCE: 88
cccggacatg gccgccaaca tgtacagggt cggagactac gtctactttg agaactcctc     60
cagcaaccca tacctgatcc ggagaatcga ggagctcaac aagacggcca atgggaacgt    120
ggaggccaaa gtggtgtgct tctaccggag gcgggacatc tccagcaccc tcatcgccct    180
ggccgacaag cacgcaaccc tgtcagtctg ctataaggcc ggaccggggg cggacaacgg    240
cgaggaaggg gaaatagaag aggaaatgga gaatccggaa atggtggacc tgcccgagaa    300
actaaagcac cagctgcggc atcgggagct gttcctctcc cggcagctgg agtctctgcc    360
cgccacgcac atcaggggca gtgcagcgt caccctgctc aacgagaccg agtcgctcaa    420
gtcctacctg gagcgggagg atttcttctt ctattctcta gtctacgacc acagcagaa    480 gaccctgctg gcagataaag gagagattcg agtaggaaac cggtaccagg cagacatcac    540
cgacttgtta aaagaaggcg aggaggatgg ccgagaccag tccaggttgg agacccaggt    600
gtgggaggcg cacaacccac tcacagacaa gcagatcgac cagttcctgg tggtggcccg    660
ctctgtgggc accttcgcac gggccctgga ctgcagcagc tccgtccgac agcccagcct    720
gcacatgagc gccgcagctg cctcccgaga catcaccctg ttccacgcca tggatactct    780
ccacaagaac atctacgaca tctccaaggc catctcggcg ctggtgccgc agggcgggcc    840
cgtgctctgc agggacgaga tggaggagtg gtctgcatca gaggccaacc ttttcgagga    900
agccctggaa aaatatggga aggatttcac ggacattcag caagattttc tcccgtggaa    960
gtcgctgacc agcatcattg agtactacta catgtggaag accaccgaca gatacgtgca   1020
gcagaaacgc ttgaaagcag ctgaagctga gagcaagtta aagcaagttt atattcccaa   1080
ctataacaag ccaaatccga accaaatcag cgtcaacaac gtcaaggccg gtgtggtgaa   1140
cggcacgggg gcgccgggcc agagccctgg ggctggccgg gcctgcgaga gctgttacac   1200
cacacagtct taccagtggt attcttgggg tccccctaac atgcagtgtc gtctctgcgc   1260
```

-continued

| | |
|---|---|
| atcttgttgg acatattgga agaaatatgg tggcttgaaa atgccaaccc ggttagatgg | 1320 |
| agagaggcca ggaccaaacc gcagtaacat gagtccccac ggcctcccag cccggagcag | 1380 |
| cgggagcccc aagtttgcca tgaagaccag gcaggctttc tatctgcaca cgacgaagct | 1440 |
| gacgcggatc gcccggcgcc tgtgccgtga gatcctgcgc ccgtggcacg ctgcgcggaa | 1500 |
| cccctacctg cccatcaaca gcgcggccat caaggccgag tgcacggcgc ggctgcccga | 1560 |
| agcctcccag agcccgctgg tgctgaagca ggcggtacgc aagccgctgg aagccgtgct | 1620 |
| tcggtatctt gagacccacc ccgccccccc caagcctgac cccgtgaaaa gcgtgtccag | 1680 |
| cgtgctcagc agcctgacgc cgccaaggt ggccccgtc atcaacaacg ctccccac | 1740 |
| catcctgggc aagcgcagct acgagcagca acggggtg acggcaaca tgaagaagcg | 1800 |
| cctcttgatg cccagtaggg gtctggcaaa ccacggacag accaggcaca tgggaccaag | 1860 |
| ccggaacctc ctgctcaacg ggaagtccta ccccaccaaa gtgcgcctga tccggggggg | 1920 |
| ctccctgccc ccagtcaagc ggcggcggat gaactggatc gacgcccgg gtgacgtgtt | 1980 |
| ctacatgccc aaagaggaga ccaggaagat ccgcaagctg ctctcatcct cggaaaccaa | 2040 |
| gcgtgctgcc cgccggccct acaagcccat cgccctgcgc cagagccagg ccctgccgcc | 2100 |
| gcggccaccg ccacctgcgc ccgtcaacga cgagcccatc gtcatcgagg actaggggcc | 2160 |
| gcccccacct gcggccgccc cccgcccctc gcccgcccac acggccccctt ccagccagc | 2220 |
| ccgccgcccg cccctcagtt tggtagtgcc ccacctcccg ccctcacctg aagagaaacg | 2280 |
| cgctccttgg cggacactgg gggaggagag gaagaagcgc ggctaactta ttccgagaat | 2340 |
| gccgaggagt tgtcgttttt agctttgtgt ttacttttg gctggagcgg agatgagggg | 2400 |
| ccaccccgtg cccctgtgct gcggggcctt tgcccggag gccgggccct aaggttttgt | 2460 |
| tgtgttctgt tgaaggtgcc atttaaatt ttatttat tactttttt gtagatgaac | 2520 |
| ttgagctctg taacttacac ctggaatgtt aggatcgtgc ggccgcggcc ggccgagctg | 2580 |
| cctggcgggg ttggcccttg tcttttcaag taattttcat attaaacaaa aacaaagaaa | 2640 |
| aaaaatctta taaaaggaa aa | 2662 |

<210> SEQ ID NO 89
<211> LENGTH: 552
<212> TYPE: DNA
<213> ORGANISM: Homo sapiens

<400> SEQUENCE: 89

| | |
|---|---|
| atgagagagt acaaagtggt ggtgctgggc tcgggcggcg tgggcaagtc cgcgctcacc | 60 |
| gtgcagttcg tgacgggctc cttcatcgag aagtacgacc cgaccatcga agacttttac | 120 |
| cgcaaggaga ttgaggtgga ctcgtcgccg tcggtgctgg agatcctgga tacggcgggc | 180 |
| accgagcagt tcgcgtccat gcgggacctg tacatcaaga acggccaggg cttcatcctg | 240 |
| gtctacagcc tcgtcaacca gcagagcttc aggacatca gcccatgcg ggaccagatc | 300 |
| atccgcgtga gcggtacga gcgcgtgccc atgatcctgg tgggcaacaa ggtggacctg | 360 |
| gagggtgagc gcgaggtctc gtacggggag ggcaaggccc tggctgagga gtggagctgc | 420 |
| cccttcatgg agacgtcggc caaaaacaaa gcctcggtag acgagctatt tgccgagatc | 480 |
| gtgcggcaga tgaactacgc ggcgcagtcc acggcgatg agggctgctg ctcggcctgc | 540 |
| gtgatcctct ga | 552 |

<210> SEQ ID NO 90
<211> LENGTH: 2198

<212> TYPE: DNA
<213> ORGANISM: Homo sapiens

<400> SEQUENCE: 90

| | | | | | |
|---|---|---|---|---|---|
| gagctgcggg | cgctgctgct | gtggggccgc | cgcctgcggc | ctttgctgcg | ggcgccggcg | 60 |
| ctggcggccg | tgccgggagg | aaaaccaatt | ctgtgtcctc | ggaggaccac | agcccagttg | 120 |
| ggccccaggc | gaaacccagc | ctggagcttg | caggcaggac | gactgttcag | cacgcagacc | 180 |
| gccgaggaca | aggaggaacc | cctgcactcg | attatcagca | gcacagagag | cgtgcagggt | 240 |
| tccacttcca | acatgagtt | ccaggccgag | acaaagaagc | ttttggacat | tgttgcccgg | 300 |
| tccctgtact | cagaaaaaga | ggtgtttata | cgggagctga | tctccaatgc | cagcgatgcc | 360 |
| ttggaaaaac | tgcgtcacaa | actggtgtct | gacggccaag | cactgccaga | aatggagatt | 420 |
| cacttgcaga | ccaatgccga | gaaaggcacc | atcaccatcc | aggatactgg | tatcgggatg | 480 |
| acacaggaag | agctggtgtc | caacctgggg | acgattgcca | gatcggggtc | aaaggccttc | 540 |
| ctggatgctc | tgcagaacca | ggctgaggcc | agcagcaaga | tcatcggcca | gtttggagtg | 600 |
| ggtttctact | cagctttcat | ggtggctgac | agagtggagg | tctattcccg | ctcggcagcc | 660 |
| ccggggagcc | tgggttacca | gtggctttca | gatggttctg | gagtgtttga | aatcgccgaa | 720 |
| gcttcgggag | ttagaaccgg | gacaaaaatc | atcatccacc | tgaaatccga | ctgcaaggag | 780 |
| ttttccagcg | aggcccgggt | gcgagatgtg | gtaacgaagt | acagcaactt | cgtcagcttc | 840 |
| cccttgtact | tgaatggaag | gcggatgaac | accttgcagg | ccatctggat | gatggacccc | 900 |
| aaggatgtcc | gtgagtggca | acatgaggag | ttctaccgct | acgtcgcgca | ggctcacgac | 960 |
| aagcccccgct | acaccctgca | ctataagacg | gacgcaccgc | tcaacatccg | cagcatcttc | 1020 |
| tacgtgcccg | acatgaaacc | gtccatgttt | gatgtgagcc | gggagctggg | ctccagcgtt | 1080 |
| gcactgtaca | gccgcaaagt | cctcatccag | accaaggcca | cggacatcct | gcccaagtgg | 1140 |
| ctgcgcttca | tccgaggtgt | ggtggacagt | gaggacattc | ccctgaacct | cagccgggag | 1200 |
| ctgctgcagg | agagcgcact | catcaggaaa | ctccgggacg | ttttacagca | gaggctgatc | 1260 |
| aaattcttca | ttgaccagag | taaaaaagat | gctgagaagt | atgcaaagtt | ttttgaagat | 1320 |
| tacggcctgt | tcatgcggga | gggcattgtg | accgccaccg | agcaggaggt | caaggaggac | 1380 |
| atagcaaagc | tgctgcgcta | cgagtcctcg | gcgctgcccct | ccgggcagct | aaccagcctc | 1440 |
| tcagaatacg | ccagccgcat | gcgggccggc | acccgcaaca | tctactacct | gtgcgccccc | 1500 |
| aaccgtcacc | tggcagagca | ctcaccctac | tatgaggcca | tgaagaagaa | agacacagag | 1560 |
| gttctcttct | gctttgagca | gtttgatgag | ctcacccctgc | tgcaccttcg | tgagtttgac | 1620 |
| aagaagaagc | tgatctctgt | ggagacggac | atagtcgtgg | atcactacaa | ggaggagaag | 1680 |
| tttgaggaca | ggtccccagc | cgccgagtgc | ctatcagaga | aggagacgga | ggagctcatg | 1740 |
| gcctggatga | gaaatgtgct | ggggtcgcgt | gtcaccaacg | tgaaggtgac | cctccgactg | 1800 |
| gacacccacc | ctgccatggt | caccgtgctg | gagatggggg | ctgcccgcca | cttcctgcgc | 1860 |
| atgcagcagc | tggccaagac | ccaggaggag | cgcgcacagc | tcctgcagcc | cacgctggag | 1920 |
| atcaaccca | ggcacgcgct | catcaagaag | ctgaatcagc | tgcgcgcaag | cgagcctggc | 1980 |
| ctggctcagc | tgctggtgga | tcagatatac | gagaacgcca | tgattgctgc | tggacttgtt | 2040 |
| gacgacccta | gggccatggt | gggccgcttg | aatgagctgc | ttgtcaaggc | cctggagcga | 2100 |
| cactgacagc | caggggggcca | gaaggactga | caccacagat | gacagcccca | cctccttgag | 2160 |
| ctttatttac | ctaaatttaa | aggtatttct | taacccga | | | 2198 |

<210> SEQ ID NO 91
<211> LENGTH: 1790
<212> TYPE: DNA
<213> ORGANISM: Homo sapiens

<400> SEQUENCE: 91

| | | | | | | |
|---|---|---|---|---|---|---|
| agtgatgtcc | ttgcattgcc | cattttaag | caagaagagt | cgagtttgcc | tcctgataat | 60 |
| gagaataaaa | tcctgccttt | tcaatatgtg | ctttgtgctg | ctacctctcc | agcagtgaaa | 120 |
| ctccatgatg | aaaccctaac | gtatctcaat | caaggacagt | cttatgaaat | tcgaatgcta | 180 |
| gacaatagga | aacttggaga | acttccagaa | attaatggca | aattggtgaa | gagtatattc | 240 |
| cgtgtggtgt | tccatgacag | aaggcttcag | tacactgagc | atcagcagct | agagggctgg | 300 |
| aggtggaacc | gacctggaga | cagaattctt | gacatagata | tcccgatgtc | tgtgggtata | 360 |
| atcgatccta | gggctaatcc | aactcaacta | atacagtgg | agttcctgtg | ggaccctgca | 420 |
| aagaggacat | ctgtgtttat | tcaggtgcac | tgtattagca | cagagttcac | tatgaggaaa | 480 |
| catggtggag | aaaagggggt | gccattccga | gtacaaatag | ataccttcaa | ggagaatgaa | 540 |
| aacgggaat | atactgagca | cttacactcg | gccagctgcc | agatcaaagt | tttcaagcca | 600 |
| aaggtgcaga | cagaaagcaa | aaaacggata | gggaaaaaat | ggagaaacga | acacctcatg | 660 |
| aaaaggagaa | atatcagcct | tcctatgaga | caaccatact | cacagagtgt | tctccatggc | 720 |
| ccgagatcac | gtatgtcaat | aactccccat | cacctggctt | caacagttcc | catagcagtt | 780 |
| tttctcttgg | ggaaggaaat | ggttcaccaa | accaccagcc | agagccaccc | cctccagtca | 840 |
| cagataaccct | cttaccaaca | accacacctc | aggaagctca | gcagtggttg | catcgaaatc | 900 |
| gttttctac | attcacaagg | cttttcacaa | acttctcagg | ggcagattta | ttgaaattaa | 960 |
| ctagagatga | tgtgatccaa | atctgtggcc | ctgcagatgg | aatcagactt | tttaatgcat | 1020 |
| taaaaggccg | gatggtgcgt | ccaaggttaa | ccatttatgt | ttgtcaggaa | tcactgcagt | 1080 |
| tgagggagca | gcaacaacag | cagcagcaac | agcagcagaa | gcatgaggat | ggagactcaa | 1140 |
| atggtactt | cttcgtttac | catgctatct | atctagaaga | actaacagct | gttgaattga | 1200 |
| cagaaaaaat | tgctcagctt | ttcagcattt | ccccttgcca | gatcagccag | atttacaagc | 1260 |
| aggggccaac | aggaattcat | gtgctcatca | gtgatgagat | gatacagaac | tttcaggaag | 1320 |
| aagcatgttt | tattctggac | acaatgaaag | cagaaaccaa | tgatagctat | catatcatac | 1380 |
| tgaagtagga | gtgcggcgtt | tcgtgcccag | tggctgctcc | ttccttcacc | tctgaaaacg | 1440 |
| gccctcttga | aggggatat | gaatggagat | ttgaaggtct | gcaagaacct | gactcgtctg | 1500 |
| actgtgtgtg | gaggagtcca | ggccatggag | gcagaatcct | ggccctctgt | gttggcccaa | 1560 |
| gctcttgtgg | tacacacaga | ttactgccca | atatgcagtt | ctgcagctgt | tttagttaaa | 1620 |
| tttctggacc | ttgttgttgt | taaatatcag | tagaaactct | acataattta | gagtgtatgt | 1680 |
| agggcataat | gatgatggga | attgtgtgat | gtttaacagg | aagatcttaa | attttgtgat | 1740 |
| atggagccct | gtaattttt | tcttatataa | aaatgggtat | ctatattcat | | 1790 |

<210> SEQ ID NO 92
<211> LENGTH: 652
<212> TYPE: DNA
<213> ORGANISM: Homo sapiens

<400> SEQUENCE: 92

| | | | | | | |
|---|---|---|---|---|---|---|
| aggtctgttc | cgcatgaaac | tcctgctggg | gaaggacttc | cctgcctccc | cacccaaggg | 60 |
| ctacttcctg | accaagatct | tccacccgaa | cttgggcgcc | aatggcgaga | tgtgcgtcaa | 120 |

```
cgtgctcaag agggactgga cggctgagct gggcatccga cacgtactgc tgaccatcaa    180
gtgcctgctg atccacccta accccgagtc tgcactcaac gaggaggcgg ccgcctgct    240 cttggagaac tacgaggagt atgcggctcg ggcccgtctg ctcacagaga tccacggggg    300
cgccggcggg cccagcggca gggccaaagc cgggcgggcc ctggccagtg gcactgcagc    360
ttcctccacc gactctgggg ccccagggg cttgggaggg gctgagggtc ccatggccaa    420
gaagcatgct ggcgagcgcg ataagaagct ggcggccaag aaaaagacgg acaagaagcg    480
ggcgctacgg cggctgtagt gggctctctt cctccttcca ccgtgacccc aacctctcct    540
gtcccctccc tccaactctg tctctaagtt atttaaatta tggctggggt cggggagggt    600 acaggggca ctgagacctg gatttgtttt tttaaataaa gttggaaaag ca            652
```

<210> SEQ ID NO 93
<211> LENGTH: 771
<212> TYPE: DNA
<213> ORGANISM: Homo sapiens

<400> SEQUENCE: 93

```
gtcgtgttct ccgagttcct gtctctctgc caacgccgcc cggatggctt cccaaaaccg    60
cgacccagcc gccactagcg tcgccgccgc ccgtaaagga gctgagccga gcggggcgc    120 cgcccggggt ccggtgggca aaggctaca gcaggagctg atgaccctca tgatgtctgg    180
cgataaaggg atttctgcct tccctgaatc agacaacctt ttcaaatggg tagggaccat    240
ccatggagca gctggaacag tatatgaaga cctgaggtat aagctctcgc tagagttccc    300
cagtggctac ccttacaatg cgcccacagt gaagttcctc acgccctgct atcaccccaa    360
cgtggacacc cagggtaaca tatgcctgga catcctgaag gaaaagtggt ctgccctgta    420
tgatgtcagg accattctgc tctccatcca gagccttcta ggagaaccca acattgatag    480
tcccttgaac acacatgctg ccgagctctg gaaaaacccc acagctttta agaagtacct    540
gcaagaaacc tactcaaagc aggtcaccag ccaggagccc tgacccaggc tgcccagcct    600
gtccttgtgt cgtctttta atttttcctt agatggtctg tccttttgt gatttctgta    660 taggactctt tatcttgagc tgtggtattt ttgttttgtt tttgtctttt aaattaagcc    720
tcggttgagc cctgtatat taaataaatg cattttgtc cttttttaga c              771
```

<210> SEQ ID NO 94
<211> LENGTH: 2527
<212> TYPE: DNA
<213> ORGANISM: Homo sapiens

<400> SEQUENCE: 94

```
ctccagcagc acccgagagg gtcaggagaa aagcggagga agctgggtag gccctgaggg    60
gcctcggtaa gccatcatga ccacccggca agccacgaag gatcccctcc tccgggtgt    120 atctcctacc cctagcaaga ttccggtacg ctctcagaaa cgcacgcctt tccccactgt    180
tacatcgtgc gccgtggacc aggagaacca agatccaagg agatgggtgc agaaaccacc    240
gctcaatatt caacgccccc tcgttgattc agcaggcccc aggccgaaag ccaggcacca    300
ggcagagaca tcacaaagat tggtggggat cagtcagcct cggaacccct ggaagagct    360 caggcctagc cctaggggtc aaaatgtggg gcctgggccc cctgcccaga cagaggctcc    420
agggaccata gagtttgtgg ctgaccctgc agccctggcc accatcctgt caggtgaggg    480
tgtgaagagc tgtcacctgg ggcgccagcc tagtctggct aaaagagtac tggttcgagg    540
```

```
aagtcaggga ggcaccaccc agagggtcca gggtgttcgg gcctctgcat atttggcccc      600 cagaacccccc acccaccgac tggaccctgc cagggcttcc tgcttctcta ggctggaggg    660
accaggacct cgaggccgga cattgtgtcc ccagaggcta caggctctga tttcaccttc      720
aggaccttcc tttcaccctt ccactcgccc cagtttccag gagctaagaa gggagacagc     780
tggcagcagc cggacttcag tgagccaggc ctcaggattg ctcctggaga ccccagtcca     840
gcctgctttc tctcttccta aggagaacg cgaggttgtc actcactcag atgaaggagg      900
tgtggcctct cttggtctgg cccagcgagt accattaaga gaaaaccgag aaatgtcaca      960
taccagggac agccatgact cccacctgat gccctcccct gccctgtgg cccagccctt      1020 gcctggccat gtggtgccat gtccatcacc ctttggacgg gctcagcgtg taccctcccc     1080
aggccctcca actctgacct catattcagt gttgcgcgt ctcaccgttc aacctaaaac      1140
ccggttcaca cccatgccat caaccccag agttcagcag gcccagtggc tgcgtggtgt      1200
ctcccctcag tcctgctctg aagatcctgc cctgccctgg gagcaggttg ccgtccggtt     1260
gtttgaccag gagagttgta taaggtcact ggagggttct gggaaaccac cggtggccac    1320
tccttctgga ccccactcta acagaacccc cagcctccag gaggtgaaga ttcaacgcat     1380
cggtatcctg caacagctgt tgagacagga agtagagggg ctggtagggg gccagtgtgt    1440
ccctcttaat ggaggctctt ctctggatat ggttgaactt cagcccctgc tgactgagat    1500
ttctagaact ctgaatgcca cagagcataa ctctgggact tcccaccttc ctggactgtt    1560
aaaacactca gggctgccaa agccctgtct tccagaggag tgcggggaac cacagccctg    1620
ccctccggca gagcctgggc ccccagaggc cttctgtagg agtgagcctg agataccaga   1680
gccctccctc caggaacagc ttgaagtacc agagccctac cctccagcag aacccaggcc    1740
cctagagtcc tgctgtagga gtgagcctga gataccggag tcctctcgcc aggaacagct   1800
tgaggtacct gagccctgcc ctccagcaga acccaggccc ctagagtcct actgtaggat   1860
tgagcctgag ataccggagt cctctcgcca ggaacagctt gaggtacctg agccctgccc   1920
tccagcagaa cccgggcccc ttcagcccag cacccagggg cagtctggac ccccagggcc   1980
ctgccctagg gtagagctgg gggcatcaga gccctgcacc ctggaacata aagtctaga    2040 gtccagtcta ccaccctgct gcagtcagtg ggctccagca accaccagcc tgatcttctc   2100
ttcccaacac ccgctttgtg ccagcccccc tatctgctca ctccagtctt tgagacccc    2160 agcaggccag gcaggcctca gcaatctggc ccctcgaacc ctagccctga gggagcgcct   2220
caaatcgtgt ttaaccgcca tccactgctt ccacgaggct cgtctggacg atgagtgtgc    2280
cttttacacc agccgagccc ctccctcagg ccccacccgg gtctgcacca acctgtggc    2340 tacattactc gaatggcagg atgccctgtg tttcattcca gttggttctg ctgccccca    2400 gggctctcca tgatgagaca accactcctg ccctgccgta cttcttcctt ttagccctta   2460
tttattgtcg gtctgccat gggactggga gccgcccact tttgtcctca ataaagtttc    2520
taaagta                                                               2527

<210> SEQ ID NO 95
<211> LENGTH: 2512
<212> TYPE: DNA
<213> ORGANISM: Homo sapiens

<400> SEQUENCE: 95
agaataatca tgggccagac tgggaagaaa tctgagaagg gaccagtttg ttggcggaag    60
cgtgtaaaat cagagtacat gcgactgaga cagctcaaga ggttcagacg agctgatgaa    120
```

-continued

```
gtaaaggtat gtttagttcc aatcgtcaga aaattttgga aagaacggaa atcttaaacc      180
aagaatggaa acagcgaagg atacagcctg tgcacatcct gacttctgtg agctcattgc      240
gcgggactag ggagtgttcg gtgaccagtg acttggattt tccaacacaa gtcatcccat      300
taaagactct gaatgcagtt gcttcagtac ccataatgta ttcttggtct ccctacagc       360 agaattttat ggtggaagat gaaactgttt tacataacat tccttatatg ggagatgaag      420
ttttagatca ggatggtact ttcattgaag aactaataaa aaattatgat gggaaagtac      480
acggggatag agaatgtggg tttataaatg atgaaatttt tgtggagttg gtgaatgccc      540
ttggtcaata taatgatgat gacgatgatg atgatggaga cgatcctgaa gaaagagaag      600
aaaagcagaa agatctggag gatcaccgag atgataaaga aagccgccca cctcggaaat      660
ttccttctga taaaattttt gaagccattt cctcaatgtt tccagataag ggcacagcag      720
aagaactaaa ggaaaaatat aaagaactca ccgaacagca gctcccaggc gcacttcctc      780
ctgaatgtac ccccaacata gatggaccaa atgctaaatc tgttcagaga gagcaaagct      840
tacactcctt tcatacgctt ttctgtaggc gatgttttaa atatgactgc ttcctacatc      900
cttttcatgc aacacccaac acttataagc ggaagaacac agaaacagct ctagacaaca      960
aaccttgtgg accacagtgt taccagcatt tggagggagc aaaggagttt gctgctgctc     1020
tcaccgctga gcggataaag accccaccaa aacgtccagg aggccgcaga agaggacggc     1080
ttcccaataa cagtagcagg cccagcaccc ccaccattaa tgtgctggaa tcaaaggata     1140
cagacagtga tagggaagca gggactgaaa cgggggagga aacaatgat aaagaagaag      1200 aagagaagaa agatgaaact tcgagctcct ctgaagcaaa ttctcggtgt caaacaccaa     1260
taaagatgaa gccaaatatt gaacctcctg agaatgtgga gtggagtggt gctgaagcct     1320
caatgtttag agtcctcatt ggcacttact atgacaattt ctgtgccatt gctaggttaa     1380
ttgggaccaa aacatgtaga caggtgtatg agtttagagt caaagaatct agcatcatag     1440
ctccagctcc cgctgaggat gtggatactc ctccaaggaa aaagaagagg aaacaccggt     1500
tgtgggctgc acactgcaga aagatacagc tgaaaaagga cggctcctct aaccatgttt     1560
acaactatca accctgtgat catccacggc agccttgtga cagttcgtgc ccttgtgtga     1620
tagcacaaaa ttttttgtgaa aagttttgtc aatgtagttc agagtgtcaa aaccgctttc     1680
cgggatgccg ctgcaaagca cagtgcaaca ccaagcagtg cccgtgctac ctggctgtcc     1740
gagagtgtga ccctgacctc tgtcttactt gtggagccgc tgaccattgg acagtaaaa      1800 atgtgtcctg caagaactgc agtattcagc ggggctccaa aaagcatcta ttgctggcac     1860
catctgacgt ggcaggctgg gggattttta tcaaagatcc tgtgcagaaa atgaattca      1920 tctcagaata ctgtggagag attatttctc aagatgaagc tgacagaaga gggaaagtgt     1980
atgataaata catgtgcagc tttctgttca acttgaacaa tgattttgtg gtggatgcaa     2040
cccgcaaggg taacaaaatt cgttttgcaa atcattcggt aaatccaaac tgctatgcaa     2100
aagttatgat ggttaacggt gatcacagga taggtatttt tgccaagaga gccatccaga     2160
ctggcgaaga gctgtttttt gattacagat acagccaggc tgatgccctg aagtatgtcg     2220
gcatcgaaag agaaatggaa atcccttgac atctgctacc tcctccccc tcctctgaaa     2280 cagctgcctt agcttcagga acctcgagta ctgtgggcaa tttagaaaaa gaacatgcag     2340
tttgaaattc tgaatttgca aagtactgta agaataattt atagtaatga gtttaaaaat     2400 caactttttα ttgccttctc accagctgca aagtgttttg taccagtgaa tttttgcaat     2460
```

-continued

| aatgcagtat ggtacatttt tcaactttga ataaagaata cttgaacttg tc | 2512 |

<210> SEQ ID NO 96
<211> LENGTH: 3403
<212> TYPE: DNA
<213> ORGANISM: Homo sapiens

<400> SEQUENCE: 96

| caggtctgag gcgaagctag gtgagccgtg ggaagaaaag agggagcagc tagggcgcgg | 60 |
| gtctccctcc tcccggagtt tggaacggct gaagttcacc ttccagcccc tagcgccgtt | 120 |
| cgcgccgcta ggcctggctt ctgaggcggt tgcggtgctc ggtcgccgcc taagcggggc | 180 |
| agggtgcgaa caggggcttc gggccacgct tctcttggcg acaggatttt gctgtgaagt | 240 |
| ccgtccggga aacggaggaa aaaagagtt gcgggaggct gtctgctaat aacgttctt | 300 |
| gatacatatt tgccagactt caagatttca gaaaggggt gaaagagaag attgcaactt | 360 |
| tgagtcagac ctgtaggcct gatagactga ttaaaccaca gaaggtgacc tgctgagaaa | 420 |
| agtggtacaa atactgggaa aaacctgctc ttctgcgtta agtgggagac aatgtcacaa | 480 |
| gttaaaagct cttattccta tgatgccccc tcggatttca tcaattttc atccttggat | 540 |
| gatgaaggag atactcaaaa catagattca tggtttgagg agaaggccaa tttggagaat | 600 |
| aagttactgg ggaagaatgg aactggaggg cttttttcagg gcaaaactcc tttgagaaag | 660 |
| gctaatcttc agcaagctat tgtcacacct ttgaaaccag ttgacaacac ttactacaaa | 720 |
| gaggcagaaa agaaaatct tgtggaacaa tccattccgt caaatgcttg ttcttccctg | 780 |
| gaagttgagg cagccatatc aagaaaaact ccagcccagc ctcagagaag atctcttagg | 840 |
| ctttctgctc agaaggattt ggaacagaaa gaaaagcatc atgtaaaaat gaaagccaag | 900 |
| agatgtgcca ctcctgtaat catcgatgaa attctaccct ctaagaaaat gaaagtttct | 960 |
| aacaacaaaa agaagccaga ggaagaaggc agtgctcatc aagatactgc tgaaaacaat | 1020 |
| gcatcttccc cagagaaagc caagggtaga catactgtgc cttgtatgcc acctgcaaag | 1080 |
| cagaagtttc taaaaagtac tgaggagcaa gagctggaga agagtatgaa aatgcagcaa | 1140 |
| gaggtggtgg agatgcggaa aaagaatgaa gaattcaaga aacttgctct ggctggaata | 1200 |
| gggcaacctg tgaagaaatc agtgagccag gtcaccaaat cagttgactt ccacttccgc | 1260 |
| acagatgagc gaatcaaaca acatcctaag aaccaggagg aatataagga agtgaacttt | 1320 |
| acatctgaac tacgaaagca tccttcatct cctgcccgag tgactaaggg atgtaccatt | 1380 |
| gttaagcctt tcaacctgtc ccaaggaaag aaaagaacat tgatgaaac agtttctaca | 1440 |
| tatgtgcccc ttgcacagca agttgaagac ttccataaac gaacccctaa cagatatcat | 1500 |
| ttgaggagca agaaggatga tattaacctg ttaccctcca atcttctgt gaccaagatt | 1560 |
| tgcagagacc cacagactcc tgtactgcaa accaaacacc gtgcacgggc tgtgacctgc | 1620 |
| aaaagtacag cagagctgga ggctgaggag ctcgagaaat gcaacaata caaattcaaa | 1680 |
| gcacgtgaac ttgatcccag aatacttgaa ggtgggccca tcttgcccaa gaaaccacct | 1740 |
| gtgaaaccac ccaccgagcc tattggcttt gatttggaaa ttgagaaaag aatccaggag | 1800 |
| cgagaatcaa agaagaaaac agaggatgaa cactttgaat ttcattccag accttgccct | 1860 |
| actaagattt tggaagatgt tgtgggtgtt cctgaaaaga aggtacttcc aatcaccgtc | 1920 |
| cccaagtcac cagcctttgc attgaagaac agaattcgaa tgcccaccaa agaagatgag | 1980 |
| gaagaggacg aaccggtagt gataaaagct caacctgtgc cacattatgg ggtgcctttt | 2040 |
| aagcccccaaa tcccagaggc aagaactgtg gaaatatgcc cttctcgtt tgattctcga | 2100 |

-continued

```
gacaaagaac gtcagttaca gaaggagaag aaaataaaag aactgcagaa agggaggtg      2160 cccaagttca aggcacttcc cttgcctcat tttgacacca ttaacctgcc agagaagaag      2220
gtaaagaatg tgacccagat tgaacctttc tgcttggaga ctgacagaag aggtgctctg      2280
aaggcacaga cttggaagca ccagctggaa gaagaactga cagcagaa agaagcagct       2340 tgtttcaagg ctcgtccaaa caccgtcatc tctcaggagc cctttgttcc caagaaagag     2400
aagaaatcag ttgctgaggg cctttctggt tctctagttc aggaaccttt tcagctggct     2460
actgagaaga gagccaaaga gcggcaggag ctggagaaga aatggctga ggtagaagcc      2520 cagaaagccc agcagttgga ggaggccaga ctacaggagg aagagcagaa aaagaggag     2580 ctggccaggc tacggagaga actggtgcat aaggcaaatc caatacgcaa gtaccagggt     2640
ctggagataa agtcaagtga ccagcctctg actgtgcctg tatctcccaa attctccact    2700
cgattccact gctaaactca gctgtgagct gcggataccg cccggcaatg ggacctgctc    2760
ttaacctcaa acctaggacc gtcttgcttt gtcattgggc atggagagaa cccatttctc    2820 cagacttttta cctacccgtg cctgagaaag catacttgac aactgtggac tccagttttg   2880
ttgagaattg ttttcttaca ttactaaggc taataatgag atgtaactca tgaatgtctc    2940
gattagactc catgtagtta cttcctttaa accatcagcc ggccttttat atgggtcttc    3000
actctgacta gaatttagtc tctgtgtcag cacagtgtaa tctctattgc tattgcccct    3060
tacgactctc accctctccc cactttttttt aaaaatttta accagaaaat aaagatagtt   3120
aaatcctaag atagagatta agtcatggtt taaatgagga caatcagta aatcagattc     3180 tgtcctcttc tctgcatacc gtgaatttat agttaaggat cccttgctg tgagggtaga     3240 aaacctcacc aactgcacca gtgaggaaga agactgcgtg gattcatggg gagcctcaca    3300
gcagccacgc agcaggctct gggtgggct gccgttaagg cacagttctt tccttactgg     3360
tgctgataac aacagggaac cgtgcagtgt gcattttaag acc                      3403
```

<210> SEQ ID NO 97
<211> LENGTH: 2688
<212> TYPE: DNA
<213> ORGANISM: Homo sapiens

<400> SEQUENCE: 97

```
cttcaacccg cgccggcggc gactgcagtt cctgcgagcg aggagcgcgg gacctgctga      60
cacgctgacg ccttcgagcg cggcccgggg cccggagcgg ccggagcagc ccgggtcctg     120
accccggccc ggctcccgct ccgggctctg ccggcgggcg ggcgagcgcg cgcgcggtccg    180 ggccgggggg atgtctcggc ggacgcgctg cgaggatctg gatgagctgc actaccagga    240
cacagattca gatgtgccgg agcagaggga tagcaagtgc aaggtcaaat ggacccatga    300
ggaggacgag cagctgaggg ccctggtgag gcagtttgga cagcaggact ggaagttcct    360
ggccagccac ttccctaacc gcactgacca gcaatgccag tacaggtggc tgagagtttt    420
gaatccagac cttgtcaagg ggccatggac caaagaggaa gaccaaaaag tcatcgagct    480
ggttaagaag tatggcacaa agcagtggac actgattgcc aagcacctga agggccggct    540
ggggaagcag tgccgtgaac gctggcacaa ccacctcaac cctgaggtga agaagtcttg    600
ctggaccgag gaggaggacc gcatcatctg cgaggcccac aaggtgctgg caaccgctg     660 ggccagagatc gccaagatgt tgccagggag gacagacaat gctgtgaaga atcactggaa   720
ctctaccatc aaaaggaagg tggacacagg aggcttcttg agcgagtcca aagactgcaa    780
```

-continued

| | |
|---|---|
| gcccccagtg tacttgctgc tggagctcga ggacaaggac ggcctccaga gtgcccagcc | 840 |
| cacggaaggc cagggaagtc ttctgaccaa ctggccctcc gtccctccta ccataaagga | 900 |
| ggaggaaaac agtgaggagg aacttgcagc agccaccaca tcgaaggaac aggagcccat | 960 |
| cggtacagat ctggacgcag tgcgaacacc agagcccttg gaggaattcc cgaagcgtga | 1020 |
| ggaccaggaa ggctccccac cagaaacgag cctgccttac aagtgggtgg tggaggcagc | 1080 |
| taacctcctc atccctgctg tgggttctag cctctctgaa gccctggact tgatcgagtc | 1140 |
| ggaccctgat gcttggtgtg acctgagtaa atttgacctc cctgaggaac catctgcaga | 1200 |
| ggacagtatc aacaacagcc tagtgcagct gcaagcgtca catcagcagc aagtcctgcc | 1260 |
| accccgccag ccttccgccc tggtgcccag tgtgaccgag taccgcctgg atggccacac | 1320 |
| catctcagac ctgagccgga gcagccgggg cgagctgatc cccatctccc ccagcactga | 1380 |
| agtcgggggc tctggcattg gcacaccgcc ctctgtgctc aagcggcaga ggaagaggcg | 1440 |
| tgtggctctg tcccctgtca ctgagaatag caccagtctg tccttcctgg attcctgtaa | 1500 |
| cagcctcacg cccaagagca cacctgttaa gaccctgccc ttctcgccct cccagtttct | 1560 |
| gaacttctgg aacaaacagg acacattgga gctggagagc ccctcgctga catccacccc | 1620 |
| agtgtgcagc cagaaggtgg tggtcaccac accactgcac cgggacaaga caccctgca | 1680 |
| ccagaaacat gctgcgtttg taaccccaga tcagaagtac tccatggaca cactccccca | 1740 |
| cacgccaacc ccgttcaaga cgccctgga gaagtacgga ccccctgaagc ccctgccaca | 1800 |
| gaccccgcac ctggaggagg acttgaagga ggtgctgcgt tctgaggctg gcatcgaact | 1860 |
| catcatcgag gacgacatca ggcccgagaa gcagaagagg aagcctgggc tgcggcggag | 1920 |
| ccccatcaag aaagtccgga agtctctggc tcttgacatt gtggatgagg atgtgaagct | 1980 |
| gatgatgtcc acactgccca agtctctatc cttgccgaca actgcccctt caaactcttc | 2040 |
| cagcctcacc ctgtcaggta tcaaagaaga caacagcttg ctcaaccagg gcttcttgca | 2100 |
| ggccaagccc gagaaggcag cagtggccca gaagccccga agccacttca cgacacctgc | 2160 |
| ccctatgtcc agtgcctgga agacggtggc ctgcggggg accagggacc agcttttcat | 2220 |
| gcaggagaaa gcccggcagc tcctgggccg cctgaagccc agccacacat ctcggaccct | 2280 |
| catcttgtcc tgaggtgttg agggtgtcac gagcccattc tcatgtttac aggggttgtg | 2340 |
| ggggcagagg gggtctgtga atctgagagt cattcaggtg acctcctgca gggagccttc | 2400 |
| tgccaccagc ccctcccag actctcaggt ggaggcaaca gggccatgtg ctgccctgtt | 2460 |
| gccgagccca gctgtgggcg gctcctggtg ctaacaacaa agttccactt ccaggtctgc | 2520 |
| ctggttccct ccccaaggcc acagggagct ccgtcagctt ctcccaagcc cacgtcaggc | 2580 |
| ctggcctcat ctcagaccct gcttaggatg ggggatgtgg ccaggggtgc tcctgtgctc | 2640 |
| accctctctt ggtgcatttt tttggaagaa taaaattgcc tctctctt | 2688 |

<210> SEQ ID NO 98
<211> LENGTH: 1883
<212> TYPE: DNA
<213> ORGANISM: Homo sapiens

<400> SEQUENCE: 98

| | |
|---|---|
| atgaggttga cgctactttg ttgcacctgg agggaagaac gtatgggaga ggaaggaagc | 60 |
| gagttgcccg tgtgtgcaag ctgcggccag aggatctatg atggccagta cctccaggcc | 120 |
| ctgaacgcgg actggcacgc agactgcttc agtgttgtg actgcagtgc ctccctgtcg | 180 |
| caccagtact atgagaagga tgggcagctc ttctgcaaga aggactactg gcccgctat | 240 |

```
ggcgagtcct gccatgggtg ctctgagcaa atcaccaagg gactggttat ggtggctggg    300
gagctgaagt accaccccga gtgtttcatc tgcctcacgt gtgggacctt tatcggtgac    360
ggggacacct acacgctggt ggagcactcc aagctgtact gcgggcactg ctactaccag    420
actgtggtga cccccgtcat cgagcagatc ctgcctgact ccctggctc ccacctgccc     480 cacaccgtca cctggtgtc catcccagcc tcatctcatg gcaagcgtgg actttcagtc     540
tccattgacc ccccgcacgg cccaccgggc tgtggcaccg agcactcaca caccgtccgc    600
gtccagggag tggatccggg ctgcatgagc ccagatgtga agaattccat ccacgtcgga    660
gaccggatct tggaaatcaa tggcacgccc atccgaaatg tgcccctgga cgagattgac    720
ctgctgattc aggaaaccag ccgcctgctc cagctgaccc tcgagcatga ccctcacgat    780
acactgggcc acgggctggg gcctgagacc agccccctga gctctccggc ttatactccc    840
agcggggagg cgggcagctc tgcccggcag aaacctgtct tcgcaaggac ctgggtcgct    900
ctgagtccct ccgcgtagtc tgccggccac accgcatctt ccggccgtcg acctcatcc     960 acggggaggt gctgggcaag ggctgcttcg gccaggctat caaggtgaca caccgtgaga   1020
caggtgaggt gatggtgatg aaggagctga tccggttcga cgaggagacc cagaggacgt   1080
tcctcaagga ggtgaaggtc atgcgatgcc tggaacaccc caacgtgctc aagttcatcg   1140
gggtgctcta caaggacaag aggctcaact tcatcactga gtacatcaag gcggcacgc    1200 tccggggcat catcaagagc atggacagcc agtacccatg gagccagaga gtgagctttg   1260
ccaaggacat cgcatcaggg atggcctacc tccactccat gaacatcatc caccgagacc   1320
tcaactccca caactgcctg gtccgcgaga caagaatgt ggtggtggct gacttcgggc    1380
tggcgcgtct catggtggac gagaagactc agcctgaggg cctgcggagc ctcaagaagc   1440
cagaccgcaa gaagcgctac accgtggtgg gcaacccta ctggatggca cctgagatga    1500 tcaacgccg cagctatgat gagaaggtgg atgtgttctc ctttgggatc gtcctgtgcg    1560
agatcatcgg gcgggtgaac gcagaccctg actacctgcc ccgcaccatg gactttggcc   1620
tcaacgtgcg aggattcctg gaccgctact gccccccaaa ctgcccccg agcttcttcc    1680 ccatcaccgt gcgctgttgc gatctggacc ccgagaagag gccatccttt gtgaagctgg   1740
aacactggct ggagaccctc cgcatgcacc tggccggcca cctgccactg ggcccacagc   1800
tggagcagct ggacagaggt ttctgggaga cctaccggcg cggcgagagc ggactgcctg   1860
cccaccctga ggtccccgac tga                                           1883

<210> SEQ ID NO 99
<211> LENGTH: 597
<212> TYPE: DNA
<213> ORGANISM: Homo sapiens

<400> SEQUENCE: 99
atgcctggct tcgactacaa gttcctggag aagcccaagc gacggctgct gtgcccactg     60
tgcgggaagc ccatgcgcga gcctgtgcag gtttccacct cgccaccg tttctgcgat      120 acctgcctgc aggagttcct cagtgaagga gtcttcaagt gccctgagga ccagcttcct    180
ctggactatg ccaagatcta cccagacccg gagctggaag tacaagtatt gggcctgcct    240
atccgctgca tccacagtga ggagggctgc cgctggagtg ggccactacg tcatctacag    300 ggccaccctga atacctgcag cttcaatgtc attcctgcc taatcgctg ccccatgaag     360 ctgagccgcc gtgatctacc tgcacacttg cagcatgact gccccaagcg gcgcctcaag    420
```

| | |
|---|---|
| tgcgagtttt gtggctgtga cttcagtggg gaggcctatg aggtggatga gagttctctg | 480 |
| ggctttggtt atcccaagtt catctcccac caggacattc gaaagcgaaa ctatgtgcgg | 540 |
| gatgatgcag tcttcatccg tgctgctgtt gaactgcccc ggaagatcct cagctga | 597 |

<210> SEQ ID NO 100
<211> LENGTH: 23
<212> TYPE: DNA
<213> ORGANISM: Artificial
<220> FEATURE:
<223> OTHER INFORMATION: Synthetic

<400> SEQUENCE: 100

| | |
|---|---|
| cgtatgcccc gctgaatctc gtg | 23 |

<210> SEQ ID NO 101
<211> LENGTH: 24
<212> TYPE: DNA
<213> ORGANISM: Artificial
<220> FEATURE:
<223> OTHER INFORMATION: Synthetic

<400> SEQUENCE: 101

| | |
|---|---|
| tggccaatca tccgtgctca tctg | 24 |

<210> SEQ ID NO 102
<211> LENGTH: 24
<212> TYPE: DNA
<213> ORGANISM: Artificial
<220> FEATURE:
<223> OTHER INFORMATION: Synthetic

<400> SEQUENCE: 102

| | |
|---|---|
| cggagtcaac ggatttggtc gtat | 24 |

<210> SEQ ID NO 103
<211> LENGTH: 24
<212> TYPE: DNA
<213> ORGANISM: Artificial
<220> FEATURE:
<223> OTHER INFORMATION: Synthetic

<400> SEQUENCE: 103

| | |
|---|---|
| agccttctcc atggtggtga agac | 24 |

<210> SEQ ID NO 104
<211> LENGTH: 2005
<212> TYPE: DNA
<213> ORGANISM: Homo sapiens

<400> SEQUENCE: 104

| | |
|---|---|
| ttgcaggctg ctgggctggg gctaagggct gctcagtttc cttcagcggg gcactgggaa | 60 |
| gcgccatggc actgcagggc atctcggtcg tggagctgtc cggcctggcc ccgggcccgt | 120 |
| tctgtgctat ggtcctggct gacttcgggg cgcgtgtggt acgcgtggac cggcccggct | 180 |
| cccgctacga cgtgagccgc ttgggccggg gcaagcgctc gctagtgctg gacctgaagc | 240 |
| agccgcgggg agccgccgtg ctgcggcgtc tgtgcaagcg gtcggatgtg ctgctggagc | 300 |
| ccttccgccg cggtgtcatg gagaaactcc agctgggccc agagattctg cagcgggaaa | 360 |
| atccaaggct tatttatgcc aggctgagtg gatttggcca gtcaggaagc ttctgccggt | 420 |
| tagctggcca cgtatcaac tatttggctt tgtcaggtgt tctctcaaaa attggcagaa | 480 |
| gtggtgagaa tccgtatgcc ccgctgaatc tcctggctga ctttgctggt ggtggcctta | 540 |

```
tgtgtgcact gggcattata atggctcttt ttgaccgcac acgcactggc aagggtcagg    600
tcattgatgc aaatatggtg aaggaacag catatttaag ttcttttctg tggaaaactc    660
agaaatcgag tctgtgggaa gcacctcgag gacagaacat gttggatggt ggagcacctt   720
tctatacgac ttacaggaca gcagatgggg aattcatggc tgttggagca atagaacccc   780
agttctacga gctgctgatc aaaggacttg gactaaagtc tgatgaactt cccaatcaga   840
tgagcatgga tgattggcca gaaatgaaga agaagtttgc agatgtattt gcaaagaaga   900
cgaaggcaga gtggtgtcaa atctttgacg gcacagatgc ctgtgtgact ccggttctga   960
cttttgagga ggttgttcat catgatcaca acaaggaacg gggctcgttt atcaccagtg   1020
aggagcagga cgtgagcccc cgccctgcac ctctgctgtt aaacacccca gccatcccnt   1080 cttcaaaag ggatccttc ataggagaac acactgagga gatacttgaa gaatttggat    1140
tcagccgcga agagatttat cagcttaact cagataaaat cattgaaagt aataaggtaa   1200
aagctagtct ctaacttcca ggcccacggc tcaagtgaat ttgaatactg catttacagt   1260
gtagagtaac acataacatt gtatgcatgg aaacatggag gaacagtatt acagtgtcct   1320
accactctaa tcaagaaaag aattacagac tctgattcta cagtgatgat tgaattctaa   1380
aaatggttat cattagggct tttgatttat aaaactttgg gtacttatac taaattatgg   1440
tagttattct gccttccagt ttgcttgata tatttgttga tattaagatt cttgacttat   1500
attttgaatg ggttctagtg aaaaaggaat gatatattct tgaagacatc gatatacatt   1560
tatttacact cttgattcta caatgtagaa atgaggaaa tgccacaaat tgtatggtga    1620
taaaagtcac gtgaaacaga gtgattggtt gcatccaggc cttttgtctt ggtgttcatg   1680
atctccctct aagcacattc caaactttag caacagttat cacactttgt aatttgcaaa   1740
gaaaagtttc acctgtattg aatcagaatg ccttcaactg aaaaaaacat atccaaaata   1800
atgaggaaat gtgttggctc actacgtaga gtccagaggg acagtcagtt ttagggttgc   1860
ctgtatccag taactcgggg cctgtttccc cgtgggtctc tgggctgtca gctttccttt   1920
ctccatgtgt ttgatttctc ctcaggctgg tagcaagttc tggatcttat acccaacaca   1980
cagcaacatc cagaaataaa gatct                                         2005
```

<210> SEQ ID NO 105
<211> LENGTH: 24
<212> TYPE: DNA
<213> ORGANISM: Artificial
<220> FEATURE:
<223> OTHER INFORMATION: Synthetic

<400> SEQUENCE: 105

```
tggccaatca tccgtgctca tctg                                          24
```

<210> SEQ ID NO 106
<211> LENGTH: 24
<212> TYPE: DNA
<213> ORGANISM: Artificial
<220> FEATURE:
<223> OTHER INFORMATION: Synthetic

<400> SEQUENCE: 106

```
agccttctcc atggtggtga agac                                          24
```

<210> SEQ ID NO 107
<211> LENGTH: 24
<212> TYPE: DNA

<213> ORGANISM: Artificial
<220> FEATURE:
<223> OTHER INFORMATION: Synthetic

<400> SEQUENCE: 107
agccttctcc atggtggtga agac                                    24

<210> SEQ ID NO 108
<211> LENGTH: 21
<212> TYPE: DNA
<213> ORGANISM: Artificial
<220> FEATURE:
<223> OTHER INFORMATION: Synthetic

<400> SEQUENCE: 108
gccagactgg gaagaaatct g                                       21

<210> SEQ ID NO 109
<211> LENGTH: 21
<212> TYPE: DNA
<213> ORGANISM: Artificial
<220> FEATURE:
<223> OTHER INFORMATION: Synthetic

<400> SEQUENCE: 109
tgtgctggaa aatccaagtc a                                       21

<210> SEQ ID NO 110
<211> LENGTH: 24
<212> TYPE: DNA
<213> ORGANISM: Artificial
<220> FEATURE:
<223> OTHER INFORMATION: Synthetic

<400> SEQUENCE: 110
cggagtcaac ggatttggtc gtat                                    24

<210> SEQ ID NO 111
<211> LENGTH: 24
<212> TYPE: DNA
<213> ORGANISM: Artificial
<220> FEATURE:
<223> OTHER INFORMATION: Synthetic

<400> SEQUENCE: 111
agccttctcc atggtggtga agac                                    24

<210> SEQ ID NO 112
<211> LENGTH: 35
<212> TYPE: DNA
<213> ORGANISM: Artificial
<220> FEATURE:
<223> OTHER INFORMATION: Synthetic

<400> SEQUENCE: 112
ggggtaccat gggcggccgc gaacaaaagt tgatt                        35

<210> SEQ ID NO 113
<211> LENGTH: 33
<212> TYPE: DNA
<213> ORGANISM: Artificial
<220> FEATURE:
<223> OTHER INFORMATION: Synthetic

<400> SEQUENCE: 113
ggggaattct catgccagca atagatgctt ttt                          33

<210> SEQ ID NO 114
<211> LENGTH: 3042
<212> TYPE: DNA
<213> ORGANISM: Homo sapiens

<400> SEQUENCE: 114

```
cggaggcgct gggcgcacgg cgcggagccg gccggagctc gaggccggcg gcggcgggag      60
agcgacccgg gcggcctcgt agcggggccc cggatccccg agtggcggcc ggagcctcga     120
aaagagattc tcagcgctga ttttgagatg atgggcttgg aaacgggcg tcgcagcatg      180
aagtcgccgc ccctcgtgct ggccgccctg gtggcctgca tcatcgtctt gggcttcaac     240
tactggattg cgagctcccg gagcgtggac ctccagacac ggatcatgga gctggaaggc     300
agggtccgca gggcggctgc agagagaggc gccgtggagc tgaagaagaa cgagttccag     360
ggagagctgg agaagcagcg ggagcagctt gacaaaatcc agtccagcca caacttccag     420
ctggagagcg tcaacaagct gtaccaggac gaaaaggcgg ttttggtgaa taacatcacc     480
acaggtgaga ggctcatccg agtgctgcaa gaccagttaa agaccctgca gaggaattac     540
ggcaggctgc agcaggatgt cctccagttt cagaagaacc agaccaacct ggagaggaag     600
ttctcctacg acctgagcca gtgcatcaat cagatgaagg aggtgaagga acagtgtgag     660
gagcgaatag aagaggtcac caaaaagggg aatgaagctg tagcttccag agacctgagt     720
gaaaacaacg accagagaca gcagctccaa gccctcagtg agcctcagcc caggctgcag     780
gcagcaggcc tgccacacac agaggtgcca caagggaagg gaaacgtgct tggtaacagc     840
aagtcccaga caccagcccc cagttccgaa gtggttttgg attcaaagag acaagttgag     900
aaagaggaaa ccaatgagat ccaggtggtg aatgaggagc ctcagaggga caggctgccg     960
caggagccag gccgggagca ggtggtggaa gacagacctg taggtggaag aggcttcggg    1020
ggagccggaa actgggcca gaccccacag gtgcaggctg ccctgtcagt gagccaggaa    1080
aatccagaga tggagggccc tgagcgagac cagcttgtca tccccgacgg acaggaggag    1140
gagcaggaag ctgccgggga agggagaaac cagcagaaac tgagaggaga agatgactac    1200
aacatggatg aaaatgaagc agaatctgag acagacaagc aagcagccct ggcagggaat    1260
gacagaaaca tagatgtttt taatgttgaa gatcagaaaa gagacaccat aaatttactt    1320
gatcagcgtg aaaagcggaa tcatacactc tgaattgaac tggaatcaca tatttcacaa    1380
cagggccgaa gagatgacta taaaatgttc atgagggact gaatactgaa actgtgaaa    1440
tgtactaaat aaaatgtaca tctgaagatg attattgtga aattttagta tgcactttgt    1500
gtaggaaaaa atggaatggt cttttaaaca gcttttgggg gggtactttg gaagtgtcta    1560
ataaggtgtc acaattttg gtagtaggta tttcgtgaga agttcaacac caaaactgga    1620
acatagttct ccttcaagtg ttggcgacag cggggcttcc tgattctgga atataacttt    1680
gtgtaaatta acagccacct atagaagagt ccatctgctg tgaaggagag acagagaact    1740
ctgggttccg tcgtcctgtc cacgtgctgt accaagtgct ggtgccagcc tgttacctgt    1800
tctcactgaa aagtctggct aatgctcttg tgtagtcact tctgattctg acaatcaatc    1860
aatcaatggc ctagagcact gactgttaac acaaacgtca ctagcaaagt agcaacagct    1920
ttaagtctaa atacaaagct gttctgtgtg agaatttttt aaaaggctac ttgtataata    1980
accccttgtca tttttaatgt acaaaacgct attaagtggc ttagaatttg aacatttgtg    2040
gtctttattt actttgcttc gtgtgtgggc aaagcaacat cttccctaaa tatatattac    2100
```

-continued

```
caagaaaagc aagaagcaga ttaggttttt gacaaaacaa acaggccaaa aggggggctga    2160 cctggagcag agcatggtga gaggcaaggc atgagagggc aagtttgttg tggacagatc    2220
tgtgcctact ttattactgg agtaaaagaa aacaaagttc attgatgtcg aaggatatat    2280
acagtgttag aaattaggac tgtttagaaa acaggaata caatggttgt ttttatcata    2340
gtgtacacat ttagcttgtg gtaaatgact cacaaaactg attttaaaat caagttaatg    2400
tgaattttga aaattactac ttaatcctaa ttcacaataa caatggcatt aaggtttgac    2460
ttgagttggt tcttagtatt atttatggta aataggctct taccacttgc aaataactgg    2520
ccacatcatt aatgactgac ttcccagtaa ggctctctaa ggggtaagta ggaggatcca    2580
caggatttga gatgctaagg ccccagagat cgtttgatcc aaccctctta ttttcagagg    2640
ggaaaatggg gcctagaagt tacagagcat ctagctggtg cgctggcacc cctggcctca    2700
cacagactcc cgagtagctg ggactacagg cacacagtca ctgaagcagg ccctgtttgc    2760
aattcacgtt gccacctcca acttaaacat tcttcatatg tgatgtcctt agtcactaag    2820
gttaaacttt cccacccaga aaaggcaact tagataaaat cttagagtac tttcatactc    2880
ttctaagtcc tcttccagcc tcactttgag tcctccttgg ggttgatagg aattttctct    2940
tgctttctca ataaagtctc tattcatctc atgtttaatt tgtacgcata gaattgctga    3000
gaaataaaat gttctgttca acttaaaaaa aaaaaaaaa aa                        3042
```

<210> SEQ ID NO 115
<211> LENGTH: 2368
<212> TYPE: DNA
<213> ORGANISM: Homo sapiens

<400> SEQUENCE: 115

```
cgggcgatgc cgcgctgcgg gggggccgca cagccgccgc caccgccacc gccgccgggt      60 gggggtgggag gggcgggaac gcgcgccgcc gcctccaggg tgggcgcctt tcgccgtgga    120
cgccgaccgt ccgggacgag ggtttcatca ccttaaatgg ttttgaacca atgaaggtgt    180
attcccttaa aaagacggac agcccatcgt gtgaactata gagtttgtgg acagattat     240 attgggttca tagtggcgtc atgcacgcag actcctgcaa gttccccctaa gttcttagag    300 gactgctttg cctttgatc tgagagttgc aaagttccat aaagaatggc ccttgtggat     360
aagcacaaag tcaagagaca gcgattggac agaatttgtg aaggtatccg ccccagatc    420 atgaacggcc cctgcaccc ccgcccctg gtggcgctgc tggacggccg cgactgcact    480
gtggagatgc ccatcctgaa ggacctggcc actgtgcct tctgtgacgc gcagtcgacg    540
caggaaatcc acgagaaggt tctaaacgaa gccgtgggcg ccatgatgta ccacaccatc    600
accctcacca gggaggacct ggagaagttc aaggccctga gagtgatcgt gcggataggc    660
agtggctatg acaacgtgga catcaaggct gccggcgagc tcggaattgc cgtgtgcaac    720
atcccgtctg cagccgtgga agagacagcg gactctacca tctgccacat cctcaacctg    780
taccggagga cacgtggct gtaccaggca ctgcgggaag gcacgcgggt tcagagcgtg    840
gagcagatcc gcgaggtggc ctcgggagcg gcccgcatcc gtgggagac gctgggcctc    900 attggctttg gtcgcacggg gcaggcggtt gcagttcgag ccaaggcctt tggattcagc    960
gtcatatttt atgaccccta cttgcaggat gggatcgagc ggtccctggg cgtgcagagg    1020
gtctacaccc tgcaggattt gctgtatcag agcgactgcg tctccttgca ctgcaatctc    1080
aacgaacata accaccacct catcaatgac tttaccataa agcagatgag gcagggagca    1140
ttccttgtga acgcagcccg tggcggcctg gtggacgaga aagccttagc acaagccctc    1200
```

-continued

```
aaggagggca ggatacgagg ggcagccctc gacgtgcatg agtcagagcc cttcagcttt      1260
gctcagggtc cgttgaaaga tgccccgaat ctcatctgca ctcctcacac tgcctggtac      1320
agtgagcagg cgtcactgga gatgagggag gcagctgcca ccgagatccg ccgagccatc      1380
acaggtcgca tcccagaaag cttaagaaat tgtgtgaaca aggaattctt tgtcacatca      1440
gcgccttggt cagtaataga ccagcaagca attcatcctg agctcaatgg tgccacatac      1500
agatatccgc caggcatcgt gggtgtggct ccaggaggac ttcctgcagc catggaaggg      1560
atcatccctg gaggcatccc agtgactcac aacctcccga cagtggcaca tccttcccaa      1620
gcgccctctc ccaaccagcc cacaaaacac ggggacaatc gagagcaccc caacgagcaa      1680
tagcagagaa tgccagaagg taatcactca gatacacttg ggaccaagag acagtgaaaa      1740
atagatgaac taagagaaaa agaatcggat ggtctttgta actgattctg acatatgca      1800 tcattgatgt tgcagtgttg aaactacaag agctagaaaa ctgaagatgt cgtctgctta      1860
cggaagcgct gaaagactag gatgtgattt attaacgacc aacttctgtt attgtgtgtt      1920
aagtttttca tctgtgcatc aaatcacaaa agaataaat agagcttttt cctttatcag      1980
tcccttgggc acagcaggtc ctgaacaccc tgctctacaa tgttgcatca agagttcaaa      2040
caacaaaata aaaatatta agaggaaatc cccatcctgt gacttgagtc ccttaagtct      2100 acagggctg gtgacctctt tttgctaata ggaaaatcac attactacaa aatgggaga      2160 aaactgtttg cctgtggtag acacctgcac gcataggatt gaagacagta caggctgctg      2220
tacagagaag cgcctctcac atctgaactg catactgagc gggcaagtcg gttgtaagtt      2280
cagtaaaacc ctctgatgat gcaaaaaaaa aaaaaagta ttaagtttca caagctgttt      2340
gtactcaaat atattttctc agtttcag                                        2368
```

<210> SEQ ID NO 116
<211> LENGTH: 1362
<212> TYPE: DNA
<213> ORGANISM: Homo sapiens

<400> SEQUENCE: 116

```
catttgggga cgctctcagc tctcggcgca cggcccagct tccttcaaaa tgtctactgt      60
tcacgaaatc ctgtgcaagc tcagcttgga gggtgatcac tctacacccc caagtgcata     120
tgggtctgtc aaagcctata ctaactttga tgctgagcgg gatgctttga acattgaaac     180
agccatcaag accaaggtg tggatgaggt caccattgtc aacatttga ccaaccgcag      240 caatgcacag agacaggata ttgccttcgc ctaccagaga aggaccaaaa aggaacttgc     300
atcagcactg aagtcagcct tatctggcca cctggagacg tgattttgg gcctattgaa      360 gacacctgct cagtatgacg cttctgagct aaaagcttcc atgaaggggc tgggaaccga     420
cgaggactct ctcattgaga tcatctgctc cagaaccaac caggagctgc aggaaattaa      480
cagagtctac aaggaaatgt acaagactga tctggagaag gacattattt cggacacatc     540
tggtgacttc cgcaagctga tggttgccct ggcaaagggt agaagagcag aggatggctc     600
tgtcattgat tatgaactga ttgaccaaga tgctcgggat ctctatgacg ctggagtgaa      660
gaggaaagga actgatgttc ccaagtggat cagcatcatg accgagcgga gcgtgccca      720 cctccagaaa gtatttgata ggtacaagag ttacagccct tatgacatgt tggaaagcat     780
caggaaagag gttaaggag acctggaaaa tgctttcctg aacctggttc agtgcattca      840
gaacaagccc ctgtatttg ctgatcggct gtatgactcc atgaagggca aggggacgcg      900
```

| | |
|---|---:|
| agataaggtc ctgatcagaa tcatggtctc ccgcagtgaa gtggacatgt tgaaaattag | 960 |
| gtctgaattc aagagaaagt acggcaagtc cctgtactat tatatccagc aagacactaa | 1020 |
| gggcgactac cagaaagcgc tgctgtacct gtgtggtgga gatgactgaa gcccgacacg | 1080 |
| gcctgagcgt ccagaaatgg tgctcaccat gcttccagct aacaggtcta gaaaaccagc | 1140 |
| ttgcgaataa cagtccccgt ggccatccct gtgagggtga cgttagcatt accccccaacc | 1200 |
| tcattttagt tgcctaagca ttgcctggcc ttcctgtcta gtctctcctg taagccaaag | 1260 |
| aaatgaacat tccaaggagt tggaagtgaa gtctatgatg tgaaacactt tgcctcctgt | 1320 |
| gtactgtgtc ataaacagat gaataaactg aatttgtact tt | 1362 |

<210> SEQ ID NO 117
<211> LENGTH: 2137
<212> TYPE: DNA
<213> ORGANISM: Homo sapiens

<400> SEQUENCE: 117

| | |
|---|---:|
| gccccaggtg cgcttcccct agagagggat tttccggtct cgtgggcaga ggaacaacca | 60 |
| ggaacttggg ctcagtctcc accccacagt ggggcggatc cgtcccggat aagacccgct | 120 |
| gtctggccct gagtagggtg tgacctccgc agccgcagag gaggagcgca gcccggcctc | 180 |
| gaagaacttc tgcttgggtg gctgaactct gatcttgacc tagagtcatg gccatggcaa | 240 |
| ccaaaggagg tactgtcaaa gctgcttcag gattcaatgc catggaagat gcccagaccc | 300 |
| tgaggaaggc catgaaaggg ctcggcaccg atgaagacgc cattattagc gtccttgcct | 360 |
| accgcaacac cgcccagcgc caggagatca ggacagccta caagagcacc atcggcaggg | 420 |
| acttgataga cgacctgaag tcagaactga gtggcaactt cgagcaggtg attgtgggga | 480 |
| tgatgacgcc cacggtgctg tatgacgtgc aagagctgcg aagggccatg aagggagccg | 540 |
| gcactgatga gggctgccta attgagatcc tggcctcccg gacccctgag gagatccggc | 600 |
| gcataagcca aacctaccag cagcaatatg gacggagcct gaagatgac attcgctctg | 660 |
| acacatcgtt catgttccag cgagtgctgg tgtctctgtc agctggtggg agggatgaag | 720 |
| gaaattatct ggacgatgct ctcgtgagac aggatgccca ggacctgtat gaggctggag | 780 |
| agaagaaatg ggggacagat gaggtgaaat ttctaactgt tctctgttcc cggaaccgaa | 840 |
| atcacctgtt gcatgtgttt gatgaataca aaaggatatc acagaaggat attgaacaga | 900 |
| gtattaaatc tgaaacatct ggtagctttg aagatgctct gctggctata gtaaagtgca | 960 |
| tgaggaacaa atctgcatat tttgctgaaa agctctataa atcgatgaag ggcttgggca | 1020 |
| ccgatgataa caccctcatc agagtgatgg tttctcgagc agaaattgac atgttggata | 1080 |
| tccgggcaca cttcaagaga ctctatggaa agtctctgta ctcgttcatc aagggtgaca | 1140 |
| catctggaga ctacaggaaa gtactgcttg ttctctgtgg aggagatgat taaaataaaa | 1200 |
| atcccagaag gacaggagga ttctcaacac tttgaatttt tttaacttca tttttctaca | 1260 |
| ctgctattat cattatctca gaatgcttat ttccaattaa aacgcctaca gctgcctcct | 1320 |
| agaatataga ctgtctgtat tattattcac ctataattag tcattatgat gctttaaagc | 1380 |
| tgtacttgca tttcaaagct tataagatat aaatggagat tttaagtag aaataaatat | 1440 |
| gtattccatg ttttttaaaag attactttct actttgtgtt tcacagacat tgaatatatt | 1500 |
| aaattattcc atattttctt ttcagtgaaa aattttttaa atggaagact gttctaaaat | 1560 |
| cacttttttc cctaatccaa tttttagagt ggctagtagt ttcttcattt gaattgtaa | 1620 |
| gcatccggtc agtaagaatg cccatccagt tttctatatt tcatagtcaa agccttgaaa | 1680 |

-continued

```
gcatctacaa atctcttttt ttaggttttg tccatagcat cagttgatcc ttactaagtt    1740
tttcatggga gacttccttc atcacatctt atgttgaaat cactttctgt agtcaaagta    1800
taccaaaacc aatttatctg aactaaattc taaagtatgg ttatacaaac catatacatc    1860
tggttaccaa acataaatgc tgaacattcc atattattat agttaatgtc ttaatccagc    1920
ttgcaagtga atgaaaaaa aataagctt caaactaggt attctgggaa tgatgtaatg    1980
ctctgaattt agtatgatat aaagaaaact tttttgtgct aaaaatactt tttaaaatca    2040
attttgttga ttgtagtaat ttctatttgc actgtgcctt tcaactccag aaacattctg    2100
aagatgtact tggatttaat taaaaagttc actttgt                              2137
```

<210> SEQ ID NO 118
<211> LENGTH: 1958
<212> TYPE: DNA
<213> ORGANISM: Homo sapiens

<400> SEQUENCE: 118

```
gctgctgcgc ccgcggctcc ccagtgcccc gagtgccccg cgggccccgc gagcgggagt      60
gggacccagc cctaggcaga acccaggcgc cgcgcccggg acgcccgcgg agagagccac     120
tcccgcccac gtcccatttc gcccctcgcg tccggagtcc ccgtggccag atctaaccat     180
gagctaccct ggctatcccc cgcccccagg tggctaccca ccagctgcac caggtggtgg     240
tccctgggga ggtgctgcct accctcctcc gcccagcatg cccccatcg ggctggataa     300 cgtggccacc tatgcggggc agttcaacca ggactatctc tcgggaatgg cggccaacat     360
gtctgggaca tttggaggag ccaacatgcc caacctgtac cctggggccc ctggggctgg     420
ctacccacca gtgccccctg gcggctttgg gcagcccccc tctgcccagc agcctgttcc     480
tccctatggg atgtatccac cccaggagg aaacccaccc tccaggatgc cctcatatcc     540
gccataccca ggggcccctg tgccgggcca gccatgcca ccccccggac agcagccccc     600 agggcctac cctgggcagc caccagtgac ctaccctggt cagcctccag tgccactccc     660
tgggcagcag cagccagtgc cgagctaccc aggatacccg ggtctgggga ctgtcacccc     720
cgctgtgccc ccaacccagt ttggaagccg aggcaccatc actgatgctc ccggctttga     780 cccctgcga gatgccgagg tcctgcggaa ggccatgaaa ggcttcggga cggatgagca     840
ggccatcatt gactgcctgg ggagtcgctc caacaagcag cggcagcaga tcctacttc     900 cttcaagacg gcttacggca aggatttgat caaagatctg aaatctgaac tgtcaggaaa     960
ctttgagaag acaatcttgg ctctgatgaa gaccccagtc ctctttgaca tttatgagat    1020
aaaggaagcc atcaagggg ttggcactga tgaagcctgc ctgattgaga tcctcgcttc    1080
ccgcagcaat gagcacatcc gagaattaaa cagagcctac aaagcagaat caaaaagac    1140 cctggaagag gccattcgaa gcgacacatc agggcacttc cagcggctcc tcatctctct    1200
ctctcaggga aaccgtgatg aaagcacaaa cgtggacatg tcactcgccc agagagatgc    1260
ccaggagctg tatgcggccg gggagaaccg cctgggaaca gacgagtcca gttcaatgc    1320 ggttctgtgc tcccggagcc gggcccacct ggtagcagtt ttcaatgagt accagagaat    1380
gacaggccgg gacattgaga agagcatctg ccgggagatg tccggggacc tggaggaggg    1440
catgctggcc gtggtgaaat gtctcaagaa tacccagcc ttctttgcgg agaggctcaa    1500
caaggccatg aggggggcag gaacaaagga ccggaccctg attcgcatca tggtgtctcg    1560
cagcgagacc gacctcctgg acatcagatc agagtataag cggatgtacg gcaagtcgct    1620
```

-continued

| | |
|---|---|
| gtaccacgac atctcgggag atacttcagg ggattaccgg aagattctgc tgaagatctg | 1680 |
| tggtggcaat gactgaacag tgactggtgg ctcacttctg cccacctgcc ggcaacacca | 1740 |
| gtgccaggaa aaggccaaaa gaatgtctgt ttctaacaaa tccacaaata gccccgagat | 1800 |
| tcaccgtcct agagcttagg cctgtcttcc acccctcctg acccgtatag tgtgccacag | 1860 |
| gacctgggtc ggtctagaac tctctcagga tgccttttct accccatccc tcacagcctc | 1920 |
| ttgctgctaa aatagatgtt tcattttct gaaaaaaa | 1958 |

<210> SEQ ID NO 119
<211> LENGTH: 5791
<212> TYPE: DNA
<213> ORGANISM: Homo sapiens

<400> SEQUENCE: 119

| | |
|---|---|
| ggctcatgct cgggagcgtg gttgagcggc tggcgcggtt gtcctggagc aggggcgcag | 60 |
| gaattctgat gtgaaactaa cagtctgtga gccctggaac ctccactcag agaagatgaa | 120 |
| ggatatcgac ataggaaaag agtatatcat ccccagtcct gggtatagaa gtgtgaggga | 180 |
| gagaaccagc acttctggga cgcacagaga ccgtgaagat tccaagttca ggagaactcg | 240 |
| accgttggaa tgccaagatg ccttggaaac agcagcccga gccgagggcc tctctcttga | 300 |
| tgcctccatg cattctcagc tcagaatcct ggatgaggag catcccaagg gaaagtacca | 360 |
| tcatggcttg agtgctctga gcccatccg gactacttcc aaacaccagc acccagtgga | 420 |
| caatgctggg cttttttcct gtatgacttt ttcgtggctt tcttctctgg cccgtgtggc | 480 |
| ccacaagaag ggggagctct caatggaaga cgtgtggtct ctgtccaagc acgagtcttc | 540 |
| tgacgtgaac tgcagaagac tagagagact gtggcaagaa gagctgaatg aagttgggcc | 600 |
| agacgctgct tccctgcgaa gggttgtgtg gatcttctgc cgcaccaggc tcatcctgtc | 660 |
| catcgtgtgc ctgatgatca cgcagctggc tggcttcagt ggaccagcct tcatggtgaa | 720 |
| acacctcttg gagtataccc aggcaacaga gtctaacctg cagtacagct tgttgttagt | 780 |
| gctgggcctc ctcctgacgg aaatcgtgcg gtcttggtcg cttgcactga cttgggcatt | 840 |
| gaattaccga accggtgtcc gcttgcgggg ggccatccta accatggcat ttaagaagat | 900 |
| ccttaagtta aagaacatta aagagaaatc cctgggtgag ctcatcaaca tttgctccaa | 960 |
| cgatgggcag agaatgtttg aggcagcagc cgttggcagc ctgctggctg gaggacccgt | 1020 |
| tgttgccatc ttaggcatga tttataatgt aattattctg ggaccaacag gcttcctggg | 1080 |
| atcagctgtt tttatcctct tttacccagc aatgatgttt gcatcacggc tcacagcata | 1140 |
| tttcaggaga aaatgcgtgg ccgccacgga tgaacgtgtc cagaagatga atgaagttct | 1200 |
| tacttacatt aaatttatca aaatgtatgc ctgggtcaaa gcattttctc agagtgttca | 1260 |
| aaaaatccgc gaggaggagc gtcggatatt ggaaaaagct gggtacttcc agagcatcac | 1320 |
| tgtgggtgtg gctcccattg tggtggtgat tgccagcgtg gtgaccttct ctgttcatat | 1380 |
| gaccctgggc ttcgatctga cagcagcaca ggctttcaca gtggtgacag tcttcaattc | 1440 |
| catgactttt gctttgaaag taacaccgtt ttcagtaaag tccctctcag aagcctcagt | 1500 |
| ggctgttgac agatttaaga gtttgtttct aatggaagag gttcacatga taaagaacaa | 1560 |
| accagccagt cctcacatca agatagagat gaaaaatgcc accttggcat gggactcctc | 1620 |
| ccactccagt atccagaact cgcccaagct gacccccaaa atgaaaaaag acaagagggc | 1680 |
| ttccaggggc aagaaagaga aggtgaggca gctgcagcgc actgagcatc aggcggtgct | 1740 |
| ggcagagcag aaaggccacc tcctcctgga cagtgacgag cggcccagtc ccgaagagga | 1800 |

-continued

```
agaaggcaag cacatccacc tgggccacct gcgcttacag aggacactgc acagcatcga      1860
tctggagatc caagagggta aactggttgg aatctgtggc agtgtgggaa gtggaaaaac      1920
ctctctcatt tcagccattt taggccagat gacgcttcta gagggcagca ttgcaatcag      1980
tggaaccttc gcttatgtgg cccagcaggc ctggatcctc aatgctactc tgagagacaa      2040
catcctgttt gggaaggaat atgatgaaga aagatacaac tctgtgctga acagctgctg      2100
cctgaggcct gacctggcca ttcttcccag cagcgacctg acggagattg agagcgagg       2160 agccaacctg agcggtgggc agcgccagag gatcagcctt gcccgggcct tgtatagtga      2220
caggagcatc tacatcctgg acgacccct cagtgcctta gatgcccatg tgggcaacca      2280
catcttcaat agtgctatcc ggaaacatct caagtccaag acagttctgt ttgttaccca      2340
ccagttacag tacctggttg actgtgatga agtgatcttc atgaaagagg gctgtattac      2400
ggaaagaggc acccatgagg aactgatgaa tttaaatggt gactatgcta ccattttaa      2460 taacctgttg ctgggagaga caccgccagt tgagatcaat tcaaaaaagg aaaccagtgg      2520
ttcacagaag aagtcacaag acaagggtcc taaaacagga tcagtaaaga aggaaaaagc      2580
agtaaagcca gaggaagggc agcttgtgca gctggaagag aaagggcagg gttcagtgcc      2640
ctggtcagta tatggtgtct acatccaggc tgctggggc ccttggcat tcctggttat       2700 tatggcccett ttcatgctga atgtaggcag caccgccttc agcacctggt ggttgagtta      2760
ctggatcaag caaggaagcg ggaacaccac tgtgactcga gggaacgaga cctcggtgag      2820
tgacagcatg aaggacaatc ctcatatgca gtactatgcc agcatctacg ccctctccat      2880
ggcagtcatg ctgatcctga aagccattcg aggagttgtc tttgtcaagg gcacgctgcg      2940
agcttcctcc cggctgcatg acgagctttt ccgaaggatc cttcgaagcc ctatgaagtt      3000
ttttgacacg accccacag ggaggattct caacaggttt ccaaagaca tggatgaagt       3060 tgacgtgcgg ctgccgttcc aggccgagat gttcatccag aacgttatcc tggtgttctt      3120
ctgtgtggga atgatcgcag gagtcttccc gtggttcctt gtggcagtgg ggccccttgt      3180
catcctcttt tcagtcctgc acattgtctc caggtcctg attcgggagc tgaagcgtct       3240
ggacaatatc acgcagtcac ctttcctctc ccacatcacg tccagcatac agggccttgc      3300
caccatccac gcctacaata aagggcagga gtttctgcac agataccagg agctgctgga      3360
tgacaaccaa gctccttttt ttttgtttac gtgtgcgatg cggtggctgg ctgtgcggct      3420
ggacctcatc agcatcgccc tcatcaccac cacggggctg atgatcgttc ttatgcacgg      3480
gcagattccc ccagcctatg cgggtctcgc catctcttat gctgtccagt taacggggct      3540
gttccagttt acggtcagac tggcatctga gacagaagct cgattcacct cggtggagag      3600
gatcaatcac tacattaaga ctctgtcctt ggaagcacct gccagaatta agaacaaggc      3660
tccctcccct gactggcccc aggagggaga ggtgacctt gagaacgcag agatgaggta       3720
ccgagaaaac ctccctctcg tcctaaagaa agtatccttc acgatcaaac taaagagaa      3780 gattggcatt gtggggcgga caggatcagg gaagtcctcg ctggggatgg ccctcttccg      3840
tctggtggag ttatctggag gctgcatcaa gattgatgga gtgagaatca gtgatattgg      3900
ccttgccgac ctccgaagca aactctctat cattcctcaa gagccggtgc tgttcagtgg      3960
cactgtcaga tcaaatttgg accccttcaa ccagtacact gaagaccaga tttgggatgc      4020
cctggagagg acacacatga aagaatgtat tgctcagcta cctctgaaac ttaatctga       4080 agtgatggag aatggggata acttctcagt gggggaacgg cagctcttgt gcatagctag      4140
```

-continued

| | |
|---|---|
| agccctgctc cgccactgta agattctgat tttagatgaa gccacagctg ccatggacac | 4200 |
| agagacagac ttattgattc aagagaccat ccgagaagca tttgcagact gtaccatgct | 4260 |
| gaccattgcc catcgcctgc acacggttct aggctccgat aggattatgg tgctggccca | 4320 |
| gggacaggtg gtggagtttg acccccatc ggtccttctg tccaacgaca gttcccgatt | 4380 |
| ctatgccatg tttgctgctg cagagaacaa ggtcgctgtc aagggctgac tcctccctgt | 4440 |
| tgacgaagtc tcttttcttt agagcattgc cattccctgc ctggggcggg ccctcatcg | 4500 |
| cgtcctccta ccgaaacctt gcctttctcg attttatctt tcgcacagca gttccggatt | 4560 |
| ggcttgtgtg tttcactttt agggagagtc atattttgat tattgtattt attccatatt | 4620 |
| catgtaaaca aaatttagtt tttgttctta attgcactct aaaaggttca gggaaccgtt | 4680 |
| attataattg tatcagaggc ctataatgaa gctttatacg tgtagctata tctatatata | 4740 |
| attctgtaca tagcctatat ttacagtgaa aatgtaagct gtttatttta tattaaaata | 4800 |
| agcactgtgc taataacagt gcatattcct ttctatcatt tttgtacagt ttgctgtact | 4860 |
| agagatctgg ttttgctatt agactgtagg aagagtagca tttcattctt ctctagctgg | 4920 |
| tggtttcacg gtgccaggtt ttctgggtgt ccaaaggaag acgtgtggca atagtgggcc | 4980 |
| ctccgacagc cccctctgcc gcctccccac ggccgctcca ggggtggctg agacgggtg | 5040 |
| ggcggctgga gaccatgcag agcgccgtga gttctcaggg ctcctgcctt ctgtcctggt | 5100 |
| gtcacttact gtttctgtca ggagagcagc ggggcgaagc ccaggcccct tttcactccc | 5160 |
| tccatcaaga atggggatca cagagacatt cctccgagcc ggggagtttc tttcctgcct | 5220 |
| tcttcttttt gctgttgttt ctaaacaaga atcagtctat ccacagagag tcccactgcc | 5280 |
| tcaggttcct atggctggcc actgcacaga gctctccagc tccaagacct gttggttcca | 5340 |
| agccctggag ccaactgctg cttttgagg tggcactttt tcatttgcct attcccacac | 5400 |
| ctccacagtt cagtggcagg gctcaggatt tcgtgggtct gttttccttt ctcaccgcag | 5460 |
| tcgtcgcaca gtctctctct ctctctcccc tcaaagtctg caactttaag cagctcttgc | 5520 |
| taatcagtgt ctcacactgg cgtagaagtt tttgtactgt aaagagacct acctcaggtt | 5580 |
| gctggttgct gtgtggtttg gtgtgttccc gcaaaccccc tttgtgctgt ggggctggta | 5640 |
| gctcaggtgg gcgtggtcac tgctgtcatc aattgaatgg tcagcgttgc atgtcgtgac | 5700 |
| caactagaca ttctgtcgcc ttagcatgtt tgctgaacac cttgtggaag caaaaatctg | 5760 |
| aaaatgtgaa taaaattatt ttggatttg t | 5791 |

<210> SEQ ID NO 120
<211> LENGTH: 1992
<212> TYPE: DNA
<213> ORGANISM: Homo sapiens

<400> SEQUENCE: 120

| | |
|---|---|
| aaacttcccg cacgcgttac aggagccagg tcggtataag cgccacgcct cgccgcccgt | 60 |
| caagctgtcc acatccctgg cctcagcccg ccacatcacc ctgacctgct tacgcccaga | 120 |
| ttttcttcaa tcacatctga ataaatcact tgaagaaagc ttatagcttc attgcaccat | 180 |
| gtgtggcatt tgggcgctgt ttggcagtga tgattgcctt tctgttcagt gtctgagtgc | 240 |
| tatgaagatt gcacacagag gtccagatgc attccgtttt gagaatgtca atggatacac | 300 |
| caactgctgc tttggatttc accggttggc ggtagttgac ccgctgtttg aatgcagcc | 360 |
| aattcgagtg aagaaatatc cgtatttgtg gctctgttac aatggtgaaa tctacaacca | 420 |
| taagaagatg caacagcatt ttgaatttga ataccagacc aaagtggatg gtgagataat | 480 |

```
ccttcatctt tatgacaaag gaggaattga gcaaacaatt tgtatgttgg atggtgtgtt    540
tgcatttgtt ttactggata ctgccaataa gaaagtgttc ctgggtagag atacatatgg    600
agtcagacct ttgtttaaag caatgacaga gatggattt ttggctgtat gttcagaagc    660
taaaggtctt gttacattga agcactccgc gactcccttt ttaaaagtgg agccttttct    720
tcctggacac tatgaagttt tggatttaaa gccaaatggc aaagttgcat ccgtggaaat    780
ggttaaatat catcactgtc gggatgtacc cctgcacgcc ctctatgaca atgtggagaa    840
actctttcca ggttttgaga tagaaactgt gaagaacaac ctcaggatcc tttttaataa    900
tgctgtaaag aaacgtttga tgacagacag aaggattggc tgcctttat cagggggctt     960 ggactccagc ttggttgctg ccactctgtt gaagcagctg aaagaagccc aagtacagta   1020
tcctctccag acatttgcaa ttggcatgga agacagcccc gatttactgg ctgctagaaa   1080
ggtggcagat catattggaa gtgaacatta tgaagtcctt tttaactctg aggaaggcat   1140
tcaggctctg gatgaagtca tattttcctt ggaaacttat gacattacaa cagttcgtgc   1200
ttcagtaggt atgtatttaa tttccaagta tattcggaag aacacagata gcgtggtgat   1260
cttctctgga gaaggatcag atgaacttac gcagggttac atatattttc acaaggctcc   1320
ttctcctgaa aaagccgagg aggagagtga gaggcttctg agggaactct atttgtttga   1380
tgttctccgc gcagatcgaa ctactgctgc ccatggtctt gaactgagag tcccatttct   1440
agatcatcga tttttttcct attacttgtc tctgccacca gaaatgagaa ttccaaagaa   1500
tgggatagaa aaacatctcc tgagagagac gtttgaggat tccaatctga tacccaaaga   1560
gattctctgg cgaccaaaag aagccttcag tgatggaata acttcagtta agaattcctg   1620
gtttaagatt ttacaggaat acgttgaaca tcaggttgat gatgcaatga tggcaaatgc   1680
agcccagaaa tttcccttca atactcctaa aaccaaagaa ggatattact accgtcaagt   1740
ctttgaacgc cattacccag gccgggctga ctggctgagc cattactgga tgcccaagtg   1800
gatcaatgcc actgacccct ctgcccgcac gctgacccac tacaagtcag ctgtcaaagc   1860
ttaggtggtc tttatgctgt aatgtgaaag caaatatttc ttcgtgttgg atggggactg   1920
tgggtagata ggggaacaat gagagtcaac tcaggctaac ttgggtttga aaaaaataaa   1980
attcctaaat tt                                                       1992
```

<210> SEQ ID NO 121
<211> LENGTH: 5698
<212> TYPE: DNA
<213> ORGANISM: Homo sapiens

<400> SEQUENCE: 121

```
aggttcaagt ggagctctcc taaccgacgc gcgtctgtgg agaagcggct tggtcggggg     60
tggtctcgtg gggtcctgcc tgtttagtcg ctttcagggt tcttgagccc cttcacgacc    120
gtcaccatgg aagtgtcacc attgcagcct gtaaatgaaa atatgcaagt caacaaaata    180
aagaaaaatg aagatgctaa gaaaagactg tctgttgaaa gaatctatca aaagaaaaca    240
caattggaac atattttgct ccgcccagac acctacattg gttctgtgga attagtgacc    300
cagcaaatgt gggtttacga tgaagatgtt ggcattaact atagggaagt cacttttgtt    360 cctggttttgt acaaaatctt tgatgagatt ctagttaatg ctgcggacaa caaacaaagg    420
gacccaaaaa tgtcttgtat tagagtcaca attgatccgg aaaacaattt aattagtata    480
tggaataatg gaaaggtat tcctgttgtt gaacacaaag ttgaaaagat gtatgtccca    540
```

-continued

```
gctctcatat ttggacagct cctaacttct agtaactatg atgatgatga aaagaaagtg    600
acaggtggtc gaaatggcta tggagccaaa ttgtgtaaca tattcagtac caaatttact    660
gtggaaacag ccagtagaga atacaagaaa atgttcaaac agacatggat ggataatatg    720
ggaagagctg gtgagatgga actcaagccc ttcaatggag aagattatac atgtatcacc    780
tttcagcctg atttgtctaa gtttaaaatg caaagcctgg acaaagatat tgttgcacta    840
atggtcagaa gagcatatga tattgctgga tccaccaaag atgtcaaagt ctttcttaat    900
ggaaataaac tgccagtaaa aggatttcgt agttatgtgg acatgtattt gaaggacaag    960
ttggatgaaa ctggtaactc cttgaaagta atacatgaac aagtaaacca caggtgggaa    1020
gtgtgtttaa ctatgagtga aaaaggcttt cagcaaatta gctttgtcaa cagcattgct    1080
acatccaagg gtggcagaca tgttgattat gtagctgatc agattgtgac taaacttgtt    1140
gatgttgtga agaagaagaa caagggtggt gttgcagtaa agcacatca ggtgaaaaat    1200 cacatgtgga tttttgtaaa tgccttaatt gaaaacccaa cctttgactc tcagacaaaa    1260
gaaaacatga ctttacaacc aagagctttt ggatcaacat gccaattgag tgaaaaattt    1320
atcaaagctg ccattggctg tggtattgta gaaagcatac taaactgggt gaagtttaag    1380
gcccaagtcc agttaaacaa gaagtgttca gctgtaaaac ataatagaat caagggaatt    1440
cccaaactcg atgatgccaa tgatgcaggg ggccgaaact ccactgagtg tacgcttatc    1500
ctgactgagg gagattcagc caaaactttg gctgtttcag gccttggtgt ggttgggaga    1560
gacaaatatg gggttttccc tcttagagga aaaatactca atgttcgaga agcttctcat    1620
aagcagatca tggaaaatgc tgagattaac aatatcatca agattgtggg tcttcagtac    1680
aagaaaaact atgaagatga agattcattg aagacgcttc gttatgggaa gataatgatt    1740
atgacagatc aggaccaaga tggttcccac atcaaaggct tgctgattaa ttttatccat    1800
cacaactggc cctctcttct gcgacatcgt tttctggagg aatttatcac tcccattgta    1860
aaggtatcta aaaacaagca agaaatggca ttttacagcc ttcctgaatt tgaagagtgg    1920
aagagttcta ctccaaatca taaaaatgg aaagtcaaat attacaaagg tttgggcacc    1980
agcacatcaa aggaagctaa agaatacttt gcagatatga aaagacatcg tatccagttc    2040
aaatattctg gtcctgaaga tgatgctgct atcagcctgg cctttagcaa aaaacagata    2100
gatgatcgaa aggaatggtt aactaatttc atggaggata aagacaacg aaagttactt    2160 gggcttcctg aggattactt gtatggacaa actaccacat atctgacata taatgacttc    2220
atcaacaagg aacttatctt gttctcaaat tctgataacg agagatctat cccttctatg    2280
gtggatggtt tgaaaccagg tcagagaaag gttttgttta cttgcttcaa acggaatgac    2340
aagcgagaag taaggttgc ccaattagct ggatcagtgg ctgaaatgtc ttcttatcat    2400
catggtgaga tgtcactaat gatgaccatt atcaatttgg ctcagaattt tgtgggtagc    2460
aataatctaa acctcttgca gcccattggt cagtttggta ccaggctaca tggtggcaag    2520
gattctgcta gtccacgata catctttaca atgctcagct ctttggctcg attgttattt    2580
ccaccaaaag atgatcacac gttgaagttt ttatatgatg acaaccagcg tgttgagcct    2640
gaatggtaca ttcctattat tcccatggtg ctgataaatg gtgctgaagg aatcggtact    2700
gggtggtcct gcaaaatccc caactttgat gtgcgtgaaa ttgtaaataa catcaggcgt    2760
ttgatggatg gagaagaacc tttgccaatg cttccaagtt acaagaactt caagggtact    2820
attgaagaac tggctccaaa tcaatatgtg attagtggtg aagtagctat tcttaattct    2880
acaaccattg aaatctcaga gcttcccgtc agaacatgga cccagacata caagaacaa    2940
```

```
gttctagaac ccatgttgaa tggcaccgag aagacacctc ctctcataac agactatagg    3000
gaataccata cagataccac tgtgaaattt gttgtgaaga tgactgaaga aaaactggca    3060
gaggcagaga gagttggact acacaaagtc ttcaaactcc aaactagtct cacatgcaac    3120
tctatggtgc ttttttgacca cgtaggctgt ttaaagaaat atgacacggt gttggatatt    3180
ctaagagact tttttgaact cagacttaaa tattatggat taagaaaaga atggctccta    3240
ggaatgcttg gtgctgaatc tgctaaactg aataatcagg ctcgctttat cttagagaaa    3300
atagatggca aaataatcat tgaaaataag cctaagaaag aattaattaa agttctgatt    3360
cagaggggat atgattcgga tcctgtgaag gcctggaaag aagcccagca aaaggttcca    3420
gatgaagaag aaaatgaaga gagtgacaac gaaaaggaaa ctgaaaagag tgactccgta    3480
acagattctg gaccaacctt caactatctt cttgatatgc ccctttggta tttaaccaag    3540
gaaaagaaag atgaactctg caggctaaga atgaaaaag aacaagagct ggacacatta    3600
aaaagaaaga gtccatcaga tttgtggaaa gaagacttgg ctacatttat tgaagaattg    3660
gaggctgttg aagccaagga aaacaagat gaacaagtcg acttcctgg aaaggggg    3720 aaggccaagg ggaaaaaaac acaaatggct gaagttttgc cttctccgcg tggtcaaaga    3780
gtcattccac gaataaccat agaaatgaaa gcagaggcag aaaagaaaaa taaaagaaa    3840 attaagaatg aaaatactga aggaagccct caagaagatg tgtggaact agaaggccta    3900 aaacaaagat tagaaaagaa acagaaaaga gaaccaggta caaagacaaa gaaacaaact    3960
acattggcat ttaagccaat caaaaaagga aagaagagaa atccctggtc tgattcagaa    4020
tcagatagga gcagtgacga agtaatttt gatgtccctc cacgagaaac agagccacgg    4080
agagcagcaa caaaaacaaa attcacaatg gatttggatt cagatgaaga tttctcagat    4140
tttgatgaaa aaactgatga tgaagatttt gtcccatcag atgctagtcc acctaagacc    4200
aaaacttccc caaaacttag taacaaagaa ctgaaaccac agaaaagtgt cgtgtcagac    4260
cttgaagctg atgatgttaa gggcagtgta ccactgtctt caagccctc tgctacacat    4320 ttcccagatg aaactgaaat tacaaaccca gttcctaaaa agaatgtgac agtgaagaag    4380
acagcagcaa aaagtcagtc ttccaccctcc actaccggtg ccaaaaaag gctgccca    4440 aaaggaacta aagggatcc agctttgaat tctggtgtct ctcaaaagcc tgatcctgcc    4500
aaaaccaaga atcgccgcaa aaggaagcca tccacttctg atgattctga ctctaatttt    4560
gagaaaattg tttcgaaagc agtcacaagc aagaaatcca agggggagag tgatgacttc    4620
catatggact ttgactcagc tgtggctcct cgggcaaaat ctgtacgggc aaagaaacct    4680
ataaagtacc tggaagagtc agatgaagat gatctgtttt aaaatgtgag gcgattattt    4740
taagtaatta tcttaccaag cccaagactg gttttaaagt tacctgaagc tcttaacttc    4800
ctcccctctg aatttagtt ggggaaggtg tttttagtac aagacatcaa agtgaagtaa    4860
agcccaagtg ttctttagct ttttataata ctgtctaaat agtgaccatc tcatgggcat    4920
tgttttcttc tctgctttgt ctgtgttttg agtctgcttt cttttgtctt taaaacctga    4980 ttttaagtt cttctgaact gtagaaatag ctatctgatc acttcagcgt aaagcagtgt    5040
gtttattaac catccactaa gctaaaacta gagcagtttg attttaaagt gtcactcttc    5100
ctccttttct actttcagta gatatgagat agagcataat tatctgtttt atcttagttt    5160
tatacataat ttaccatcag atagaacttt atggttctag tacagatact ctactacact    5220
cagcctctta tgtgccaagt ttttctttaa gcaatgagaa attgctcatg ttcttcatct    5280
```

-continued

| | |
|---|---|
| tctcaaatca tcagaggcca aagaaaaaca ctttggctgt gtctataact tgacacagtc | 5340 |
| aatagaatga agaaaattag agtagttatg tgattatttc agctcttgac ctgtcccctc | 5400 |
| tggctgcctc tgagtctgaa tctcccaaag agagaaacca atttctaaga ggactggatt | 5460 |
| gcagaagact cggggacaac atttgatcca agatcttaaa tgttatattg ataaccatgc | 5520 |
| tcagcaatga gctattagat tcattttggg aaatctccat aatttcaatt tgtaaacttt | 5580 |
| gttaagacct gtctacattg ttatatgtgt gtgacttgag taatgttatc aacgttttg | 5640 |
| taaatattta ctatgttttt ctattagcta aattccaaca attttgtact ttaataaa | 5698 |

<210> SEQ ID NO 122
<211> LENGTH: 2753
<212> TYPE: DNA
<213> ORGANISM: Homo sapiens

<400> SEQUENCE: 122

| | |
|---|---|
| gcgccatgga gcagtggcgg cagtgcggcc gctggctcat cgattgcaag gtcctgccgc | 60 |
| ccaaccaccg ggtggtgtgg ccctcggccg tggtcttcga cctggcgcag gcgctgcgcg | 120 |
| acggggtcct tctgtgccag ctgctgcaca acctctcccc cggctccatc gacctcaagg | 180 |
| acatcaactt ccggccgcag atgtcccagt ttctgtgttt gaagaacata cgcaccttcc | 240 |
| tgaaagtctg ccacgataaa tttggattaa ggaacagcga gctgtttgac ccctttgacc | 300 |
| tcttcgatgt gcgagacttt ggaaaggtca tctccgcggt gtcgaggctc tccctgcaca | 360 |
| gcatcgcgca gaacaaaggg atcaggcctt tccctcaga ggagaccaca gagaatgacg | 420 |
| atgacgtcta ccgcagcctg gaggagctgg ccgacgagca tgacctgggg gaggacatct | 480 |
| acgactgcgt cccgtgtgag gatggagggg acgacatcta cgaggacatc atcaaggtgg | 540 |
| aggtgcagca gcccatgatt agatacatgc agaaaatggg catgactgaa gatgacaaga | 600 |
| ggaactgctg cctgctggag atccaggaga ccgaggccaa gtactaccgc accctggagg | 660 |
| acattgagaa gaactacatg agcccctgc ggctggtgct gagcccggcg gacatggcag | 720 |
| ctgtcttcat taacctggag gacctgatca aggtgcatca cagcttcctg agggccatcg | 780 |
| acgtgtccgt gatggtgggg ggcagcacgc tggccaaggt cttcctcgat ttcaaggaaa | 840 |
| ggcttctgat ctacggggag tactgcagcc acatggagca cgcccagaac acactgaacc | 900 |
| agctcctggc cagccgggag gacttcaggc agaaagtcga ggagtgcaca ctgaaggtcc | 960 |
| aggatggaaa atttaagctg caagacctgc tggtggtccc catgcagagg gtgctcaaat | 1020 |
| accacctgct cttgaaggag cttctgagcc attctgcgga acggcctgag aggcagcagc | 1080 |
| tcaaagaagc actggaagcc atgcaggact tggcgatgta catcaatgaa gttaaacggg | 1140 |
| acaaggagac cttgaggaaa atcagcgaat tcagagttc tatagaaaat ttgcaagtga | 1200 |
| aactggagga atttggaaga ccaaagattg acggggaact gaaagtccgg tccatagtca | 1260 |
| accacaccaa gcaggacagg tacttgttcc tgtttgacaa ggtggtcatc gtctgcaagc | 1320 |
| ggaagggcta cagctacgag ctcaaggaga tcatcgagct gctgttccac aagatgaccg | 1380 |
| acgacccat gaacaacaag gacgtcaaga agtctcacgg gaaaatgtgg tcctacggct | 1440 |
| tctacctaat tcaccttcaa ggaaagcagg gcttccagtt tttctgcaaa acagaagata | 1500 |
| tgaagaggaa gtggatggag cagtttgaga tggccatgtc aaacatcaag ccagacaaag | 1560 |
| ccaatgccaa ccaccacagt ttccagatgt acacgtttga caagaccacc aactgcaaag | 1620 |
| cctgcaaaat gttcctcagg ggcaccttct accaggata catgtgtacc aagtgtggcg | 1680 |
| tcggggcaca caaggagtgc ctggaagtga tacctccctg caagttcact tctcctgcag | 1740 |

```
atctggacgc ctccggagcg ggaccaggtc ccaagatggt ggccatgcag aattaccatg    1800
gcaacccagc ccctcccggg aagcctgtgc tgaccttcca gacgggcgac gtgcttgagc    1860
tgctgagggg cgaccctgag tctccgtggt gggagggtcg tctggtacaa accaggaagt    1920
cagggtattt ccccagctca tctgtgaagc cctgccctgt ggatggaagg ccgcccatca    1980
gccggccgcc atcccgggag atcgactaca ctgcataccc ctggtttgca ggtaacatgg    2040
agaggcagca gacggacaac ctgctcaagt cccacgccag cgggacctac ctgatcaggg    2100
agcggcctgc cgaggctgag cgctttgcaa taagcatcaa gttcaatgat gaggtgaagc    2160
acatcaaggt ggtggagaag gacaactgga tccacatcac agaggccaag aaattcgaca    2220
gcctcctgga gttggtggag tactaccagt gccactcact gaaggagagc ttcaagcagc    2280
tggacaccac actcaagtac ccctacaagt cccgggaacg ttcggcctcc agggcctcca    2340
gccggtcccc agcttcctgt gcttcctaca acttttcttt tctcagtcct cagggcctca    2400
gctttgcttc tcagggcccc tccgctccct tctggtcagt gttcacgccc cgcgtcatcg    2460
gcacagctgt ggccaggtat aactttgccg cccgagatat gagggagctt tcgctgcggg    2520
agggtgacgt ggtgaggatc tacagccgca tcggcggaga ccagggctgg tggaagggcg    2580
agaccaacgg acggattggc tggtttcctt caacgtacgt agaagaggag ggcatccagt    2640
gacggcagga acgtggacaa gactcgcaga ttttcttggg agagtcactc cagccctgaa    2700
gtctgtctct agctcctctg tgactcagag gggaaatacc aacctcccag tct           2753
```

<210> SEQ ID NO 123
<211> LENGTH: 23
<212> TYPE: DNA
<213> ORGANISM: Artificial
<220> FEATURE:
<223> OTHER INFORMATION: Synthetic

<400> SEQUENCE: 123
cgtatgcccc gctgaatctc gtg                                              23